US009365583B2

(12) United States Patent
Siu et al.

(10) Patent No.: US 9,365,583 B2
(45) Date of Patent: Jun. 14, 2016

(54) SUBSTITUTED PYRAZOLES AND USES THEREOF

(71) Applicant: Genentech, Inc., South San Francisco, CA (US)

(72) Inventors: Michael Siu, Burlingame, CA (US); Anthony Estrada, San Carlos, CA (US); Wen Liu, Foster City, CA (US); Joseph P. Lyssikatos, Piedmont, CA (US); Snahel Patel, Foster City, CA (US); Guibai Liang, Shanghai (CN); Kevin Chen, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/576,890

(22) Filed: Dec. 19, 2014

(65) Prior Publication Data

US 2015/0175619 A1    Jun. 25, 2015

Related U.S. Application Data

(63) Continuation of application No. PCT/CN2013/090153, filed on Dec. 20, 2013.

(30) Foreign Application Priority Data

Dec. 20, 2013    (WO) ................. PCT/CN2013/090153

(51) Int. Cl.
| | |
|---|---|
| *C07D 491/107* | (2006.01) |
| *C07D 401/14* | (2006.01) |
| *C07D 405/14* | (2006.01) |
| *C07D 407/14* | (2006.01) |
| *C07D 413/14* | (2006.01) |
| *C07D 471/04* | (2006.01) |
| *C07D 487/04* | (2006.01) |
| *C07D 491/08* | (2006.01) |
| *C07D 498/04* | (2006.01) |
| *C07D 498/10* | (2006.01) |
| *C07D 401/04* | (2006.01) |

(52) U.S. Cl.
CPC .......... *C07D 491/107* (2013.01); *C07D 401/04* (2013.01); *C07D 401/14* (2013.01); *C07D 405/14* (2013.01); *C07D 407/14* (2013.01); *C07D 413/14* (2013.01); *C07D 471/04* (2013.01); *C07D 487/04* (2013.01); *C07D 491/08* (2013.01); *C07D 498/04* (2013.01); *C07D 498/10* (2013.01)

(58) Field of Classification Search
CPC ............. C07D 491/107; C07D 401/14; C07D 405/14; C07D 407/14; C07D 413/14; C07D 471/04; C07D 487/04; C07D 491/08; C07D 498/04; C07D 498/10
See application file for complete search history.

(56) References Cited

FOREIGN PATENT DOCUMENTS

| WO | 2011/050192 A1 | 4/2011 |
| WO | 2011/149950 A2 | 12/2011 |
| WO | WO 2013174780 | * 11/2013 |
| WO | WO 2014111496 | * 7/2014 |

OTHER PUBLICATIONS

International Search Report issued in Internatonal Application No. PCT/EP2014/050860, dated Mar. 3, 2014.

* cited by examiner

*Primary Examiner* — Rebecca Anderson
(74) *Attorney, Agent, or Firm* — Mark D. Kafka

(57) ABSTRACT

The present invention provides for compounds of formula 0 and various embodiments thereof, and compositions comprising compounds of formula 0 and various embodiments thereof.

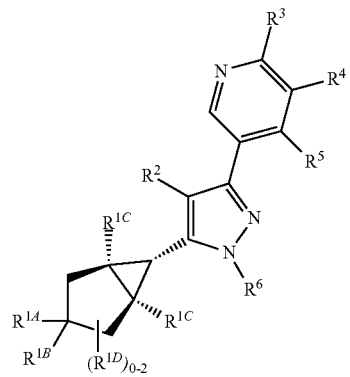

In compounds of formula 0, the groups $R^{1A}$, $R^{1B}$, $R^{1C}$, $R^{1D}$, $R^2$, $R^3$, $R^4$, $R^5$ and $R^6$ have the meaning as described herein. The present invention also provides for methods of using compounds of formula 0 and compositions comprising compounds of formula 0 as DLK inhibitors and for treating neurodegeneration diseases and disorders.

40 Claims, No Drawings

SUBSTITUTED PYRAZOLES AND USES THEREOF

CROSS-REFERENCE TO RELATED APPLICATION

This patent application claims the benefit under 35 U.S.C. §119(a) of International Application No. PCT/CN2013/090153, filed Dec. 20, 2013. This entire content of this application is hereby incorporated herein by reference.

FIELD OF THE INVENTION

The present invention relates to organic compounds useful for therapy and/or prophylaxis in a mammal, and in particular to inhibitors of DLK useful for treating neurodegeneration diseases and disorders.

BACKGROUND OF THE INVENTION

Neuron or axon degeneration plays a central role in the proper development of the nervous system and is a hallmark of many neurodegenerative diseases including, for example, amyotrophic lateral sclerosis (ALS), glaucoma, Alzheimer's disease, and Parkinson's disease, as well as traumatic injury to the brain and spinal cord. Recent patent publication WO 2011/050192, incorporated herein by reference, describes the role of the Dual Leucine Zipper Kinase (DLK), also referred to as MAP3K12, to cause neuronal cell death. Neurodegenerative diseases and injuries are devastating to patients and caregivers, and also result in great financial burdens, with annual costs currently exceeding several hundred billion dollars in the United States alone. Most current treatments for these diseases and conditions are inadequate. Adding to the urgency of the problems created by these diseases is the fact that many such diseases are age-related, and thus their incidence is increasing rapidly as population demographics change. There is a great need for the development of effective approaches to treating neurodegenerative diseases and nervous system injuries, including for example, the development of inhibitors of DLK.

SUMMARY OF THE INVENTION

In one aspect the present invention provides for novel compounds. In a first embodiment of such compounds (Embodiment 0; abbreviated as "E0") the invention provides for compounds of formula 0:

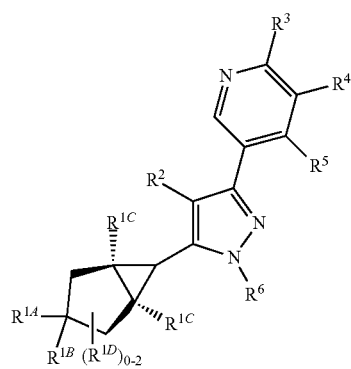

and salts thereof; wherein in formula 0

$R^{1A}$ is selected from the group consisting of H, —F, —Cl, a 3 to 12 membered heterocycloalkyl, 5 or 6 membered heteroaryl, —$(X^{1A})_{0-1}$—$OR^{1A-1}$, —$(X^{1A})_{0-1}$—$SR^{1A-1}$, —$(X^{1A})_{0-1}$—$S(O)R^{1A-1}$, —$(X^{1A})_{0-1}$—$S(O)_2R^{1A-1}$ and —$(X^{1A})_{0-1}$—$N(R^{1A-1})_2$, each $X^{1A}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{1A-1}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl-, 3-7 membered heterocycloalkyl, 3-7 membered heterocycloalkyl-$C_{1-4}$ alkyl-, 5-6 membered heteroaryl, 5-6 membered heteroaryl-$C_{1-4}$ alkyl-, phenyl and phenyl-$C_{1-4}$ alkyl-, or any two $R^{1A-1}$ groups attached to the same nitrogen atom are optionally combined to form a 3 to 6 membered heterocyclic ring optionally comprising 1 to 2 additional heteroatom selected from N, O and S, and wherein a $R^{1A}$ group at each occurrence is independently optionally further substituted with 1 to 5 $R^{1A-2}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ dialkylamino, $C_{1-6}$ alkyl, $C_{1-6}$ heteroalkyl, $C_{1-6}$ haloalkyl, oxo, —S(=O)$_{1-2}$—$C_{1-6}$ alkyl and 3 to 7 membered heterocycloalkyl;

$R^{1B}$ is selected from the group consisting of H, —OH, —F, —Cl, —Br, —I, —CN, —NH$_2$, —N(CH$_3$)C(O)CH$_3$, $C_{1-6}$ alkylamino, $C_{1-6}$ dialkylamino, $C_{1-6}$ alkoxy, $C_{1-6}$ alkyl, $C_{1-6}$ haloalkyl and $C_{1-6}$ heteroalkyl;

or $R^{1A}$ and $R^{1B}$ together form an oxo group or a 3 to 7 membered heterocycloalkyl comprising 1 to 2 heteroatoms selected from N, O and S and wherein said 3 to 7 membered heterocycloalkyl is optionally further substituted with 1 to 5 $R^{1A-2}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ dialkylamino, $C_{1-6}$ alkyl, $C_{1-6}$ heteroalkyl, oxo, —S(=O)$_{1-2}$—$C_{1-6}$ alkyl and 3 to 7 membered heterocycloalkyl;

$R^{1C}$ at each occurrence is independently selected from the group consisting of hydrogen, —F, —Cl, —Br, —I, $C_{1-4}$ alkyl and $C_{1-4}$ haloalkyl;

$R^{1D}$ at each occurrence is independently selected from the group consisting of hydrogen, —F, —Cl, —Br, —I, —OH, $C_{1-4}$ alkyl, $C_{1-4}$ haloalkyl, 3 to 7 membered heterocycloalkyl;

or $R^{1A}$ and $R^{1D}$ together form a 3-7 membered cycloalkyl or 3-7 membered heterocycloalkyl, each optionally substituted by $C_{1-4}$ alkyl;

$R^2$ is selected from the group consisting of hydrogen, —F, —Cl, —Br, —I, —NO$_2$, —CN, $C_{1-6}$ alkyl and $C_{1-6}$ haloalkyl;

$R^3$ is N(R$^{3A}$)$_2$, wherein each $R^{3A}$ is independently selected from the group consisting of hydrogen, $C_{1-6}$ alkyl, and $C_{1-6}$ haloalkyl;

$R^4$ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^4)_{0-1}$—CN, —$(X^4)_{0-1}$—NO$_2$, —$(X^4)_{0-1}$—SF$_5$, —$(X^4)_{0-1}$—OSF$_5$, —$(X^4)_{0-1}$—OR$^{4A}$, —$(X^4)_{0-1}$—N(R$^{4A}$)$_2$, —$(X^4)_{0-1}$—SR$^{4A}$, —$(X^4)_{0-1}$—CF$_3$, 3 to 7 membered cycloalkyl-$(X^4)_{0-1}$—, 3 to 7 membered heterocycloalkyl-$(X^4)_{0-1}$—, 5 to 6 membered heteroaryl-$(X^4)_{0-1}$—, phenyl-$(X^4)_{0-1}$—, —$(X^4)_{0-1}$—C(=O)N(R$^{4A}$)(R$^{4A}$), —$(X^4)_{0-1}$—C(=O)OR$^{4A}$, —$(X^4)_{0-1}$—N(R$^{4A}$)C(=O)(R$^{4A}$), —$(X^4)_{0-1}$—N(R$^{4A}$)C(=O)OR$^{4A}$, —$(X^4)_{0-1}$—S(=O)$_{1-2}$R$^{4A}$, —$(X^4)_{0-1}$—N(R$^{4A}$)S(=O)$_{1-2}$—R$^{4A}$, —$(X^4)_{0-1}$—S(=O)$_{1-2}$N(R$^{4A}$)$_2$, —$(X^4)_{0-1}$—C(=O)R$^{4A}$, —$(X^4)_{0-1}$—C(=NOR$^{4A}$)R$^{4A}$, —$(X^4)_{0-1}$—N(R$^{4A}$)C(=O)N(R$^{4A}$)$_2$, —$(X^4)_{0-1}$—OC(=O)R$^{4A}$, —$(X^4)_{0-1}$—OP(=O)(OR$^{4A}$)$_2$, —$(X^4)$—SC(=O)OR$^{4A}$ and —(X⁴)—SC(=O)N(R⁴⁴)₂, each X⁴ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring optionally comprising 1 to 2 additional heteroatoms selected from N, O and S, and wherein a $R^4$ group is independently optionally further substituted with 1 to 5 $R^{4A-1}$ substituents independently selected from the group consisting of —F, —Cl, —Br, —I, —OH, —CN, —NO₂, —SF₅, —NH₂, $C_{1-6}$ alkoxy, $C_{1-6}$ alkylamino, $C_{1-6}$ alkyl and $C_{1-6}$ dialkylamino;

or $R^3$ and $R^4$ together with the atoms to which they are attached form a 5 or 6 membered heteroaryl wherein the 5 or 6 membered heteroaryl is optionally substituted with 1 to 3 $R^{3/4cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X^{3/4})₀₋₁—CN, —(X^{3/4})₀₋₁—NO₂, —(X^{3/4})₀₋₁—SF₅, —(X^{3/4})₀₋₁—OSF₅, —(X^{3/4})₀₋₁—OR^{3/4A}, —(X^{3/4})₀₋₁—N(R^{3/4A})₂, —(X^{3/4})₀₋₁—SR^{3/4A}, —(X^{3/4})₀₋₁—CF₃, 3 to 12 membered cycloalkyl-(X^{3/4})₀₋₁—, 3 to 12 membered heterocycloalkyl-(X^{3/4})₀₋₁—, 5 to 6 membered heteroaryl-(X^{3/4})₀₋₁, phenyl-(X^{3/4})₀₋₁—, —(X^{3/4})₀₋₁—C(=O)N(R^{3/4A})(R^{3/4A}), —(X^{3/4})₀₋₁—C(=O)OR^{3/4A}, —(X^{3/4})₀₋₁—N(R^{3/4A})C(=O)(R^{3/4A}), —(X^{3/4})₀₋₁—N(R^{3/4A})C(=O)OR^{3/4A}, —(X^{3/4})₀₋₁—S(=O)₁₋₂—R^{3/4A}, —(X^{3/4})₀₋₁—N(R^{3/4A})S(=O)₁₋₂R^{3/4A}, —(X^{3/4})₀₋₁—S(=O)₁₋₂N(R^{3/4A})₂, —(X^{3/4})₀₋₁—C(=O)R^{3/4A}, —(X^{3/4})₀₋₁—C(=NOR^{3/4A})R^{3/4A}, —(X^{3/4})₀₋₁—N(R^{3/4A})C(=O)N(R^{3/4A})₂ and —(X^{3/4})₀₋₁—OC(=O)R^{3/4A}, —(X^{3/4})₀₋₁—OP(=O)(OR^{3/4A})₂, —(X^{3/4})—SC(=O)OR^{3/4A} and —(X^{3/4})—SC(=O)N(R^{3/4A})₂, each X^{3/4} is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{3/4A}$ at each occurrence is each independently selected from the group consisting of hydrogen, $C_{1-6}$ alkyl, $C_{1-6}$ haloalkyl and $C_{1-6}$ heteroalkyl, or any two $R^{3/4A}$ groups attached to the same nitrogen atom are optionally combined to form a 3 to 6 membered heterocyclic ring optionally comprising 1 to 2 additional heteroatom selected from N, O and S, and wherein a $R^{3/4cy}$ substituent at each occurrence is independently optionally further substituted with 1 to 5 $R^{3/4cy-1}$ substituents independently selected from the group consisting of —F, —Cl, —Br, —I, —OH, —CN, —NO₂, —SF₅, —NH₂, $C_{1-6}$ alkoxy, $C_{1-6}$ alkylamino, $C_{1-6}$ alkyl and $C_{1-6}$ dialkylamino;

$R^5$ is hydrogen, —F, —Cl, —Br or —I; and $R^6$ is selected from the group consisting of $C_{1-12}$ alkyl, $C_{1-12}$ haloalkyl, $C_{1-12}$ heteroalkyl-(L)₀₋₁-, $C_{2-12}$ alkenyl-(L)₀₋₁-, $C_{2-12}$ alkynyl-(L)₀₋₁-, 3 to 12 membered cycloalkyl-(L)₀₋₁- and 3 to 12 membered heterocycloalkyl-(L)₀₋₁-, wherein L is selected from the group consisting of $C_{1-4}$ alkylene, $C_{1-4}$ haloalkylene, heteroalkylene, $C_{2-4}$ alkenylene and $C_{2-4}$ alkynylene, wherein a $R^6$ group is optionally further substituted with 1 to 5 $R^{6A}$ substituents independently selected from the group consisting of —F, —Cl, —Br, —I, —OH, —CN, —NO₂, —SF₅, —OSF₅, —NH₂, $C_{1-6}$ alkyl, $C_{1-6}$ haloalkyl, 3 to 5 membered cycloalkyl, 3 to 5 membered heterocycloalkyl, $C_{1-6}$ alkoxy, $C_{1-6}$ alkylthio, $C_{1-6}$ alkylamino and $C_{1-6}$ dialkylamino In a further embodiment of such compounds (Embodiment 1; abbreviated as "E1") the invention provides for compounds of formula I:

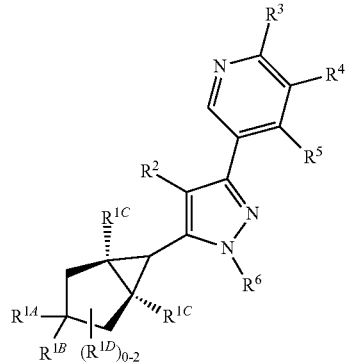

I and salts thereof; wherein in formula I $R^{1A}$ is selected from the group consisting of a 3 to 12 membered heterocycloalkyl, 5 or 6 membered heteroaryl, —(X^{1A})₀₋₁—OR^{1A-1}, —(X^{1A})₀₋₁—SR^{1A-1}, —(X^{1A})₀₋₁—S(O)R^{1A-1}, —(X^{1A})₀₋₁—S(O)₂R^{1A-1} and —(X^{1A})₀₋₁—N(R^{1A-1})₂, each X^{1A} is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{1A-1}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl-, 3-7 membered heterocycloalkyl, 3-7 membered heterocycloalkyl-$C_{1-4}$ alkyl-, 5-6 membered heteroaryl, 5-6 membered heteroaryl-$C_{1-4}$ alkyl-, phenyl and phenyl-$C_{1-4}$ alkyl-, or any two $R^{1A-1}$ groups attached to the same nitrogen atom are optionally combined to form a 3 to 6 membered heterocyclic ring optionally comprising 1 to 2 additional heteroatom selected from N, O and S, and wherein a $R^{1A}$ group at each occurrence is independently optionally further substituted with 1 to 5 $R^{1A-2}$ substituents independently selected from the group consisting of —F, —Cl, —Br, —I, —OH, —CN, —NO₂, —SF₅, —NH₂, $C_{1-6}$ alkoxy, $C_{1-6}$ alkylamino, $C_{1-6}$ dialkylamino, $C_{1-6}$ alkyl, oxo, —S(=O)₁₋₂—$C_{1-6}$ alkyl and 3 to 7 membered heterocycloalkyl;

$R^{1B}$ is selected from the group consisting of hydrogen, —OH, —F, —Cl, —Br, —I, —CN, NH₂, $C_{1-6}$ alkylamino, $C_{1-6}$ dialkylamino, $C_{1-6}$ alkoxy, $C_{1-6}$ alkyl, $C_{1-6}$ haloalkyl and $C_{1-6}$ heteroalkyl;

or $R^{1A}$ and $R^{1B}$ together form an oxo group or a 3 to 7 membered heterocycloalkyl comprising 1 to 2 heteroatoms selected from N, O and S and wherein said 3 to 7 membered heterocycloalkyl is optionally further substituted with 1 to 5 $R^{1A-2}$ substituents independently selected from the group consisting of —F, —Cl, —Br, —I, —OH, —CN, —NO₂, —SF₅, —NH₂, $C_{1-6}$ alkoxy, $C_{1-6}$ alkylamino, $C_{1-6}$ dialkylamino, $C_{1-6}$ alkyl, oxo, —S(=O)₁₋₂—$C_{1-6}$ alkyl and 3 to 7 membered heterocycloalkyl;

$R^{1C}$ at each occurrence is independently selected from the group consisting of hydrogen, —F, —Cl, —Br, —I, $C_{1-4}$ alkyl and $C_{1-4}$ haloalkyl;

$R^{1D}$ at each occurrence is independently selected from the group consisting of hydrogen, —F, —Cl, —Br, —I, $C_{1-4}$ alkyl and $C_{1-4}$ haloalkyl;

R² is selected from the group consisting of hydrogen, —F, —Cl, —Br, —I, —NO₂, —CN, $C_{1-6}$ alkyl and $C_{1-6}$ haloalkyl;

R³ is N(R$^{3A}$)₂, wherein each R$^{3A}$ is independently selected from the group consisting of hydrogen, $C_{1-6}$ alkyl, and $C_{1-6}$ haloalkyl;

R⁴ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X⁴)$_{0-1}$—CN, —(X⁴)$_{0-1}$—NO₂, —(X⁴)$_{0-1}$—SF₅, —(X⁴)$_{0-1}$—OSF₅, —(X⁴)$_{0-1}$—OR$^{4A}$, —(X⁴)$_{0-1}$—N(R$^{4A}$)₂, —(X⁴)$_{0-1}$—SR$^{4A}$, —(X⁴)$_{0-1}$—CF₃, 3 to 7 membered cycloalkyl-(X⁴)$_{0-1}$—, 3 to 7 membered heterocycloalkyl-(X⁴)$_{0-1}$—, 5 to 6 membered heteroaryl-(X⁴)$_{0-1}$—, phenyl-(X⁴)$_{0-1}$—, —(X⁴)$_{0-1}$—C(═O)N(R$^{4A}$)(R$^{4A}$), —(X⁴)$_{0-1}$—C(═O)OR$^{4A}$, —(X⁴)$_{0-1}$—N(R$^{4A}$)C(═O)(R$^{4A}$), —(X⁴)$_{0-1}$—N(R$^{4A}$)C(═O)OR$^{4A}$, —(X⁴)$_{0-1}$—S(═O)$_{1-2}$—R$^{4A}$, —(X⁴)$_{0-1}$—N(R$^{4A}$)S(═O)$_{1-2}$—R$^{4A}$, —(X⁴)$_{0-1}$—S(═O)$_{1-2}$N(R$^{4A}$)₂, —(X⁴)$_{0-1}$—C(═O)R$^{4A}$, —(X⁴)$_{0-1}$—C(═NOR$^{4A}$)R$^{4A}$, —(X⁴)$_{0-1}$—N(R$^{4A}$)C(═O)N(R$^{4A}$)₂, —(X⁴)$_{0-1}$—OC(═O)R$^{4A}$, —(X⁴)$_{0-1}$—OP(═O)(OR$^{4A}$)₂, —(X⁴)—SC(═O)OR$^{4A}$ and —(X⁴)—SC(═O)N(R$^{4A}$)₂, each X⁴ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, R$^{4A}$ at each occurrence is each independently selected from the group consisting of hydrogen, $C_{1-6}$ alkyl, $C_{1-6}$ haloalkyl and $C_{1-6}$ heteroalkyl, or any two R$^{4A}$ groups attached to the same nitrogen atom are optionally combined to form a 3 to 6 membered heterocyclic ring optionally comprising 1 to 2 additional heteroatoms selected from N, O and S, and wherein a R⁴ group is independently optionally further substituted with 1 to 5 R$^{4A-1}$ substituents independently selected from the group consisting of —F, —Cl, —Br, —I, —OH, —CN, —NO₂, —SF₅, —NH₂, $C_{1-6}$ alkoxy, $C_{1-6}$ alkylamino, $C_{1-6}$ alkyl and $C_{1-6}$ dialkylamino;

or R³ and R⁴ together with the atoms to which they are attached form a 5 or 6 membered heteroaryl wherein the 5 or 6 membered heteroaryl is optionally substituted with 1 to 3 R$^{3/4cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X$^{3/4}$)$_{0-1}$—CN, —(X$^{3/4}$)$_{0-1}$—NO₂, —(X$^{3/4}$)$_{0-1}$—SF₅, —(X$^{3/4}$)$_{0-1}$—OSF₅, —(X$^{3/4}$)$_{0-1}$—OR$^{3/4A}$, —(X$^{3/4}$)$_{0-1}$—N(R$^{3/4A}$)₂, —(X$^{3/4}$)$_{0-1}$—SR$^{3/4A}$, —(X$^{3/4}$)$_{0-1}$—CF₃, 3 to 12 membered cycloalkyl-(X$^{3/4}$)$_{0-1}$—, 3 to 12 membered heterocycloalkyl-(X$^{3/4}$)$_{0-1}$—, 5 to 6 membered heteroaryl-(X$^{3/4}$)$_{0-1}$—, phenyl-(X$^{3/4}$)$_{0-1}$—, —(X$^{3/4}$)$_{0-1}$—C(═O)N(R$^{3/4A}$)(R$^{3/4A}$), —(X$^{3/4}$)$_{0-1}$—C(═O)OR$^{3/4A}$, —(X$^{3/4}$)$_{0-1}$—N(R$^{3/4A}$)C(═O(R$^{3/4A}$), —(X$^{3/4}$)$_{0-1}$—N(R$^{3/4A}$)C(═O)OR$^{3/4A}$, —(X$^{3/4}$)$_{0-1}$—S(═O)$_{1-2}$—R$^{3/4A}$, —(X$^{3/4}$)$_{0-1}$—N(R$^{3/4A}$)S(═O)$_{1-2}$—R$^{3/4A}$, —(X$^{3/4}$)$_{0-1}$—S(═O)$_{1-2}$N(R$^{3/4A}$)₂, —(X$^{3/4}$)$_{0-1}$—C(═O)R$^{3/4A}$, —(X$^{3/4}$)$_{0-1}$—C(═NOR$^{3/4A}$)R$^{3/4A}$, —(X$^{3/4}$)$_{0-1}$—N(R$^{3/4A}$)C(═O)N(R$^{3/4A}$)₂ and —(X$^{3/4}$)$_{0-1}$—OC(═O)R$^{3/4A}$, (X$^{3/4}$)$_{0-1}$—OP(═O)(OR$^{3/4A}$)₂, —(X$^{3/4}$)—SC(═O)OR$^{3/4A}$ and —(X$^{3/4}$)—SC(═O)N(R$^{3/4A}$)₂, each X$^{3/4}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, R$^{3/4A}$ at each occurrence is each independently selected from the group consisting of hydrogen, $C_{1-6}$ alkyl, $C_{1-6}$ haloalkyl and $C_{1-6}$ heteroalkyl, or any two R$^{3/4A}$ groups attached to the same nitrogen atom are optionally combined to form a 3 to 6 membered heterocyclic ring optionally comprising 1 to 2 additional heteroatom selected from N, O and S, and wherein a R$^{3/4cy}$ substituent at each occurrence is independently optionally further substituted with 1 to 5 R$^{3/4cy-1}$ substituents independently selected from the group consisting of —F, —Cl, —Br, —I, —OH, —CN, —NO₂, —SF₅, —NH₂, $C_{1-6}$ alkoxy, $C_{1-6}$ alkylamino, $C_{1-6}$ alkyl and $C_{1-6}$ dialkylamino;

R⁵ is hydrogen, —F, —Cl, —Br or —I; and

R⁶ is selected from the group consisting of $C_{1-12}$ alkyl, $C_{1-12}$ haloalkyl, $C_{1-12}$ heteroalkyl-(L)$_{0-1}$-, $C_{2-12}$ alkenyl-(L)$_{0-1}$-, $C_{2-12}$ alkynyl-(L)$_{0-1}$-, 3 to 12 membered cycloalkyl-(L)$_{0-1}$-and 3 to 12 membered heterocycloalkyl-(L)$_{0-1}$-, wherein L is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, wherein a R⁶ group is optionally further substituted with 1 to 5 R$^{6A}$ substituents independently selected from the group consisting of —F, —Cl, —Br, —I, —OH, —CN, —NO₂, —SF₅, —OSF₅, —NH₂, $C_{1-6}$ alkyl, $C_{1-6}$ haloalkyl, 3 to 5 membered cycloalkyl, 3 to 5 membered heterocycloalkyl, $C_{1-6}$ alkoxy, $C_{1-6}$ alkylthio, $C_{1-6}$ alkylamino and $C_{1-6}$ dialkylamino.

Further embodiments (E) of the first embodiment of compounds of the invention are described below.

E2 The compound of E0 which is a compound of formula Ia, Ib or Ic:

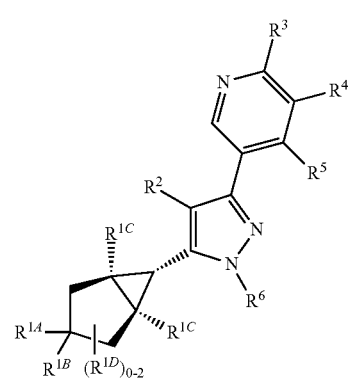

Ia

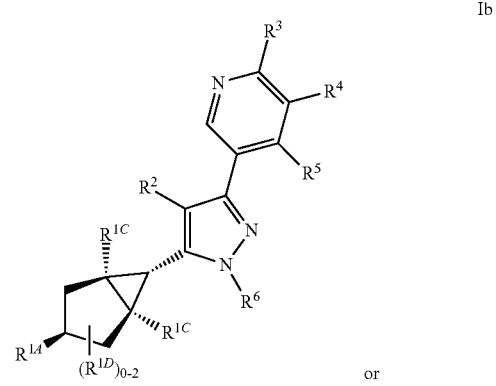

Ib or

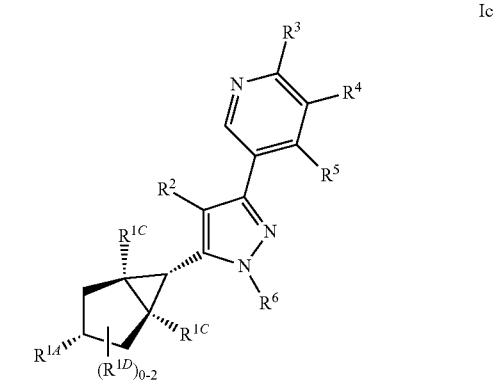

Ic or a salt thereof.

E3 The compound of E0, E1 or E2, wherein R² is hydrogen.
E4 The compound of any one of E0-E3, wherein R⁵ is hydrogen or —F.

E5 The compound of any one of E0-E3, wherein $R^5$ is hydrogen.

E6 The compound of any one of E0-E5, wherein $R^{1C}$ and $R^{1D}$ at each occurrence are each hydrogen.

E7 The compound of E0 which is a compound of formula Id or Ie:

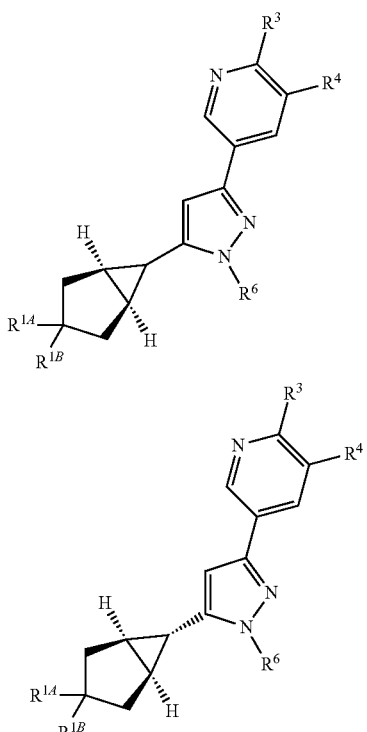

or a salt thereof.

E8 The compound of E0 which is a compound of formula If or Ig:

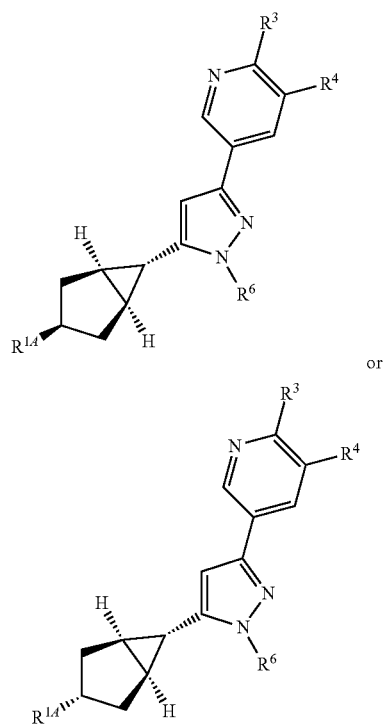

or a salt thereof.

E9 The compound of any one E0-E8, wherein $R^6$ is $C_{1-12}$ alkyl or a 3 to 7 membered cycloalkyl-(L)$_{0-1}$, wherein L is a $C_{1-4}$ alkylene, and wherein said $C_{1-12}$ alkyl group and 3 to 7 membered cycloalkyl-(L)$_{0-1}$ are each independently optionally substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ haloalkyl, $C_{1-6}$ alkoxy, $C_{1-6}$ alkylthio, $C_{1-6}$ alkylamino and $C_{1-6}$ dialkylamino.

E10 The compound of any one of E0-E8, wherein $R^6$ is $C_{1-6}$ alkyl, wherein the $C_{1-6}$ alkyl is optionally substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ haloalkyl, $C_{1-6}$ alkoxy, $C_{1-6}$ alkylthio, $C_{1-6}$ alkylamino and $C_{1-6}$ dialkylamino.

E11 The compound of any one of E0-E8, wherein $R^6$ is —CH(CH$_3$)$_2$ or —CH$_2$CHF$_2$.

E12 The compound of any one of E0-E8, wherein $R^6$ is 3 to 7 membered cycloalkyl-(L)$_{0-1}$, wherein L is $C_{1-4}$ alkylene; and wherein $R^6$ is optionally substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ haloalkyl, $C_{1-6}$ alkoxy, $C_{1-6}$ alkylthio, $C_{1-6}$ alkylamino and $C_{1-6}$ dialkylamino.

E13 The compound of any one of E0-E8, wherein $R^6$ is selected from the group consisting of:

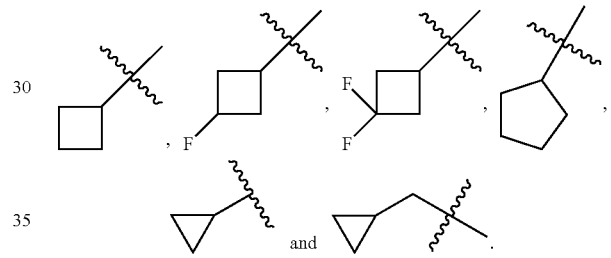

E14 The compound of any one of E0-E8, wherein $R^6$ is $C_{1-6}$ alkyl, wherein the $C_{1-6}$ alkyl group is optionally substituted with 1 to 5 $R^{6A}$ substituents independently selected from the group consisting of —F, —Cl, —Br, —I, —OH, —CN, —NO$_2$ and —NH$_2$.

E15 The compound of any one of E0-E8, wherein $R^6$ is $C_{1-12}$ alkyl.

E16 The compound of any one of E0-E8, wherein $R^6$ is $C_{1-6}$ alkyl.

E17 The compound of any one of E0-E8, wherein $R^6$ is —CH(CH$_3$)$_2$.

E18 The compound of any one of E0-E8, wherein $R^6$ is 3 to 7 membered cycloalkyl, wherein the 3 to 7 membered cycloalkyl is optionally substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ haloalkyl, $C_{1-6}$ alkoxy, $C_{1-6}$ alkylthio, $C_{1-6}$ alkylamino and $C_{1-6}$ dialkylamino E19 The compound of any one of E0-E8, wherein $R^6$ is 3 to 7 membered cycloalkyl, wherein the 3 to 7 membered cycloalkyl is optionally substituted with 1 to 5 $R^{6A}$ substituents independently selected from the group consisting of —F, —Cl, —Br, —I, —OH, —CN, —NO$_2$, —NH$_2$, $C_{1-3}$ haloalkyl, $C_{1-3}$ alkoxy, $C_{1-3}$ alkylthio, $C_{1-3}$ alkylamino and $C_{1-3}$ dialkylamino.

E20 The compound of any one of E0-E19, wherein $R^3$ is $N(R^{3A})_2$, and $R^4$ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X$^4$)$_{0-1}$—CN, —(X$^4$)$_{0-1}$—NO$_2$, —(X$^4$)$_{0-1}$—SF$_5$, —(X$^4$)$_{0-1}$—OSF$_5$, —(X$^4$)$_{0-1}$—OR$^{4A}$, —(X$^4$)$_{0-1}$—N(R$^{4A}$)$_2$, —(X$^4$)$_{0-1}$—SR$^{4A}$, —(X$^4$)$_{0-1}$—CF$_3$, 3 to 7 membered cycloalkyl-(X$^4$)$_{0-1}$—, 3 to 7 membered heterocycloalkyl- ($X^4$)$_{0-1}$—, 5 to 6 membered heteroaryl-($X^4$)$_{0-1}$—, phenyl-($X^4$)$_{0-1}$, —($X^4$)$_{0-1}$—C(=O)N($R^{4A}$)($R^{4A}$), —($X^4$)$_{0-1}$—C(=O)O$R^{4A}$, ($X^4$)$_{0-1}$—N($R^{4A}$)C(=O)($R^{4A}$), —($X^4$)$_{0-1}$—N($R^{4A}$)C(=O)O$R^{4A}$, —($X^4$)$_{0-1}$—S(=O)$_{1-2}$—$R^{4A}$, —($X^4$)$_{0-1}$—N($R^{4A}$)C(=O)N($R^{4A}$)$_2$, —($X^4$)$_{0-1}$—OC(=O)$R^{4A}$, —($X^4$)$_{0-1}$—OP(=O)(O$R^{4A}$)$_2$, —($X^4$)—SC(=O)O$R^{4A}$ and —($X^4$)—SC(=O)N($R^{4A}$)$_2$, each $X^4$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatoms selected from N, O and S; and wherein a $R^4$ group is independently optionally further substituted with 1 to 5 $R^{4A-1}$ substituents independently selected from the group consisting of —F, —Cl, —Br, —I, —OH, —CN, —NO$_2$, —SF$_5$, —NH$_2$, $C_{1-6}$ alkoxy and $C_{1-6}$ alkylamino.

E21 The compound of any one of E0-E20, wherein each $R^{3A}$ is independently selected from the group consisting of hydrogen and methyl.

E22 The compound of any one of E0-E20, wherein $R^3$ is —NH$_2$.

E23 The compound of E0, which is a compound of formula Ii:

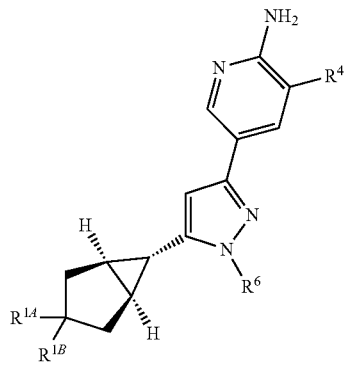

Ii or a salt thereof.

E24 The compound of E0, which is a compound of formula Ih, Ii, Ij or Ik:

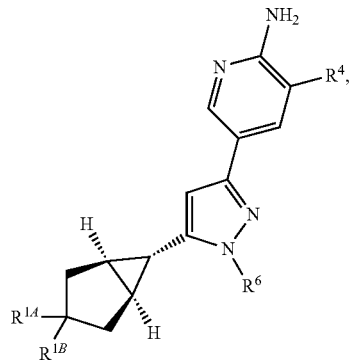

Ih

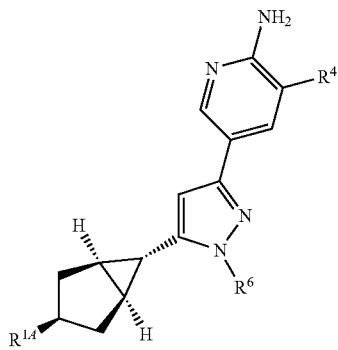

Ii

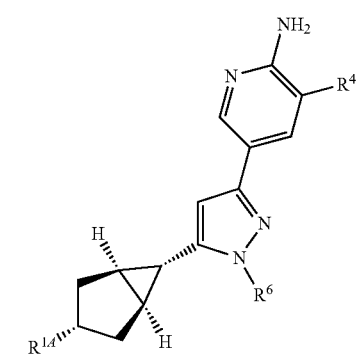

Ij or

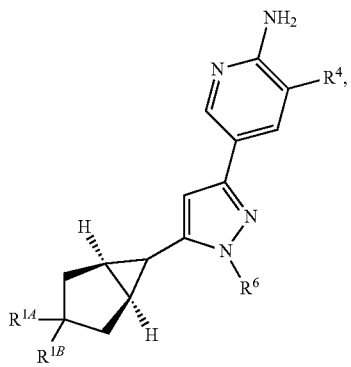

Ik or a salt thereof.

E25 The compound of any one of E0-E24, wherein $R^4$ is selected from the group consisting of $C_{1-12}$ alkyl, $C_{1-12}$ haloalkyl, $C_{2-12}$ alkenyl, $C_{2-12}$ alkynyl, —($X^4$)$_{0-1}$—O$R^{4A}$, —($X^4$)$_{0-1}$—S$R^{4A}$ and —($X^4$)$_{0-1}$—C(=O)N($R^{4A}$)($R^{4A}$) each $X^4$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatoms selected from N, O and S, and wherein a $R^4$ group is independently optionally further substituted with 1 to 5 $R^{4A-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ alkyl and $C_{1-6}$ dialkylamino E26 The compound of any one of E0-E24, wherein $R^4$ is selected from the group consisting of $C_{1-6}$ alkyl, $C_{1-6}$ haloalkyl, $C_{2-6}$ alkenyl, $C_{2-6}$ alkynyl, —O$R^{4A}$, —S$R^{4A}$ and —C(=O)N($R^{4A}$)($R^{4A}$), $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatoms selected from N, O and S, and wherein a $R^4$ group is independently optionally further substituted with 1 to 5 $R^{4,4-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ alkyl and $C_{1-6}$ dialkylamino E27 The compound of any one of E0-E24, wherein $R^4$ is selected from the group consisting of $C_{1-6}$ haloalkyl, —OC$_{1-6}$ haloalkyl, —SC$_{1-6}$ haloalkyl and —C(═O)N(R$^{4,4}$)(R$^{4,4}$), and the two $R^{4,4}$ groups attached to the same nitrogen atom are combined to form a 3 to 6 membered heterocyclic ring comprising 1 to 2 additional heteroatoms selected from N, O and S.

E28 The compound of any one of E0-E24, wherein $R^4$ is selected from the group consisting of $C_{1-3}$ haloalkyl, —O(C$_{1-3}$ haloalkyl) and —S(C$_{1-3}$ haloalkyl).

E29 The compound of any one of E0-E24, wherein $R^4$ is selected from the group consisting of CF$_3$, —OCF$_3$, —OCHF$_2$, —OCH$_2$CF$_3$, —SCF$_3$ and —C(═O)-(pyrrolidin-1-yl).

E30 The compound of any one of E0-E24, wherein $R^4$ is selected from the group consisting of CF$_3$, —OCF$_3$, —OCHF$_2$, —OCH$_2$CF$_3$ and —SCF$_3$.

E31 The compound of any one of E0-E24, wherein $R^4$ is selected from the group consisting of $C_{1-3}$ alkyl, $C_{1-3}$ haloalkyl, $C_{2-3}$ alkenyl, $C_{2-3}$ alkynyl and —OR$^{4,4}$, wherein $R^{4,4}$ is selected from the group consisting of $C_{1-3}$ alkyl, $C_{1-3}$ haloalkyl and $C_{1-3}$ heteroalkyl.

E32 The compound of any one of E0-E24, wherein $R^4$ is selected from the group consisting of $C_{1-12}$ alkyl, $C_{1-12}$ haloalkyl and —OR$^{4,4}$, wherein $R^{4,4}$ is selected from the group consisting of $C_{1-6}$ alkyl and $C_{1-6}$ haloalkyl.

E33 The compound of any one of E0-E24, wherein $R^4$ is selected from the group consisting of $C_{1-3}$ alkyl, $C_{1-3}$ haloalkyl and —OR$^{4,4}$, wherein $R^{4,4}$ is selected from the group consisting of $C_{1-3}$ alkyl and $C_{1-3}$ haloalkyl.

E34 The compound of any one of E0-E24, wherein $R^4$ is selected from the group consisting of $C_{1-6}$ haloalkyl and —O(C$_{1-6}$ haloalkyl).

E35 The compound of any one of E0-E24, wherein $R^4$ is selected from the group consisting of $C_{1-3}$ haloalkyl and —O(C$_{1-3}$ haloalkyl).

E36 The compound of any one of E0-E24, wherein $R^4$ is selected from the group consisting of CF$_3$, —OCF$_3$, —OCHF$_2$ and —OCH$_2$CF$_3$.

E37 The compound of any one of E0-E24, wherein $R^4$ is selected from the group consisting of CF$_3$, —OCF$_3$ and —OCHF$_2$.

E38 The compound of any one of E0-E19, wherein $R^3$ and $R^4$ together with the atoms to which they are attached form a 5 membered heteroaryl, wherein the 5 membered heteroaryl is optionally substituted with 1 to 3 $R^{3/4cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X$^{3/4}$)$_{0-1}$—CN, —(X$^{3/4}$)$_{0-1}$—NO$_2$, —(X$^{3/4}$)$_{0-1}$—SF$_5$, —(X$^{3/4}$)$_{0-1}$—OSF$_5$, —(X$^{3/4}$)$_{0-1}$—OR$^{3/4,4}$, —(X$^{3/4}$)$_{0-1}$—N(R$^{3/4,4}$)$_2$, —(X$^{3/4}$)$_{0-1}$—SR$^{3/4,4}$, —(X$^{3/4}$)$_{0-1}$—CF$_3$, 3 to 12 membered cycloalkyl-(X$^{3/4}$)$_{0-1}$—, 3 to 12 membered heterocycloalkyl-(X$^{3/4}$)$_{0-1}$—, 5 to 6 membered heteroaryl-(X$^{3/4}$)$_{0-1}$—, phenyl-(X$^{3/4}$)$_{0-1}$—, —(X$^{3/4}$)$_{0-1}$—C(═O)N(R$^{3/4,4}$)(R$^{3/4,4}$), —(X$^{3/4}$)$_{0-1}$—C(═O)OR$^{3/4,4}$, —(X$^{3/4}$)$_{0-1}$—N(R$^{3/4,4}$)C(═O)(R$^{3/4,4}$), —(X$^{3/4}$)$_{0-1}$—N(R$^{3/4,4}$)C(═O)OR$^{3/4,4}$, —(X$^{3/4}$)$_{0-1}$—S(═O)$_{1-2}$—R$^{3/4,4}$, —(X$^{3/4}$)$_{0-1}$—N(R$^{3/4,4}$)S(═O)$_{1-2}$—R$^{3/4,4}$, —(X$^{3/4}$)$_{0-1}$—S(═O)$_{1-2}$N(R$^{3/4,4}$)$_2$, —(X$^{3/4}$)$_{0-1}$—C(═O)R$^{3/4,4}$, —(X$^{3/4}$)$_{0-1}$—C(═NOR$^{3/4,4}$)R$^{3/4,4}$, —(X$^{3/4}$)$_{0-1}$—N(R$^{3/4,4}$)C(═O)N(R$^{3/4,4}$)$_2$ and —(X$^{3/4}$)$_{0-1}$—OC(═O)R$^{3/4,4}$, —(X$^{3/4}$)$_{0-1}$—OP(═O)(OR$^{3/4,4}$)$_2$, —(X$^{3/4}$)—SC(═O)OR$^{3/4,4}$ and —(X$^{3/4}$)—SC(═O)N(R$^{3/4,4}$)$_2$, each X$^{3/4}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, R$^{3/4,4}$ at each occurrence is each independently selected from the group consisting of hydrogen, $C_{1-6}$ alkyl, $C_{1-6}$ haloalkyl and $C_{1-6}$ heteroalkyl, or any two R$^{3/4,4}$ groups attached to the same nitrogen atom are optionally combined to form a 3 to 6 membered heterocyclic ring comprising 1 to 2 additional heteroatoms selected from N, O and S, and wherein a R$^{3/4cy}$ substituent at each occurrence is independently optionally further substituted with 1 to 5 R$^{3/4cy-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino E39 The compound of any one of E0-E19, wherein $R^3$ and $R^4$ together with the atoms to which they are attached form a pyrrolyl or pyrazolyl, wherein the pyrrolyl or pyrazolyl is optionally substituted with 1 to 3 R$^{3/4cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X$^{3/4}$)$_{0-1}$—CN, —(X$^{3/4}$)$_{0-1}$—NO$_2$, —(X$^{3/4}$)$_{0-1}$—SF$_5$, —(X$^{3/4}$)$_{0-1}$—OSF$_5$, —(X$^{3/4}$)$_{1-1}$—OR$^{3/4,4}$, —(X$^{3/4}$)$_{0-1}$—N(R$^{3/4,4}$)$_2$, —(X$^{3/4}$)$_{0-1}$—SR$^{3/4,4}$, —(X$^{3/4}$)$_{0-1}$—CF$_3$, 3 to 12 membered cycloalkyl-(X$^{3/4}$)$_{0-1}$—, 3 to 12 membered heterocycloalkyl-(X$^{3/4}$)$_{0-1}$—, 5 to 6 membered heteroaryl-(X$^{3/4}$)$_{0-1}$, phenyl-(X$^{3/4}$)$_{0-1}$—, —(X$^{3/4}$)$_{0-1}$—C(═O)N(R$^{3/4,4}$)(R$^{3/4,4}$), —(X$^{3/4}$)$_{0-1}$—C(═O)OR$^{3/4,4}$, —(X$^{3/4}$)$_{0-1}$—N(R$^{3/4,4}$)C(═O)(R$^{3/4,4}$), —(X$^{3/4}$)$_{0-1}$—N(R$^{3/4,4}$)C(═O)OR$^{3/4,4}$, —(X$^{3/4}$)$_{0-1}$—S(═O)$_{1-2}$—R$^{3/4,4}$, —(X$^{3/4}$)$_{0-1}$—N(R$^{3/4,4}$)S(═O)$_{1-2}$—R$^{3/4,4}$, —(X$^{3/4}$)$_{0-1}$—S(═O)$_{1-2}$N(R$^{3/4,4}$)$_2$, —(X$^{3/4}$)$_{0-1}$—C(═O)R$^{3/4,4}$, —(X$^{3/4}$)$_{0-1}$—C(═NOR$^{3/4,4}$)R$^{3/4,4}$, —(X$^{3/4}$)$_{0-1}$—N(R$^{3/4,4}$)C(═O)N(R$^{3/4,4}$)$_2$ and —(X$^{3/4}$)$_{0-1}$—OC(═O)R$^{3/4,4}$, —(X$^{3/4}$)$_{0-1}$—OP(═O)(OR$^{3/4,4}$)$_2$, —(X$^{3/4}$)—SC(═O)OR$^{3/4,4}$ and —(X$^{3/4}$)—SC(═O)N(R$^{3/4,4}$)$_2$, each X$^{3/4}$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, R$^{3/4,4}$ at each occurrence is each independently selected from the group consisting of hydrogen, $C_{1-6}$ alkyl, $C_{1-6}$ haloalkyl and $C_{1-6}$ heteroalkyl, or any two R$^{3/4,4}$ groups attached to the same nitrogen atom are optionally combined to form a 3 to 6 membered heterocyclic ring comprising 1 to 2 additional heteroatoms selected from N, O and S; and wherein a R$^{3/4cy}$ substituent at each occurrence is independently optionally further substituted with 1 to 5 R$^{3/4cy-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino E40 The compound of any one of E0-E19, wherein $R^3$ and $R^4$ together with the atoms to which are attached and the remainder of the compound of formula 0 form a compound of formula II:

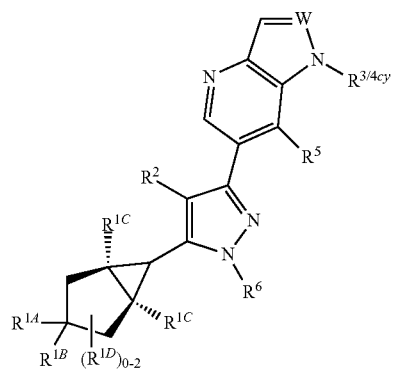

II wherein W is CH or N, or a salt thereof.

E41 The compound of any one of E0-E19, wherein $R^3$ and $R^4$ together with the atoms to which are attached and the remainder of the compound of formula 0 form a compound of formula IIa, IIb or IIc:

IIa
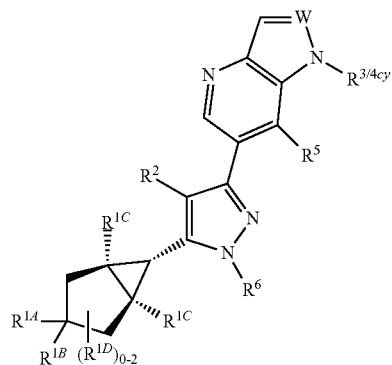

IIb
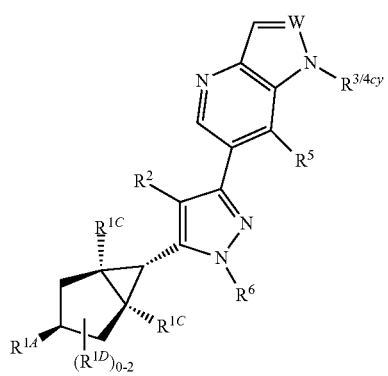

or

IIc
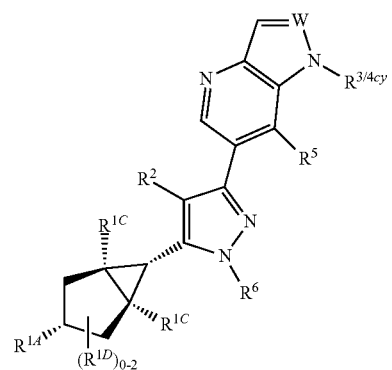

wherein W is CH or N, or a salt thereof.

E42 The compound of any one of E0-E13, wherein $R^3$ and $R^4$ together with the atoms to which are attached and the remainder of the compound of formula 0 form a compound of formula IId, IIe, IIf or IIg

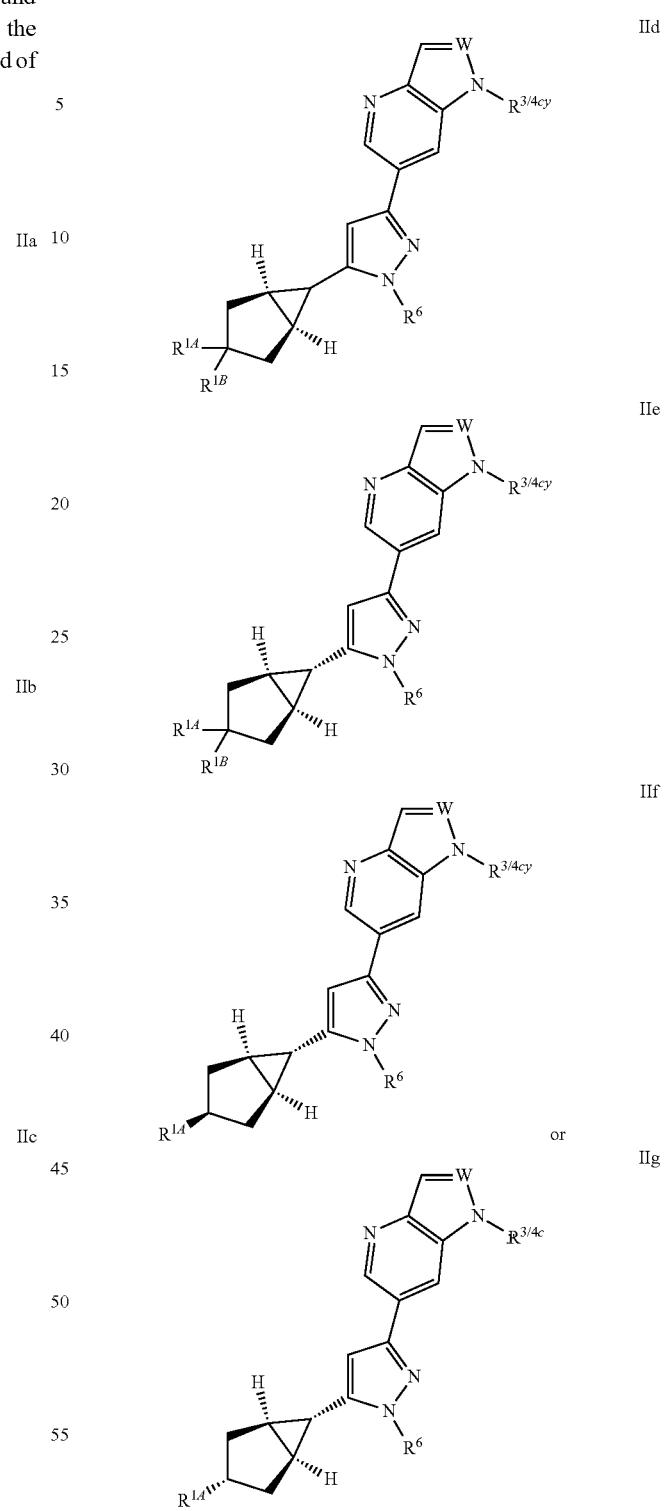

wherein W is CH or N, or a salt thereof.

E43 The compound of any one of E0-E13 or E38-E42, wherein each $R^{3/4cy}$ substituent is selected from the group consisting of 3 to 12 membered cycloalkyl-$(X^{3/4})_{0-1}$—, 3 to 12 membered heterocycloalkyl-$(X^{3/4})_{0-1}$, 5 to 6 membered heteroaryl-$(X^{3/4})_{0-1}$— and phenyl-$(X^{3/4})_{0-1}$—, each $X^{3/4}$ is independently selected from the group consisting of $C_{1-4}$ alkylene, $C_{1-4}$ haloalkylene, $C_{1-4}$ heteroalkylene, $C_{2-4}$ alkenylene and C$_{2-4}$ alkynylene, and wherein a R$^{3/4cy}$ substituent at each occurrence is independently optionally further substituted with 1 to 5 R$^{3/4cy-1}$ substituents independently selected from the group consisting of —F, —Cl, —Br, —I, —OH, —CN, —NO$_2$, —SF$_5$, —NH$_2$, C$_{1-6}$ alkoxy, C$_{1-6}$ alkylamino and C$_{1-6}$ dialkylamino.

E44 The compound of any one of E0-E13 or E38-E42, wherein each R$^{3/4cy}$ substituent is selected from the group consisting of 5 to 6 membered heteroaryl-(X$^{3/4}$)$_{0-1}$— and phenyl-(X$^{3/4}$)$_{0-1}$—, each X$^{3/4}$ is C$_{1-4}$ alkylene, and wherein a R$^{3/4cy}$ substituent at each occurrence is independently optionally further substituted with 1 to 5 R$^{3/4cy-1}$ substituents independently selected from the group consisting of —F, —Cl, —Br, —I, —OH, —CN, —NO$_2$, —SF$_5$, —NH$_2$, C$_{1-6}$ alkoxy, C$_{1-6}$ alkylamino and C$_{1-6}$ dialkylamino E45 The compound of any one of E0-E13 or E38-E42, wherein each R$^{3/4cy}$ substituent is a 6 membered heteroaryl-(X$^{3/4}$)$_{0-1}$—, X$^{3/4}$ is C$_{1-4}$ alkylene, and wherein a R$^{3/4cy}$ substituent at each occurrence is independently optionally further substituted with 1 to 5 R$^{3/4cy-1}$ substituents independently selected from the group consisting of —F, —Cl, —Br, —I, —OH, —CN, —NO$_2$, —SF$_5$, —NH$_2$, C$_{1-6}$ alkoxy, C$_{1-6}$ alkylamino and C$_{1-6}$ dialkylamino.

E46 The compound of any one of E0-E13 or E38-E42, wherein each R$^{3/4cy}$ is pyridinyl-(X$^{3/4}$)$_1$—, wherein X$^{3/4}$ is C$_{1-4}$ alkylene.

E47 The compound of any one of E0-E13 or E38-E42, wherein R$^{3/4cy}$ is:

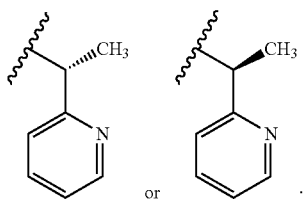

or

E48 The compound of any one of E0-E13 or E38-E42, wherein each R$^{3/4cy}$ substituent is selected from the group consisting pyridinyl-(X$^{3/4}$)$_1$, X$^{3/4}$ is C$_{1-4}$ alkylene, and wherein a R$^{3/4cy}$ substituent at each occurrence is independently optionally further substituted with 1 to 5 R$^{3/4cy-1}$ substituents selected from the group consisting of —F, —Cl, —Br, —I, —OH, —CN, —NO$_2$, —SF$_5$, —NH$_2$, C$_{1-6}$ alkoxy, C$_{1-6}$ alkylamino and C$_{1-6}$ dialkylamino.

E49 The compound of any one of E0-E48, wherein R$^{1A}$ is selected from the group consisting of morpholinyl, thiomorpholinyl, thiomorpholinyl-1,1-dioxide, piperazinyl, azetidinyl, pyrrolidin-2-onyl, 2-oxa-6-azaspiro[3.3]heptanyl, (1R,4R)-2-oxa-5-azabicyclo[2.2.1]heptanyl, oxazolidin-2-only, piperazinyl, (1S,4S)-2-oxa-5-azabicyclo[2.2.1]heptanyl, pyrrolidinyl, 1,4-oxazepanyl, octahydropyrrolo[1,2-a]pyrazinyl, pyrazolyl, —OH and —N(R$^{1A-1}$)$_2$, wherein R$^{1A-1}$ at each occurrence is each independently selected from the group consisting of hydrogen, C$_{1-6}$ alkyl, 3-7 membered heterocycloalkyl and 3-7 membered heterocycloalkyl-C$_{1-4}$ alkyl-, and wherein a R$^{1A}$ group at each occurrence is independently optionally further substituted with 1 to 5 R$^{1A-2}$ substituents selected from the group consisting of —F, —Cl, —Br, —I, —OH, —CN, —NO$_2$, —SF$_5$, —NH$_2$, C$_{1-6}$ alkoxy, C$_{1-6}$ alkylamino, C$_{1-6}$ dialkylamino, C$_{1-6}$ alkyl, oxo and —S(=O)$_{1-2}$—C$_{1-6}$ alkyl, and R$^{1b}$ is H.

E50 The compound of any one of E0-E48, wherein R$^{1A}$ is morpholinyl, thiomorpholinyl, thiomorpholinyl-1,1-dioxide, piperazinyl, azetidinyl, pyrrolidin-2-onyl, 2-oxa-6-azaspiro[3.3]heptanyl, (1R,4R)-2-oxa-5-azabicyclo[2.2.1]heptanyl, oxazolidin-2-only, piperazinyl, (1S,4S)-2-oxa-5-azabicyclo[2.2.1]heptanyl, pyrrolidinyl, 1,4-oxazepanyl, octahydropyrrolo[1,2-a]pyrazinyl and pyrazolyl wherein a R$^{1A}$ group at each occurrence is independently optionally further substituted with 1 to 5 R$^{1A-2}$ substituents selected from the group consisting of —F, —CN, C$_{1-6}$ alkoxy, C$_{1-6}$ alkyl, oxo and —S(=O)$_{1-2}$—C$_{1-6}$ alkyl, and R$^{1B}$ is H.

E51 The compound of any one of E0-E48, wherein R$^{1B}$ is H, and R$^{1A}$ is:

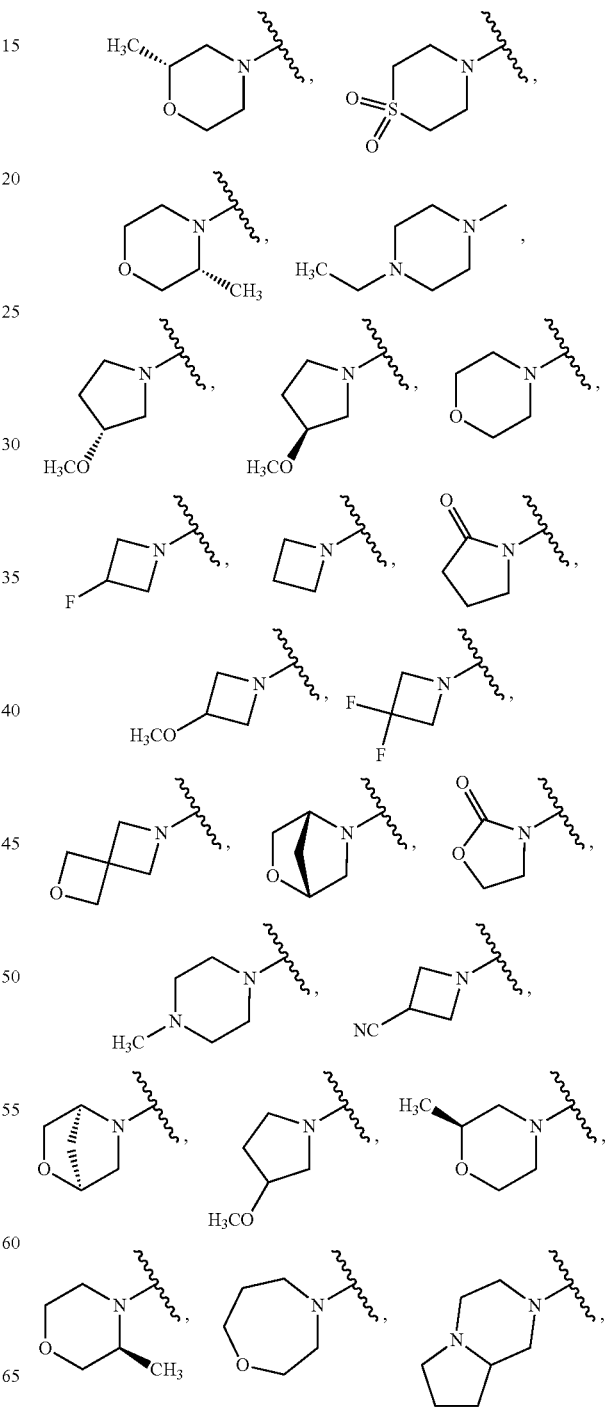

-continued

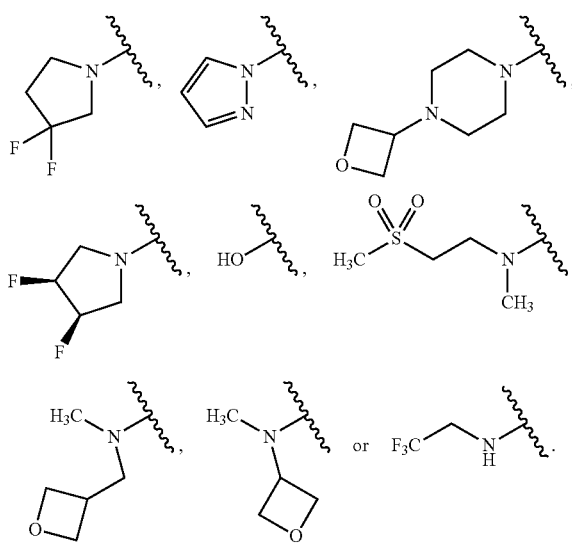

E52 The compound of any one of E0-E48, wherein $R^{1B}$ is H, and $R^{1A}$ is:

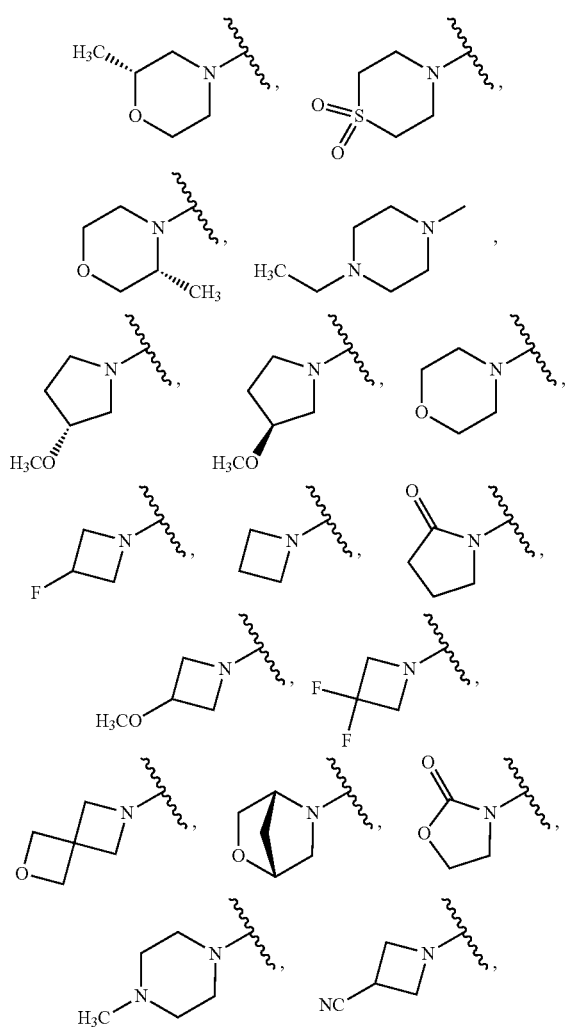

-continued

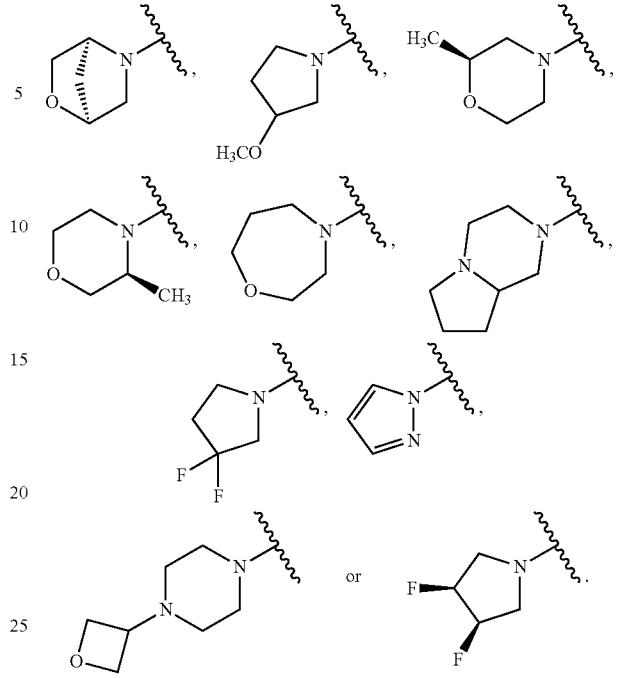

E53 The compound of any one of E0-E48, wherein $R^{1A}$ is morpholinyl, thiomorpholinyl, thiomorpholinyl-1,1-dioxide, piperazinyl, azetidinyl, pyrrolidinyl.

The compound of any one of E1-E48, wherein $R^{1B}$ is H, and $R^{1A}$ is:

E54 The compound of any one of E0-E48, wherein or $R^{1A}$ and $R^{1B}$ together form an oxo group.

E55 The compound of any one of E0-E48, wherein or $R^{1A}$ and $R^{1B}$ together form a 3 to 7 membered heterocycloalkyl comprising 1 to 2 heteroatoms selected from N, O and S and wherein said 3 to 7 membered heterocycloalkyl is optionally further substituted with 1 to 5 $R^{1A\text{-}2}$ substituents independently selected from the group consisting of —F, —Cl, —Br, —I, —OH, —CN, —NO$_2$, —SF$_5$, —NH$_2$, C$_{1-6}$ alkoxy, C$_{1-6}$ alkylamino, C$_{1-6}$ dialkylamino, C$_{1-6}$ alkyl, oxo, —S(=O)$_{1-2}$—C$_{1-6}$ alkyl and $R^{1b}$ is H.

E56 The compound of any one of E0-E48, wherein or $R^{1A}$ and $R^{1B}$ together form an oxetanyl, wherein the oxetanyl is optionally further substituted with 1 to 5 $R^{1A\text{-}2}$ substituents independently selected from the group consisting of —F, —Cl, —Br, —I, —OH, —CN, —NO$_2$, —SF$_5$, —NH$_2$, C$_{1-6}$ alkoxy, C$_{1-6}$ alkylamino, C$_{1-6}$ dialkylamino, C$_{1-6}$ alkyl, oxo, —S(=O)$_{1-2}$—C$_{1-6}$ alkyl and $R^{1b}$ is H.

E57 The compound of any one of E0-E48, wherein $R^{1A}$ is morpholinyl, thiomorpholinyl, thiomorpholinyl-1,1-dioxide, piperazinyl, azetidinyl, pyrrolidin-2-onyl, 2-oxa-6-azaspiro[3.3]heptanyl, (1R,4R)-2-oxa-5-azabicyclo[2.2.1]heptanyl, oxazolidin-2-only, piperazinyl, (1S,4S)-2-oxa-5-azabicyclo[2.2.1]heptanyl, pyrrolidinyl, 1,4-oxazepanyl and octahydropyrrolo[1,2-a]pyrazinyl, wherein a $R^{1A}$ group at each occurrence is independently optionally further substituted with 1 to 5 $R^{1A-2}$ substituents independently selected from the group consisting of —F, —CN, $C_{1-6}$ alkoxy, $C_{1-6}$ alkyl, oxo and —S(=O)$_{1-2}$—$C_{1-6}$ alkyl, and $R^{1b}$ is H.

E58 The compound of E0 selected from:

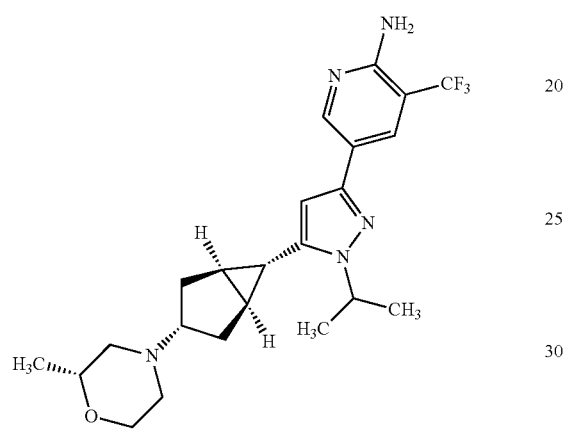

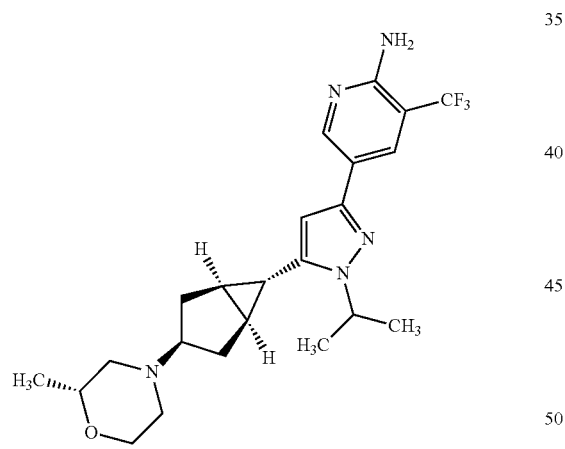

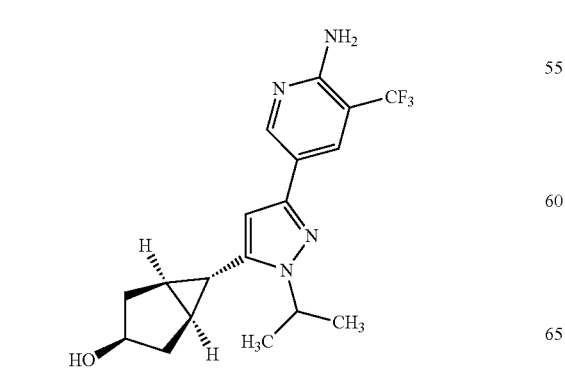

-continued

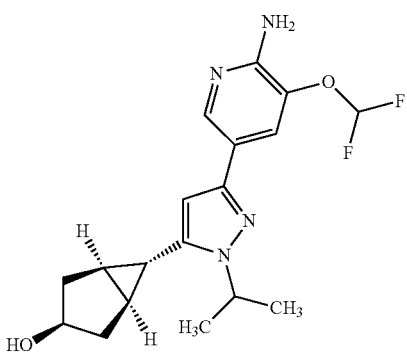

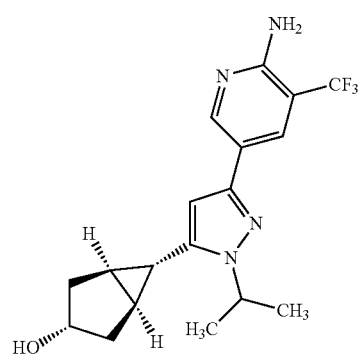

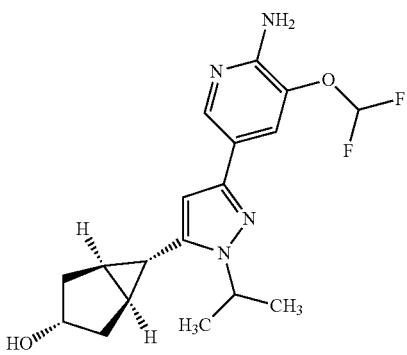

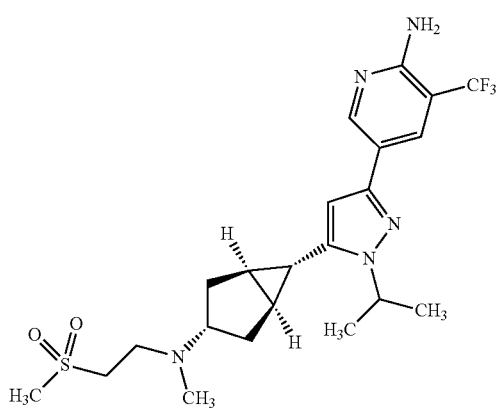

-continued
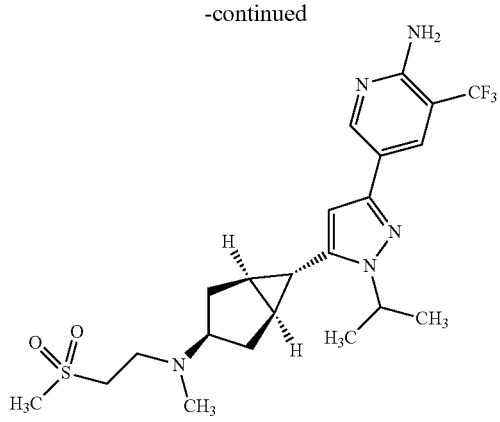
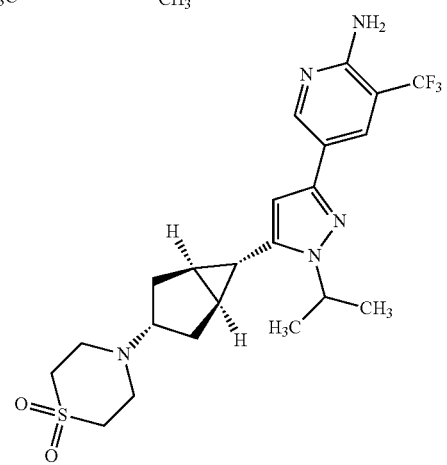
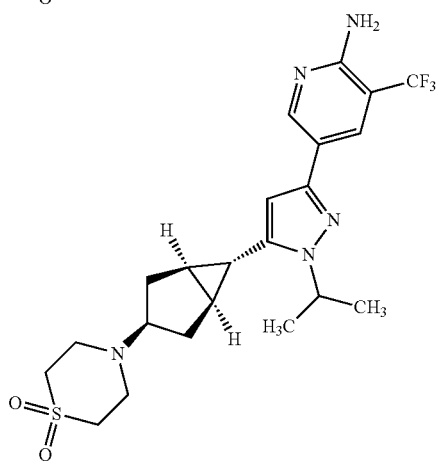
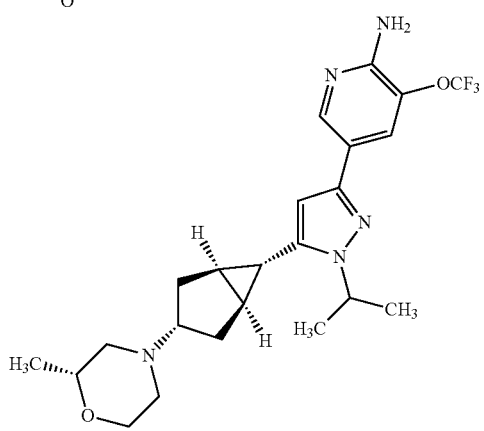
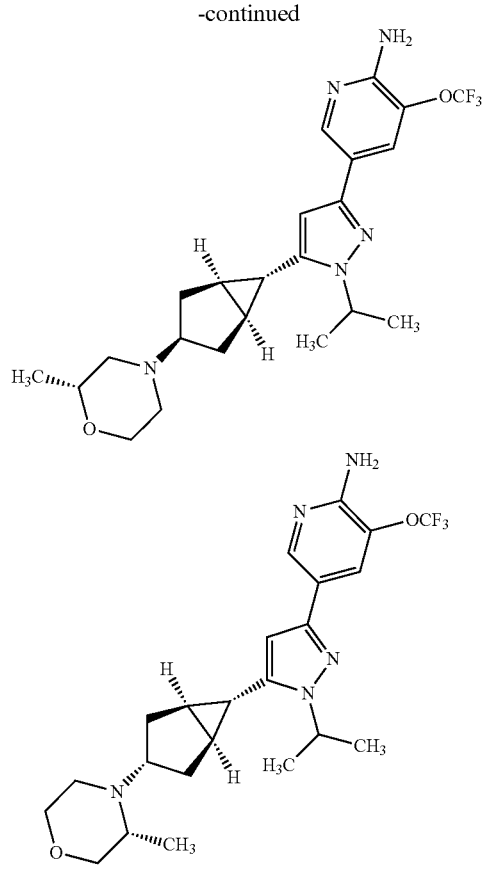
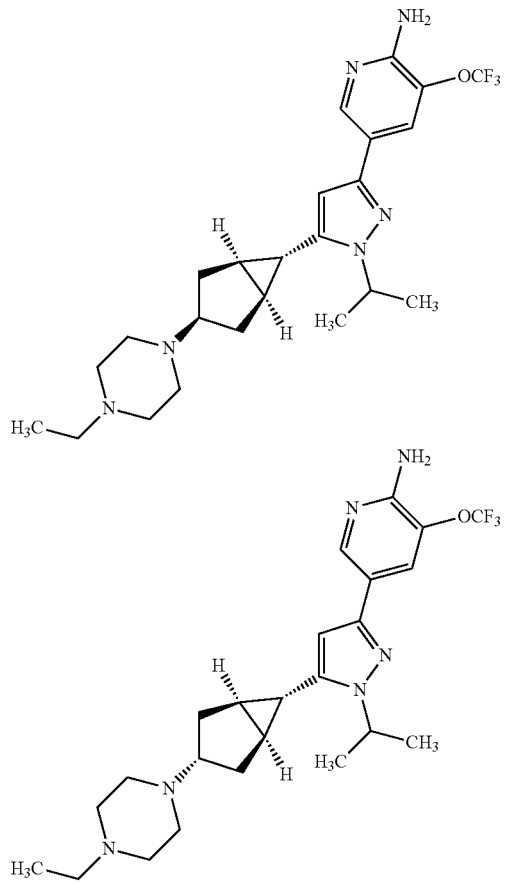

23
-continued
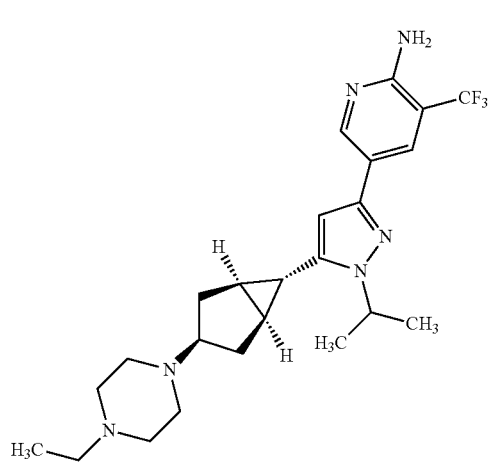
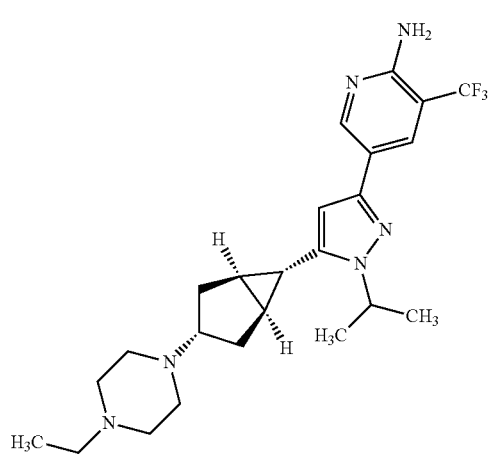
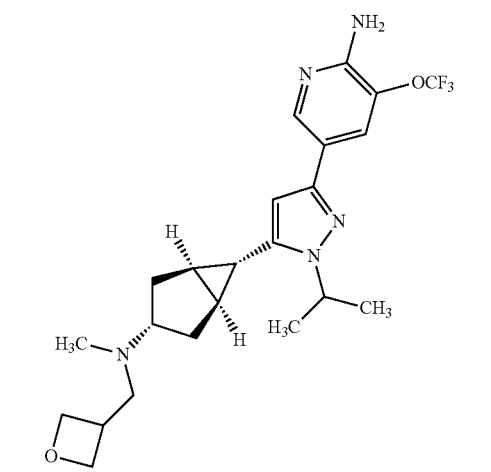
24
-continued
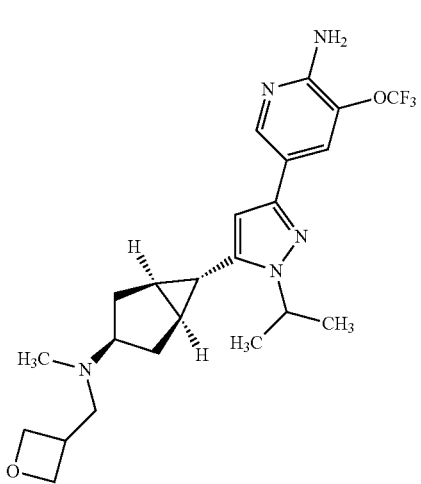
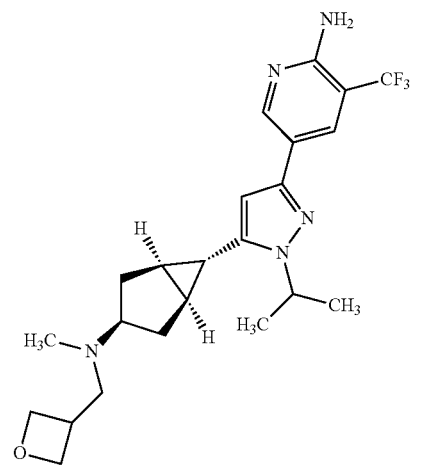
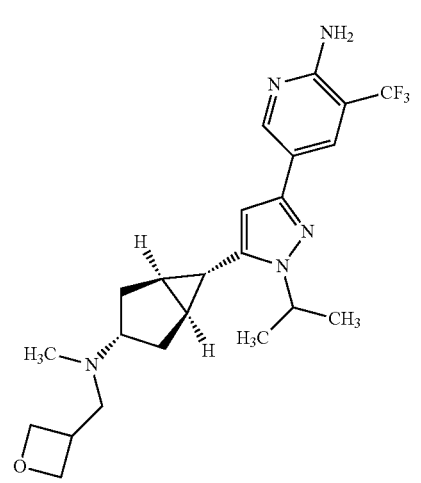

25
-continued
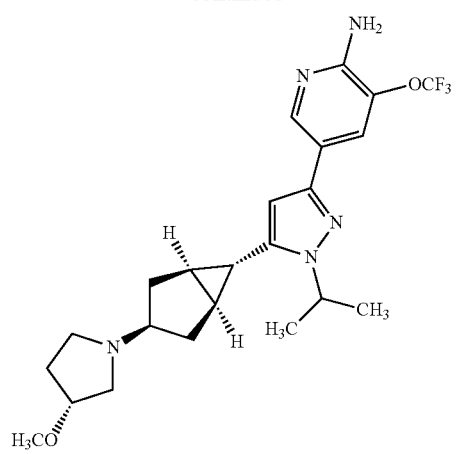
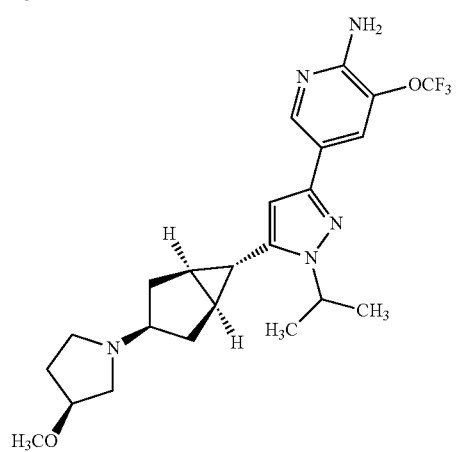
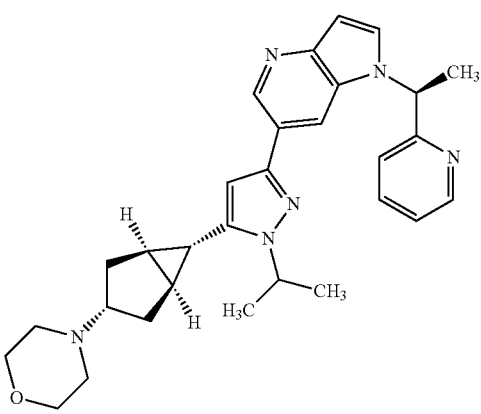
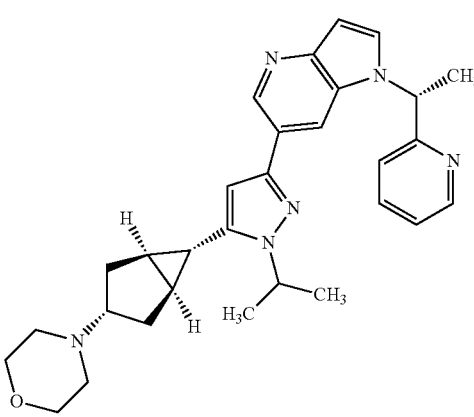
26
-continued
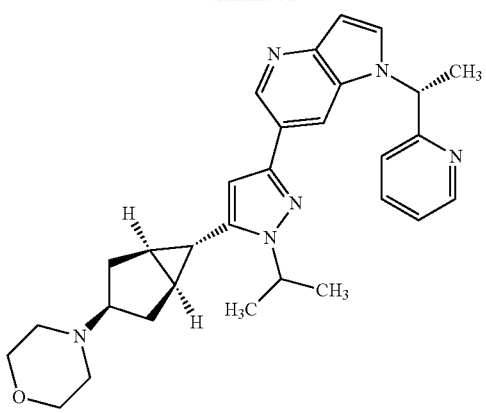
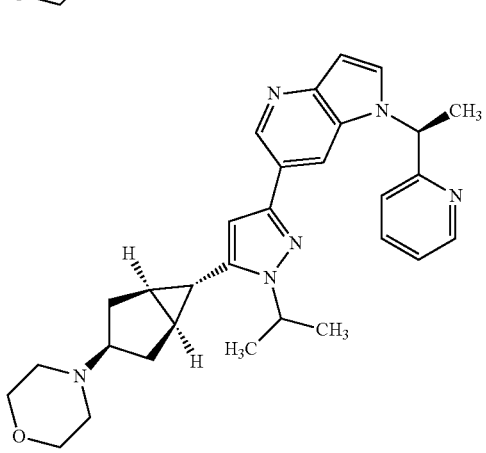
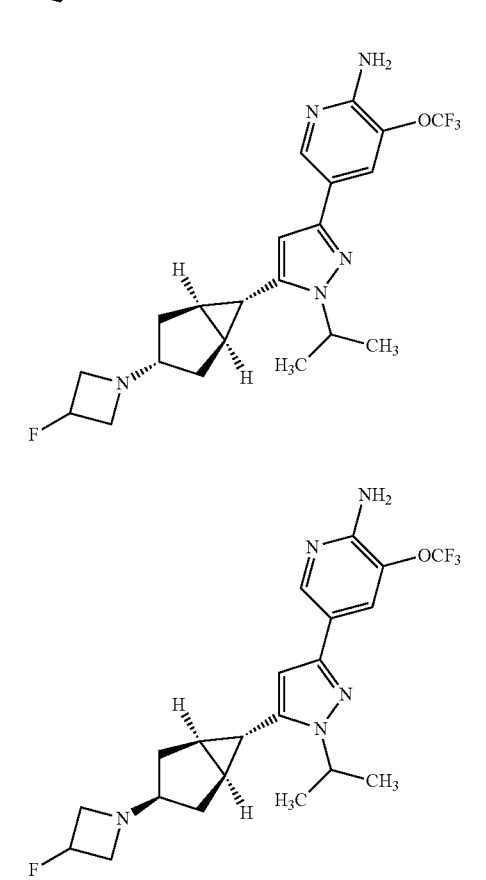

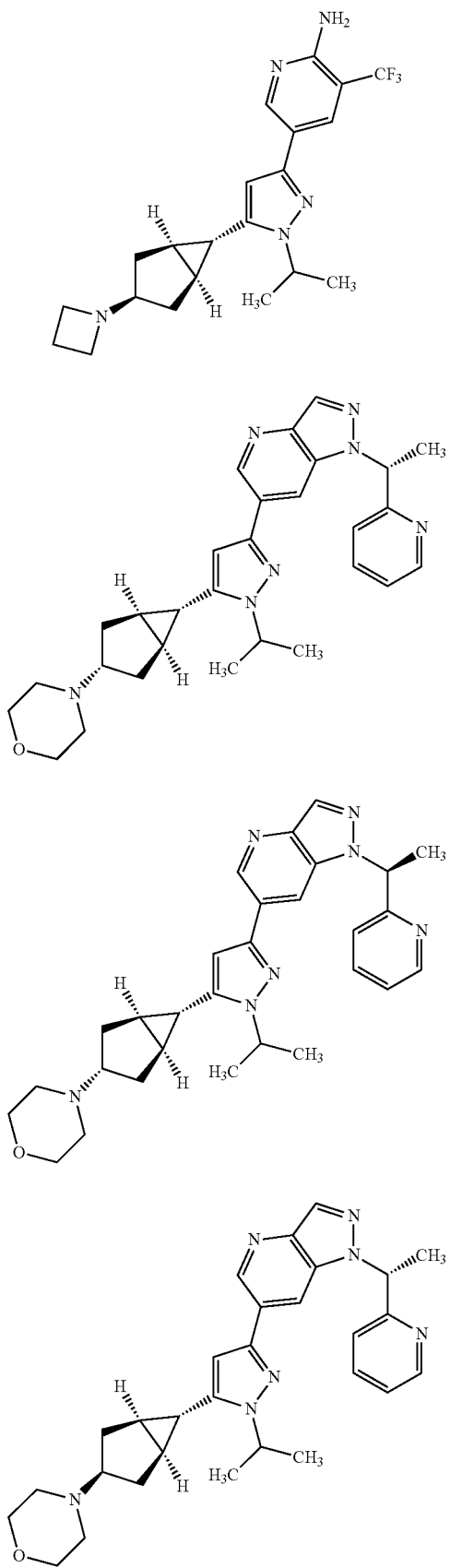
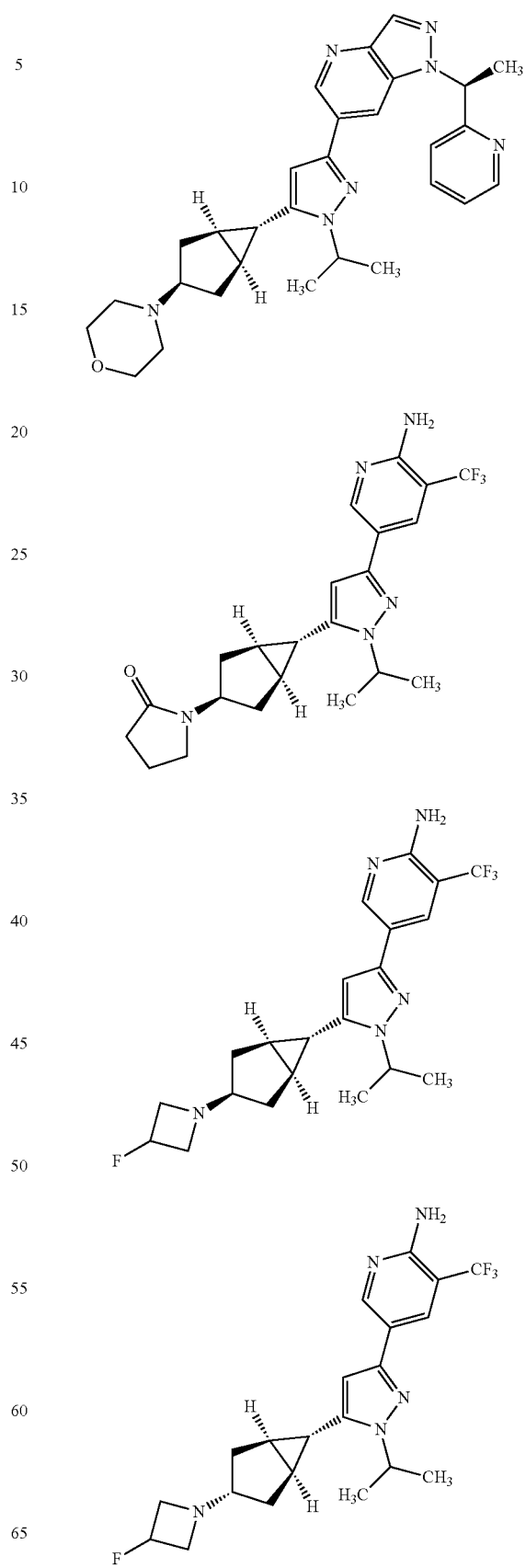

-continued
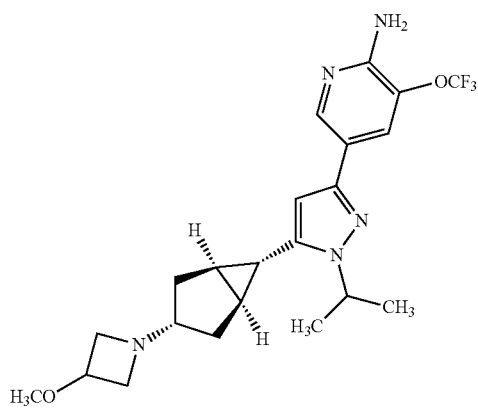
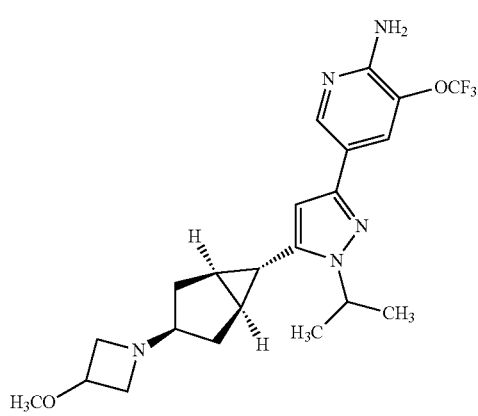
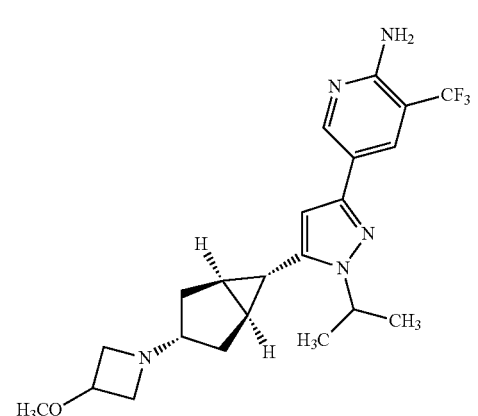
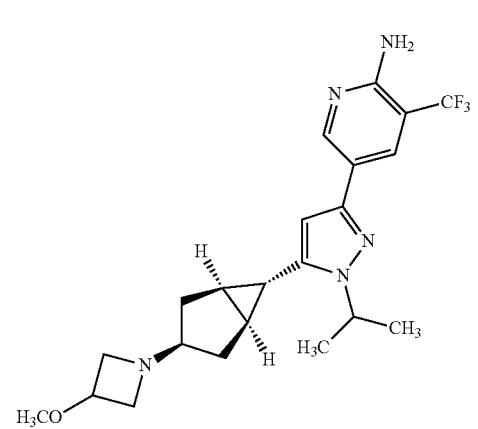
-continued
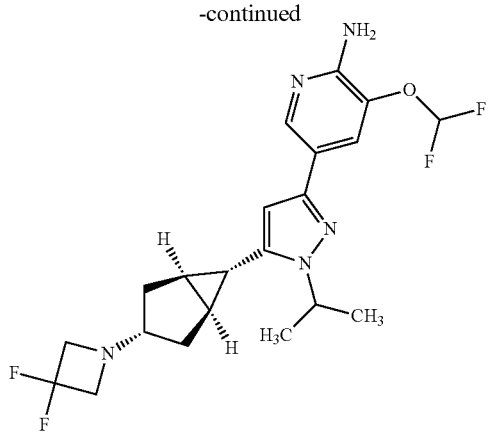
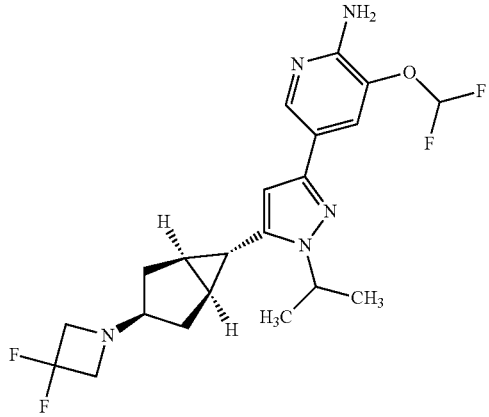
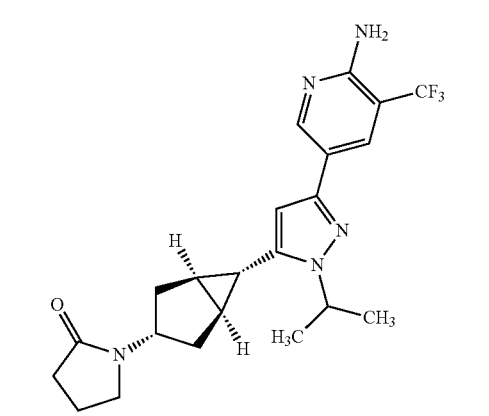
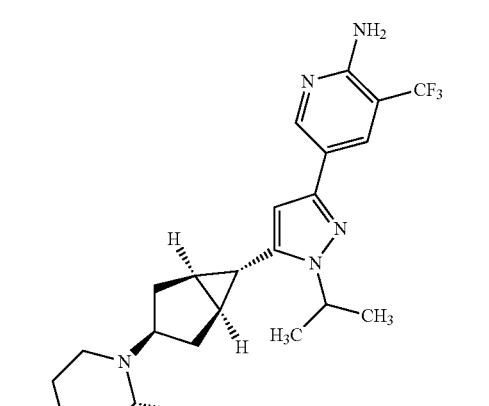

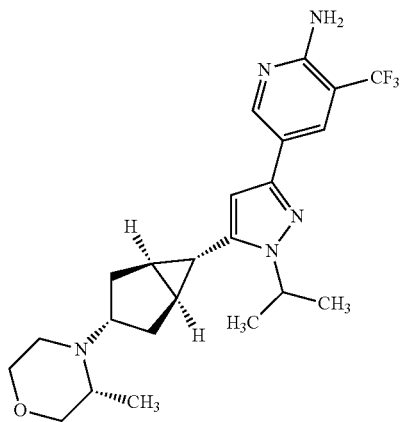
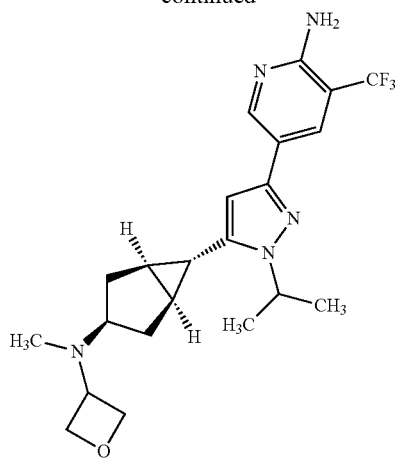
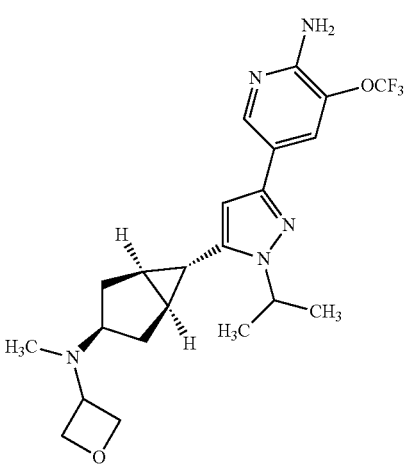
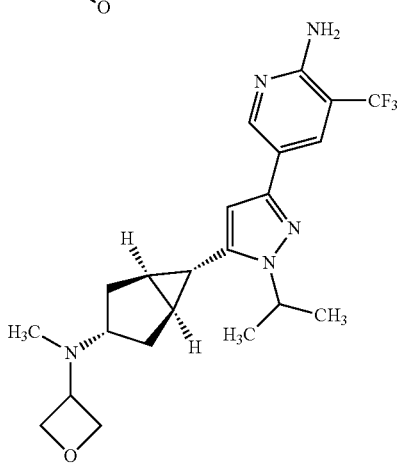
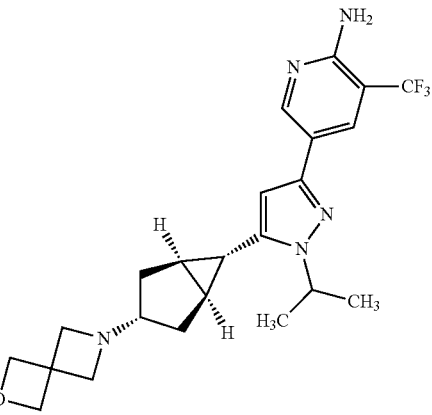
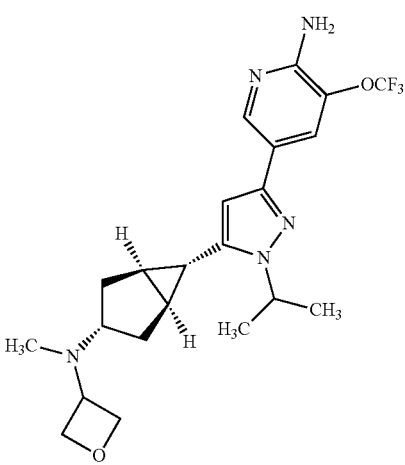
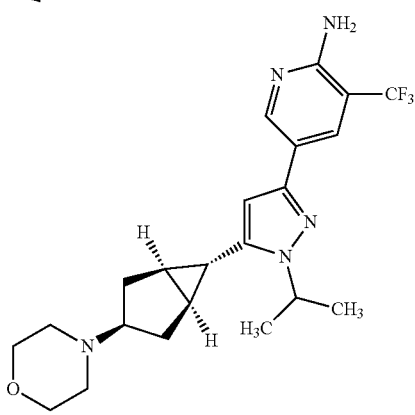

33
-continued
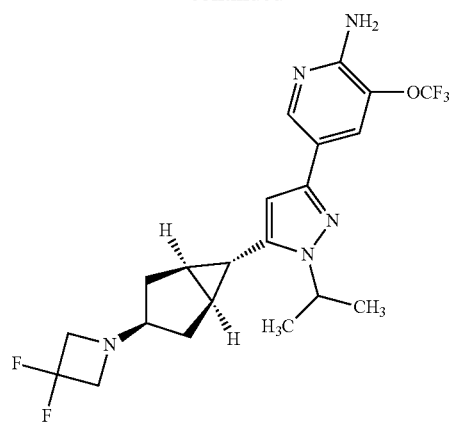
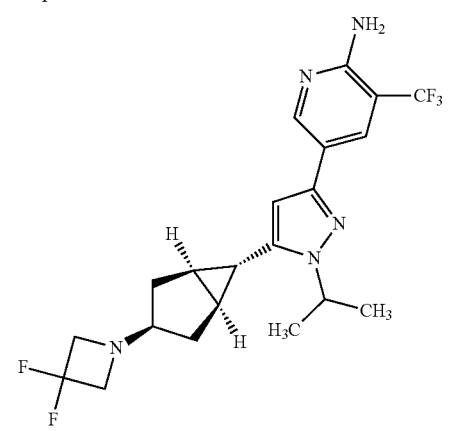
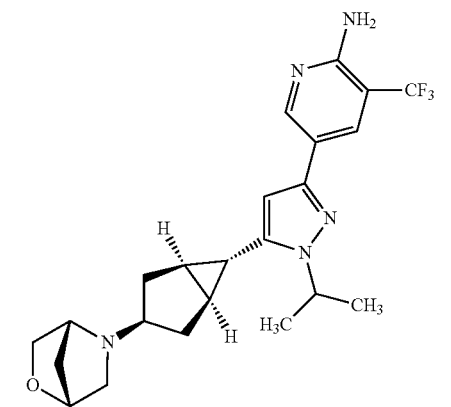
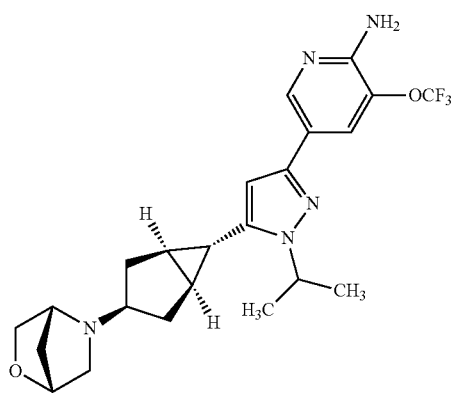
34
-continued
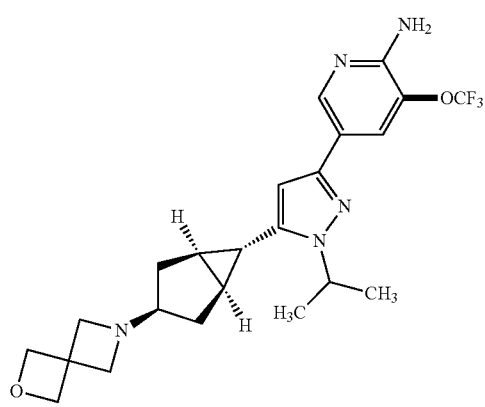
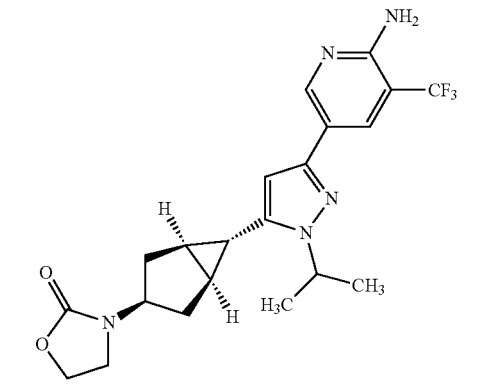
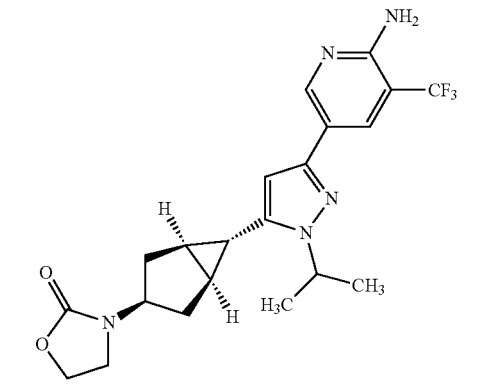
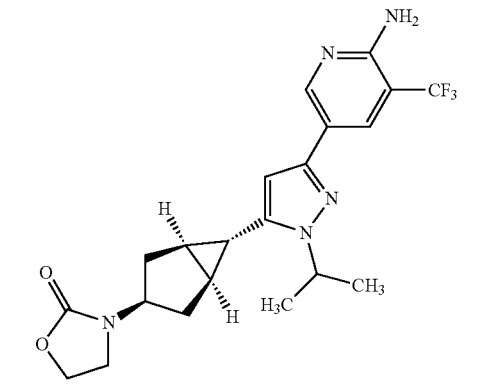

-continued
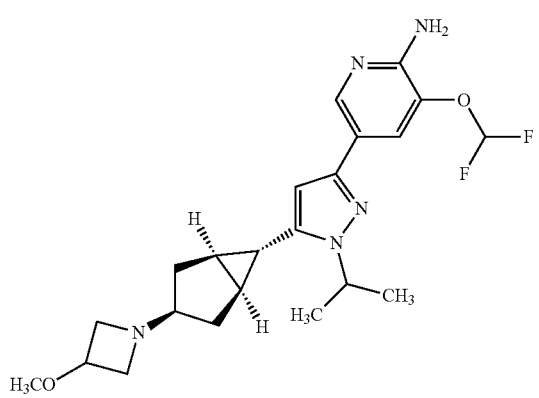
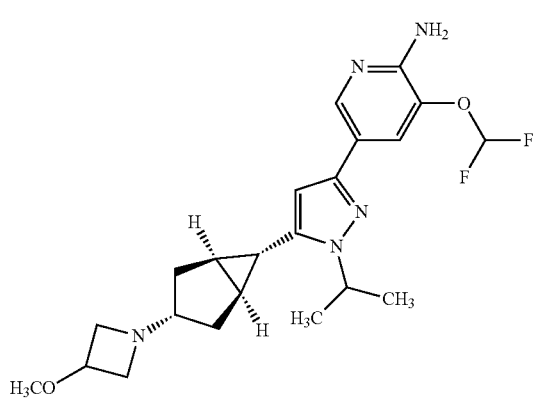
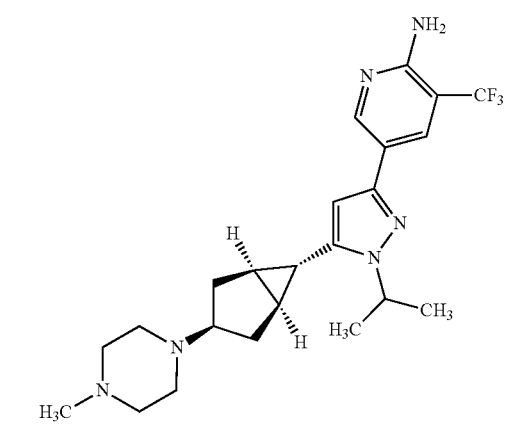
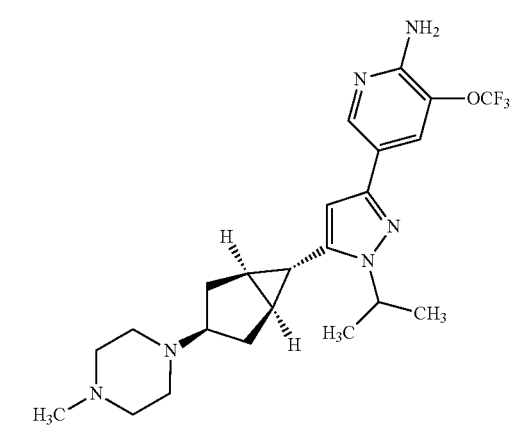
-continued
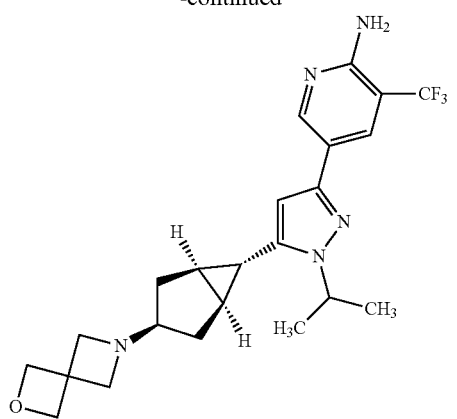
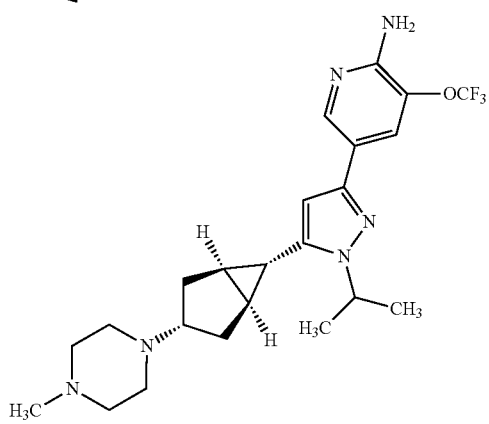
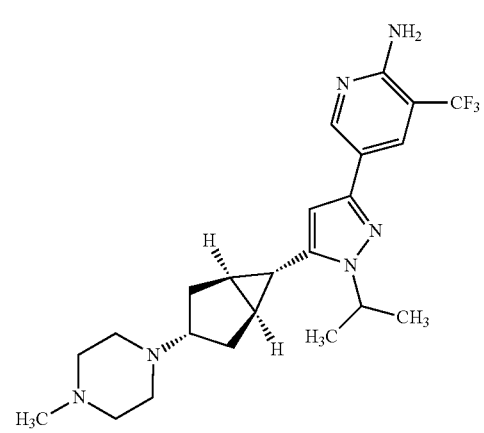
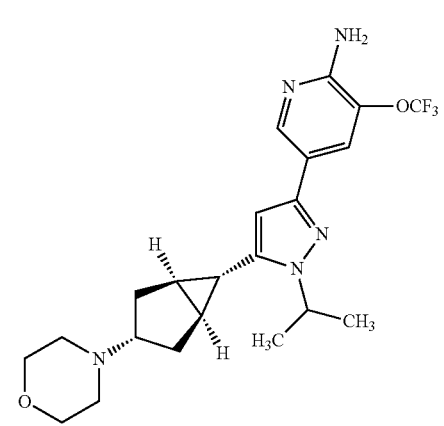

37
-continued
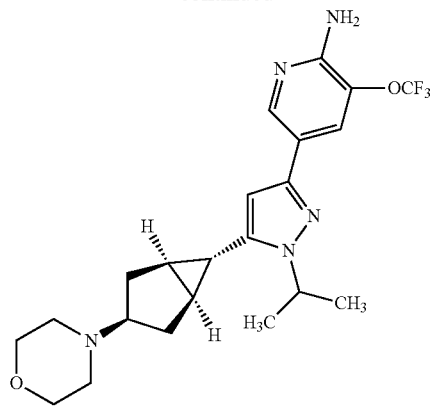

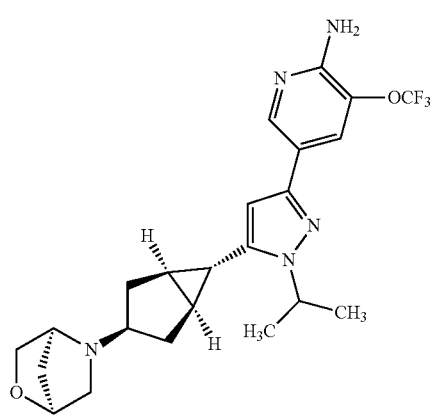
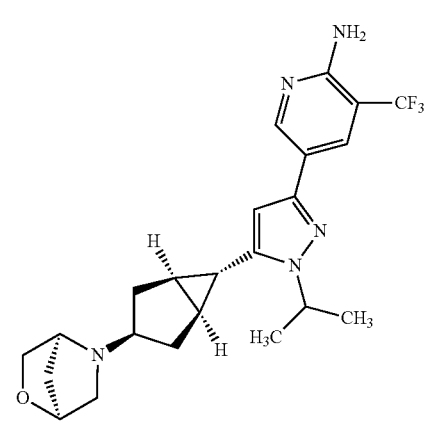
38
-continued
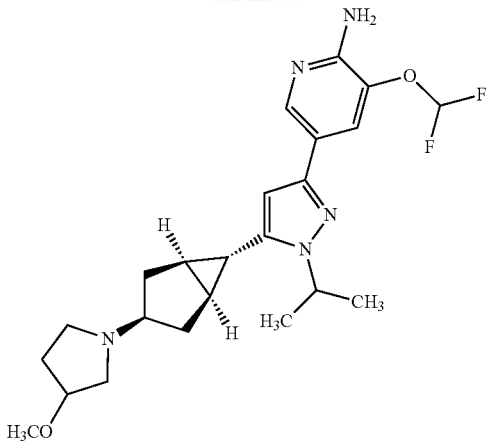
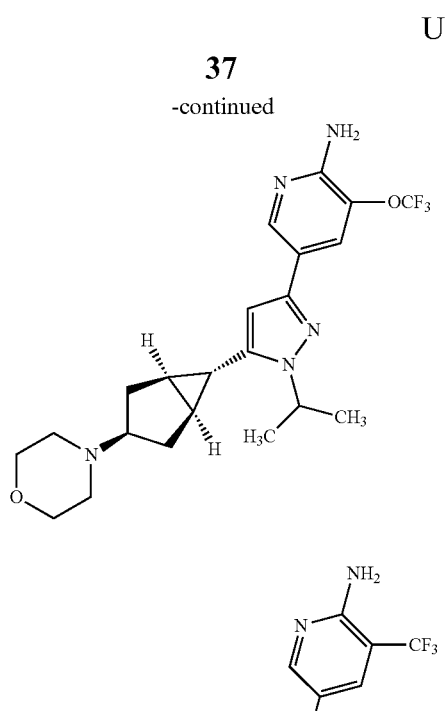
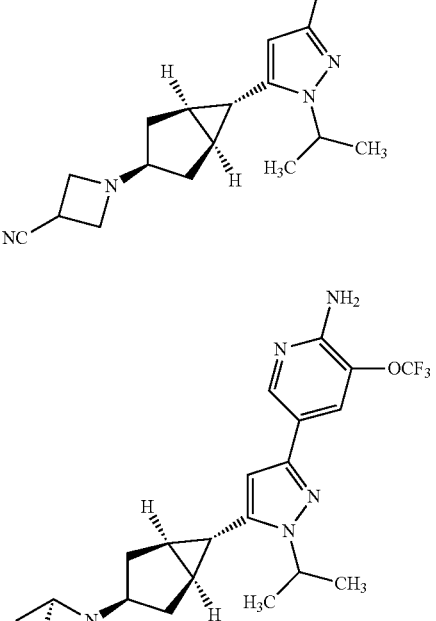
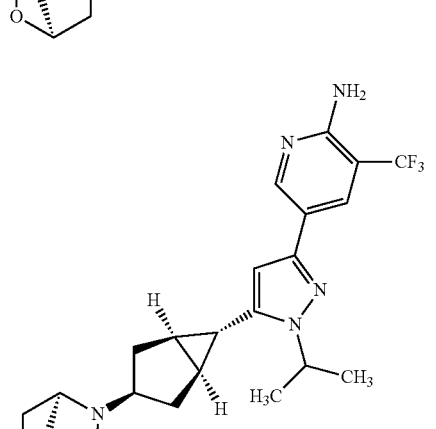

39
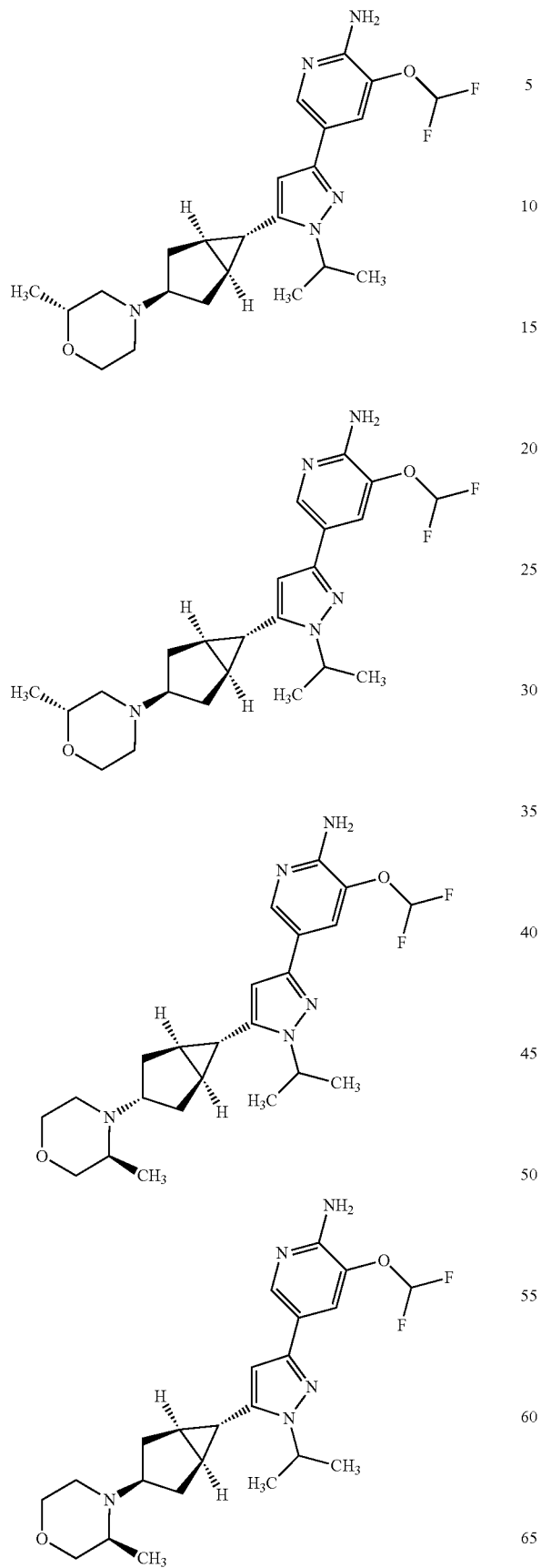
40
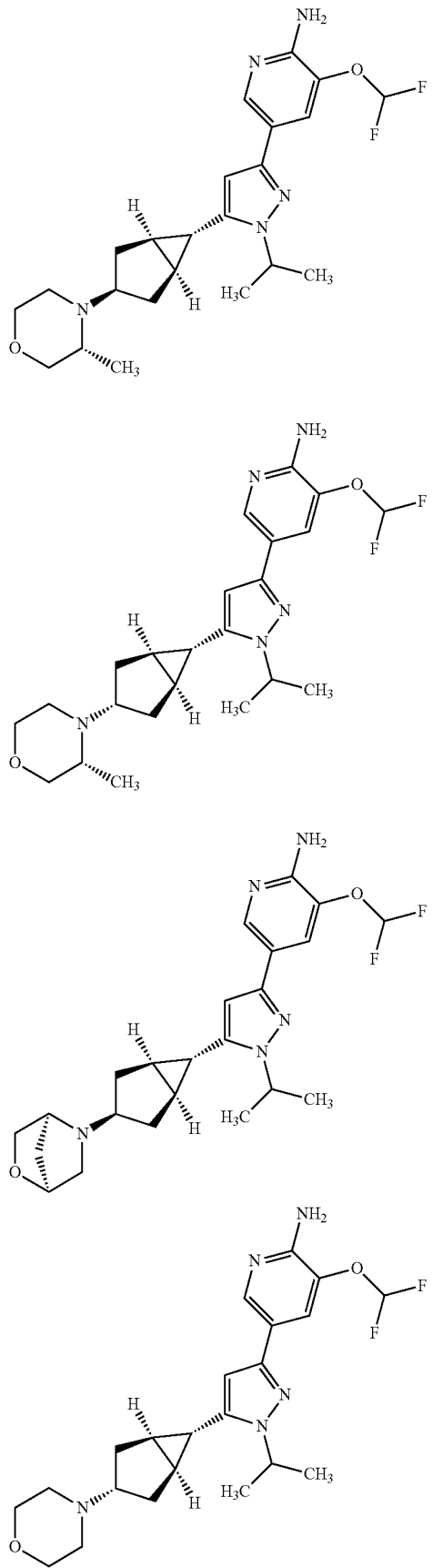

41
-continued
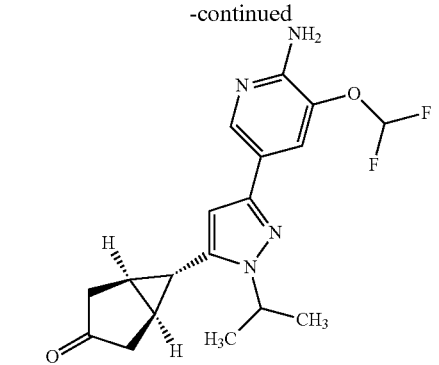
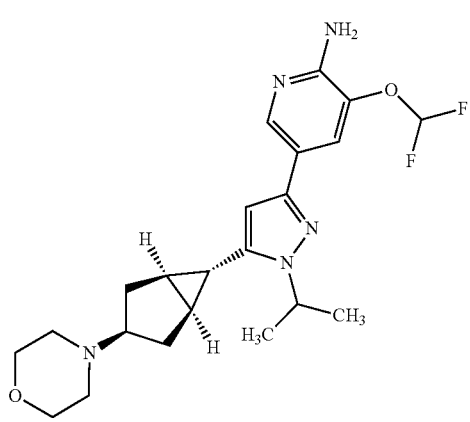
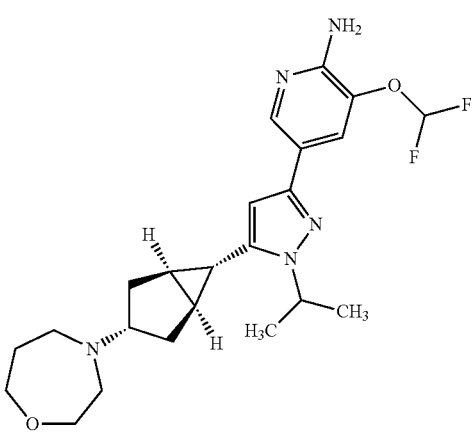
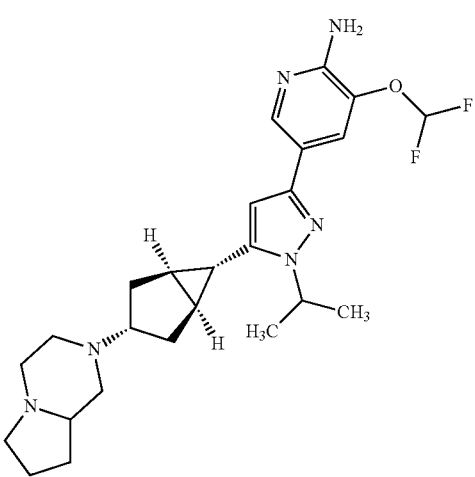
42
-continued
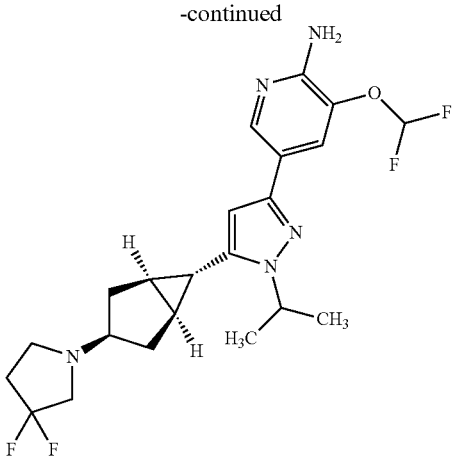
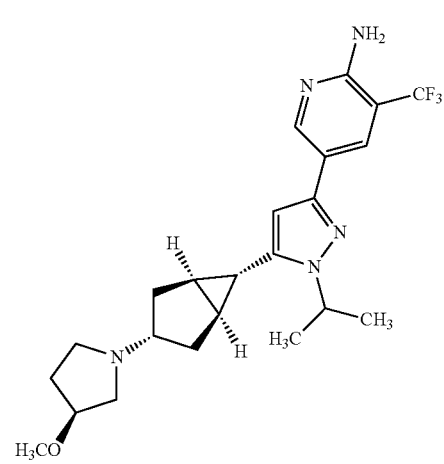
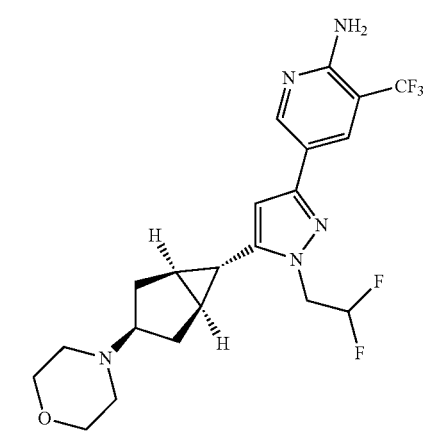
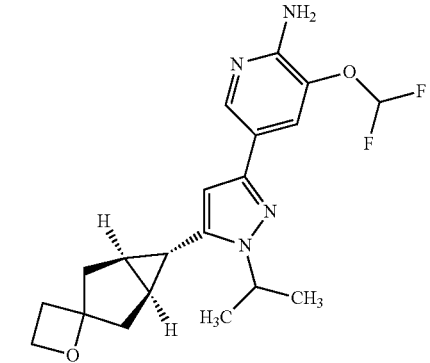

-continued
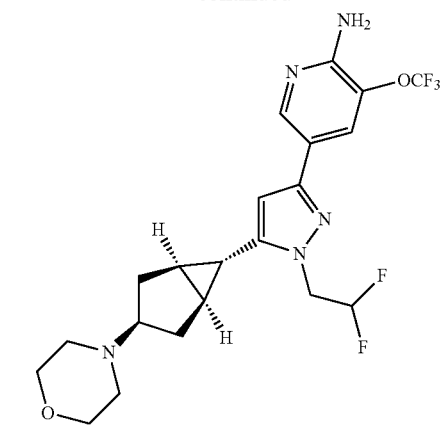
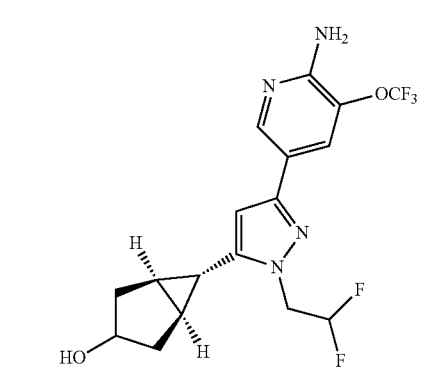
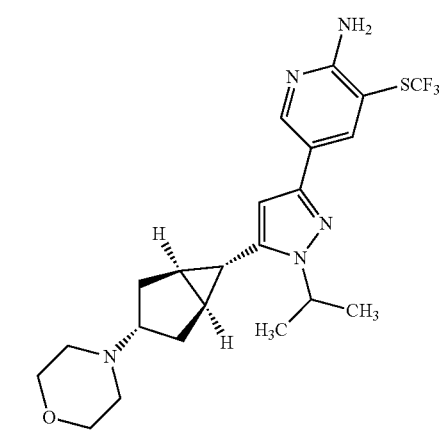
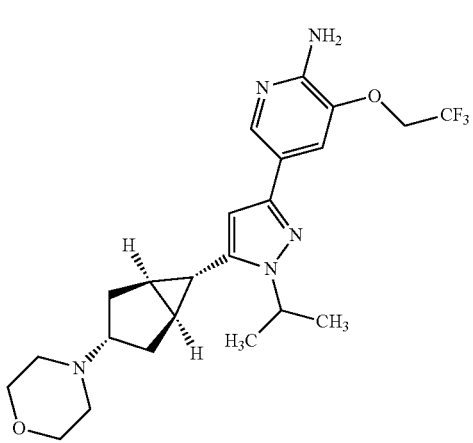
-continued
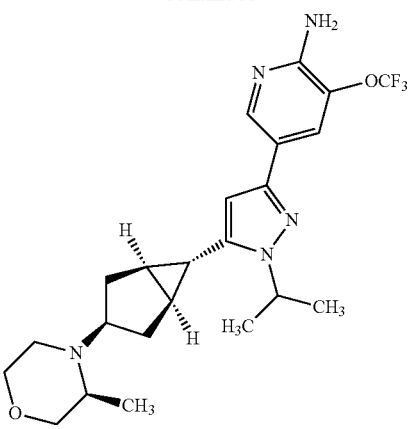
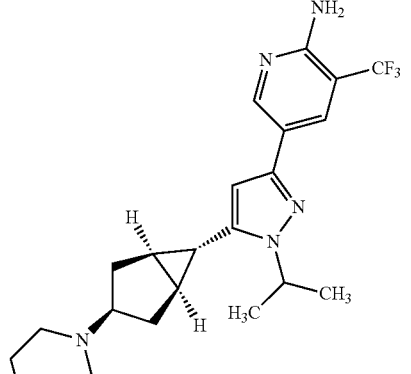
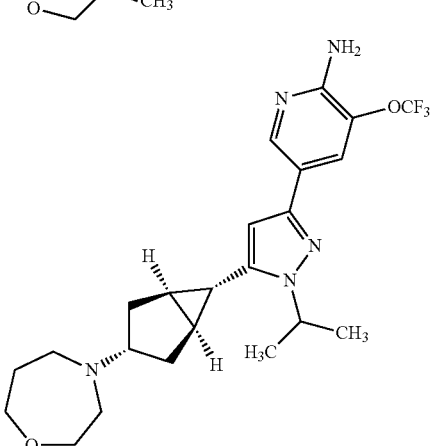
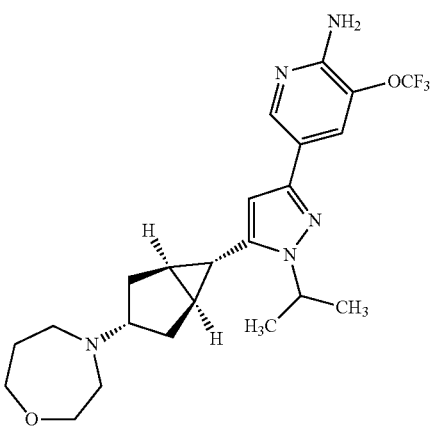

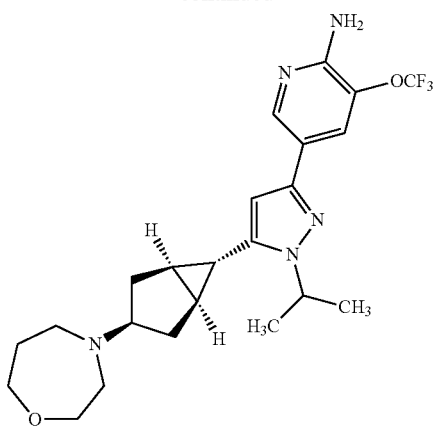
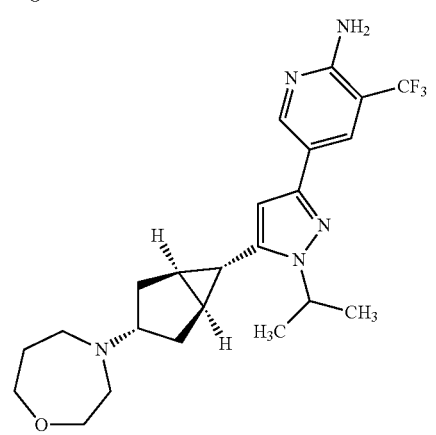
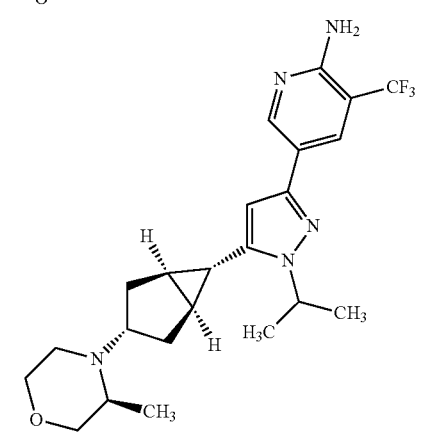

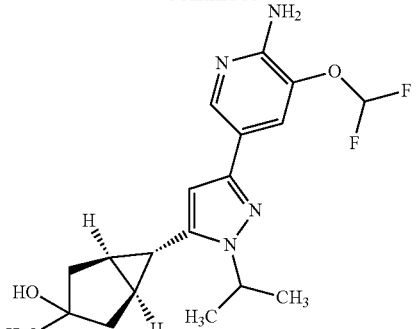
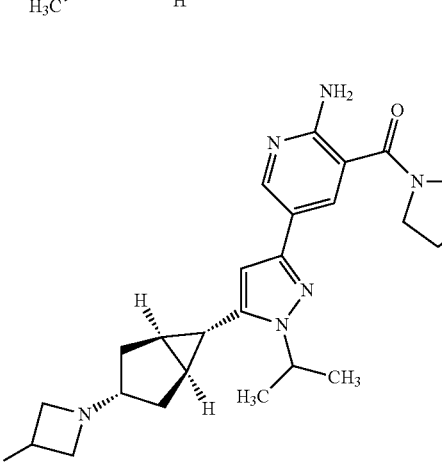
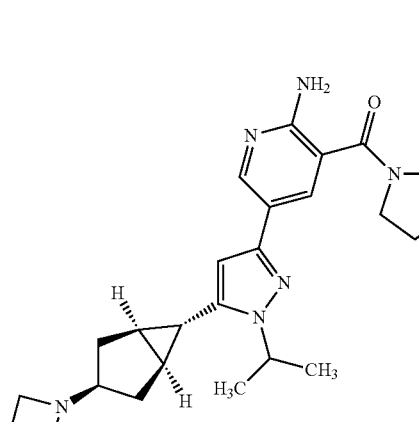
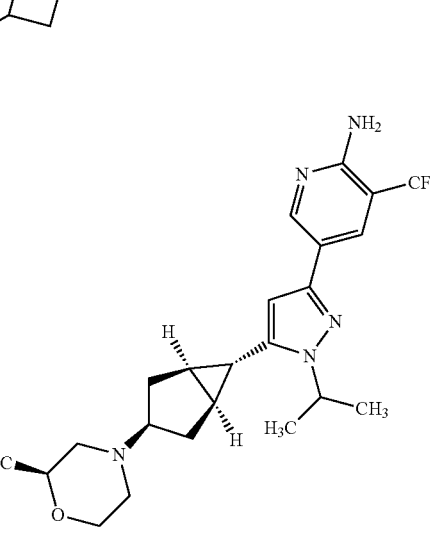

-continued
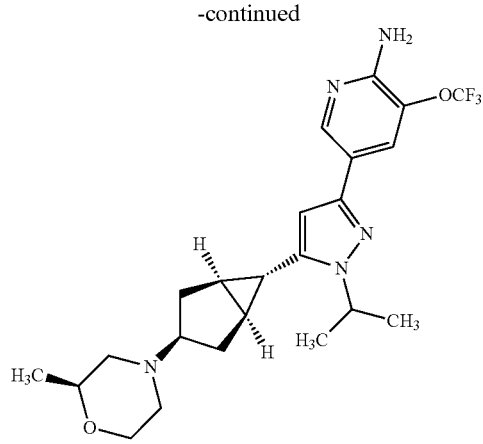
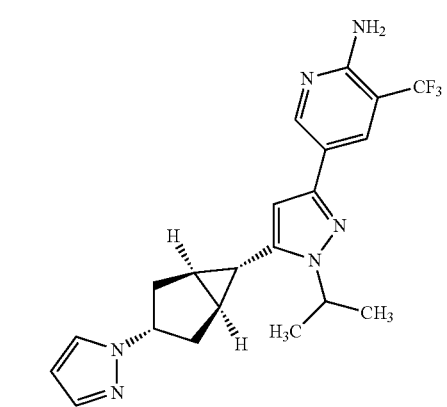
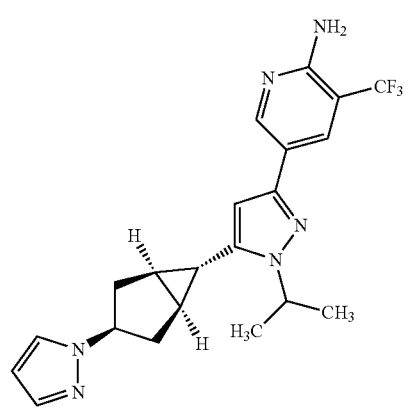
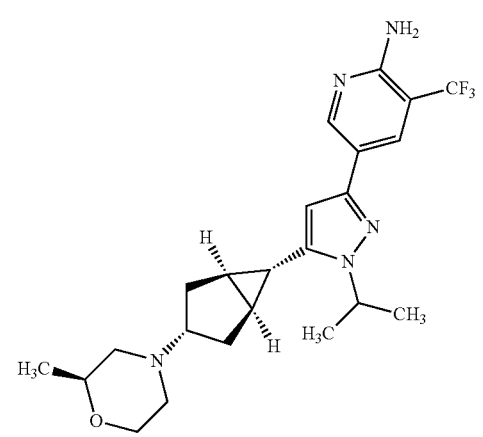
-continued
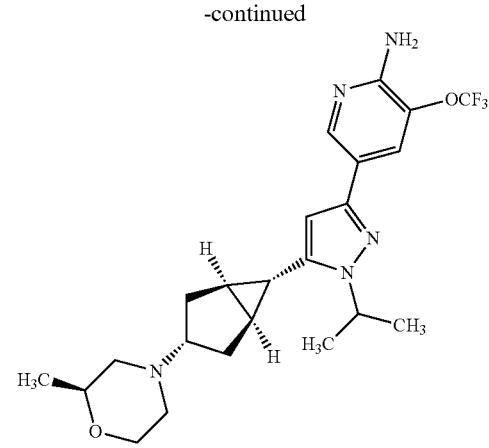
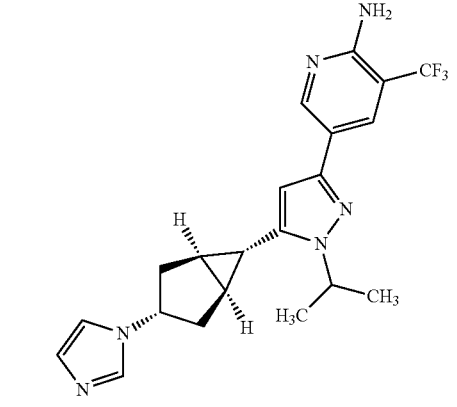
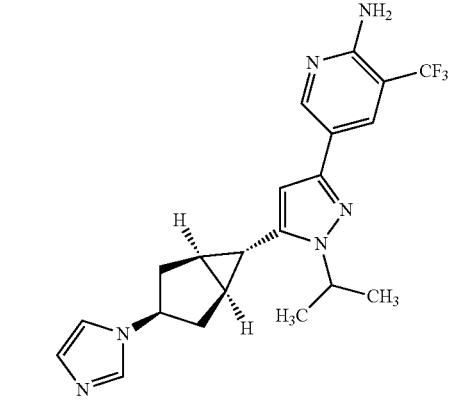
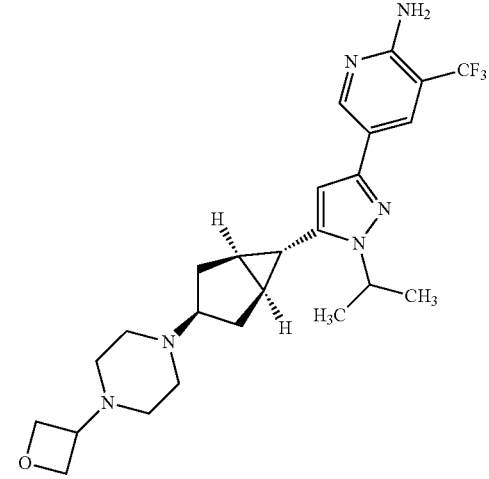

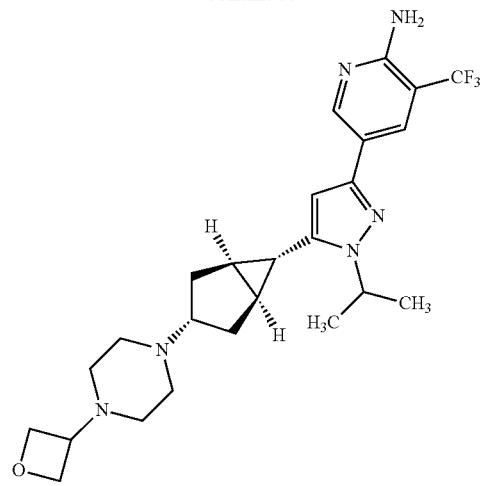
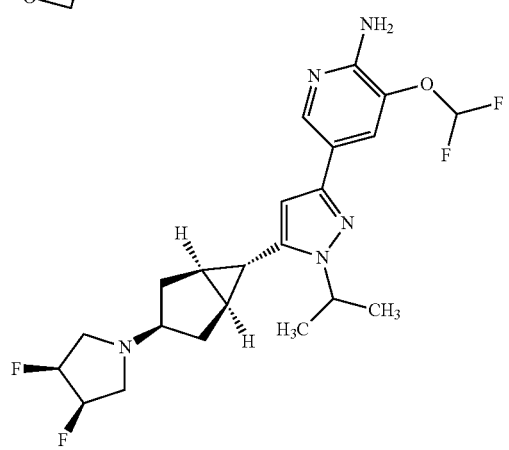
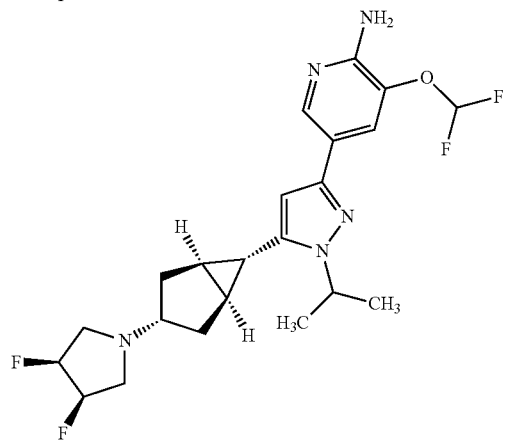
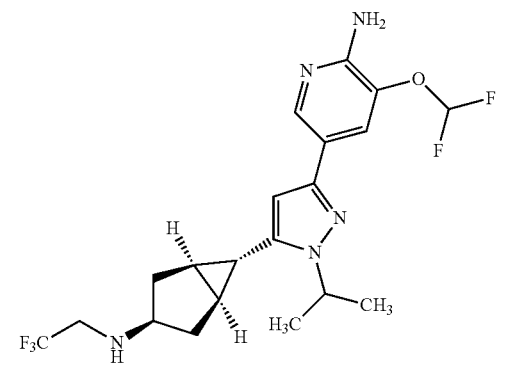
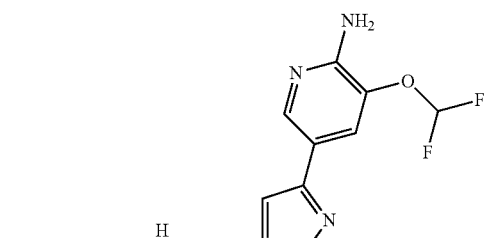
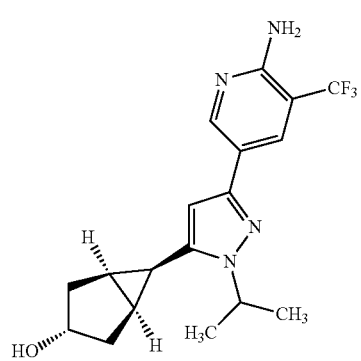
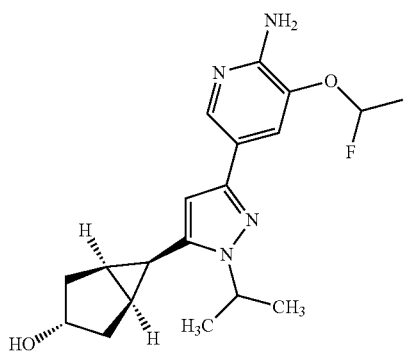
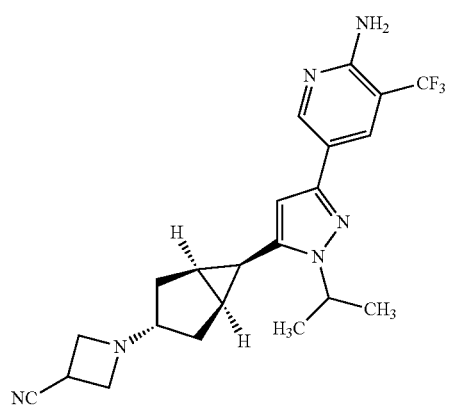

51
-continued
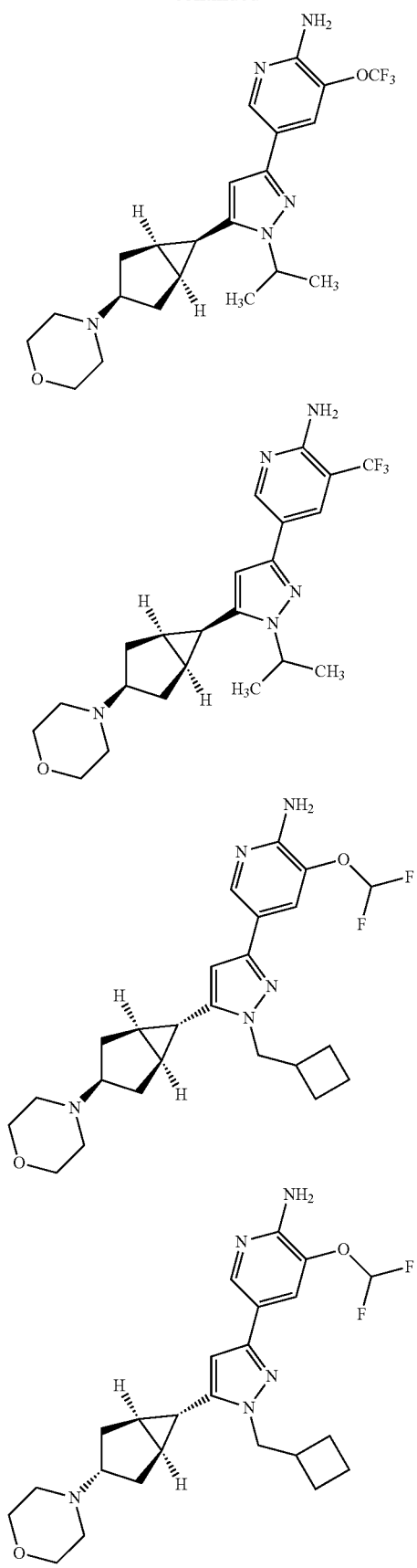
52
-continued
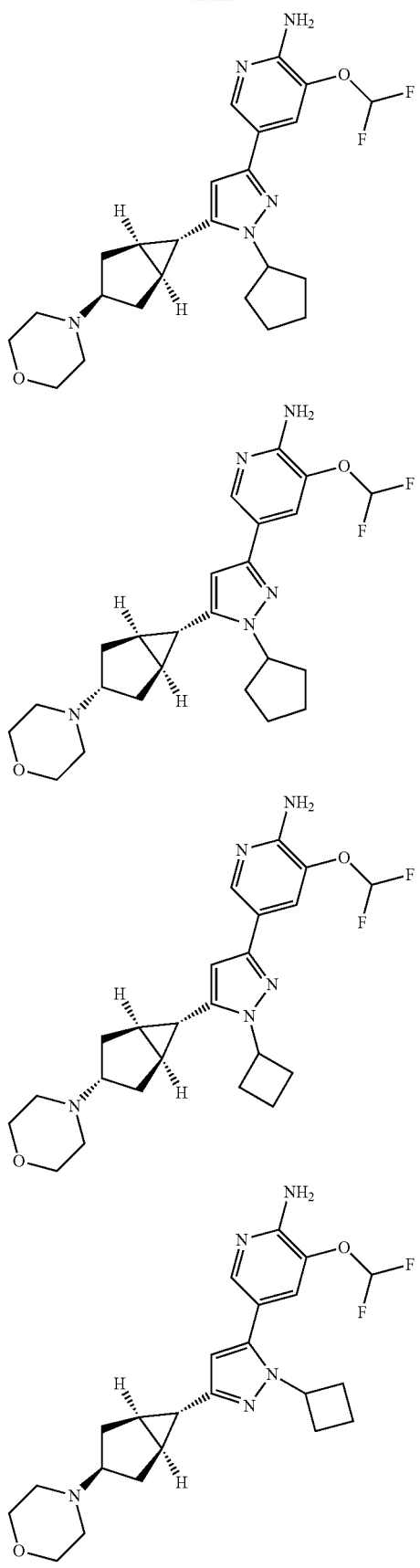

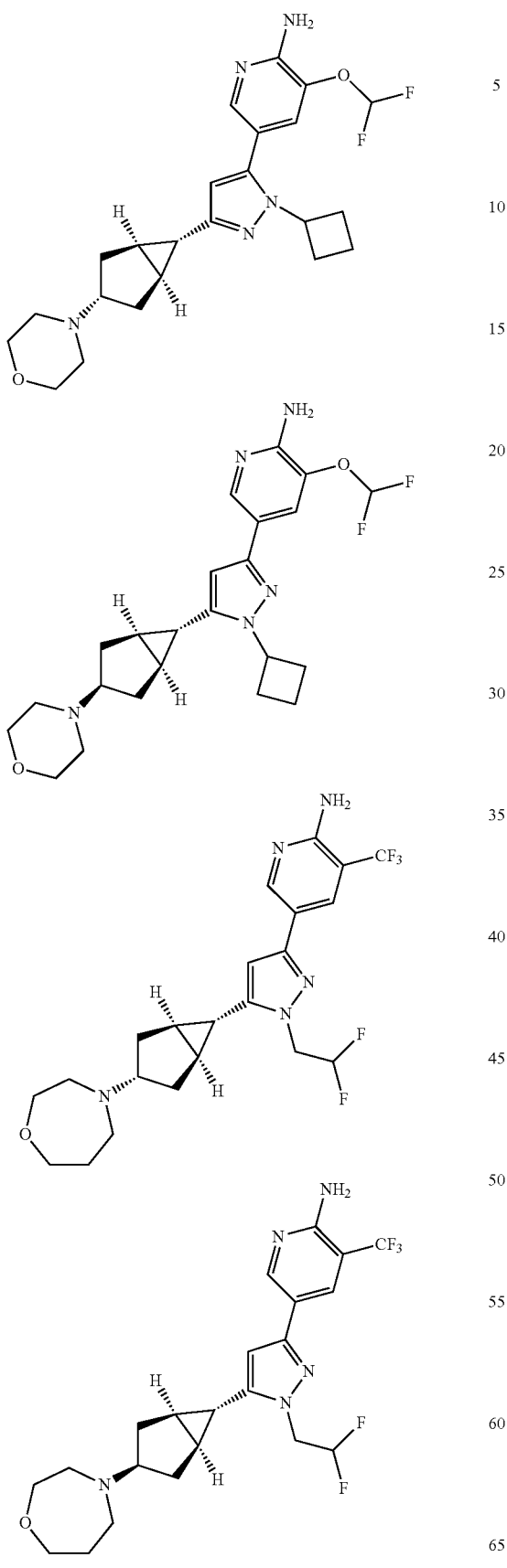
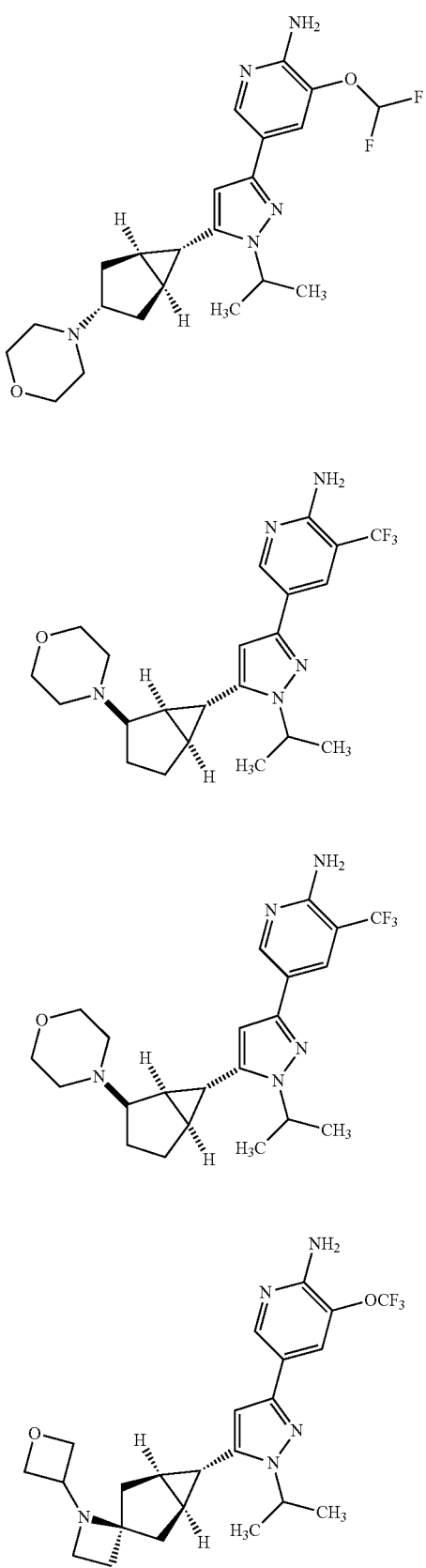

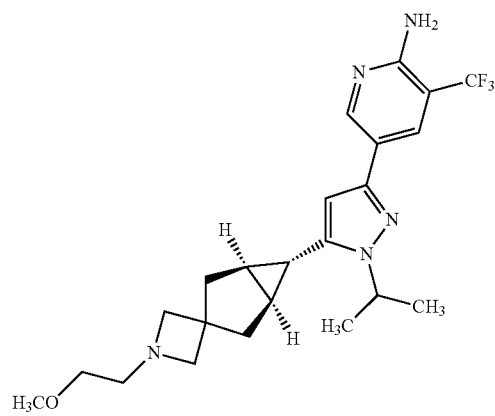
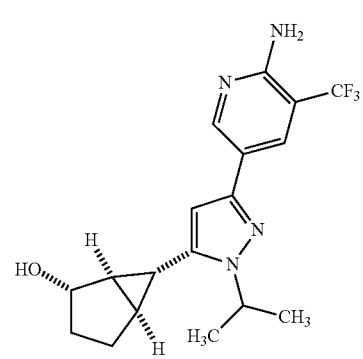
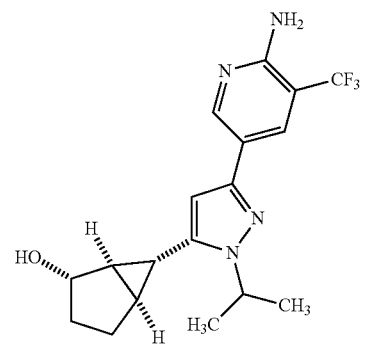
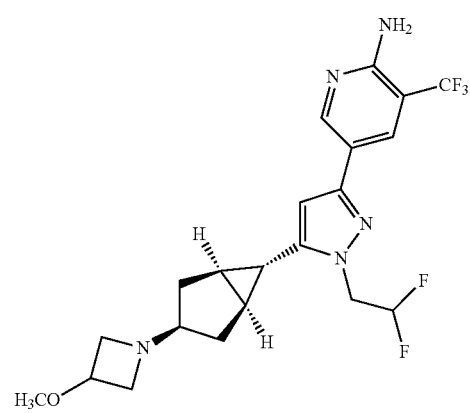
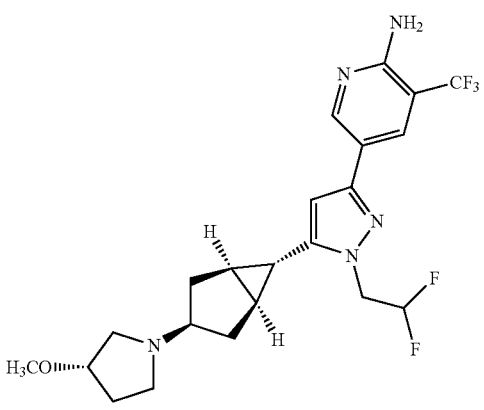
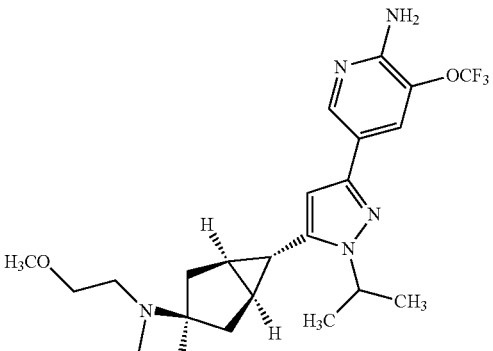
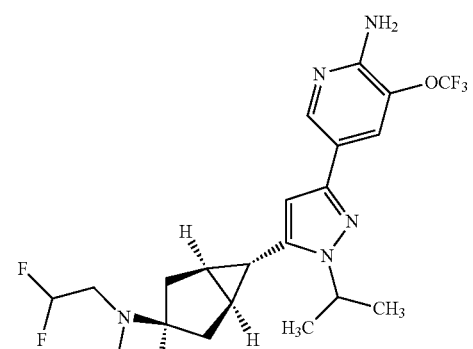
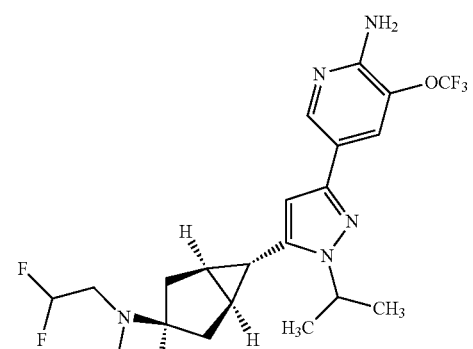

-continued
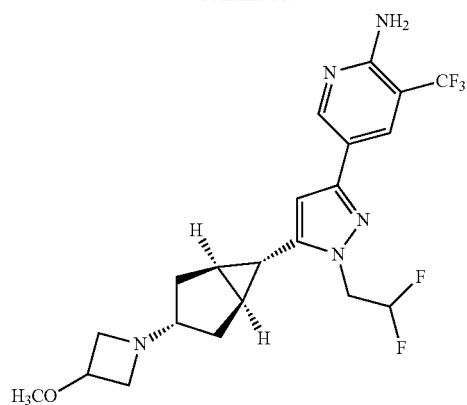
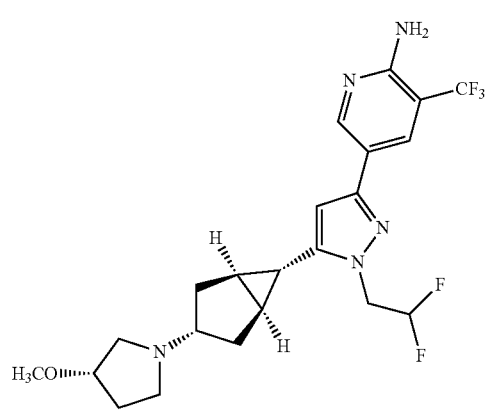
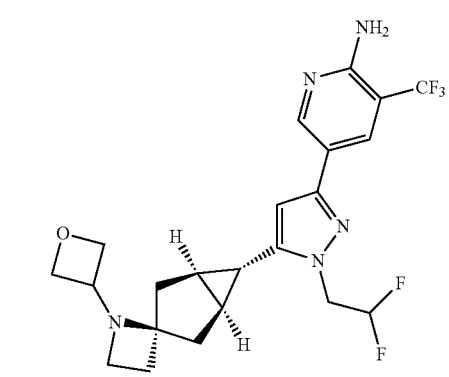
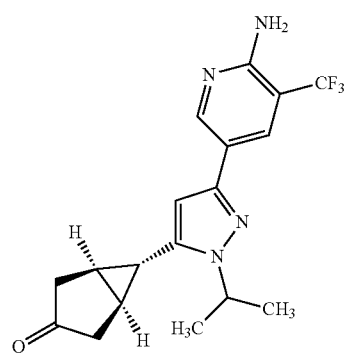
-continued
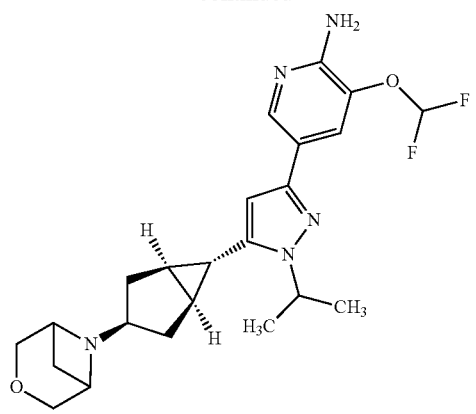
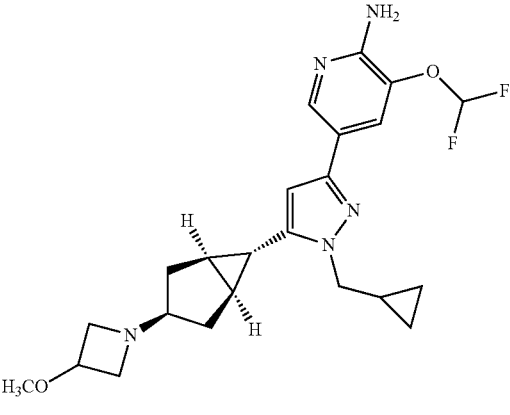
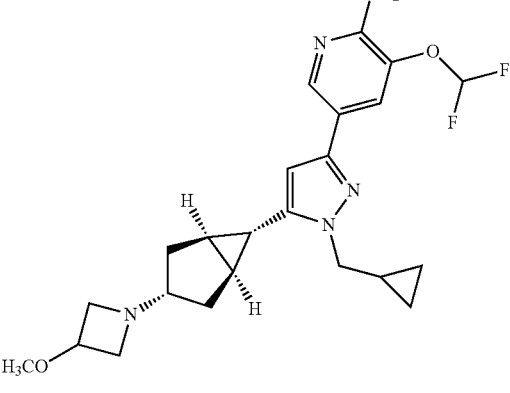
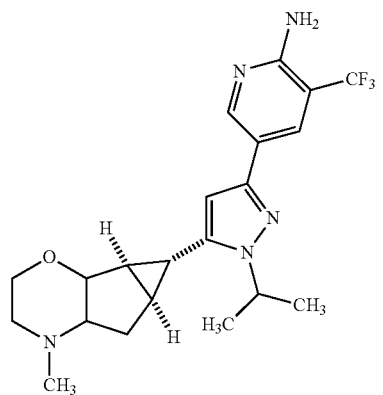

59
-continued
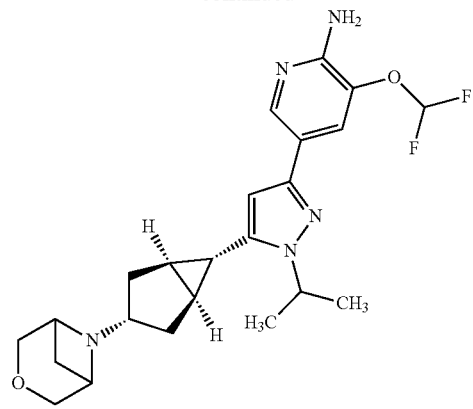
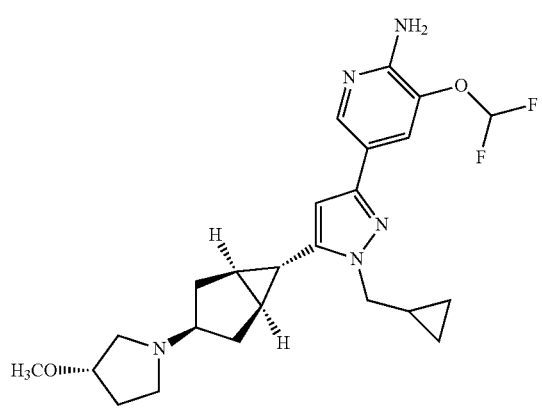
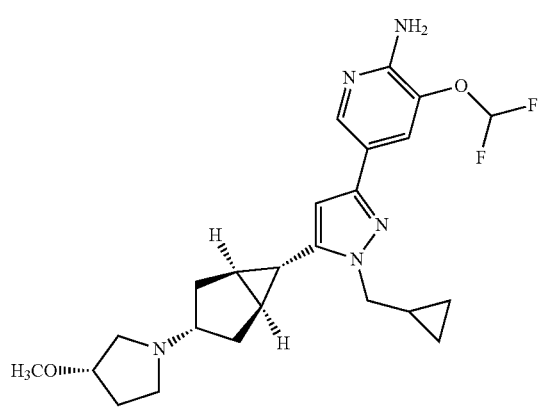
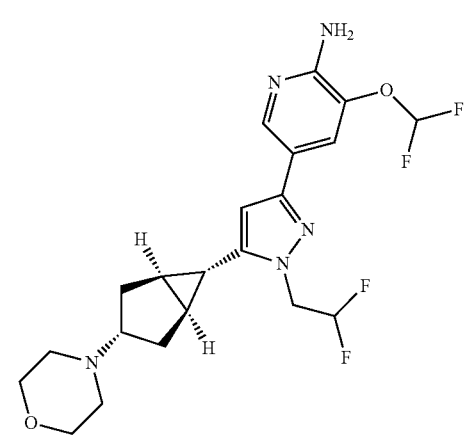
60
-continued
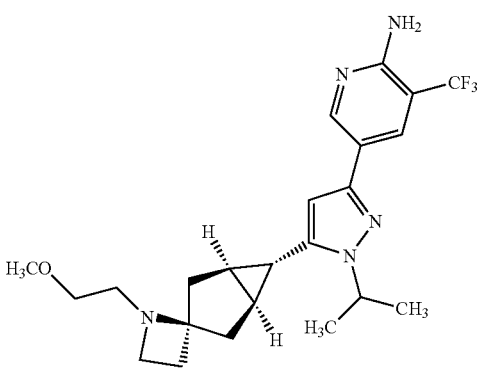
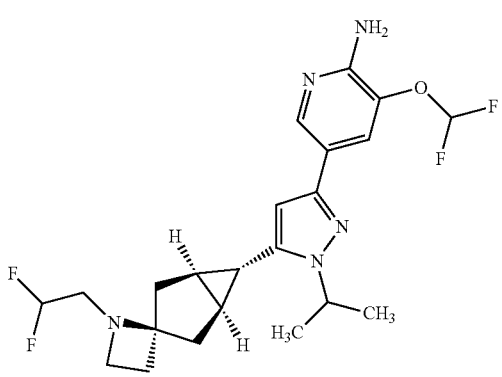
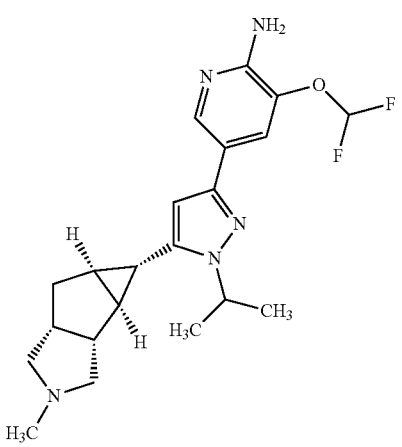
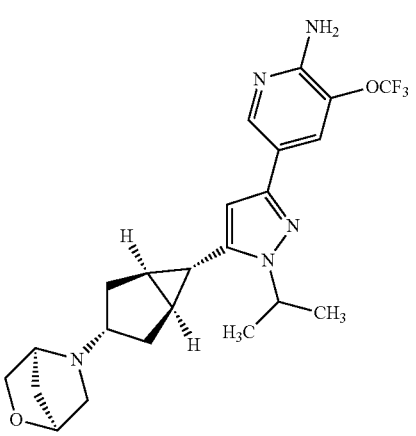

-continued
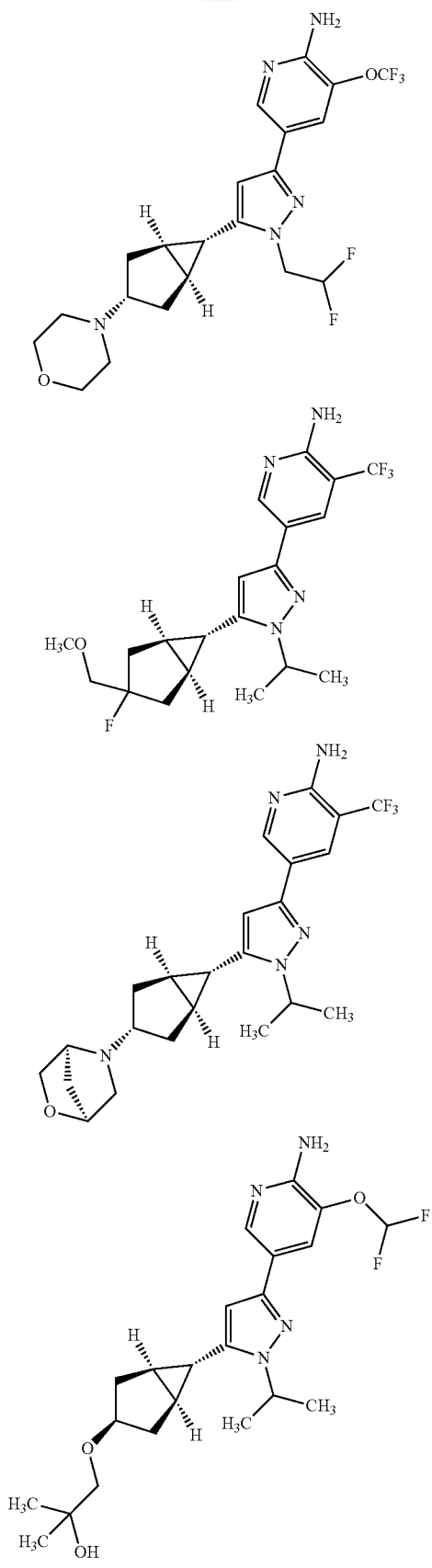
-continued
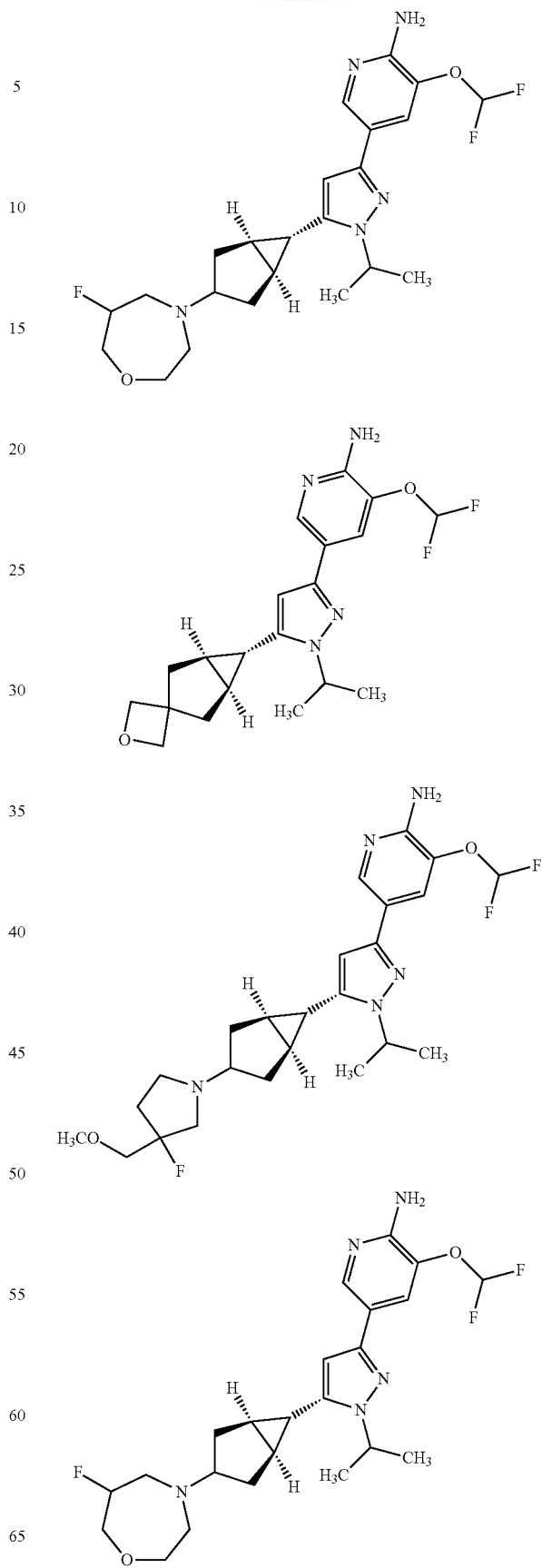

63
-continued
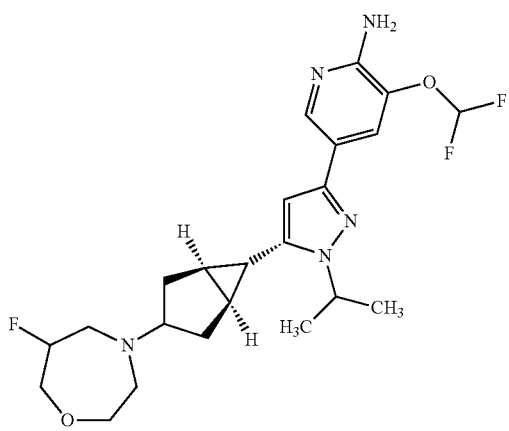
64
-continued
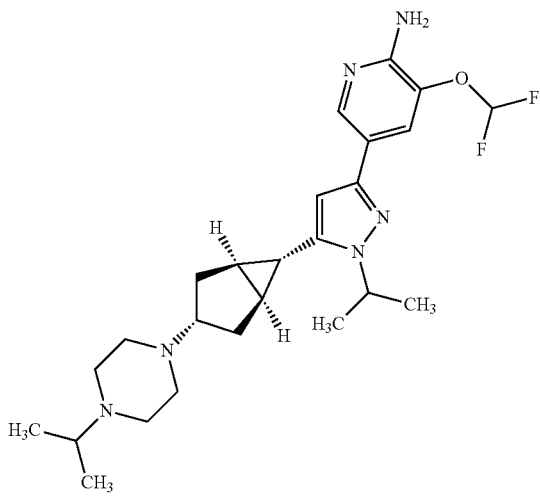
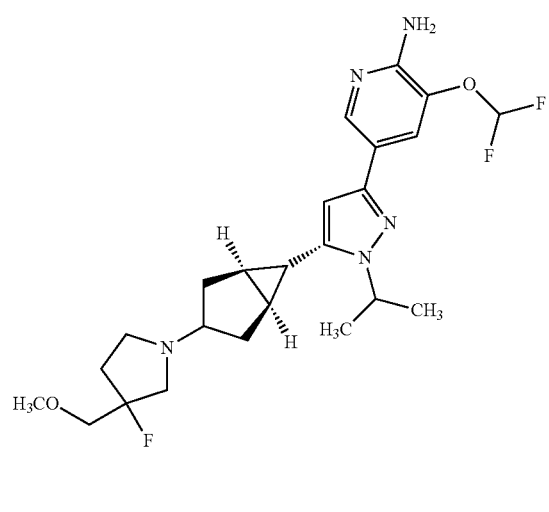
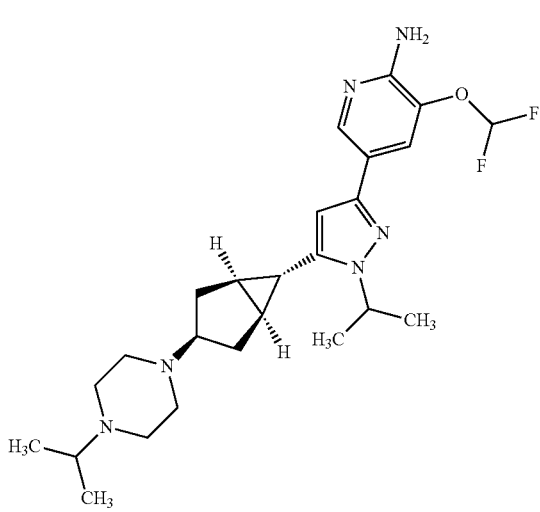
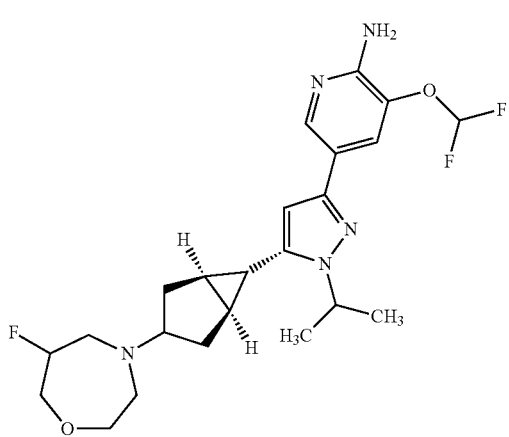
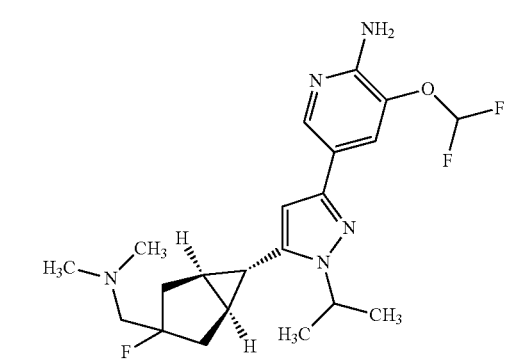

65
-continued
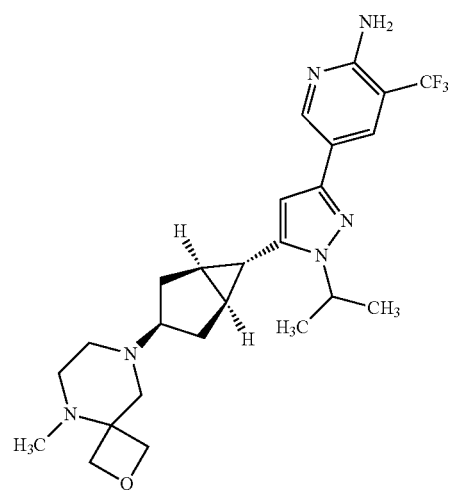
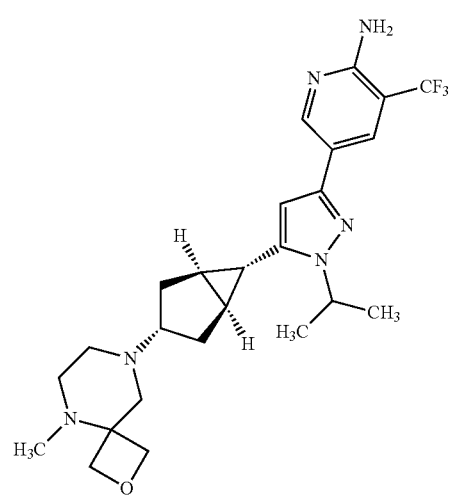
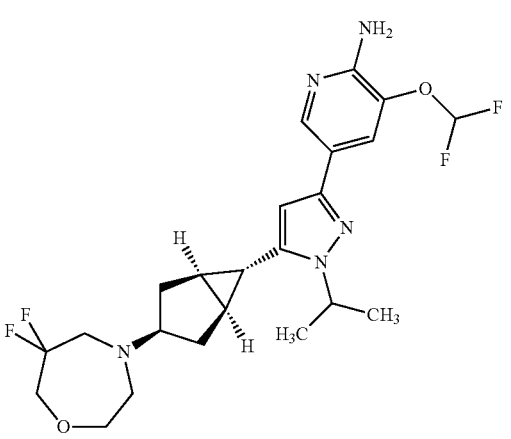
66
-continued
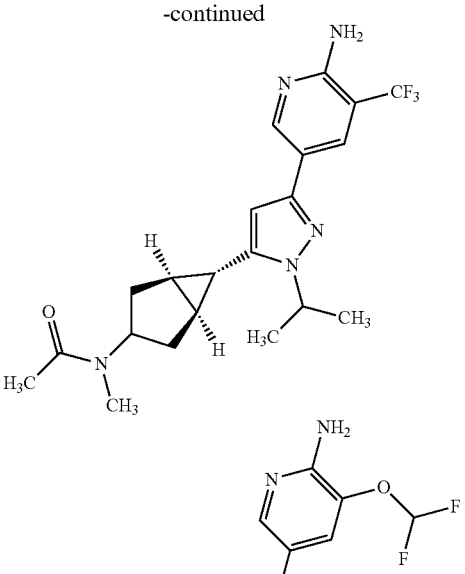
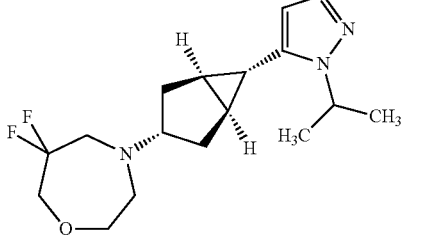
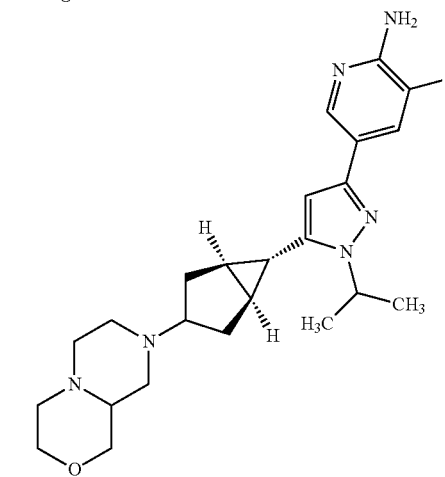
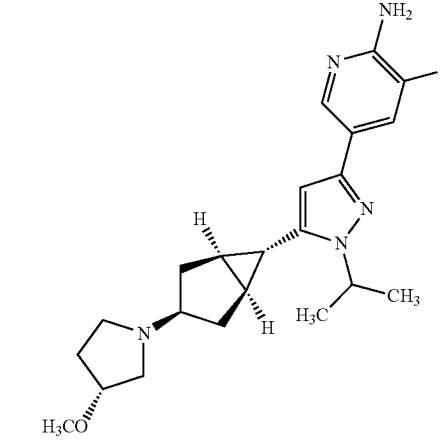

67
-continued
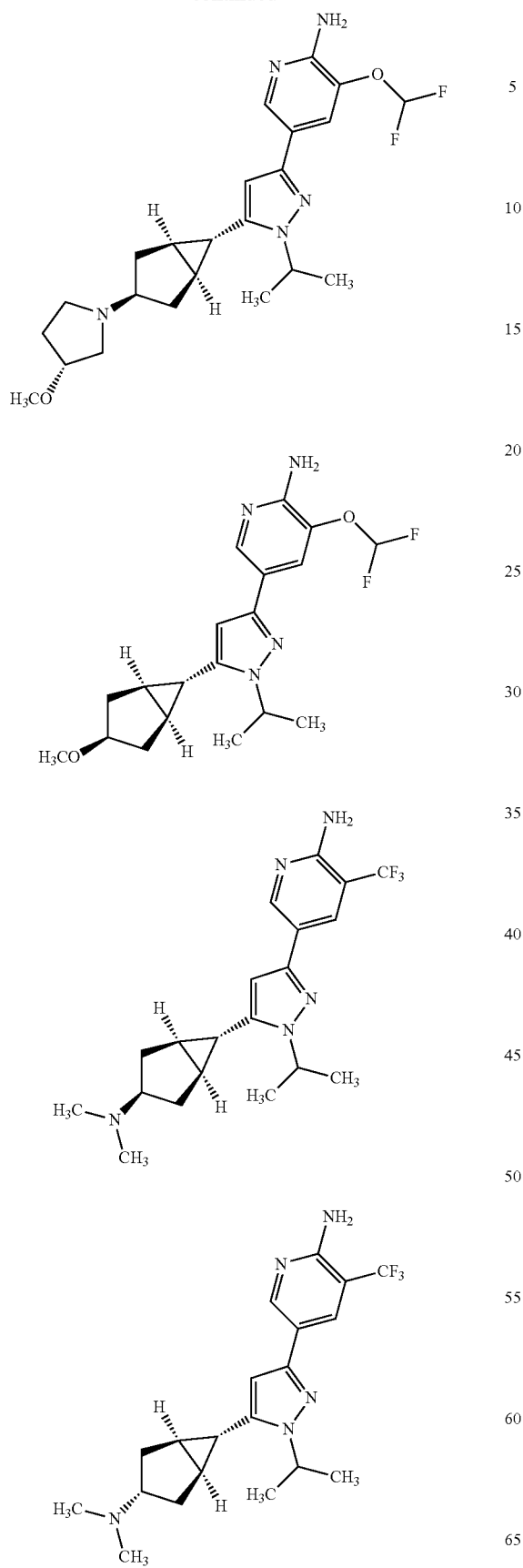
68
-continued
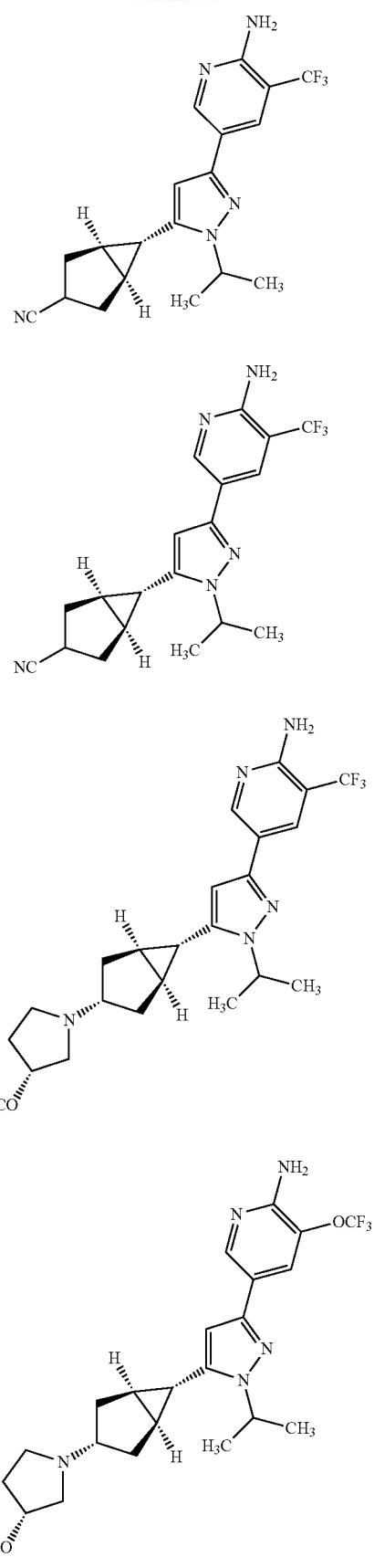

69
-continued
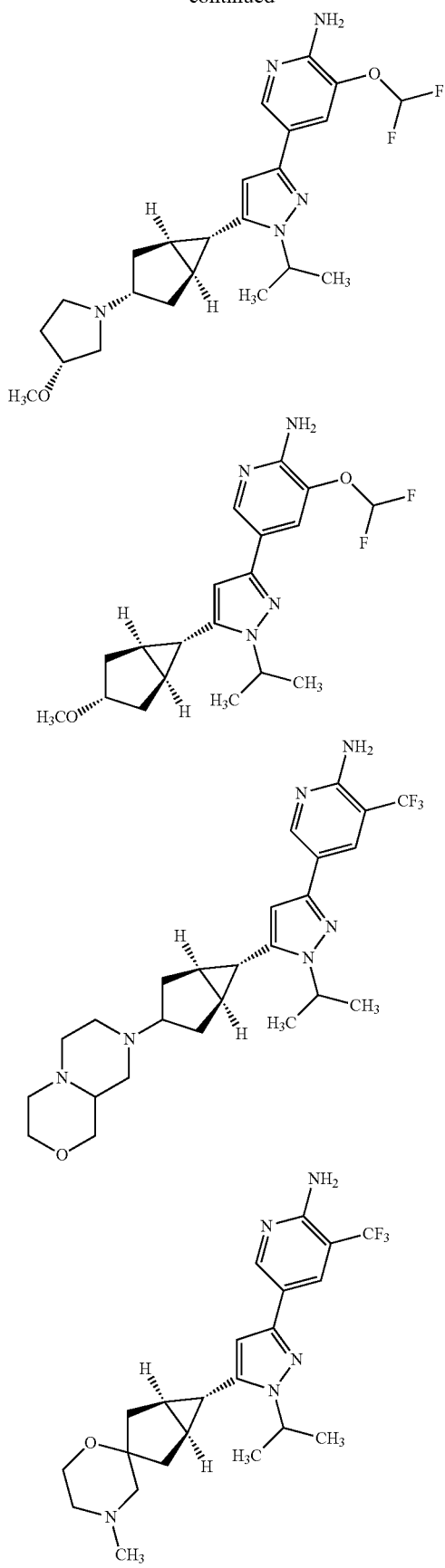
70
-continued
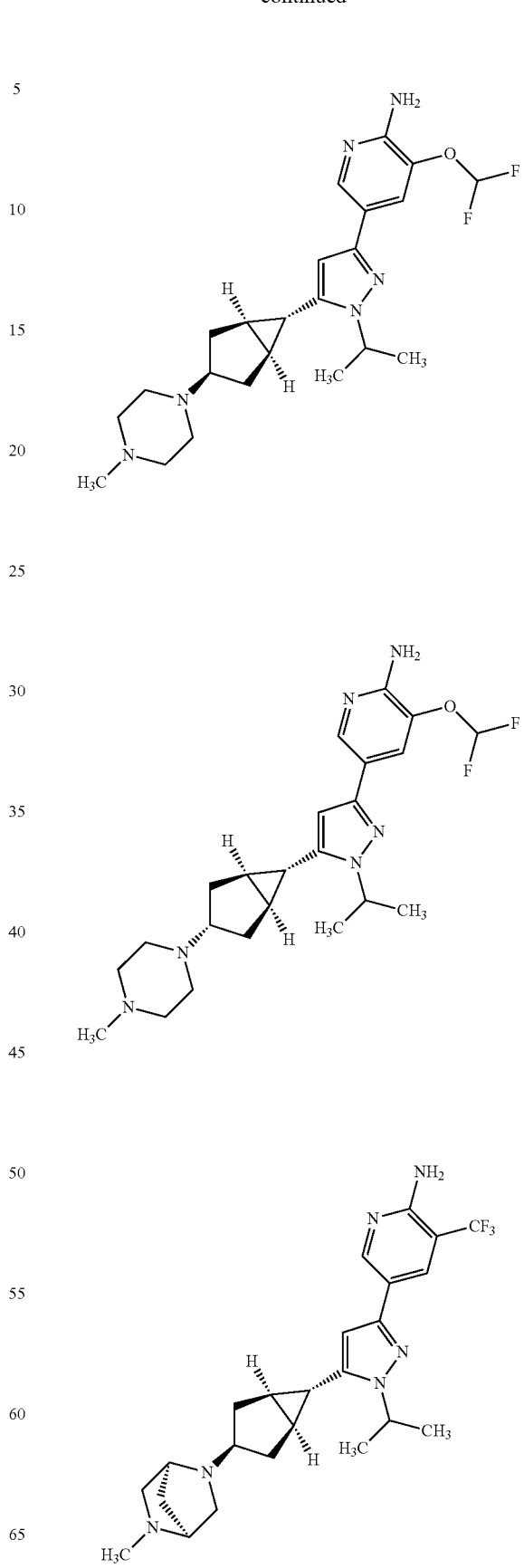

71
-continued
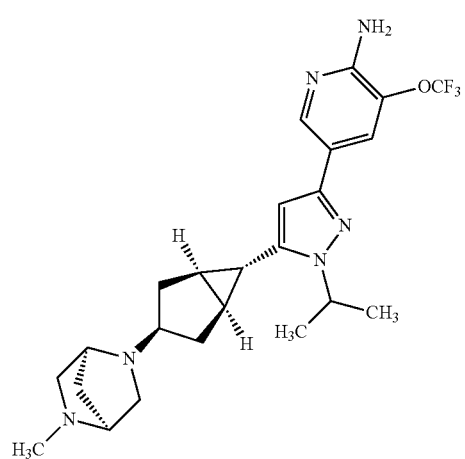
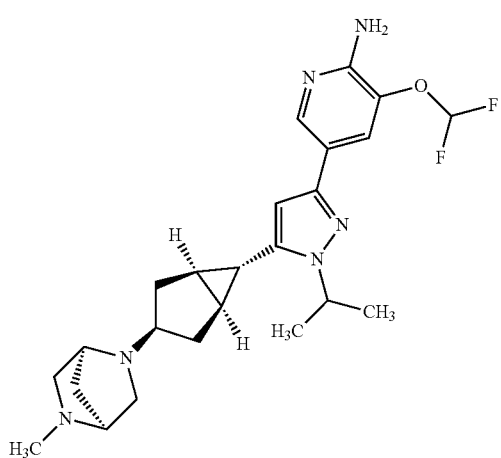
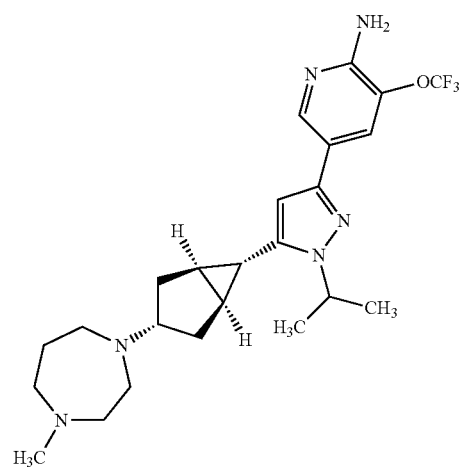
72
-continued
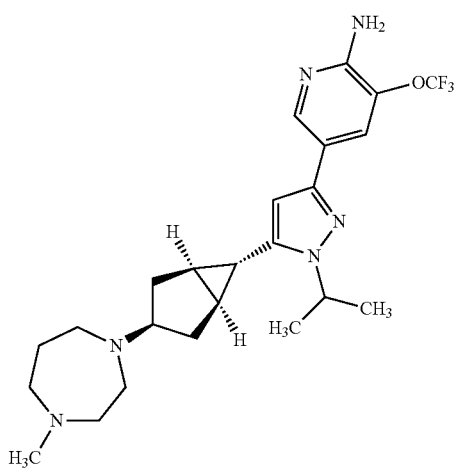
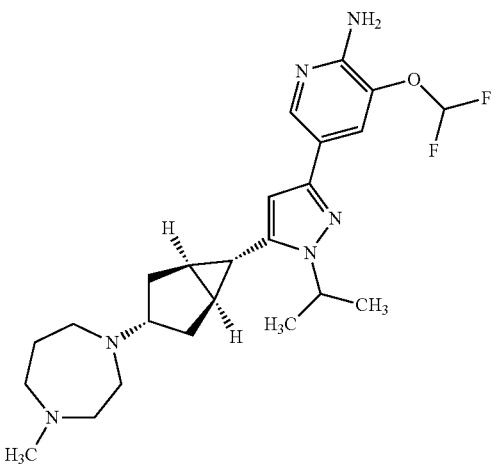
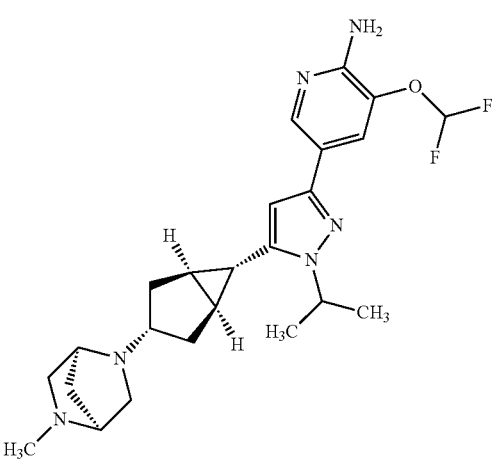

73
-continued
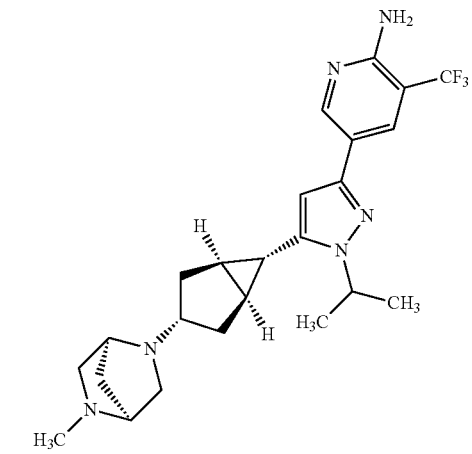
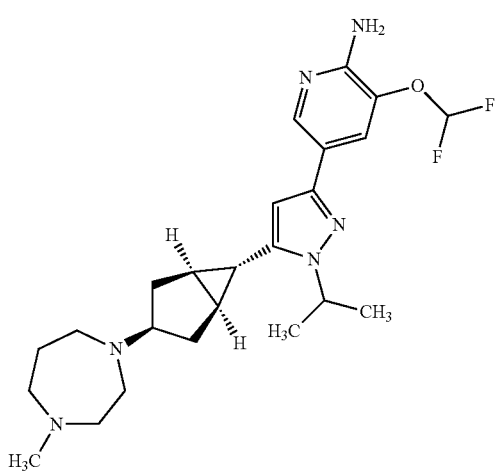
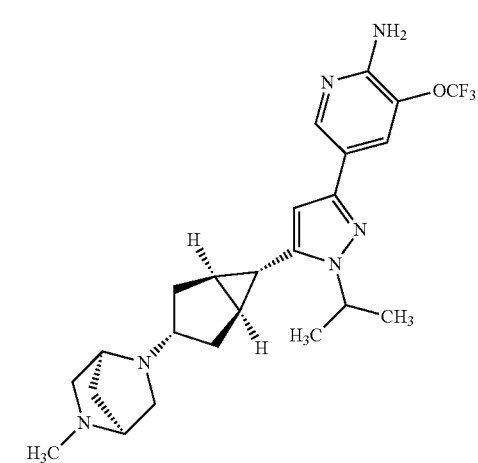
74
-continued
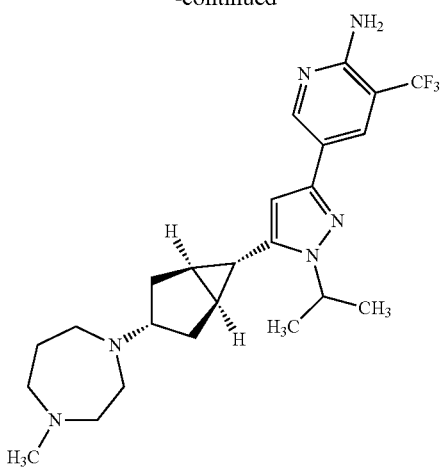
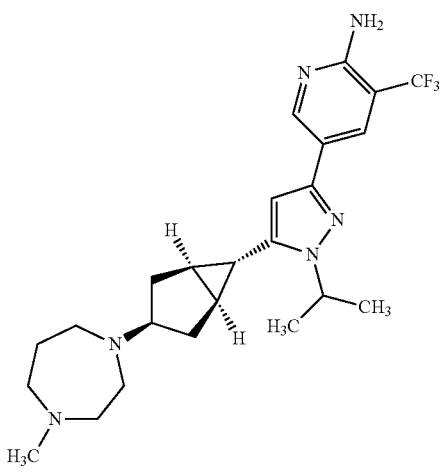
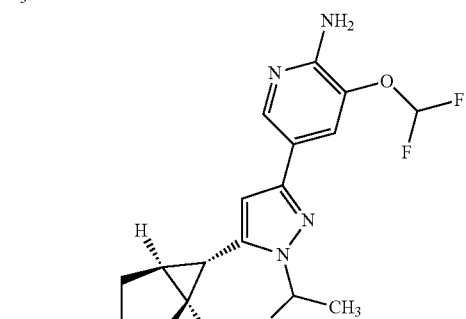
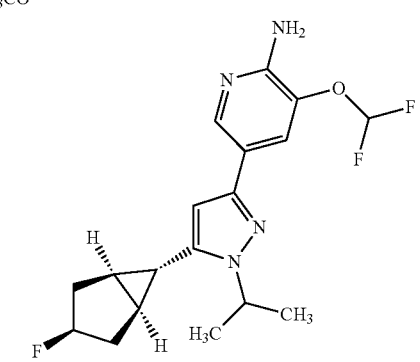

75
-continued
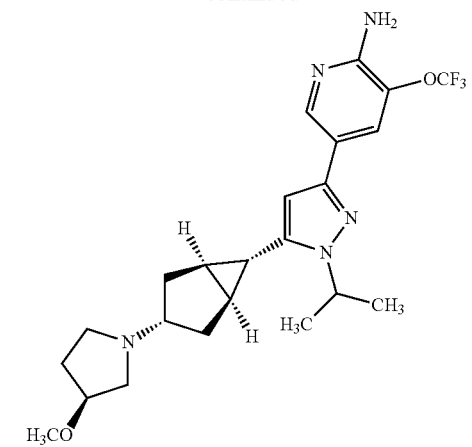
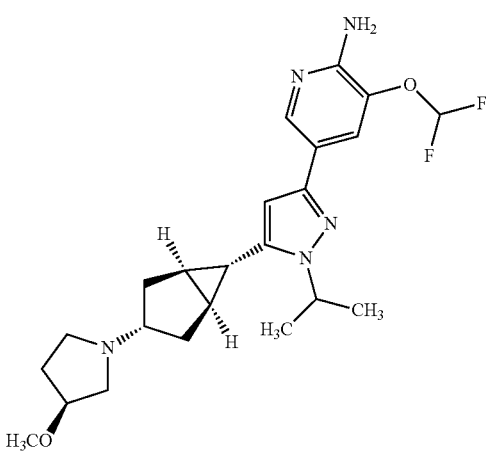
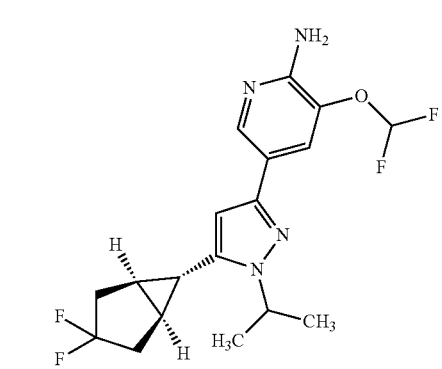
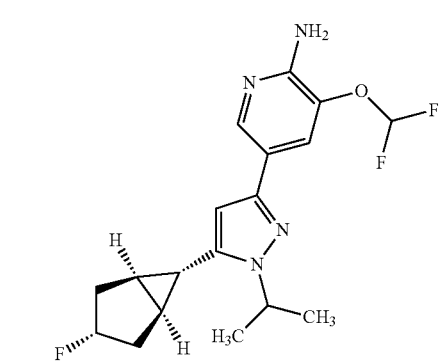
76
-continued
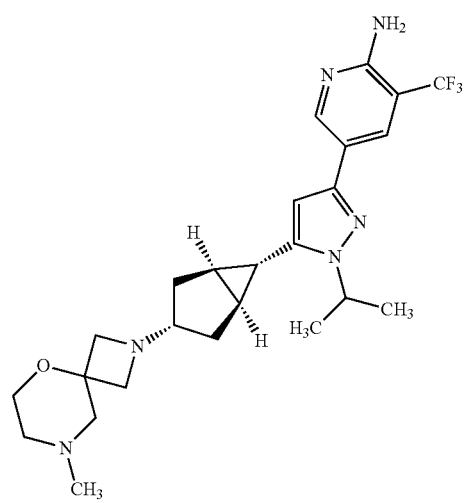
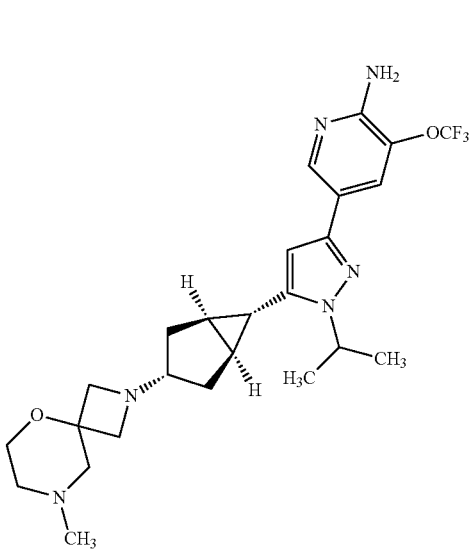

77
-continued
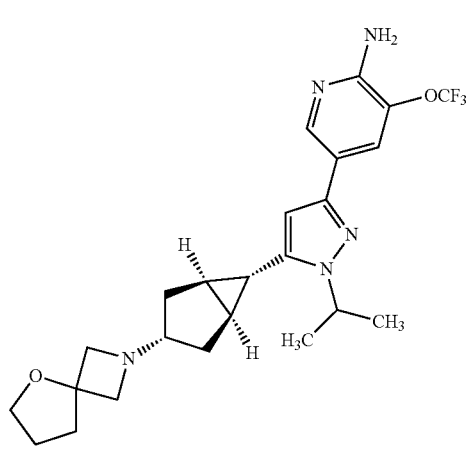
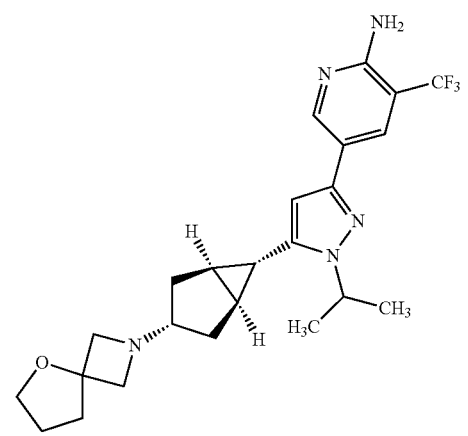
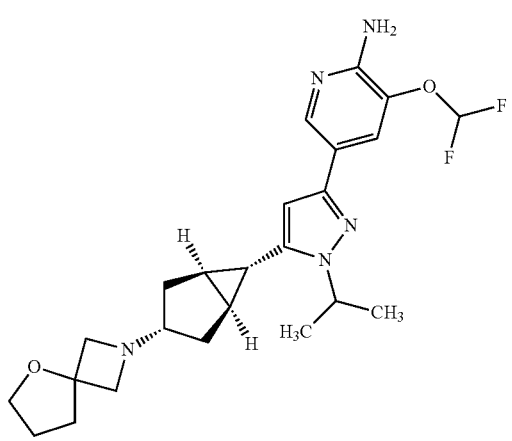
78
-continued
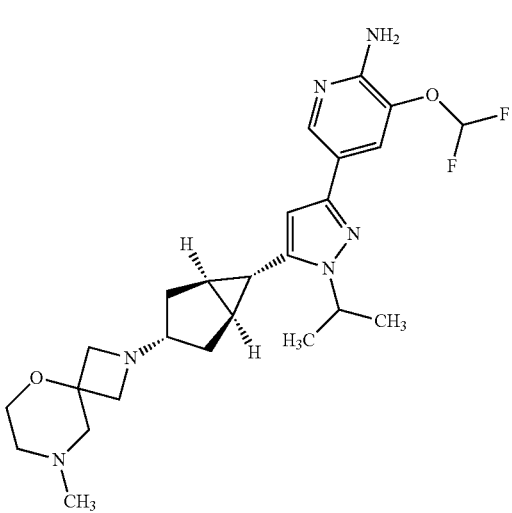
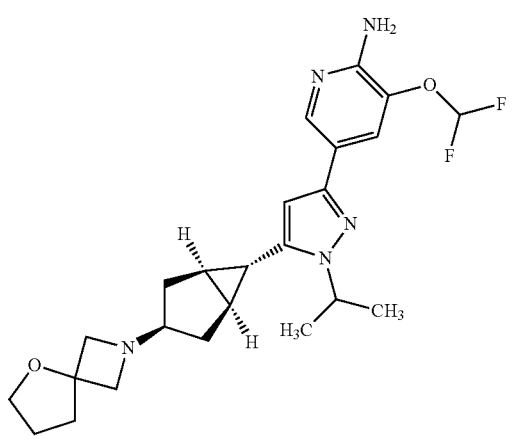
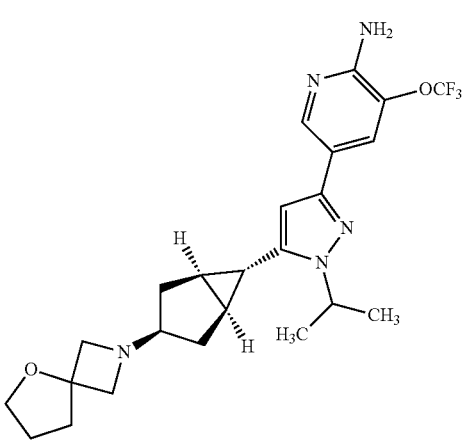

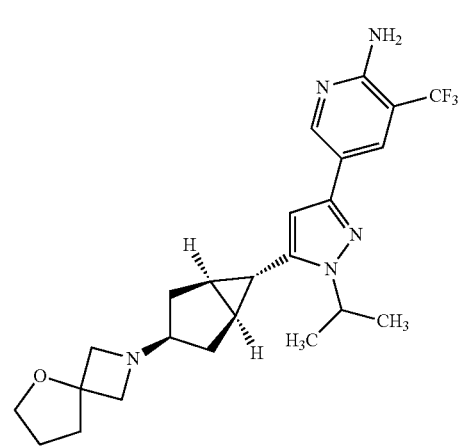
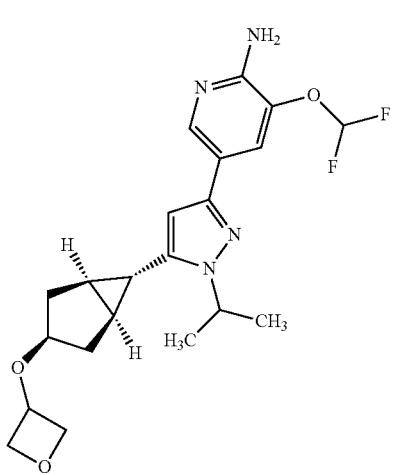
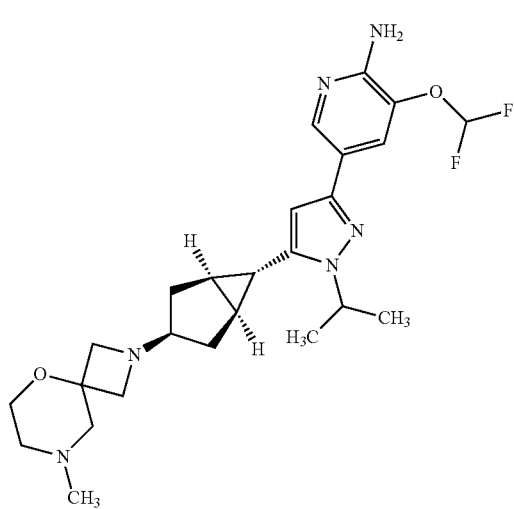
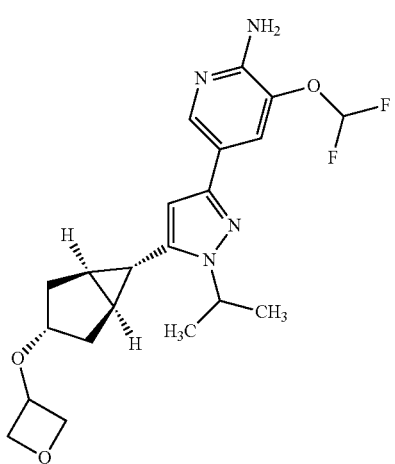
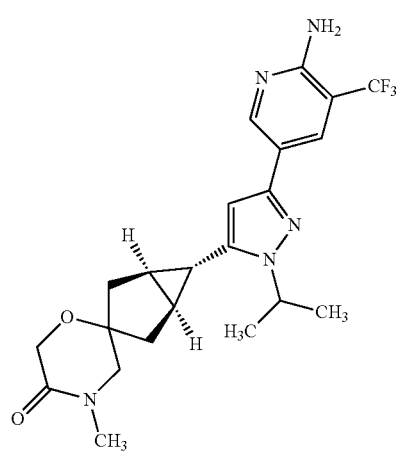
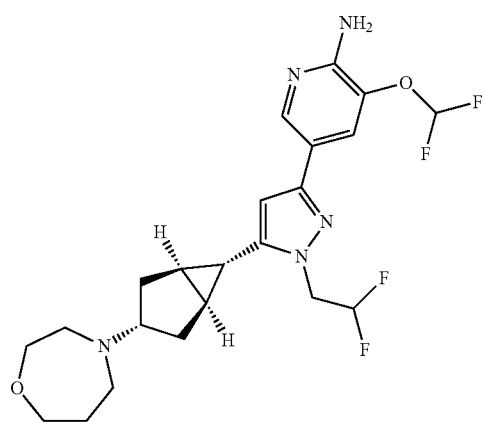

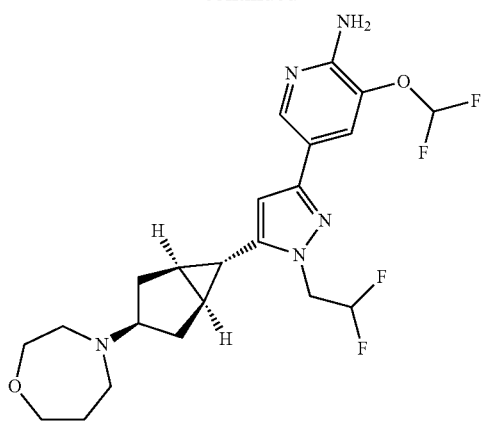

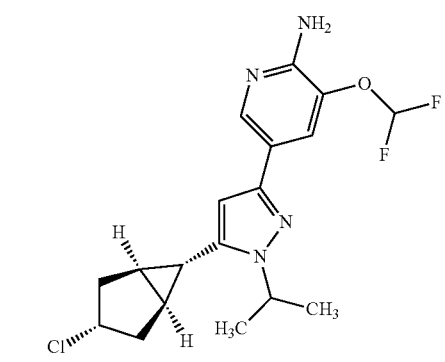
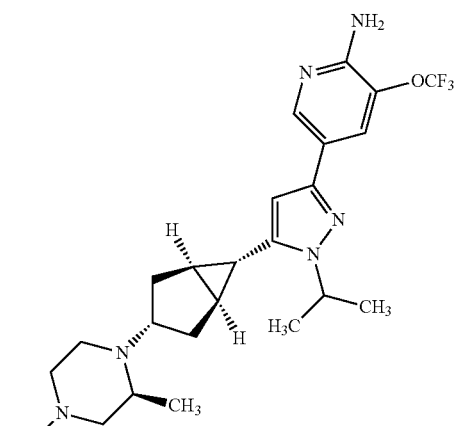

83
-continued
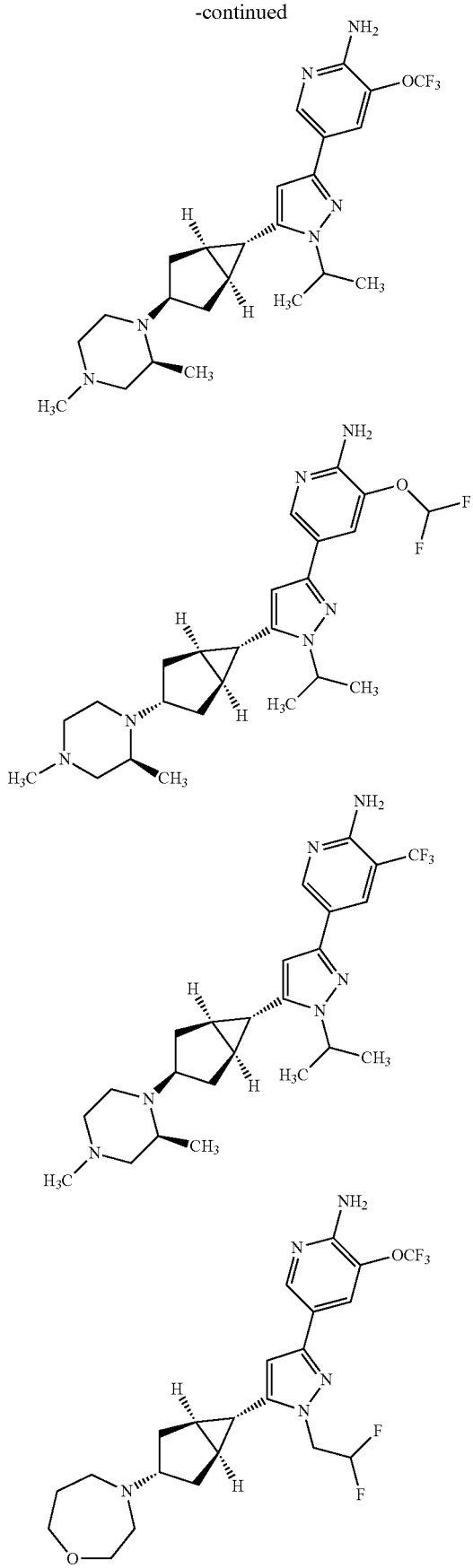
84
-continued
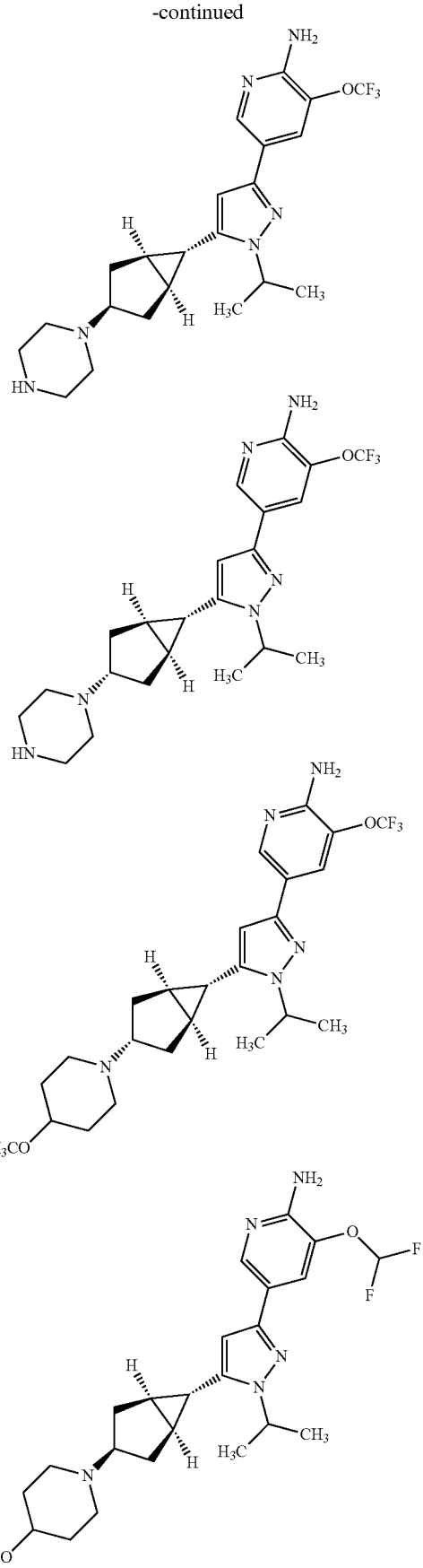

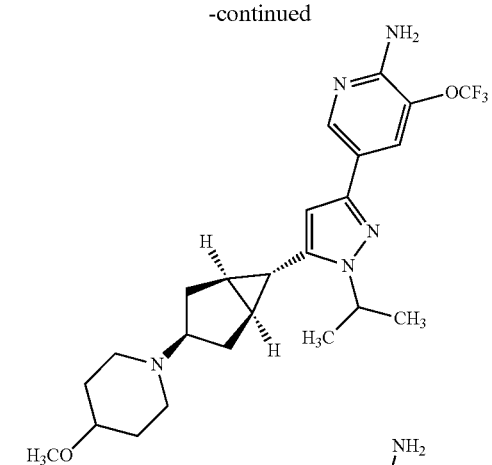
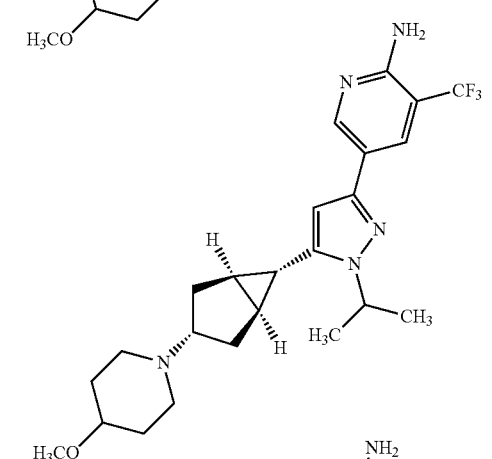

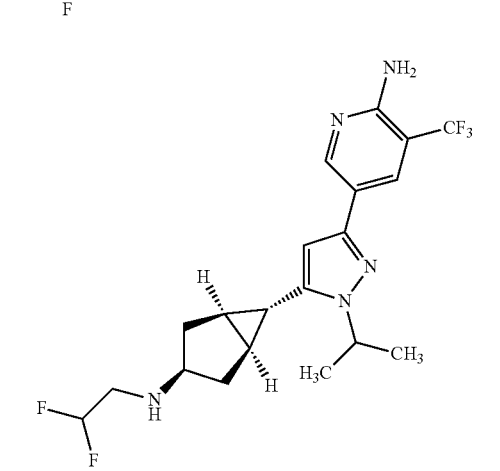
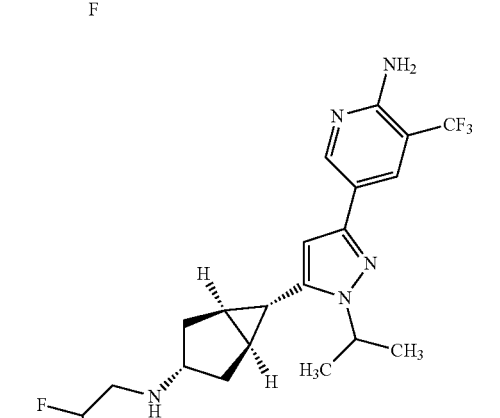
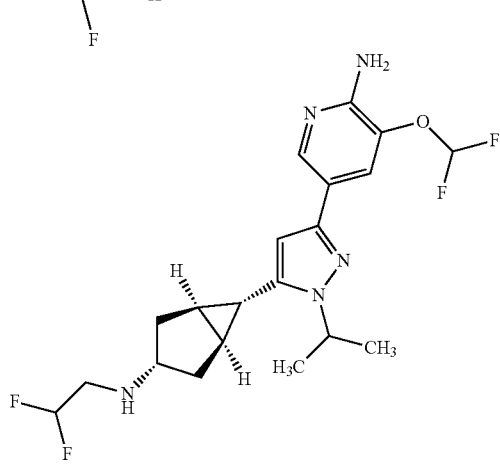

87
-continued
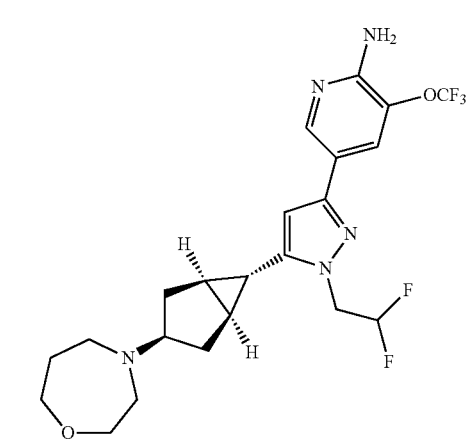
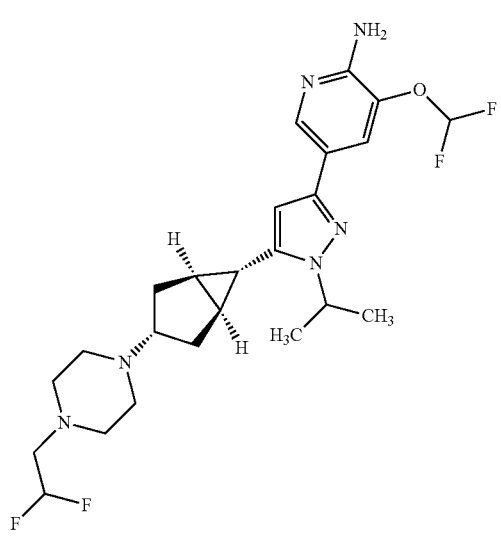
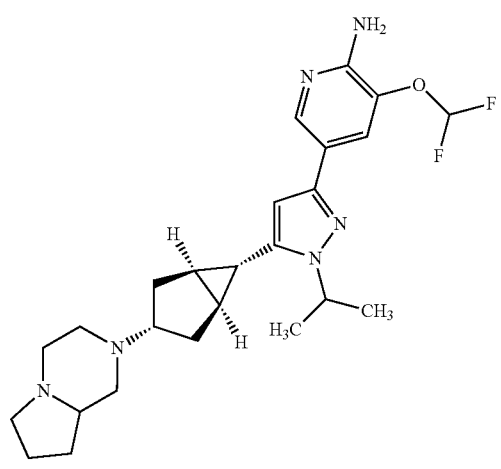
88
-continued
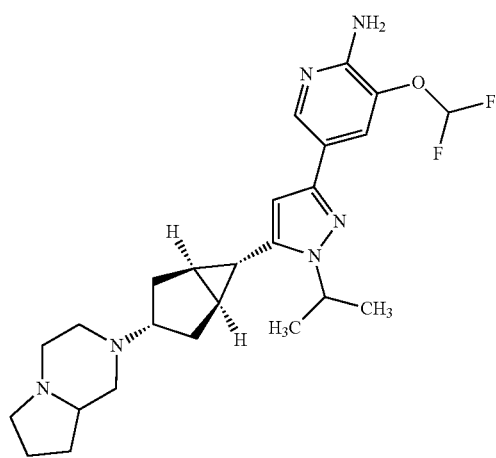
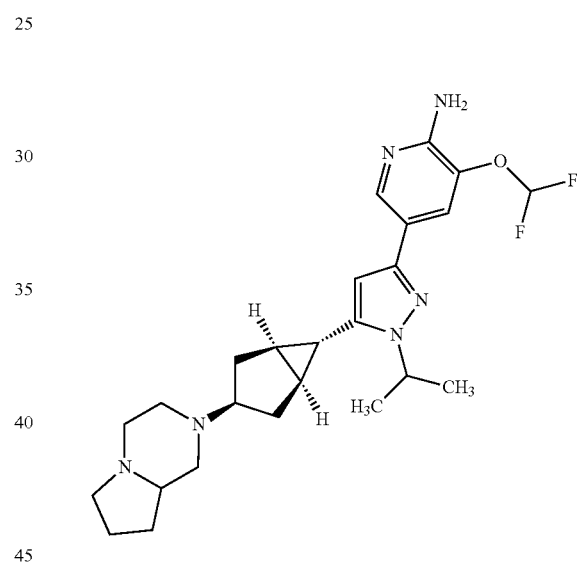
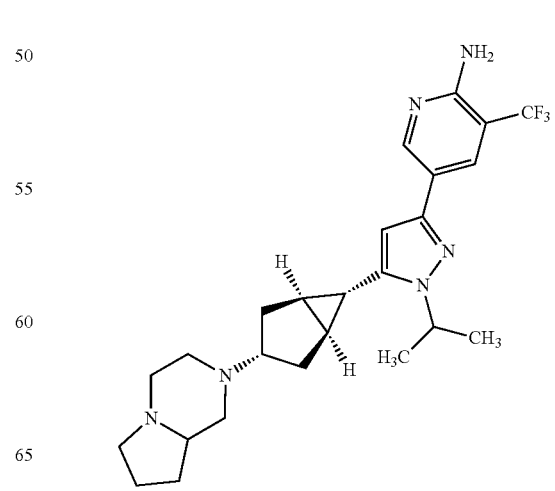

-continued
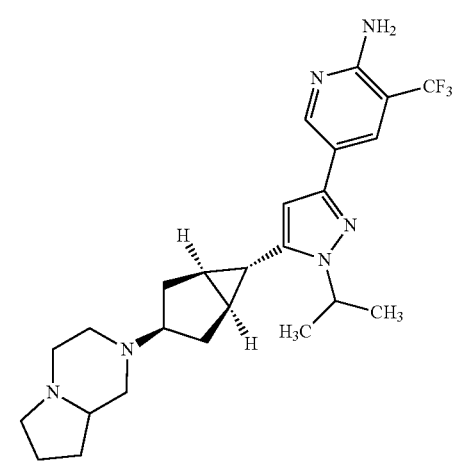
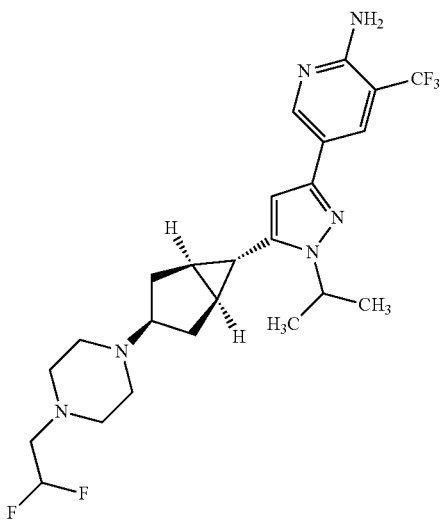
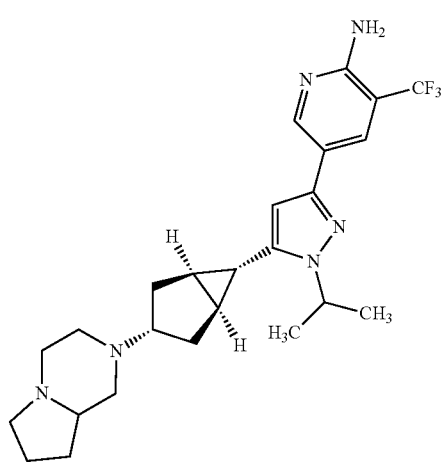
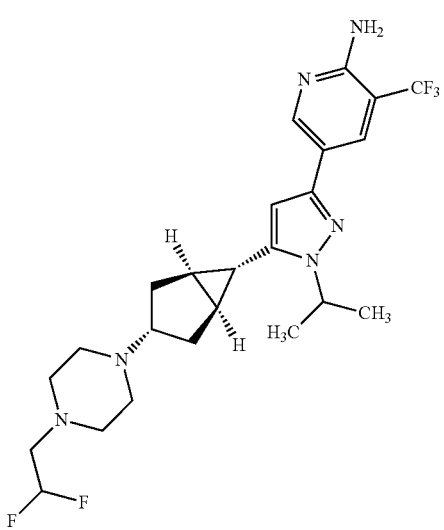
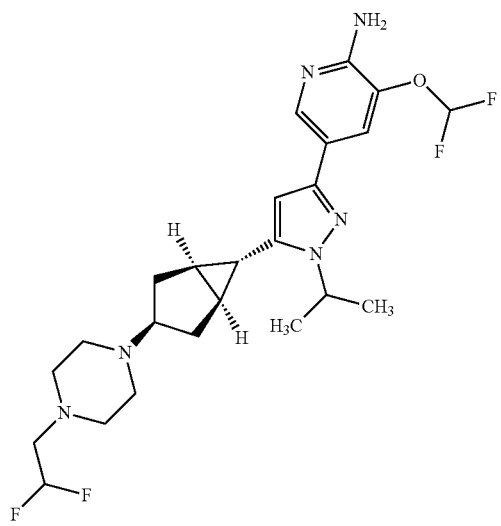
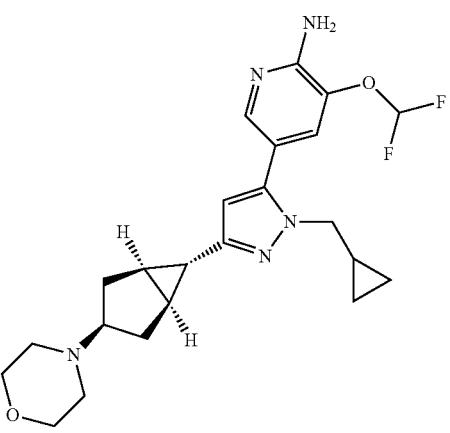

91
-continued
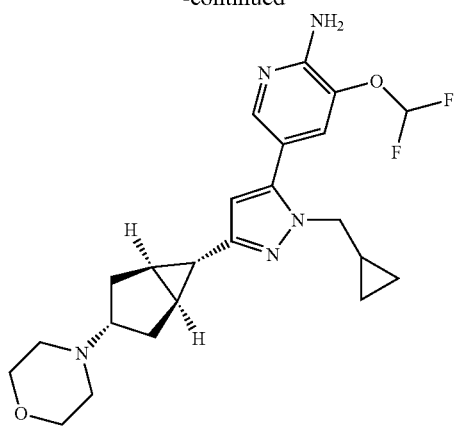
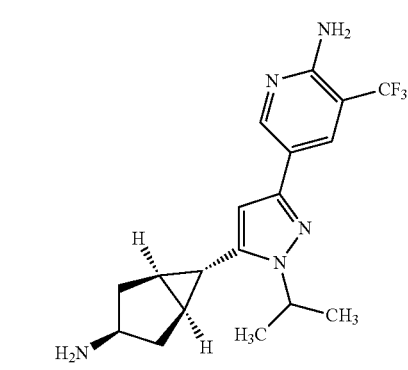
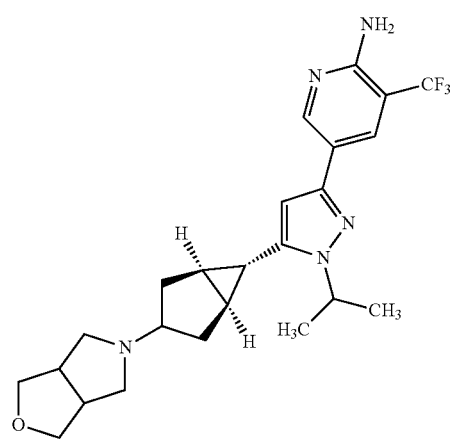
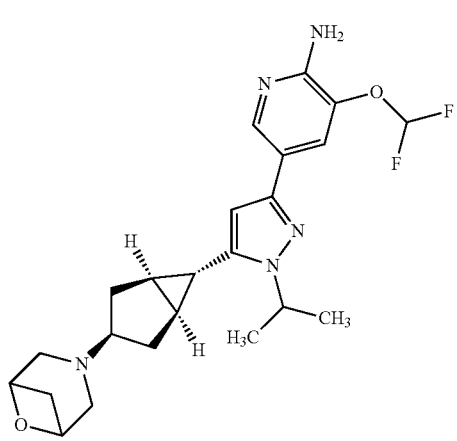
92
-continued
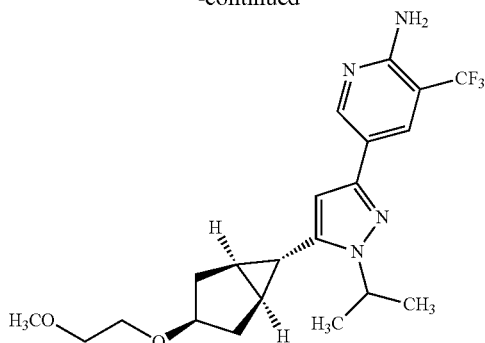
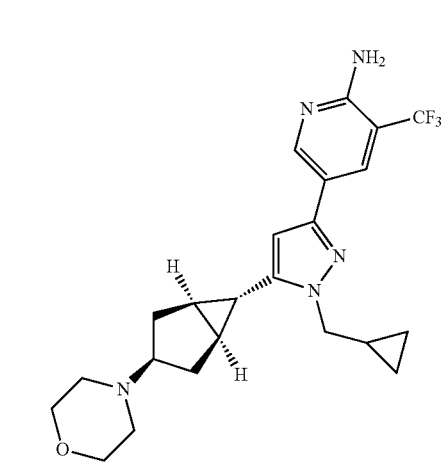
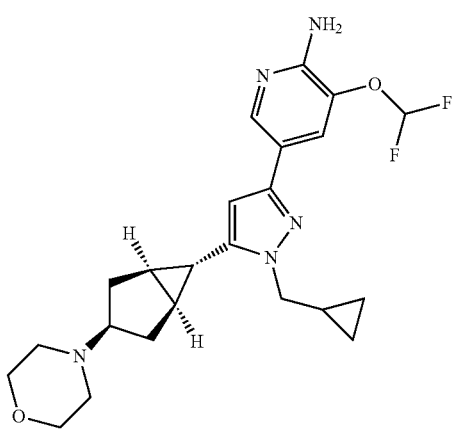
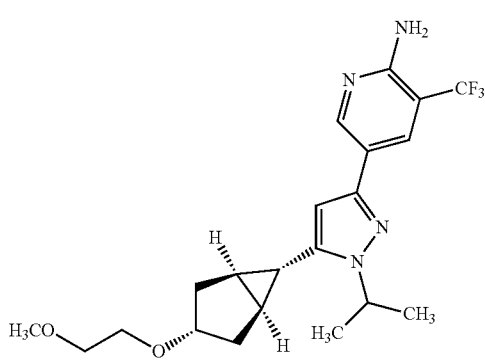

-continued
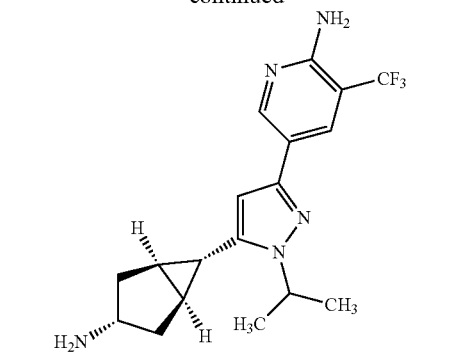
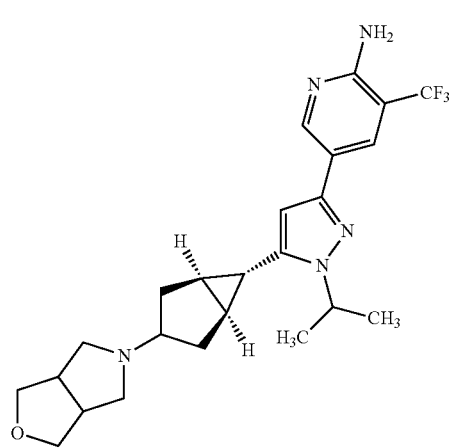
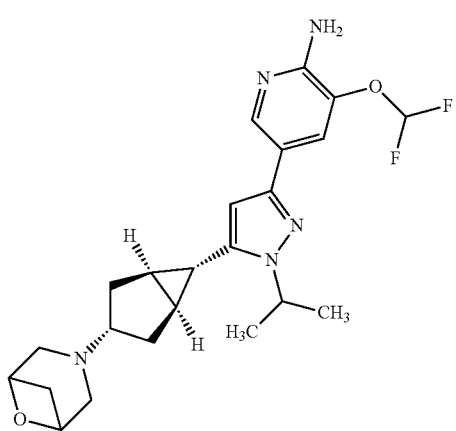
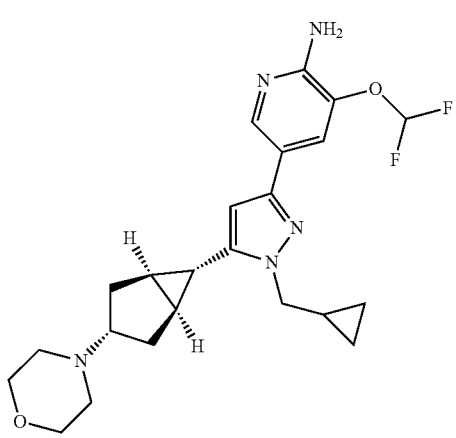
-continued
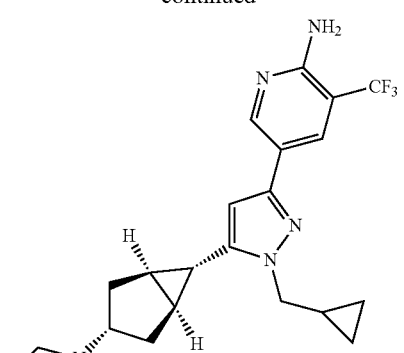
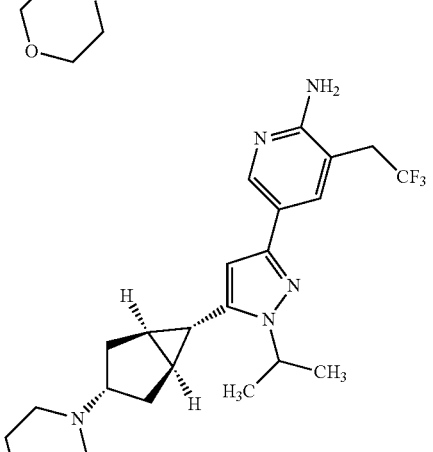
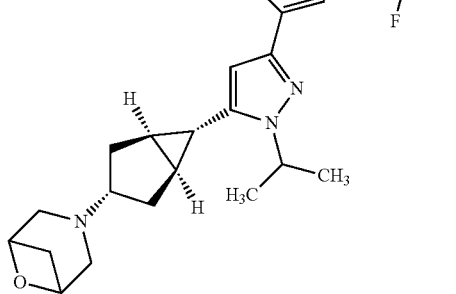
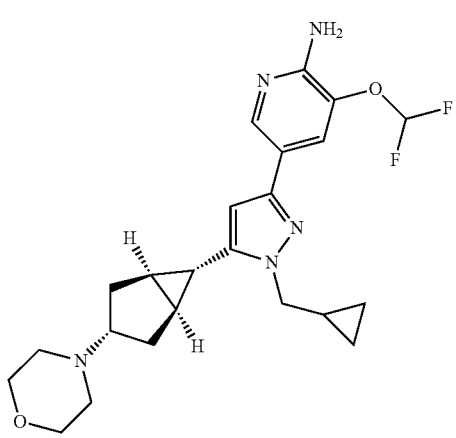

95
-continued
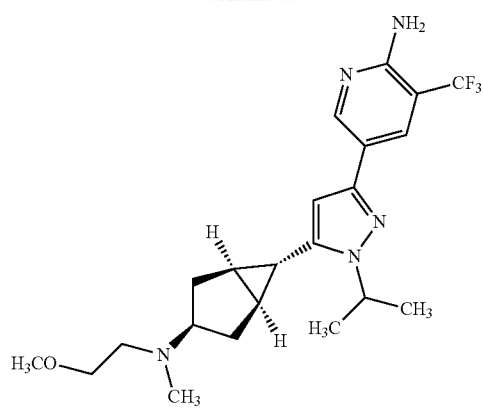
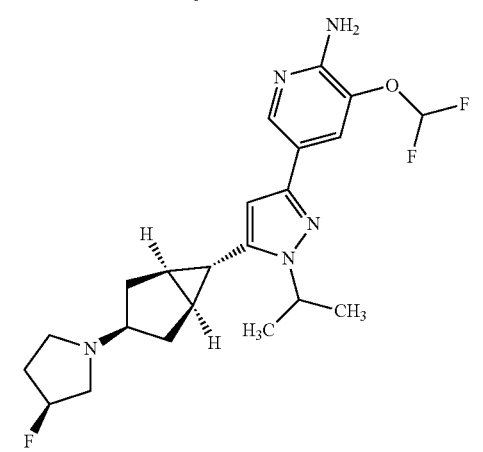
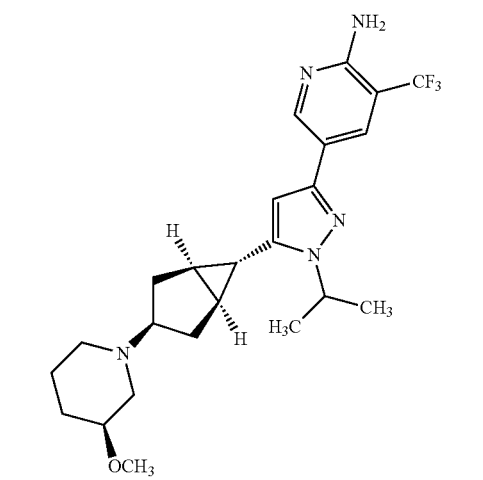
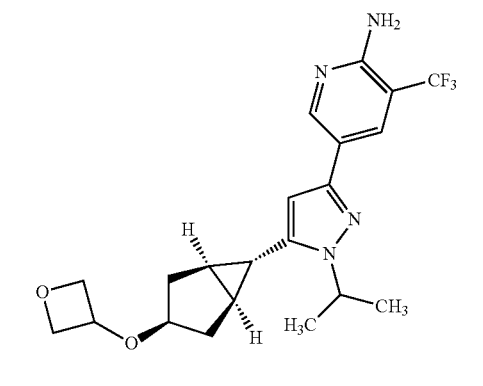
96
-continued
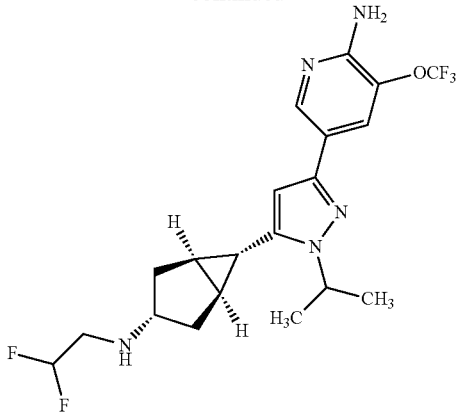

-continued

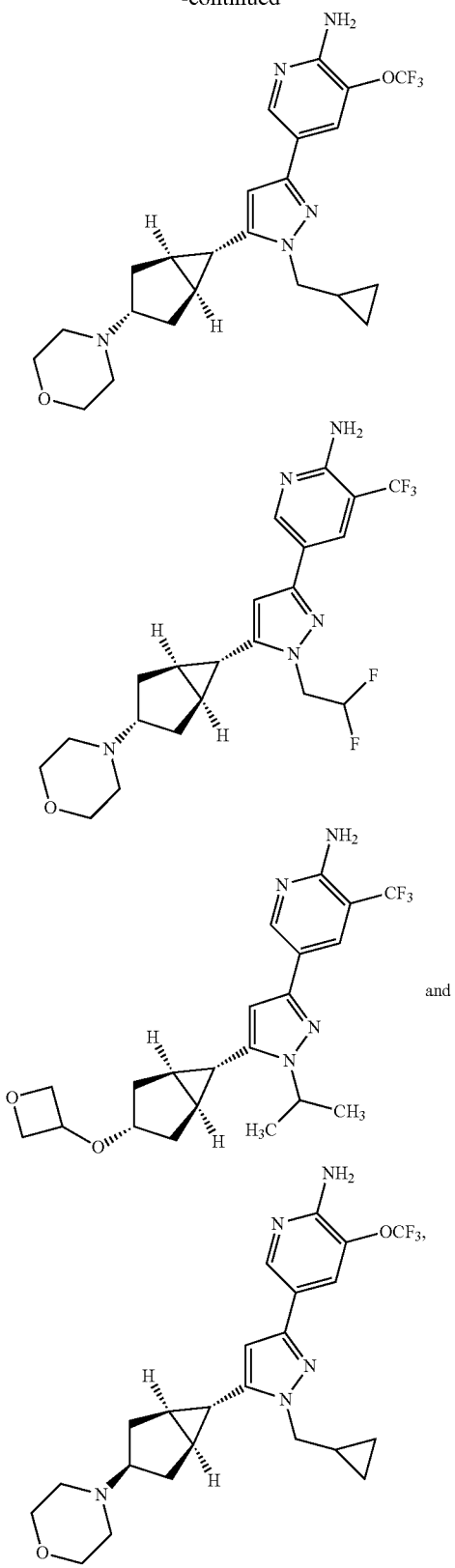

and salts thereof.

E59 A compound of E0, selected from the group consisting of compounds set forth in Table A presented herein.

In another aspect, the compounds formula 0, including compounds in Table A, having a bicyclo[3.1.0]hexane ring display surprisingly superior in vitro and in vivo metabolism profile as compared to related compound that do not have a bicyclo[3.1.0]hexane group.

In another aspect the present invention provides for a pharmaceutical composition comprising a compound of formula 0 or any embodiment thereof and a pharmaceutically acceptable carrier, diluent or excipient.

In another aspect the present invention provides a method for inhibiting or preventing degeneration of a central nervous system (CNS) neuron or a portion thereof, the method comprising administering to the CNS neuron a compound of formula 0 or any embodiment thereof.

In another aspect the present invention provides a method for inhibiting or preventing degeneration of a central nervous system (CNS) neuron in a patient having or at risk of developing a neurodegenerative disease or condition comprising administering to said patient a therapeutically effective amount of a compound of formula 0 or any embodiment thereof, or a pharmaceutically acceptable salt thereof.

In another aspect the present invention provides a method for decreasing or preventing one or more symptoms of a neurodegenerative disease or condition in a patient suffering therefrom comprising administering to said patient a therapeutically effective amount of a compound of formula 0 or any embodiment thereof, or a pharmaceutically acceptable salt thereof.

In another aspect the present invention provides method for decreasing the progression of a neurodegenerative disease or condition in a patient suffering therefrom comprising administering to said patient a therapeutically effective amount of a compound of formula 0 or any embodiment thereof, or a pharmaceutically acceptable salt thereof.

In another aspect the present invention provides a compound of formula 0 or any embodiment thereof, or a pharmaceutically acceptable salt thereof for use in medical therapy.

In another aspect the present invention provides the use of a compound of formula 0 or any embodiment thereof, or a pharmaceutically acceptable salt thereof for the preparation of a medicament for inhibiting or preventing degeneration of a central nervous system (CNS) neuron in a patient having or at risk of developing a neurodegenerative disease or condition.

In another aspect the present invention provides use of a compound of formula 0 or any embodiment thereof, or a pharmaceutically acceptable salt thereof for the preparation of a medicament for decreasing or preventing one or more symptoms of a neurodegenerative disease or condition in a patient suffering therefrom.

In another aspect the present invention provides the use of a compound of formula 0 or any embodiment thereof, or a pharmaceutically acceptable salt thereof for the preparation of a medicament for decreasing the progression of a neurodegenerative disease or condition in a patient suffering therefrom.

In another aspect the present invention provides a compound of formula 0 or any embodiment thereof, or a pharmaceutically acceptable salt thereof for the therapeutic or prophylactic treatment of central nervous system (CNS) neuron degeneration.

In another aspect the present invention provides a compound of formula 0 or any embodiment thereof, or a pharmaceutically acceptable salt thereof for the therapeutic or prophylactic treatment of a neurodegenerative disease or condition.

DETAILED DESCRIPTION OF THE INVENTION

A. Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include linear and branched groups including vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon ring system having specified overall number of ring atoms (e.g., 3 to 12 ring atoms in a 3 to 12 membered cycloalkyl or $C_{3-12}$ cycloalkyl) and being fully saturated or having no more than one double bond between ring vertices for a 3-5 membered cycloalkyl and being saturated or having no more than two double bonds between ring vertices for 6 or larger membered cycloalkyl. The monocyclic or polycyclic ring may be optionally substituted with one or more oxo groups. The terms "cycloalkyl," "carbocyclic," or "carbocycle" also include polycyclic ring systems wherein the ring radical attached to the remainder of the molecule is a saturated or partially unsaturated ring as defined above and wherein such polycyclic ring systems can also include fused aryl rings and fused heteroaryl rings as defined herein within the polycyclic ring systems. As used herein, "cycloalkyl," "carbocyclic," or "carbocycle" is also meant to refer to polycyclic (including fused and bridged bicyclic, fused and bridged polycyclic and spirocyclic) hydrocarbon ring system such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH=N($CH_3$)—$CH_3$. Up to two heteroatoms can be consecutive, such as, for example, —$CH_2$—NH—$OCH_3$ and —$CH_2$—O—Si($CH_3$)$_3$.

The term "heterocycloalkyl," "heterocyclic," or "heterocycle" refers to a saturated or partially unsaturated ring system radical having from the indicated number of overall number of stated ring atoms and containing from one to five heteroatoms selected from N, O, and S, wherein the nitrogen and sulfur atoms are optionally oxidized, nitrogen atom(s) are optionally quaternized, as ring atoms (e.g., a 3 to 12 membered heterocycloalkyl that would have 3 to 12 ring atoms and include at least one heteroatom, which also could be referred to as a $C_{2-11}$ heterocycloalkyl). Unless otherwise stated, a "heterocycloalkyl," "heterocyclic," or "heterocycle" ring system can be a monocyclic or a fused, bridged, or spirocyclic polycyclic (including a fused bicyclic, bridged bicyclic or spirocyclic) ring system. The monocyclic or polycyclic ring may be optionally substituted with one or more oxo groups. The terms "heterocycloalkyl," "heterocyclic," and "heterocycle" also include polycyclic ring systems wherein the ring radical attached to the remainder of the molecule is a saturated or partially unsaturated ring that contains from one to five heteroatoms selected from N, O, and S, as defined above and wherein such polycyclic ring systems can also include fused aryl rings and fused heteroaryl rings as defined herein within the polycyclic ring systems. A "heterocycloalkyl," "heterocyclic," or "heterocycle" group can be attached to the remainder of the molecule through one or more ring carbons or heteroatoms. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2, 4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane, azetidine, pyrrolidin-2-one, 2-oxa-6-azaspiro[3.3]heptane, (1R,4R)-2-oxa-5-azabicyclo[2.2.1]heptane, oxazolidin-2-one, (1S,4S)-2-oxa-5-azabicyclo[2.2.1]heptane and the like. A "heterocycloalkyl," "heterocyclic," or "heterocycle" can include mono- and poly-halogenated variants thereof.

The term "alkylene" by itself or as part of another substituent means a divalent radical derived from an alkane, as exemplified by —$CH_2CH_2CH_2CH_2$—, and can be branched. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively, and further include mono- and poly-halogenated variants thereof. Additionally, for dialkylamino groups, the alkyl portions can be the same or different.

The terms "alkoxy," "alkylamino" and "alkylthio", are used in their conventional sense, and refer to those alkyl groups attached to the remainder of the molecule via an oxygen atom ("oxy"), an amino group ("amino") or thio group, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like. The term "(halo)alkyl" as used herein includes optionally halogenated alkyl. Thus the term "(halo)alkyl" includes both alkyl and haloalkyl (e.g., monohaloalkyl and polyhaloalkyl).

The term "aryl" means, unless otherwise stated, a polyunsaturated, typically aromatic, hydrocarbon ring, which can be a single ring or multiple rings (up to three rings) which are fused together. In one embodiment the aryl ring can have 6 to 12 carbon atoms (i.e., $C_{6-12}$ aryl). The term "heteroaryl" refers to a poly unsaturated, typically aromatic ring(s) that contain in addition to carbon atoms from one to five heteroatoms selected from N, O, and S, wherein the nitrogen and sulfur atoms are optionally oxidized, and the nitrogen atom(s) are optionally quaternized. In one embodiment that heteroaryl can have 5 to 12 ring atoms (i.e., 5 to 12 membered heteroaryl) including carbon atoms and one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon atom or a heteroatom. Non-limiting examples of aryl groups include phenyl and naphthyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "  " that intersects a bond in a chemical structure fragment indicates the point of attachment of the bond to which the wavy bond intersects in the chemical structure fragment to the remainder of a molecule or structural formula.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-1}$ means the group $X^d$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996) 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy) ethyl, $(C_{1-6})$alkoxycarbonyloxymethyl, N—$(C_{1-6})$alkoxycarbonylaminomethyl, succinoyl, $(C_{1-6})$alkanoyl, alpha-amino $(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some embodiments, a therapeutically effective amount is an amount of a chemical entity described herein sufficient to significantly decrease or delay neuronal cell death.

The term "administering" as used herein refers to contacting a neuron or portion thereof with a compound described herein. This includes administration of the compound to a subject in which the neuron or portion thereof is present, as well as introducing the inhibitor into a medium in which a neuron or portion thereof is cultured.

The term "patient" as used herein refers to any mammal, including humans, higher non-human primates, rodents, domestic and farm animals such as cow, horses, dogs and cats. In one embodiment, the patient is a human patient.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The phrases "preventing axon degeneration," "preventing neuron degeneration," "preventing CNS neuron degeneration," "inhibiting axon degeneration," "inhibiting neuron degeneration" "inhibiting CNS neuron degeneration" as used herein include (i) the ability to inhibit or prevent axon or neuron degeneration in patients diagnosed as having a neurodegenerative disease or risk of developing a neurodegenerative disease and (ii) the ability to inhibit or prevent further axon or neuron degeneration in patients who are already suffering from, or have symptoms of a neurodegenerative disease. Preventing axon or neuron degeneration includes decreasing or inhibiting axon or neuron degeneration, which may be characterized by complete or partial inhibition or neuron or axon degeneration. This can be assessed, for example, by analysis of neurological function. The above-listed terms also include in vitro and ex vivo methods. Further, the phrases "preventing neuron degeneration" and "inhibiting neuron degeneration" include such inhibition with respect to the entire neuron or a portion thereof, such as the neuron cell body, axons and dendrites. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease in one or more symptoms of a disorder of the nervous system, a condition of the nervous system that is secondary to a disease, condition, or therapy having a primary effect outside of the nervous system; an injury to the nervous system caused by physical, mechanical or chemical trauma, pain; and ocular related neurodegeneration; memory loss; or a psychiatric disorder (e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity) in a subject or population compared to a control subject or population that does not receive the one or more agent described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein. The administration of one or more agents as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder in a subject or a subject population compared to a control subject or population not treated with the one or more compounds described herein.

The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column) Certain specific examples of neuron types that may be subject to treatment according to the invention include cerebellar granule neurons, dorsal root ganglion neurons, and cortical neurons.

B. Synthesis of Compounds

Compounds (including intermediates) of the invention can be synthesized according to any of the General Methods A-($X^{3/4}$) as described in the Examples section and as described below and in the Schemes 1 and 2.

General Preparation of Compounds of Formula 0

The starting materials and reagents used in preparing these compounds generally are either available from commercial suppliers, such as Aldrich Chemical Co., or are prepared by methods known to those skilled in the art following literature procedures, for example, such as procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds and intermediates of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds, including intermediates of the invention may be made by any number of conventional means. Solely for illustrative purpose, for example, intermediates of the invention can be prepared according to the processes outlined in Scheme 1 below. Solely for illustrative purpose, for example, compounds of formula 0 as described herein can be prepared according the processes outlined in Scheme 2 below.

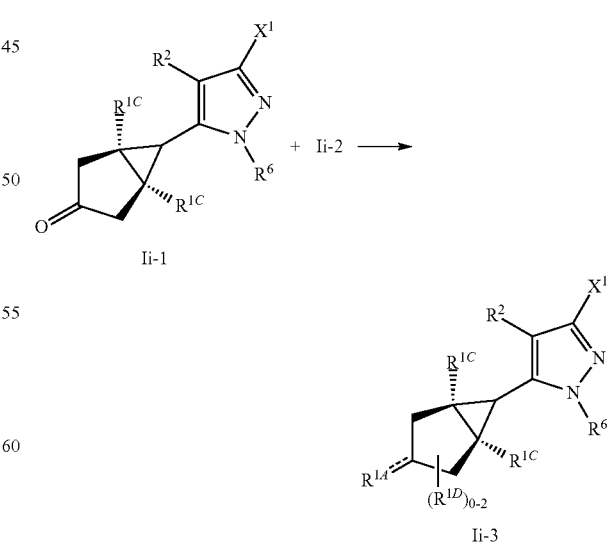

Intermediates of formula Ii-3 can be prepared by allowing a keto intermediate of formula Ii-1 to react with the compound of formula Ii-2 (as defined below) wherein: $R^{1C}$, $R^2$, $R^6$ and $X^1$ are each non-interfering groups (including those groups as defined for formula 0) to the reaction that is outlined in Scheme 1 I; Ii-2 is a nucleophilic reagent such as for example, but not limited to, amine, hydride, Wittig reagent, among others.

These transformations are well-documented in the chemical literature and familiar to those skilled in the art and proceeds under various reactions conditions. For example, the keto intermediate Ii-1 and the amine intermediate of formula Ii-2 can be combined in a solvent such as aprotic solvent including an alcohol solvent (e.g., methanol or ethanol) and treated with a reducing agent such as sodium cyanoborohydride. In one embodiment, in formula Ii-1 and Ii-3 $X^1$ is a halogen (e.g., —I, —Br, —Cl) and in some embodiments, $X^1$ is —I.

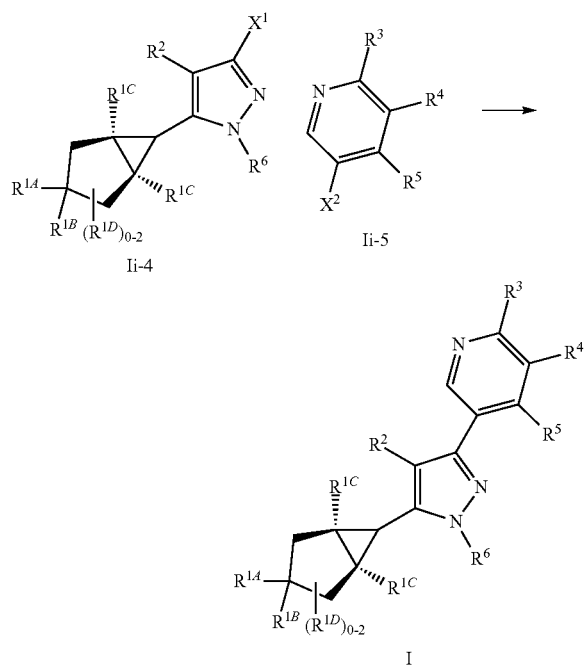

Scheme 2

Compounds of formula 0 can be prepared by coupling an intermediate of formula Ii-4 (including intermediates of formula Ii-3) with an intermediate of formula Ii-5 wherein $X^1$ is a group such as a halogen (e.g., I, Br, Cl), boronate (e.g., —B(OR)$_2$ reagent, wherein R, $R^2$, $R^6$, $R^{1A}$, $R^{1B}$, $R^{1C}$, $R^{1D}$, $R^3$, $R^4$ and $R^5$ where they appear in formula Ii-4, Ii-5 and formula 0, are each non-interfering groups (including those groups as defined for formula 0) to the reaction outlined in Scheme 2.

This transformation is well-documented in the chemical literature and familiar to those skilled in the art and proceeds under various reactions conditions. For example, intermediate Ii-4 (or Ii-3) and intermediate Ii-5 can be combined in a solvent such as organic solvent (e.g., dioxane) in the presence of a base such as an amine base or an inorganic base (e.g., cesium carbonate) and treated with a coupling agent such as catalyst including a palladium catalyst (e.g., 1,1'-bis(diphenylphosphino)ferrocene-palladium(II) dichloride). In one embodiment, in formula Ii-4, $X^1$ is a halogen (e.g., —I, —Br, —Cl). In one embodiment $X^1$ is —I. In one embodiment in formula Ii-5, $X^2$ is a boronate (e.g., —B(OR)$_2$ and sometimes $X^2$ is 4,4,5,5-tetramethyl-1,3,2-dioxaborolan-2-yl.

C. Pharmaceutical Compositions and Administrations

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of formula 0 or any subformula thereof and at least one pharmaceutically acceptable carrier, diluent or excipient. The compositions of the invention can be used for inhibiting DLK activity in patients (e.g., humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of formula 0 (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula 0 and compositions comprising compounds of formula 0 or any embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit DLK activity as required to prevent or treat the undesired disease or disorder, such as for example, neurodegeneration, amyloidosis, formation of neurofibrillary tangles, or undesired cell growth. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily dose is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further inactive agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula 0 any embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula 0 or any embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philidelphia, Pa.

Sustained-release preparations of a compound of the invention (e.g., compound of formula 0 or any embodiment thereof) can be prepared. Suitable examples of sustained-release preparations include semipermeable matrices of solid hydrophobic polymers containing a compound of formula 0 or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of formula 0 or any embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula 0 or an embodiment thereof is formulated in an acetate buffer, at pH 5. In another embodiment, the compounds of formula 0 or an embodiment thereof are sterile. The compound may be stored, for example, as a solid or amorphous composition, as a lyophilized formulation or as an aqueous solution.

Formulations of a compound of the invention (e.g., compound of formula 0 or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula 0 or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of formula 0 or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of formula 0) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula 0 (or an embodiment thereof) to traverse the blood-brain barrier. Certain neurodegenerative diseases are associated with an increase in permeability of the blood-brain barrier, such that a compound of formula 0 (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula 0 (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford).

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula 0 (or an embodiment thereof) across the blood-brain barrier include, but are not limited to, encapsulating the a compound of formula 0 (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula 0 (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula 0 (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula 0 (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula 0 (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula 0 (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula 0 (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 µg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula 0 (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg/kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

D. Indications and Methods of Treatment

In another aspect, the invention provides for methods of inhibiting the Dual Leucine Zipper Kinase (DLK) in an in vitro (e.g., a nerve graft of nerve transplant) or in vivo setting (e.g., in a patient) by contacting DLK present in an in vitro or in vivo setting with compounds of formula 0 or an embodiment thereof. In these methods of the invention, the inhibition of DLK signaling or expression with a compound of formula 0 or an embodiment thereof results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, administering one or more compounds of formula 0 or an embodiment thereof according to the methods of the invention can result in decrease in activity of kinase targets downstream of the DLK signaling cascade, e.g., (i) a decrease in JNK phosphorylation, JNK activity, and/or JNK expression, (ii) a decrease in cJun phosphorylation, cJun activity, and/or cJun expression, and/or (iii) a decrease in p38 phosphorylation, p38 activity, and/or p38 expression.

Compounds of the invention can be used in methods for inhibiting neuron or axon degeneration. The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS dememtial complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy.

Examples of types of pain that can be treated according to the methods of the invention include those associated with the following conditions: chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neuogenic or neuropathic pain, nerve inflammation or damage, shingles, herniated disc, torn ligament, and diabetes.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine. Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the inhibitors described herein can be useful as components of culture media for use in culturing nerve cells in vitro.

Accordingly, in another aspect, the invention provides for a method for inhibiting or preventing degeneration of a central nervous system (CNS) neuron or a portion thereof, the method comprising administering to the CNS neuron a compound of formula 0 or an embodiment thereof.

In one embodiment, of the method for inhibiting or preventing degeneration of a central nervous system neuron or a portion thereof, the administering to the CNS neuron is performed in vitro.

In another embodiment, of the method for inhibiting or preventing degeneration of a central nervous system neuron or a portion thereof, the method further comprises grafting or implanting the CNS neuron into a human patient after administration of the agent.

In another embodiment, of the method for inhibiting or preventing degeneration of a central nervous system neuron or a portion thereof, the CNS neuron is present in a human patient.

In another embodiment, of the method for inhibiting or preventing degeneration of a central nervous system neuron or a portion thereof, the administering to the CNS neuron comprises administration of said compound of formula 0 or an embodiment thereof in a pharmaceutically acceptable carrier, diluent or excipient.

In another embodiment, of the method for inhibiting or preventing degeneration of a central nervous system neuron or a portion thereof, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

In another embodiment, of the method for inhibiting or preventing degeneration of a central nervous system neuron or a portion thereof, the method further comprises administering one or more additional pharmaceutical agents.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits comprising combinations as described herein.

In addition to the combinations noted above, other combinations included in the invention are combinations of inhibitors of degeneration of different neuronal regions. Thus, the invention includes combinations of agents that (i) inhibit degeneration of the neuron cell body, and (ii) inhibit axon degeneration. For example, inhibitors of GSK and transcription are found to prevent degeneration of neuron cell bodies, while inhibitors of EGFR and p38 MAPK are found to prevent degeneration of axons. Thus, the invention includes combinations of inhibitors of GSK and EGFR (and/or p38 MAPK), combinations of transcription inhibitors and EGF (and/or p38 MAPK), and further combinations of inhibitors of dual leucine zipper-bearing kinase (DLK), glycogen synthase kinase 3β (GSK3), p38 MAPK, EGFF, phosphoinositide 3-kinase (PI3K), cyclin-dependent kinase 5 (cdk5), adenylyl cyclase, c-Jun N-terminal kinase (JNK), BCL2-associated ($X^{3/4}$)protein (Bax), In channel, calcium/calmodulin-dependent protein kinase kinase (CaMKK), a G-protein, a G-protein coupled receptor, transcription factor 4 (TCF4), and β-catenin. The inhibitors used in these combinations can be any of those described herein, or other inhibitors of these targets as described in WO 2011/050192, incorporated herein by reference.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

EXAMPLES

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. ¹H NMR spectra were recorded on a Varian instrument operating at 400 MHz. ¹H NMR spectra were obtained in deuterated CDCl₃, d₆-DMSO, CH₃OD or d₆-acetone solutions (reported in ppm), using tetramethylsilane (TMS) as the reference standard (0 ppm). When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography-Mass Spectrometry (LCMS) experiments to performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150E($X^{3/4}$) using a Phenomenex DNYC monolithic C18 column with a linear gradient of 5%-95% acetonitrile/water (with 0.1% trifluoroacetic acid in each mobile phase) within 5 minutes and held at 95% for 1 minute to determine retention times ($R_T$) and associated mass ions.

All abbreviations used to described reagents, reaction conditions, or equipment used are consistent with the definitions set forth in the "List of standard abbreviations and acronyms" published yearly by the Journal of Organic Chemistry (an American Chemical Society journal). The chemical names of discrete compounds of the invention were obtained using the structure naming feature ChemBioDraw Version 11.0 or from Accelrys' Pipeline Pilot IUPAC compound naming program.

Example 1

Preparation of Intermediates

Synthesis of 3-(difluoromethoxy)-5-(4,4,5,5-tetramethyl-1,3,2-dioxaborolan-2-yl)pyridin-2-amine Step 1: Synthesis of 3-(difluoromethoxy)-2-nitropyridine

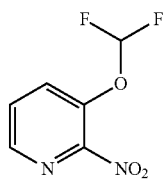

To a stirred solution of 2-nitropyridin-3-ol (5 g, 35.69 mmol) and sodium 2,2-dichloro-2-fluoroacetate (8.16 g, 53.53 mmol) in N,N-dimethylmethanamide (20 mL) and water (15 mL) was added potassium carbonate (9.86 g, 71.38 mmol) slowly. The reaction mixture was heated to 105° C. for 20 h. After cooling down the reaction mixture was diluted with water (150 mL), and the mixture was extracted with ethyl acetate (3×50 mL). The combined organic layers were dried over sodium sulfate and concentrated to dryness in vacuo affording 3-(difluoromethoxy)-2-nitropyridine (5 g, 74%). The residue was used in next step directly without further purification. ¹H NMR (400 MHz, DMSO-d6) δ 8.48 (dd, J₁=4.4 Hz, J₂=1.2 Hz, 1H), 8.18 (dd, J₁=4.4 Hz, J₂=0.8 Hz, 1H), 7.95-7.91 (m, 1H), 7.45 (t, J=72.0 Hz, 1H).

Step 2: Synthesis of 3-(difluoromethoxy)pyridin-2-amine

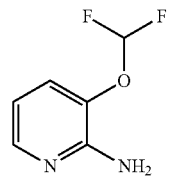

To a stirred solution of 3-(difluoromethoxy)-2-nitropyridine (5 g, 2.63 mmol) and ammonium chloride (4.22 g, 78.9 mmol) in ethanol (40 mL) and water (30 mL) was added iron powder (7.34 g, 131.51 mmol). The reaction mixture was heated to 90° C. for 1 h. After cooling down the reaction mixture was filtered and the solid was washed with ethyl acetate. The mother liquid was concentrated to dryness in vacuo. The residue was diluted with water and extracted with ethyl acetate (3×70 mL). The combined organic layers were dried over sodium sulfate and concentrated to dryness in vacuo affording 3-(difluoromethoxy)pyridin-2-amine (2.3 g, 55%). The residue was used in next step directly without further purification. ¹H NMR (400 MHz, DMSO-d6) δ 7.90 (dd, J₁=4.8 Hz, J₂=1.6 Hz, 1H), 7.28 (dd, J₁=8.0 Hz, J₂=0.8 Hz, 1H), 7.07 (t, J=74.0 Hz, 1H), 6.53 (dd, J₁=8.0 Hz, J₂=0.8 Hz, 1H), 6.01 (s, 2H).

Step 3: Synthesis of 5-bromo-3-(difluoromethoxy)pyridin-2-amine

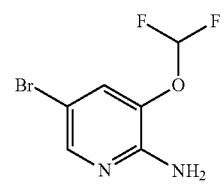

To a solution of 3-(difluoromethoxy)pyridin-2-amine (2.3 g, 14.36 mmol) in acetonitrile (15 mL) was added N-bromosuccinimide (2.61 g, 14.65 mmol) over 3 min at 0° C. The reaction mixture was stirred at the same temperature for another 20 min and subsequently concentrated to dryness in vacuo. The resulting viscous mass was diluted with water and extracted with ethyl acetate (3×60 mL). The combined organic layers were dried over sodium sulfate and concentrated to dryness in vacuo. The resulting residue was purified by column chromatography (silica gel, 100-200 mesh, 20% ethyl acetate in hexane) affording 5-bromo-3-(difluoromethoxy)pyridin-2-amine (3.2 g, 93%): ¹H NMR (400 MHz, DMSO-d6) δ 7.89 (s, 1H), 7.51 (s, 1H), 7.16 (t, J=73.6 Hz, 1H), 6.34 (s, 2H).

Step 4: Synthesis of 3-(difluoromethoxy)-5-(4,4,5,5-tetramethyl-1,3,2-dioxaborolan-2-yl)pyridin-2-amine

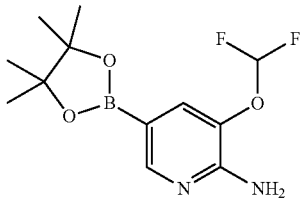 [SMILES: CC1(C)OB(c2cnc(N)c(OC(F)F)c2)OC1(C)C]

To a solution of 5-bromo-3-(difluoromethoxy)pyridin-2-amine (3.2 g, 13.39 mmol) in 1,4-dioxane (60 mL) were added 4,4,4',4',5,5,5',5'-octamethyl-2,2'-bi(1,3,2-dioxaborolane) (3.74 g, 14.73 mmol), tricyclohexylphosphine (525 mg, 1.87 mmol), potassium acetate (3.28 g, 33.47 mmol) and tris(dibenzylideneacetone)dipalladium(0) (490 mg, 0.53 mmol). The reaction mixture was purged with nitrogen for 2 min and heated to 110° C. for 16 h and subsequently concentrated to dryness in vacuo. The resulting viscous mass was diluted with water and extracted with ethyl acetate (3×75 mL). The combined organic layers were dried over sodium sulfate and concentrated to dryness in vacuo. The resulting residue was purified by column chromatography (silica gel, 100-200 mesh, 25% ethyl acetate in hexane) affording 3-(difluoromethoxy)-5-(4,4,5,5-tetramethyl-1,3,2-dioxaborolan-2-yl)pyridin-2-amine (1.3 g, 34%): ¹H NMR (400 MHz, DMSO-d6) δ 8.03 (s, 1H), 7.33 (s, 1H), 7.11 (t, J=73.6 Hz, 1H), 6.44 (s, 2H), 1.25 (s, 12H).

Synthesis of 5-(4,4,5,5-tetramethyl-1,3,2-dioxaborolan-2-yl)-3-(trifluoromethoxy)pyridin-2-amine Step 1: Synthesis of 3-(bromodifluoromethoxy)-2-nitropyridine

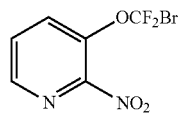

To a stirred solution of sodium hydride (856 mg, 21.41 mmol) in N-methylpyrrolidinone (20 mL) was added a solution of 2-nitropyridin-3-ol (2 g, 14.28 mmol) in N-methylpyrrolidinone (10 mL). The reaction mixture was stirred at 20° C. for 30 min followed by heating at 50° C. for another 30 min before cooling to 20° C. CF₂Br₂ (4.49 g, 21.41 mmol) was added dropwise and the resulting mixture was stirred at 20° C. for 18 h. Then CF₂Br₂ (8.99 g, 42.83 mmol) was added dropwise and the mixture was stirred at 20° C. for another 18 h. The reaction mixture was slowly quenched into saturated aqueous ammonium chloride solution (30 mL) and extracted with ethyl acetate (2×50 mL). The combined organic layers were washed with water (2×50 mL), brine (2×50 mL), dried over anhydrous sodium sulfate and concentrated in vacuo. The resulting residue was purified by column chromatography (silica gel, 100-200 mesh, 15% ethyl acetate in petroleum ether) affording product (890 mg, 23%): ¹H NMR (400 MHz, chloroform-d) δ 8.53-8.51 (m, 1H), 7.99-7.97 (m, 1H), 7.72-7.69 (m, 1H).

Step 2: Synthesis of 2-nitro-3-(trifluoromethoxy)pyridine

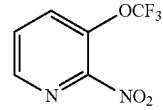

A solution of 3-(bromodifluoromethoxy)-2-nitropyridine (500 mg, 1.86 mmol) in dichloromethane (10 mL) was cooled to −78° C., then silver tetrafluoroborate (796 mg, 4.09 mmol) was added. The resulting mixture was slowly warmed to 20° C. and allowed to stir for 18 h. Saturated sodium bicarbonate solution (10 mL) was added, and the mixture was filtered. The filtrate was extracted with dichloromethane (3×10 mL). The combined organic layers were dried over anhydrous sodium sulfate and concentrated to dryness in vacuo. The residue was used in the next step directly without further purification (300 mg, 78%): LCMS (ESI) m/z 209.0 [M+H]⁺.

Step 3: Synthesis of 3-(trifluoromethoxy)pyridin-2-amine

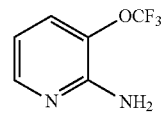

To a stirred solution of 2-nitro-3-(trifluoromethoxy)pyridine (370 mg, 1.78 mmol) in ethanol (5 mL) were added aqueous ammonium chloride (951 mg, 17.78 mmol, in 10 mL of water) and iron powder (993 mg, 17.78 mmol). The reaction mixture was heated to 70° C. for 2 h. After cooling down the reaction mixture was filtered and the solid was washed with ethyl acetate. The mother liquid was concentrated to dryness in vacuo. The residue was diluted with water and extracted with ethyl acetate (3×15 mL). The combined organic layers were dried over anhydrous sodium sulfate and concentrated to dryness in vacuo. The residue was used in next step directly without further purification (250 mg, 79%): ¹H NMR (400 MHz, DMSO-d₆) δ 7.93-7.91 (m, 1H), 7.48-7.46 (m, 1H), 6.59-6.56 (m, 1H), 6.35 (brs, 2H).

Step 4: Synthesis of 5-bromo-3-(trifluoromethoxy)pyridin-2-amine

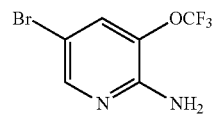

To a solution of 3-(trifluoromethoxy)pyridin-2-amine (300 mg, 1.68 mmol) in dichloromethane (8 mL) was added N-bromosuccinimide (450 mg, 2.53 mmol) at 20° C. The reaction mixture was stirred at the same temperature for another 5 min and subsequently concentrated to dryness in vacuo. The resulting residue was purified by column chromatography (silica gel, 100-200 mesh, 15% ethyl acetate in petroleum ether) affording product (220 mg, 51%): $^1$H NMR (400 MHz, DMSO-d$_6$) δ 8.03 (d, J=2.0 Hz, 1H), 7.75-7.74 (m, 1H), 6.68 (brs, 2H).

Step 5: Synthesis of 5-(4,4,5,5-tetramethyl-1,3,2-dioxaborolan-2-yl)-3-(trifluoromethoxy)pyridin-2-amine

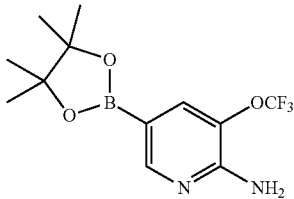 [SMILES: CC1(C)OB(c2cnc(N)c(OC(F)(F)F)c2)OC1(C)C]

To a solution of 5-bromo-3-(trifluoromethoxy)pyridin-2-amine (220 mg, 0.856 mmol) in dioxane (5 mL) were added 4,4,4',4',5,5,5',5'-octamethyl-2,2'-bi(1,3,2-dioxaborolane) (261 mg, 1.03 mmol), 1,1'-bis(diphenylphosphino)ferrocene-palladium(II)dichloride (63 mg, 0.0856 mmol) and potassium acetate (252 mg, 2.57 mmol). The reaction mixture was purged with nitrogen for 2 min and heated to 80° C. for 2 h and subsequently concentrated to dryness in vacuo. The resulting residue was purified by column chromatography (silica gel, 100-200 mesh, 15% ethyl acetate in petroleum ether) affording product (220 mg, 84%): $^1$H NMR (400 MHz, DMSO-d$_6$) δ 8.14 (d, J=2.0 Hz, 1H), 7.46-7.45 (m, 1H), 6.86 (br s, 2H), 1.27 (s, 12H).

Synthesis of 1-(1-(pyridin-2-yl)ethyl)-6-(4,4,5,5-tetramethyl-1,3,2-dioxaborolan-2-yl)-1H-pyrazolo[4,3-b]pyridine Step 1: Synthesis of 5-bromo-2-methylpyridin-3-amine

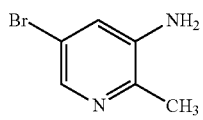

To a solution of 5-bromo-2-methyl-3-nitropyridine (8.0 g, 37 mmol) in 4:1 ethanol/water (250 mL) was added iron (16.5 g, 295 mmol) and ammonium chloride (15.8 g, 295 mmol). The mixture was stirred at 80° C. for 3 h. The mixture was filtered, and the filtrate was concentrated in vacuo to give 5-bromo-2-methylpyridin-3-amine (6.8 g, 99% crude yield), which was without further purification.

Step 2: Synthesis of N-(5-bromo-2-methylpyridin-3-yl)acetamide

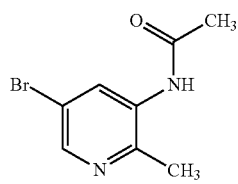

To a solution of 5-bromo-2-methylpyridin-3-amine (3.2 g, 17 mmol) in dichloromethane (100 mL) was added pyridine (2.03 g, 25.7 mmol) and acetic anhydride (2.63 g, 25.7 mmol). The mixture was stirred at 80° C. for 16 h. The mixture was poured into water (80 mL) and extracted with dichloromethane (3×150 mL). The organic layer was concentrated in vacuo, and the resultant residue was purified by flash column chromatography (15→30% ethyl acetate in petroleum ether) to afford N-(5-bromo-2-methylpyridin-3-yl)acetamide (3.1 g, 80% yield). $^1$H NMR (400 MHz, Chloroform-d) δ 8.48 (s, 1 H), 8.32 (s, 1 H), 7.09 (br s. 1 H), 2.45 (s, 3 H), 2.23 (s, 3 H).

Step 3: Synthesis of 1-(6-bromo-1H-pyrazolo[4,3-b]pyridin-1-yl)ethanone

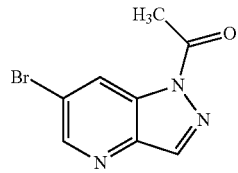

A solution of N-(5-bromo-2-methylpyridin-3-yl)acetamide (2.8 g, 12 mmol) and potassium acetate (3.59 g, 36.6 mmol) in toluene (50 mL) was heated at 80° C. under nitrogen. After 30 min, 2-methyl-2-nitropropane (3.77 g, 36.6 mmol) and acetic anhydride (3.73 g, 36.6 mmol) were added, and the resulting mixture was stirred at 80° C. for another 18 h. The reaction mixture was concentrated in vacuo, and the residue was diluted with water (50 mL). The aqueous mixture was extracted with ethyl acetate (3×60 mL). The collected organic extractions were concentrated in vacuo. Purification by flash column chromatography (5→10% ethyl acetate in petroleum ether) afforded 1-(6-bromo-1H-pyrazolo[4,3-b]pyridin-1-yl)ethanone (1.4 g, 48.% yield). $^1$H NMR (400 MHz, Chloroform-d) δ 8.90 (s, 1 H), 8.75 (s, 1 H), 8.32 (s, 1 H), 2.79 (s, 3 H).

Step 4: Synthesis of 6-bromo-1H-pyrazolo[4,3-b]pyridine

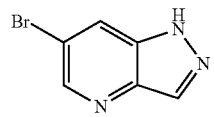

To a solution of 1-(6-bromo-1H-pyrazolo[4,3-b]pyridin-1-yl)ethanone (1.4 g, 5.9 mmol) in tetrahydrofuran (20 mL) and methanol (15 mL) was added a solution of sodium hydroxide (0.71 g, 18 mmol) in water (5 mL) at 27° C. After 5 h, the reaction was neutralized with hydrogen chloride acid (2 mol/L, 10 mL), and the resulting mixture was extracted with ethyl acetate (3×50 mL). The collected organic extracts were concentrated in vacuo. Purification by flash column chromatography (15→30% ethyl acetate in petroleum ether) afforded 6-bromo-1H-pyrazolo[4,3-b]pyridine (1.0 g, 86% yield). ¹H NMR (400 MHz, Chloroform-d) δ 10.46 (brs, 1 H), 8.58 (s, 1 H), 8.25 (s, 1 H), 7.98 (s, 1 H).

Step 5: Synthesis of 6-bromo-1-(1-(pyridin-2-yl)ethyl)-1H-pyrazolo[4,3-b]pyridine

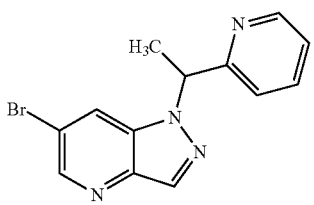 [SMILES: CC(c1ccccn1)n1ncc2ncc(Br)cc21]

To an ice-cooled solution of 6-bromo-1H-pyrazolo[4,3-b]pyridine (0.60 g, 3.0 mmol) in N,N-dimethylformamide (30 mL) was added sodium hydride (60%, 488 mg, 12.2 mmol). After 30 min, 2-(1-chloroethyl)pyridine (1.73 g, 12.2 mmol) was added to reaction mixture, and the resulting suspension was warmed to 27° C. After 17 h, the reaction mixture was poured into water (50 mL), and the resulting solution was extracted with ethyl acetate (3×30 mL). The organic extracts were concentrated in vacuo. Purification by flash column chromatography (6→15% ethyl acetate in petroleum ether) afforded 6-bromo-1-(1-(pyridin-2-yl)ethyl)-1H-pyrazolo[4,3-b]pyridine (450 mg, 49% yield). LRMS (ESI): [MH]+= 304.6.

Step 6: Synthesis of 1-(1-(pyridin-2-yl)ethyl)-6-(4,4,5,5-tetramethyl-1,3,2-dioxaborolan-2-yl)-1H-pyrazolo[4,3-b]pyridine

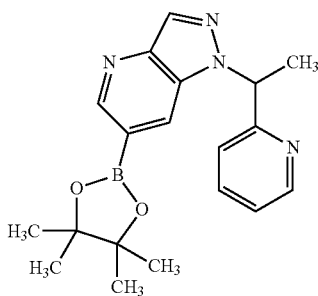 [SMILES: CC(c1ccccn1)n1ncc2ncc(B3OC(C)(C)C(C)(C)O3)cc21]

A solution of 6-bromo-1-(1-(pyridin-2-yl)ethyl)-1H-pyrazolo[4,3-b]pyridine (240 mg, 0.80 mmol), 4,4,4',4',5,5,5',5'-octamethyl-2,2'-bi(1,3,2-dioxaborolane) (222 mg, 0.875 mmol), tricyclohexylphosphine (11 mg, 0.040 mmol), potassium acetate (156 mg, 1.59 mmol) and tris(dibenzylideneacetone)dipalladium(0) (37 mg, 0.040 mmol) in anhydrous dioxane (5 mL) was heated at 110° C. for 2 h. The mixture was diluted with ethyl acetate (10 mL) and filtered. The filtrate was concentrated in vacuo to afford crude 1-(1-(pyridin-2-yl)ethyl)-6-(4,4,5,5-tetramethyl-1,3,2-dioxaborolan-2-yl)-1H-pyrazolo[4,3-b]pyridine (300 mg), which was used without further purification. LRMS (ESI): [MH]+=351.1.

Synthesis of 1-(1-(pyridin-2-yl)ethyl)-6-(4,4,5,5-tetramethyl-1,3,2-dioxaborolan-2-yl)-1H-pyrrolo[3,2-b]pyridine Step 1: Synthesis of 1-(pyridin-2-yl)ethanol

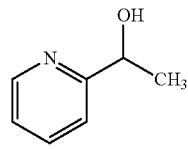

To an ice-cooled solution of 1-(pyridin-2-yl)ethanone (11 g, 91 mmol) in methanol (120 mL) was slowly added sodium borohydride (8.58 g, 227 mmol). Upon complete addition, the mixture was warmed to 25° C. After 16 h, the reaction was diluted with water (100 mL), and the mixture was concentrated in vacuo. The resulting aqueous solution was extracted with ethyl acetate (3×100 mL). The combined organic extracted were washed with saturated aqueous sodium chloride (2×50 mL), dried over anhydrous sodium sulfate, filtered, and concentrated. Purification by flash column chromatography (10→30% ethyl acetate in petroleum ether) afforded 1-(pyridin-2-yl)ethanol (10.3 g, 92% yield). ¹H NMR (400 MHz, Chloroform-d) δ 8.54 (d, J=4.8 Hz, 1 H), 7.72-7.68 (m, 1 H), 7.30 (d, J=8.0 Hz, 1 H), 7.22-7.20 (m, 1 H), 4.93-4.88 (m, 1 H), 4.39 (br s, 1 H), 1.52 (d, J=6.4 Hz, 3 H).

Step 2: Synthesis of 2-(1-chloroethyl)pyridine

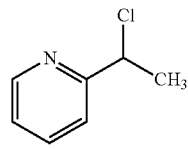

To an ice-cooled solution of 1-(pyridin-2-yl)ethanol (4.5 g, 36 mmol) in dry dichloromethane (100 mL) was slowly added thionyl dichloride (20 mL). The mixture was then warmed to 20° C. After 2 h, the reaction was concentrated in vacuo, and the resulting residue was diluted with water (40 mL) and dichloromethane (60 mL). The solution was neutralized with saturated aqueous sodium carbonate solution. The organic layer was washed with saturated aqueous sodium chloride solution (3×30 mL), dried over anhydrous sodium sulfate, filtered, and concentrated to afford crude 2-(1-chloroethyl)pyridine (5.0 g, 97% yield). The product was used without further purification.

Step 3: Synthesis of 6-bromo-1-(1-(pyridin-2-yl)ethyl)-1H-pyrrolo[3,2-b]pyridine

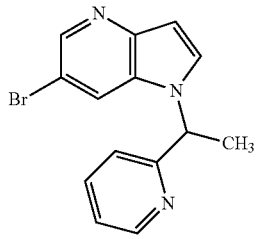 [SMILES: CC(c1ccccn1)n1ccc2ncc(Br)cc21]

To an ice-cooled suspension of 6-bromo-1H-pyrrolo[3,2-b]pyridine (7.0 g, 35 mmol) in N,N-dimethylformamide (100 mL) was slowly added a solution of sodium hydride (2.12 g, 88.28 mmol, 60% in mineral oil) in N,N-dimethylformamide (20 mL). After 30 min at 0° C., a solution of 2-(1-chloroethyl)

pyridine (5.0 g, 35 mmol) in N,N-dimethylformamide (20 mL) was slowly added. The mixture was then warmed to room temperature. After 16 h, saturated aqueous ammonium chloride solution (20 mL) was slowly added to the reaction mixture, and the resulting solution was concentrated in vacuo. The resulting residue was purified by flash column chromatography (10→30% ethyl acetate in petroleum ether) to afford 6-bromo-1-(1-(pyridin-2-yl)ethyl)-1H-pyrrolo[3,2-b]pyridine (6.0 g, 56% yield). $^1$H NMR (400 MHz, Chloroform-d) δ 8.61 (d, J=4.4 Hz, 1 H), 8.47 (d, J=2.0 Hz, 1 H), 7.70 (s, 1 H), 7.62-7.57 (m, 2 H), 7.21-7.18 (m, 1 H), 6.81-6.76 (m, 2 H), 5.66-5.61 (m, 1 H), 2.00 (d, J=7.2 Hz, 3 H).

Step 4: Synthesis of 1-(1-(pyridin-2-yl)ethyl)-6-(4,4,5,5-tetramethyl-1,3,2-dioxaborolan-2-yl)-1H-pyrrolo[3,2-b]pyridine

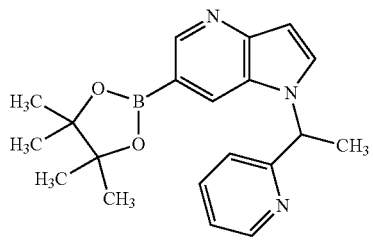 [SMILES: CC(c1ccccn1)n1ccc2ncc(B3OC(C)(C)C(C)(C)O3)cc21]

A solution of 6-bromo-1-(1-(pyridin-2-yl)ethyl)-1H-pyrrolo[3,2-b]pyridine (5.5 g, 18 mmol), 4,4,4',4',5,5,5',5'-octamethyl-2,2'-bi(1,3,2-dioxaborolane) (4.85 g, 19.1 mmol), potassium acetate (3.57 g, 36.4 mmol), tricyclohexylphosphine (255 mg, 0.91 mmol) and tris(dibenzylideneacetone)dipalladium(0) (333 mg, 0.36 mmol) in anhydrous dioxane (50 mL) was heated to reflux for 2 h. After cooling to room temperature, the mixture was filtered, and the filtrate was concentrated in vacuo to yield crude 1-(1-(pyridin-2-yl)ethyl)-6-(4,4,5,5-tetramethyl-1,3,2-dioxaborolan-2-yl)-1H-pyrrolo[3,2-b]pyridine (4.6 g, 72% crude yield) LRMS (ESI): [MH+-82] 267.9, which was used without further purification.

Example 2

General Methods

General Method A

Preparation of 5-(1-isopropyl-5-((1R,3 s,5 S,6r)-3-morpholinobicyclo[3.1.0]hexan-6-yl)-1H-pyrazol-3-yl)-3-(trifluoromethoxy)pyridin-2-amine and 5-(1-isopropyl-5-((1R,3r,5 S,6r)-3-morpholinobicyclo[3.1.0]hexan-6-yl)-1H-pyrazol-3-yl)-3-(trifluoromethoxy)pyridin-2-amine

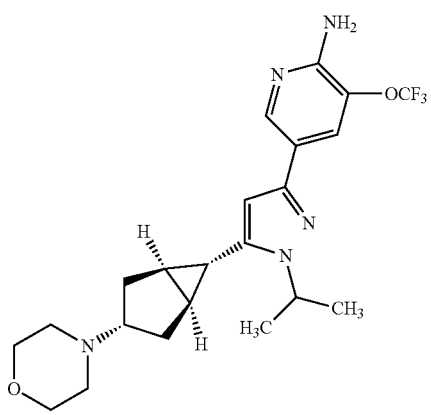

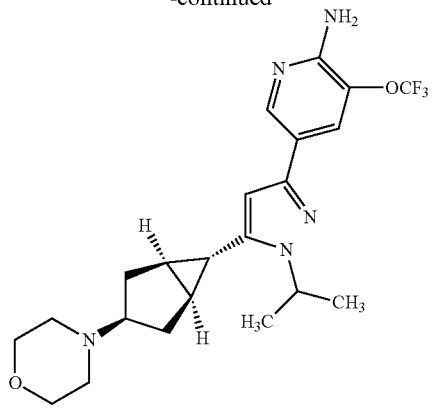

Step 1: Synthesis of tert-butyl(cyclopent-3-en-1-yloxy)diphenylsilane

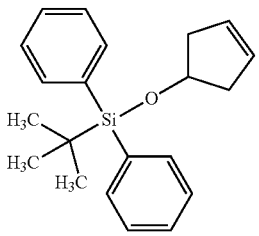 [SMILES: CC(C)(C)[Si](OC1CC=CC1)(c1ccccc1)c1ccccc1]

To an ice-cooled solution of 4-hydroxycyclopentene (50.0 g, 0.594 mol) and imidazole (80.9 g, 1.19 mol) in N,N-dimethylformamide (300 mL) was slowly added tert-butyldiphenylsilyl chloride (180 g, 0.65 mmol). The reaction mixture was warmed to room temperature. After 16 h, the reaction mixture was diluted with water (1 L) and ethyl acetate (500 mL). The aqueous layer was extracted with ethyl acetate (2×200 mL). The combined organics were washed sequentially with water (3×300 mL) and saturated aqueous sodium chloride solution (2×200 mL). The collected organic was dried over anhydrous sodium sulfate, filtered, and concentrated. Purification by flash column chromatography (15:1 petroleum ether/ethyl acetate) provided tert-butyl(cyclopent-3-en-1-yloxy)diphenylsilane (188 g, 98%) as a colorless oil. $^1$H NMR (400 MHz, CDCl$_3$): δ 7.69-7.66 (m, 4H), 7.43-7.38 (m, 6H), 5.63-5.60 (m, 2H), 4.58-4.53 (m, 1H), 2.46-2.38 (m, 4H), 1.61 (s, 9H).

Step 2: Synthesis of ethyl 3-((tert-butyldiphenylsilyl)oxy)bicyclo[3.1.0]hexane-6-carboxylate

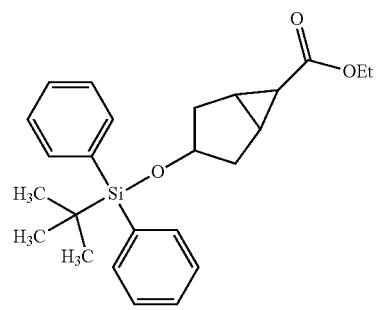

To a stirred solution of tert-butyl(cyclopent-3-en-1-yloxy)diphenylsilane (0.100 kg, 310 mmol) and rhodium acetate dimer (1.37 g, 3.10 mmol) in anhydrous dichloromethane (1.2 L) at room temperature was added a solution of ethyl 2-diazoacetate (63.68 mmol) in dichloromethane (300 mL) over 8 h. After an additional 12 h. The reaction mixture was filtered through Celite. Concentration of the filtrate afforded crude ethyl 3-((tert-butyldiphenylsilyl)oxy)bicyclo[3.1.0] hexane-6-carboxylate (140 g) which was used without further purification.

Step 3: Synthesis of 3-((tert-butyldiphenylsilyl)oxy)-N-methoxy-N-methylbicyclo[3.1.0]hexane-6-carboxamide

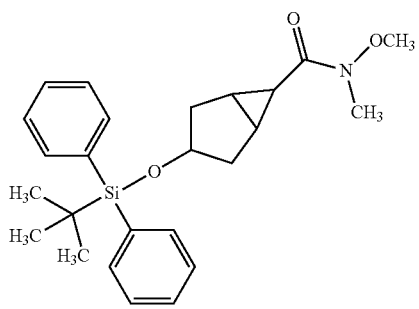 [SMILES: CON(C)C(=O)C1C2CC(O[Si](c3ccccc3)(c3ccccc3)C(C)(C)C)CC21]

To a solution of ethyl 3-((tert-butyldiphenylsilyl)oxy)bicyclo[3.1.0]hexane-6-carboxylate (70.0 g, 171 mmol) in ethanol (400 mL) was slowly added a solution of sodium hydroxide (20.56 g, 513.94 mmol) in water (100 mL). After 20 h, the reaction mixture was concentrated and the resulting residue was diluted with water (200 mL). The aqueous solution was adjusted to pH=3 by dropwise addition of 3 M aqueous hydrochloric acid. The aqueous mixture was extracted with ethyl acetate (2×200 mL). The combined organics were washed with saturated aqueous sodium chloride (200 mL), dried over anhydrous sodium sulfate, filtered, and concentrated to yield 3-((tert-butyldiphenylsilyl)oxy)bicyclo[3.1.0]hexane-6-carboxylic acid as a yellow solid (53 g). To an ice-cooled suspension of crude acid in dichloromethane (600 mL) was added carbonyldiimidazole (25.5 g, 158 mmol). After 2 h, N,O-dimethylhydroxylamine hydrochloride (32 g, 0.33 mmol) was added. After 3 h, the reaction mixture was filtered and the filtrate was concentrated. Purified by flash column chromatography (6:1 petroleum ether/ethyl acetate) afforded 3-((tert-butyldiphenylsilyl)oxy)-N-methoxy-N-methylbicyclo[3.1.0]hexane-6-carboxamide (37 g, 60%) as a colorless oil. $^1$H NMR (400 MHz, CDCl$_3$): δ 7.63-7.61 (m, 4H), 7.42-7.33 (m, 6H), 4.33-4.31 (m, 1H), 3.74 (s, 2H), 3.57 (s, 1H), 3.21 (s, 2H), 3.10 (s, 1H), 2.21-2.18 (m, 1H), 2.00-1.80 (m, 6H), 1.06-1.01 (m, 9H).

Step 4: Synthesis of 1-(3-((tert-butyldiphenylsilyl)oxy)bicyclo[3.1.0]hexan-6-yl)ethanone

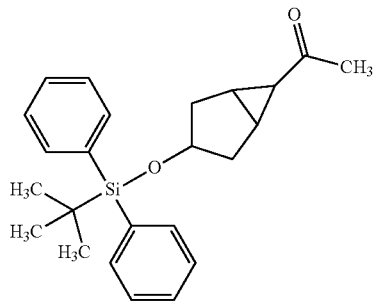 [SMILES: CC(=O)C1C2CC(O[Si](c3ccccc3)(c3ccccc3)C(C)(C)C)CC21]

To an ice-cooled solution of 3-((tert-butyldiphenylsilyl)oxy)-N-methoxy-N-methylbicyclo[3.1.0]hexane-6-carboxamide (37 g, 87 mmol) in anhydrous tetrahydrofuran (500 mL) was added dropwise methylmagnesium bromide (87 mL, 262 mmol, 3.0 M in diethyl ether). After 3 h, saturated aqueous ammonium chloride was added to the reaction mixture. The resulting aqueous solution was extracted with ethyl acetate (3×100 mL). The combined organics were washed with saturated aqueous sodium chloride solution, dried over anhydrous sodium sulfate, filtered, and concentrated to yield crude 1-(3-((tert-butyldiphenylsilyl)oxy)bicyclo[3.1.0]hexan-6-yl)ethanone as a light brown solid (30.0 g, 91%) which was used without further purification.

Step 5: Synthesis of ethyl 4-(3-((tert-butyldiphenylsilyl)oxy)bicyclo[3.1.0]hexan-6-yl)-2,4-dioxobutanoate

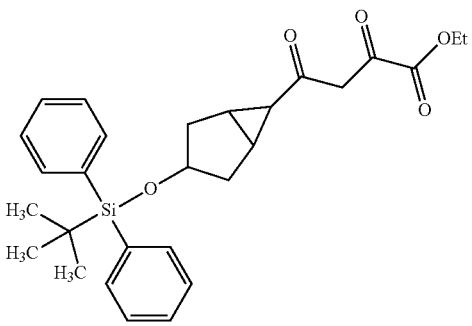 [SMILES: CCOC(=O)C(=O)CC(=O)C1C2CC(O[Si](c3ccccc3)(c3ccccc3)C(C)(C)C)CC21]

To a solution of 1-(3-((tert-butyldiphenylsilyl)oxy)bicyclo [3.1.0]hexan-6-yl)ethanone (27 g, 71 mmol) in anhydrous tetrahydrofuran (300 mL) was added lithium bis(trimethylsilyl)amide (106 mL, 106 mmol, 1 M in tetrahydrofuran) slowly at −78° C. under nitrogen. After 0.5 h, diethyl oxalate (15.63 g, 107.0 mmol) was added, and the reaction mixture was warmed to room temperature. After 6 h, the reaction mixture was quenched with 3 M aqueous hydrochloric acid until the solution reached pH ~3. The mixture was extracted with ethyl acetate (2×200 mL). The combined organics were washed with saturated aqueous sodium chloride solution, dried over anhydrous sodium sulfate, filtered, and concentrated to provided ethyl 4-(3-((tert-butyldiphenylsilyl)oxy) bicyclo[3.1.0]hexan-6-yl)-2,4-dioxobutanoate as an orange solid (40 g), which was used without further purification. LCMS: [M+H]$^+$ 479.0, [M+Na]$^+$ 501.0, [M+Na+CH$_3$CN]$^+$ 542.0.

Step 6: Synthesis of ethyl 5-(3-((tert-butyldiphenylsilyl)oxy)bicyclo[3.1.0]hexan-6-yl)-1-isopropyl-1H-pyrazole-3-carboxylate

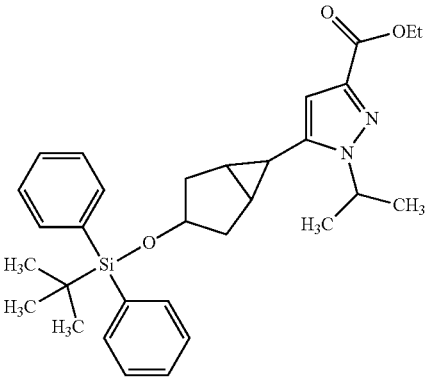 [SMILES: CC(C)n1nc(C(=O)O)cc1C1C2CC(O[Si](c3ccccc3)(c3ccccc3)C(C)(C)C)CC21]

To a solution of ethyl 4-(3-((tert-butyldiphenylsilyl)oxy) bicyclo[3.1.0]hexan-6-yl)-2,4-dioxobutanoate (0.40 kg, 84 mmol) in ethanol (500 mL) was added N-isopropylhydrazine hydrochloride (9.7 g, 84 mmol) at room temperature. After 16 h, triethylamine was added, and the resulting mixture was concentrated in vacuo. Purification of the residue by flash column chromatography (9% ethyl acetate in petroleum ether) afforded ethyl 5-(3-((tert-butyldiphenylsilyl)oxy)bicyclo[3.1.0]hexan-6-yl)-1-isopropyl-1H-pyrazole-3-carboxylate (19.5 g, 45%) as a colorless oil. LRMS: [M+H]$^+$=517.1.

Step 7: Synthesis of 5-(3-((tert-butyldiphenylsilyl)oxy)bicyclo[3.1.0]hexan-6-yl)-1-isopropyl-1H-pyrazole-3-carboxylic acid

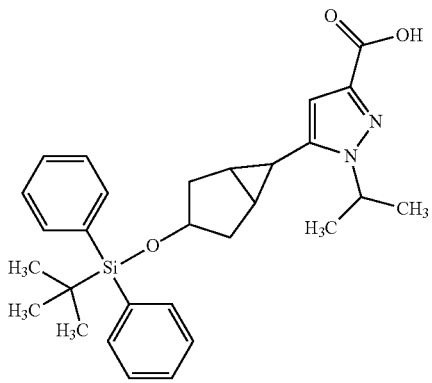

To a stirred solution of ethyl 5-(3-((tert-butyldiphenylsilyl)oxy)bicyclo[3.1.0]hexan-6-yl)-1-isopropyl-1H-pyrazole-3-carboxylate (19.5 g, 37.7 mmol) in ethanol (200 mL) was added a solution of sodium hydroxide (6.30 g, 151 mmol) in water (50 mL) at room temperature. After 6 h, the reaction mixture was concentrated in vacuo, and the resulting aqueous solution was diluted with water (10 mL). 2 M aqueous hydrochloric acid was added until the solution reached pH ~3. The aqueous mixture was extracted with ethyl acetate (2×100 mL). The combined organic extracts were washed with saturated aqueous sodium chloride solution, dried over anhydrous sodium sulfate, filtered, and concentrated to provide crude 5-(3-((tert-butyldiphenylsilyl)oxy)bicyclo[3.1.0]hexan-6-yl)-1-isopropyl-1H-pyrazole-3-carboxylic (18 g, 92%) as a brown yellow solid.

Step 8: Synthesis of benzyl (5-(3-((tert-butyldiphenylsilyl)oxy)bicyclo[3.1.0]hexan-6-yl)-1-isopropyl-1H-pyrazol-3-yl)carbamate

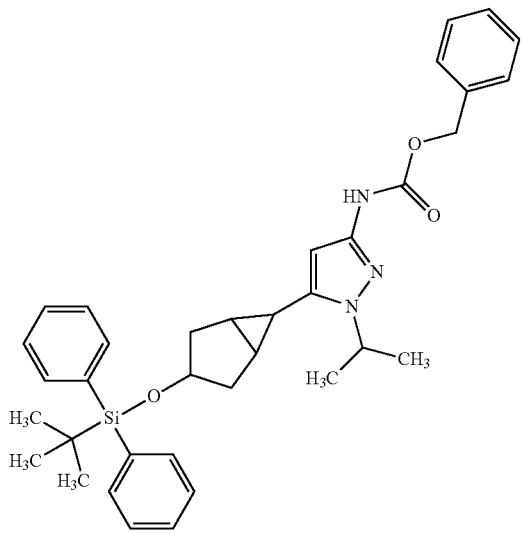 [SMILES: CC(C)n1nc(NC(=O)OCc2ccccc2)cc1C1C2CC(O[Si](c3ccccc3)(c3ccccc3)C(C)(C)C)CC21]

A 500 mL three-neck flask was charged with 5-(3-((tert-butyldiphenylsilyl)oxy)bicyclo[3.1.0]hexan-6-yl)-1-isopropyl-1H-pyrazole-3-carboxylic acid (26 g, 53 mmol), diisopropylethylamine (14 mL, 0.080 mol), benzyl alcohol (17.26 g, 159.6 mmol) and anhydrous toluene (300 mL). The reaction mixture was purged with nitrogen for 2 min and heated to 100° C. Diphenyl phosphorazidate (17.2 mL, 79.85 mmol) was added dropwise to the reaction mixture, and the reaction was maintained at 100° C. After 16 h, the reaction mixture was concentrated in vacuo. The resulting residue was purified by flash column chromatography (20:1 petroleum ether/ethyl acetate) to afford benzyl (5-(3-((tert-butyldiphenylsilyl)oxy)bicyclo[3.1.0]hexan-6-yl)-1-isopropyl-1H-pyrazol-3-yl)carbamate as a yellow oil (28 g, 89%). LRMS: [M+H]$^+$ 594.0.

Step 9: Synthesis of 5-(3-((tert-butyldiphenylsilyl)oxy)bicyclo[3.1.0]hexan-6-yl)-3-iodo-1-isopropyl-1H-pyrazole

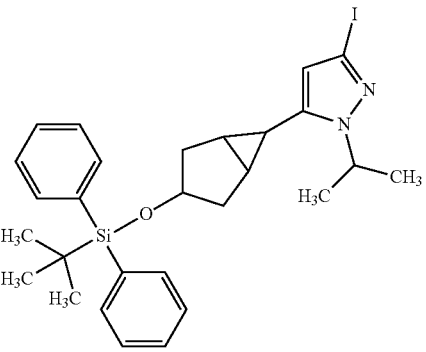 [SMILES: CC(C)n1nc(I)cc1C1C2CC(O[Si](c3ccccc3)(c3ccccc3)C(C)(C)C)CC21]

To a solution of benzyl (5-(3-((tert-butyldiphenylsilyl)oxy)bicyclo[3.1.0]hexan-6-yl)-1-isopropyl-1H-pyrazol-3-yl)carbamate (28 g, 47 mmol) in methanol (200 mL) was added 10% palladium on carbon (2.8 g). The reaction mixture was stirred at room temperature under 1 atm of hydrogen. After 16 h, the reaction mixture was filtered through Celite. The filtrate was concentrated in vacuo to provide crude 5-(3-((tert-butyldiphenylsilyl)oxy)bicyclo[3.1.0]hexan-6-yl)-1-isopropyl-1H-pyrazol-3-amine which was dissolved in acetonitrile (200 mL). A solution of 4-methylbenzenesulfonic acid monohydrate (22.34 g, 117.5 mmol) in water (25 mL) was added at room temperature. After 30 min at room temperature, the reaction mixture was cooled to 0° C. A solution of sodium nitrite (5.4 g, 78 mmol) and sodium iodide (1174 g, 78.31 mmol) in water (25 mL) was added dropwise to the reaction mixture.

After 30 min, saturated aqueous sodium sulfite was added to the reaction, and the resulting aqueous mixture was extracted with ethyl acetate (2×100 mL). The combined organic layers were washed with saturated aqueous sodium chloride, dried over anhydrous sodium sulfate, filtered, and concentrated. Purified of the residue by flash column chromatography (3-5% ethyl acetate in petroleum ether) afforded 5-(3-((tert-butyldiphenylsilyl)oxy)bicyclo[3.1.0]hexan-6-yl)-3-iodo-1-isopropyl-1H-pyrazole as a colorless oil (11.2 g, 50%). LRMS: [M+H]$^+$ 570.9.

Step 10: Synthesis of 6-(3-iodo-1-isopropyl-1H-pyrazol-5-yl)bicyclo[3.1.0]hexan-3-ol

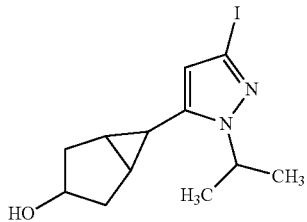 [SMILES: CC(C)n1nc(I)cc1C1C2CC(O)CC21]

A solution of 5-(3-((tert-butyldiphenylsilyl)oxy)bicyclo[3.1.0]hexan-6-yl)-3-iodo-1-isopropyl-1H-pyrazole (11.2 g, 19.7 mmol) and triethylamine trihydrofluoride (63 g, 391 mmol) in anhydrous tetrahydrofuran (100 mL) was heated at 70° C. for 6 h. Saturated aqueous sodium bicarbonate solution was added until the solution reached pH=7. The resulting aqueous mixture was extracted with ethyl acetate (2×100 mL). The combined organic layers were washed with saturated aqueous sodium chloride solution, dried over anhydrous sodium sulfate, filtered, and concentrated. Purification by flash column chromatography (5:1 petroleum either/ethyl acetate) afforded crude 6-(3-iodo-1-isopropyl-1H-pyrazol-5-yl)bicyclo[3.1.0]hexan-3-ol as a pale yellow oil (6.6 g, 100%). LRMS: [M+H]$^+$ 332.9.

Step 11: Synthesis of (1R,5S,6r)-6-(3-iodo-1-isopropyl-1H-pyrazol-5-yl)bicyclo[3.1.0]hexan-3-one

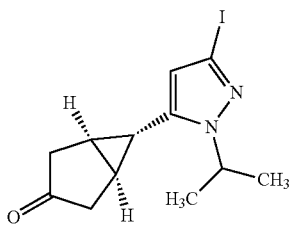 [SMILES: CC(C)n1nc(I)cc1[C@H]1[C@@H]2CC(=O)C[C@@H]21]

To a solution of 6-(3-iodo-1-isopropyl-1H-pyrazol-5-yl)bicyclo[3.1.0]hexan-3-ol (6.0 g, 18 mmol) in dichloromethane (200 mL) was added Dess-Martin periodinane (11.5 g, 27.1 mmol) at room temperature. After 2 h, saturated aqueous sodium bicarbonate solution (100 mL) and saturated aqueous sodium sulfite solution (100 mL) were added sequentially to the reaction mixture. The heterogeneous solution was stirred for 0.5 h. The organic layer was separated and the aqueous layer was extracted with dichloromethane (2×100 mL). The combined organic layers were washed with saturated aqueous sodium chloride solution, dried over anhydrous sodium sulfate, filtered, and concentrated. Purified by flash column chromatography (5:1 petroleum ether/ethyl acetate) afforded (1R,5S,6r)-6-(3-iodo-1-isopropyl-1H-pyrazol-5-yl)bicyclo[3.1.0]hexan-3-one as a white solid (3.5 g). LRMS: [M+H]$^+$ 330.7; $^1$H NMR (400 MHz, CDCl$_3$): δ 6.03 (s, 1H), 4.59-4.49 (m, 1H), 2.78-2.72 (m, 2H), 2.42 (s, 1H), 2.37 (s, 1H), 1.89 (t, J=3.6 Hz, 2H), 1.49 (s, 6H), 1.33 (t, J=3.2 Hz, 1H). (1R,5S,6s)-6-(3-iodo-1-isopropyl-1H-pyrazol-5-yl)bicyclo[3.1.0]hexan-3-one (1.5 g) was also isolated as a white solid.

Step 12: Synthesis of 4-((1R,3r,5S,6r)-6-(3-iodo-1-isopropyl-1H-pyrazol-5-yl)bicyclo[3.1.0]hexan-3-yl)morpholine and 4-((1R,3s,5S,6r)-6-(3-iodo-1-isopropyl-1H-pyrazol-5-yl)bicyclo[3.1.0]hexan-3-yl)morpholine

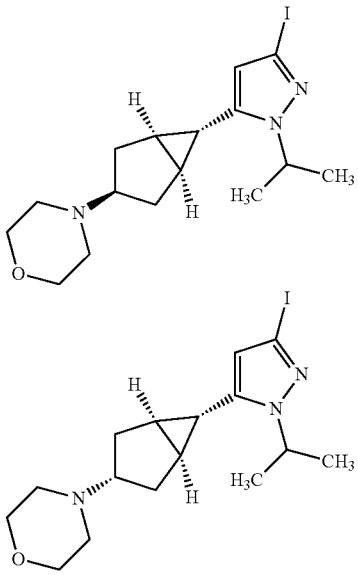

A solution of (1R,5S,6r)-6-(3-iodo-1-isopropyl-1H-pyrazol-5-yl)bicyclo[3.1.0]hexan-3-one (1.5 g, 4.5 mmol), morpholine (1.98 g, 22.7 mmol), sodium cyanoborohydride (857 mg, 13.6 mmol) acetic acid (25 µL) in anhydrous methanol (50 mL) was heated at 60° C. under nitrogen. After 16 h, the reaction mixture was concentrated in vacuo, and the resulting residue was diluted with ethyl acetate (50 mL) and saturated aqueous sodium bicarbonate solution (100 mL). The layers were separated, and the aqueous layer was extracted with ethyl acetate (50 mL). The combined organic layers were dried over anhydrous sodium sulfate, filtered, and concentrated. Purification by flash column chromatography (50% ethyl acetate in hexanes) afforded a mixture of 4-((1R,3r,5S,6r)-6-(3-iodo-1-isopropyl-1H-pyrazol-5-yl)bicyclo[3.1.0]hexan-3-yl)morpholine and 4-((1R,3s,5S,6r)-6-(3-iodo-1-isopropyl-1H-pyrazol-5-yl)bicyclo[3.1.0]hexan-3-yl)morpholine as white solid (1.6 g, 88% yield).

Step 13: Synthesis of 5-(1-isopropyl-5-((1R,3r,5S,6r)-3-morpholinobicyclo[3.1.0]hexan-6-yl)-1H-pyrazol-3-yl)-3-(trifluoromethoxy)pyridin-2-amine and 5-(1-isopropyl-5-((1R,3s,5S,6r)-3-morpholinobicyclo[3.1.0]hexan-6-yl)-1H-pyrazol-3-yl)-3-(trifluoromethoxy)pyridin-2-amine A mixture of 4-((1R,3r,5S,6r)-6-(3-iodo-1-isopropyl-1H-pyrazol-5-yl)bicyclo[3.1.0]hexan-3-yl)morpholine and 4-((1R,3s,5S,6r)-6-(3-iodo-1-isopropyl-1H-pyrazol-5-yl)bicyclo[3.1.0]hexan-3-yl)morpholine (1.6 g, 3.99 mmol), 5-(4,4,5,5-tetramethyl-1,3,2-dioxaborolan-2-yl)-3-(trifluoromethoxy)-pyridine-2-amine (1.45 g, 3.99 mmol), cesium carbonate (2.6 g, 8.0) and 1,1'-bis(diphenylphosphino)ferrocene-palladium(II) dichloride (146 mg, 0.20 mmol) in 5:1 dioxane/water (30 mL) was flushed with nitrogen. The reaction mixture was heated at 90° C. for 2 h. The reaction mixture was diluted with dichloromethane (20 mL) and then filtered through Celite. The filtrate was concentrated, and the resulting residue was purified by flash column chromatography (50% ethyl acetate in petroleum ether→100% ethyl acetate) to afford 5-(1-isopropyl-5-((1R,3r,5S,6r)-3-morpholinobicyclo[3.1.0]hexan-6-yl)-1H-pyrazol-3-yl)-3-(trifluoromethoxy)pyridin-2-amine as a white solid (340 mg, 19% yield). LRMS (ESI): [MH]$^+$=452.15; $^1$H NMR (400 MHz, CDCl$_3$) δ 8.32 (s, 1 H), 7.81 (s, 1 H), 5.95 (s, 1 H), 4.71 (br s, 2 H), 4.64 (m, 1 H), 3.73-3.71 (m, 4 H), 2.92 (m, 1 H), 2.45 (m, 4 H), 2.28 (m, 2 H), 1.81 (m, 1 H), 1.69-1.65 (m, 4 H), 1.53 (d, J=6.8 Hz, 6 H) and 5-(1-isopropyl-5-((1R,3s,5S,6r)-3-morpholinobicyclo[3.1.0]hexan-6-yl)-1H-pyrazol-3-yl)-3-(trifluoromethoxy)pyridin-2-amine as a white solid (206 mg, 11% yield). LRMS (ESI): [MH]$^+$=452.20; $^1$H NMR (400 MHz, CDCl$_3$) δ 8.31 (s, 1 H), 7.79 (s, 1 H), 5.98 (s, 1 H), 4.70 (br s, 2 H), 4.59 (m, 1 H), 3.73 (m, 4 H), 2.45 (m, 4 H), 2.36 (m, 1 H), 2.22 (m, 2 H), 1.84 (m, 2 H), 1.68 (m, 2 H), 1.55-1.50 (m, 7 H).

General Method A was also used to prepare 5-(1-isopropyl-5-((1R,3r,5S,6r)-3-morpholinobicyclo[3.1.0]hexan-6-yl)-1H-pyrazol-3-yl)-3-(trifluoromethyl)pyridin-2-amine

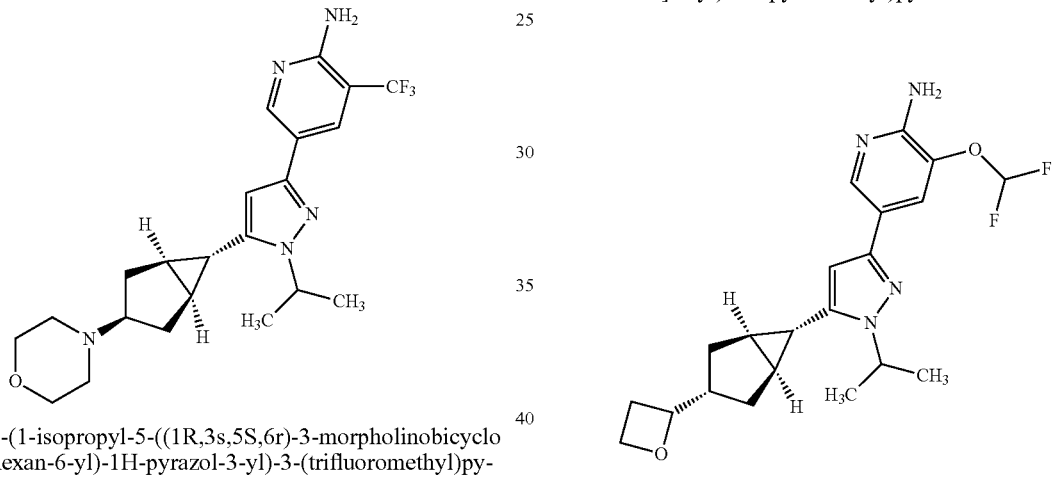

and 5-(1-isopropyl-5-((1R,3s,5S,6r)-3-morpholinobicyclo[3.1.0]hexan-6-yl)-1H-pyrazol-3-yl)-3-(trifluoromethyl)pyridin-2-amine

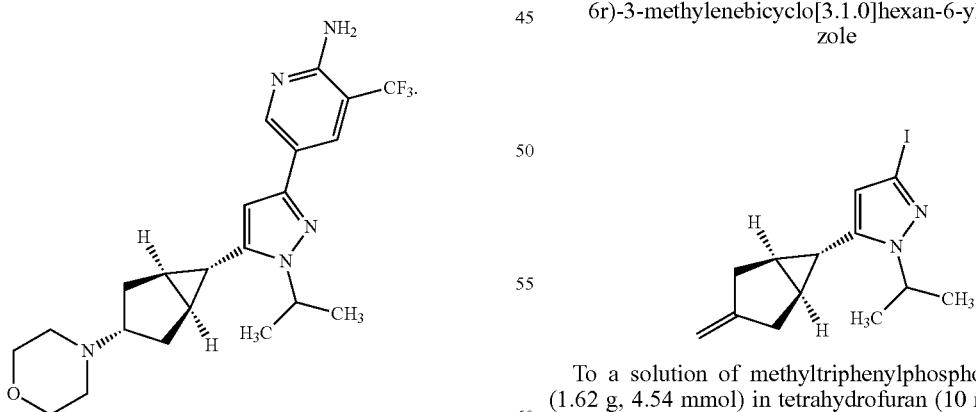

A mixture of crude 4-((1R,5S,6r)-6-(3-iodo-1-isopropyl-1H-pyrazol-5-yl)bicyclo[3.1.0]hexan-3-yl)-morpholine (6.2 g, 15 mmol), 5-(4,4,5,5-tetramethyl-1,3,2-dioxaborolan-2-yl)-3-(trifluoromethyl)pyridin-2-amine (5.22 g, 18.1 mmol), cesium carbonate (9.82 g, 30.2 mmol) and 1,1'-bis(diphenylphosphino)ferrocene-palladium(II) dichloride (554 mg, 0.76 mmol) in 10:1 dioxane/water (200 mL) was evacuated and flushed with nitrogen (3×). The reaction mixture was heated at 90° C. for 3 h. The reaction mixture was diluted with ethyl acetate (200 mL) and filtered through celite. The filtrate was concentrated, and the resulting residue was purified by flash column chromatography to afford 5-(1-isopropyl-5-((1R,3r,5S,6r)-3-morpholinobicyclo[3.1.0]-hexan-6-yl)-1H-pyrazol-3-yl)-3-(trifluoromethyl)pyridin-2-amine (1.61 g) as a white solid. LRMS (ESI): [MH]$^+$=435.9; $^1$H NMR (400 MHz, Methanol-d4) δ 8.47 (s, 1 H), 8.09 (s, 1 H), 6.12 (s, 1 H), 4.76-4.74 (m, 1 H), 3.69-3.67 (m, 4 H), 2.95 (m, 1 H), 2.47 (m, 4 H), 2.33 (m, 2 H), 1.81 (m, 1 H), 1.69-1.61 (m, 4 H), 1.51 (d, J=6.8 Hz, 6 H);

and 5-(1-isopropyl-5-((1R,3s,5S,6r)-3-morpholinobicyclo[3.1.0]-hexan-6-yl)-1H-pyrazol-3-yl)-3-(trifluoromethyl)pyridin-2-amine (700 mg) as a white solid. LRMS (ESI): [MH]$^+$=435.9; $^1$H NMR (400 MHz, Chloroform-d) δ 8.53 (s, 1 H), 8.09 (s, 1 H), 6.00 (s, 1 H), 4.92 (br s, 2 H), 4.64-4.57 (m, 1 H), 3.73-3.71 (m, 4 H), 2.45 (m, 4 H), 2.35-2.33 (m, 1 H), 2.24-2.19 (m, 2 H), 1.90-1.82 (m, 2 H), 1.68 (m, 2 H), 1.55-1.51 (m, 7 H).

General Method B

Preparation of 3-(difluoromethoxy)-5-(1-isopropyl-5-((1R,5S,6r)-spiro[bicyclo[3.1.0]hexane-3,2'-oxetan]-6-yl)-1H-pyrazol-3-yl)pyridin-2-amine Step 1: Synthesis of 3-iodo-1-isopropyl-5-((1R,5S,6r)-3-methylenebicyclo[3.1.0]hexan-6-yl)-1H-pyrazole To a solution of methyltriphenylphosphonium bromide (1.62 g, 4.54 mmol) in tetrahydrofuran (10 mL) was added n-butyllithium (1.82 mL, 4.54 mmol, 2.5 M in hexanes) dropwise at −78° C. The mixture was warmed to 0° C. for 1 h and cooled to −78° C. before the addition of a solution of (1R,5S,6r)-6-(3-iodo-1-isopropyl-1H-pyrazol-5-yl)bicyclo[3.1.0]hexan-3-one (1.0 g, 3.0 mmol) in tetrahydrofuran (5 mL). The mixture was warmed to 0° C. After 4 h, saturated aqueous ammonium chloride solution was added to the reaction and the resulting mixture was extracted with ethyl acetate (3×50 mL). The combined organic layers were dried over anhydrous sodium sulfate, filtered, and concentrated. Purification by flash column chromatography (10→20% ethyl acetate in petroleum ether) yielded 3-iodo-1-isopropyl-5-((1R,5 S,6r)-3-methylenebicyclo[3.1.0]hexan-6-yl)-1H-pyrazole (0.40 g, 40% crude yield) as yellow solid.

Step 2: Synthesis of 3-iodo-1-isopropyl-5-((1R,5S, 6r)-spiro[bicyclo[3.1.0]hexane-3,2'-oxiran]-6-yl)-1H-pyrazole

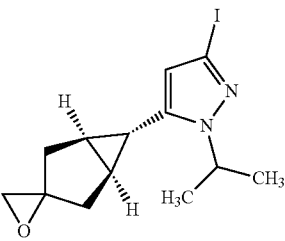

To a solution of 3-iodo-1-isopropyl-5-((1R,5 S,6r)-3-methylenebicyclo[3.1.0]hexan-6-yl)-1H-pyrazole (150 mg, 0.46 mmol) in dichloromethane (5 mL) was added m-chloroperbenzoic acid (237 mg, 1.37 mmol) at 20° C. After 16 h, saturated aqueous sodium sulfite solution was added to the reaction, and the resulting mixture was extracted with dichloromethane (3×20 mL). The organic layers were dried over anhydrous sodium sulfate, filtered, and concentrated. Purification by preparative thin layer chromatography (11% ethyl acetate in petroleum ether) afforded 3-iodo-1-isopropyl-5-((1R,5S,6r)-spiro[bicyclo[3.1.0]hexane-3,2'-oxiran]-6-yl)-1H-pyrazole (0.090 g, 57% yield).

Step 3: Synthesis of 3-iodo-1-isopropyl-5-((1R,5S, 6r)-spiro[bicyclo[3.1.0]hexane-3,2'-oxetan]-6-yl)-1H-pyrazole

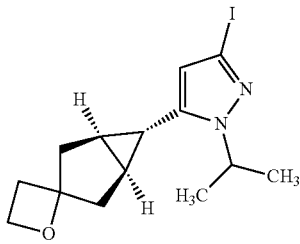

A solution of trimethylsulfoxonium iodide (86 mg, 0.40 mmol) in 2-methylpropan-2-ol (3 mL) and potassium tert-butoxide (44 mg, 0.39 mmol) was warmed to 50° C. After 1 h, 3-iodo-1-isopropyl-5-((1R,5S,6r)-spiro[bicyclo[3.1.0]hexane-3,2'-oxiran]-6-yl)-1H-pyrazole (45 mg, 0.13 mmol) was added, and the reaction mixture was maintained at 50° C. After 16 h, the mixture was quenched with saturated ammonium chloride solution, and the resulting solution was extracted with dichloromethane (3×30 mL). The organic layers were dried over anhydrous sodium sulfate, filtered, and concentrated. Purification by preparative thin layer chromatography (25% ethyl acetate in petroleum ether) afforded 3-iodo-1-isopropyl-5-((1R,5S,6r)-spiro[bicyclo[3.1.0]hexane-3,2'-oxetan]-6-yl)-1H-pyrazole (55 mg, 59% yield).

Step 4: Synthesis of 3-(difluoromethoxy)-5-(1-isopropyl-5-((1R,5 S,6r)-spiro[bicyclo[3.1.0]hexane-3, 2'-oxetan]-6-yl)-1H-pyrazol-3-yl)pyridin-2-amine To a microwave vial charged with 3-iodo-1-isopropyl-5-((1R,5S,6r)-spiro[bicyclo[3.1.0]hexane-3,2'-oxetan]-6-yl)-1H-pyrazole (55 mg, 0.15 mmol), 3-(difluoromethoxy)-5-(4,4,5,5-tetramethyl-1,3,2-dioxaborolan-2-yl)pyridin-2-amine (83 mg, 0.38 mmol) and cesium carbonate (48 mg, 0.31 mmol) in 5:1 1,4-dioxane/water (2.5 mL) was added 1,1'-bis(diphenylphosphino)ferrocene-palladium(II) dichloride (11 mg, 0.015 mmol) under nitrogen. The vial was sealed and heated by microwave irradiation at 100° C. for 30 min. The reaction mixture was concentrated in vacuo, and the resulting residue was purified by preparative HPLC (base) to afford 3-(difluoromethoxy)-5-(1-isopropyl-5-((1R,5 S,6r)-spiro[bicyclo[3.1.0]hexane-3,2'-oxetan]-6-yl)-1H-pyrazol-3-yl)pyridin-2-amine (34 mg, 56% yield). LRMS (ESI): [MH]$^+$= 391.2; $^1$H NMR (400 MHz, Chloroform-d) δ 8.25 (s, 1 H), 7.71 (s, 1 H), 6.55 (t, J$_{HF}$=73.6 Hz, 1 H), 5.96 (s, 1H), 4.71 (br s, 2 H), 4.64 (m, 1 H), 4.48 (t, J=7.6 Hz, 2 H), 2.64 (t, J=8.0 Hz, 2 H), 2.56 (d, J=14.4 Hz, 2 H), 2.09-2.05 (m, 2 H), 1.70 (m, 1 H), 1.62 (m, 2 H), 1.50 (d, J=6.8 Hz, 6 H).

General Method C

Preparation of (1R,5S,6r)-6-(3-(6-amino-5-(difluoromethoxy)pyridin-3-yl)-1-isopropyl-1H-pyrazol-5-yl)-3-methylbicyclo[3.1.0]hexan-3-ol

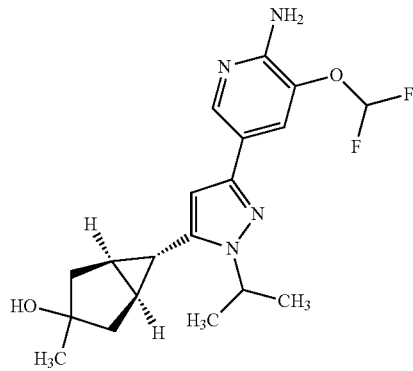

Step 1: Synthesis of (1R,5S,6r)-6-(3-(6-amino-5-(difluoromethoxy)pyridin-3-yl)-1-isopropyl-1H-pyrazol-5-yl)bicyclo[3.1.0]hexan-3-one

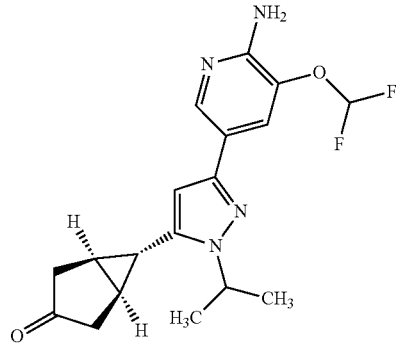 [SMILES: CC(C)n1nc(-c2cnc(N)c(OC(F)F)c2)cc1[C@H]1[C@@H]2CC(=O)C[C@@H]21]

To a microwave vial charged with (1R,5S,6r)-6-(3-iodo-1-isopropyl-1H-pyrazol-5-yl)bicycle-[3.1.0]hexan-3-one (0.10 g, 0.30 mmol), 3-(difluoromethoxy)-5-(4,4,5,5-tetramethyl-1,3,2-dioxaborolan-2-yl)pyridin-2-amine (95 mg, 0.33 mmol) and cesium carbonate (197 mg, 0.606 mmol) in 5:1 1,4-dioxane/water (3 mL) was added 1,1'-bis(diphenylphosphino)ferrocene-palladium(II) dichloride (22 mg, 0.030 mmol) under nitrogen. The vial was sealed and heated by microwave irradiation at 120° C. for 20 min. The reaction mixture was concentrated in vacuo, and the resulting residue was purified by preparative thin layer chromatography (50% ethyl acetate in petroleum ether) to afford (1R,5S,6r)-6-(3-

(6-amino-5-(difluoromethoxy)pyridin-3-yl)-1-isopropyl-1H-pyrazol-5-yl)bicyclo[3.1.0]hexan-3-one (120 mg) as a brown solid. LRMS (ESI): [MH]+=363.0.

Step 2: Synthesis of (1R,5S,6r)-6-(3-(6-amino-5-(difluoromethoxy)pyridin-3-yl)-1-isopropyl-1H-pyrazol-5-yl)-3-methylbicyclo[3.1.0]hexan-3-ol To a solution of (1R,5S,6r)-6-(3-(6-amino-5-(difluoromethoxy)pyridin-3-yl)-1-isopropyl-1H-pyrazol-5-yl)bicyclo[3.1.0]hexan-3-one (0.060 g, 0.17 mmol) in tetrahydrofuran (3 mL) was added methyllithium (1.0 mL, 1.6 mmol, 1.6 M) at −78° C. under nitrogen. After 1.5 h, water (15 mL) was added to the reaction, and the resulting mixture was extracted with ethyl acetate (2×20 mL). The combined organic extracts were washed by saturated aqueous sodium chloride solution (20 mL), dried over anhydrous sodium sulfate, filtered and concentrated. Purification by preparative HPLC (base) afforded (1R,5S,6r)-6-(3-(6-amino-5-(difluoromethoxy)pyridin-3-yl)-1-isopropyl-1H-pyrazol-5-yl)-3-methylbicyclo[3.1.0]hexan-3-ol (3 mg, 5% yield) as a white solid. LRMS (ESI): [MH]+=379.17. $^1$H NMR (400 MHz, Chloroform-d) δ 8.22 (s, 1 H), 7.69 (s, 1 H), 6.53 (t, $J_{HF}$=73.6 Hz, 1 H), 5.95 (s, 1 H), 4.70 (br s, 2 H), 4.66 (m, 1 H), 2.35 (m, 1 H), 2.08 (m, 2 H), 1.96 (m, 2 H), 1.70 (m, 1 H), 1.63 (m, 2 H), 1.50 (d, J=6.8 Hz, 6 H), 1.38 (s, 3 H).

General Method D

Preparation of 5-(1-cyclobutyl-5-((1R,3s,5S,6r)-3-morpholinobicyclo[3.1.0]hexan-6-yl)-1H-pyrazol-3-yl)-3-(difluoromethoxy)pyridin-2-amine and 5-(1-cyclobutyl-5-((1R,3r,5S,6r)-3-morpholinobicyclo[3.1.0]hexan-6-yl)-1H-pyrazol-3-yl)-3-(difluoromethoxy)pyridin-2-amine

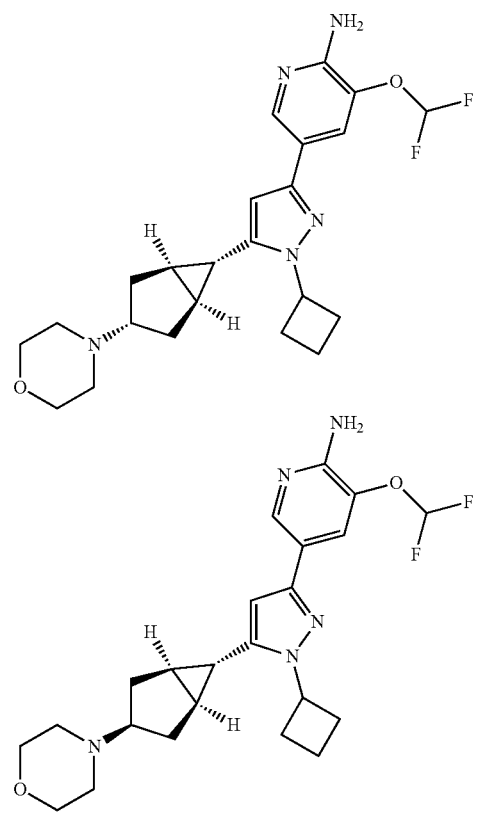

Step 1—Synthesis of 3-((1R,5 S,6r)-3-((tert-butyldiphenylsilyl)oxy)bicyclo[3.1.0]hexan-6-yl)-3-oxopropanenitrile

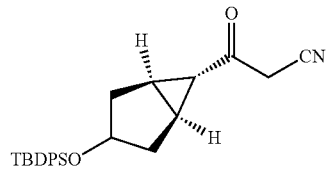

To 3 ice-cooled solutions each containing ethyl 3-((tert-butyldiphenylsilyl)oxy)bicyclo[3.1.0]hexane-6-carboxylate (0.300 kg, 734 mmol) in anhydrous tetrahydrofuran (2 L) and acetonitrile (193 mL, 3.67 mol) were each added potassium tert-butoxide (98.9 g, 881 mmol) portion-wise. The resulting mixtures were warmed to 25° C. After 12 h, the reactions were combined and poured into ice water (3 L), and the resulting mixture was acidified to pH=1 with 12 M hydrochloric acid while keeping the solution between 0-10° C. The resulting mixture was extracted with ethyl acetate (2×3 L), and the combined organic was washed with saturated aqueous sodium chloride solution (1 L), dried over anhydrous sodium sulfate, filtered, and concentrated. Purification by flash column chromatography (petroleum ether→5:1 petroleum ether/ethyl acetate) provided a yellow oil (300 g, 34% yield). $^1$H NMR (1.3:1 C3 isomer ratio, * denotes minor isomer peaks, 400 MHz, CDCl$_3$): δ 7.26-7.64 (m, 20 H), 4.35* (m, 1 H), 3.96 (m, 1H), 3.59* (s, 2 H), 3.42 (s, 2 H), 2.72* (m, 1H), 1.91-2.08 (m, 15 H), 1.51 (m, 1 H), 1.09* (s, 9 H), 1.03 (s, 9 H).

Step 2—Synthesis of 5-((1R,5S,6r)-3-((tert-butyldiphenylsilyl)oxy)bicyclo[3.1.0]hexan-6-yl)-1H-pyrazol-3-amine

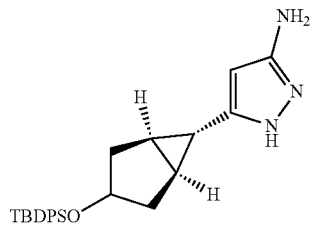

Four reaction solutions each containing 3-((1R,5 S,6r)-3-((tert-butyldiphenylsilyl)oxy)bicyclo[3.1.0]hexan-6-yl)-3-oxopropanenitrile (0.250 kg, 619 mmol) and hydrazine monohydrate (60.2 mL, 1.24 mol) in 2-propanol (2 L) were heated to 80° C. for 2 h. The 4 reactions were combined and concentrated. The crude residue was dissolved in dichloromethane (8 L), and the resulting solution was washed with saturated aqueous sodium chloride solution (1 L). The collected organic phase was dried over anhydrous sodium sulfate, filtered, and concentrated to afford a yellow solid (833 g, 80% crude yield). The crude product was used without further purification.

Step 3—Synthesis of 5-((1R,5S,6r)-3-((tert-butyldiphenylsilyl)oxy)bicyclo[3.1.0]hexan-6-yl)-3-iodo-1H-pyrazole

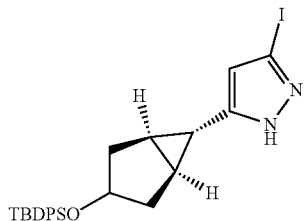

To 2 ice-cooled solutions each containing 5-((1R,5S,6r)-3-((tert-butyldiphenylsilyl)oxy)bicyclo[3.1.0]hexan-6-yl)-1H-pyrazol-3-amine (0.300 kg, 718 mmol) in acetonitrile (3 L) were each added 4-methylbenzenesulfonic acid hydrate (542 g, 2.16 mol) in water (1 L). After 30 min, sodium nitrite (149 g, 2.16 mol) in water (600 mL) were added dropwise via addition funnel to each reaction at 0° C. After 30 min, sodium iodide (323 g, 2.16 mol) in water (600 mL) were added dropwise to each reaction. The resulting dark reaction mixtures were warmed to 25° C. for 30 min. The 2 reactions were combined and concentrated. The aqueous solution was extracted with ethyl acetate (2×4 L), and the collected organic was concentrated. Purification by flash column chromatography (petroleum ether→10:1 petroleum ether/ethyl acetate) provided a brown oil, which was triturated with methanol (400 mL). Filtration afforded product as an off-white solid. The filtrate was purified by prep-HPLC to provide additional product. The combined products were dissolved in dichloromethane and concentrated to afford a tan solid (203 g, 27% yield). $^1$H NMR (1.3:1 C3 isomer ratio, * denotes minor isomer peaks, 400 MHz, CDCl$_3$): δ 7.26-7.64 (m, 20 H), 6.04* (s, 1 H), 5.86 (s, 1 H), 4.37* (m, 1 H), 3.98 (m, 1 H), 2.42* (m, 1 H), 1.91-2.12 (m, 10 H), 1.57* (m, 2H), 1.50 (m, 2H), 1.39* (m, 1H), 1.26 (m, 1 H), 1.06* (s, 9 H), 1.03 (s, 9 H); LCMS: [MH]$^+$=529.1.

Step 4—Synthesis of (1R,5S,6r)-6-(3-iodo-1H-pyrazol-5-yl)bicyclo[3.1.0]hexan-3-ol

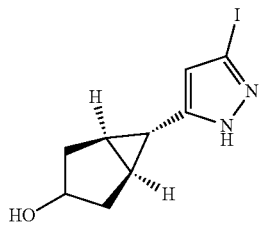

A solution of 5-((1R,5S,6r)-3-((tert-butyldiphenylsilyl)oxy)bicyclo[3.1.0]hexan-6-yl)-3-iodo-1H-pyrazole (2.0 g, 3.8 mmol) and triethylamine trihydrofluoride (6.17 mL, 37.8 mmol) in tetrahydrofuran (40 mL) was heated at 70° C. overnight. The reaction mixture was concentrated in vacuo, and the resulting residue was diluted with saturated aqueous sodium bicarbonate solution until pH 7-8. The aqueous solution was extracted with ethyl acetate (2×40 mL). The collected organic was washed with saturated aqueous sodium chloride solution (80 mL), dried over anhydrous sodium sulfate, filtered, and concentrated in vacuo. Purification by flash column chromatography (dichloromethane→6% methanol in dichloromethane+0.6% aqueous ammonium hydroxide to provide the title compound (1.1 g, 100% yield). LCMS: [MH]$^+$=291.1.

Step 5—Synthesis of (1R,5S,6r)-6-(3-iodo-1H-pyrazol-5-yl)bicyclo[3.1.0]hexan-3-one

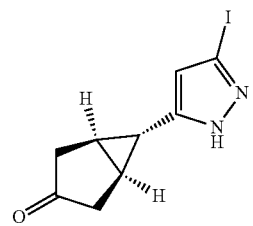 [SMILES: O=C1C[C@@H]2[C@H](C1)[C@H]2c1cc(I)n[nH]1]

To a solution of (1R,5S,6r)-6-(3-iodo-1H-pyrazol-5-yl)bicyclo[3.1.0]hexan-3-ol (0.97 g, 3.3 mmol) in dichloromethane (10 mL) was added Dess-Martin periodinane (1.56 g, 3.68 mmol) at room temperature. After 2 h, the reaction mixture was diluted with dichloromethane (10 mL), saturated aqueous sodium bicarbonate solution (20 mL), and 10% sodium thiosulfate aqueous solution (20 mL). The heterogeneous solution was stirred vigorously for 30 min until the organic phase became clear. The layers were separated, and the aqueous layer was extracted with dichloromethane (2×20 mL). The combined organic was washed with saturated aqueous sodium chloride solution (20 mL), dried over anhydrous sodium sulfate, filtered, and concentrated in vacuo. Purification by flash column chromatography (dichloromethane→2.5% methanol in dichloromethane+0.25% aqueous ammonium hydroxide) afforded the title product (0.60 g, 62% yield). LCMS: [MH]$^+$=288.9.

Step 6—Synthesis of 4-((1R,5S,6r)-6-(3-iodo-1H-pyrazol-5-yl)bicyclo[3.1.0]hexan-3-yl)morpholine

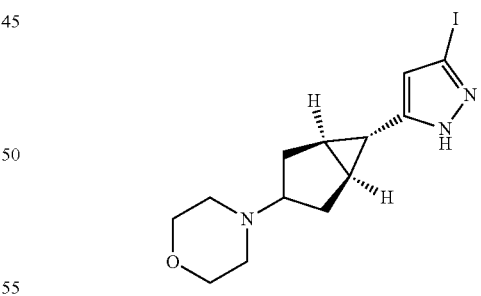

To a solution (1R,5S,6r)-6-(3-iodo-1H-pyrazol-5-yl)bicyclo[3.1.0]hexan-3-one (0.60 g, 2.1 mmol) in toluene (10 mL) was sequentially added morpholine (1.82 mL, 20.8 mmol), sodium cyanoborohydride (206 mg, 3.12 mmol), and acetic acid (1.4 mL, 25 mmol). The solution was heated at 110° C. with microwave irradiation for 15 min. The reaction was diluted with saturated aqueous sodium bicarbonate solution (10 mL). The resulting solution was extracted with ethyl acetate (2×20 mL). The collected organic was washed with saturated aqueous sodium chloride solution, dried over anhydrous sodium sulfate, filtered, and concentrated in vacuo.

Purification by flash column chromatography (dichloromethane→5% methanol in dichloromethane+0.5% aqueous ammonium hydroxide) afforded product (0.30 g, 40% yield). LCMS: [MH]⁺=360.0.

Step 7—Synthesis of 4-((1R,5S,6r)-6-(1-cyclobutyl-3-iodo-1H-pyrazol-5-yl)bicyclo[3.1.0]hexan-3-yl)morpholine

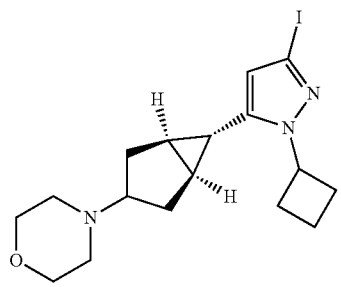

A suspension of 4-((1R,5S,6r)-6-(3-iodo-1H-pyrazol-5-yl)bicyclo[3.1.0]hexan-3-yl)morpholine (0.50 g, 1.4 mmol), bromocyclobutane (0.39 mL, 4.2 mmol), and cesium carbonate (0.50 g, 1.5 mmol) in N,N-dimethylformamide (10 mL) was heated at 120° C. for 30 min. The reaction mixture was diluted with water (10 mL), and the resulting mixture extracted with ethyl acetate (3×10 mL). The collected organic was washed with saturated aqueous sodium chloride solution, dried over anhydrous sodium sulfate, and concentrated in vacuo. Purification by flash column chromatography (dichloromethane→5% methanol in dichloromethane+0.5% aqueous ammonium hydroxide) afforded the title compound (210 mg, 37% yield). LCMS: [MH]⁺=414.1.

Step 8—Synthesis of 5-(1-cyclobutyl-5-((1R,5S,6r)-3-morpholinobicyclo[3.1.0]hexan-6-yl)-1H-pyrazol-3-yl)-3-(difluoro methoxy)pyridin-2-amine To a solution of 4-((1R,5S,6r)-6-(1-cyclobutyl-3-iodo-1H-pyrazol-5-yl)bicyclo[3.1.0]hexan-3-yl)morpholine (88 mg, 0.30 mmol), (3-(difluoromethoxy)-5-(4,4,5,5-tetramethyl-1,3,2-dioxaborolan-2-yl)pyridin-2-amine (76 mg, 0.35 mmol) and cesium carbonate (77 mg, 0.32 mmol) in 1,4-dioxane (3 mL) and water (0.3 mL) was added 1,1'-bis(diphenylphosphino)ferrocene-palladium(II)dichloride dichloromethane complex (49 mg, 0.059 mmol) under nitrogen. The mixture was heated at 100° C. under microwave irradiation for 15 min. The reaction was diluted with water (10 mL), and the resulting solution was extracted with ethyl acetate (2×50 mL). The collected organic was washed with saturated aqueous sodium chloride solution, dried over anhydrous sodium sulfate, filtered, and concentrated in vacuo. Purification by preparative HPLC provided the title compounds.

5-(1-cyclobutyl-5-((1R,3s,5S,6r)-3-morpholinobicyclo[3.1.0]hexan-6-yl)-1H-pyrazol-3-yl)-3-(difluoromethoxy)pyridin-2-amine: (30 mg, 31% yield) ¹H NMR (400 MHz, CDCl₃) δ: 8.25 (d, J=1.9 Hz, 1 H), 7.75-7.59 (m, 1 H), 6.55 (t, J=73.6 Hz, 1 H), 6.00 (d, J=0.7 Hz, 1 H), 4.91-4.77 (m, 1 H), 4.71 (s, 2 H), 3.80-3.67 (m, 4 H), 2.87-2.67 (m, 2 H), 2.52-2.31 (m, 8 H), 2.29-2.16 (m, 2 H), 2.00-1.73 (m, 4 H), 1.71-1.60 (m, 2 H), 1.57-1.46 (m, 1 H). LCMS: [MH]⁺=446.2.

5-(1-cyclobutyl-5-((1R,3r,5 S,6r)-3-morpholinobicyclo[3.1.0]hexan-6-yl)-1H-pyrazol-3-yl)-3-(difluoromethoxy)pyridin-2-amine: (27 mg, 28% yield) ¹H NMR (400 MHz, DMSO-d₆) δ: 8.17 (d, J=1.9 Hz, 1 H), 7.63-7.57 (m, 1 H), 7.16 (t, J=73.9 Hz, 1 H), 6.20 (d, J=0.6 Hz, 1 H), 6.10 (s, 2 H), 5.02-4.81 (m, 1 H), 3.56 (t, J=4.6 Hz, 4 H), 2.84-2.71 (m, 1 H), 2.63-2.53 (m, 3 H), 2.41-2.30 (m, 6 H), 2.14-2.05 (m, 2 H), 1.97-1.86 (m, 1 H), 1.86-1.76 (m, 2 H), 1.75-1.65 (m, 2 H), 1.61-1.52 (m, 2 H). LCMS: [MH]⁺=446.2.

General Method E

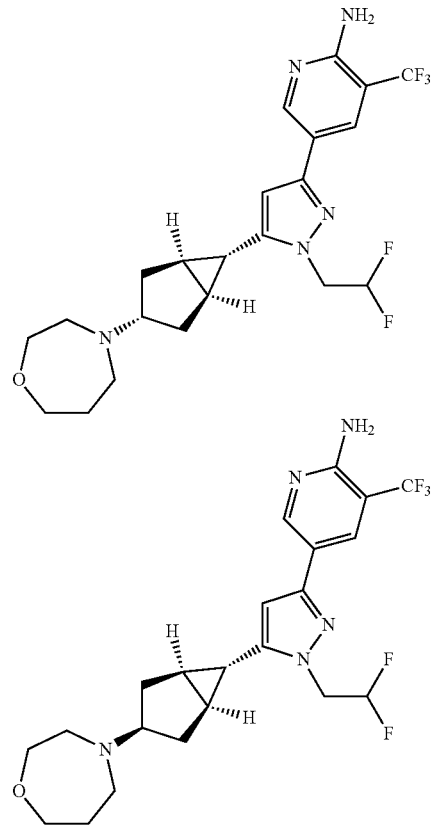

Preparation of 5-(5-((1R,3s,5S,6r)-3-(1,4-oxazepan-4-yl)bicyclo[3.1.0]hexan-6-yl)-1-(2,2-difluoroethyl)-1H-pyrazol-3-yl)-3-(trifluoromethyl)pyridin-2-amine and 5-(5-((1R,3r,5S,6r)-3-(1,4-oxazepan-4-yl)bicyclo[3.1.0]hexan-6-yl)-1-(2,2-difluoroethyl)-1H-pyrazol-3-yl)-3-(trifluoromethyl)pyridin-2-amine Step 1—Synthesis of (1R,5S,6r)-6-(3-(6-amino-5-(trifluoromethyl)pyridin-3-yl)-1H-pyrazol-5-yl)bicyclo[3.1.0]hexan-3-one

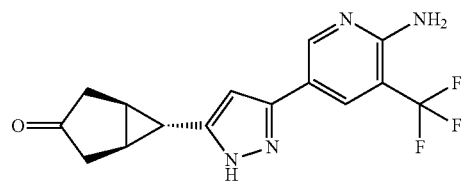 [SMILES: Nc1ncc(-c2cc([C@H]3[C@@H]4CC(=O)C[C@@H]43)[nH]n2)cc1C(F)(F)F]

To a solution of (1R,5S,6r)-6-(3-iodo-1H-pyrazol-5-yl)bicyclo[3.1.0]hexan-3-one (350 mg, 1.22 mmol) and 5-(4,4,5, 5-tetramethyl-1,3,2-dioxaborolan-2-yl)-3-(trifluoromethyl) pyridin-2-amine (398 mg, 1.46 mmol) in toluene/ethanol/water (5 mL/1.5 mL/0.5 mL) was added tripotassium phosphate tribasic (776 mg, 3.66 mmol) and 1,1'-bis(diphenylphosphino)ferrocene-palladium(II) dichloride (277 mg, 0.378 mmol) under nitrogen. The mixture was stirred at 95° C. for 16 h. The mixture was filtered through Celite, and the filtrate was concentrated in vacuo. Purification by flash column chromatography (20%-50% ethyl acetate in petroleum ether) afforded a yellow solid (346 mg, 88% yield). LCMS: [MH]$^+$=323.1.

Step 2—Synthesis of (1R,5 S,6r)-6-(3-(6-amino-5-(trifluoromethyl)pyridin-3-yl)-1-(2,2-difluoroethyl)-1H-pyrazol-5-yl)bicyclo[3.1.0]hexan-3-one

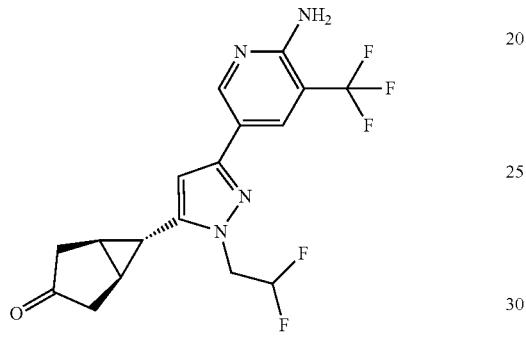

The mixture of (1R,5S,6r)-6-(3-(6-amino-5-(trifluoromethyl)pyridin-3-yl)-1H-pyrazol-5-yl)bicyclo[3.1.0]hexan-3-one (0.100 g, 0.155 mmol), 2,2-difluoroethyl trifluoromethanesulfonate (66 mg, 0.31 mmol) and cesium carbonate (151 mg, 0.465 mmol) in N,N-dimethylformamide (1 mL) was stirred at room temperature for 5 h. The mixture was diluted with water (10 mL) and extracted with ethyl acetate (3×15 mL). The combined organic was concentrated to give a crude residue, which was purified by preparative thin layer chromatography (25% ethyl acetate in petroleum ether) to afford product as a white solid (80 mg, 66% yield). LCMS: [MH]$^+$=387.0.

Step 3—Synthesis of 5-(5-((1 R,5 S,6r)-3-(1,4-oxazepan-4-yl)bicyclo[3.1.0]hexan-6-yl)-1-(2,2-difluoroethyl)-1H-pyrazol-3-yl)-3-(trifluoromethyl)pyridin-2-amine To a solution of (1R,5S,6r)-6-(3-(6-amino-5-(trifluoromethyl)pyridin-3-yl)-1-(2,2-difluoroethyl)-1H-pyrazol-5-yl)bicyclo[3.1.0]hexan-3-one (0.080 mg, 0.21 mmol) in methanol (5 mL) was added 1,4-oxazepane (42 mg, 0.41 mmol) and sodium cyanoborohydride (39 mg, 0.62 mmol). The mixture was stirred at 50° C. After 6 h, the reaction was concentrated in vacuo. Purification by preparative HPLC provided the title compounds as white solids.

5-(5-((1 R,3 s,5 S,6r)-3-(1,4-oxazepan-4-yl)bicyclo[3.1.0] hexan-6-yl)-1-(2,2-difluoroethyl)-1H-pyrazol-3-yl)-3-(trifluoromethyl)pyridin-2-amine: (7.7 mg, 7.9% yield)$^1$H NMR (400 MHz, CDCl$_3$) δ: 8.53 (s, 1 H), 8.06 (d, J=1.2 Hz, 1 H), 6.35-6.02 (m, 1 H), 6.06 (s, 1 H), 5.03 (br s, 2 H), 4.53-4.43 (m, 2 H), 3.79 (t, J=6.0 Hz, 2 H), 3.74 (t, J=4.8 Hz, 2 H), 2.82-2.74 (m, 1 H), 2.73-2.67 (m, 4 H), 2.42-2.17 (m, 2 H), 1.92-1.81 (m, 4H), 1.72-1.66 (m, 2 H), 1.57 (t, J=2.8 Hz, 1 H). LCMS: [MH]$^+$=472.1.

5-(5-((1 R,3r,5 S,6r)-3-(1,4-oxazepan-4-yl)bicyclo[3.1.0] hexan-6-yl)-1-(2,2-difluoroethyl)-1H-pyrazol-3-yl)-3-(trifluoromethyl)pyridin-2-amine: (4.6 mg, 4.7% yield)$^1$H NMR (400 MHz, CDCl$_3$) δ: 8.53 (d, J=1.2 Hz, 1 H), 8.06 (d, J=1.2 Hz, 1 H), 6.34-6.02 (m, 1 H), 6.01 (s, 1 H), 5.03 (br s, 2 H), 4.55-4.45 (m, 2 H), 3.78 (t, J=6.0 Hz, 2 H), 3.73 (t, J=4.8 Hz, 2 H), 3.35-3.25 (m, 1 H), 2.74-2.65 (m, 4 H), 2.33-2.23 (m, 2 H), 1.91-1.84 (m, 2 H), 1.82 (t, J=3.0 Hz, 1 H), 1.70-1.61 (m, 4 H). LCMS: [MH]$^+$=472.1.

General Method F

Synthesis of 5-(1-isopropyl-5-(2-morpholinobicyclo [3.1.0]hexan-6-yl)-1H-pyrazol-3-yl)-3-(trifluoromethyl)pyridin-2-amine (exo-anti enantiomers)

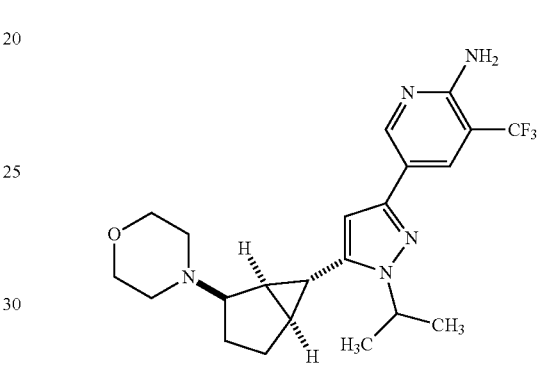

Step 1—Synthesis of 3-iodo-1-isopropyl-5-(3-oxatricyclo[4.1.0.0$^{2,4}$]heptan-7-yl)-1H-pyrazole (exo-syn enantiomers)

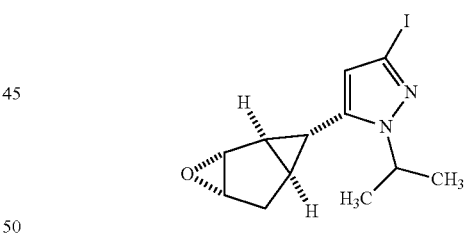

To an ice-cooled solution of (±)-exo-5-(bicyclo[3.1.0]hex-2-en-6-yl)-3-iodo-1-isopropyl-1H-pyrazole (6.0 g, 19 mmol) in anhydrous dichloromethane (100 mL) was added m-chloroperoxybenzoic acid (6.2 g, 28 mmol) portionwise. The reaction mixture was warmed to 20° C. After 16 h, the reaction mixture was filtered, and the filtrate was washed sequentially with saturated aqueous sodium sulfite and aqueous sodium hydroxide (15%, 100 mL). The collected organic was dried over anhydrous sodium sulfate, filtered and concentrated in vacuo. Purification by flash column chromatography (300-400 mesh neutral aluminum oxide, 100% petroleum ether to 10% ethyl acetate in petroleum ether) afforded product as a yellow solid (3.5 g, 56% yield). LCMS (ESI): [MH]$^+$=330.8.

Step 2—Synthesis of (±)-6-(3-iodo-1-isopropyl-1H-pyrazol-5-yl)bicyclo[3.1.0]hexan-2-ol

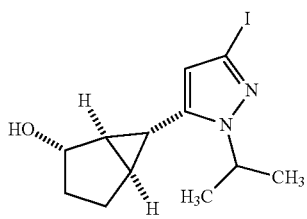

To an ice-cooled solution of 3-iodo-1-isopropyl-5-(3-oxatricyclo[4.1.0.0²,⁴]heptan-7-yl)-1H-pyrazole (0.500 g, 1.52 mmol) in anhydrous tetrahydrofuran (5 mL) was added lithium triethylhydroborate (10 mL, 1 M in THF) dropwise. The reaction mixture was warmed to 20° C. After 1 h, the reaction mixture was cooled to 0° C. and diluted with saturated aqueous ammonium chloride solution (10 mL). The resulting mixture was extracted with ethyl acetate (2×10 mL). The collected organic was concentrated in vacuo. Purification by flash column chromatography (17% ethyl acetate in petroleum ether) afforded product as a colorless oil (460 mg, 91% yield).

Step 3—Synthesis of (±)-exo-6-(3-iodo-1-isopropyl-1H-pyrazol-5-yl)bicyclo[3.1.0]hexan-2-one

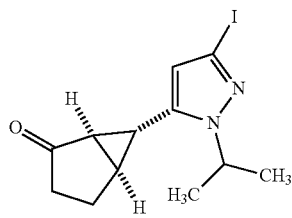

To a solution of (±)-6-(3-iodo-1-isopropyl-1H-pyrazol-5-yl)bicyclo[3.1.0]hexan-2-ol (470 mg, 1.4 mmol) in anhydrous dichloromethane (10 mL) was added Dess-Martin periodinane (1.19 g, 2.22 mmol) at 20° C. After 16 h, the reaction mixture was diluted with saturated aqueous sodium sulfite. Sodium carbonate was added until the solution reached pH>7. The mixture was extracted with dichloromethane (2×10 mL), and the collected organic was concentrated in vacuo. The residue was purified by flash column chromatography (17% ethyl acetate in petroleum ether) to afford a white solid (230 mg, 49% yield). LCMS (ESI): [MH]⁺=330.8.

Step 4—Synthesis of (±)-exo-6-(3-(6-amino-5-(trifluoromethyl)pyridin-3-yl)-1-isopropyl-1H-pyrazol-5-yl)bicyclo[3.1.0]hexan-2-one

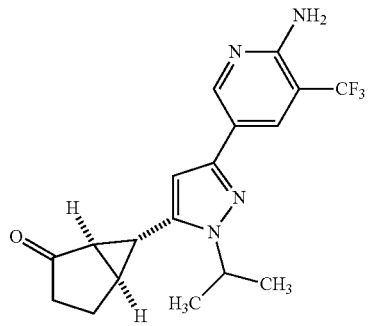

A mixture of (±)-exo-6-(3-iodo-1-isopropyl-1H-pyrazol-5-yl)bicyclo[3.1.0]hexan-2-one (100 mg, 0.3 mmol), 5-(4,4,5,5-tetramethyl-1,3,2-dioxaborolan-2-yl)-3-(trifluoromethyl)pyridin-2-amine (0.10 g, 0.36 mmol), 1,1'-bis(diphenylphosphino)ferrocene-palladium(II) dichloride (20 mg, 0.03 mol) and cesium carbonate (200 mg, 0.6 mmol) in 5:1 1,4-dioxane/water (0.6 mL) was purged with nitrogen for 1 min. The reaction mixture was sealed in a microwave vial and heated by microwave irradiation at 110° C. for 15 min. The reaction mixture was concentrated in vacuo, and the resulting residue was purified by preparative thin layer chromatography (50% ethyl acetate in petroleum ether) to afford a colorless oil (84 mg, 76% yield). LCMS (ESI): [MH]⁺=365.0.

Step 5—Synthesis of 5-(1-isopropyl-5-(2-morpholinobicyclo[3.1.0]hexan-6-yl)-1H-pyrazol-3-yl)-3-(trifluoromethyl)pyridin-2-amine (exo anti enantiomers)

A mixture of (±)-exo-6-(3-(6-amino-5-(trifluoromethyl)pyridin-3-yl)-1-isopropyl-1H-pyrazol-5-yl)bicyclo[3.1.0]hexan-2-one (0.070 g, 0.19 mmol), morpholine (84 mg, 0.96 mmol), sodium cyanoborohydride (36 mg, 0.57 mol) and acetate acid (50 μL) in methanol (5 mL) was heated at 70° C. for 1 h. The reaction was concentrated in vacuo, and the resulting residue was diluted with ethyl acetate (10 mL) and water (5 mL). The organic layer was collected and concentrated in vacuo. Purification by preparative thin layer chromatography (ethyl acetate) afforded a racemic mixture (0.060 g, 63% yield), which were separated by chiral SFC.

Enantiomer 1:
exo-anti-5-(1-isopropyl-5-((2-morpholinobicyclo[3.1.0]hexan-6-yl)-1H-pyrazol-3-yl)-3-(trifluoromethyl)pyridin-2-amine as a white solid (11 mg, 11%). LCMS (ESI): [MH]⁺=436.1, ¹H NMR (400 MHz, CDCl₃) δ: 8.53 (s, 1 H), 8.10 (s, 1 H), 5.96 (s, 1 H), 4.95 (s, 2 H), 4.72 (m, 1 H), 3.74 (m, 4 H), 2.90 (s, 1 H), 2.63-2.55 (m, 4 H), 2.05-1.85 (m, 5 H), 1.70 (m, 2 H), 1.56-1.51 (m, 6 H).

Enantiomer 2:
exo-anti-5-(1-isopropyl-5-(2-morpholinobicyclo[3.1.0]hexan-6-yl)-1H-pyrazol-3-yl)-3-(trifluoromethyl)pyridin-2-amine as a white solid (14 mg, 14%). LCMS (ESI): [MH]⁺=436.1, ¹H NMR (400 MHz, CDCl₃) δ: 8.53 (s, 1 H), 8.10 (s, 1 H), 5.98 (s, 1 H), 4.96 (s, 2 H), 4.73 (m, 1 H), 3.75 (m, 4 H), 2.92 (s, 1 H), 2.63-2.55 (m, 4 H), 2.05-1.85 (m, 5 H), 1.72 (m, 2 H), 1.58-1.52 (m, 6 H).

General Method G

Preparation of 5-(1-isopropyl-5-((1'R,2r,5'S,6'r)-1-(oxetan-3-yl)spiro[azetidine-2,3'-bicyclo[3.1.0]hexan]-6'-yl)-1H-pyrazol-3-yl)-3-(trifluoromethoxy)pyridin-2-amine

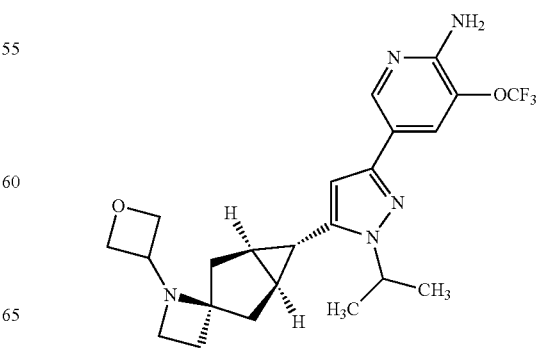

Step 1—Synthesis of (S)—N-((1R,5S,6R)-6-(3-iodo-1-isopropyl-1H-pyrazol-5-yl)bicyclo[3.1.0]hexan-3-ylidene)-2-methylpropane-2-sulfinamide

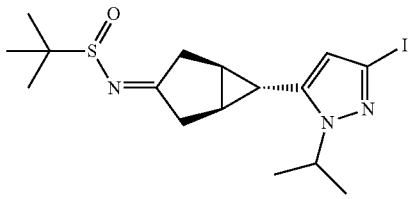 [SMILES: CC(C)n1nc(I)cc1[C@H]1[C@@H]2C/C(=N\S(=O)C(C)(C)C)C[C@@H]21]

To a solution of (1R,5S,6r)-6-(3-iodo-1-isopropyl-1H-pyrazol-5-yl)bicyclo[3.1.0]hexan-3-one (3.0 g, 9.1 mmol), (S)-2-methylpropane-2-sulfinamide (2.2 g, 18 mmol) in tetrahydrofuran (100 mL) was added titanium (IV) isopropoxide (10 g, 36 mmol) dropwise. The reaction was heated at 70° C. for 20 h. Water (100 mL) was added to the reaction, and the resulting mixture was filtered. The filter cake was rinsed with ethyl acetate (3×50 mL). The collected organic was washed with saturated aqueous sodium chloride solution (100 mL), dried over anhydrous sodium sulfate, filtered, and concentrated in vacuo. Purification by flash column chromatography (0→30% ethyl acetate in petroleum ether) yielded a yellow solid (2.75 g, 40% yield). $^1$H NMR (400 MHz, CDCl$_3$) δ 5.99 (s, 1 H), 4.52-4.56 (m, 1 H), 3.50 (m, 1 H), 3.14-3.15 (m, 1 H), 3.01-3.11 (m, 1 H), 2.73-2.80 (m, 1 H), 1.83-1.87 (m, 1 H), 1.74-1.80 (m, 1 H), 1.48 (d, J=6.4 Hz, 6 H), 1.19-1.31 (m, 10 H).

Step 2—Synthesis of Ethyl 2-((1R,3r,5 S,6S)-3-((S)-1,1-dimethylethylsulfinamido)-6-(3-iodo-1-isopropyl-1H-pyrazol-5-yl)bicyclo[3.1.0]hexan-3-yl)acetate

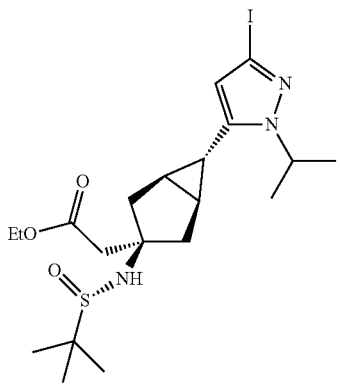 [SMILES: CCOC(=O)C[C@]1(N[S@@](=O)C(C)(C)C)C[C@@H]2[C@H](C1)[C@H]2c1cc(I)nn1C(C)C]

To a suspension of activated zinc (25 g, 38 mmol) in tetrahydrofuran (240 mL) at 40-50° C. was added chlorotrimethylsilane (5.17 g, 47.6 mmol) dropwise under a nitrogen atmosphere. The reaction mixture was stirred at 45° C. for 15 min before the addition of ethyl 2-bromoacetate (53 g, 320 mmol) at a rate that maintained reflux. Upon completion of the addition, the reaction temperature was maintained between 60-65° C. for 2 h until the color of the reaction mixture became light orange. The reaction was cooled to −10° C. before the dropwise addition of (S)—N-((1R,5S,6R)-6-(3-iodo-1-isopropyl-1H-pyrazol-5-yl)bicyclo[3.1.0]hexan-3-ylidene)-2-methyl propane-2-sulfinamide (2.75 g, 6.35 mmol) in tetrahydrofuran (10 mL). The reaction was stirred at −10° C. for 3 h before warming to 24° C. After 16 h, the reaction was diluted with saturated aqueous ammonium chloride solution (150 mL), and the mixture was extracted with ethyl acetate (3×70 mL). The collected organic was washed with saturated aqueous sodium bicarbonate solution (100 mL), saturated aqueous sodium chloride solution (100 mL), dried over anhydrous sodium sulfate, filtered, and concentrated in vacuo. Purification by flash column chromatography (5:1 petroleum ether/ethyl acetate) provided a yellow solid (2.15 g, 65% yield). $^1$H NMR (400 MHz, CDCl$_3$) δ: 5.90 (s, 1 H), 4.81 (s, 1 H), 4.51-4.57 (m, 1 H), 4.15 (q, J=7.2 Hz, 2 H), 3.20 (m, 1 H), 2.64 (m, 1 H), 2.49 (m, 1 H), 2.27 (m, 1 H), 2.09-2.14 (m, 2 H), 2.00-2.14 (m, 1 H), 1.63-1.64 (m, 2 H), 1.45 (d, J=6.8 Hz, 6 H), 1.23-1.28 (m, 12 H).

Step 3—Synthesis of N-((1R,3r,5 S,6S)-3-(2-hydroxyethyl)-6-(3-iodo-1-isopropyl-1H-pyrazol-5-yl)bicyclo[3.1.0]hexan-3-yl)-2-methylpropane-2-sulfinamide

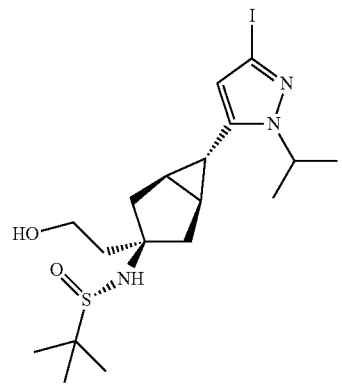 [SMILES: CC(C)n1nc(I)cc1[C@H]1[C@@H]2C[C@](CCO)(N[S@@](=O)C(C)(C)C)C[C@@H]21]

To an ice-cooled solution of ethyl 2-((1R,3r,5 S,6S)-3-((S)-1,1-dimethylethylsulfinamido)-6-(3-iodo-1-isopropyl-1H-pyrazol-5-yl)bicyclo[3.1.0]hexan-3-yl)acetate (2.15 g, 4.12 mmol) in tetrahydrofuran (40 mL) was added lithium borohydride (450 mg, 21 mmol). After stirring for 5 h at 0° C., the reaction was diluted with saturated aqueous ammonium chloride solution (50 mL). The resulting mixture was extracted with ethyl acetate (3×50 mL). The collected organic was washed with saturated aqueous sodium bicarbonate solution (30 mL), saturated aqueous sodium chloride solution (80 mL), dried over anhydrous sodium sulfate, filtered, and concentrated in vacuo. Purification by flash column chromatography (50% ethyl acetate in petroleum ether) provided a yellow solid (1.75 g, 88% yield). LCMS (ESI): [MH]$^+$=480.1.

Step 4—Synthesis of 2-((1R,3r,5S,6S)-3-((S)-1,1-dimethylethylsulfinamido)-6-(3-iodo-1-isopropyl-1H-pyrazol-5-yl)bicyclo[3.1.0]hexan-3-yl)ethyl methanesulfonate

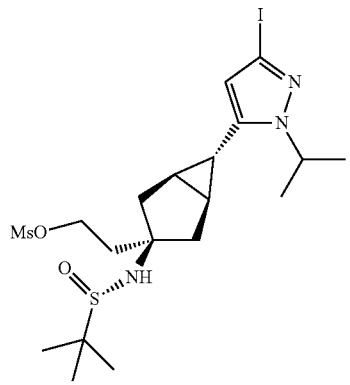 [SMILES: CC(C)n1nc(I)cc1[C@H]1[C@@H]2C[C@](CCOS(C)(=O)=O)(N[S@@](=O)C(C)(C)C)C[C@@H]21]

To an ice-cooled solution of (S)—N-((1R,3r,5S,6S)-3-(2-hydroxyethyl)-6-(3-iodo-1-isopropyl-1H-pyrazol-5-yl)bicyclo[3.1.0]hexan-3-yl)-2-methylpropane-2-sulfinamide (1.74 g, 3.63 mmol) and triethylamine (3.67 g, 36.3 mmol) in dichloromethane (35 mL) was added methanesulfonyl chloride (2.10 g, 18.3 mmol) dropwise. After 30 min, the reaction was concentrated in vacuo. Purification by flash column chromatography (50% ethyl acetate in petroleum ether) provided a yellow solid (1.28 g, 63% yield). LCMS (ESI): [MH]$^+$=557.9; $^1$H NMR (400 MHz, CDCl$_3$) δ: 5.92 (s, 1 H), 4.73-4.79 (m, 1 H), 4.51-4.54 (m, 1 H), 4.32-4.37 (m, 1 H), 3.84 (s, 1 H), 3.05 (s, 3 H), 2.56 (m, 1 H), 2.37-2.41 (m, 1 H), 2.27-2.31 (m, 1 H), 1.96-2.13 (m, 4 H), 1.63-1.67 (m, 2 H), 1.44-1.47 (m, 6 H), 1.26 (s, 9 H).

Step 5—Synthesis of (1'R,2r,5'S,6'S)-1-((S)-tert-butylsulfinyl)-6'-(3-iodo-1-isopropyl-1H-pyrazol-5-yl)spiro[azetidine-2,3'-bicyclo[3.1.0]hexane]

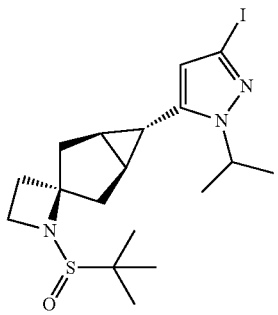 [SMILES: CC(C)n1nc(I)cc1[C@H]1[C@@H]2C[C@@]3(CCN3S(=O)C(C)(C)C)C[C@@H]21]

To an ice-cooled solution of 2-((1R,3r,5 S,6S)-3-((S)-1,1-dimethylethylsulfinamido)-6-(3-iodo-1-isopropyl-1H-pyrazol-5-yl)bicyclo[3.1.0]hexan-3-yl)ethyl methanesulfonate (1.28 g, 2.30 mmol) in N,N-dimethylformamide (2.5 mL) was added sodium hydride (185 mg, 4.62 mmol, 60% dispersion in mineral oil). After 1 h at 0° C., excess sodium hydride was quenched with water (20 mL). The resulting solution was extracted with ethyl acetate (3×30 mL). The collected organic was washed with saturated aqueous sodium chloride solution (30 mL), dried over anhydrous sodium sulfate, filtered, and concentrated in vacuo. Purification by flash column chromatography (30% ethyl acetate in petroleum ether) provided a white solid (750 mg, 71% yield). LCMS (ESI): [MH]$^+$=462.0.

Step 6—Synthesis of (1'R,2r,5'S,6'r)-6'-(3-iodo-1-isopropyl-1H-pyrazol-5-yl)spiro[azetidine-2,3'-bicyclo[3.1.0]hexane]

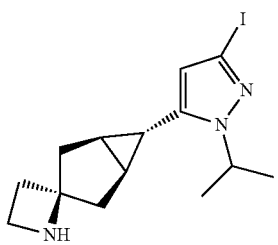 [SMILES: CC(C)n1nc(I)cc1[C@H]1[C@@H]2C[C@@]3(CCN3)C[C@@H]21]

To an ice-cooled solution of (1'R,2r,5'S,6'S)-1-((S)-tert-butylsulfinyl)-6'-(3-iodo-1-isopropyl-1H-pyrazol-5-yl)spiro[azetidine-2,3'-bicyclo[3.1.0]hexane] (0.750 g, 1.63 mmol) in ethanol (10 mL) was added 4M HCl in ethyl acetate (10 mL). After 1.5 h at 0° C., the reaction was concentrated in vacuo. The residue was partitioned between ethyl acetate (50 mL) and saturated aqueous sodium bicarbonate solution (50 mL). The heterogeneous solution was filtered, and the solids were sequentially rinsed with water (2×10 mL) and ethyl acetate (2×10 mL). The collected white solid was dried in vacuo (460 mg, 79% yield). LRMS (ESI): [MH]$^+$=357.8.

Step 7—Synthesis of (1'R,2r,5'S,6'r)-6'-(3-iodo-1-isopropyl-1H-pyrazol-5-yl)-1-(oxetan-3-yl)spiro[azetidine-2,3'-bicyclo[3.1.0]hexane]

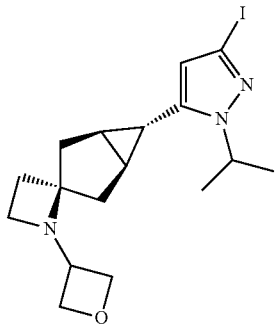 [SMILES: CC(C)n1nc(I)cc1[C@H]1[C@@H]2C[C@@]3(CCN3C3COC3)C[C@@H]21]

To a solution of (1'R,2r,5'S,6'r)-6'-(3-iodo-1-isopropyl-1H-pyrazol-5-yl)spiro[azetidine-2,3'-bicyclo[3.1.0]hexane] (110 mg, 0.31 mmol), 3-oxetanone (133 mg, 1.85 mmol) in methanol (2 mL) was added titanium (IV) isopropoxide (356 mg, 1.23 mmol). The reaction was heated at 60° C. for 2 h before cooling to 25° C. Sodium cyanoborohydride (116 mg, 1.85 mmol) was added, and the reaction was heated at 60° C. After 16 h, the reaction was diluted with water (10 mL), and the resulting suspension was filtered. The solids were rinsed with ethyl acetate (3×10 mL). The filtrate was extracted with ethyl acetate (2×10 mL). The collected organic was washed with saturated aqueous sodium chloride solution (10 mL), dried over anhydrous sodium sulfate, filtered, and concentrated in vacuo. Purification by preparative thin layer chromatography (ethyl acetate) afforded a yellow solid (65 mg, 51% yield). LCMS (ESI): [MH]$^+$=413.8.

Step 8—Synthesis of 5-(1-isopropyl-5-((1'R,2r,5'S,6'r)-1-(oxetan-3-yl)spiro[azetidine-2,3'-bicyclo[3.1.0]hexane]-6'-yl)-1H-pyrazol-3-yl)-3-(trifluoromethoxy)pyridin-2-amine To a mixture of (1'R,2r,5'S,6'r)-6'-(3-iodo-1-isopropyl-1H-pyrazol-5-yl)-1-(oxetan-3-yl)spiro[azetidine-2,3'-bicyclo[3.1.0]hexane] (0.060 g, 0.15 mmol), 5-(4,4,5,5-tetramethyl-1,3,2-dioxaborolan-2-yl)-3-(trifluoromethoxy)pyridin-2-amine (0.050 g, 0.17 mmol) and cesium carbonate (114 mg, 0.35 mmol) in 5:1 1,4-dioxane/water (1.8 mL) was added 1,1'-bis(diphenylphosphino)ferrocene-palladium(II) dichloride (11 mg, 0.015 mmol) under nitrogen. The resulting mixture was heated at 105° C. by microwave irradiation for 30 min. The reaction mixture was filtered, and the solids were rinsed with ethyl acetate (3×15 mL). The collected filtrate was concentrated in vacuo. Purification by preparative thin layer chromatography (1% methanol in ethyl acetate) followed by preparative HPLC afforded a yellow solid (33 mg, 50% yield). LRMS (ESI): [MH]$^+$=464.2; $^1$H NMR (400 MHz, CDCl$_3$), δ: 8.30 (s, 1 H), 7.81 (s, 1 H), 5.96 (s, 1 H), 4.78-4.68 (m, 2 H), 4.67-4.59 (m, 5 H), 4.05-4.00 (m, 1 H), 3.44-3.40 (m, 2 H), 2.27-2.19 (m, 4 H), 1.59 (m, 4 H), 1.54-1.52 (d, J=8 Hz, 6 H), 1.39 (m, 1 H).

General Method H

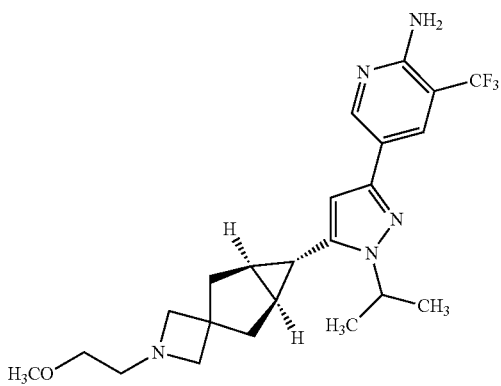 [SMILES: COCCN1CC2(C[C@@H]3[C@H](C2)[C@H]3c2cc(-c3cnc(N)c(C(F)(F)F)c3)nn2C(C)C)C1]

Preparation of 5-(1-isopropyl-5-((1'R,5'S,6'r)-1-(2-methoxyethyl)spiro[azetidine-3,3'-bicyclo[3.1.0]hexan]-6'-yl)-1H-pyrazol-3-yl)-3-(trifluoromethyl)pyridin-2-amine Step 1—Synthesis of (1 R,5 S,6r)-6-(3-iodo-1-isopropyl-1H-pyrazol-5-yl)bicyclo[3.1.0]hexane-3-carbaldehyde

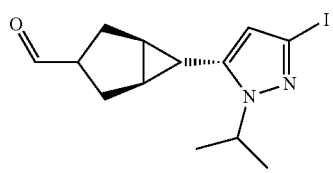

To an ice-cooled solution of 3-iodo-1-isopropyl-5-((1R,5S,6r)-spiro[bicyclo[3.1.0]hexane-3,2'-oxirane]-6-yl)-1H-pyrazole (1.5 g, 4.4 mmol) in dichloromethane (100 mL) was added boron trifluoride diethyl etherate (9 mL) under nitrogen. The cooling bath was removed. After 16 h, the reaction mixture diluted with saturated aqueous sodium bicarbonate solution (100 mL). The resulting mixture was extracted with dichloromethane (2×50 mL). The collected organic was washed with saturated aqueous sodium chloride solution (100 mL), dried over anhydrous sodium sulfate, filtered, and concentrated in vacuo. Purification by flash column chromatography (5% ethyl acetate in petroleum ether) provided a yellow oil (510 mg, 34% yield). LCMS (ESI): [MH]$^+$=344.9.

Step 2—Synthesis of ((1R,5S,6r)-6-(3-iodo-1-isopropyl-1H-pyrazol-5-yl)bicyclo[3.1.0]hexane-3,3-diyl)dimethanol

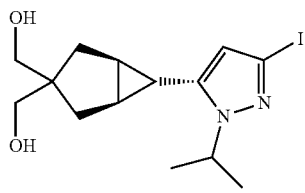

To a solution of (1R,5 S,6r)-6-(3-iodo-1-isopropyl-1H-pyrazol-5-yl)bicyclo[3.1.0]hexane-3-carbaldehyde (250 mg, 0.72 mmol) in tetrahydrofuran (3 mL) was added 50% wt/wt potassium hydroxide solution (2.6 mL) and paraformaldehyde (950 mg). The reaction was heated at 75° C. under nitrogen. After 7 h, the reaction was cooled to 0° C. and diluted with water (100 mL). The pH of the mixture was adjusted to ~7 with 2 M aqueous hydrochloric acid. The resulting mixture was extracted with ethyl acetate (4×25 mL). The collected organic was washed with saturated aqueous sodium chloride solution (30 mL), dried over anhydrous sodium sulfate, filtered, and concentrated in vacuo. Purification by flash column chromatography (50% ethyl acetate in petroleum ether) provided a yellow oil (150 mg, 55% yield). LCMS (ESI): [MH]$^+$=377.0. $^1$H NMR (400 MHz, CDCl$_3$) δ 5.90 (s, 1 H), 4.56-4.62 (m, 1 H), 3.62 (d, J=5.2 Hz, 4 H), 1.98-2.03 (dd, J=14.6 Hz, 5.0 Hz, 2 H), 1.64-1.67 (m, 4 H), 1.48 (d, J=6.4 Hz, 6 H), 1.40-1.41 (m, 1 H).

Step 3—Synthesis of ((1 R,5 S,6r)-6-(3-iodo-1-isopropyl-1H-pyrazol-5-yl)bicyclo[3.1.0]hexane-3,3-diyl)bis(methylene)bis(trifluoromethanesulfonate)

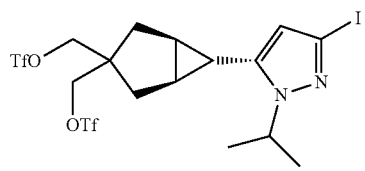

To a solution of ((1R,5S,6r)-6-(3-iodo-1-isopropyl-1H-pyrazol-5-yl)bicyclo[3.1.0]hexane-3,3-diyl)dimethanol (75 mg, 0.20 mmol) in dichloromethane (8 mL) was added triflate anhydride (450 mg, 1.6 mmol) and pyridine (0.090 g, 2.4 mmol) at −78° C. The cooling bath was removed and the reaction mixture was allowed to warm to room temperature. After 16 h, the reaction was concentrated in vacuo to provide a brown oil (160 mg). LCMS (ESI): [MH]$^+$=640.7.

Step 4—Synthesis of (1'R,5'S,6'r)-6'-(3-iodo-1-isopropyl-1H-pyrazol-5-yl)-1-(2-methoxyethyl)spiro[azetidine-3,3'-bicyclo[3.1.0]hexane]

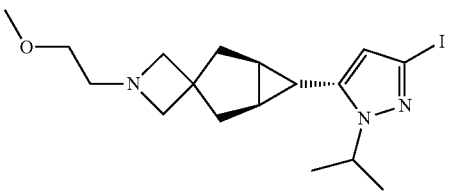

The solution of ((1R,5S,6r)-6-(3-iodo-1-isopropyl-1H-pyrazol-5-yl)bicyclo[3.1.0]hexane-3,3-diyl)bis(methylene)bis(trifluoromethanesulfonate) (130 mg, 0.20 mmol), 2-methoxyethanamine (46 mg, 0.61 mmol), diisopropylethylamine (105 mg, 0.81 mmol) in tetrahydrofuran (4 mL) was heated at 66° C. for 2 h. The reaction was diluted with water (10 mL), and the resulting mixture was extracted with ethyl acetate (3×15 mL). The collected organic was washed with saturated aqueous ammonium chloride solution (10 mL), saturated aqueous sodium chloride solution (20 mL), dried over anhydrous sodium sulfate, filtered, and concentrated in vacuo. Purification by preparative thin layer chromatography (9% methanol in ethyl acetate) provided the title compound as a yellow solid (25 mg, 30%). LCMS (ESI): [MH]⁺=415.8.

Step 5—Synthesis of 5-(1-isopropyl-5-((1'R,5'S,6'r)-1-(2-methoxyethyl)spiro[azetidine-3,3'-bicyclo[3.1.0]hexane]-6'-yl)-1H-pyrazol-3-yl)-3-(trifluoromethyl)pyridin-2-amine To a mixture of (1'R,5'S,6'r)-6'-(3-iodo-1-isopropyl-1H-pyrazol-5-yl)-1-(2-methoxyethyl)spiro[azetidine-3,3'-bicyclo[3.1.0]hexane] (35 mg, 0.084 mmol), 5-(4,4,5,5-tetramethyl-1,3,2-dioxaborolan-2-yl)-3-(trifluoromethyl)pyridin-2-amine (27 mg, 0.093 mmol) and cesium carbonate (0.060 g, 0.19 mmol) in 1,4-dioxane (9 mL) and water (1.8 mL) was added 1,1'-bis(diphenylphosphino)ferrocene-palladium(II) dichloride (6 mg, 0.008 mmol) under nitrogen. The mixture heated to 110° C. with microwave irradiation for 20 min. The reaction mixture was diluted with ethyl acetate (10 mL) and filtered. The filtrate was concentrated in vacuo. Purification by preparative thin layer chromatography (12.5% methanol in ethyl acetate) afforded a yellow solid (24.5 mg, 60% yield). LRMS (ESI): [MH]⁺=450.0; ¹H NMR (400 MHz, CDCl₃) δ: 8.53 (s, 1 H), 8.11 (s, 1 H), 6.03 (s, 1 H), 5.08 (s, 2 H), 4.51-4.57 (m, 1 H), 3.82 (t, J=4.4 Hz, 2 H), 3.37 (s, 3 H), 3.26 (t, J=4.2 Hz, 2 H), 2.20-2.24 (m, 2 H), 1.71 (s, 2 H), 1.51 (d, J=7.2 Hz, 6 H), 1.26-1.29 (m, 6 H), 0.98 (s, 1 H).

General Method I

Preparation of 6-(3-(6-amino-5-(trifluoromethyl)pyridin-3-yl)-1-isopropyl-1H-pyrazol-5-yl)bicyclo[3.1.0]hexan-2-ol (exo syn enantiomers)

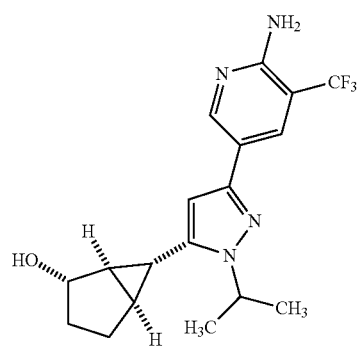

A solution of (±)-6-(3-iodo-1-isopropyl-1H-pyrazol-5-yl)bicyclo[3.1.0]hexan-2-ol (30 mg, 90.3 µmol), 5-(4,4,5,5-tetramethyl-1,3,2-dioxaborolan-2-yl)-3-(trifluoromethyl)pyridin-2-amine (39 mg, 0.14 mmol), 1,1'-bis(diphenylphosphino)ferrocene-palladium(II) dichloride (6 mg, 0.009 mmol) and cesium carbonate (59 mg, 0.18 mmol) in 1,4-dioxane (0.5 mL) and water (0.1 mL) was purged with nitrogen. The reaction mixture was heated to 110° C. by microwave irradiation for 20 min. The mixture was concentrated, and the resulting residue was diluted with ethyl acetate (2 mL), and the solution was filtered. The filtrate was concentrated. Purification by preparation HPLC followed by chiral SFC separation afforded the title compounds:
Enantiomer 1 (white solid, 2.4 mg, 7%)¹H NMR (400 MHz, CDCl₃) δ: 8.55 (s, 1 H), 8.12 (s, 1 H), 6.07 (s, 1 H), 4.97 (s, 2 H), 4.63-4.56 (m, 1 H), 4.47-4.46 (d, J=4.8 Hz, 1 H), 2.20-2.11 (m, 1 H), 1.96-1.94 (m, 1 H), 1.80-1.74 (m, 4 H), 1.54-1.52 (m, 6 H), 1.43 (m, 1 H) LCMS: [MH]⁺=367.0.

Enantiomer 2 (white solid, 2.8 mg, 8%)¹H NMR (400 MHz, CDCl₃) δ: 8.55 (s, 1 H), 8.12 (s, 1 H), 6.07 (s, 1 H), 4.97 (s, 2 H), 4.61-4.56 (m, 1 H), 4.47-4.46 (d, J=4.4 Hz, 1 H), 2.20-2.11 (m, 1 H), 1.94-1.90 (m, 1 H), 1.80-1.74 (m, 4 H), 1.54-1.52 m, 6 H), 1.43 (m, 1 H) LCMS: [MH]⁺=367.0.

General Method J

Preparation of (±)-5-(1-isopropyl-5-(4-methyloctahydro-2H-cyclopropa[4,5]cyclopenta[1,2-b][1,4]oxazin-6-yl)-1H-pyrazol-3-yl)-3-(trifluoromethyl)pyridin-2-amine

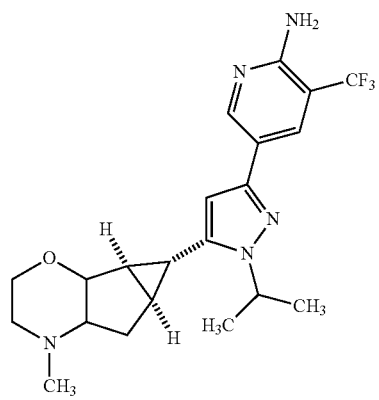

Step 1-(±)-6-(3-iodo-1-isopropyl-1H-pyrazol-5-yl)-3-(methylamino)-exo-bicyclo[3.1.0]hexan-2-ol

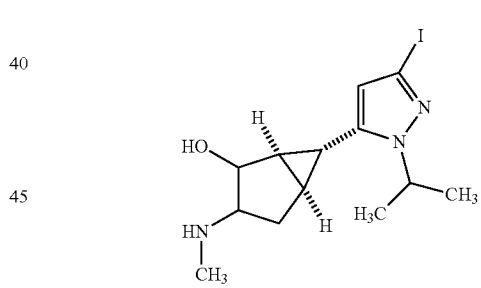

A reaction vessel charged with 3-iodo-1-isopropyl-5-(3-oxatricyclo[4.1.0.0²,⁴]heptan-7-yl)-1H-pyrazole (exo-syn enantiomers) (3.9 g, 12 mmol), methylamine methanol solution (10 mL), and ethanol (10 mL) was sealed and heated at 80° C. After 16 h, the reaction mixture was cooled to room temperature and concentrated in vacuo. The resulting residue was diluted with dichloromethane (30 mL), and the solution was washed with saturated aqueous sodium chloride solution, dried over sodium sulfate, filtered, and concentrated in vacuo. Purification by flash column (25% ethyl acetate in petroleum→5% methanol in ethyl acetate) afforded the crude title compound as an orange oil (2.2 g, 56% purity by LCMS) which was used without further purification. LCMS (ESI): [MH]⁺=362.0.

Step 2—(±)-2-chloro-N-(2-hydroxy-6-(3-iodo-1-isopropyl-1H-pyrazol-5-yl)-exo-bicyclo[3.1.0]hexan-3-yl)-N-methylacetamide

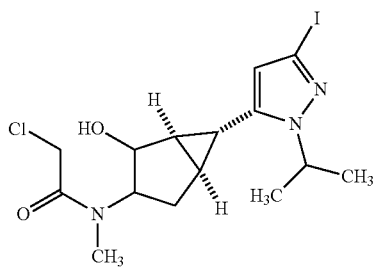

To a solution of (±)-6-(3-iodo-1-isopropyl-1H-pyrazol-5-yl)-3-(methylamino)-exo-bicyclo[3.1.0]hexan-2-ol (2.2 g, 3.4 mmol, 56% purity), triethylamine (690 mg, 6.8 mmol), in anhydrous dichloromethane (200 mL) was added 2-chloroacetyl chloride (390 mg, 3.4 mmol) in dichloromethane (1 mL) at −48° C. under nitrogen. After 2 h, the reaction mixture was diluted with water (50 mL). The collected organic was washed with saturated aqueous sodium chloride solution, dried over sodium sulfate, filtered, and concentrated in vacuo. Purification by flash column chromatography (50% ethyl acetate in petroleum ether) afforded a colorless oil (660 mg, 44% yield). LCMS (ESI): [MH]$^+$=437.8.

Step 3—(±)-6-(3-iodo-1-isopropyl-1H-pyrazol-5-yl)-4-methylhexahydro-2H-cyclopropa[4,5]cyclopenta[1,2-b][1,4]oxazin-3(6bH)-one

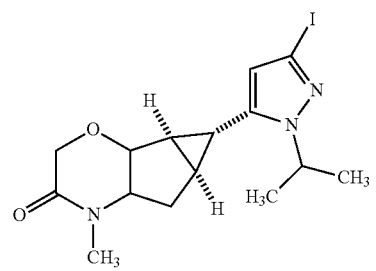

To an ice-cooled solution of (±)-2-chloro-N-(2-hydroxy-6-(3-iodo-1-isopropyl-1H-pyrazol-5-yl)-exo-bicyclo[3.1.0]hexan-3-yl)-N-methylacetamide (0.10 g, 0.23 mmol) in dichloromethane (10 mL) was added potassium tert-butoxide (39 mg, 0.35 mmol). After 1 h, the reaction mixture was concentrated. Purification by preparative thin layer chromatography (ethyl acetate) afforded a colorless oil (50 mg) which was used without further purification. LCMS (ESI): [MH]$^+$=401.9

Step 4—(±)-6-(3-(6-amino-5-(trifluoromethyl)pyridin-3-yl)-1-isopropyl-1H-pyrazol-5-yl)-4-methylhexahydro-2H-cyclopropa[4,5]cyclopenta[1,2-b][1,4]oxazin-3(6bH)-one

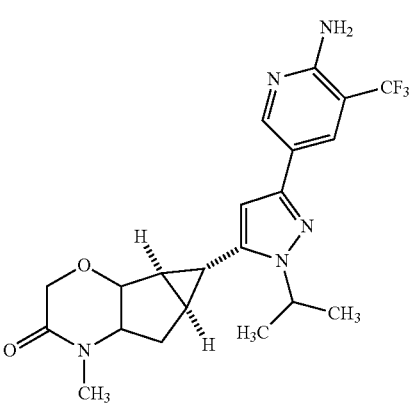

A mixture of (±)-6-(3-iodo-1-isopropyl-1H-pyrazol-5-yl)-4-methylhexahydro-2H-cyclopropa[4,5]cyclopenta[1,2-b][1,4]oxazin-3(6bH)-one (0.050 g, 0.12 mmol), 5-(4,4,5,5-tetramethyl-1,3,2-dioxaborolan-2-yl)-3-(trifluoromethyl)pyridin-2-amine (54 mg, 0.19 mmol), cesium carbonate (78 mg, 0.24 mmol), and 1,1'-bis(diphenylphosphino)ferrocenepalladium(II) dichloride (9 mg, 0.01 mmol) in 1.4-dioxane (2 mL) and water (0.5 mL) was purged with nitrogen. The mixture was heated to 110° C. by microwave irradiation for 30 min. The reaction was concentrated in vacuo, and the resulting residue was purified by preparative thin layer chromatography (ethyl acetate) to afford a white solid (40 mg, 77% yield).

Step 5: (±)-5-(1-isopropyl-5-(4-methyloctahydro-2H-cyclopropa[4,5]cyclopenta[1,2-b][1,4]oxazin-6-yl)-1H-pyrazol-3-yl)-3-(trifluoromethyl)pyridin-2-amine To a stirred solution of (±)-6-(3-(6-amino-5-(trifluoromethyl)pyridin-3-yl)-1-isopropyl-1H-pyrazol-5-yl)-4-methylhexahydro-2H-cyclopropa[4,5]cyclopenta[1,2-b][1,4]oxazin-3(6bH)-one (0.040 g, 0.092 mmol) in tetrahydrofuran (5 mL) was added borane tetrahydrofuran complex (5 mL, 5 mmol). The reaction mixture was heated at 70° C. for 2 h under nitrogen. Methanol was added and the resulting solution was concentrated in vacuo. Purification by preparative HPLC afforded a 1.5:1 mixture of diastereomers (15 mg, 39%). LCMS (ESI): [MH]$^+$=401.9 $^1$H NMR (400 MHz, Methanol-d$_4$) δ: 8.52 (d, J=3.6 Hz, 1 H), 8.32 (s, 1 H), 8.13 (s, 1 H), 6.31 (s, 0.6 H), 6.22 (s, 0.4 H), 4.85-4.82 (m, 1H), 4.06-4.02 (m, 1 H), 3.85-3.70 (m, 1.6 H), 3.50-3.45 (m, 0.4 H), 3.40-3.30 (m, 0.6 H), 3.20-3.17 (m, 0.4 H), 2.90-2.85 (m, 0.6 H), 2.79-2.65 (m, 3.4 H), 2.60 (s, 1 H), 2.37-2.36 (m, 1 H), 2.05-1.95 (m, 2 H), 1.90-1.80 (m, 1 H), 1.55-1.52 (m, 6 H).

General Method K

Preparation of (±)-3-(difluoromethoxy)-5-(1-isopropyl-5-((3aS,3bR,4S,4aR,5aR)-2-methyloctahydro-1H-cyclopropa[3,4]cyclopenta[1,2-c]pyrrol-4-yl)-1H-pyrazol-3-yl)pyridin-2-amine

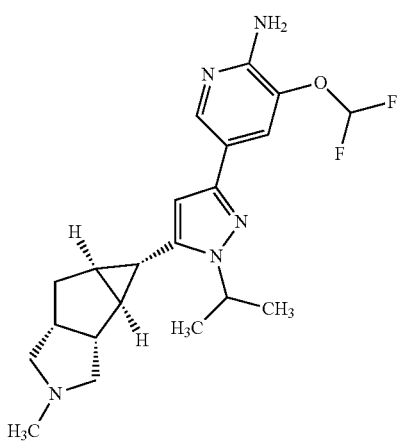 [SMILES: CC(C)n1nc(-c2cnc(N)c(OC(F)F)c2)cc1[C@H]1[C@@H]2C[C@H]3CN(C)C[C@H]3[C@@H]21]

Step 1—Synthesis of (±)-(3 aS,3bR,4S,4aR)-4-(3-iodo-1-isopropyl-1H-pyrazol-5-yl)-2-methyloctahydro-1H-cyclopropa[3,4]cyclopenta[1,2-c]pyrrole

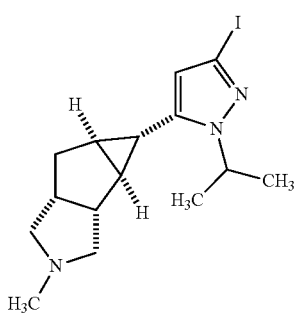

To an ice-cooled solution of trimethylamine (10 mL, methanol solution) in methanol (10 mL) was added 30% hydrogen peroxide (10 mL). The reaction mixture was warmed to room temperature for 16 h. The solvent was removed in vacuo to afford crude trimethylamine oxide (9.5 g) as a white solid.

To an ice-cooled solution of trimethylamine oxide (717 mg, 9.55 mmol) and 5-((1S,5R,6S)-bicyclo[3.1.0]hex-2-en-6-yl)-3-iodo-1-isopropyl-1H-pyrazole (2.0 g, 6.4 mmol) in tetrahydrofuran (10 mL) under nitrogen was added lithium diisopropylamide (28 mmol). After 1 h at 0° C., the reaction mixture was diluted with water (50 mL), and the resulting solution was extracted with ethyl acetate (2×20 mL). The collected organic was washed with saturated aqueous sodium chloride solution, dried over anhydrous sodium sulfate, filtered, and concentrated. Purification by flash column chromatography (17% ethyl acetate in petroleum ether) afforded a brown oil (110 mg, 4.7%). LCMS (ESI): [MH]$^+$=372.2.

Step 2—Synthesis of (±)-3-(difluoromethoxy)-5-(1-isopropyl-5-((3 aS,3bR,4S,4aR,5aR)-2-methyloctahydro-1H-cyclopropa[3,4]cyclopenta[1,2-c]pyrrol-4-yl)-1H-pyrazol-3-yl)pyridin-2-amine A mixture of (±)-(3aS,3bR,4S,4aR)-4-(3-iodo-1-isopropyl-1H-pyrazol-5-yl)-2-methyloctahydro-1H-cyclopropa[3,4]cyclopenta[1,2-c]pyrrole (0.10 g, 0.27 mmol), 5-(4,4,5,5-tetramethyl-1,3,2-dioxaborolan-2-yl)-3-(trifluoromethyl)pyridin-2-amine (92 mg, 0.32 mmol), cesium carbonate (176 mg, 0.540 mmol) and bis(diphenylphosphino)ferrocene-palladium(II) dichloride (20 mg, 0.03 mmol) in 5:1 1,4-dioxane/water (6 mL) was purged with nitrogen. The reaction mixture was heated at 80° C. under nitrogen. After 2h, the reaction mixture was concentrated, and the resulting residue was purified by preparative HPLC to afford the title compound as a white solid (15 mg, 13% yield). LCMS (ESI): [MH]$^+$=404.0. $^1$H NMR (400 MHz, CDCl$_3$) δ 8.39 (s, 1 H), 8.11 (s, 1 H), 7.69 (s, 1 H), 6.85 (t, J=73.6 Hz, 1 H), 6.14 (s, 1 H), 4.75-4.70 (m, 1 H), 3.50-3.74 (m, 2 H), 3.32-3.29 (m, 2 H), 3.18-3.16 (m, 1 H), 2.92 (s, 3 H), 2.90-2.80 (m, 1H), 2.38-2.25 (m, 1 H), 1.86-1.75 (m, 3 H), 1.63 (t, J=6.4 Hz, 1 H), 1.53 (m, 6 H)

General Method L

Preparation of 5-(5-((1 R,5 S,6r)-3-fluoro-3-(methoxymethyl)bicyclo[3.1.0]hexan-6-yl)-1-isopropyl-1H-pyrazol-3-yl)-3-(trifluoromethyl)pyridin-2-amine

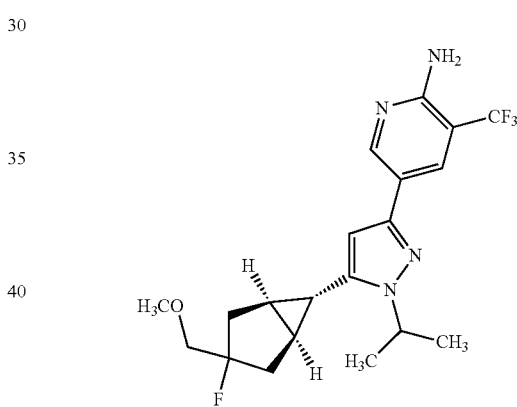

Step 1—Synthesis of ((1 R,5 S,6r)-3-fluoro-6-(3-iodo-1-isopropyl-1H-pyrazol-5-yl)bicyclo[3.1.0]hexan-3-yl)methanol

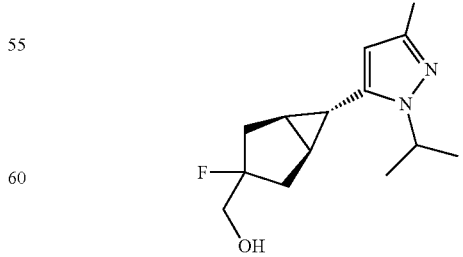

To an ice-cooled solution of 3-iodo-1-isopropyl-5-((1R,5S,6r)-spiro[bicyclo[3.1.0]hexane-3,2'-oxiran]-6-yl)-1H-pyrazole (172 mg, 0.500 mmol) in dichloromethane (2 mL)

was added triethylamine trihydrofluoride (1 mL). After 2 h, the reaction was diluted with saturated aqueous sodium bicarbonate solution, and the resulting mixture was extracted with 10:1 dichloromethane/methanol (2×15 mL). The collected organic was washed with saturated aqueous sodium chloride solution and concentrated to provide crude ((1R,5S,6r)-3-fluoro-6-(3-iodo-1-isopropyl-1H-pyrazol-5-yl)bicyclo[3.1.0]hexan-3-yl)methanol as an oil (210 mg) which was used without further purification. LCMS (ESI): [MH]+=344.9.

Step 2—Synthesis of 5-((1R,5S,6r)-3-fluoro-3-(methoxymethyl)bicyclo[3.1.0]hexan-6-yl)-3-iodo-1-isopropyl-1H-pyrazole

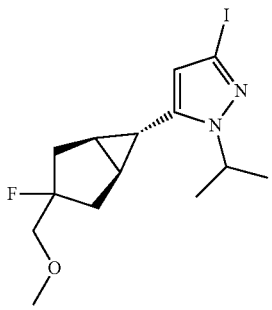 [SMILES: COCC1(F)C[C@@H]2[C@H](C1)[C@H]2c1cc(I)nn1C(C)C]

To an ice-cooled solution of ((1R,5S,6r)-3-fluoro-6-(3-iodo-1-isopropyl-1H-pyrazol-5-yl)bicyclo[3.1.0]hexan-3-yl)methanol (210 mg, 0.58 mmol) in N,N-dimethylformamide (2 mL) was added sodium hydride (46 mg, 1.2 mmol, 60% in mineral oil) followed by iodomethane (830 mg, 5.8 mmol). The mixture was stirred at 0° C. for 2 h. Water was added to the reaction mixture, and the resulting mixture was extracted with ethyl acetate (2×20 mL). The collected organic was washed with saturated aqueous sodium chloride solution and concentrated. Purification by flash column chromatography (9% ethyl acetate in petroleum ether) provided product as an oil (200 mg, 92% yield). LCMS (ESI): [MH]+=379.1.

Step 3—5-(5-((1 R,5 S,6r)-3-fluoro-3-(methoxymethyl)bicyclo[3.1.0]hexan-6-yl)-1-isopropyl-1H-pyrazol-3-yl)-3-(trifluoromethyl)pyridin-2-amine To a solution of 5-((1R,5S,6r)-3-fluoro-3-(methoxymethyl)bicyclo[3.1.0]hexan-6-yl)-3-iodo-1-isopropyl-1H-pyrazole (180 mg, 0.48 mmol), 5-(4,4,5,5-tetramethyl-1,3,2-dioxaborolan-2-yl)-3-(trifluoromethyl)pyridin-2-amine (151 mg, 0.524 mmol) and cesium carbonate (310 mg, 0.95 mmol) in 5:1 dioxane/water (5 mL) was added 1,1'-bis(diphenylphosphino)ferrocene-palladium(II)dichloride (35 mg, 0.048 mmol). The mixture was purged with nitrogen and heated to 110° C. by microwave irradiation for 30 min. The reaction was concentrated in vacuo, and the resulting residue was purified by preparative HPLC to give product as a yellow solid (54 mg, 27% yield). LCMS (ESI): [MH]+=413.2. 1H NMR (400 MHz, CDCl3) δ: 8.56 (s, 1 H), 8.38 (s, 1 H), 7.51 (br s, 2 H), 6.07 (s, 1 H), 4.59 (t, J=6.4 Hz, 1 H), 3.47-3.41 (m, 2 H), 3.39 (s, 3 H), 2.49-2.34 (m, 2 H), 2.08-1.94 (m, 2 H), 1.83 (m, 2 H), 1.48 (d, J=6.8 Hz, 6 H), 1.39 (m, 1 H).

General Method M

Preparation of 1-(((1R,3r,5S,6r)-6-(3-(6-amino-5-(difluoromethoxy)pyridin-3-yl)-1-isopropyl-1H-pyrazol-5-yl)bicyclo[3.1.0]hexan-3-yl)oxy)-2-methylpropan-2-ol

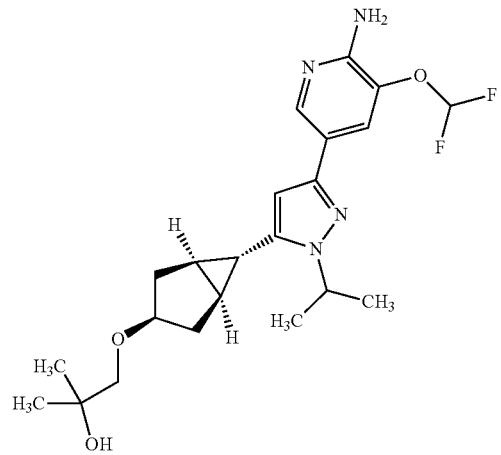 [SMILES: CC(C)n1nc(-c2cnc(N)c(OC(F)F)c2)cc1[C@H]1[C@@H]2C[C@H](OCC(C)(C)O)C[C@@H]21]

Step 1—Synthesis of 1-(((1R,5S,6r)-6-(3-iodo-1-isopropyl-1H-pyrazol-5-yl)bicyclo[3.1.0]hexan-3-yl)oxy)-2-methylpropan-2-ol

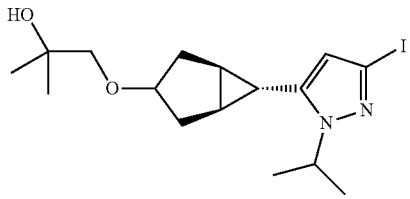 [SMILES: CC(C)n1nc(I)cc1[C@H]1[C@@H]2CC(OCC(C)(C)O)C[C@@H]21]

To an ice-cooled solution of (1R,5S,6r)-6-(3-iodo-1-isopropyl-1H-pyrazol-5-yl)bicyclo[3.1.0]hexan-3-ol (0.40 g, 1.5 mmol) in anhydrous N,N-dimethylformamide (5 mL) was added sodium hydride (0.180 g, 4.52 mmol, 60% in mineral oil). The reaction mixture was warmed to room temperature. After 1 h, the reaction mixture was cooled to 0° C. before the addition of 2,2-dimethyloxirane (180 mg, 15 mmol). The reaction mixture was warmed to room temperature for 16 h. The reaction mixture diluted with water, and the resulting solution was extracted with ethyl acetate (2×20 mL). The collected organic was washed with saturated aqueous sodium chloride solution (2×10 mL), dried over anhydrous sodium sulfate, filtered and concentrated to afford the title compound as a yellow oil (300 mg) which was used without further purification. LCMS (ESI): [MH]+=405.1.

Step 2—Synthesis of 1-(((1R,3r,5 S,6r)-6-(3-(6-amino-5-(difluoromethoxy)pyridin-3-yl)-1-isopropyl-1H-pyrazol-5-yl)bicyclo[3.1.0]hexan-3-yl)oxy)-2-methylpropan-2-ol To a solution of 1-(((1R,5 S,6r)-6-(3-iodo-1-isopropyl-1H-pyrazol-5-yl)bicyclo[3.1.0]hexan-3-yl)oxy)-2-methylpropan-2-ol (96 mg, 0.24 mmol), 5-(4,4,5,5-tetramethyl-1,3,2-dioxaborolan-2-yl)-3-(trifluoromethyl)pyridin-2-amine (74.7 mg, 0.261 mmol) and cesium carbonate (155 mg, 0.475 mmol) in 5:1 dioxane/water (2 mL) was added 1,1'-bis(diphenylphosphino)ferrocene-palladium(II) dichloride (17 mg, 0.024 mmol). The mixture was purged with nitrogen, and heated to 100° C. by microwave irradiation for 15 min. The reaction was concentrated in vacuo, and resulting residue was purified by preparative HPLC to give product as a white solid (5 mg, 5% yield). LCMS (ESI): [MH]+=437.2; $^1$H NMR (400 MHz, CDCl$_3$) 8.19 (s, 1H), 8.06 (d, J=1.2 Hz, 1H), 7.13 (t, J=72 Hz, 1H), 6.29 (s, 1H), 4.82-4.72 (m, 1H), 4.02 (t, J=5.6 Hz, 1H), 3.21 (s, 2H), 2.20-2.06 (m, 5H), 1.69 (m, 2H), 1.50 (d, J=6.8 Hz, 6H), 1.20 (s, 6H).

General Method N

Preparation of 3-(difluoromethoxy)-5-(1-isopropyl-5-((1R,5 S,6r)-spiro[bicyclo[3.1.0]hexane-3,3'-oxetan]-6-yl)-1H-pyrazol-3-yl)pyridin-2-amine

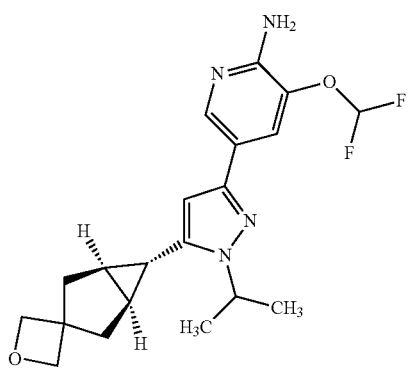 [SMILES: CC(C)n1nc(-c2cnc(N)c(OC(F)F)c2)cc1[C@H]1[C@@H]2CC3(COC3)C[C@@H]21]

Step 1—Synthesis of (Z)-1,4-dichlorobut-2-ene

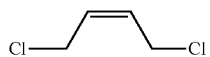

To an ice-cooled solution of (Z)-but-2-ene-1,4-diol (150 g, 1.7 mol) was added thionyl chloride (250 mL) over 40 min. The resulting mixture was warmed to 20° C. After 16 h, the reaction mixture was diluted with water (500 mL), and the resulting mixture was extracted with ethyl acetate (2 L). The collected organic was dried over anhydrous sodium sulfate, filtered, and concentrated to give product as a brown oil (180 g, 84% yield).

Step 2—Synthesis of diethyl cyclopent-3-ene-1,1-dicarboxylate

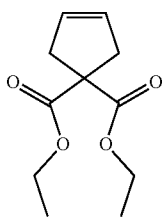

To an ice-cooled solution of diethyl malonate (75.01 g, 468.3 mmol) in tetrahydrofuran (1.5 L) was added sodium hydride (28.1 g, 1.17 mmol) portionwise. After 1 h, (Z)-1,4-dichlorobut-2-ene (75.0 g, 468 mmol) in tetrahydrofuran (500 mL) was added over 40 min at 0° C. After 1 h, the reaction mixture was diluted with saturated aqueous ammonia chloride solution (500 mL), and the resulting mixture was extracted with ethyl acetate (2×2 L). The collected organic was dried over anhydrous sodium sulfate, filtered, and concentrated. Purification by flash column chromatography (petroleum ether) provided product as a yellow oil (85 g, 86% yield).

Step 3—Synthesis of cyclopent-3-ene-1,1-diyldimethanol

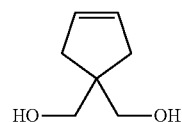

To an ice-cooled suspension of lithium aluminum hydride (25.54 g, 672.8 mmol) in tetrahydrofuran (2 L) was added a solution of diethyl cyclopent-3-ene-1,1-dicarboxylate (42.0 g, 198 mmol) in tetrahydrofuran (100 mL) over 30 min. The reaction mixture was warmed to 26° C. After 2 h, the reaction was diluted sequentially with water (26 mL), 3M aqueous sodium hydroxide solution (26 mL), and water (78 mL). The mixture was stirred at 0° C. for 15 min and filtered. The filtrate was concentrated to afford product as a colorless oil (45 g, 89% yield).

Step 4—Synthesis of (1-(hydroxymethyl)cyclopent-3-en-1-yl)methyl 4-methylbenzenesulfonate

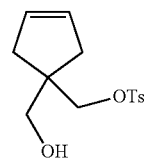 [SMILES: Cc1ccc(S(=O)(=O)OCC2(CO)CC=CC2)cc1]

To an ice-cooled solution of cyclopent-3-ene-1,1-diyldimethanol (44.0 g, 343 mmol), triethylamine (34.7 g, 343 mmol) and 4-dimethylaminopyridine (4.19 g, 34.3 mmol) in dichloromethane (2 L) was added tosyl chloride (58.9 g, 309 mmol) portionwise. The reaction mixture was warmed to 26° C. After 16 h, the mixture was concentrated, and the resulting residue was purified by flash column chromatography (30% ethyl acetate in petroleum ether)) to afford product as a brown solid (34 g, 35% yield).

Step 5—Synthesis of 2-oxaspiro[3.4]oct-6-ene

A suspension of sodium hydride (8.66 g, 361 mmol) in tetrahydrofuran (1.5 L) and (1-(hydroxymethyl)cyclopent-3-en-1-yl)methyl 4-methylbenzenesulfonate (34 g, 60.21 mmol) was heated at 60° C. for 16 h. The reaction was diluted with saturated aqueous ammonia chloride, and the resulting solution was extracted with dichloromethane (2×2 L). The collected organic was concentrated, and the resulting oil was distilled to provide a colorless oil (3 g, 20% yield).

Step 6—Synthesis of ethyl spiro[bicyclo[3.1.0]hexane-3,3'-oxetane]-6-carboxylate

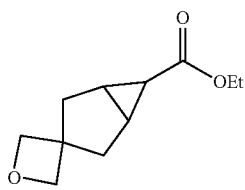 [SMILES: CCOC(=O)C1C2CC3(COC3)CC21]

To a solution of 2-oxaspiro[3.4]oct-6-ene (1.0 g, 9.2 mmol) and copper sulfate (145 mg, 0.907 mmol) in toluene (5 mL) was added a solution of ethyl 2-diazoacetate (2.64 g, 22.7 mmol) in toluene (20 mL) at 100° C. over 16 h. The reaction mixture was concentrated, and the resulting residue was purified by flash column chromatography (10% ethyl acetate in petroleum ether) to afford product as a brown oil (1.5 g, 84% yield).

Step 7—Synthesis of spiro[bicyclo[3.1.0]hexane-3,3'-oxetane]-6-carboxylic Acid

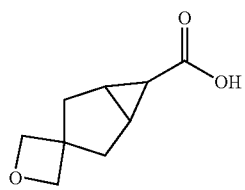 [SMILES: O=C(O)C1C2CC3(COC3)CC21]

To a solution of ethyl spiro[bicyclo[3.1.0]hexane-3,3'-oxetane]-6-carboxylate (1.5 g, 7.6 mmol) in ethanol (15 mL) was added sodium hydroxide (917 mg, 22.9 mmol) in water (5 mL). After 16 h, the reaction mixture was concentrated, and the resulting residue was dissolved with water (20 mL). The resulting solution was extracted with ethyl acetate (15 mL). The aqueous layer was acidified with 1 M aqueous HCl solution to pH=3, and the aqueous solution was extracted with dichloromethane (20 mL). The collected organic was dried over anhydrous sodium sulfate, filtered, and concentrated to provide a white solid (0.80 g, 62% yield).

Step 8—Synthesis of N-methoxy-N-methylspiro[bicyclo[3.1.0]hexane-3,3'-oxetane]-6-carboxamide

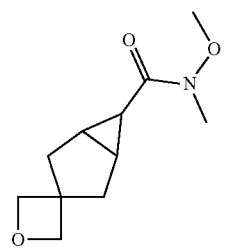

To a solution of spiro[bicyclo[3.1.0]hexane-3,3'-oxetane]-6-carboxylic acid (0.70 g, 4.2 mmol) in dichloromethane (21 mL) was added carbonyl diimidazole (1.35 g, 8.33 mmol) at 15° C. After 30 min, N,O-dimethylhydroxylamine hydrochloride (487 mg, 4.99 mmol) was added in one portion. After 16 h, the reaction mixture was diluted with dichloromethane (50 mL), and the resulting mixture was washed with saturated aqueous sodium chloride solution (2×20 mL). The collected organic was concentrated, and the resulting residue was purified by flash column chromatography (30% ethyl acetate in petroleum ether) to afford product as a white solid (0.30 g, 34% yield).

Step 9—Synthesis of 1-(spiro[bicyclo[3.1.0]hexane-3,3'-oxetan]-6-yl)ethanone

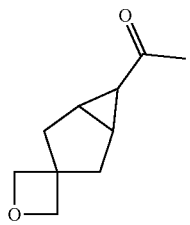

To an ice-cooled solution of N-methoxy-N-methylspiro[bicyclo[3.1.0]hexane-3,3'-oxetane]-6-carboxamide (0.30 g, 1.4 mmol) in tetrahydrofuran (15 mL) was added methylmagnesium bromide (1 mL, 3M in tetrahydrofuran) dropwise. After 1 h, the reaction mixture was diluted with saturated aqueous ammonia chloride solution (10 mL), and the resulting solution was extracted with ethyl acetate (3×20 mL). The collected organic was concentrated to provide product as a brown oil (220 mg, 93% yield).

Step 10—Synthesis of 3,3-bis(methylthio)-1-(spiro[bicyclo[3.1.0]hexane-3,3'-oxetan]-6-yl)prop-2-en-1-one

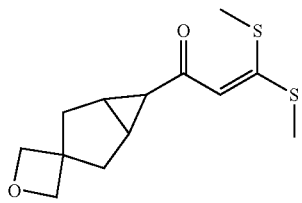 [SMILES: CSC(=CC(=O)C1C2CC3(COC3)CC21)SC]

To an ice-cooled solution of 1-(spiro[bicyclo[3.1.0]hexane-3,3'-oxetan]-6-yl)ethanone (0.20 g, 1.2 mmol) in tetrahydrofuran (10 mL) was added lithium bis(trimethylsilyl)amide (2.5 mL, 1M in THF). After 30 min, carbon disulfide (91.6 mg 1.20 mmol) was added dropwise. After 30 min, iodomethane (976 mg 2.65 mmol) was added dropwise. The mixture was warmed to 20° C. for 1 h. The reaction mixture was diluted with saturated aqueous ammonia chloride solution, and the resulting solution was extracted with ethyl acetate (5×10 mL). The collected organic was concentrated, and the resulting residue was purified by flash column chromatography (30% ethyl acetate in petroleum ether) to afford a yellow solid (270 mg, 83% yield).

Step 11—Synthesis of (E)-3-(6-amino-5-(difluoromethoxy)pyridin-3-yl)-3-(methylthio)-1-(spiro[bicyclo[3.1.0]hexane-3,3'-oxetan]-6-yl)prop-2-en-1-one

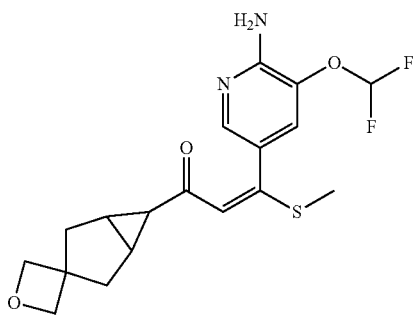 [SMILES: CS/C(=C/C(=O)C1C2CC3(COC3)CC21)c1cnc(N)c(OC(F)F)c1]

To a solution of 3,3-bis(methylthio)-1-(spiro[bicyclo[3.1.0]hexane-3,3'-oxetan]-6-yl)prop-2-en-1-one (250 mg, 924 mmol) in 6:1 tetrahydrofuran/water (3.5 mL) was added 3-(difluoromethoxy)-5-(4,4,5,5-tetramethyl-1,3,2-dioxaborolan-2-yl)pyridin-2-amine (317 mg, 1.11 mmol), copper (I) thiophene-2-carboxylate (353 mg, 1.85 mmol), cesium carbonate (602 mg, 1.85 mmol), and bis(triphenylphosphine)palladium(II) dichloride (65 mg, 92 mmol). The reaction mixture was heated at 110° C. with microwave irradiation for 1.5 h. The reaction mixture was concentrated, and the resulting residue was purified by flash column chromatography (ethyl acetate) to afford product as a white solid (0.080 g, 23%).

Step 12—Synthesis of 3-(difluoromethoxy)-5-(5-(spino[bicyclo[3.1.0]hexane-3,3'-oxetan]-6-yl)-1H-pyrazol-3-yl)pyridin-2-amine

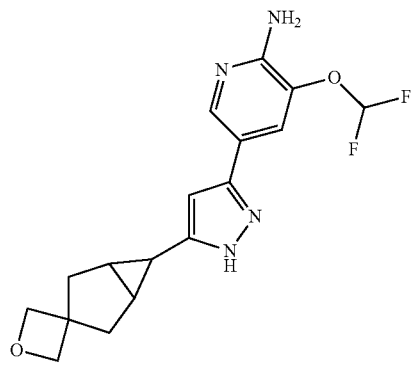 [SMILES: Nc1ncc(-c2cc(C3C4CC5(COC5)CC43)[nH]n2)cc1OC(F)F]

A solution of (E)-3-(6-amino-5-(difluoromethoxy)pyridin-3-yl)-3-(methylthio)-1-(spiro[bicyclo[3.1.0]hexane-3,3'-oxetan]-6-yl)prop-2-en-1-one (0.080 g, 0.21 mmol) in ethanol (2 mL) was added hydrazine hydrate (2 mL). The reaction mixture was heated at 100° C. with microwave irradiation for 1 h. The reaction mixture was concentrated to provide product (200 mg), which was used without further purification.

Step 13—Synthesis of 3-(difluoromethoxy)-5-(1-isopropyl-5-((1R,5 S,6r)-spiro[bicyclo[3.1.0]hexane-3,3'-oxetan]-6-yl)-1H-pyrazol-3-yl)pyridin-2-amine A solution of crude 3-(difluoromethoxy)-5-(5-(spiro[bicyclo[3.1.0]hexane-3,3'-oxetan]-6-yl)-1H-pyrazol-3-yl)pyridin-2-amine (0.20 g, 0.21 mmol), 2-bromopropane (78 mg, 0.63 mmol), and cesium carbonate (561 mg, 1.72 mmol) in N,N-dimethylformamide (2 mL) was heated at 110° C. for 1.5 h. The reaction mixture was concentrated, and the resulting residue was purified by preparative HPLC to afford product as a yellow solid (5 mg, 6% yield over two steps) LCMS (ESI): [MH]$^+$=391. $^1$H NMR (400 MHz, DMSO-$d_6$) δ: 8.13 (s, 1 H), 7.66 (s, 1 H), 7.38-7.01 (t, 1 H), 6.57 (brs, 1 H), 6.29 (s, 2 H), 4.62-4.56 (m, 1 H), 4.49 (s, 2 H), 4.39 (s, 2 H), 2.76 (m, 1H), 2.44-2.37 (m, 2 H), 2.05-2.02 (m, 2 H), 1.60 (m, 2 H), 1.40-1.39 (m, 6 H).

General Method O

Preparation of 3-(difluoromethoxy)-5-(5-((1R,5S,6r)-3-((dimethylamino)methyl)-3-fluorobicyclo[3.1.0]hexan-6-yl)-1-isopropyl-1H-pyrazol-3-yl)pyridin-2-amine

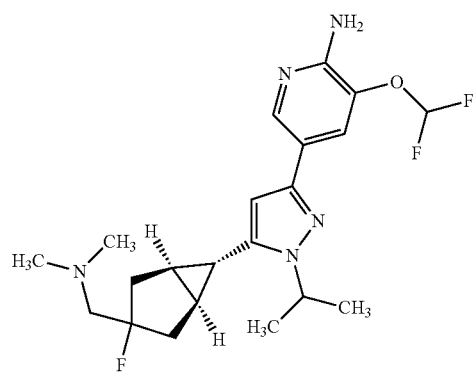

Step 1—Synthesis of (1R,5S,6r)-3-((dimethylamino)methyl)-6-(3-iodo-1-isopropyl-1H-pyrazol-5-yl)bicyclo[3.1.0]hexan-3-ol

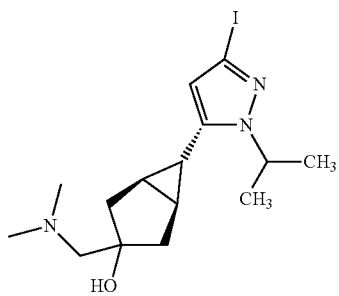

A solution of 3-iodo-1-isopropyl-5-((1R,5 S,6r)-spiro[bicyclo[3.1.0]hexane-3,2'-oxiran]-6-yl)-1H-pyrazole (138 mg, 0.401 mmol), dimethylamine hydrochloride (97 mg, 1.2 mmol) and N,N-diisopropylethylamine (155 mg, 1.20 mmol) in ethanol (4 mL) was stirred at 80° C. After 2 h, reaction mixture was concentrated, and the resulting residue was partitioned between dichloromethane (5 mL) and water (5 mL). The collected organic was dried over anhydrous sodium sulfate, filtered and concentrated to afford product as a brown solid (150 mg, 96% yield). LCMS (ESI): [MH]$^+$=390.0.

Step 2—Synthesis of 1-((1R,5S,6r)-3-fluoro-6-(3-iodo-1-isopropyl-1H-pyrazol-5-yl)bicyclo[3.1.0]hexan-3-yl)-N,N-dimethylmethanamine

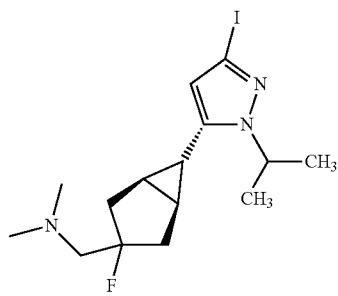

To an ice-cooled solution of (1 R,5 S,6r)-3-((dimethylamino)methyl)-6-(3-iodo-1-isopropyl-1H-pyrazol-5-yl)bicyclo[3.1.0]hexan-3-ol (0.070 g, 0.18 mmol) in N,N-dimethylformamide (5 mL) was added diethylaminosulfur trifluoride (87 mg, 0.54 mmol). After 2 h, the reaction mixture was diluted with saturated aqueous sodium bicarbonate solution (10 mL), and the resulting solution was extracted with dichloromethane (3×10 mL). The collected organic was dried over anhydrous sodium sulfate, filtered, and concentrated. Purification by flash column chromatography (50% ethyl acetate in petroleum ether) provided product as a brown solid (150 mg, 57% yield). LCMS (ESI): [MH]$^+$=391.8.

Step 3—Synthesis of 3-(difluoromethoxy)-5-(5-((1R,5 S,6r)-3-((dimethylamino)methyl)-3-fluorobicyclo[3.1.0]hexan-6-yl)-1-isopropyl-1H-pyrazol-3-yl)pyridin-2-amine A mixture of 1-((1R,5 S,6r)-3-fluoro-6-(3-iodo-1-isopropyl-1H-pyrazol-5-yl)bicyclo[3.1.0]hexan-3-yl)-N,N-dimethylmethanamine (0.050 g, 0.13 mmol), 3-(difluoromethoxy)-5-(4,4,5,5-tetramethyl-1,3,2-dioxaborolan-2-yl)pyridin-2-amine (40 mg, 0.14 mmol) and cesium carbonate (104.32 mg, 0.32 mmol) in 5:1 1,4-dioxane/water (2.5 mL) was added 1,1'-bis(diphenylphosphino)ferrocene-palladium(II) dichloride (9.4 mg, 0.013 mmol). The reaction mixture was heated to 100° C. by microwave irradiation for 30 min. The reaction mixture was concentrated in vacuo, and the resulting residue was purified by preparative HPLC to afford product (2.7 mg, 10% yield). $^1$H NMR (400 MHz, CDCl$_3$) δ 8.24 (s, 1 H), 7.71 (s, 1 H), 6.56 (t, J$_{HF}$=73.6 Hz, 1 H), 6.00 (s, 1 H), 4.78-4.63 (m, 3 H), 2.73-2.71 (m, 2 H), 2.58-2.52 (m, 7 H), 2.10-2.02 (m, 3 H), 1.90 (s, 2 H), 1.52 (d, J=6.8 Hz, 6 H), 1.26 (s, 1 H). LCMS (ESI): [MH]$^+$=423.9.

General Method P

Preparation of N-((1R,5S,6r)-6-(3-(6-amino-5-(trifluoromethyl)pyridin-3-yl)-1-isopropyl-1H-pyrazol-5-yl)bicyclo[3.1.0]hexan-3-yl)-N-methylacetamide

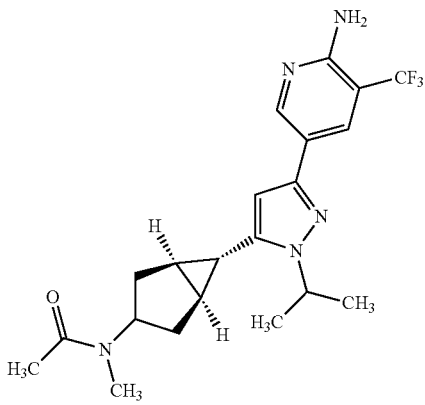

Step 1—Synthesis of (1R,5S,6r)-6-(3-iodo-1-isopropyl-1H-pyrazol-5-yl)-N-methylbicyclo[3.1.0]hexan-3-amine

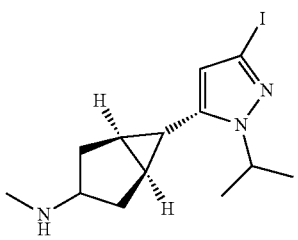

To a solution of (1R,5S,6r)-6-(3-iodo-1-isopropyl-1H-pyrazol-5-yl)bicyclo[3.1.0]hexan-3-one (150 mg, 0.45 mmol) in methanol (4 mL) was added methylamine hydrochloride (167 mg, 1.35 mmol), acetic acid (135 mg, 2.25 mmol) followed by sodium cyanoborohydride (142 mg, 2.25 mmol). The mixture was stirred at 50° C. for 16 h under a nitrogen atmosphere. The reaction mixture was diluted with water (30 mL), and the resulting solution was extracted with ethyl acetate (2×30 mL). The collected organic was concentrated in vacuo to afford crude product as a yellow oil (75 mg) which was used without further purification.

Step 2—Synthesis of N-((1R,5S,6r)-6-(3-iodo-1-isopropyl-1H-pyrazol-5-yl)bicyclo[3.1.0]hexan-3-yl)-N-methylacetamide

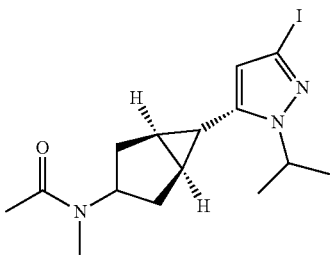

To an ice-cooled solution of crude (1R,5S,6r)-6-(3-iodo-1-isopropyl-1H-pyrazol-5-yl)-N-methylbicyclo[3.1.0]hexan-3-amine (75 mg, 0.22 mmol) and triethylamine (67 mg, 0.66 mmol) in dichloromethane (10 mL) was added acetyl chloride (34 mg, 0.44 mmol). After 30 min, the reaction mixture was diluted with water (20 mL), and the resulting solution was extracted with dichloromethane (2×30 mL). The collected organic was concentrated in vacuo, and the resulting residue was purified by preparative thin layer chromatography (ethyl acetate) to provide product as a yellow oil (0.060 g, 71% yield).

Step 3—Synthesis of N-((1 R,5 S,6r)-6-(3-(6-amino-5-(trifluoromethyl)pyridin-3-yl)-1-isopropyl-1H-pyrazol-5-yl)bicyclo[3.1.0]hexan-3-yl)-N-methylacetamide To a solution of N-((1 R,5 S,6r)-6-(3-iodo-1-isopropyl-1H-pyrazol-5-yl)bicyclo[3.1.0]hexan-3-yl)-N-methylacetamide (0.060 g, 0.15 mmol), 5-(4,4,5,5-tetramethyl-1,3,2-dioxaborolan-2-yl)-3-(trifluoromethyl)pyridin-2-amine (52 mg, 0.18 mmol) and cesium carbonate (98 mg, 0.30 mmol) in 5:1 1,4-dioxane/water (2.5 mL) was added 1,1'-bis(diphenylphosphino)ferrocene-palladium(II)dichloride (14 mg, 0.02 mmol) under nitrogen. The reaction mixture was heat to 110° C. by microwave irradiation for 30 min. The reaction mixture was concentrated in vacuo, and the resulting residue was purified by preparative HPLC to provide product as a white solid (17 mg, 27% yield). $^1$H NMR (400 MHz, Methanol-$d_4$) δ 8.50 (s, 1H), 8.10 (s, 1H), 6.17 (s, 1H), 4.84-4.81 (m, 2H), 2.92-2.78 (m, 3H), 2.38-2.31 (m, 2H), 2.18-2.08 (m, 3H), 1.81-1.68 (m, 5H), 1.54 (d, J=6.4 Hz, 6H).

General Method Q

Preparation of 3-(difluoromethoxy)-5-(1-isopropyl-5-((1R,3s,5S,6r)-3-methoxybicyclo[3.1.0]hexan-6-yl)-1H-pyrazol-3-yl)pyridin-2-amine

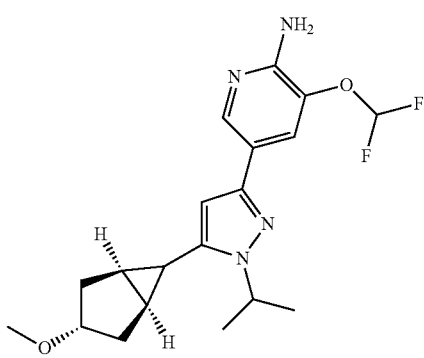 [SMILES: CO[C@H]1C[C@@H]2C(c3cc(-c4cnc(N)c(OC(F)F)c4)nn3C(C)C)[C@@H]2C1]

Step 1—Synthesis of 3-iodo-1-isopropyl-5-((1R,3s,5S,6r)-3-methoxybicyclo[3.1.0]hexan-6-yl)-1H-pyrazole

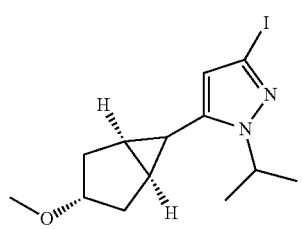 [SMILES: CO[C@H]1C[C@@H]2C(c3cc(I)nn3C(C)C)[C@@H]2C1]

To an ice-cooled solution of sodium hydride (11 mg, 0.15 mmol) in N,N-dimethylformamide (3 mL) was added (1R,3s,5S,6r)-6-(3-iodo-1-isopropyl-1H-pyrazol-5-yl)bicyclo[3.1.0]hexan-3-ol (0.050 g, 0.15 mmol). After 10 min, iodomethane (64 mg, 0.45 mmol) was added, and the resulting mixture was warmed to 12° C. After 16 h, the reaction mixture was diluted with ethyl acetate (30 mL), and the resulting solution was washed with saturated aqueous sodium chloride (5×20 mL). The collected organic was concentrated to afford product as a yellow oil (0.040 g, 77% yield).

Step 2—Synthesis of 3-(difluoromethoxy)-5-(1-isopropyl-5-((1R,3s,5S,6r)-3-methoxybicyclo[3.1.0]hexan-6-yl)-1H-pyrazol-3-yl)pyridin-2-amine To a solution of 3-iodo-1-isopropyl-5-((1R,3s,5S,6r)-3-methoxybicyclo[3.1.0]hexan-6-yl)-1H-pyrazole (52 mg, 0.15 mmol), 3-(difluoromethoxy)-5-(4,4,5,5-tetramethyl-1,3,2-dioxaborolan-2-yl)pyridin-2-amine (52 mg, 0.18 mmol) and cesium carbonate (98 mg, 0.30 mmol) in 5:1 1,4-dioxane/water (2 mL) was added 1,1'-bis(diphenylphosphino)ferrocene-palladium(II)dichloride (11 mg, 0.015 mmol) under nitrogen. The reaction mixture was heated to 110° C. for 30 min by microwave irradiation. The reaction mixture was concentrated, and the resulting residue was purified by preparative-HPLC to give product as a yellow solid (13 mg, 25% yield). LCMS (ESI): [M+H]$^+$=379.2. $^1$H NMR (400 MHz, Methanol-$d_4$) δ 8.14 (s, 1H), 7.71 (s, 1H), 6.87 (t, J=73.2 Hz, 1H), 6.12 (s, 1H), 4.76-4.70 (m, 1H), 3.81-3.74 (m, 1H), 3.31 (s, 3H), 2.42-2.37 (m, 2H), 1.84-1.79 (m, 2H), 1.69 (m, 2H), 1.57 (m, 1H), 1.50 (d, J=6.8 Hz, 6H).

General Method R

Preparation of (1 R,3r,5 S,6r)-6-(3-(6-amino-5-(trifluoromethyl)pyridin-3-yl)-1-isopropyl-1H-pyrazol-5-yl)bicyclo[3.1.0]hexane-3-carbonitrile and (1 R,3 s,5 S,6r)-6-(3-(6-amino-5-(trifluoromethyl)pyridin-3-yl)-1-isopropyl-1H-pyrazol-5-yl)bicyclo[3.1.0]hexane-3-carbonitrile

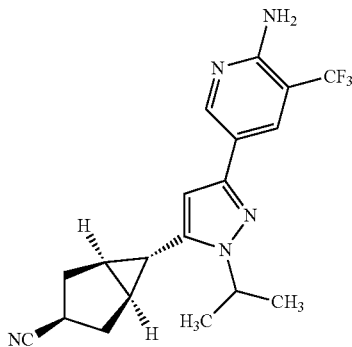

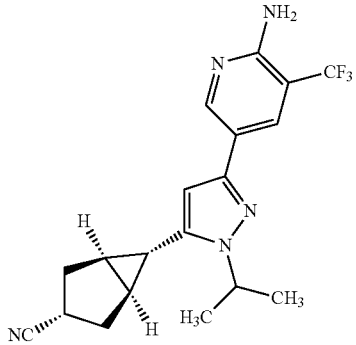

177

Step 1—Synthesis of (1R,5 S,6r)-6-(3-iodo-1-isopropyl-1H-pyrazol-5-yl)bicyclo[3.1.0]hexane-3-carbonitrile

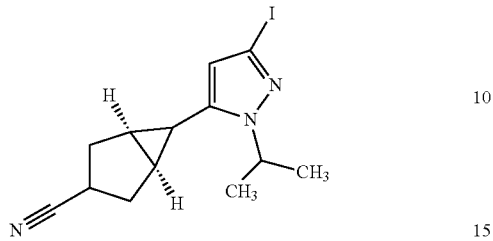

To a solution of toluenesulfonylmethyl isocyanide (141 mg, 0.72 mmol) in tetrahydrofuran (15 mL) was added potassium tert-butoxide (1.5 mL, 1.5 mmol) over 3 min at −70° C. After 15 min, a solution of (1R,5S,6r)-6-(3-iodo-1-isopropyl-1H-pyrazol-5-yl)bicyclo[3.1.0]hexan-3-one (150 mg, 0.45 mmol) in tetrahydrofuran (3 mL) was added to the reaction. After 1.5 h, methanol (6 mL) was added, and the resulting mixture was heated to reflux. After 30 min, the reaction solution was diluted with saturated aqueous ammonium chloride solution (15 mL), and the resulting mixture was extracted with ethyl acetate (3×20 mL). The collected organic was dried over anhydrous sodium sulfate, filtered, and concentrated. Purification by flash column chromatography (18% ethyl acetate in petroleum ether) provided product (115 mg, 75% yield). LCMS (ESI) [MH]$^+$=342.0.

Step 2—Synthesis of (1 R,3r,5 S,6r)-6-(3-(6-amino-5-(trifluoromethyl)pyridin-3-yl)-1-isopropyl-1H-pyrazol-5-yl)bicyclo[3.1.0]hexane-3-carbonitrile and (1R,3s,5S,6r)-6-(3-(6-amino-5-(trifluoromethyl)pyridin-3-yl)-1-isopropyl-1H-pyrazol-5-yl)bicyclo[3.1.0]hexane-3-carbonitrile The a microwave vial charged with (1R,5S,6r)-6-(3-iodo-1-isopropyl-1H-pyrazol-5-yl)bicyclo[3.1.0]hexane-3-carbonitrile (150 mg, 0.44 mmol), 5-(4,4,5,5-tetramethyl-1,3,2-dioxaborolan-2-yl)-3-(trifluoromethyl)pyridin-2-amine (139 mg, 0.48 mmol) and cesium carbonate (359 mg, 1.1 mmol) in 5:1 1,4-dioxane/water (2.5 mL) was added 1,1'-bis(diphenylphosphino)ferrocene-palladium(II) dichloride (32 mg, 0.044 mmol) under nitrogen. The vial was sealed and heated to 100° C. for 30 min by microwave irradiation. The reaction mixture was concentrated in vacuo, and the resulting residue was purified by preparative HPLC to afford product:

Diastereomer 1 (16 mg, 14% yield) $^1$H NMR (400 MHz, CDCl$_3$) δ 8.54 (s, 1 H), 8.11-8.10 (m, 1 H), 6.05 (s, 1 H), 4.96 (s, 2 H), 4.57-4.54 (m, 1 H), 2.57-2.46 (m, 3 H), 2.31-2.28 (m, 2 H), 1.81-1.80 (m, 2 H), 1.59-1.51 (m, 7 H).

Diastereomer 2 (32 mg, 28% yield)$^1$H NMR (400 MHz, CDCl$_3$) δ 8.56 (m, 1 H), 8.12 (m, 1 H), 6.03 (s, 1 H), 4.95 (s, 2 H), 4.67-4.63 (m, 1 H), 3.13-3.10 (m, 1 H), 2.38-2.37 (m, 4 H), 2.12-2.10 (m, 1 H), 1.83 (m, 2 H), 1.58-1.55 (m, 6 H). LCMS: [MH]$^+$=376.2.

178

General Method S

Preparation of 5-(1-isopropyl-5-((1R,5 S,6r)-4'-methylspiro[bicyclo[3.1.0]hexane-3,2'-morpholin]-6-yl)-1H-pyrazol-3-yl)-3-(trifluoromethyl)pyridin-2-amine

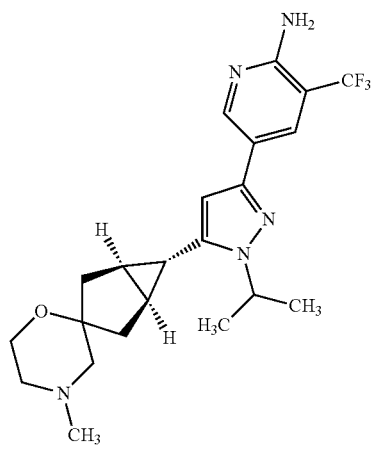

Step 1—Synthesis of 2-chloro-N-(((1 R,5 S,6r)-3-hydroxy-6-(3-iodo-1-isopropyl-1H-pyrazol-5-yl)bicyclo[3.1.0]hexan-3-yl)methyl)-N-methylacetamide

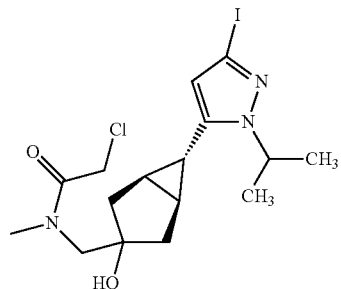

To an ice-cooled solution of (1R,5S,6r)-6-(3-iodo-1-isopropyl-1H-pyrazol-5-yl)-3 ((methylamino)methyl)bicyclo[3.1.0]hexan-3-ol (360 mg, 0.96 mmol) and diisopropylethylamine (248 mg, 1.92 mmol) in dichloromethane (10 mL) was added 2-chloroacetyl chloride (129 mg, 1.15 mmol). After 2 h, the reaction mixture was diluted with water (8 mL), and the resulting solution was extracted with dichloromethane (3×10 mL). The collected organic was dried over anhydrous sodium sulfate, filtered, and concentrated. Purification by flash column chromatography (50% ethyl acetate in petroleum ether) provide product (290 mg, 67% yield). LCMS (ESI) [MH]$^+$=451.8.

Step 2—Synthesis of (1R,5 S,6r)-6-(3-iodo-1-isopropyl-1H-pyrazol-5-yl)-4'-methylspiro[bicyclo[3.1.0]hexane-3,2'-morpholin]-5'-one

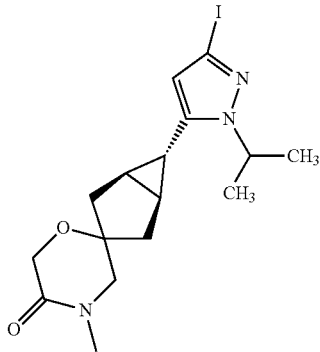

To an ice-cooled solution of 2-chloro-N-(((1 R,5 S,6r)-3-hydroxy-6-(3-iodo-1-isopropyl-1H-pyrazol-5-yl)bicyclo[3.1.0]hexan-3-yl)methyl)N-methylacetamide (290 mg, 0.64 mmol) in N,N-dimethylformamide (7 mL) was added sodium hydride (77 mg, 1.9 mmol). After 2 h, the reaction mixture was diluted with saturated aqueous ammonium chloride solution (10 mL), and the resulting solution was extracted with 2-methoxy-2-methylpropane (3×15 mL). The collected organic was dried over anhydrous sodium sulfate, filtered, and concentrated. Purification by flash column chromatography (66% ethyl acetate in petroleum ether) provided product (150 mg, 57% yield). LCMS (ESI) [MH]$^+$=415.9.

Step 3—Synthesis of (1 R,5 S,6r)-6-(3-iodo-1-isopropyl-1H-pyrazol-5-yl)-4'-methylspiro[bicyclo[3.1.0]hexane-3,2'-morpholine]

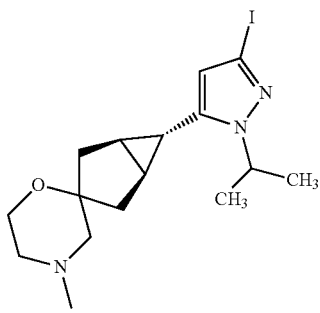 [SMILES: CC(C)n1nc(I)cc1[C@H]1[C@@H]2CC3(C[C@@H]21)CN(C)CCO3]

A solution of (1R,5S,6r)-6-(3-iodo-1-isopropyl-1H-pyrazol-5-yl)-4'-methylspiro[bicyclo[3.1.0]hexane-3,2'-morpholin]-5'-one (124 mg, 0.3 mmol) in tetrahydrofuran (10 mL) was added borane (3 mL, 1M in tetrahydrofuran). The reaction mixture was refluxed for 2 h under nitrogen. The reaction mixture was cooled to 0° C., and methanol (3 mL) followed by 2 M aqueous HCl (2 mL) were sequentially added. The resulting mixture was refluxed for 1 h. After cooling to room temperature, the reaction mixture was added 10% sodium hydroxide aqueous solution. The mixture was extracted with ethyl acetate (3×30 mL), and the collected organic was concentrated. Purification by flash column chromatography (50% ethyl acetate in petroleum ether) provided product (150 mg, 57% yield). LCMS (ESI) [MH]$^+$=401.8.

Step 4—Synthesis of 5-(1-isopropyl-5-((1R,5 S,6r)-4'-methylspiro[bicyclo[3.1.0]hexane-3,2'-morpholin]-6-yl)-1H-pyrazol-3-yl)-3-(trifluoromethyl)pyridin-2-amine To a microwave vial charged with (1R,5 S,6r)-6-(3-iodo-1-isopropyl-1H-pyrazol-5-yl)-4'-methylspiro[bicyclo[3.1.0]hexane-3,2'-morpholine] (0.110 g, 0.274 mmol), 5-(4,4,5,5-tetramethyl-1,3,2-dioxaborolan-2-yl)-3-(trifluoromethyl)pyridin-2-amine (86.9 mg, 0.302 mmol), and cesium carbonate (223 mg, 0.685 mmol) in 5:1 1,4-dioxane/water (2.5 mL) was added 1,1'-bis(diphenylphosphino)ferrocene-palladium(II) dichloride (0.020 mg, 0.027 mmol) under nitrogen. The vial was capped, and the mixture was heated at 100° C. by microwave irradiation for 30 min. The reaction mixture was concentrated in vacuo, and the resulting residue was purified by preparative HPLC to afford product (31 mg, 36% yield): LCMS (ESI): [MH]$^+$=436.2; $^1$H NMR (400 MHz, CDCl$_3$) δ 11.20 (s, 2 H), 8.45 (s, 1 H), 8.30 (s, 2 H), 8.14 (s, 1 H), 5.97 (s, 1 H), 5.64 (s, 2 H), 4.63-4.60 (m, 1 H), 3.90 (s, 2 H), 2.81-2.75 (m, 4 H), 2.53 (s, 3 H), 2.33-2.29 (m, 2 H), 2.06 (s, 3H), 1.67 (s, 2 H), 1.51 (d, J=6.0 Hz, 6 H).

General Method T

Preparation of 3-(difluoromethoxy)-5-(5-((1R,3r,5 S,6r)-3-fluorobicyclo[3.1.0]hexan-6-yl)-1-isopropyl-1H-pyrazol-3-yl)pyridin-2-amine and 3-(difluoromethoxy)-5-(5-((1R,3 s,5 S,6r)-3-fluorobicyclo[3.1.0]hexan-6-yl)-1-isopropyl-1H-pyrazol-3-yl)pyridin-2-amine

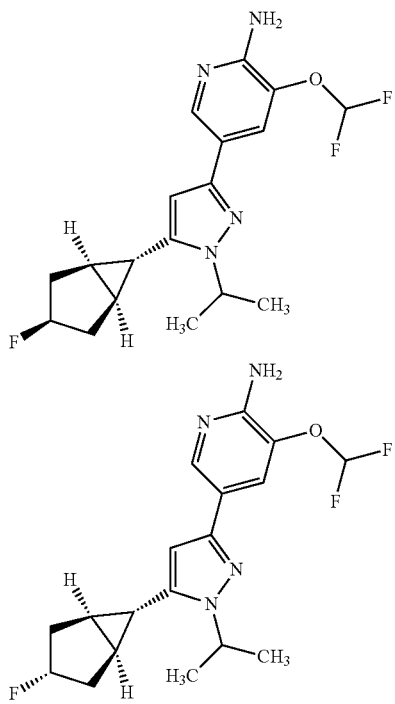

Step 1—Synthesis of (1R,3r,5S,6r)-6-(3-iodo-1-isopropyl-1H-pyrazol-5-yl)bicyclo[3.1.0]hexan-3-ol and (1R,3s,5S,6r)-6-(3-iodo-1-isopropyl-1H-pyrazol-5-yl)bicyclo[3.1.0]hexan-3-ol

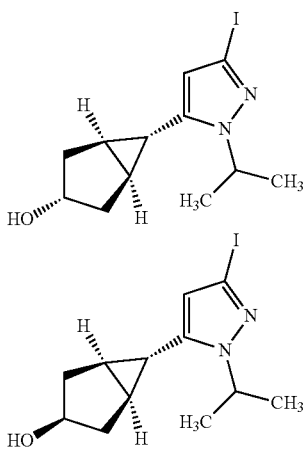

To an ice-cooled solution of (1R,5S,6r)-6-(3-iodo-1-isopropyl-1H-pyrazol-5-yl)bicyclo[3.1.0]hexan-3-one (25 g, 76 mmol) in 9:1 tetrahydrofuran/water (3 L) was added L-selectride (115 mL, 115 mmol) slowly under a nitrogen atmosphere. The reaction mixture was maintained at <10° C. After 6 h, 2 M HCl aqueous solution (150 mL) was added to the reaction mixture, and the resulting solution was concentrated in vacuo. The resulting residue was dissolved in water (400 mL), and the aqueous solution was extracted with ethyl acetate (3×500 mL). The collected organic was washed with saturated aqueous sodium chloride solution (2×100 mL), dried over anhydrous sodium sulfate, filtered, and concentrated in vacuo. Purification by flash column chromatography (16% ethyl acetate in petroleum ether) afforded (1R,3r,5S,6r)-6-(3-iodo-1-isopropyl-1H-pyrazol-5-yl)bicyclo[3.1.0]hexan-3-ol (17 g, 67% yield) and (1R,3s,5S,6r)-6-(3-iodo-1-isopropyl-1H-pyrazol-5-yl)-bicyclo[3.1.0]hexan-3-ol (6 g, 23% yield). LCMS (ESI) [MH]$^+$=333.0.

Step 2—Synthesis of 5-((1R,3s,5S,6r)-3-fluorobicyclo[3.1.0]hexan-6-yl)-3-iodo-1-isopropyl-1H-pyrazole

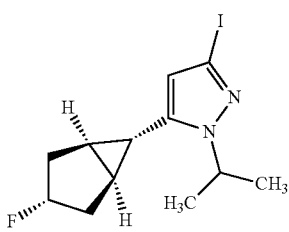 [SMILES: CC(C)n1nc(I)cc1[C@H]1[C@@H]2C[C@@H](F)C[C@@H]21]

To a solution of (1R,3r,5S,6r)-6-(3-iodo-1-isopropyl-1H-pyrazol-5-yl)bicyclo[3.1.0]hexan-3-ol (0.050 g, 0.15 mmol) in dichloromethane (2 mL) was added diethylaminosulfur trifluoride (2 mL) at 15° C. After 16 h, saturated aqueous sodium bicarbonate solution was added to the reaction mixture. The mixture was further diluted with water (15 mL), and the resulting solution was extracted with dichloromethane (3×15 mL). The collected organic was washed with saturated aqueous sodium chloride solution (15 mL), dried over anhy-drous sodium sulfate, filtered, and concentrated in vacuo to afford crude product as a brown solid (40 mg) which was used without further purification. LCMS (ESI) [MH]$^+$=334.7.

Synthesis of 5-((1R,3r,5S,6r)-3-fluorobicyclo[3.1.0]hexan-6-yl)-3-iodo-1-isopropyl-1H-pyrazole

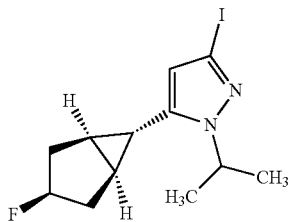 [SMILES: CC(C)n1nc(I)cc1[C@H]1[C@@H]2C[C@H](F)C[C@@H]21]

Reaction of (1R,3s,5S,6r)-6-(3-iodo-1-isopropyl-1H-pyrazol-5-yl)bicyclo[3.1.0]hexan-3-ol (0.050 mg, 0.15 mmol) following the procedure for the preparation of 5-((1R,3 s,5 S,6r)-3-fluorobicyclo[3.1.0]hexan-6-yl)-3-iodo-1-isopropyl-1H-pyrazole afforded the crude title compound as a brown solid (50 mg, 80% purity). LCMS (ESI) [MH]$^+$=334.7.

Step 3—Synthesis of 3-(difluoromethoxy)-5-(5-((1R, 3 s,5 S,6r)-3-fluorobicyclo[3.1.0]hexan-6-yl)-1-isopropyl-1H-pyrazol-3-yl)pyridin-2-amine To a microwave vial charged with 5-((1R,3s,5S,6r)-3-fluorobicyclo[3.1.0]hexan-6-yl)-3-iodo-1-isopropyl-1H-pyrazole (0.040 g, 0.12 mmol), 3-(difluoromethoxy)-5-(4,4,5,5-tetramethyl-1,3,2-dioxaborolan-2-yl)pyridin-2-amine (41 mg, 0.14 mmol) and cesium carbonate (120 mg, 0.36 mmol) in 5:1 1,4-dioxane/water (2 mL) was added 1,1'-bis(diphenylphosphino)ferrocene-palladium(II) dichloride (9 mg, 0.01 mmol) under nitrogen. The vial was sealed and heated by microwave irradiation at 120° C. for 30 min. The reaction mixture was concentrated in vacuo, and the residue was dissolved in ethyl acetate (20 mL). The resulting solution was washed sequentially with water (2×5 mL) and saturated aqueous sodium chloride solution (5 mL). The collected organic was dried over anhydrous sodium sulfate, filtered, and concentrated in vacuo. Purification by preparative HPLC afforded product as a white solid (8 mg, 18% yield). LCMS (ESI): [MH]$^+$=367.0; $^1$H NMR (400 MHz, Methanol-d4) δ 8.13 (d, J=1.6 Hz, 1 H), 7.70 (s, 1H), 6.87 (t, J$_{HF}$=73.6 Hz, 1 H), 6.13 (s, 1 H), 5.13-5.09 (m, 1 H), 4.74-4.68 (m, 1H), 2.37-2.13 (m, 4 H), 1.78 (s, 2 H), 1.52-1.48 (m, 7H).

Synthesis of 3-(difluoromethoxy)-5-(5-((1R,3r,5 S,6r)-3-fluorobicyclo[3.1.0]hexan-6-yl)-1-isopropyl-1H-pyrazol-3-yl)pyridin-2-amine Reaction of 5-((1R,3r,5 S,6r)-3-fluorobicyclo[3.1.0]hexan-6-yl)-3-iodo-1-isopropyl-1H-pyrazole (50 mg, 80% purity) following the procedure for the preparation of 3-(difluoromethoxy)-5-(5-((1R,3 s,5 S,6r)-3-fluorobicyclo[3.1.0]hexan-6-yl)-1-isopropyl-1H-pyrazol-3-yl)pyridin-2-amine afforded the title compound as a white solid (9 mg, 16% yield). LCMS (ESI): [MH]+=367.2; $^1$H NMR (400 MHz, Methanol-d4) δ 8.14 (d, J=2 Hz, 1 H), 7.71 (d, J=0.8 Hz, 1 H), 6.87 (t, J$_{HF}$=73.2 Hz, 1 H), 6.15 (s, 1 H), 5.26-5.11 (m, 1 H), 4.73-4.68 (m, 1 H), 2.29-2.20 (m, 4 H), 1.81-1.76 (m, 3 H), 1.52-1.48 (m, 6 H).

General Method U

Preparation of 5-(5-((1 R,5 S,6r)-3,3-difluorobicyclo[3.1.0]hexan-6-yl)-1-isopropyl-1H-pyrazol-3-yl)-3-(difluoromethoxy)pyridin-2-amine

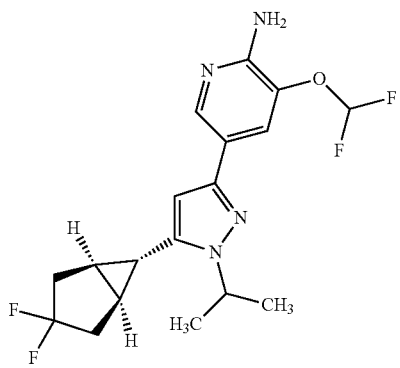 [SMILES: CC(C)n1nc(-c2cnc(N)c(OC(F)F)c2)cc1[C@H]1[C@@H]2CC(F)(F)C[C@@H]21]

Step 1—Synthesis of 5-((1R,5S,6r)-3,3-difluorobicyclo[3.1.0]hexan-6-yl)-3-iodo-1-isopropyl-1H-pyrazole

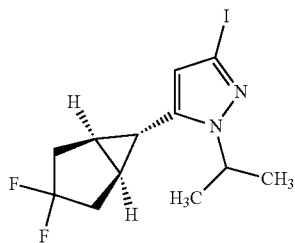 [SMILES: CC(C)n1nc(I)cc1[C@H]1[C@@H]2CC(F)(F)C[C@@H]21]

Reaction of (1R,5 S,6r)-6-(3-iodo-1-isopropyl-1H-pyrazol-5-yl)bicyclo[3.1.0]hexan-3-one (45 mg, 0.12 mmol) following the procedure for the preparation of 5-((1R,3r,5 S,6r)-3-fluorobicyclo[3.1.0]hexan-6-yl)-3-iodo-1-isopropyl-1H-pyrazole afforded the crude product as a brown solid (45 mg, 68%) which was used without further purification. LCMS (ESI): [MH]+352.8.

Step 2—Synthesis of 5-(5-((1 R,5 S,6r)-3,3-difluorobicyclo[3.1.0]hexan-6-yl)-1-isopropyl-1H-pyrazol-3-yl)-3-(difluoromethoxy)pyridin-2-amine To a microwave vial charged with 5-((1R,5S,6r)-3,3-difluorobicyclo[3.1.0]hexan-6-yl)-3-iodo-1-isopropyl-1H-pyrazole (45 mg, 0.12 mmol), 3-(difluoromethoxy)-5-(4,4,5,5-tetramethyl-1,3,2-dioxaborolan-2-yl)pyridin-2-amine (43 mg, 0.15 mmol), and cesium carbonate (97 mg, 0.3 mmol) in 5:1 1,4-dioxane/water (2 mL) was added 1,1'-bis(diphenylphosphino)ferrocene-palladium(II) dichloride (13 mg, 0.018 mmol) under nitrogen. The vial was sealed and heated by microwave irradiation at 120° C. for 30 min. The reaction mixture was concentrated in vacuo, and the residue was dissolved in ethyl acetate (20 mL). The organic solution was sequentially washed with water (2×5 mL) and saturated aqueous sodium chloride solution (5 mL). The collected organic was dried over anhydrous sodium sulfate, filtered, and concentrated in vacuo. Purification by preparative HPLC afforded product as a white solid (6 mg, 13% yield). LCMS (ESI): [MH]+=385.4; $^1$H NMR (400 MHz, Methanol-$d_4$) δ 8.14 (d, J=2 Hz, 1 H), 7.71 (s, 1 H), 6.87 (t, J=73.6 Hz, 1 H), 6.19 (s, 1 H), 4.72-4.66 (m, 1 H), 2.57-2.31 (m, 4H), 1.83-1.77 (m, 3 H), 1.51 (d, J=6.8 Hz, 6 H)

General Method V

Preparation of 5-(5-((1 R,3 s,5 S,6r)-3-((2,2-difluoroethyl)amino)bicyclo[3.1.0]hexan-6-yl)-1-isopropyl-1H-pyrazol-3-yl)-3-(trifluoromethyl)pyridin-2-amine and 5-(5-((1R,3r,5 S,6r)-3-((2,2-difluoroethyl)amino)bicyclo[3.1.0]hexan-6-yl)-1-isopropyl-1H-pyrazol-3-yl)-3-(trifluoromethyl)pyridin-2-amine

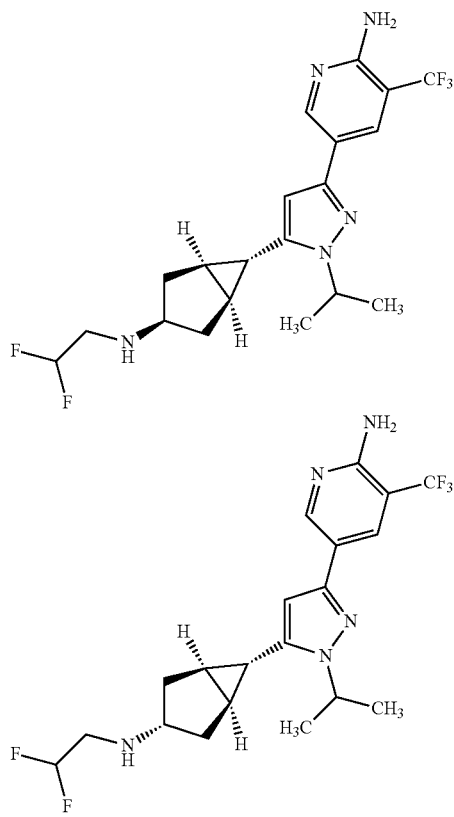

Step 1—Synthesis of N-((1 R,5 S,6r)-6-(3-iodo-1-isopropyl-1H-pyrazol-5-yl)bicyclo[3.1.0]hexan-3-yl)-2-methylpropane-2-sulfinamide

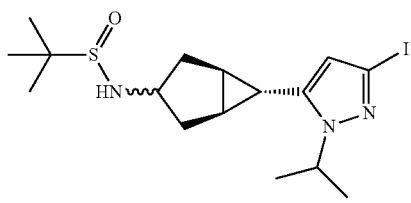

A solution of (1R,5S,6r)-6-(3-iodo-1-isopropyl-1H-pyrazol-5-yl)bicyclo[3.1.0]hexan-3-one (440 mg, 1.3 mmol), (S)-

2-methylpropane-2-sulfinamide (322 mg, 2.66 mmol), and titanium (IV) isopropoxide (1.51 g, 5.32 mmol) in tetrahydrofuran (13 mL) was heated at 70° C. After 3 h, the reaction mixture was cooled to −60° C. before the dropwise addition of L-selectride (5 mL). The reaction mixture was warmed to 20° C. After 16 h, the reaction mixture was diluted with water, and the resulting suspension was filtered. The filtrate was concentrated and diluted with ethyl acetate (60 mL). The resulting solution was washed with saturated aqueous sodium chloride solution (3×8 mL), dried over anhydrous sodium sulfate, filtered and concentrated. Purification by flash column chromatography (ethyl acetate) provided product as a yellow oil (320 mg, 56% yield). LCMS (ESI) [MH]$^+$=435.8.

Step 2—Synthesis of N-(2,2-difluoroethyl)-N-((1R, 5S,6r)-6-(3-iodo-1-isopropyl-1H-pyrazol-5-yl)bicyclo[3.1.0]hexan-3-yl)-2-methylpropane-2-sulfinamide

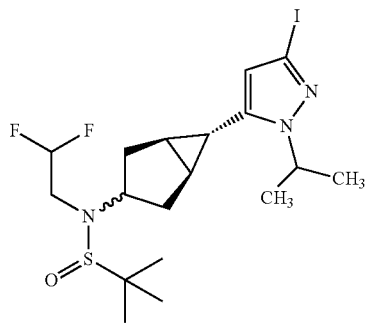

To an ice-cooled solution of N-((1 R,5 S,6r)-6-(3-iodo-1-isopropyl-1H-pyrazol-5-yl)bicyclo[3.1.0]hexan-3-yl)-2-methylpropane-2-sulfinamide (230 mg, 0.53 mmol) in tetrahydrofuran (10 mL) was added sodium hydride (106 mg, 2.65 mmol). After 1 h, 2,2-difluoroethyl trifluoromethanesulfonate (340 mg, 1.6 mmol) was added dropwise, and the resulting mixture was warmed to 20° C. for 16 h. Methanol was added to the reaction mixture, and the resulting mixture was concentrated in vacuo. The residue was dissolved in ethyl acetate (20 mL), and the solution was washed with saturated aqueous sodium chloride solution (2×8 mL). The collected organic was dried over anhydrous sodium sulfate, filtered, and concentrated. Purification by flash column chromatography (20% ethyl acetate in petroleum ether) provided product as a colorless oil (256 mg, 95%). LCMS (ESI) [MH]$^+$=367.1.

Step 3—Synthesis of (1 R,5 S,6r)-N-(2,2-difluoroethyl)-6-(3-iodo-1-isopropyl-1H-pyrazol-5-yl)bicyclo[3.1.0]hexan-3-amine

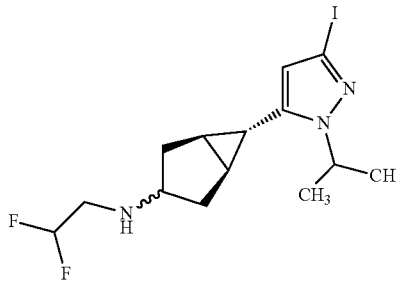

A solution of N-(2,2-difluoroethyl)-N-((1R,5S,6r)-6-(3-iodo-1-isopropyl-1H-pyrazol-5-yl)bicyclo[3.1.0]hexan-3-yl)-2-methylpropane-2-sulfinamide (350 mg, 0.7 mmol) in methanol (2 mL) was added 4 M hydrogen chloride in methanol at 20° C. After 3 h, the solution was concentrated in vacuo, and the resulting residue was dissolved in ethyl acetate (30 mL). The organic solution was washed with saturated aqueous sodium bicarbonate solution (2×5 mL), dried over anhydrous sodium sulfate, filtered, and concentrated in vacuo to give crude product as a brown solid (150 mg, 54% crude yield). LCMS (ESI) [MH]$^+$=395.9.

Step 4—Synthesis of 5-(5-((1 R,3 s,5 S,6r)-3-((2,2-difluoroethyl)amino)bicyclo[3.1.0]hexan-6-yl)-1-isopropyl-1H-pyrazol-3-yl)-3-(trifluoromethyl)pyridin-2-amine and 5-(5-((1R,3r,5 S,6r)-3-((2,2-difluoroethyl)amino)bicyclo[3.1.0]hexan-6-yl)-1-isopropyl-1H-pyrazol-3-yl)-3-(trifluoromethyl)pyridin-2-amine To a microwave vial charged with (1R,5S,6r)-N-(2,2-difluoroethyl)-6-(3-iodo-1-isopropyl-1H-pyrazol-5-yl)bicyclo[3.1.0]hexan-3-amine (0.030 g, 0.075 mmol), 5-(4,4,5,5-tetramethyl-1,3,2-dioxaborolan-2-yl)-3-(trifluoromethyl)pyridin-2-amine (23 mg, 0.08 mmol) and cesium carbonate (0.050 g, 0.15 mmol) in 5:1 1,4-dioxane/water (2 mL) was added 1,1'-bis(diphenylphosphino)ferrocene-palladium(II) dichloride (11 mg, 0.015 mmol) under nitrogen. The vial was sealed and heated by microwave irradiation at 110° C. for 30 min. The reaction mixture was concentrated in vacuo, and the residue was diluted with ethyl acetate (20 mL). The organic solution was sequentially washed with water (2×5 mL) and saturated aqueous sodium chloride solution (5 mL). The collected organic was dried over anhydrous sodium sulfate, filtered, and concentrated. Purification by preparative HPLC afforded products as white solids.

Diastereomer 1 (6.5 mg, 12%): LCMS (ESI): [MH]$^+$=430.2; $^1$H NMR (400 MHz, Methanol-d4) δ 8.49 (m, 1 H), 8.10 (d, J=2 Hz, 1 H), 6.17 (s, 1 H), 6.05-5.74 (m, 1 H), 4.78-4.72 (m, 1 H), 3.06-2.88 (m, 3 H), 2.37-2.32 (m, 2 H), 1.72-1.66 (m, 5 H), 1.50 (d, J=7.2 Hz, 6 H)

Diastereomer 2 (5.1 mg, 9.4%): LCMS (ESI): [MH]$^+$=430.2; $^1$H NMR (400 MHz, Methanol-d4) δ 8.48 (s, 1 H), 8.10 (s, 1 H), 6.12 (s, 1 H), 6.01-5.72 (m, 1 H), 4.78-4.73 (m, 1 H), 3.43-3.40 (m, 1 H), 2.94-2.86 (m, 2 H), 2.34-2.25 (m, 3 H), 1.78-1.67 (m, 4 H), 1.51 (d, J=6.8 Hz, 6 H)

General Method W

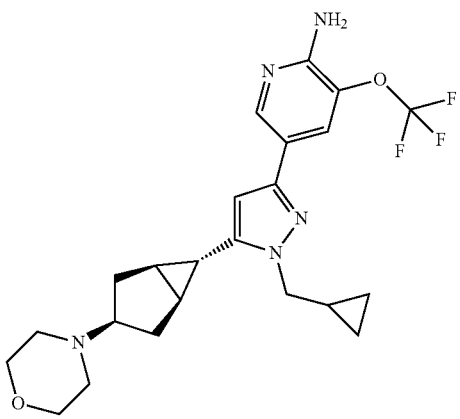

-continued

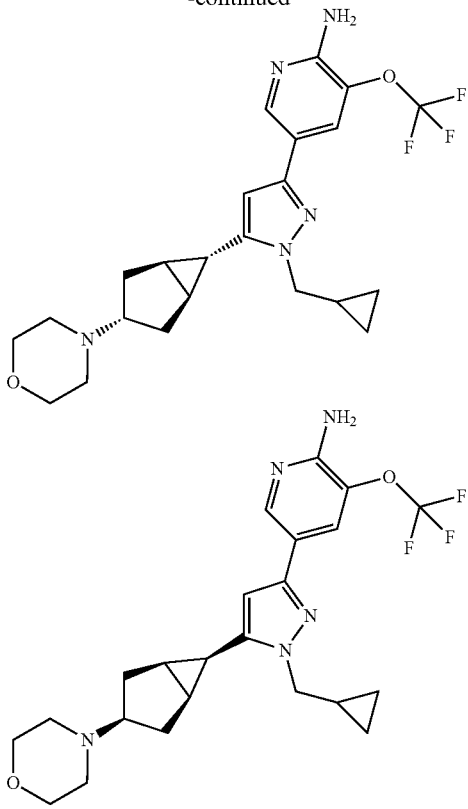

Preparation of: 5-(1-(cyclopropylmethyl)-5-((1R,3r,5S,6r)-3-morpholinobicyclo[3.1.0]hexan-6-yl)-1H-pyrazol-3-yl)-3-(trifluoromethoxy)pyridin-2-amine 5-(1-(cyclopropylmethyl)-5-((1R,3s,5S,6r)-3-morpholinobicyclo[3.1.0]hexan-6-yl)-1H-pyrazol-3-yl)-3-(trifluoromethoxy)pyridin-2-amine 5-(1-(cyclopropylmethyl)-5-((1R,3r,5S,6s)-3-morpholinobicyclo[3.1.0]hexan-6-yl)-1H-pyrazol-3-yl)-3-(trifluoromethoxy)pyridin-2-amine Step 1—Synthesis of 1-(3-((tert-butyldiphenylsilyl)oxy)bicyclo[3.1.0]hexan-6-yl)-3,3-bis(methylthio)prop-2-en-1-one

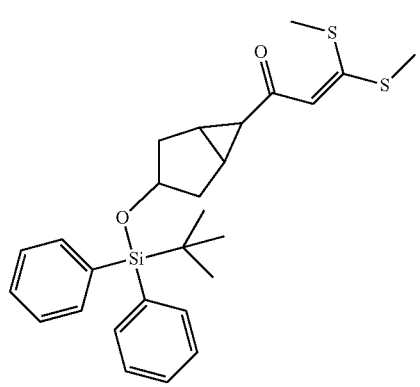 [SMILES: CSC(=CC(=O)C1C2CC(O[Si](c3ccccc3)(c3ccccc3)C(C)(C)C)CC21)SC]

To a solution of 1-(3-((tert-butyldiphenylsilyl)oxy)bicyclo[3.1.0]hexan-6-yl)ethanone (10 g, 26 mmol) in tetrahydrofuran (60 mL) was added lithium bis(trimethylsilyl)amide (79.24 mL, 79.24 mmol, 1.0 in tetrahydrofuran) at −40° C. over 30 min. The mixture was warmed to 0° C. for 30 min, before the dropwise addition of carbon disulfide (2.2 g, 29 mmol). After 10 min, the cooled bath was removed, and the mixture was allowed to stir at 20° C. for 30 min. The reaction was cooled to −40° C., and iodomethane (15 g, 105 mmol) was added. After 10 min, the reaction mixture was warmed to 20° C. for 18 h. Methanol (5 mL) was added, and the resulting solution was concentrated in vacuo. Purification by flash column chromatography (30% ethyl acetate in petroleum ether) afforded product as a yellow oil (12 g, 80% yield). LCMS (ESI) [MH]$^+$=483.0.

Step 2—Synthesis of (E)-3-(6-amino-5-(trifluoromethoxy)pyridin-3-yl)-1-(3-((tert-butyldiphenylsilyl)oxy)bicyclo[3.1.0]hexan-6-yl)-3-(methylthio)prop-2-en-1-one

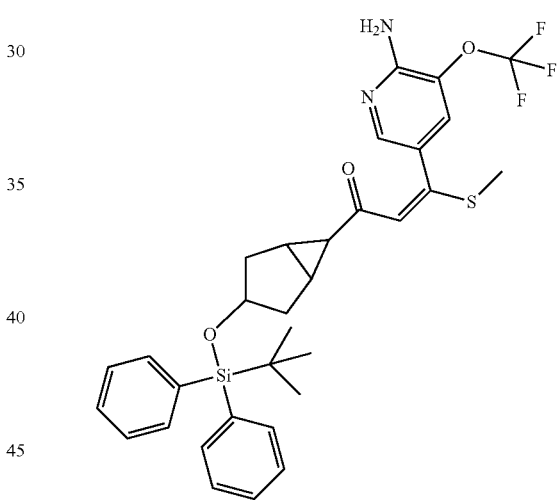

A microwave vial charged with 1-(3-((tert-butyldiphenylsilyl)oxy)bicyclo[3.1.0]hexan-6-yl)-3,3-bis(methylthio)prop-2-en-1-one (2.0 g, 4.1 mmol), 5-(4,4,5,5-tetramethyl-1,3,2-dioxaborolan-2-yl)-3-(trifluoro-methoxy)-pyridin-2-amine (1.89 g, 6.23 mmol), ((thiophene-2-carbonyl)oxy) copper (1.58 g, 8.29 mmol), cesium carbonate (2.7 g, 8.3 mmol) and tetra(triphenylphosphine)palladium (0) (957 mg, 0.83 mmol) in 10:1 tetrahydrofuran/water (22 mL) was purged with nitrogen for 3 min. The reaction mixture was sealed and heated by microwave irradiation at 100° C. for 1.5 h. The reaction mixture was concentrated in vacuo, and the resulting residue was purified by flash column chromatography (40% ethyl acetate in petroleum ether) to provide product as a yellow oil (0.70 g, 26% yield). LCMS (ESI) [MH]$^+$=613.1.

Step 3—Synthesis of 5-(5-(3-((tert-butyldiphenylsilyl)oxy)bicyclo[3.1.0]hexan-6-yl)-1H-pyrazol-3-yl)-3-(trifluoromethoxy)pyridin-2-amine

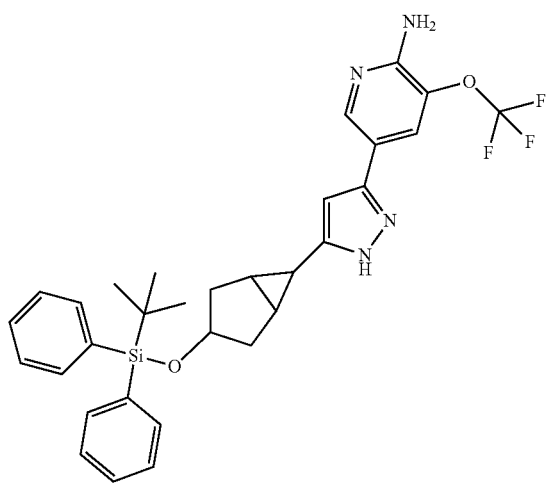 [SMILES: CC(C)(C)[Si](OC1CC2C(C1)C2c1cc(-c2cnc(N)c(OC(F)(F)F)c2)n[nH]1)(c1ccccc1)c1ccccc1]

A solution of (E)-3-(6-amino-5-(trifluoromethoxy)pyridin-3-yl)-1-(3-((tert-butyldiphenylsilyl)oxy)bicyclo[3.1.0]hexan-6-yl)-3-(methylthio)prop-2-en-1-one (0.70 g, 1.1 mmol) and hydrazine hydrate (5 mL) in ethanol (5 mL) was sealed in a microwave vessel and heated at 100° C. by microwave irradiation for 1 h. The reaction mixture was concentrated, and the resulting residue was purified by flash column chromatography (60% ethyl acetate in petroleum ether) to product as a white solid (0.50 g, 76% yield). LCMS (ESI) [MH]$^+$=579.1.

Step 4—Synthesis of 5-(5-(3-((tert-butyldiphenylsilyl)oxy)bicyclo[3.1.0]hexan-6-yl)-1-(cyclopropylmethyl)-1H-pyrazol-3-yl)-3-(trifluoromethoxy)pyridin-2-amine

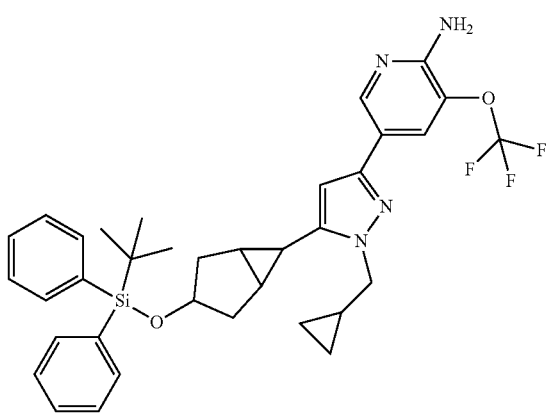 [SMILES: CC(C)(C)[Si](OC1CC2C(C1)C2c1cc(-c2cnc(N)c(OC(F)(F)F)c2)nn1CC1CC1)(c1ccccc1)c1ccccc1]

To a round-bottomed flask charged with 5-(5-(3-((tert-butyldiphenylsilyl)oxy)bicyclo[3.1.0]hexan-6-yl)-1H-pyrazol-3-yl)-3-(trifluoromethoxy)pyridin-2-amine (0.40 g, 0.35 mmol) and cesium carbonate (0.68 g, 2.1 mmol) in N,N-dimethylformamide (4 mL) was added bromomethylcyclopropane (0.28 mg, 2.1 mmol) at 20° C. After 16 h, the reaction mixture was partitioned between ethyl acetate (20 mL) and water (10 mL). The aqueous layer was extracted with ethyl acetate (3×10 mL). The combined organics were washed with saturated aqueous sodium chloride solution (2×10 mL), dried over anhydrous sodium sulfate, filtered, and concentrated. Purification by flash column chromatography (30% ethyl acetate in petroleum ether) afforded product as an orange oil (0.30 g, 69% yield). LCMS (ESI) [MH]$^+$=633.1.

Step 5—Synthesis of 6-(3-(6-amino-5-(trifluoromethoxy)pyridin-3-yl)-1-(cyclopropylmethyl)-1H-pyrazol-5-yl)bicyclo[3.1.0]hexan-3-ol

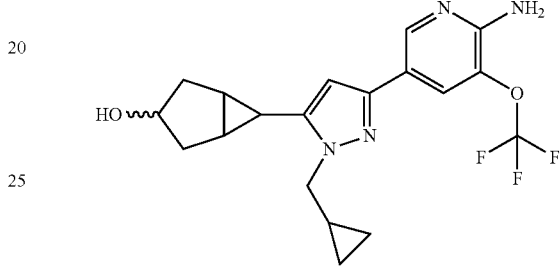

A solution of 5-(5-(3-((tert-butyldiphenylsilyl)oxy)bicyclo[3.1.0]hexan-6-yl)-1-(cyclopropylmethyl)-1H-pyrazol-3-yl)-3-(trifluoromethoxy)pyridin-2-amine (0.30 g, 0.47 mmol) in tetrahydrofuran (2 mL) and triethylamine trihydrofluoride (2 mL) was heated to 60° C. for 16 h. The reaction was diluted with saturated aqueous sodium bicarbonate, and the resulting mixture was extracted with ethyl acetate (2×10 mL). The collected organic was washed with saturated aqueous sodium chloride solution, dried over anhydrous sodium sulfate, filtered, and concentrated. Purification by flash column chromatography (50% ethyl acetate in petroleum ether) provided product as a solid (140 mg, 75% yield). LCMS (ESI) [MH]$^+$=394.9.

Step 6—Synthesis of 6-(3-(6-amino-5-(trifluoromethoxy)pyridin-3-yl)-1-(cyclopropylmethyl)-1H-pyrazol-5-yl)bicyclo[3.1.0]hexan-3-ylmethanesulfonate

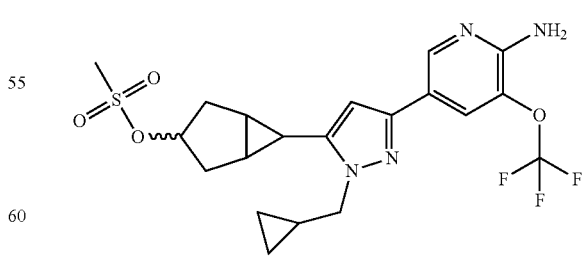

To an ice-cooled solution of 6-(3-(6-amino-5-(trifluoromethoxy)pyridin-3-yl)-1-(cyclopropylmethyl)-1H-pyrazol-5-yl)bicyclo[3.1.0]hexan-3-ol (140 mg, 0.35 mmol) and triethylamine (72 mg, 0.71 mmol) in dichloromethane (20 mL) was added methanesulfonyl chloride (45 mg, 110 mmol) in dichloromethane (1 mL). After 1 h at 0° C., the reaction mixture was diluted with water, and the resulting solution was extracted with dichloromethane (20 mL). The collected organic was washed with saturated aqueous sodium chloride solution, dried over anhydrous sodium sulfate, filtered and concentrated. Purification by flash column chromatography (80% ethyl acetate in petroleum ether) afforded product as a colorless oil (110 mg, 66% yield). LCMS: [MH]⁺=472.8.

Step 7—Synthesis of 5-(1-(cyclopropylmethyl)-5-((1R,3r,5S,6r)-3-morpholinobicyclo[3.1.0]hexan-6-yl)-1H-pyrazol-3-yl)-3-(trifluoromethoxy)pyridin-2-amine and 5-(1-(cyclopropylmethyl)-5-((1R,3 s,5 S,6r)-3-morpholinobicyclo[3.1.0]hexan-6-yl)-1H-pyrazol-3-yl)-3-(trifluoromethoxy)pyridin-2-amine and 5-(1-(cyclopropylmethyl)-5-((1R,3r,5 S,6s)-3-morpholinobicyclo[3.1.0]hexan-6-yl)-1H-pyrazol-3-yl)-3-(trifluoromethoxy)pyridin-2-amine A solution of 6-(3-(6-amino-5-(trifluoromethoxy)pyridin-3-yl)-1-(cyclopropylmethyl)-1H-pyrazol-5-yl)bicyclo [3.1.0]hexan-3-ylmethanesulfonate (110 mg, 0.23 mmol) in morpholine (1 mL) was heated at 160° C. by microwave irradiation for 1.5 h. The reaction mixture was diluted with N,N-dimethylformamide (3 mL) and filtered. The filtrate was concentrated, and the resulting residue was purified by preparative HPLC to afford title compounds as white solids.
Stereoisomer 1:
5-(1-(cyclopropylmethyl)-5-((1R,3s,5S,6r)-3-morpholinobicyclo[3.1.0]hexan-6-yl)-1H-pyrazol-3-yl)-3-(trifluoromethoxy)pyridin-2-amine (7 mg, 7%). LCMS (ESI): [MH]⁺=463.9. ¹H NMR (400 MHz, CDCl₃) δ 8.33 (s, 1 H), 7.80 (s, 1 H), 5.96 (s, 1 H), 4.71 (s, 2 H), 4.04 (d, J=6.8 Hz, 2 H), 3.72 (s, 4 H), 2.89-2.87 (m, 1 H), 2.46 (br s, 4 H), 2.25-2.20 (m, 2 H), 1.89 (s, 1 H), 1.73-1.66 (m, 4 H), 1.32 (m, 1 H), 0.61 (m, 2 H), 0.43 (m, 2 H)
Stereoisomer 2:
5-(1-(cyclopropylmethyl)-5-((1R,3r,5S,6s)-3-morpholinobicyclo[3.1.0]hexan-6-yl)-1H-pyrazol-3-yl)-3-(trifluoromethoxy)pyridin-2-amine (2.6 mg, 6%). LCMS (ESI): [MH]⁺=463.9. ¹H NMR (400 MHz, Chloroform-d) δ 8.00 (s, 1 H), 7.39 (s, 1 H), 5.90 (s, 1 H), 4.92 (s, 2 H), 3.88-3.77 (m, 6 H), 3.04 (br s, 1 H), 2.56 (br s, 4 H), 2.31 (br s, 2 H), 1.90 (s, 1 H), 1.67 (br s, 4 H), 1.14 (br s, 1 H), 0.48 (d, J=7.2 Hz, 2 H), 0.16 (d, J=4.4 Hz, 2 H)
Stereoisomer 3:
5-(1-(cyclopropylmethyl)-5-((1R,3r,5 S,6r)-3-morpholinobicyclo[3.1.0]hexan-6-yl)-1H-pyrazol-3-yl)-3-(trifluoromethoxy)pyridin-2-amine (6.2 mg, 6%). LCMS (ESI): [MH]⁺=464.0. ¹H NMR (400 MHz, Chloroform-d) δ 8.32 (s, 1 H), 7.80 (s, 1 H), 6.00 (s, 1 H), 4.81 (br s, 2 H), 4.03 (d, J=6.8 Hz, 2 H), 3.76 (s, 4 H), 2.51 (br s, 4 H), 2.41-2.39 (m, 1 H), 2.25-2.20 (m, 2 H), 1.92-1.90 (m, 2 H), 1.72-1.68 (m, 2 H), 1.57 (s, 1 H), 1.32 (br s, 1 H), 0.61 (d, J=7.6 Hz, 2 H), 0.43 (d, J=4.4 Hz, 2 H).

General Method X

Preparation of 5-(1-isopropyl-5-((1'R,2r,5'S,6'r)-1-(2-methoxyethyl)spiro[azetidine-2,3'-bicyclo[3.1.0] hexan]-6'-yl)-1H-pyrazol-3-yl)-3-(trifluoromethoxy) pyridin-2-amine

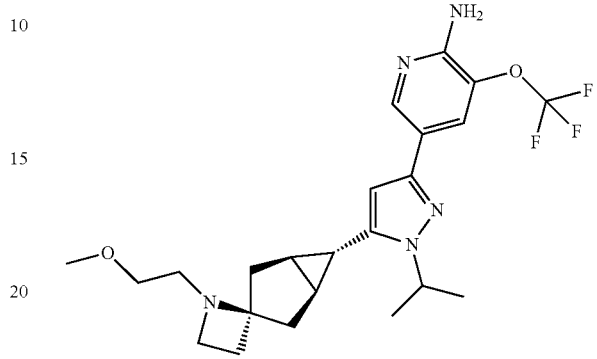

Step 1—Synthesis of (1'R,2r,5'S,6'r)-6'-(3-iodo-1-isopropyl-1H-pyrazol-5-yl)-1-(2-methoxyethyl)spiro [azetidine-2,3'-bicyclo[3.1.0]hexane]

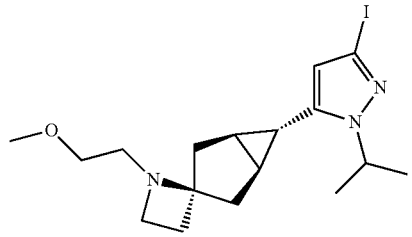 [SMILES: COCCN1CC[C@@]12C[C@@H]1[C@H](C2)[C@H]1c1cc(I)nn1C(C)C]

A suspension of (1'R,2r,5'S,6'r)-6'-(3-iodo-1-isopropyl-1H-pyrazol-5-yl)spiro[azetidine-2,3'-bicyclo[3.1.0]hexane] (0.070 g, 0.20 mmol), 1-bromo-2-methoxyethane (54 mg, 0.39 mmol), potassium carbonate (54 mg, 0.39 mmol) in N,N-dimethylacetamide (1 mL) was heated at 60° C. for 2 h. The reaction was diluted with water (12 mL), and the resulting mixture was extracted with ethyl acetate (3×10 mL). The collected organic was washed with saturated aqueous sodium chloride solution (15 mL), dried over anhydrous sodium sulfate, filtered, and concentrated. Purification by preparative thin layer chromatography (11% methanol in ethyl acetate) provided product as a yellow solid (65 mg, 80%). LCMS: [M+H]⁺ 415.8.

Step 2—Synthesis of 5-(1-isopropyl-5-((1'R,2r,5'S, 6'r)-1-(2-methoxyethyl)spiro[azetidine-2,3'-bicyclo [3.1.0]hexan]-6'-yl)-1H-pyrazol-3-yl)-3-(trifluoromethoxy)pyridin-2-amine To a microwave vial charged with (1'R,2r,5'S,6'r)-6'-(3-iodo-1-isopropyl-1H-pyrazol-5-yl)-1-(2-methoxyethyl) spiro[azetidine-2,3'-bicyclo[3.1.0]hexane] (0.060 g, 0.14 mmol), 5-(4,4,5,5-tetramethyl-1,3,2-dioxaborolan-2-yl)-3-(trifluoromethoxy)pyridin-2-amine (53 mg, 0.17 mmol) and cesium carbonate (113 mg, 0.347 mmol) in 5:1 1,4-dioxane/water (1.8 mL) was added 1,1'-bis(diphenylphosphino)ferrocene-palladium(II) dichloride (11 mg, 0.015 mmol) under nitrogen. The vial was sealed and heated by microwave irradiation at 110° C. for 30 min. The reaction mixture was diluted with ethyl acetate (15 mL) and filtered. The filtrate was concentrated in vacuo, and the resulting residue was purified by preparative thin layer chromatography (17% methanol in ethyl acetate) followed by preparative HPLC to afford product as a solid (21 mg, 32%). LCMS: [M+H]+ 466.0; $^1$H NMR (400 MHz, CDCl$_3$) δ8.31 (s, 1 H), 7.80 (s, 1 H), 5.96 (s, 1 H), 4.75 (s, 2 H), 4.61-4.68 (m, 1 H), 3.40 (t, J=5.6 Hz, 2 H), 3.34 (s, 3 H), 3.21 (t, J=7.0 Hz, 2 H), 2.62 (t, J=5.8 Hz, 2 H), 2.24 (m, 1 H), 2.16-2.21 (m, 3 H), 1.88 (m, 2 H), 1.57 (m, 2 H), 1.53 (d, J=6.8 Hz, 6 H), 1.40 (t, J=3.0 Hz, 1 H).

Example 3

Compounds

The compounds disclosed in Table A were prepared following General Methods A-(X$^{3/4}$) as described above in Example 2 with modifying the starting reactants in those methods as would be known to one skilled in the art as necessary to arrive at the compounds in Table A.

TABLE A

| Cmpd No. | Structure | $^1$H NMR | MS [MH]+ | Method |
|---|---|---|---|---|
| 1 | 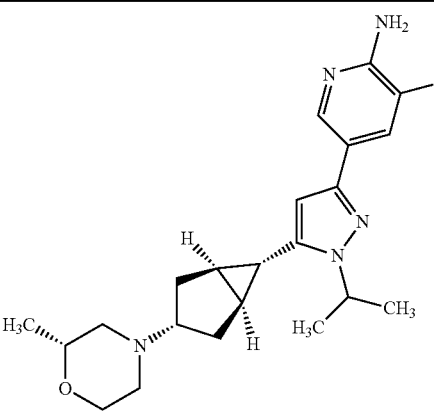<br>5-(1-isopropyl-5-((1R,3s,5S,6R)-3-((R)-2-methylmorpholino)bicyclo[3.1.0]hexan-6-yl)-1H-pyrazol-3-yl)-3-(trifluoromethyl)pyridin-2-amine | $^1$H NMR (400 MHz, Chloroform-d) δ 8.30 (s, 1 H), 7.79 (s, 1 H), 5.98 (s, 1 H), 4.69 (s, 2 H), 4.62-4.55 (m, 1 H), 3.88-3.85 (m, 1 H), 3.70 (m, 2 H), 2.85-2.75 (m, 2 H), 2.38-2.35 (m, 1 H), 2.25-2.10 (m, 2 H), 2.12-2.10 (m, 1 H), 1.90-1.75 (m, 3 H), 1.69 (s, 3 H), 1.50 (d, J = 6.4 Hz, 6 H), 1.15 (d, J = 6.4 Hz, 3 H) | 466.3 | A |
| 2 | 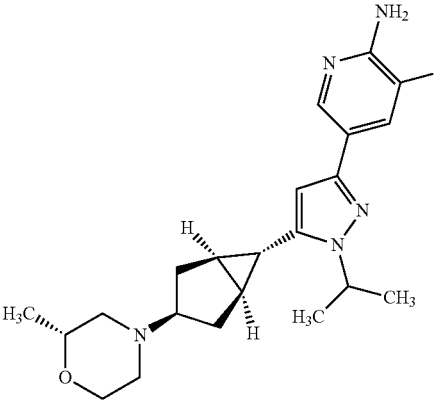<br>5-(1-isopropyl-5-((1R,3r,5S,6R)-3-((R)-2-methylmorpholino)bicyclo[3.1.0]hexan-6-yl)-1H-pyrazol-3-yl)-3-(trifluoromethyl)pyridin-2-amine | $^1$H NMR (400 MHz, Chloroform-d) δ 8.30 (s, 1 H), 7.79 (s, 1 H), 5.92 (s, 1 H), 4.68 (s, 2 H), 4.66-4.60 (m, 1 H), 3.90-3.84 (m, 1 H), 3.70-3.55 (m, 2 H), 2.88-2.55 (m, 3 H), 2.30-2.20 (m, 2 H), 2.10-2.03 (m, 1 H), 1.83-1.75 (m, 1 H), 1.65-1.63 (m, 5 H), 1.51 (d, J = 6.4 Hz, 6 H), 1.15 (d, J = 5.2 Hz, 3 H) | 466.3 | A |

TABLE A-continued

| Cmpd No. | Structure | ¹H NMR | MS [MH]⁺ | Method |
|---|---|---|---|---|
| 3 | 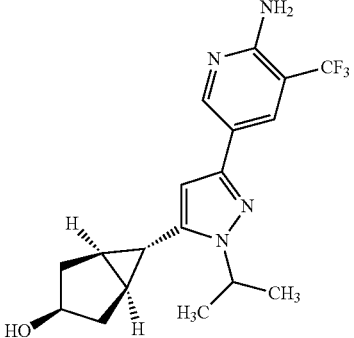 [SMILES: CC(C)n1nc(-c2cnc(N)c(C(F)(F)F)c2)cc1[C@H]1[C@@H]2C[C@H](O)C[C@@H]21]<br>(1R,3r,5S,6r)-6-(3-(6-ammo-5-(trifluoromethyl)pyridin-3-yl)-1-isopropyl-1H-pyrazol-5-yl)cbicylo[3.1.0]hexan-3-ol | ¹H NMR (DMSO-$d_6$) δ: 8.57-8.52 (m, 1H), 7.98 (d, J = 2.2 Hz, 1H), 6.44 (br s, 2H), 6.30 (s, 1H), 4.67-4.55 (m, 2H), 4.26 (m, 1H), 3.30 (d, J = 19.9 Hz, 1H), 2.17-2.01 (m, 3H), 1.83 (d, J = 13.9 Hz, 2H), 1.61 (t, J = 3.3 Hz, 2H), 1.43 (d, J = 6.6 Hz, 6H) | 367.2 | A |
| 4 | 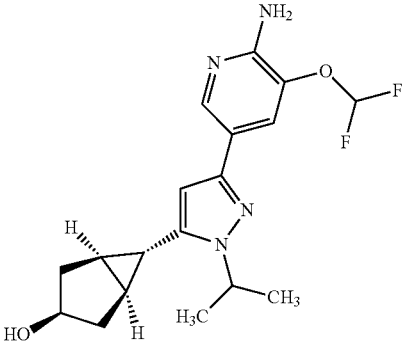 [SMILES: CC(C)n1nc(-c2cnc(N)c(OC(F)F)c2)cc1[C@H]1[C@@H]2C[C@H](O)C[C@@H]21]<br>(1R,3r,5S,6r)-6-(3-(6-amino-5-(difluoromethoxy)pyridin-3-yl)-1-isopropyl-1H-pyrazol-5-yl)bicyclo[3.1.0]hexan-3-ol | ¹H NMR (DMSO-$d_6$) δ: 8.17 (d, J = 1.9 Hz, 1H), 7.61-7.55 (m, 1H), 7.15 (t, $J_{HF}$ = 73.9 Hz, 1H), 6.20 (s, 1H), 6.06 (s, 2H), 4.66-4.55 (m, 2H), 4.30-4.22 (m, 1H), 3.30 (m, 2H), 2.16-2.01 (m, 3H), 1.82 (m, 2H), 1.60 (m, 2H), 1.43 (d, J = 6.6 Hz, 6H) | 365.2 | A |
| 5 | 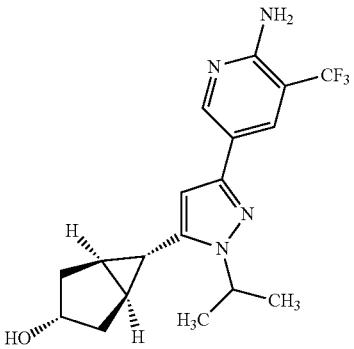<br>(1R,3s,5S,6r)-6-(3-(6-amino-5-(trifluoromethyl)pyridin-3-yl)-1-isopropyl-1H-pyrazol-5-yl)bicyclo[3.1.0]hexan-3-ol | ¹HNMR (CDCl₃) δ: 8.54 (m, 1H), 8.10 (dd, J = 2.2, 0.8 Hz, 1H), 6.00 (d, J = 0.7 Hz, 1H), 4.95 (br s, 2H), 4.59 (hept, J = 6.7 Hz, 1H), 4.29-4.07 (m, 1H), 2.36 (dd, J = 13.1, 7.0 Hz, 2H), 1.94-1.78 (m, 2H), 1.67 (m, 2H), 1.52 (m, 7H), 1.42 (t, J = 3.4 Hz, 1H) | 367.2 | A |

TABLE A-continued

| Cmpd No. | Structure | ¹H NMR | MS [MH]⁺ | Method |
|---|---|---|---|---|
| 6 | (1R,3s,5S,6r)-6-(3-(6-amino-5-(difluoromethoxy)pyridin-3-yl)-1-isopropyl-1H-pyrazol-5-yl)bicyclo[3.1.0]hexan-3-ol | ¹H NMR (CDCl₃) δ: 8.23 (d, J = 1.9 Hz, 1H), 7.70 (m, 1H), 5.99 (d, J = 0.7 Hz, 1H), 4.76 (br s, 2H), 4.66-4.50 (m, 1H), 4.18 (m, 1H), 2.36 (dd, J = 13.1, 7.0 Hz, 2H), 1.87 (m, 2H), 1.67 (m, 3H), 1.51 (d, J = 6.7 Hz, 6H), 1.41 (t, J = 3.4 Hz, 1H) | 365.2 | A |
| 7 | 5-(1-isopropyl-5-((1R,3s,5S,6r)-3-(methyl(2-(methylsulfonyl)ethyl)amino)bicyclo[3.1.0]hexan-6-yl)-1H-pyrazol-3-yl)-3-(trifluoromethyl)pyridin-2-amine | ¹H NMR (400 MHz, Methanol-d4) δ 8.49 (s, 1 H), 8.10 (s, 1 H), 6.17 (s, 1 H), 4.79-4.72 (m, 1 H), 4.60 (m, 1 H), 3.31-3.29 (m, 2 H), 3.04 (s, 3 H), 2.95-2.92 (m, 2 H), 2.76-2.74 (m, 1 H), 2.27 (s, 3 H), 2.26-2.22 (m, 1 H), 1.88-1.82 (m, 2 H), 1.74-1.71 (m, 3 H), 1.50 (d, J = 6.8 Hz, 6 H) | 486.1 | A |
| 8 | 5-(1-isopropyl-5-((1R,3r,5S,6r)-3-(methyl(2-(methylsulfonyl)ethyl)amino)bicyclo[3.1.0]hexan-6-yl)-1H-pyrdzol-3-yl)-3-(trifluoromethyl)pyridin-2-amine | ¹H NMR (400 MHz, Methanol-d4) δ 8.49 (s, 1 H), 8.10 (s, 1 H), 6.13 (s, 1 H), 4.82-4.76 (m, 1 H), 4.60 (m, 1 H), 3.31-3.28 (m, 2 H), 3.16-3.14 (m, 1 H), 3.03 (s, 3 H), 2.93-2.89 (m, 2 H), 2.34-2.29 (m, 2 H), 2.25 (s, 3H), 1.76-1.75 (m, 2 H), 1.73-1.68 (m, 2 H), 1.51 (d, J = 6.8 Hz, 6 H) | 486.1 | A |

TABLE A-continued

| Cmpd No. | Structure | ¹H NMR | MS [MH]⁺ | Method |
|---|---|---|---|---|
| 9 | 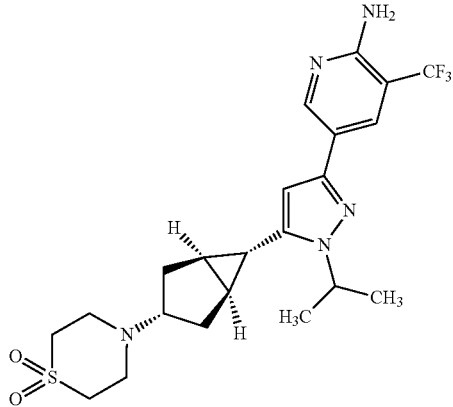 [SMILES: CC(C)n1nc(-c2cnc(N)c(C(F)(F)F)c2)cc1[C@H]1[C@@H]2C[C@@H](N3CCS(=O)(=O)CC3)C[C@@H]21]<br>4-((1R,3s,5S,6r)-6-(3-(6-amino-5-(trifluoromethyl)pyridin-3-yl)-1-isopropyl-1H-pyrazol-5-yl)bicyclo[3.1.0]hexan-3-yl)thiomorpholine 1,1-dioxide | ¹H NMR (400 MHz, Chloroform-d) δ 8.48 (s, 1 H), 8.17 (s, 1 H), 6.00 (s, 1 H), 5.37 (br s, 2 H), 4.60-4.56 (m, 1 H), 3.12-3.05 (m, 8 H), 2.75-2.70 (m, 1 H), 2.26-2.21 (m, 2 H), 2.00-1.92 (m, 2 H), 1.71 (m, 3 H), 1.51 (d, J = 6.8 Hz, 6 H) | 484.3 | A |
| 10 | 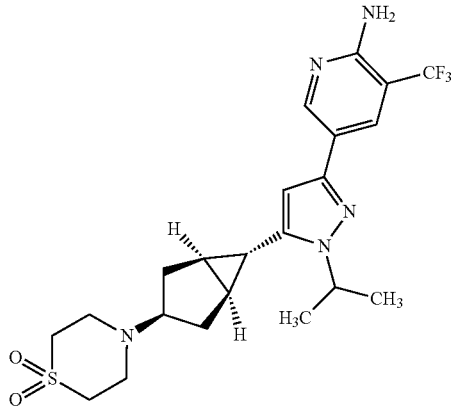 [SMILES: CC(C)n1nc(-c2cnc(N)c(C(F)(F)F)c2)cc1[C@H]1[C@@H]2C[C@H](N3CCS(=O)(=O)CC3)C[C@@H]21]<br>4-((1R,3r,5S,6r)-6-(3-(6-amino-5-(trifluoromethyl)pyridin-3-yl)-1-isopropyl-1H-pyrazol-5-yl)bicyclo[3.1.0]hexan-3-yl)thiomorpholine 1,1-dioxide | ¹H NMR (400 MHz, Chloroform-d) δ 8.45 (s, 1 H), 8.05 (s, 1 H), 5.90 (s, 1 H), 5.00 (br s, 2 H), 4.60-4.53 (m, 1 H), 3.28-3.24 (m, 1 H), 3.00-2.97 (m, 8 H), 2.33-2.30 (m, 2 H), 1.75-1.67 (m, 3 H), 1.60-1.56 (m, 2 H), 1.46 (d, J = 6.8 Hz, 6 H) | 484.2 | A |
| 11 | 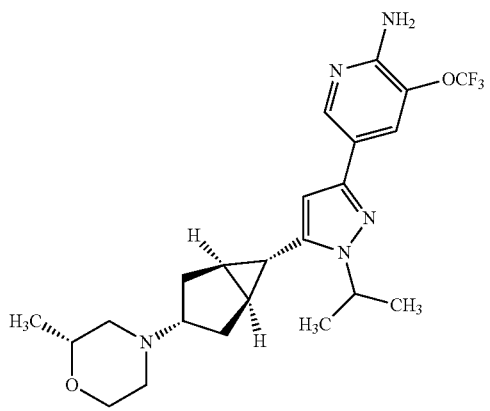 [SMILES: CC(C)n1nc(-c2cnc(N)c(OC(F)(F)F)c2)cc1[C@H]1[C@@H]2C[C@@H](N3CCO[C@H](C)C3)C[C@@H]21]<br>5-(1-isopropyl-5-((1R,3s,5S,6R)-3-((R)-2-methylmorpholino)bicyclo[3.1.0]hexan-6-yl)-1H-pyrazol-3-yl)-3-(trifluoromethoxy)pyridin-2-amine | ¹H NMR (400 MHz, Chloroform-d) δ 8.52 (s, 1 H), 8.08 (s, 1 H), 6.00 (s, 1 H), 4.92 (m, 2 H), 4.62-4.55 (m, 1 H), 3.88-3.85 (m, 1 H), 3.70 (m, 2 H), 2.85-2.75 (m, 2 H), 2.40-2.35 (m, 1 H), 2.30-2.22 (m, 3 H), 2.00-1.85 (m, 3 H), 1.69 (m, 3H), 1.51 (d, J = 6.8 Hz, 6 H), 1.15 (d, J = 6.0 Hz, 3 H) | 450.3 | A |

TABLE A-continued

| Cmpd No. | Structure | ¹H NMR | MS [MH]⁺ | Method |
|---|---|---|---|---|
| 12 | 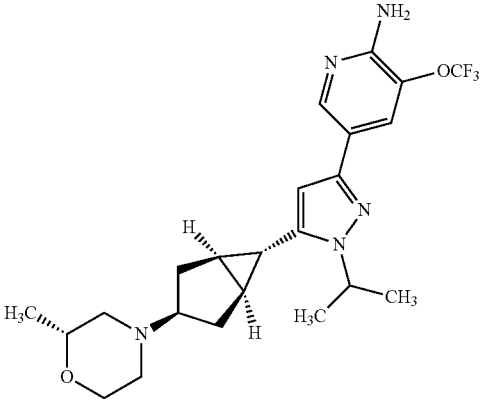 [SMILES: CC(C)n1nc(-c2cnc(N)c(OC(F)(F)F)c2)cc1[C@H]1[C@@H]2C[C@H](N3CCO[C@H](C)C3)C[C@@H]21]<br>5-(1-isopropyl-5-((1R,3r,5S,6R)-3-((R)-2-methylmorpholino)bicyclo[3.1.0]hexan-6-yl)-1H-pyrazol-3-yl)-3-(trifluoromethoxy)pyridin-2-amine | ¹H NMR (400 MHz, Chloroform-d) δ 8.52 (s, 1 H), 8.08 (s, 1 H), 5.94 (s, 1 H), 4.92 (br s, 2 H), 4.65- 4.60 (m, 1 H), 3.88-3.83 (m, 1 H), 3.62 (m, 2 H), 2.85-2.75 (m, 3 H), 2.30-2.22 (m, 2H), 2.10-2.00 (m, 1 H), 1.85-1.80 (m, 1 H), 1.65-1.55 (m, 5 H), 1.51 (d, J = 6.4 Hz, 6 H), 1.15 (d, J = 6.4 Hz, 3 H) | 450.2 | A |
| 13 | 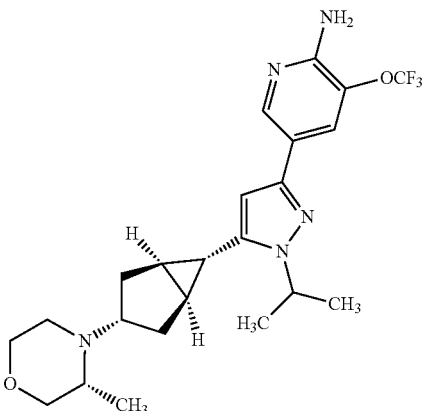<br>5-(1-isopropyl-5-((1R,3s,5S,6R)-3-((R)-3-methylmorpholino)bicyclo[3.1.0]hexan-6-yl)-1H-pyrazol-3-yl)-3-(trifluoromethoxy)pyridin-2-amine | ¹H NMR (400 MHz, Methanol-d4) δ 8.24 (s, 1 H), 7.82 (s, 1 H), 6.15 (s, 1 H), 4.79-4.74 (m, 1 H), 3.72-3.68 (m, 3 H), 3.50-3.47 (m, 1 H), 3.05-2.95 (m, 1 H), 2.80-2.75 (m, 1 H), 2.72-2.65 (m, 1 H), 2.50-2.45 (m, 1 H), 2.19-2.12 (m, 2 H), 1.90-1.88 (m, 2 H), 1.76-1.70 (m, 3 H), 1.50 (d, J = 6.8 Hz, 6 H), 1.10 (d, J = 6.4 Hz, 3 H) | 466.1 | A |
| 14 | 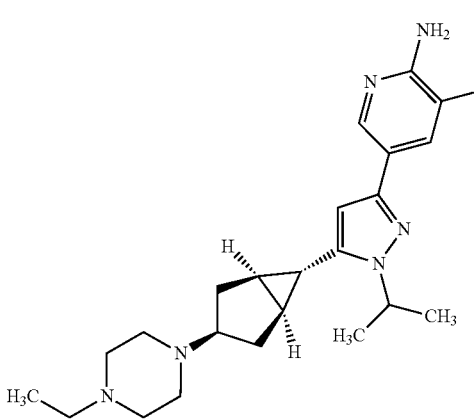<br>5-(5-((1R,3r,5S,6r)-3-(4-ethylpiperazin-1-yl)bicyclo[3.1.0]hexan-6-yl)-1-isopropyl-1H-pyrazol-3-yl)-3-(trifluoromethoxy)pyridin-2-amine | ¹H NMR (DMSO-d₆) δ: 8.28 (d, J = 1.9 Hz, 1H), 7.70 (m, 1H), 6.40 (br s, 2H), 6.21 (s, 1H), 4.66 (m, 1H), 2.84-2.70 (m, 1H), 2.47-2.17 (m, 8H), 2.17- 2.00 (m, 2H), 1.94 (t, J = 3.3 Hz, 1H), 1.69 (dd, J = 13.6, 6.2 Hz, 2H), 1.58 (m, 2H), 1.42 (d, J = 6.6 Hz, 6H), 0.97 (t, J = 7.2 Hz, 3H) | 479.2 | A |

TABLE A-continued

| Cmpd No. | Structure | ¹H NMR | MS [MH]⁺ | Method |
|---|---|---|---|---|
| 15 | <br>5-(5-((1R,3s,5S,6r)-3-(4-ethylpiperazin-1-yl)bicyclo[3.1.0]hexan-6-yl)-1-isopropyl-1H-pyrazol-3-yl)-3-(trifluoromethoxy)pyridin-2-amine | ¹H NMR (DMSO-$d_6$) δ: 8.28 (d, J = 1.9 Hz, 1H), 7.70 (m, 1H), 6.40 (br s, 2H), 6.25 (s, 1H), 4.67 (m, 1H), 2.48-2.19 (m, 9H), 2.11 (dd, J = 12.1, 6.9 Hz, 2H), 1.78-1.52 (m, 7H), 1.40 (d, J = 6.6 Hz, 6H), 0.97 (t, J = 7.2 Hz, 3H) | 479.2 | A |
| 16 | 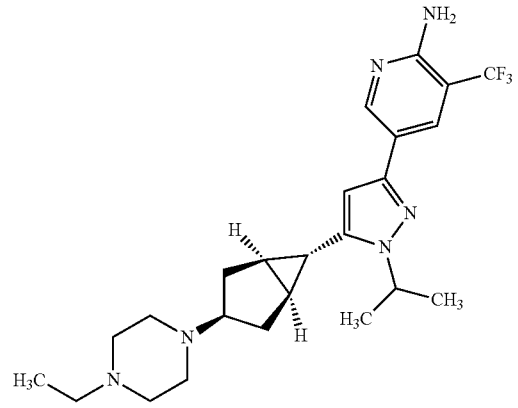 [SMILES: CCN1CCN([C@H]2C[C@@H]3[C@H](C2)[C@H]3c2cc(-c3cnc(N)c(C(F)(F)F)c3)nn2C(C)C)CC1]<br>5-(5-((1R,3r,5S,6r)-3-(4-ethylpiperazin-1-yl)bicyclo[3.1.0]hexan-6-yl)-1-isopropyl-1H-pyrazol-3-yl)-3-(trifluoromethyl)pyridin-2-amine | ¹H NMR (DMSO-$d_6$) δ: 8.57-8.44 (m, 1H), 7.97 (d, J = 2.2 Hz, 1H), 6.44 (br s, 2H), 6.26 (s, 1H), 4.67 (m, 1H), 2.77 (h, J = 6.6 Hz, 1H), 2.26 (m, 1H), 2.10 (m, 2H), 1.95 (t, J = 3.3 Hz, 1H), 1.69 (dd, J = 13.6, 6.3 Hz, 2H), 1.60 (d, J = 4.0 Hz, 2H), 1.43 (d, J = 6.6 Hz, 6H), 0.97 (t, J = 7.2 Hz, 3H) | 463.2 | A |
| 17 | 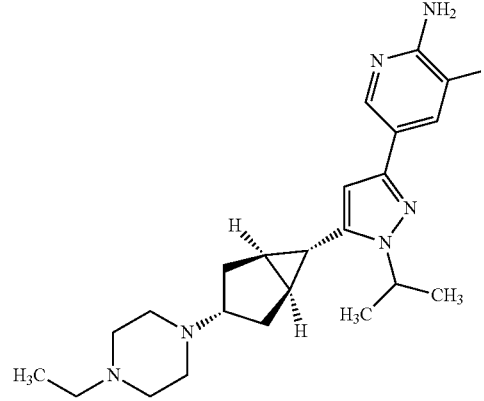<br>5-(5-((1R,3s,5S,6r)-3-(4-ethylpiperazin-1-yl)bicyclo[3.1.0]hexan-6-yl)-1-isopropyl-1H-pyrazol-3-yl)-3-(trifluoromethyl)pyridin-2-amine | ¹H NMR (DMSO-$d_6$) δ: 8.53 (d, J = 2.1 Hz, 1H), 7.97 (d, J = 2.2 Hz, 1H), 6.44 (br s, 2H), 6.30 (s, 1H), 4.68 (m, 1H), 2.47-2.18 (m, 11H), 2.11 (dd, J = 12.1, 6.9 Hz, 2H), 1.80-1.55 (m, 5H), 1.40 (d, J = 6.5 Hz, 6H), 0.97 (t, J = 7.1 Hz, 3H) | 463.2 | A |

TABLE A-continued

| Cmpd No. | Structure | ¹H NMR | MS [MH]⁺ | Method |
|---|---|---|---|---|
| 18 | 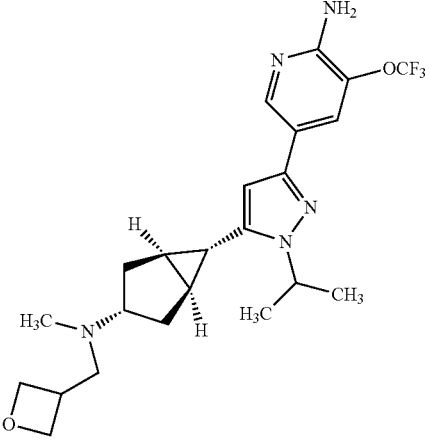 [SMILES: CC(C)n1nc(-c2cnc(N)c(OC(F)(F)F)c2)cc1[C@H]1[C@@H]2C[C@@H](N(C)CC3COC3)C[C@@H]21]<br>5-(1-isopropyl-5-((1R,3s,5S,6r)-3-(methyl(oxetan-3-ylmethyl)amino)bicyclo[3.1.0]hexan-6-yl)-1H-pyrazol-3-yl)-3-(trifluoromethoxy)pyridin-2-amine | ¹H NMR (DMSO-$d_6$) δ: 8.29 (d, J = 1.9 Hz, 1H), 7.71 (m, 1H), 6.40 (br s, 2H), 6.25 (s, 1H), 4.76-4.65 (m, 1H), 4.62 (dd, J = 7.8, 5.8 Hz, 2H), 4.22 (t, J = 6.1 Hz, 2H), 3.13 (m, 1H), 2.69-2.54 (m, 3H), 2.09 (dd, J = 12.3, 7.0 Hz, 2H), 2.02 (s, 3H), 1.79-1.53 (m, 5H), 1.41 (d, J = 6.5 Hz, 6H) | 466.2 | A |
| 19 | 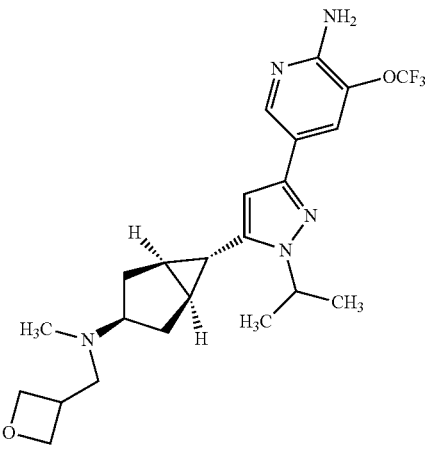 [SMILES: CC(C)n1nc(-c2cnc(N)c(OC(F)(F)F)c2)cc1[C@H]1[C@@H]2C[C@H](N(C)CC3COC3)C[C@@H]21]<br>5-(1-isopropyl-5-((1R,3r,5S,6r)-3-(methyl(oxetan-3-ylmethyl)amino)bicyclo[3.1.0]hexan-6-yl)-1H-pyrazol-3-yl)-3-(trifluoromethoxy)pyridin-2-amine | ¹HNMR (DMSO-$d_6$) δ: 8.28 (d, J = 1.9 Hz, 1H), 7.70 (m, 1H), 6.40 (br s, 2H), 6.22 (s, 1H), 4.72-4.54 (m, 3H), 4.24 (t, J = 6.0 Hz, 2H), 3.13 (m, 1H), 2.96 (m, 1H), 2.58 (d, J = 7.5 Hz, 2H), 2.22-2.07 (m, 2H), 2.01 (s, 3H), 1.82 (t, J = 3.2 Hz, 1H), 1.70-1.49 (m, 4H), 1.42 (d, J = 6.6 Hz, 6H) | 466.2 | A |

TABLE A-continued

| Cmpd No. | Structure | ¹H NMR | MS [MH]⁺ | Method |
|---|---|---|---|---|
| 20 | 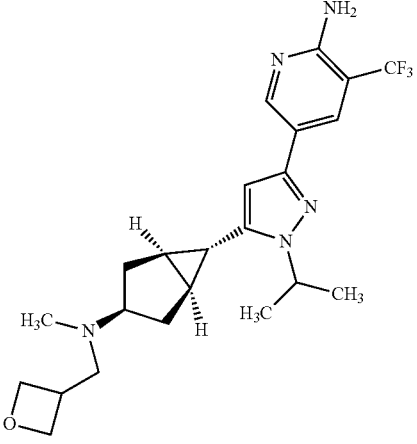 [SMILES: CC(C)n1nc(-c2cnc(N)c(C(F)(F)F)c2)cc1[C@H]1[C@@H]2C[C@H](N(C)CC3COC3)C[C@@H]21]<br>5-(1-isopropyl-5-((1R,3r,5S,6r)-3-(methyl(oxetan-3-ylmethyl)amino)bicyclo[3.1.0]hexan-6-yl)-1H-pyrazol-3-yl)-3-(trifluoromethyl)pyridin-2-amine | ¹H NMR (DMSO-$d_6$) δ: 8.56-8.48 (m, 1H), 7.97 (d, J = 2.2 Hz, 1H), 6.45 (br s, 2H), 6.27 (s, 1H), 4.75-4.55 (m, 3H), 4.24 (t, J = 6.1 Hz, 2H), 3.13 (m, 1H), 2.96 (m, 1H), 2.58 (d, J = 7.4 Hz, 2H), 2.21-2.07 (m, 2H), 2.02 (s, 3H), 1.82 (t, J = 3.3 Hz, 1H), 1.71-1.52 (m, 4H), 1.42 (d, J = 6.6 Hz, 6H) | 450.2 | A |
| 21 | 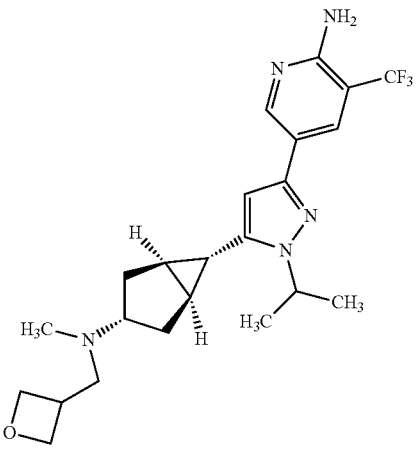 [SMILES: CC(C)n1nc(-c2cnc(N)c(C(F)(F)F)c2)cc1[C@H]1[C@@H]2C[C@@H](N(C)CC3COC3)C[C@@H]21]<br>5-(1-isopropyl-5-((1R,3s,5S,6r)-3-(methyl(oxetan-3-ylmethyl)amino)bicyclo[3.1.0]hexan-6-yl)-1H-pyrazol-3-yl)-3-(trifluoromethyl)pyridin-2-amine | ¹H NMR (DMSO-$d_6$) δ: 8.59-8.47 (m, 1H), 7.98 (d, J = 2.2 Hz, 1H), 6.45 (br s, 2H), 6.30 (s, 1H), 4.69 (m, 1H), 4.62 (dd, J = 7.8, 5.8 Hz, 2H), 4.22 (t, J = 6.1 Hz, 2H), 3.21-3.06 (m, 1H), 2.71-2.54 (m, 2H), 2.09 (dd, J = 12.3, 6.9 Hz, 2H), 2.02 (s, 3H), 1.78-1.53 (m, 5H), 1.41 (d, J = 6.6 Hz, 5H) | 450.2 | A |

| Cmpd No. | Structure | ¹H NMR | MS [MH]⁺ | Method |
|---|---|---|---|---|
| 22 | 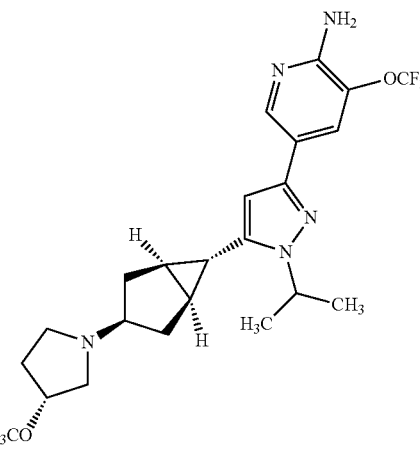<br>5-(1-isopropyl-5-((1R,3r,5S,6R)-3-((R)-3-methoxypyrrolidin-1-yl)bicyclo[3.1.0]hexan-6-yl)-1H-pyrazol-3-yl)-3-(trifluoromethoxy)pyridin-2-amine | ¹H NMR (DMSO-$d_6$) δ: 8.28 (d, J = 2.1 Hz, 1H), 7.70 (s, 1H), 6.37 (br s, 2H), 6.21 (s, 1H), 4.62 (m, 1H), 3.82 (s, 1H), 3.16 (s, 3H), 2.74 (m, 1H), 2.57 (m, 4H), 2.32 (m, 1H), 2.23 (m, 1H), 2.09-1.80 (m, 5H), 1.67-1.53 (m, 2H), 1.42 (d, J = 6.5 Hz, 6H) | 466.2 | A |
| 23 | 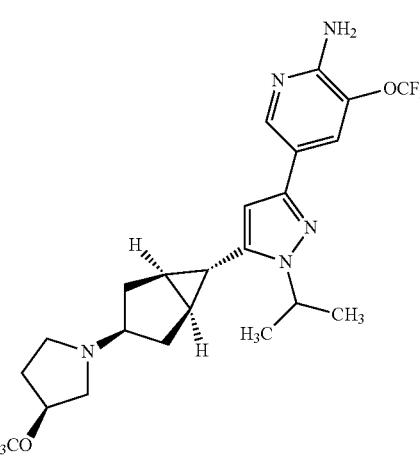<br>5-(1-isopropyl-5-((1R,3r,5S,6S)-3-((S)-3-methoxypyrrolidin-1-yl)bicyclo[3.1.0]hexan-6-yl)-1H-pyrazol-3-yl)-3-(trifluoromethoxy)pyridin-2-amine | ¹H NMR (DMSO-$d_6$) δ: 8.28 (s, 1H), 7.70 (s, 1H), 6.38 (br s, 2H), 6.21 (s, 1H), 4.62 (m, 1H), 3.90-3.74 (m, 1H), 3.17 (s, 3H), 2.74 (m, 1H), 2.67-2.49 (m, 4H), 2.32 (m, 1H), 2.23 (t, J = 3.3 Hz, 1H), 2.01 (m, 2H), 1.91 (m, 3H), 1.59 (m, 2H), 1.42 (d, J = 6.5 Hz, 6H) | 466.2 | A |

TABLE A-continued

| Cmpd No. | Structure | ¹H NMR | MS [MH]⁺ | Method |
|---|---|---|---|---|
| 24 | 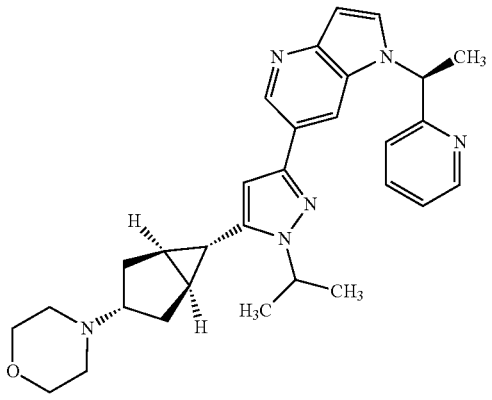 [SMILES: CC(C)n1nc(-c2cnc3ccn([C@@H](C)c4ccccn4)c3c2)cc1[C@H]1[C@@H]2C[C@@H](N3CCOCC3)C[C@@H]21]<br>4-((1R,3R,5S,6r)-6-(1-isopropyl-3-(1-((S)-1-(pyridin-2-yl)ethyl)-1H-pyrrolo[3,2-b]pyridin-6-yl)-1H-pyrazol-5-yl)bicyclo[3.1.0]hexan-3-yl)morpholine | ¹H NMR (400 MHz, Methanol-d4) δ 8.68 (s, 1 H), 8.54 (d, J = 4.4 Hz, 1 H), 8.07 (s, 1 H), 7.85 (s, 1 H), 7.73-7.69 (m, 1 H), 7.30-7.26 (m, 1 H), 7.10 (d, J = 8.0 Hz, 1 H), 6.67 (s, 1 H), 6.24 (s, 1 H), 5.91-5.89 (m, 1 H), 4.76-4.72 (m, 1 H), 3.68 (m, 4 H), 2.49 (m, 5 H), 2.30-2.25 (m, 2 H), 2.00 (d, J = 6.8 Hz, 3H), 1.83-1.72 (m, 5 H), 1.50 (d, J = 6.8 Hz, 6 H) | 497.2 | A |
| 25 | 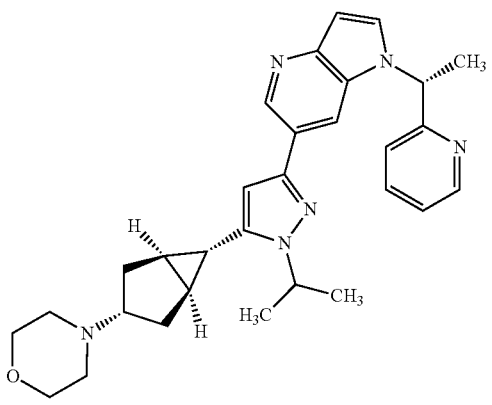 [SMILES: CC(C)n1nc(-c2cnc3ccn([C@H](C)c4ccccn4)c3c2)cc1[C@H]1[C@@H]2C[C@@H](N3CCOCC3)C[C@@H]21]<br>4-((1R,3S,5S,6r)-6-(1-isopropyl-3-(1-((R)-1-(pyridin-2-yl)ethyl)-1H-pyrrolo[3,2-b]pyridin-6-yl)-1H-pyrazol-5-yl)bicyclo[3.1.0]hexan-3-yl)morpholine | ¹H NMR (400 MHz, Methanol-d4) δ 8.60 (s, 1 H), 8.44 (d, J = 4.4 Hz, 1 H), 7.99 (s, 1 H), 7.75 (s, 1 H), 7.64-7.60 (m, 1 H), 7.20-7.17 (m, 1 H), 7.00 (d, J = 8.0 Hz, 1 H), 6.58 (s, 1 H), 6.15 (s, 1 H), 5.82-5.80 (m, 1 H), 4.66-4.63 (m, 1 H), 3.61-3.58 (m, 4 H), 2.41 (m, 5 H), 2.20-2.15 (m, 2 H), 1.90 (d, J = 6.8 Hz, 3 H), 1.74-1.63 (m, 5 H), 1.41 (d, J = 6.4 Hz, 6 H) | 497.2 | A |
| 26 | 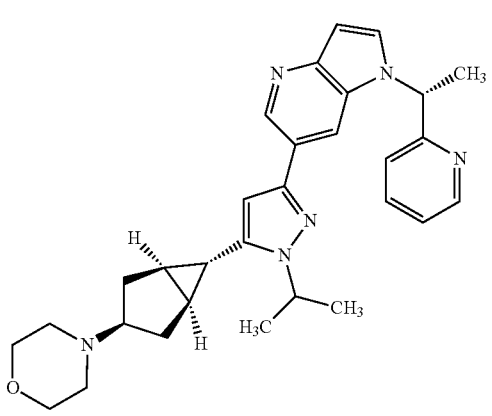 [SMILES: CC(C)n1nc(-c2cnc3ccn([C@H](C)c4ccccn4)c3c2)cc1[C@H]1[C@@H]2C[C@H](N3CCOCC3)C[C@@H]21]<br>4-((1R,3R,5S,6r)-6-(1-isopropyl-3-(1-((R)-1-(pyridin-2-yl)ethyl)-1H-pyrrolo[3,2-b]pyridin-6-yl)-1H-pyrazol-5-yl)bicyclo[3.1.0]hexan-3-yl)morpholine | ¹H NMR (400 MHz, Methanol-d4) δ 8.69 (s, 1 H), 8.53 (d, J = 4.4 Hz, 1 H), 8.09 (s, 1 H), 7.86 (s, 1 H), 7.73-7.69 (m, 1 H), 7.29-7.26 (m, 1 H), 7.10 (d, J = 8.0 Hz, 1 H), 6.67 (s, 1 H), 6.20 (s, 1 H), 5.91-5.89 (m, 1 H), 4.78-4.75 (m, 1 H), 3.70-3.68 (m, 4 H), 3.05-3.03 (m, 1 H), 2.53 (m, 4 H), 2.36-2.33 (m, 2 H), 1.99 (d, J = 7.2 Hz, 3H), 1.82 (m, 1 H), 1.69-1.61 (m, 4 H), 1.28 (d, J = 8.4 Hz, 6 H) | 497.2 | A |

TABLE A-continued

| Cmpd No. | Structure | ¹H NMR | MS [MH]⁺ | Method |
|---|---|---|---|---|
| 27 | 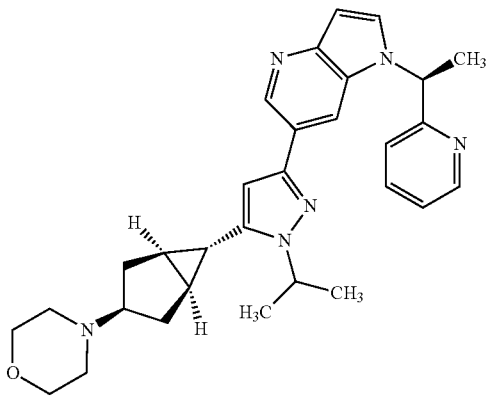 [SMILES: CC(C)n1nc(-c2cnc3ccn([C@@H](C)c4ccccn4)c3c2)cc1[C@H]1[C@@H]2C[C@H](N3CCOCC3)C[C@@H]21]<br>4-((1R,3S,5S,6r)-6-(1-isopropyl-3-1-((S)-1-(pyridin-2-yl)ethyl)-1H-pyrrolo[3,2-b]pyridin-6-yl)-1H-pyrazol-5-yl)bicyclo[3.1.0]hexan-3-yl)morpholine | ¹H NMR (400 MHz, Methanol-d4) δ 8.68 (s, 1 H), 8.53 (d, J = 4.0 Hz, 1 H), 8.09 (s, 1 H), 7.86 (s, 1 H), 7.73-7.69 (m, 1 H), 7.29-7.26 (m, 1 H), 7.10 (d, J = 8.0 Hz, 1 H), 6.68 (s, 1 H), 6.20 (s, 1 H), 5.91-5.90 (m, 1 H), 4.80-4.75 (m, 1 H), 3.71 (m, 4 H), 3.12-3.09 (m, 1 H), 2.59 (m, 4 H), 2.40-2.35 (m, 2 H), 1.99 (d, J = 6.8 Hz, 3 H), 1.83 (m, 1 H), 1.70-1.63 (m, 4H), 1.52 (d, J = 6.4 Hz, 6 H) | 497.2 | A |
| 28 | 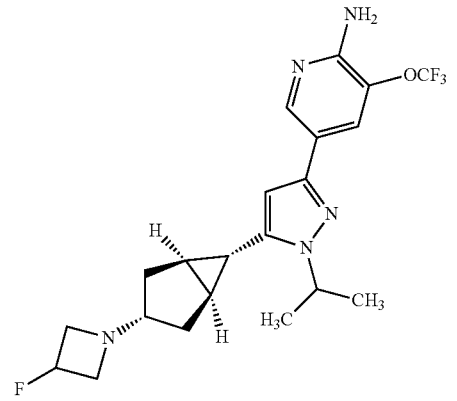 [SMILES: CC(C)n1nc(-c2cnc(N)c(OC(F)(F)F)c2)cc1[C@H]1[C@@H]2C[C@@H](N3CC(F)C3)C[C@@H]21]<br>5-(5-((1R,3s,5S,6r)-3-(3-fluoro-azetidin-1-yl)bicyclo[3.1.0]hexan-6-yl)-1-isopropyl-1H-pyrazol-3-yl)-3-(trifluoromethoxy)pyridin-2-amine | ¹H NMR (400 MHz, Methanol-d4) δ 8.24 (s, 1 H), 7.81 (s, 1 H), 6.14 (s, 1 H), 5.22-5.04 (m, 1 H), 4.77-4.70 (m, 1 H), 3.68-3.60 (m, 2 H), 3.36-3.35 (m, 2 H), 2.88-2.80 (m, 1 H), 2.21-2.16 (m, 2 H), 1.71-1.65 (m, 5 H), 1.50 (d, J = 6.8 Hz, 6 H) | 439.9 | A |
| 29 | 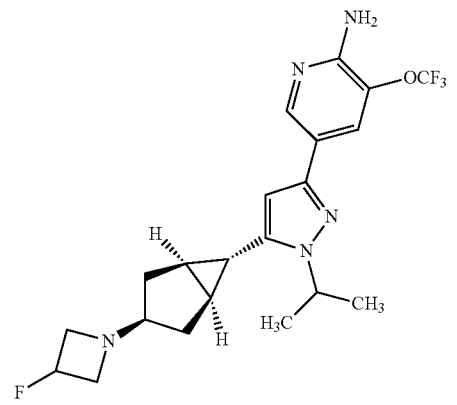 [SMILES: CC(C)n1nc(-c2cnc(N)c(OC(F)(F)F)c2)cc1[C@H]1[C@@H]2C[C@H](N3CC(F)C3)C[C@@H]21]<br>5-(5-((1R,3r,5S,6r)-3-(3-fluoro-azetidin-1-yl)bicyclo[3.1.0]hexan-6-yl)-1-isopropyl-1H-pyrazol-3-yl)-3-(trifluoromethoxy)pyridin-2-amine | ¹H NMR (400 MHz, Methanol-d4) δ 8.24 (s, 1 H), 7.81 (s, 1 H), 6.08 (s, 1 H), 5.14-4.97 (m, 1 H), 4.76-4.71 (m, 1 H), 3.61-3.54 (m, 2 H), 3.08-3.05 (m, 1 H), 3.02-2.99 (m, 2 H), 2.36 (m, 1 H), 2.07-2.02 (m, 2 H), 1.78 (m, 1 H), 1.75 (m, 1 H), 1.66 (m, 2 H), 1.51 (d, J = 6.8 Hz, 6 H) | 439.9 | A |

TABLE A-continued

| Cmpd No. | Structure | ¹H NMR | MS [MH]⁺ | Method |
|---|---|---|---|---|
| 30 | 5-(5-((1R,3r,5S,6r)-3-(azetidin-1-yl)bicyclo[3.1.0]hexan-6-yl)-1-isopropyl-1H-pyrazol-3-yl)-3-(trifluoromethyl)pyridin-2-amine | ¹H NMR (400 MHz, Methanol-d4) δ 8.48 (s, 1 H), 8.10 (s, 1 H), 6.11 (s, 1 H), 4.82-4.75 (m, 1 H), 3.22 (s, 4 H), 3.13-3.11 (m, 1 H), 2.19-2.14 (m, 1 H), 2.12-2.04 (m, 4 H), 1.71-1.70 (m, 1 H), 1.67-1.66 (m, 3 H), 1.52 (d, J = 6.4 Hz, 6 H) | 405.9 | A |
| 31 | 4-((1R,3S,5S,6r)-6-(1-isopropyl-3-(1-((R)-1-(pyridin-2-yl)ethyl)-1H-pyrazolo[4,3-b]pyridin-6-yl)-1H-pyrazol-5-yl)bicyclo[3.1.0]hexan-3-yl)morpholine | ¹H NMR (400 MHz, Methanol-d4) δ 8.94 (s, 1 H), 8.51-8.50 (m, 1 H), 8.28 (s, 1 H), 8.23 (s, 1 H), 7.76-7.72 (m, 1 H), 7.31-7.28 (m, 1 H), 7.19 (d, J = 8.0 Hz, 1 H), 6.38 (s, 1 H), 6.11-6.09 (m, 1 H), 4.78-4.75 (m, 1 H), 3.71-3.68 (m, 4 H), 2.51 (m, 5 H), 2.31-2.26 (m, 2 H), 2.07 (d, J = 7.2 Hz, 3 H), 1.85-1.75 (m, 5 H), 1.52 (d, J = 6.4 Hz, 6 H) | 498.2 | A |
| 32 | 4-((1R,3R,5S,6r)-6-(1-isopropyl-3-(1-((S)-1-(pyridin-2-yl)ethyl)-1H-pyrazolo[4,3-b]pyridin-6-yl)-1H-pyrazol-5-yl)bicyclo[3.1.0]hexan-3-yl)morpholine | ¹H NMR (400 MHz, Methanol-d4) δ 8.93 (s, 1 H), 8.50 (d, J = 4.8 Hz, 1 H), 8.28 (s, 1 H), 8.23 (s, 1 H), 7.76-7.72 (m, 1 H), 7.31-7.27 (m, 1 H), 7.18 (d, J = 8.0 Hz, 1 H), 6.38 (s, 1 H), 6.11-6.09 (m, 1 H), 4.78-4.75 (m, 1 H), 3.70-3.68 (m, 4 H), 2.49 (m, 5 H), 2.30-2.25 (m, 2 H), 2.07 (d, J = 6.8 Hz, 3H), 1.83-1.78 (m, 2 H), 1.74 (m, 3 H), 1.51 (d, J = 6.4 Hz, 6 H) | 498.2 | A |

TABLE A-continued

| Cmpd No. | Structure | ¹H NMR | MS [MH]⁺ | Method |
|---|---|---|---|---|
| 33 | 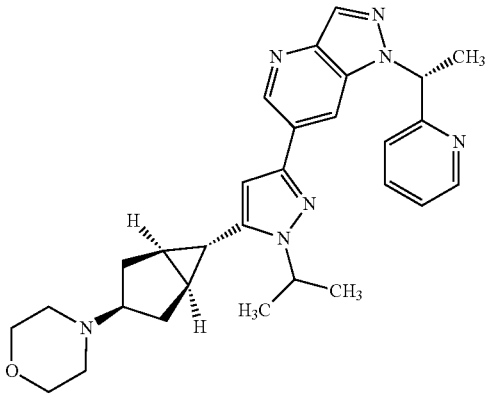 [SMILES: CC(C)n1nc(-c2cnc3cnn([C@H](C)c4ccccn4)c3c2)cc1[C@H]1[C@@H]2C[C@H](N3CCOCC3)C[C@@H]21]<br>4-((1R3R,5S,6r)-6-(1-isopropyl-3-(1-((R)-1-(pyridin-2-yl)ethyl)-1H-pyrazolo[4,3-b]pyridin-6-yl)-1H-pyrazol-5-yl)bicyclo[3.10]hexan-3-yl)morpholine | ¹H NMR (400 MHz, Methanol-d4) δ 8.93 (s, 1 H), 8.49 (d, J = 4.8 Hz, 1 H), 8.27 (s, 1 H), 8.22 (s, 1 H), 7.73-7.69 (m, 1 H), 7.29-7.25 (m, 1 H), 7.17 (d, J = 8.0 Hz, 1 H), 6.30 (s, 1 H), 6.09-6.06 (m, 1 H), 4.79-4.75 (m, 1 H), 3.67-3.65 (m, 4 H), 2.93-2.91 (m, 1 H), 2.44 (m, 4 H), 2.31-2.29 (m, 2 H), 2.05 (d, J = 7.2 Hz, 3 H), 1.83-1.82 (m, 1 H), 1.66-1.59 (m, 4 H), 1.52 (d, J = 6.4 Hz, 6 H) | 498.2 | A |
| 34 | 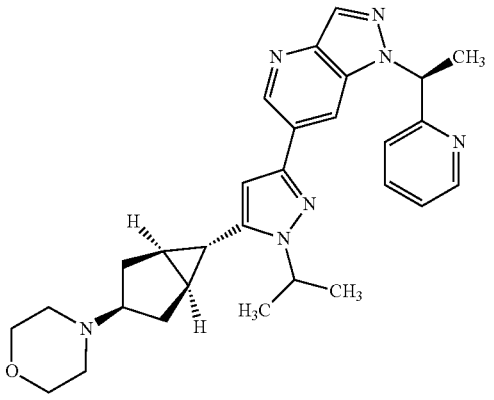 [SMILES: CC(C)n1nc(-c2cnc3cnn([C@@H](C)c4ccccn4)c3c2)cc1[C@H]1[C@@H]2C[C@H](N3CCOCC3)C[C@@H]21]<br>4-((1R,3S,5S,6r)-6-(1-isopropyl-3-(1-((S)-1-(pyridin-2-yl)ethyl)-1H-pyrazolo[4,3-b]pyridin-6-yl)-1H-pyrazol-5-yl)bicyclo[3.1.0]hexan-3-yl)morpholine | ¹HNMR (400 MHz, Methanol-d4) δ 8.93 (s, 1 H), 8.49 (d, J = 4.4 Hz, 1 H), 8.27 (s, 1 H), 8.22 (s, 1 H), 7.74-7.70 (m, 1 H), 7.29-7.26 (m, 1 H), 7.17 (d, J = 8.0 Hz, 1 H), 6.30 (s, 1 H), 6.11-6.06 (m, 1 H), 4.81-4.74 (m, 1 H), 3.67-3.65 (m, 4 H), 2.94-2.92 (m, 1 H), 2.44 (m, 4 H), 2.31-2.29 (m, 2 H), 2.05 (d, J = 7.2 Hz, 3 H), 1.84-1.83 (m, 1 H), 1.67-1.59 (m, 4 H), 1.52 (d, J = 6.8 Hz, 6 H) | 498.2 | A |
| 35 | 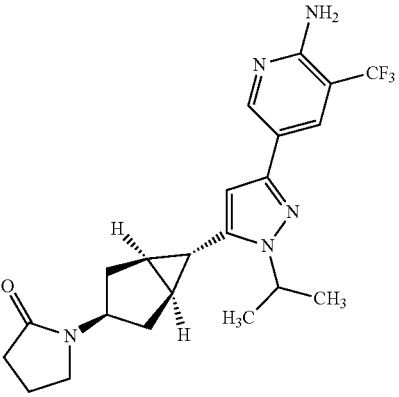 [SMILES: CC(C)n1nc(-c2cnc(N)c(C(F)(F)F)c2)cc1[C@H]1[C@@H]2C[C@H](N3CCCC3=O)C[C@@H]21]<br>1-((1R,3r,5S,6r)-6-(3-(6-amino-5-(trifluoromethyl)pyridin-3-yl)-1-isopropyl-1H-pyrazol-5-yl)bicyclo[3.1.0]hexan-3-yl)pyrrolidin-2-one | ¹H NMR (400 MHz, Methanol-d4) δ 8.49 (s, 1 H), 8.11 (s, 1 H), 6.20-6.17 (m, 1 H), 4.77-7.74 (m, 1 H), 4.38-4.29 (m, 1 H), 3.48-3.43 (m, 2 H), 2.42-2.38 (m, 3 H), 2.09-2.02 (m, 5 H), 1.86-1.85 (m, 1 H), 1.75 (m, 2 H), 1.51 (d, J = 6.8 Hz, 6 H) | 434.0 | A |

TABLE A-continued

| Cmpd No. | Structure | ¹H NMR | MS [MH]⁺ | Method |
|---|---|---|---|---|
| 36 | 5-(5-((1R,3r,5S,6r)-3-(3-fluoro-azetidin-1-yl)bicyclo[3.1.0]hexan-6-yl)-1-isopropyl-1H-pyrazol-3-yl)-3-(trifluoromethyl)pyridin-2-amine | ¹H NMR (400 MHz, Methanol-d4) δ 8.48 (s, 1 H), 8.10 (s, 1 H), 6.11 (s, 1 H), 5.14-4.97 (m, 1 H), 4.76-4.71 (m, 1 H), 3.59-3.54 (m, 2 H), 3.07-3.05 (m, 1 H), 3.02-2.98 (m, 2 H), 2.37-2.35 (m, 1 H), 2.04-2.02 (m, 2 H), 1.76 (m, 1 H), 1.66 (m, 2 H), 1.51 (d, J = 6.4 Hz, 6 H) | 424.2 | A |
| 37 | 5-(5-((1R,3s,5S,6r)-3-(3-fluoro-azetidin-1-yl)bicyclo[3.1.0]hexan-6-yl)-1-isopropyl-1H-pyrazol-3-yl)-3-(trifluoromethyl)pyridin-2-amine | ¹HNMR (400 MHz, Methanol-d4) δ 8.48 (s, 1 H), 8.10 (s, 1 H), 6.17 (s, 1 H), 5.19-5.03 (m, 1 H), 4.77-4.71 (m, 1 H), 3.63-3.57 (m, 2 H), 3.27-3.25 (m, 2 H), 2.85-2.79 (m, 1 H), 2.20-2.15 (m, 2 H), 2.71-2.65 (m, 5 H), 1.50 (d, J = 6.4 Hz, 6 H) | 423.9 | A |
| 38 | 5-(1-isopropyl-5-((1R,3s,5S,6r)-3-(3-methoxyazetidin-1-yl)bicyclo[3.1.0]hexan-6-yl)-1H-pyrazol-3-yl)-3-(trifluoromethoxy)pyridin-2-amine | ¹H NMR (400 MHz, Methanol-d4) δ 8.14 (s, 1 H), 7.71 (s, 1 H), 6.07 (s, 1 H), 4.67-4.60 (m, 1 H), 4.21-4.15 (m, 3 H), 3.82-3.80 (m, 2 H), 3.51-3.42 (m, 1 H), 3.25 (s, 3 H), 2.35-2.30 (m, 2 H), 1.81-1.68 (m, 5 H), 1.41 (d, J = 6.4 Hz, 6 H) | 452.0 | A |

| Cmpd No. | Structure | ¹H NMR | MS [MH]⁺ | Method |
|---|---|---|---|---|
| 39 | 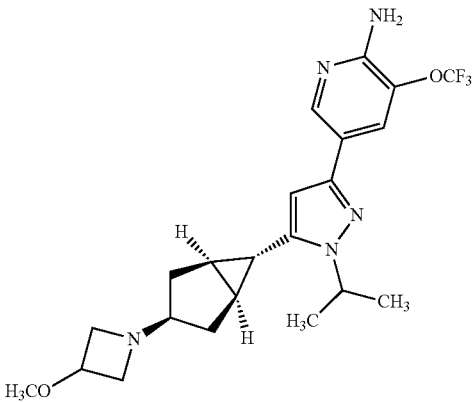 [SMILES: COC1CN([C@H]2C[C@@H]3[C@H](C2)[C@H]3c2cc(-c3cnc(N)c(OC(F)(F)F)c3)nn2C(C)C)C1]<br>5-(1-isopropyl-5-((1R,3r,5S,6r)-3-(3-methoxyazetidin-1-yl)bicyclo[3.1.0]hexan-6-yl)-1H-pyrazol-3-yl)-3-(trifluoromethoxy)pyridin-2-amine | ¹HNMR (400 MHz, Methanol-d4) δ 8.22 (s, 1 H), 7.80 (s, 1 H), 6.09 (s, 1 H), 4.76-4.73 (m, 1 H), 4.14-4.08 (m, 1 H), 3.95-3.93 (m, 2 H), 3.57 (m, 1 H), 3.40 (m, 2 H), 3.29 (s, 3 H), 2.37-2.32 (m, 2 H), 2.10 (m, 1 H), 1.75-1.71 (m, 4 H), 1.50 (d, J = 6.8 Hz, 6 H) | 452.0 | A |
| 40 | 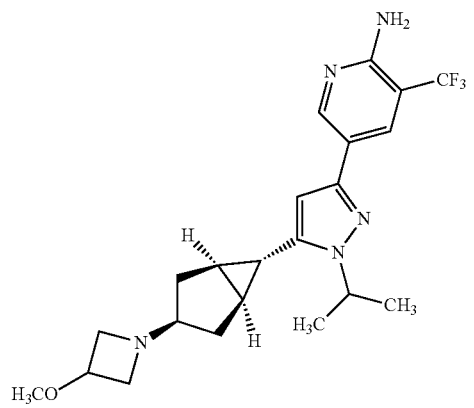 [SMILES: COC1CN([C@H]2C[C@@H]3[C@H](C2)[C@H]3c2cc(-c3cnc(N)c(C(F)(F)F)c3)nn2C(C)C)C1]<br>5-(1-isopropyl-5-((1R,3s,5S,6r)-3-(3-methoxyazetidin-1-yl)bicyclo[3.1.0]hexan-6-yl)-1H-pyrazol-3-yl)-3-(trifluoromethyl)pyridin-2-amine | ¹HNMR (400 MHz, Methanol-d4) δ 8.47 (s, 1 H), 8.08 (s, 1 H), 6.19 (s, 1 H), 4.76-4.71 (m, 1 H), 4.30-4.25 (m, 3 H), 3.96-3.94 (m, 2 H), 3.67-3.61 (m, 1 H), 3.32 (s, 3 H), 2.45-2.40 (m, 2 H), 1.91-1.77 (m, 5 H), 1.49 (d, J = 6.4 Hz, 6 H) | 435.9 | A |
| 41 | 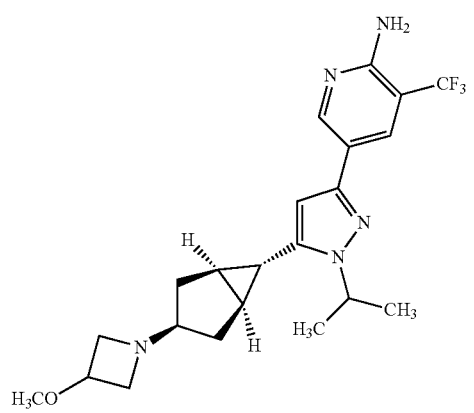 [SMILES: COC1CN([C@H]2C[C@@H]3[C@H](C2)[C@H]3c2cc(-c3cnc(N)c(C(F)(F)F)c3)nn2C(C)C)C1]<br>5-(1-isopropyl-5-((1R,3r,5S,6r)-3-(3-methoxyazetidin-1-yl)bicyclo[3.1.0]hexan-6-yl)-1H-pyrazol-3-yl)-3-(trifluoromethyl)pyridin-2-amine | ¹H NMR (400 MHz, Methanol-d4) δ 8.49 (s, 1 H), 8.11 (s, 1 H), 6.15 (s, 1 H), 4.81-4.76 (m, 1 H), 4.14-4.11 (m, 1 H), 3.92 (m, 2 H), 3.55 (m, 1 H), 3.37-3.32 (m, 5 H), 2.40-2.35 (m, 2 H), 2.14 (m, 1 H), 1.78-1.70 (m, 4 H), 1.53 (d, J = 6.8 Hz, 6H) | 435.9 | A |

TABLE A-continued

| Cmpd No. | Structure | ¹H NMR | MS [MH]⁺ | Method |
|---|---|---|---|---|
| 42 | 5-(5-((1R,3s,5S,6r)-3-(3,3-difluoroazetidin-1-yl)bicyclo[3.1.0]hexan-6-yl)-1-isopropyl-1H-pyrazol-3-yl)-3-(difluoromethoxy)pyridin-2-amine | ¹H NMR (400 MHz, Methanol-d4) δ 8.13 (s, 1 H), 7.70 (s, 1 H), 6.86 (t, $J_{HF}$ = 73.2 Hz, 1 H), 6.12 (s, 1 H), 4.74-4.71 (m, 1 H), 3.63 (t, J = 12.0 Hz, 4 H), 2.90-2.85 (m, 1 H), 2.22-2.15 (m, 2 H), 1.71 (m, 5 H), 1.49 (d, J = 5.6 Hz, 6 H) | 440.2 | A |
| 43 | 5-(5-((1R,3r,5S,6r)-3-(3,3-difluoro-azetidin-1-yl)bicyclo[3.1.0]hexan-6-yl)-1-isopropyl-1H-pyrazol-3-yl)-3-(difluoromethoxy)pyridin-2-amine | ¹H NMR (400 MHz, Methanol-d4) δ 8.13 (s, 1 H), 7.70 (s, 1 H), 6.86 (t, $J_{HF}$ = 73.6 Hz, 1 H), 6.07 (s, 1 H), 4.75-4.68 (m, 1 H), 3.48 (t, J = 12.0 Hz, 4 H), 3.10-3.04 (m, 1 H), 2.46-2.44 (m, 1 H), 2.09-2.04 (m, 2 H), 1.82-1.78 (m, 2 H), 1.67 (m, 2 H), 1.51 (d, J = 6.8 Hz, 6 H) | 440.2 | A |
| 44 | 1-((1R,3s,5S,6r)-6-(3-(6-amino-5-(trifluoromethyl)pyridin-3-yl)-1-isopropyl-1H-pyrazol-5-yl)bicyclo[3.1.0]hexan-3-yl)pyrrolidin-2-one | ¹H NMR (400 MHz, Methanol-d4) δ 8.48 (s, 1 H), 8.09 (s, 1 H), 6.16 (s, 1 H), 4.78-4.72 (m, 2 H), 3.45-3.42 (m, 2 H), 2.38-2.31 (m, 4 H), 2.03-2.00 (m, 2 H), 1.77-1.72 (m, 5 H), 1.51 (d, J = 6.8 Hz, 6 H) | 433.9 | A |

TABLE A-continued

| Cmpd No. | Structure | ¹H NMR | MS [MH]⁺ | Method |
|---|---|---|---|---|
| 45 | 5-(1-isopropyl-5-((1R,3r,5S,6R)-3-((R)-3-methylmorpholino)bicyclo[3.1.0]hexan-6-yl)-1H-pyrazol-3-yl)-3-(trifluoromethyl)pyridin-2-amine | ¹H NMR (400 MHz, Methanol-d4) δ 8.47 (s, 1 H), 8.09 (s, 1 H), 6.12 (s, 1 H), 4.78-4.75 (m, 1 H), 3.73-3.65 (m, 4 H), 3.48-3.46 (m, 2 H), 2.81 (m, 1 H), 2.70-2.65 (m, 1 H), 2.49-2.47 (m, 1 H), 2.28-2.22 (m, 2 H), 1.78 (m, 1 H), 1.71-1.63 (m, 3 H), 1.51 (d, J = 6.4 Hz, 6 H), 1.08 (d, J = 6.8 Hz, 3 H) | 450.0 | A |
| 46 | 5-(1-isopropyl-5-((1R,3s,5S,6R)-3-((R)-3-methylmorpholino)bicyclo[3.1.0]hexan-6-yl)-1H-pyrazol-3-yl)-3-(trifluoromethyl)pyridin-2-amine | ¹HNMR (400 MHz, Methanol-d4) δ 8.48 (s, 1 H), 8.09 (s, 1 H), 6.17 (s, 1 H), 4.77-4.75 (m, 1 H), 3.71-3.68 (m, 3 H), 3.52-3.48 (m, 2 H), 3.02-2.05 (m, 1 H), 2.85-2.79 (m, 1 H), 2.75-2.71 (m, 1 H), 2.49-2.45 (m, 1 H), 2.20-2.11 (m, 2 H), 1.87-1.80 (m, 2 H), 1.75-1.70 (m, 2 H), 1.49 (d, J = 6.4 Hz, 6 H), 1.10 (d, J = 6.4 Hz, 3 H) | 450.0 | A |

TABLE A-continued

| Cmpd No. | Structure | ¹H NMR | MS [MH]⁺ | Method |
|---|---|---|---|---|
| 47 | 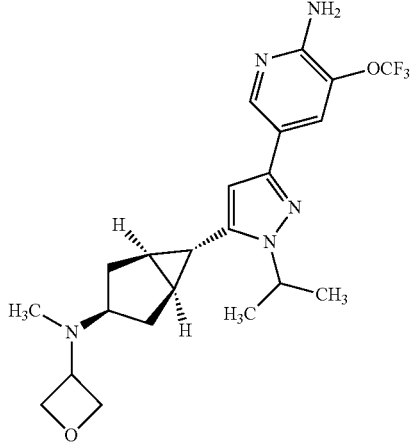 [SMILES: CC(C)n1nc(-c2cnc(N)c(OC(F)(F)F)c2)cc1[C@H]1[C@@H]2C[C@H](N(C)C3COC3)C[C@@H]21]<br>5-(1-isopropyl-5-(((1R,3r,5S,6r)-3-(methyl(oxetan-3-yl)amino)bicyclo[3.1.0]hexan-6-yl)-1H-pyrazol-3-yl)-3-(trifluoromethoxy)pyridin-2-amine | ¹H NMR (DMSO-d6) δ: 8.28 (d, J = 1.8 Hz, 1H), 7.70 (m, 1H), 6.39 (m, 2H), 6.21 (s, 1H), 4.69 (m, 1H), 4.47 (d, J = 7.0 Hz, 4H), 3.64 (m, 1H), 2.99 (m, 1H), 2.13-2.05 (m, 2H), 2.02 (s, 3H), 1.77 (t, J = 3.3 Hz, 1H), 1.56 (m, 2H), 1.47 (m, 2H), 1.42 (d, J = 6.7 Hz, 6H) | 452.2 | A |
| 48 | 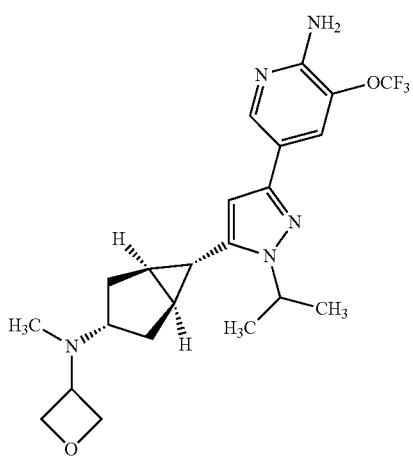 [SMILES: CC(C)n1nc(-c2cnc(N)c(OC(F)(F)F)c2)cc1[C@H]1[C@@H]2C[C@@H](N(C)C3COC3)C[C@@H]21]<br>5-(1-isopropyl-5-(((1R,3s,5S,6r)-3-(methyl(oxetan-3-yl)amino)bicyclo[3.1.0]hexan-6-yl)-1H-pyrazol-3-yl)-3-(trifluoromethoxy)pyridin-2-amine | ¹H NMR (DMSO-d₆) δ: 8.28 (d, J = 1.9 Hz, 1H), 7.69 (m, 1H), 6.38 (br s, 2H), 6.23 (s, 1H), 4.66 (m, 1H), 4.53-4.37 (m, 4H), 3.66 (m, 1H), 2.60 (m, 1H), 2.04 (s, 3H), 1.92 (dd, J = 12.3, 7.0 Hz, 2H), 1.75 (t, J = 3.2 Hz, 1H), 1.72-1.62 (m, 2H), 1.62-1.52 (m, 2H), 1.40 (d, J = 6.5 Hz, 6H) | 452.2 | A |

TABLE A-continued

| Cmpd No. | Structure | $^1$H NMR | MS [MH]$^+$ | Method |
|---|---|---|---|---|
| 49 | 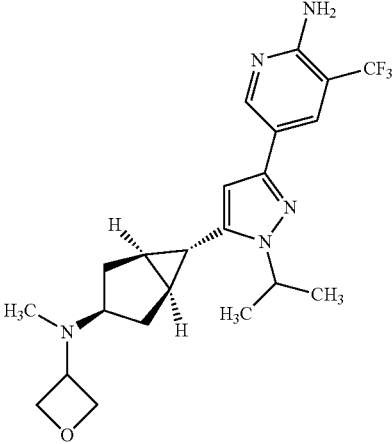 [SMILES: CC(C)n1nc(-c2cnc(N)c(C(F)(F)F)c2)cc1[C@H]1[C@@H]2C[C@H](N(C)C3COC3)C[C@@H]21]<br>5-(1-isopropyl-5-((1R,3r,5S,6r)-3-(methyl(oxetan-3-yl)amino)bicyclo[3.1.0]hexan-6-yl)-1H-pyrazol-3-yl)-3-(trifluoromethyl)pyridin-2-amine | $^1$H NMR (DMSO-d$_6$) δ: 8.53 (d, J = 2.2 Hz, 1H), 7.97 (d, J = 2.2 Hz, 1H), 6.43 (br s, 2H), 6.26 (s, 1H), 4.70 (m, 1H), 4.47 (d, J = 7.1 Hz, 4H), 3.65 (m, 1H), 2.99 (m, 1H), 2.14-2.03 (m, 2H), 2.03 (s, 3H), 1.78 (t, J = 3.3 Hz, 1H), 1.61-1.53 (m, 2H), 1.46 (m, 1H), 1.43 (d, J = 6.6 Hz, 6H) | 436.2 | A |
| 50 | 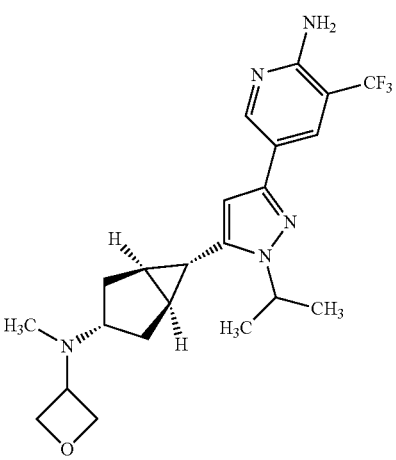 [SMILES: CC(C)n1nc(-c2cnc(N)c(C(F)(F)F)c2)cc1[C@H]1[C@@H]2C[C@@H](N(C)C3COC3)C[C@@H]21]<br>5-(1-isopropyl-5-((1R,3s,5S,6r)-3-(methyl(oxetan-3-yl)amino)bicyclo[3.1.0]hexan-6-yl)-1H-pyrazol-3-yl)-3-(trifluoromethyl)pyridin-2-amine | $^1$H NMR (DMSO-d$_6$) δ: 8.53 (d, J = 2.1 Hz, 1H), 7.97 (d, J = 2.1 Hz, 1H), 6.43 (br s, 2H), 6.29 (s, 1H), 4.68 (h, J = 6.7 Hz, 1H), 4.53-4.42 (m, 4H), 3.66 (m, 1H), 2.67-2.54 (m, 1H), 2.04 (s, 3H), 1.92 (dd, J = 12.2, 7.0 Hz, 2H), 1.80-1.62 (m, 3H), 1.57 (m, 2H), 1.40 (d, J = 6.5 Hz, 6H) | 436.2 | A |

TABLE A-continued

| Cmpd No. | Structure | $^1$H NMR | MS [MH]$^+$ | Method |
|---|---|---|---|---|
| 51 | 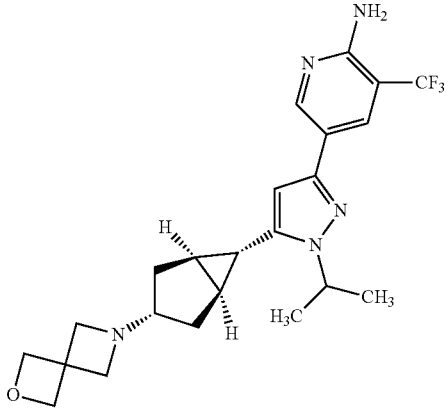 [SMILES: CC(C)n1nc(-c2cnc(N)c(C(F)(F)F)c2)cc1[C@H]1[C@@H]2C[C@@H](N3CC4(COC4)C3)C[C@@H]21]<br>5-(5-((1R,3s,5S,6r)-3-(2-oxa-6-azaspiro[3.3]heptan-6-yl)bicyclo[3.1.0]hexan-6-yl)-1-isopropyl-1H-pyrazol-3-yl)-3-(trifluoromethyl)pyridin-2-amine | $^1$H NMR (400 MHz, Methanol-d4) δ 8.47 (s, 1 H), 8.08 (s, 1 H), 6.16 (s, 1 H), 4.72 (m, 5H), 3.42 (m, 4 H), 2.69 (m, 1 H), 2.13 (m, 2 H), 1.60-1.68 (m, 5 H), 1.48 (d, J = 6.8 Hz, 6 H) | 436.0 | A |
| 52 | 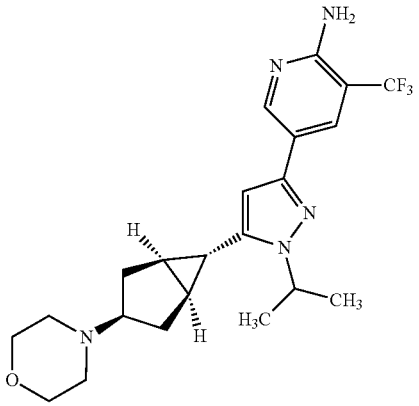 [SMILES: CC(C)n1nc(-c2cnc(N)c(C(F)(F)F)c2)cc1[C@H]1[C@@H]2C[C@H](N3CCOCC3)C[C@@H]21]<br>5-(1-isopropyl-5-((1R,3r,5S,6r)-3-morpholinobicyclo[3.1.0]hexan-6-yl)-1H-pyrazol-3-yl)-3-(trifluoromethyl)pyridin-2-amine | $^1$H NMR (400 MHz, Methanol-d4) δ 8.47 (s, 1 H), 8.09 (s, 1 H), 6.12 (s, 1 H), 4.76-4.74 (m, 1 H), 3.69-3.67 (m, 4 H), 2.95 (m, 1 H), 2.47 (m, 4 H), 2.33 (m, 2 H), 1.81 (m, 1 H), 1.69-1.61 (m, 4 H), 1.51 (d, J = 6.8 Hz, 6 H) | 435.9 | A |
| 53 | 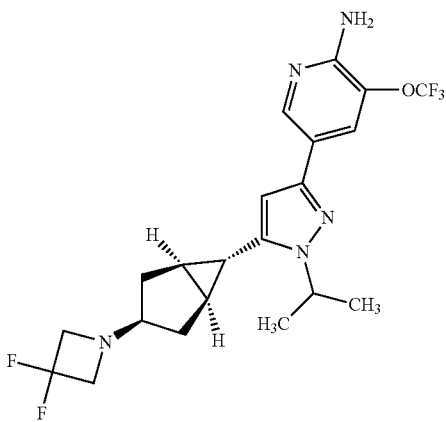 [SMILES: CC(C)n1nc(-c2cnc(N)c(OC(F)(F)F)c2)cc1[C@H]1[C@@H]2C[C@H](N3CC(F)(F)C3)C[C@@H]21]<br>5-(5-((1R,3r,5S,6r)-3-(3,3-difluoro-azetidin-1-yl)bicyclo[3.1.0]hexan-6-yl)-1-isopropyl-1H-pyrazol-3-yl)-3-(trifluoromethoxy)pyridin-2-amine | $^1$H NMR (400 MHz, Methanol-d4) δ 8.24 (s, 1 H), 7.82 (s, 1 H), 6.10 (s, 1 H), 4.74-4.70 (m, 1 H), 3.49 (t, J = 12.0 Hz, 4 H), 3.07-3.03 (m, 1 H), 2.47-2.45 (m, 1 H), 2.09-2.05 (m, 2 H), 1.83-1.79 (m, 2 H), 1.68 (m, 2 H), 1.52 (d, J = 6.8 Hz, 6 H) | 458.2 | A |

TABLE A-continued

| Cmpd No. | Structure | ¹H NMR | MS [MH]⁺ | Method |
|---|---|---|---|---|
| 54 | 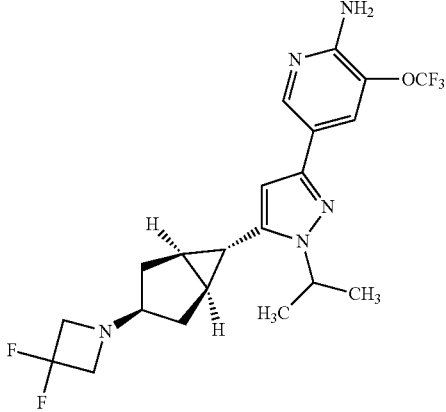 [SMILES: CC(C)n1nc(-c2cnc(N)c(OC(F)(F)F)c2)cc1[C@H]1[C@@H]2C[C@H](N3CC(F)(F)C3)C[C@@H]21]<br>5-(5-((1R,3r,5S,6r)-3-(3,3-difluoro-azetidin-1-yl)bicyclo[3.1.0]hexan-6-yl)-1-isopropyl-1H-pyrazol-3-yl)-3-(trifluoromethyl)pyridin-2-amine | ¹H NMR (400 MHz, Methanol-d4) δ 8.48 (s, 1 H), 8.10 (s, 1 H), 6.13 (s, 1 H), 4.76-4.69 (m, 1 H), 3.49 (t, J = 12.0 Hz, 4 H), 3.07-3.03 (m, 1 H), 2.47-2.46 (m, 1 H), 2.10-2.05 (m, 2 H), 1.83-1.80 (m, 2 H), 1.69 (m, 2 H), 1.52 (d, J = 6.8 Hz, 6 H) | 442.2 | A |
| 55 | 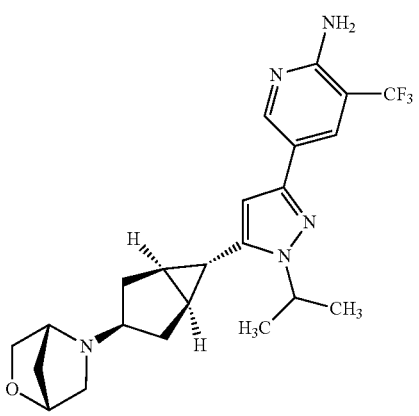 [SMILES: CC(C)n1nc(-c2cnc(N)c(C(F)(F)F)c2)cc1[C@H]1[C@@H]2C[C@H](N3C[C@H]4C[C@@H]3CO4)C[C@@H]21]<br>5-(5-((1R,3r,5S,6R)-3-((1R,4R)-2-oxa-5-azabicyclo[2.2.1]heptan-5-yl)bicyclo[3.1.0]hexan-6-yl)-1-isopropyl-1H-pyrazol-3-yl)-3-(trifluoromethyl)pyridin-2-amine | ¹H NMR (DMSO-d₆) δ: 8.54 (d, J = 2.1 Hz, 1H), 7.97 (d, J = 2.2 Hz, 1H), 6.46 (br s, 2H), 6.27 (s, 1H), 4.62 (m, 1H), 4.29 (m, 1H), 3.80 (d, J = 7.5 Hz, 1H), 3.62 (m, 1H), 3.49 (dd, J = 7.4, 1.7 Hz, 1H), 3.18 (s, 1H), 2.86-2.79 (m, 1H), 2.40 (t, J = 3.4 Hz, 1H), 2.34 (d, J = 9.6 Hz, 1H), 2.11-1.79 (m, 4H), 1.69-1.58 (m, 3H), 1.54 (m, 1H), 1.44 (d, J = 6.6 Hz, 6H) | 448.2 | A |

TABLE A-continued

| Cmpd No. | Structure | ¹H NMR | MS [MH]⁺ | Method |
|---|---|---|---|---|
| 56 | 5-(5-((1R,3r,5S,6R)-3-((1R,4R)-2-oxa-5-azabicyclo[2.2.1]heptan-5-yl)bicyclo[3.1.0]hexan-6-yl)-1-isopropyl-1H-pyrazol-3-yl)-3-(trifluoromethoxy)pyridin-2-amine | ¹H NMR (DMSO-d₆) δ: 8.28 (d, J = 2.0 Hz, 1H), 7.74-7.66 (m, 1H), 6.42 (br s, 2H), 6.22 (s, 1H), 4.61 (m, 1H), 4.29 (m, 1H), 3.80 (d, J = 7.5 Hz, 1H), 3.62 (m, 1H), 3.49 (dd, J = 7.5, 1.8 Hz, 1H), 3.17 (d, J = 7.9 Hz, 1H), 2.82 (dd, J = 9.7, 1.7 Hz, 1H), 2.40 (t, J = 3.4 Hz, 1H), 2.33 (d, J = 9.4 Hz, 1H), 2.10-1.76 (m, 4H), 1.71-1.51 (m, 4H), 1.43 (d, J = 6.5 Hz, 6H) | 464.2 | A |
| 57 | 5-(5-((1R,3r,5S,6r)-3-(2-oxa-6-azaspiro[3.3]heptan-6-yl)bicyclo[3.1.0]hexan-6-yl)-1-isopropyl-1H-pyrazol-3-yl)-3-(trifluoromethoxy)pyridin-2-amine | ¹H NMR (400 MHz, Methanol-d4) δ 8.22 (s, 1 H), 7.80 (s, 1 H), 6.07 (s, 1 H), 4.76-4.67 (m, 5 H), 3.30-3.27 (m, 4 H), 2.89-2.80 (m, 1 H), 2.28 (s, 1 H), 2.04-2.00 (m, 2 H), 1.73 (m, 1 H), 1.69 (s, 1 H), 1.64 (m, 2H), 1.50 (d, J = 1.2 Hz, 6 H) | 464.2 | A |
| 58 | 5-(5-((1R,3s,5S,6r)-3-(2-oxa-6-azaspiro[3.3]heptan-6-yl)bicyclo[3.1.0]hexan-6-yl)-1-isopropyl-1H-pyrazol-3-yl)-3-(trifluoromethoxy)pyridin-2-amine | ¹H NMR (400 MHz, Methanol-d4) δ 8.22 (s, 1 H), 7.80 (s, 1 H), 6.12 (s, 1 H), 4.74-4.68 (m, 5 H), 3.43 (m, 4 H), 2.75-2.70 (m, 1 H), 2.16-2.11 (m, 2 H), 1.68-1.60 (m, 5 H), 1.48 (d, J = 6.8 Hz, 6 H) | 464.2 | A |

TABLE A-continued

| Cmpd No. | Structure | $^1$H NMR | MS [MH]$^+$ | Method |
|---|---|---|---|---|
| 59 | 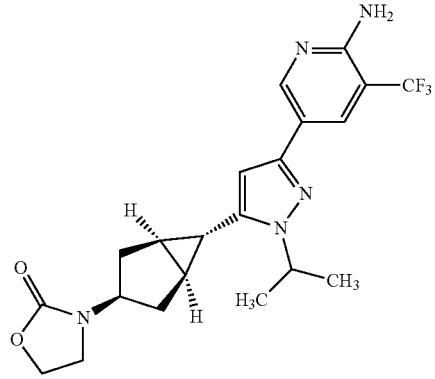 [SMILES: CC(C)n1nc(-c2cnc(N)c(C(F)(F)F)c2)cc1[C@H]1[C@@H]2C[C@H](N3CCOC3=O)C[C@@H]21]<br>3-((1R,3r,5S,6r)-6-(3-(6-amino-5-(trifluoromethyl)pyridin-3-yl)-1-isopropyl-1H-pyrazol-5-yl)bicyclo[3.1.0]hexan-3-yl)oxazolidin-2-one | $^1$H NMR (400 MHz, Methanol-d4) δ 8.48 (s, 1 H), 8.09 (s, 1 H), 6.19-6.17 (m, 1 H), 4.52-4.43 (m, 1 H), 4.34-4.30 (m, 2 H), 3.63-3.59 (m, 2 H), 2.42-2.15 (m, 2 H), 2.15-2.10 (m, 1 H), 2.08-2.00 (m, 1 H), 1.85-1.79 (m, 2 H), 1.73 (m, 2 H), 1.50 (d, J = 6.8 Hz, 6 H) | 436.1 | A |
| 60 | 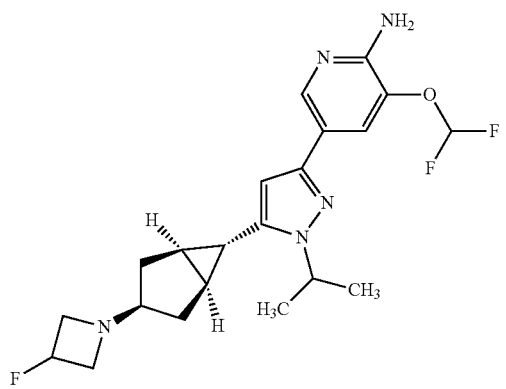 [SMILES: CC(C)n1nc(-c2cnc(N)c(OC(F)F)c2)cc1[C@H]1[C@@H]2C[C@H](N3CC(F)C3)C[C@@H]21]<br>3-(difluoromethoxy)-5-(5-((1R,3r,5S,6r)-3-(3-fluoroazetidin-1-yl)bicyclo[3.1.0]hexan-6-yl)-1-isopropyl-1H-pyrazol-3-yl)pyridin-2-amine | $^1$H NMR (400 MHz, Methanol-d4) δ 8.11 (s, 1 H), 7.68 (s, 1 H), 6.85 (t, $J_{HF}$ = 13.6 Hz, 1 H), 6.05 (s, 1 H), 4.74-4.67 (m, 1 H), 3.59-3.53 (m, 3 H), 3.03-3.00 (m, 1 H), 2.98-2.97 (m, 2 H), 2.34-2.33 (m, 1 H), 2.02-2.01 (m, 2 H), 1.77-1.73 (m, 2 H), 1.64 (m, 2 H), 1.49 (d, J = 6.4 Hz, 6 H) | 436.1 | A |
| 61 | 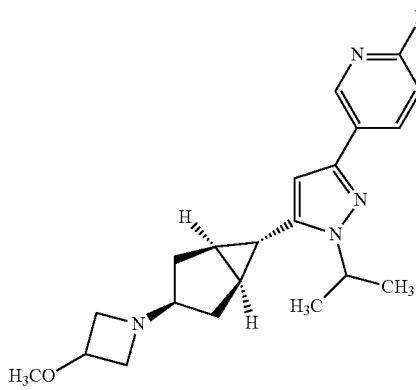<br>3-(difluoromethoxy)-5-(1-isopropyl-5-((1R,3r,5S,6r)-3-(3-methoxy-azetidin-1-yl)bicyclo[3.1.0]hexan-6-yl)-1H-pyrazol-3-yl)pyridin-2-amine | $^1$H NMR (400 MHz, Methanol-d4) δ 8.12 (s, 1 H), 7.70 (s, 1 H), 6.86 (t, $J_{HF}$ = 73.6 Hz, 1 H), 6.06 (s, 1 H), 4.78-4.71 (m, 1 H), 3.98-3.90 (m, 1 H), 3.54-3.50 (m, 2 H), 3.25 (s, 3 H), 3.05-2.99 (m, 1 H), 2.80 (m, 2 H), 2.29 (m, 1 H), 2.07-2.00 (m, 2 H), 1.75-1.65 (m, 4 H), 1.51 (d, J = 6.8 Hz, 6 H) | 422.2 | A |

TABLE A-continued

| Cmpd No. | Structure | ¹H NMR | MS [MH]⁺ | Method |
|---|---|---|---|---|
| 62 | 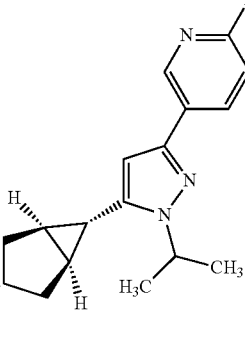<br>3-(difluoromethoxy)-5-(1-isopropyl-5-((1R,3s,5S,6r)-3-(3-methoxy-azetidin-1-yl)bicyclo[3.1.0]hexan-6-yl)-1H-pyrazol-3-yl)pyridin-2-amine | ¹H NMR (400 MHz, Methanol-d4) δ 8.13 (s, 1 H), 7.70 (s, 1 H), 6.86 (t, $J_{HF}$ = 73.6 Hz, 1 H), 6.12 (s, 1 H), 4.75-4.71 (m, 1 H), 4.03-4.01 (m, 1 H), 3.60-3.56 (m, 2 H), 3.30 (s, 3 H), 3.07-3.05 (m, 2 H), 2.80-2.75 (m, 1 H), 2.19-2.15 (m, 2 H), 1.69-1.64 (m, 5 H), 1.49 (d, J = 6.8 Hz, 6 H) | 434.2 | A |
| 63 | 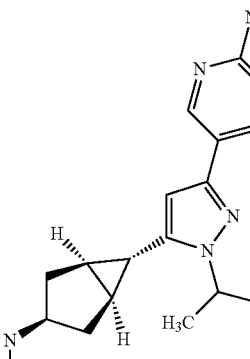<br>5-(1-isopropyl-5-((1R,3r,5S,6r)-3-(4-methylpiperazin-1-yl)bicyclo[3.1.0]hexan-6-yl)-1H-pyrazol-3-yl)-3-(trifluoromethyl)pyridin-2-amine | ¹H NMR (DMSO-d₆) δ: 8.53 (m, 1H), 7.97 (d, J = 2.2 Hz, 1H), 6.44 (br s, 2H), 6.26 (s, 1H), 4.67 (m, 1H), 2.84-2.71 (m, 1H), 2.29 (m, 8H), 2.12 (s, 3H), 2.11-2.05 (m, 2H), 1.94 (t, J = 3.3 Hz, 1H), 1.69 (dd, J = 13.5, 6.4 Hz, 2H), 1.59 (dd, J = 4.6, 2.9 Hz, 2H), 1.43 (d, J = 6.6 Hz, 6H) | 449.2 | A |
| 64 | 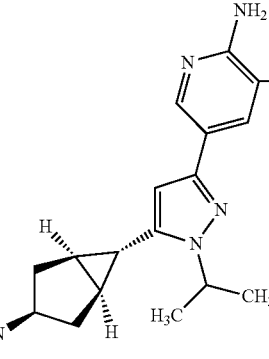<br>5-(1-isopropyl-5-((1R,3r,5S,6r)-3-(4-methylpiperazin-1-yl)bicyclo[3.1.0]hexan-6-yl)-1H-pyrazol-3-yl)-3-(trifluoromethoxy)pyridin-2-amine | ¹H NMR (DMSO-d₆) δ: 8.28 (d, J = 2.0 Hz, 1H), 7.67 (m, 1H), 6.38 (br s, 2H), 6.21 (s, 1H), 4.66 (m, 1H), 2.77 (m, 1H), 2.31 (m, 9H), 2.12 (s, 3H), 2.11-2.03 (m, 2H), 1.93 (t, J = 3.4 Hz, 1H), 1.69 (dd, J = 13.6, 6.3 Hz, 2H), 1.59 (m, 2H), 1.42 (d, J = 6.6 Hz, 6H) | 465.2 | A |

TABLE A-continued

| Cmpd No. | Structure | ¹H NMR | MS [MH]⁺ | Method |
|---|---|---|---|---|
| 65 | 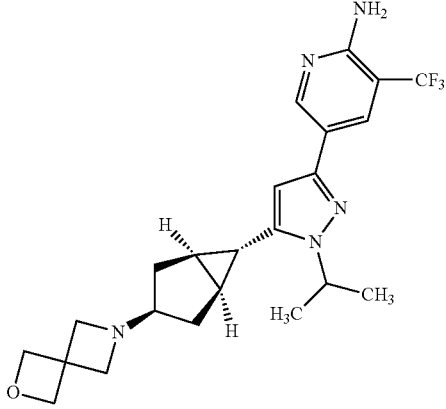 [SMILES: CC(C)n1nc(-c2cnc(N)c(C(F)(F)F)c2)cc1[C@H]1[C@@H]2C[C@H](N3CC4(COC4)C3)C[C@@H]21] 5-(5-((1R,3r,5S,6r)-3-(2-oxa-6-azaspiro[3.3]heptan-6-yl)bicyclo[3.1.0]hexan-6-yl)-1-isopropyl-1H-pyrazol-3-yl)-3-(trifluoromethyl)pyridin-2-amine | ¹H NMR (400 MHz, Chloroform-d) δ 8.52 (s, 1 H), 8.09 (s, 1 H), 5.94 (s, 1 H), 4.92 (m, 2 H), 4.70 (m, 4 H), 4.64-4.57 (m, 1 H), 3.18 (m, 4 H), 2.75-2.72 (m, 1 H), 2.40-2.38 (m, 1 H), 1.91-1.87 (m, 2 H), 1.70 (d, J = 13.2 Hz, 2H), 1.61 (m, 2 H), 1.51 (d, J = 6.8 Hz, 6 H) | 448.0 | A |
| 66 | 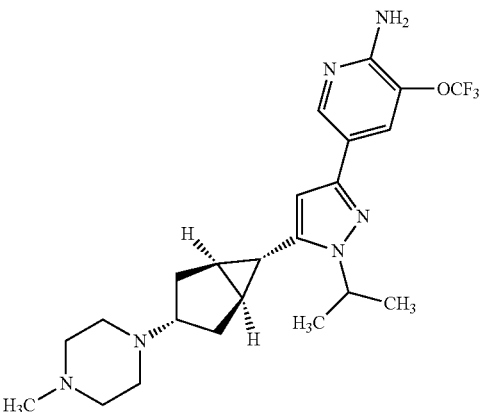 5-(1-isopropyl-5-((1R,3s,5S,6r)-3-(4-methylpiperazin-1-yl)bicyclo[3.1.0]hexan-6-yl)-1H-pyrazol-3-yl)-3-(trifluoromethoxy)pyridin-2-amine | ¹H NMR (DMSO-d₆) δ: 8.28 (d, J = 1.9 Hz, 1H), 7.74-7.61 (m, 1H), 6.38 (s, 2H), 6.24 (s, 1H), 4.67 (p, J = 6.6 Hz, 1H), 2.48-2.16 (m, 9H), 2.13 (s, 3H), 2.09 (d, J = 6.8 Hz, 2H), 1.77-1.54 (m, 5H), 1.40 (d, J = 6.5 Hz, 6H) | 465.2 | A |

TABLE A-continued

| Cmpd No. | Structure | ¹H NMR | MS [MH]+ | Method |
|---|---|---|---|---|
| 67 | 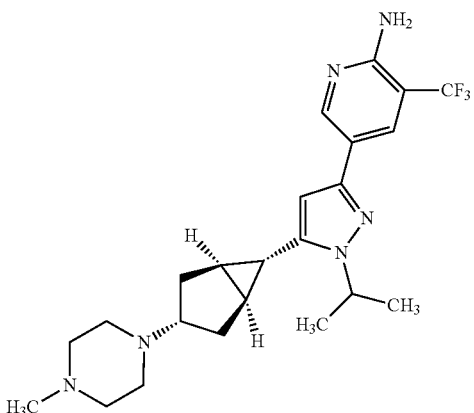 5-(1-isopropyl-5-((1R,3s,5S,6r)-3-(4-methylpiperazin-1-yl)bicyclo[3.1.0]hexan-6-yl)-1H-pyrazol-3-yl)-3-(trifluoromethyl)pyridin-2-amine | ¹H NMR (DMSO-d₆) δ: 8.53 (d, J = 2.1 Hz, 1H), 7.97 (d, J = 2.2 Hz, 1H), 6.44 (br s, 2H), 6.30 (s, 1H), 4.68 (m, 1H), 2.48-2.17 (m, 9H), 2.14 (s, 3H), 2.13-2.02 (m, 2H), 1.78-1.53 (m, 5H), 1.40 (d, J = 6.6 Hz, 6H) | 449.2 | A |
| 68 | 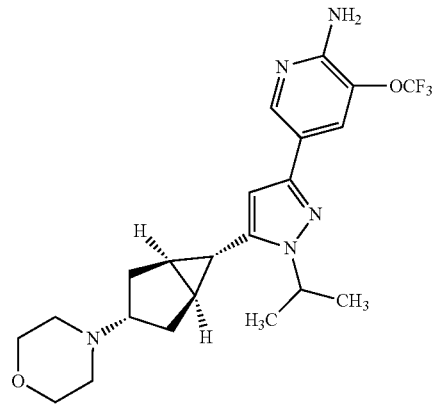 [SMILES: CC(C)n1nc(-c2cnc(N)c(OC(F)(F)F)c2)cc1[C@H]1[C@@H]2C[C@@H](N3CCOCC3)C[C@@H]21] 5-(1-isopropyl-5-((1R,3s,5S,6r)-3-morpholinobicyclo[3.1.0]hexan-6-yl)-1H-pyrazol-3-yl)-3-(trifluoromethoxy)pyridin-2-amine | ¹HNMR (400 MHz, CDCl₃) δ 8.31 (s, 1 H), 7.79 (s, 1 H), 5.98 (s, 1 H), 4.70 (br s, 2 H), 4.59 (m, 1 H), 3.73 (m, 4 H), 2.45 (m, 4 H), 2.36 (m, 1 H), 2.22 (m, 2H), 1.84 (m, 2 H), 1.68 (m, 2 H), 1.55-1.50 (m, 7 H) | 452.2 | A |
| 69 | 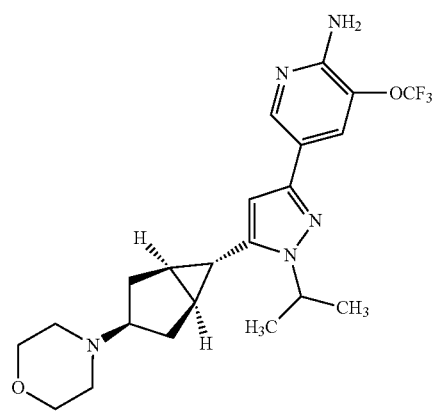 [SMILES: CC(C)n1nc(-c2cnc(N)c(OC(F)(F)F)c2)cc1[C@H]1[C@@H]2C[C@H](N3CCOCC3)C[C@@H]21] 5-(1-isopropyl-5-((1R,3r,5S,6r)-3-morpholinobicyclo[3.1.0]hexan-6-yl)-1H-pyrazol-3-yl)-3-(trifluoromethoxy)pyridin-2-amine | ¹H NMR (400 MHz, CDCl₃) δ 8.32 (s, 1 H), 7.81 (s, 1 H), 5.95 (s, 1 H), 4.71 (br s, 2 H), 4.64 (m, 1 H), 3.73-3.71 (m, 4 H), 2.92 (m, 1 H), 2.45 (m, 4 H), 2.28 (m, 2 H), 1.81 (m, 1H), 1.69-1.65 (m, 4 H), 1.53 (d, J = 6.8 Hz, 6 H) | 452.2 | A |

TABLE A-continued

| Cmpd No. | Structure | ¹H NMR | MS [MH]⁺ | Method |
|---|---|---|---|---|
| 70 | 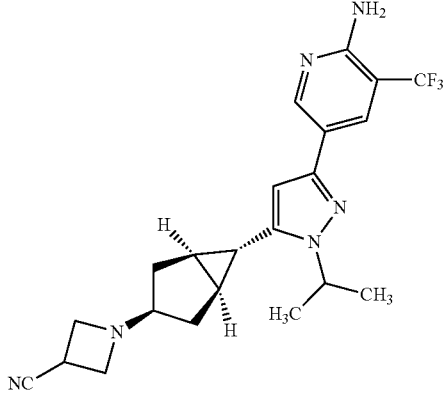 [SMILES: CC(C)n1nc(-c2cnc(N)c(C(F)(F)F)c2)cc1[C@H]1[C@@H]2C[C@H](N3CC(C#N)C3)C[C@@H]21] 1-((1R,3r,5S,6r)-6-(3-(6-amino-5-(trifluoromethyl)pyridin-3-yl)-1-isopropyl-1H-pyrazol-5-yl) bicyclo[3.1.0]hexan-3-yl)azetidine-3-carbonitrile | ¹H NMR (400 MHz, Chloroform-d) δ 8.49 (s, 1 H), 8.11 (m, 1 H), 5.94 (s, 1 H), 5.24 (br s, 2 H), 4.66-4.59 (m, 1 H), 3.47-3.44 (m, 2 H), 3.23-3.14 (m, 3 H), 2.91-2.90 (m, 1 H), 2.39-2.37 (m, 1 H), 1.96-1.93 (m, 2 H), 1.75 (m, 2 H), 1.61 (m, 2 H), 1.53 (d, J = 6.8 Hz, 6 H) | 431 | A |
| 71 | 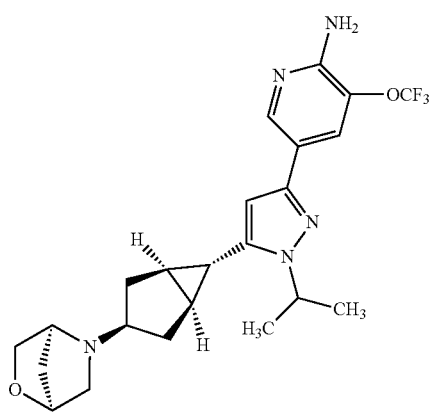 [SMILES: CC(C)n1nc(-c2cnc(N)c(OC(F)(F)F)c2)cc1[C@H]1[C@@H]2C[C@H](N3C[C@@H]4C[C@H]3CO4)C[C@@H]21] 5-(5-((1R,3r,5S,6S)-3-((1S,4S)-2-oxa-5-azabicyclo[2.2.1]heptan-5-yl)bicyclo[3.1.0]hexan-6-yl)-1-isopropyl-1H-pyrazol-3-yl)-3-(trifluoromethoxy)pyridin-2-amine | ¹H NMR (DMSO-d₆) δ: 8.28 (d, J = 1.9 Hz, 1H), 7.70 (m, 1H), 6.40 (br s, 2H), 6.21 (s, 1H), 4.61 (m, 1H), 4.29 (t, J = 1.9 Hz, 1H), 3.80 (d, J = 7.5 Hz, 1H), 3.62 (d, J = 1.9 Hz, 1H), 3.49 (dd, J = 7.5, 1.8 Hz, 1H), 3.17 (m, 1H), 2.82 (dd, J = 9.8, 1.8 Hz, 1H), 2.40 (t, J = 3.3 Hz, 1H), 2.36-2.27 (m, 1H), 2.11-1.77 (m, 4H), 1.70-1.51 (m, 4H), 1.43 (d, J = 6.6 Hz, 6H) | 464.2 | A |

TABLE A-continued

| Cmpd No. | Structure | ¹H NMR | MS [MH]⁺ | Method |
|---|---|---|---|---|
| 72 | 5-(5-((1R,3r,5S,6S)-3-((1S,4S)-2-oxa-5-azabicyclo[2.2.1]heptan-5-yl)bicyclo[3.1.0]hexan-6-yl)-1-isopropyl-1H-pyrazol-3-yl)-3-(trifluoromethyl)pyridin-2-amine | ¹H NMR (DMSO-d₆) δ: 8.54 (d, J = 2.0 Hz, 1H), 7.97 (d, J = 2.3 Hz, 1H), 6.44 (br s, 2H), 6.26 (s, 1H), 4.62 (m, 1H), 4.29 (t, J = 1.9 Hz, 1H), 3.80 (d, J = 7.5 Hz, 1H), 3.62 (s, 1H), 3.49 (dd, J = 7.6, 1.8 Hz, 1H), 3.17 (m, 1H), 2.82 (dd, J = 9.8, 1.8 Hz, 1H), 2.40 (t, J = 3.4 Hz, 1H), 2.37-2.27 (m, 1H), 2.13-1.76 (m, 4H), 1.71-1.50 (m, 4H), 1.44 (dd, J = 6.6, 0.9 Hz, 6H) | 448.2 | A |
| 73 | 3-(difluoromethoxy)-5-(1-isopropyl-5-((1R,3r,5S,6r)-3-(3-methoxypyrrolidin-1-yl)bicyclo[3.1.0]hexan-6-yl)-1H-pyrazol-3-yl)pyridin-2-amine | ¹H NMR (DMSO-d₆) δ: 8.16 (d, J = 1.8 Hz, 1H), 7.57 (d, J = 1.7 Hz, 1H), 7.15 (t, J$_{HF}$ = 73.9 Hz, 1H), 6.17 (s, 1H), 6.05 (br s, 2H), 4.62 (m, 1H), 3.82 (m, 1H), 3.17 (s, 3H), 2.73 (m, 2H), 2.58 (dd, J = 10.5, 6.3 Hz, 3H), 2.32 (m, 1H), 2.23 (t, J = 3.3 Hz, 1H), 2.02 (m, 2H), 1.90 (m, 3H), 1.60 (m, 2H), 1.42 (d, J = 6.6 Hz, 6H) | 448.2 | A |

TABLE A-continued

| Cmpd No. | Structure | ¹H NMR | MS [MH]⁺ | Method |
|---|---|---|---|---|
| 74 | 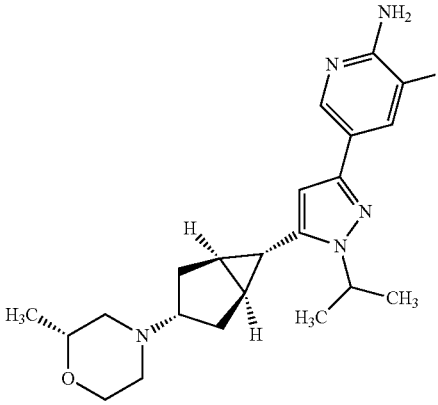<br>3-(difluoromethoxy)-5-(1-isopropyl-5-((1R,3s,5S,6R)-3-((R)-2-methylmorpholino)bicyclo[3.1.0]hexan-6-yl)-1H-pyrazol-3-yl)pyridin-2-amine | ¹H NMR (DMSO-d₆) δ: 8.16 (d, J = 1.9 Hz, 1H), 7.57 (m, 1H), 7.15 (t, $J_{HF}$ = 73.9 Hz, 1H), 6.21 (s, 1H), 6.06 (br s, 2H), 4.67 (m, 1H), 3.75-3.67 (m, 1H), 3.52-3.40 (m, 2H), 2.76-2.68 (m, 1H), 2.64 (d, J = 11.3 Hz, 1H), 2.41 (m, 1H), 2.12 (m, 2H), 1.95 (m, 1H), 1.76-1.57 (m, 6H), 1.40 (d, J = 6.5 Hz, 6H), 1.03 (d, J = 6.2 Hz, 3H) | 448.2 | A |
| 75 | 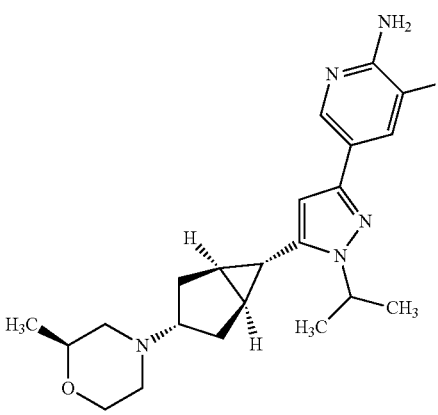<br>3-(difluoromethoxy)-5-(1-isopropyl-5-((1R,3s,5S,6S)-3-((S)-2-methylmorpholino)bicyclo[3.1.0]hexan-6-yl)-1H-pyrazol-3-yl)pyridin-2-amine | ¹HNMR(DMSO-d₆) δ: 8.16 (d, J = 1.9 Hz, 1H), 7.57 (d, J = 1.8 Hz, 1H), 7.14 (t, $J_{HF}$ = 73.9 Hz, 1H), 6.21 (s, 1H), 6.05 (br s, 2H), 4.67 (m, 1H), 3.71 (m, 1H), 3.54-3.38 (m, 2H), 2.77-2.68 (m, 1H), 2.68-2.59 (m, 1H), 2.12 (m, 2H), 1.95 (m, 1H), 1.79-1.56 (m, 6H), 1.40 (d, J = 6.5 Hz, 6H), 1.03 (d, J = 6.2 Hz, 3H) | 448.2 | A |
| 76 | 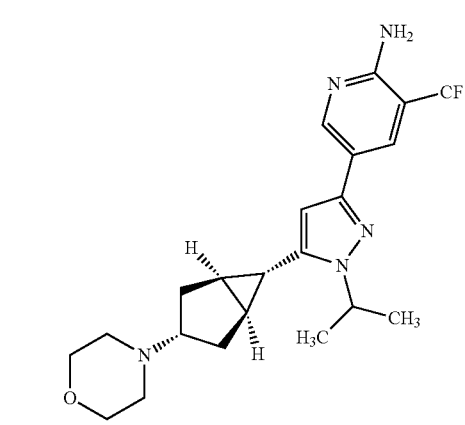<br>5-(1-isopropyl-5-((1R,3s,5S,6r)-3-morpholinobicyclo[3.1.0]hexan-6-yl)-1H-pyrazol-3-yl)-3-(trifluoromethyl)pyridin-2-amine | ¹H NMR (400 MHz, Chloroform-d) δ 8.53 (s, 1 H), 8.09 (s, 1 H), 6.00 (s, 1 H), 4.92 (br s, 2 H), 4.64-4.57 (m, 1 H), 3.73-3.71 (m, 4 H), 2.45 (m, 4 H), 2.35-2.33 (m, 1 H), 2.24-2.19 (m, 2 H), 1.90-1.82 (m, 2 H), 1.68 (m, 2H), 1.55-1.51 (m, 7 H) | 435.9 | A |

TABLE A-continued

| Cmpd No. | Structure | ¹H NMR | MS [MH]⁺ | Method |
|---|---|---|---|---|
| 77 | 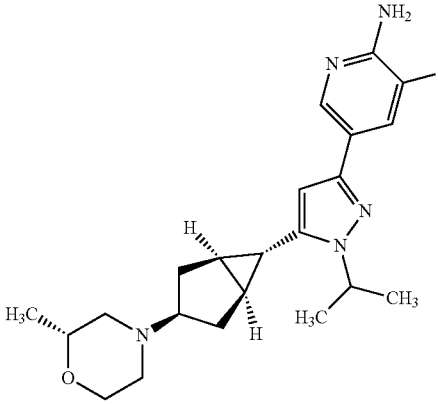<br>3-(difluoromethoxy)-5-(1-isopropyl-5-((1R,3r,5S,6R)-3-((R)-2-methylmorpholino)bicyclo[3.1.0]hexan-6-yl)-1H-pyrazol-3-yl)pyridin-2-amine | ¹H NMR (DMSO-d₆) δ: 8.15 (d, J = 1.9 Hz, 1H), 7.57 (d, J = 1.7 Hz, 1H), 7.14 ($J_{HF}$ = 73.9 Hz, 1H), 6.17 (s, 1H), 6.05 (br s, 2H), 4.66 (m, 1H), 3.79-3.67 (m, 1H), 3.52-3.37 (m, 2H), 2.86-2.67 (m, 3H), 2.18-2.05 (m, 2H), 1.98-1.81 (m, 2H), 1.71 (dd, J = 13.3, 6.2 Hz, 2H), 1.64-1.53 (m, 3H), 1.43 (d, J = 6.5 Hz, 6H), 1.04 (d, J = 6.2 Hz, 3H) | 448.2 | A |
| 78 | 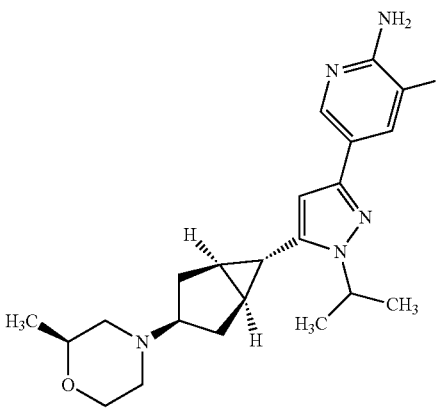<br>3-(difluoromethoxy)-5-(1-isopropyl-5-((1R,3r,5S,6S)-3-((S)-2-methylmorpholino)bicyclo[3.1.0]hexan-6-yl)-1H-pyrazol-3-yl)pyridin-2-amine | ¹H NMR (DMSO-d₆) δ: 8.15 (d, J = 1.9 Hz, 1H), 7.57 (d, J = 1.7 Hz, 1H), 7.14 (t, $J_{HF}$ = 73.9 Hz, 1H), 6.17 (s, 1H), 6.05 (br s, 2H), 4.66 (m, 1H), 3.78-3.69 (m, 1H), 3.51-3.37 (m, 2H), 2.84-2.68 (m, 3H), 2.10 (m, 2H), 1.98-1.82 (m, 2H), 1.71 (dd, J = 13.3, 6.3 Hz, 2H), 1.65-1.53 (m, 3H), 1.43 (d, J = 6.6 Hz, 6H), 1.04 (d, J = 6.2 Hz, 3H) | 448.2 | A |
| 79 | 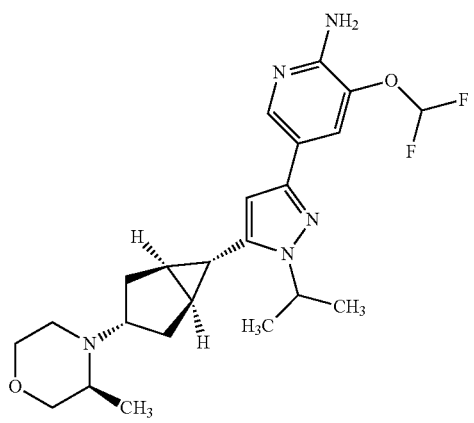 [SMILES: CC(C)n1nc(-c2cnc(N)c(OC(F)F)c2)cc1[C@H]1[C@@H]2C[C@@H](N3CCOC[C@@H]3C)C[C@@H]21]<br>3-(difluoromethoxy)-5-(1-isopropyl-5-((1R,3s,5S,6S)-3-((S)-3-methylmorpholino)bicyclo[3.1.0]hexan-6-yl)-1H-pyrazol-3-yl)pyridin-2-amine | ¹H NMR (CDCl₃) δ: 8.24 (d, J = 1.9 Hz, 1H), 7.69 (d, J = 1.8 Hz, 1H), 6.85-6.25 (m, 1H), 6.00 (s, 1H), 4.68 (br s, 2H), 4.60 (m, 1H), 3.62 (m, 4H), 3.02-2.52 (m, 3H), 2.43 (m, 1H), 2.11 (m, 2H), 1.88 (m, 2H), 1.68 (m, 3H), 1.50 (d, 6H), 1.08 (m, 3H) | 448.2 | A |

| Cmpd No. | Structure | ¹H NMR | MS [MH]⁺ | Method |
|---|---|---|---|---|
| 80 | 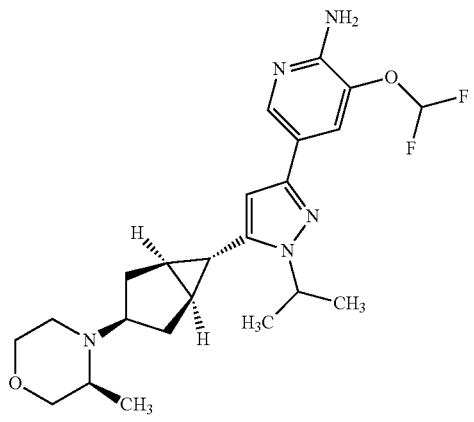 [SMILES: CC(C)n1nc(-c2cnc(N)c(OC(F)F)c2)cc1[C@H]1[C@@H]2C[C@H](N3CCOC[C@@H]3C)C[C@@H]21]<br>3-(difluoromethoxy)-5-(1-isopropyl-5-((1R,3r,5S,6S)-3-((S)-3-methylmorpholino)bicyclo[3.1.0]hexan-6-yl)-1H-pyrazol-3-yl)pyridin-2-amine | ¹H NMR (DMSO-d₆) δ: 8.16 (d, J = 1.8 Hz, 1H), 7.57 (d, J = 1.8 Hz, 1H), 7.15 (t, J$_{HF}$ = 73.9 Hz, 1H), 6.17 (s, 1H), 6.05 (br s, 2H), 4.68 (h, J = 6.5 Hz, 1H), 3.62 (m, 1H), 3.54-3.43 (m, 2H), 3.38 (dd, J = 10.9, 4.0 Hz, 1H), 3.26 (d, J = 6.9 Hz, 1H), 2.74 (m, 1H), 2.48-2.45 (m, 2H), 2.38 (m, 1H), 2.16-1.98 (m, 2H), 1.90 (t, J = 3.3 Hz, 1H), 1.68 (m, 2H), 1.58 (m, 2H), 1.43 (d, J = 6.6 Hz, 6H), 0.96 (d, J = 6.5 Hz, 3H) | 448.2 | A |
| 81 | 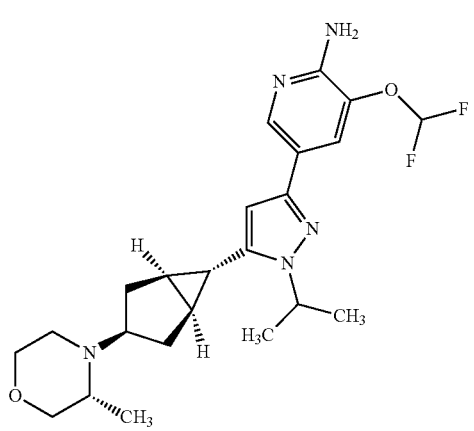 [SMILES: CC(C)n1nc(-c2cnc(N)c(OC(F)F)c2)cc1[C@H]1[C@@H]2C[C@H](N3CCOC[C@H]3C)C[C@@H]21]<br>3-(difluoromethoxy)-5-(1-isopropyl-5-((1R,3r,5S,6R)-3-((R)-3-methylmorpholino)bicyclo[3.1.0]hexan-6-yl)-1H-pyrazol-3-yl)pyridin-2-amine | ¹H NMR(DMSO-d₆) δ: 8.15 (d, J = 1.9 Hz, 1H), 7.57 (d, J = 1.8 Hz, 1H), 7.15 (t, J$_{HF}$ = 73.9 Hz, 1H), 6.17 (s, 1H), 6.06 (br s, 2H), 4.67 (m, 1H), 3.62 (m, 1H), 3.56-3.44 (m, 2H), 3.38 (dd, J = 10.8, 4.0 Hz, 2H), 2.74 (m, 1H), 2.47 (dd, J = 8.6, 3.1 Hz, 2H), 2.38 (m, 1H), 2.15-1.97 (m, 2H), 1.90 (t, J = 3.3 Hz, 1H), 1.78-1.53 (m, 5H), 1.43 (d, J = 6.5 Hz, 7H), 0.96 (d, J = 6.4 Hz, 3H) | 448.2 | A |

| Cmpd No. | Structure | ¹H NMR | MS [MH]⁺ | Method |
|---|---|---|---|---|
| 82 | 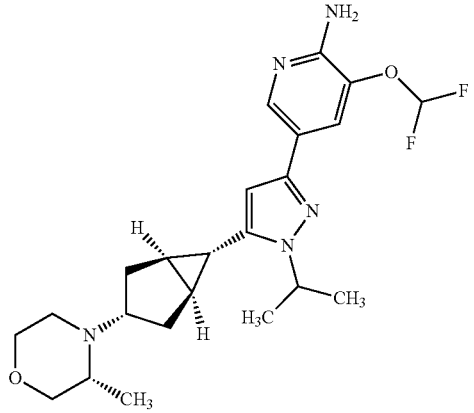 [SMILES: CC(C)n1nc(-c2cnc(N)c(OC(F)F)c2)cc1[C@H]1[C@@H]2C[C@@H](N3CCOC[C@H]3C)C[C@@H]21]<br>3-(difluoromethoxy)-5-(1-isopropyl-5-((1R,3s,5S,6R)-3-((R)-3-methylmorpholino)bicyclo[3.1.0]hexan-6-yl)-1H-pyrazol-3-yl)pyridin-2-amine | ¹H NMR (DMSO-d₆) δ: 8.16 (d, J = 1.9 Hz, 1H), 7.57 (d, J = 1.8 Hz, 1H), 7.15 (t, $J_{HF}$ = 73.9 Hz, 1H), 6.21 (s, 1H), 6.08 (br s, 2H), 4.70 (m, 1H), 3.65-3.45 (m, 2H), 2.96 (m, 1H), 2.65 (m, 1H), 2.55 (m, 2H), 2.31 (m, 1H), 1.98 (m, 2H), 1.80 (t, J = 3.2 Hz, 1H), 1.78-1.67 (m, 2H), 1.59 (m, 2H), 1.41 (m, 6H), 0.97 (d, J = 6.4 Hz, 2H) | 448.2 | A |
| 83 | 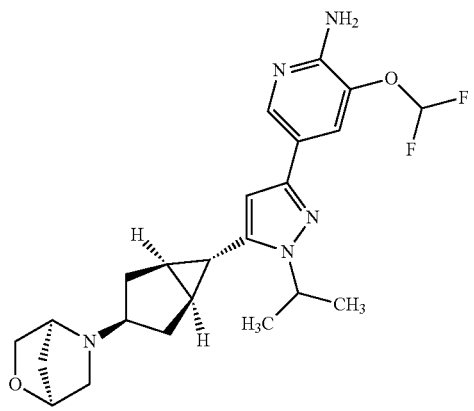 [SMILES: CC(C)n1nc(-c2cnc(N)c(OC(F)F)c2)cc1[C@H]1[C@@H]2C[C@H](N3C[C@@H]4C[C@H]3CO4)C[C@@H]21]<br>5-(5-((1R,3r,5S,6S)-3-((1S,4S)-2-oxa-5-azabicyclo[2.2.1]heptan-5-yl)bicyclo[3.1.0]hexan-6-yl)-1-isopropyl-1H-pyrazol-3-yl)-3-(difluoromethoxy)pyridin-2-amine | ¹H NMR (CDCl₃) δ: 8.24 (s, 1H), 7.75 (m, 1H), 6.54 (m, 1H), 5.93 (s, 1H), 4.67 (m, 3H), 4.37 (m, 1H), 4.00 (m, 1H), 3.58 (m, 1H), 3.27 (m, 1H), 2.91 (m, 1H), 2.49 (m, 2H), 2.13 (m, 2H), 1.87 (m, 2H), 1.81-1.60 (m, 3H), 1.57-1.46 (m, 6H) | 446.2 | A |
| 84 | 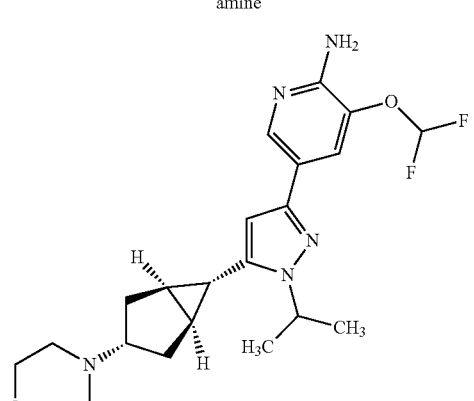<br>3-(difluoromethoxy)-5-(1-isopropyl-5-((1R,3s,5S,6r)-3-morpholinobicyclo[3.1.0]hexan-6-yl)-1H-pyrazol-3-yl)pyridin-2-amine | ¹H NMR (CDCl₃) δ: 8.23 (d, J = 1.9 Hz, 1H), 7.72-7.66 (m, 1H), 6.55 (t, $J_{HF}$ = 73.6 Hz, 1H), 5.92 (d, J = 10.0 Hz, 1H), 4.75-4.59 (m, 3H), 3.87-3.56 (m, 4H), 2.96-2.77 (m, 1H), 2.62-2.19 (m, 5H), 1.80 (d, J = 3.4 Hz, 1H), 1.72-1.59 (m, 4H), 1.53 (d, J = 6.7 Hz, 6H) | 434.2 | A |

TABLE A-continued

| Cmpd No. | Structure | ¹H NMR | MS [MH]⁺ | Method |
|---|---|---|---|---|
| 85 | (1R,5S,6r)-6-(3-(6-amino-5-(difluoromethoxy)pyridin-3-yl)-1-isopropyl-1H-pyrazol-5-yl)bicyclo[3.1.0]hexan-3-one | ¹H NMR (CDCl₃) δ: 8.25 (d, J = 1.9 Hz, 1H), 7.72 (d, J = 1.7 Hz, 1H), 6.55 (t, J$_{HF}$ = 73.5 Hz, 1H), 6.08 (s, 1H), 4.79 (s, 2H), 4.57 (m, 1H), 2.77 (m, 2H), 2.49-2.32 (m, 2H), 1.95 (m, 2H), 1.51 (d, J = 6.7 Hz, 6H), 1.37 (t, J = 3.6 Hz, 1H) | 363.2 | A |
| 86 | 3-(difluoromethoxy)-5-(1-isopropyl-5-((1R,3r,5S,6r)-3-morpholino-bicyclo[3.1.0]hexan-6-yl)-1H-pyrazol-3-yl)pyridin-2-amine | ¹H NMR (CDCl₃) δ: 8.23 (d, J = 1.9 Hz, 1H), 7.70 (d, J = 1.8 Hz, 1H), 6.54 (t, J$_{HF}$ = 73.6 Hz, 1H), 5.95 (s, 1H), 4.71 (br s, 2H), 4.62 (h, J = 6.7 Hz, 1H), 3.71 (dd, J = 5.5, 3.4 Hz, 4H), 2.90 (m, 1H), 2.45 (m, 4H), 2.32-2.19 (m, 2H), 1.80 (d, J = 3.4 Hz, 1H), 1.72-1.59 (m, 4H), 1.53 (d, J = 6.7 Hz, 6H) | 434.2 | A |
| 87 | 5-(5-((1R,3s,5S,6r)-3-(1,4-oxazepan-4-yl)bicyclo[3.1.0]hexan-6-yl)-1-isopropyl-1H-pyrazol-3-yl)-3-(difluoromethoxy)pyridin-2-amine | ¹H NMR (DMSO-d₆) δ: 8.16 (d, J = 1.9 Hz, 1H), 7.62-7.55 (m, 1H), 7.15 (t, J$_{HF}$ = 73.9 Hz, 1H), 6.20 (s, 1H), 6.05 (br s, 2H), 4.67 (h, J = 6.6 Hz, 1H), 3.69-3.61 (m, 2H), 3.61-3.55 (m, 2H), 2.88 (m, 1H), 2.65-2.56 (m, 4H), 2.09 (dd, J = 12.3, 7.0 Hz, 2H), 1.82-1.62 (m, 5H), 1.64-1.56 (m, 2H), 1.40 (d, J = 6.5 Hz, 6H) | 448.2 | A |

TABLE A-continued

| Cmpd No. | Structure | ¹H NMR | MS [MH]⁺ | Method |
|---|---|---|---|---|
| 88 | 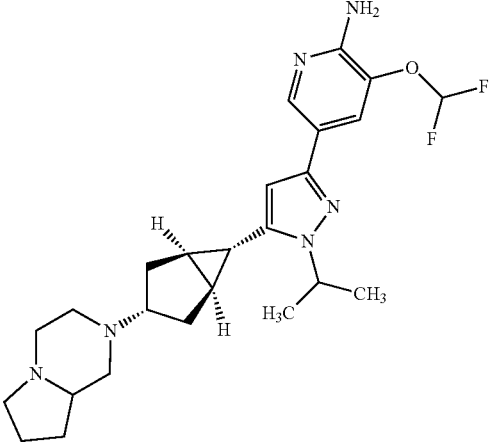 [SMILES: CC(C)n1nc(-c2cnc(N)c(OC(F)F)c2)cc1[C@H]1[C@@H]2C[C@@H](N3CCN4CCCC4C3)C[C@@H]21]<br>3-(difluoromethoxy)-5-(5-((1R,3s,5S,6r)-3-(hexahydropyrrolo[1,2-a]pyrazin-2(1H)-yl)bicyclo[3.1.0]hexan-6-yl)-1-isopropyl-1H-pyrazol-3-yl)pyridin-2-amine | 1H NMR (Chloroform-d) δ: 8.24 (d, J = 1.9 Hz, 1H), 7.69 (d, J = 0.9 Hz, 1H), 6.53 (t, $J_{HF}$ = 73.6 Hz, 1H), 5.98 (d, J = 0.6 Hz, 1H), 4.67 (s, 2H), 4.60 (m, 1H), 3.27-2.79 (m, 4H), 2.56-1.99 (m, 4H), 2.02-1.71 (m, 5H), 1.71-1.30 (m, 14H) | 473.4 | A |
| 89 | 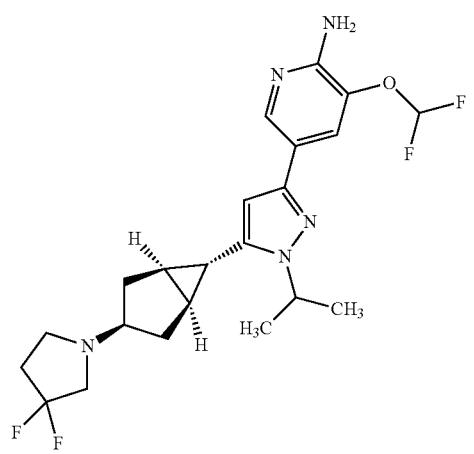 [SMILES: CC(C)n1nc(-c2cnc(N)c(OC(F)F)c2)cc1[C@H]1[C@@H]2C[C@H](N3CCC(F)(F)C3)C[C@@H]21]<br>3-(difluoromethoxy)-5-(5-((1R,3r,5S,6r)-3-(3,3-difluoropyrrolidin-1-yl)bicyclo[3.1.0]hexan-6-yl)-1-isopropyl-1H-pyrazol-3-yl)pyridin-2-amine | (400 MHz, CDCl₃), δ: 8.23 (s, 1 H), 7.70 (s, 1 H), 6.54 (t, $J_{HF}$ = 73.6 Hz, 1 H), 5.94 (s, 1 H), 4.69 (br s, 2 H), 4.66-4.57 (m, 1 H), 2.92-2.83 (m, 3 H), 2.70 (t, J = 6.8 Hz, 2 H), 2.30-2.08 (m, 5 H), 1.89 (dd, J = 14.0 Hz, 4 Hz, 2H), 1.64-1.62 (m, 2H), 1.52 (d, J = 6.4 Hz, 6 H) | 454.2 | A |

TABLE A-continued

| Cmpd No. | Structure | ¹H NMR | MS [MH]⁺ | Method |
|---|---|---|---|---|
| 90 | 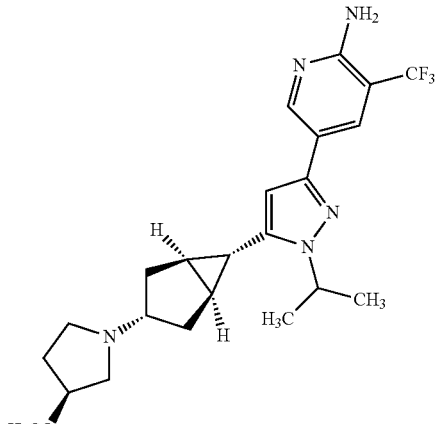<br>(1-isopropyl-5-((1R,3s,5S,6S)-3-((S)-3-methoxypyrrolidin-1-yl)bicyclo[3.1.0]hexan-6-yl)-1H-pyrazol-3-yl)-3-(trifluoromethyl)pyridin-2-amine | (400 MHz, Methanol-d₄), δ: 8.49 (s, 1 H), 8.10 (s, 1 H), 6.18 (s, 1 H), 4.74 (m, 1 H), 3.96 (m, 1 H), 3.28 (s, 3 H), 2.65-2.72 (m, 3 H), 2.48 (m, 2 H), 2.24 (m, 2 H), 2.10 (m, 1 H), 1.71-1.86 (m, 6H), 1.50 (d, J = 6.8 Hz, 6 H) | 450.2 | A |
| 91 | 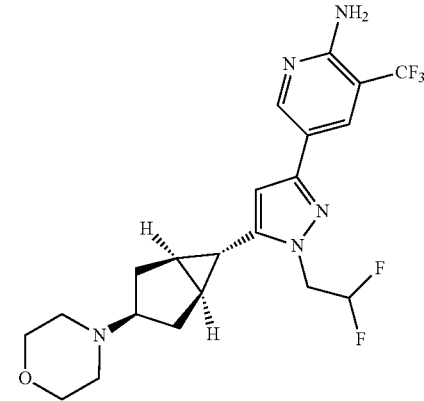 [SMILES: Nc1ncc(-c2cc([C@H]3[C@@H]4C[C@H](N5CCOCC5)C[C@@H]43)n(CC(F)F)n2)cc1C(F)(F)F]<br>5-(1-(2,2-difluoroethyl)-5-((1R,3r,5S,6r)-3-morpholinobicyclo[3.1.0]hexan-6-yl)-1H-pyrazol-3-yl)-3-(trifluoromethyl)pyridin-2-amine | (400 MHz ,CDCl₃), δ: 8.54 (s, 1 H), 8.07 (s, 1 H), 6.31-6.04 (m, 2 H), 5.00 (s, 2 H), 4.53-4.46 m, 2 H), 3.71-3.70 (m, 4 H), 2.89-2.86 (m, 1 H), 2.45 (m, 4 H), 2.23 (m, 2 H), 1.95 (m, 1 H), 1.78-1.26 (m, 6 H) | 458.0 | A |
| 92 | 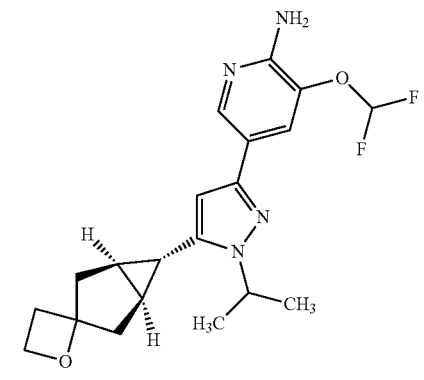<br>3-(difluoromethoxy)-5-(1-isopropyl-5-((1 R,5S,6r)-spiro[bicyclo[3.1.0]hexane-3,2'-oxetan]-6-yl)-1H-pyrazol-3-yl)pyridin-2-amine | 1H NMR (400 MHz, Chloroform-d) δ 8.25 (s, 1 H), 7.71 (s, 1 H), 6.55 (t, J_{HF} = 73.6 Hz, 1 H), 5.96 (s, 1H), 4.71 (br s, 2 H), 4.64 (m, 1H), 4.48 (t, J = 7.6 Hz, 2 H), 2.64 (t, J = 8.0 Hz, 2 H), 2.56 (d, J = 14.4 Hz, 2 H), 2.09-2.05 (m, 2 H), 1.70 (m, 1 H), 1.62 (m, 2 H), 1.50 (d, J = 6.8 Hz, 6 H) | 391.2 | B |

TABLE A-continued

| Cmpd No. | Structure | ¹H NMR | MS [MH]⁺ | Method |
|---|---|---|---|---|
| 93 | 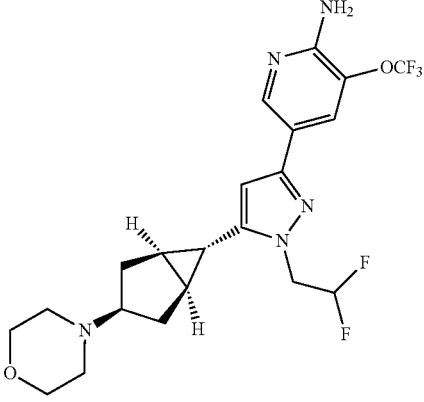 [SMILES: Nc1ncc(-c2cc([C@H]3[C@@H]4C[C@H](N5CCOCC5)C[C@@H]43)n(CC(F)F)n2)cc1OC(F)(F)F] 5-(1-(2,2-difluoroethyl)-5-((1R,3r,5S,6r)-3-morpholinobicyclo[3.1.0]hexan-6-yl)-1H-pyrazol-3-yl)-3-(trifluoromethoxy)pyridin-2-amine | (400 MHz, CDCl₃), δ: 8.31 (s, 1 H), 7.79 (s, 1 H), 6.34-6.00 (m, 2 H), 4.80 (s, 2 H), 4.56-4.50 (m, 2 H), 3.79 (m, 4 H), 3.06 (m, 1 H), 2.52 (m, 4 H), 2.31 (m, 2 H), 2.05 (m, 3 H), 1.75 (m, 2 H) | 474.0 | A |
| 94 | 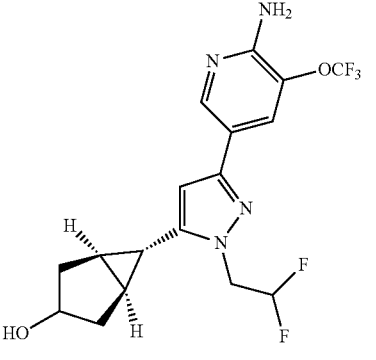 (1R,5S,6r)-6-(3-(6-amino-5-(trifluoromethoxy)pyridin-3-yl)-1-(2,2-difluoroethyl)-1H-pyrazol-5-yl)bicyclo[3.1.0]hexan-3-ol | (400 MHz, CDCl₃), δ: 8.29 (s, 1 H), 7.77 (s, 1 H), 6.32-6.02 (m, 2 H), 4.82 (br s, 2H), 4.50-4.42 (m, 2 H), 4.20-4.16 (m, 1 H), 2.39-2.34 (m, 2 H), 1.89-1.86 (m, 2 H), 1.69 (m, 2 H), 1.45-1.39 (m, 1 H) | 405.1 | A |
| 95 | 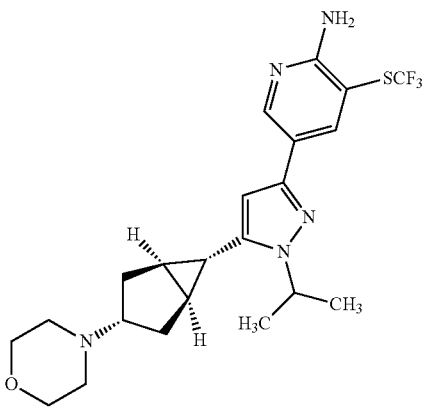 5-(1-isopropyl-5-((1R,3s,5S,6r)-3-morpholinobicyclo[3.1.0]hexan-6-yl)-1H-pyrazol-3-yl)-3-((trifluoromethyl)thio)pyridin-2-amine | (400 MHz, CDCl₃), δ: 8.52 (s, 1 H), 8.13 (s, 1 H), 5.99 (s, 1 H), 5.34 (s, 2 H), 4.63-4.60 (m, 1 H), 3.75 (m, 4 H), 2.48-2.18 (m, 7 H), 1.89-1.69 (m, 4 H), 1.56-1.52 (m, 7 H) | 468.0 | A |

TABLE A-continued

| Cmpd No. | Structure | ¹H NMR | MS [MH]⁺ | Method |
|---|---|---|---|---|
| 96 | 5-(1-isopropyl-5-((1R,3s,5S,6r)-3-morpholinobicyclo[3.1.0]hexan-6-yl)-1H-pyrazol-3-yl)-3-(2,2,2-trifluoroethoxy)pyridin-2-amine | 1H NMR (400 MHz, CDCl$_3$) δ: 8.03 (s, 1H), 7.44 (s, 1H), 6.00 (s, 1H), 4.70 (br s, 2H), 4.64-4.59 (m, 1H), 4.48 (q, J = 8.0 Hz, 2H), 3.74 (m, 4H), 2.46 (m, 4H), 2.36-2.35 (m, 1H), 2.24-2.20 (m, 2H), 1.86-1.81 (m, 2H), 1.69 (m, 3H), 1.53 (d, J = 6.8 Hz, 6H) | 466.18 | A |
| 97 | 5-(1-isopropyl-5-((1R,3r,5S,6S)-3-((S)-3-methylmorpholino)bicyclo[3.1.0]hexan-6-yl)-1H-pyrazol-3-yl)-3-(trifluoromethoxy)pyridin-2-amine | 1H NMR (DMSO-d6) δ: 8.28 (d, J = 1.9 Hz, 1H), 7.70 (m, 1H), 6.39 (br s, 2H), 6.21 (s, 1H), 4.67 (m, 1H), 3.62 (m, 1H), 3.56-3.43 (m, 2H), 3.37 (dd, J = 10.9, 4.0 Hz, 2H), 2.74 (m, 1H), 2.38 (m, 2H), 2.15-1.98 (m, 2H), 1.90 (t, J = 3.2 Hz, 1H), 1.78-1.53 (m, 4H), 1.43 (d, J = 6.5 Hz, 6H), 0.96 (d, J = 6.5 Hz, 3H) | 466.24 | A |
| 98 | 5-(1-isopropyl-5-((1R,3r,5S,6S)-3-((S)-3-methylmorpholino)bicyclo[3.1.0]hexan-6-yl)-1H-pyrazol-3-yl)-3-(trifluoromethyl)pyridin-2-amine | 1H NMR (Chloroform-d) δ: 8.54 (s, 1H), 8.15-8.05 (m, 1H), 5.96 (s, 1H), 4.91 (s, 2H), 4.70-4.59 (m, 1H), 3.80-3.60 (m, 2H), 3.51 (d, J = 11.3 Hz, 1H), 3.38-3.35 (m, 1H), 2.80 (s, 1H), 2.52 (m, 3H), 2.31-2.06 (m, 2H), 1.70 (m, 3H), 1.53-1.50 (m, 9H), 1.07 (d, J = 6.5 Hz, 2H) | 450.25 | A |

TABLE A-continued

| Cmpd No. | Structure | ¹H NMR | MS [MH]⁺ | Method |
|---|---|---|---|---|
| 99 | 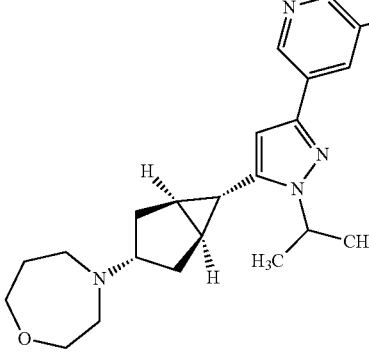<br>5-(5-((1R,3s,5S,6r)-3-(1,4-oxazepan-4-yl)bicyclo[3.1.0]hexan-6-yl)-1-isopropyl-1H-pyrazol-3-yl)-3-(trifluoromethoxy)pyridin-2-amine | 1H NMR (DMS0-d6) δ: 8.28 (d, J = 1.9 Hz, 1H), 7.70 (m, 1H), 6.39 (s, 2H), 6.25 (s, 1H), 4.68 (m, 1H), 3.65 (t, J = 5.9 Hz, 2H), 3.61-3.48 (m, 2H), 2.88 (m, 1H), 2.60 (m, 4H), 2.09 (dd, J = 12.3, 7.0 Hz, 2H), 1.82-1.64 (m, 5H), 1.64-1.53 (m, 2H), 1.40 (d, J = 6.6 Hz, 6H) | 466.24 | A |
| 100 | 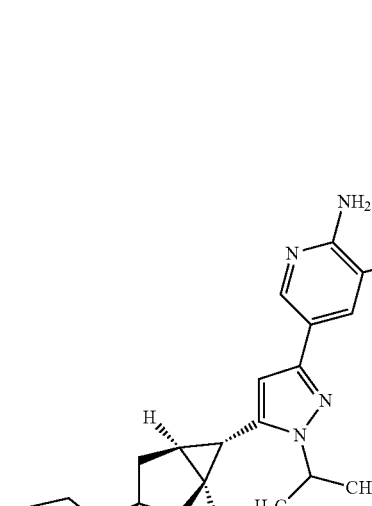<br>5-(5-((1R,3r,5S,6r)-3-(1,4-oxazepan-4-yl)bicyclo[3.1.0]hexan-6-yl)-1-isopropyl-1H-pyrazol-3-yl)-3-(trifluoromethyl)pyridin-2-amine | 1H NMR (DMSO-d6) δ: 8.53 (d, J = 2.1 Hz, 1H), 7.97 (d, J = 2.2 Hz, 1H), 6.44 (s, 2H), 6.26 (s, 1H), 4.70 (m, 1H), 3.65 (t, J = 5.9 Hz, 2H), 3.63-3.51 (m, 2H), 2.69-2.57 (m, 5H), 2.16 (m, 2H), 1.87 (t, J = 3.2 Hz, 1H), 1.75 (m, 2H), 1.64-1.54 (m, 4H), 1.43 (d, J = 6.6 Hz, 6H) | 450.2 | A |

TABLE A-continued

| Cmpd No. | Structure | ¹H NMR | MS [MH]⁺ | Method |
|---|---|---|---|---|
| 101 | 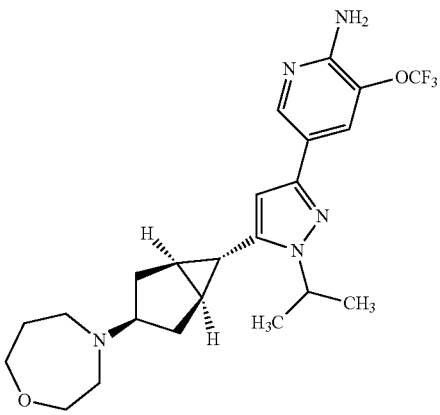 [SMILES: CC(C)n1nc(-c2cnc(N)c(OC(F)(F)F)c2)cc1[C@H]1[C@@H]2C[C@H](N3CCCOCC3)C[C@@H]21]<br>5-(5-((1R,3r,5S,6r)-3-(1,4-oxazepan-4-yl)bicyclo[3.1.0]hexan-6-yl)-1-isopropyl-1H-pyrazol-3-yl)-3-(trifluoromethoxy)pyridin-2-amine | 1H NMR (DMSO-d6) δ: 8.28 (d, J = 1.9 Hz, 1H), 7.70 (m, 1H), 6.39 (s, 2H), 6.21 (s, 1H), 4.69 (m, 1H), 3.65 (t, J = 5.9 Hz, 2H), 3.62-3.53 (m, 2H), 3.25 (d, J = 7.6 Hz, 1H), 2.69-2.55 (m, 4H), 2.22-2.10 (m, 2H), 1.86 (t, J = 3.1 Hz, 1H), 1.81-1.69 (m, 2H), 1.64-1.53 (m, 4H), 1.42 (d, J = 6.6 Hz, 6H) | 466.2 | A |
| 102 | 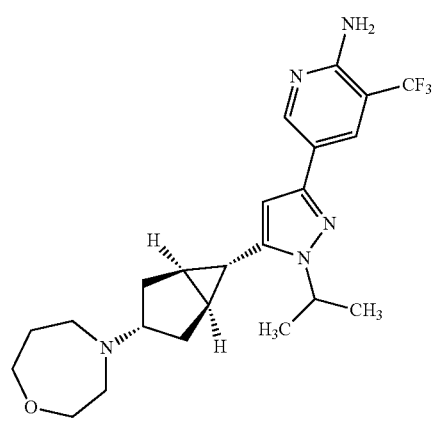 [SMILES: CC(C)n1nc(-c2cnc(N)c(C(F)(F)F)c2)cc1[C@H]1[C@@H]2C[C@@H](N3CCCOCC3)C[C@@H]21]<br>5-(5-((1R,3s,5S,6r)-3-(1,4-oxazepan-4-yl)bicyclo[3.1.0]hexan-6-yl)-1-isopropyl-1H-pyrazol-3-yl)-3-(trifluoromethyl)pyridin-2-amine | 1H NMR (DMSO-d6) δ: 8.57-8.50 (m, 1H), 7.97 (d, J = 2.2 Hz, 1H), 6.44 (s, 2H), 6.29 (s, 1H), 4.69 (m, 1H), 3.65 (t, J = 5.9 Hz, 2H), 3.62-3.51 (m, 2H), 2.88 (m, 1H), 2.66-2.54 (m, 4H), 2.09 (dd, J = 12.3, 7.0 Hz, 2H), 1.83-1.55 (m, 7H), 1.41 (d, J = 6.6 Hz, 6H) | 450.2 | A |

TABLE A-continued

| Cmpd No. | Structure | ¹H NMR | MS [MH]⁺ | Method |
|---|---|---|---|---|
| 103 | 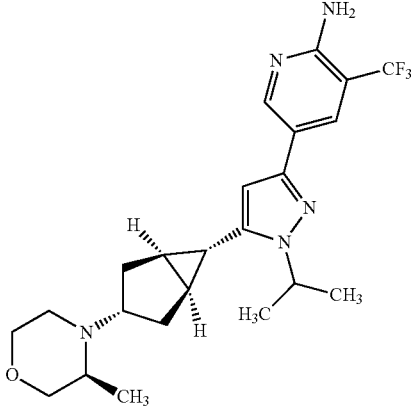 [SMILES: CC(C)n1nc(-c2cnc(N)c(C(F)(F)F)c2)cc1[C@H]1[C@@H]2C[C@@H](N3CCOC[C@@H]3C)C[C@@H]21]<br>5-(1-isopropyl-5-((1R,3s,5S,6S)-3-((S)-3-methylmorpholino)bicyclo[3.1.0]hexan-6-yl)-1H-pyrazol-3-yl)-3-(trifluoromethyl)pyridin-2-amine | 1H NMR (Chloroform-d) δ: 8.54 (dd, J = 2.1, 1.0 Hz, 1H), 8.10 (d, J = 2.1 Hz, 1H), 6.01 (s, 1H), 4.92 (s, 2H), 4.61 (m, 1H), 3.75-3.61 (m, 3H), 3.55-3.51 (m, 1H), 2.97-2.32 (m, 4H), 2.28-2.14 (m, 1H), 1.71-1.62 (m, 2H), 1.60-1.48 (m, 11H), 1.08 (s, 2H) | 450.25 | A |
| 104 | 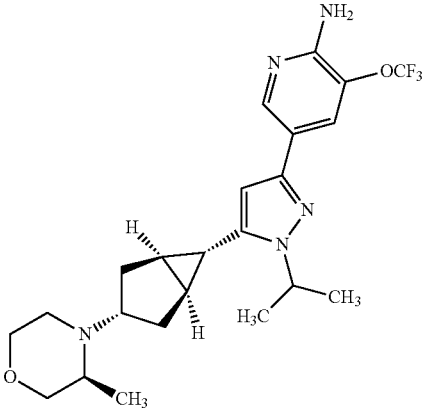 [SMILES: CC(C)n1nc(-c2cnc(N)c(OC(F)(F)F)c2)cc1[C@H]1[C@@H]2C[C@@H](N3CCOC[C@@H]3C)C[C@@H]21]<br>5-(1-isopropyl-5-((1R,3s,5S,6S)-3-((S)-3-methylmorpholino)bicyclo[3.1.0]hexan-6-yl)-1H-pyrazol-3-yl)-3-(trifluoromethoxy)pyridin-2-amine | 1H NMR (DMSO-d6) δ. 8.29 (d, J = 2.3 Hz, 1H), 7.71 (s, 1H), 6.39 (s, 2H), 6.25 (s, 1H), 4.81-4.61 (m, 1H), 3.55 (m, 4H), 3.04-2.89 (m, 1H), 2.65 (s, 1H), 2.31 (d, J = 11.6 Hz, 2H), 1.98 (m, 2H), 1.84-1.66 (m, 3H), 1.66-1.50 (m, 2H), 1.49-1.33 (m, 6H), 0.97 (d, J = 6.3 Hz, 3H) | 466.24 | A |
| 105 | 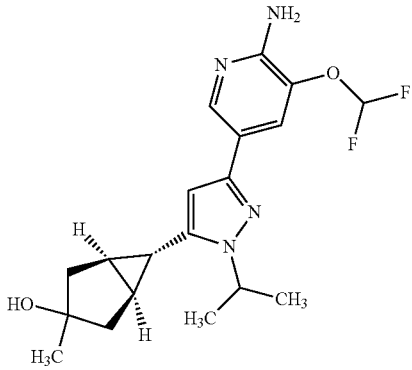<br>(1R,5S,6r)-6-(3-(6-amino-5-(difluoromethoxy)pyridin-3-yl)-1-isopropyl-1H-pyrazol-5-yl)-3-methyl-bicyclo[3.1.0]hexan-3-ol | 1H NMR (400 MHz, Chloroform-d) δ 8.22 (s, 1 H), 7.69 (s, 1 H), 6.53 (t, JHF = 73.6 Hz, 1 H), 5.95 (s, 1 H), 4.70 (br s, 2 H), 4.66 (m, 1 H), 2.35 (m, 1 H), 2.08 (m, 2 H), 1.96 (m, 2 H), 1.70 (m, 1 H), 1.63 (m, 2 H), 1.50 (d, J = 6.8 Hz, 6 H), 1.38 (s, 3 H) | 379.17 | C |

TABLE A-continued

| Cmpd No. | Structure | ¹H NMR | MS [MH]⁺ | Method |
|---|---|---|---|---|
| 106 | (2-amino-5-(5-((1R,3s,5S,6r)-3-(3-fluoroazetidin-1-yl)bicyclo[3.1.0]hexan-6-yl)-1-isopropyl-1H-pyrazol-3-yl)pyridin-3-yl)(pyrrolidin-1-yl)methanone | | 453.14 | A |
| 107 | (2-amino-5-(5-((1R,3r,5S,6r)-3-(3-fluoroazetidin-1-yl)bicyclo[3.1.0]hexan-6-yl)-1-isopropyl-1H-pyrazol-3-yl)pyridin-3-yl)(pyrrolidin-1-yl)methanone | | 453.18 | A |
| 108 | 5-(1-isopropyl-5-((1R,3r,5S,6S)-3-((S)-2-methylmorpholino)bicyclo[3.1.0]hexan-6-yl)-1H-pyrazol-3-yl)-3-(trifluoromethyl)pyridin-2-amine | 1H NMR (DMSO-d6) δ: 8.53 (dd, J = 2.1, 0.9 Hz, 1H), 7.97 (d, J = 2.2 Hz, 1H), 6.43 (s, 2H), 6.26 (s, 1H), 4.67 (m, 1H), 3.73 (m, 1H), 3.51-3.35 (m, 2H), 2.86-2.61 (m, 3H), 2.17-2.05 (m, 2H), 1.95 (t, J = 3.3 Hz, 1H), 1.88 (m, 1H), 1.78-1.64 (m, 2H), 1.64-1.51 (m, 3H), 1.43 (d, J = 6.5 Hz, 6H), 1.04 (d, J = 6.2 Hz, 3H) | 450.2 | A |

TABLE A-continued

| Cmpd No. | Structure | ¹H NMR | MS [MH]⁺ | Method |
|---|---|---|---|---|
| 109 | 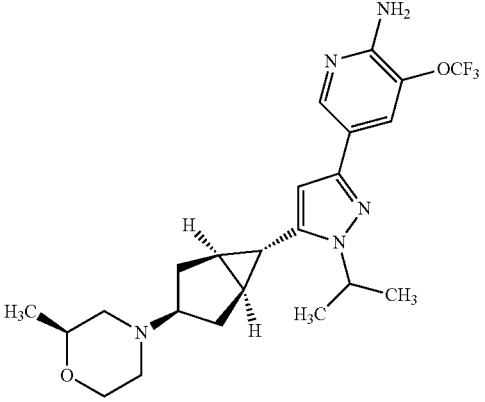 [SMILES: CC(C)n1nc(-c2cnc(N)c(OC(F)(F)F)c2)cc1[C@H]1[C@@H]2C[C@H](N3CCO[C@@H](C)C3)C[C@@H]21]<br>5-(1-isopropyl-5-((1R,3r,5S,6S)-3-((S)-2-methylmorpholino)bicyclo[3.1.0]hexan-6-yl)-1H-pyrazol-3-yl)-3-(trifluoromethoxy)pyridin-2-amine | 1H NMR (DMS0-d6) δ: 8.28 (d, J = 2.0 Hz, 1H), 7.70 (m, 1H), 6.39 (s, 2H), 6.21 (s, 1H), 4.66 (m, 1H), 3.73 (m, 1H), 3.52-3.36 (m, 2H), 2.86-2.63 (m, 3H), 2.17-2.04 (m, 2H), 1.95 (t, J = 3.3 Hz, 1H), 1.88 (m, 1H), 1.72 (dd, J = 13.2, 6.1 Hz, 2H), 1.63-1.55 (m, 3H), 1.42 (d, J = 6.6 Hz, 6H), 1.04 (d, J = 6.2 Hz, 3H) | 466.2 | A |
| 110 | 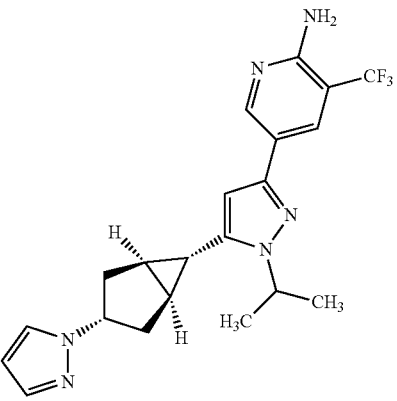 [SMILES: CC(C)n1nc(-c2cnc(N)c(C(F)(F)F)c2)cc1[C@H]1[C@@H]2C[C@@H](n3cccn3)C[C@@H]21]<br>5-(5-((1R,3s,5S,6r)-3-(1H-pyrazol-1-yl)bicyclo[3.1.0]hexan-6-yl)-1-isopropyl-1H-pyrazol-3-yl)-3-(trifluoromethyl)pyridin-2-amine |  | 416.99 |  |
| 111 | 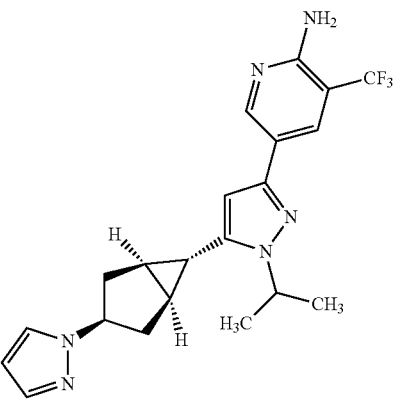 [SMILES: CC(C)n1nc(-c2cnc(N)c(C(F)(F)F)c2)cc1[C@H]1[C@@H]2C[C@H](n3cccn3)C[C@@H]21]<br>5-(5-((1R,3r,5S,6r)-3-(1H-pyrazol-1-yl)bicyclo[3.1.0]hexan-6-yl)-1-isopropyl-1H-pyrazol-3-yl)-3-(trifluoromethyl)pyridin-2-amine |  | 417.07 | A |

TABLE A-continued

| Cmpd No. | Structure | ¹H NMR | MS [MH]⁺ | Method |
|---|---|---|---|---|
| 112 | 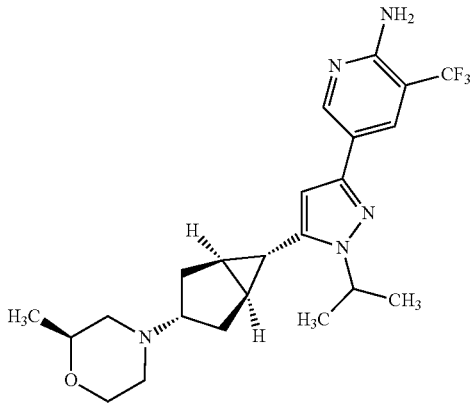 [SMILES: CC(C)n1nc(-c2cnc(N)c(C(F)(F)F)c2)cc1[C@H]1[C@@H]2C[C@@H](N3CCO[C@@H](C)C3)C[C@@H]21]<br>5-(1-isopropyl-5-((1R,3s,5S,6S)-3-((S)-2-methylmorpholino)bicyclo[3.1.0]hexan-6-yl)-1H-pyrazol-3-yl)-3-(trifluoromethyl)pyridin-2-amine | 1H NMR (DMSO-d6) δ: 8.54 (d, J = 2.3 Hz, 1H), 7.97 (d, J = 2.4 Hz, 1H), 6.44 (s, 2H), 6.30 (s, 1H), 4.68 (m, 1H), 3.71 (d, J = 10.2 Hz, 1H), 3.51-3.41 (m, 2H), 2.72 (d, J = 11.0 Hz, 1H), 2.64 (d, J = 11.4 Hz, 1H), 2.40 (m, 1H), 2.12 (m, 2H), 1.95 (m, 1H), 1.77-1.58 (m, 6H), 1.41 (d, J = 6.5 Hz, 6H), 1.03 (d, J = 6.3 Hz, 3H) | 450.25 | A |
| 113 | 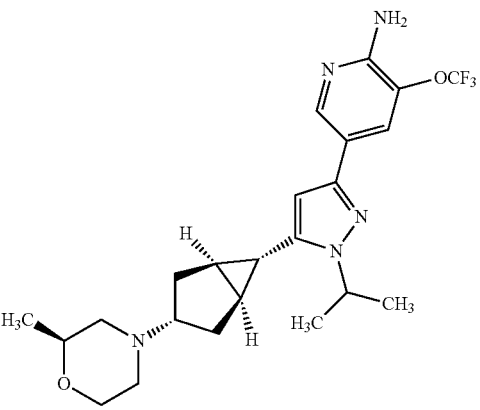 [SMILES: CC(C)n1nc(-c2cnc(N)c(OC(F)(F)F)c2)cc1[C@H]1[C@@H]2C[C@@H](N3CCO[C@@H](C)C3)C[C@@H]21]<br>5-(1-isopropyl-5-((1R,3s,5S,6S)-3-((S)-2-methylmorpholino)bicyclo[3.1.0]hexan-6-yl)-1H-pyrazol-3-yl)-3-(trifluoromethoxy)pyridin-2-amine | 1H NMR (DMSO-d6) δ: 8.28 (d, J = 1.9 Hz, 1H), 7.70 (m, 1H), 6.40 (s, 2H), 6.25 (s, 1H), 4.67 (m, 1H), 3.75-3.67 (m, 1H), 3.52- 3.40 (m, 2H), 2.72 (d, J = 11.0 Hz, 1H), 2.64 (d, J = 10.9 Hz, 1H), 2.41 (m, 1H), 2.11 (m, 2H), 1.95 (m, 1H), 1.77-1.57 (m, 6H), 1.40 (d, J = 6.5 Hz, 6H), 1.03 (d, J = 6.2 Hz, 3H) | 466.24 | A |
| 114 | 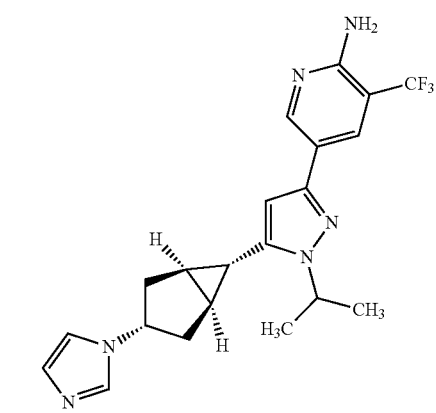 [SMILES: CC(C)n1nc(-c2cnc(N)c(C(F)(F)F)c2)cc1[C@H]1[C@@H]2C[C@@H](n3ccnc3)C[C@@H]21]<br>5-(5-((1R,3s,5S,6r)-3-(1H-imidazol-1-yl)bicyclo[3.1.0]hexan-6-yl)-1-isopropyl-1H-pyrazol-3-yl)-3-(trifluoromethyl)pyridin-2-amine | | 417.19 | A |

TABLE A-continued

| Cmpd No. | Structure | ¹H NMR | MS [MH]⁺ | Method |
|---|---|---|---|---|
| 115 | 5-(5-((1R,3r,5S,6r)-3-(1H-imidazol-1-yl)bicyclo[3.1.0]hexan-6-yl)-1-isopropyl-1H-pyrazol-3-yl)-3-(trifluoromethyl)pyridin-2-amine | | 417.14 | A |
| 116 | 5-(1-isopropyl-5-((1R,3r,5S,6r)-3-(4-(oxetan-3-yl)piperazin-1-yl)bicyclo[3.1.0]hexan-6-yl)-1H-pyrazol-3-yl)-3-(trifluoromethyl)pyridin-2-amine | | 491.4 | A |

TABLE A-continued
| Cmpd No. | Structure | ¹H NMR | MS [MH]⁺ | Method |
|---|---|---|---|---|
| 117 | 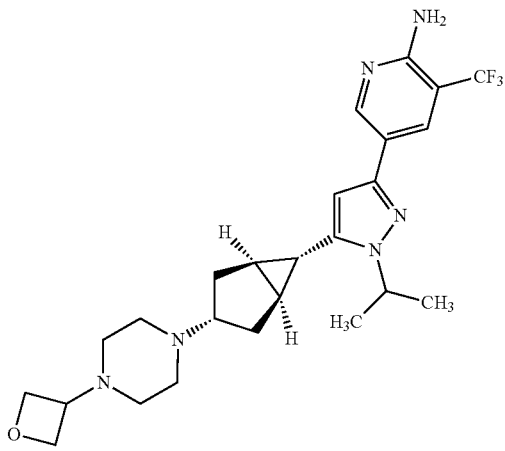 [SMILES: CC(C)n1nc(-c2cnc(N)c(C(F)(F)F)c2)cc1[C@H]1[C@@H]2C[C@@H](N3CCN(C4COC4)CC3)C[C@@H]21]<br>5-(1-isopropyl-5-(((1R,3s,5S,6r)-3-(4-(oxetan-3-yl)piperazin-1-yl)bicyclo[3.1.0]hexan-6-yl)-1H-pyrazol-3-yl)-3-(trifluoromethyl)pyridin-2-amine | | 491.2 | A |
| 118 | 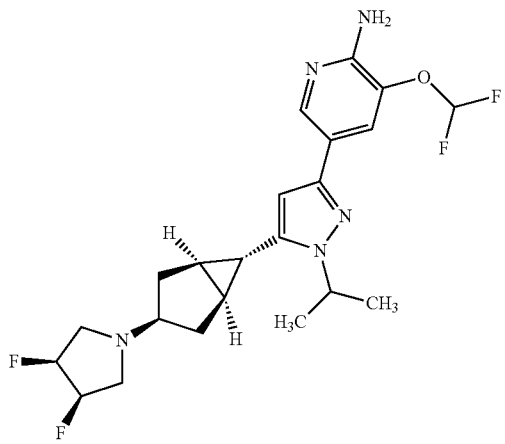 [SMILES: CC(C)n1nc(-c2cnc(N)c(OC(F)F)c2)cc1[C@H]1[C@@H]2C[C@H](N3C[C@@H](F)[C@@H](F)C3)C[C@@H]21]<br>3-(difluoromethoxy)-5-(5-((1R,3r,5S,6R)-3-((3S,4R)-3,4-difluoropyrrolidin-1-yl)bicyclo[3.1.0]hexan-6-yl)-1-isopropyl-1H-pyrazol-3-yl)pyridin-2-amine | | 454.2 | A |

TABLE A-continued

| Cmpd No. | Structure | ¹H NMR | MS [MH]⁺ | Method |
|---|---|---|---|---|
| 119 | 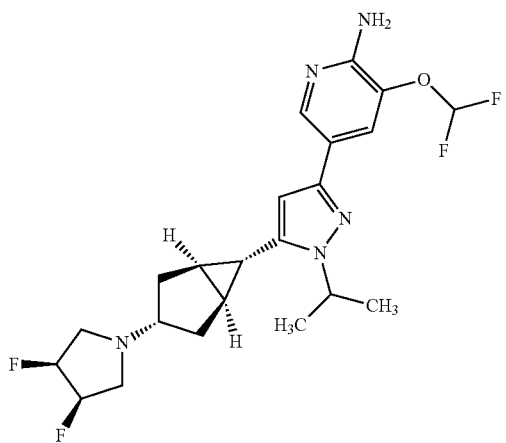 [SMILES: CC(C)n1nc(-c2cnc(N)c(OC(F)F)c2)cc1[C@H]1[C@@H]2C[C@@H](N3C[C@@H](F)[C@@H](F)C3)C[C@@H]21] 3-(difluoromethoxy)-5-(5-((1R, 3s,5S,6R)-3-((3S,4R)-3,4-difluoro-pyrrolidin-1-yl)bicyclo[3.1.0]hexan-6-yl)-1-isopropyl-1H-pyrazol-3-yl)pyridin-2-amine | | 454.2 | A |
| 120 | 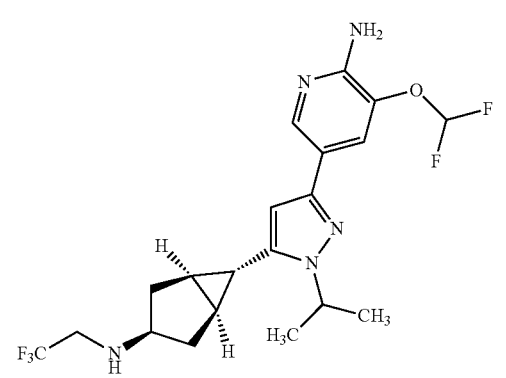 [SMILES: CC(C)n1nc(-c2cnc(N)c(OC(F)F)c2)cc1[C@H]1[C@@H]2C[C@H](NCC(F)(F)F)C[C@@H]21] 3-(difluoromethoxy)-5-(1-isopropyl-5-((1R,3r,5S,6r)-3-((2,2,2-trifluoroethyl)amino)bicyclo[3.1.0]hexan-6-yl)-1H-pyrazol-3-yl)pyridin-2-amine | | 446.2 | A |
| 121 | 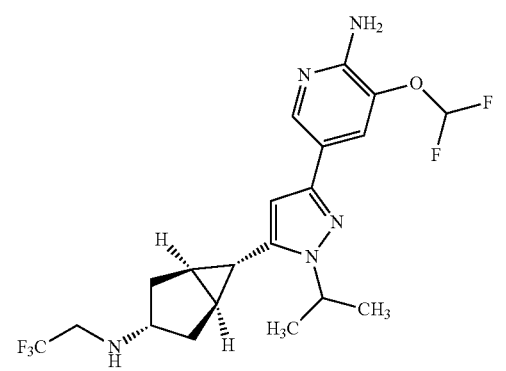 [SMILES: CC(C)n1nc(-c2cnc(N)c(OC(F)F)c2)cc1[C@H]1[C@@H]2C[C@@H](NCC(F)(F)F)C[C@@H]21] 3-(difluoromethoxy)-5-(1-isopropyl-5-((1R,3s,5S,6r)-3-((2,2,2-trifluoroethyl)amino)bicyclo[3.1.0]hexan-6-yl)-1H-pyrazol-3-yl)pyridin-2-amine | | 446.2 | A |

TABLE A-continued
| Cmpd No. | Structure | ¹H NMR | MS [MH]⁺ | Method |
|---|---|---|---|---|
| 122 | 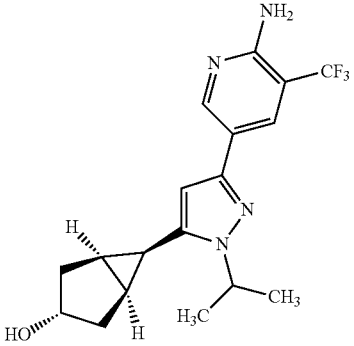 [SMILES: CC(C)n1nc(-c2cnc(N)c(C(F)(F)F)c2)cc1[C@@H]1[C@@H]2C[C@@H](O)C[C@@H]21]<br>(1R,3s,5S,6s)-6-(3-(6-amino-5-(trifluoromethyl)pyridin-3-yl)-1-isopropyl-1H-pyrazol-5-yl)bicyclo[3.1.0]hexan-3-ol | | 367.17 | A |
| 123 | 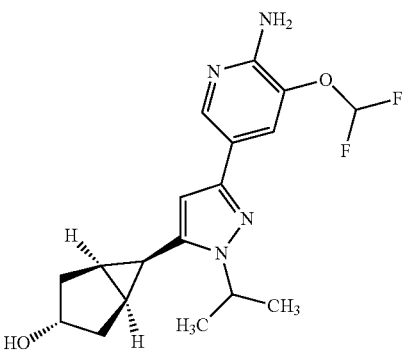 [SMILES: CC(C)n1nc(-c2cnc(N)c(OC(F)F)c2)cc1[C@@H]1[C@@H]2C[C@@H](O)C[C@@H]21]<br>(1R,3s,5S,6s)-6-(3-(6-amino-5-(difluoromethoxy)pyridin-3-yl)-1-isopropyl-1H-pyrazol-5-yl)bicyclo[3.1.0]hexan-3-ol | | 365.3 | A |
| 124 | 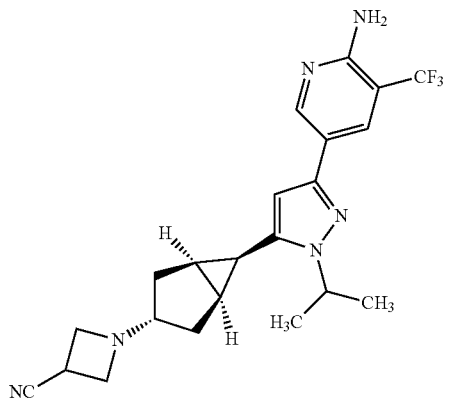 [SMILES: CC(C)n1nc(-c2cnc(N)c(C(F)(F)F)c2)cc1[C@@H]1[C@@H]2C[C@@H](N3CC(C#N)C3)C[C@@H]21]<br>1-((1R,3s,5S,6s)-6-(3-(6-amino-5-(trifluoromethyl)pyridin-3-yl)-1-isopropyl-1H-pyrazol-5-yl)bicyclo[3.1.0]hexan-3-yl)azetidine-3-carbonitrile | | 430.9 | A |

| Cmpd No. | Structure | ¹H NMR | MS [MH]⁺ | Method |
|---|---|---|---|---|
| 125 | 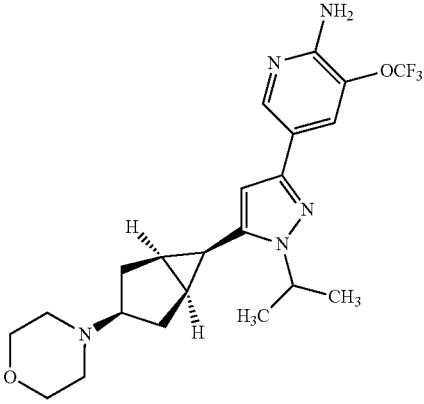 [SMILES: CC(C)n1nc(-c2cnc(N)c(OC(F)(F)F)c2)cc1[C@@H]1[C@@H]2C[C@H](N3CCOCC3)C[C@@H]21]<br>5-(1-isopropyl-5-((1R,3r,5S,6s)-3-morpholinobicyclo[3.1.0]hexan-6-yl)-1H-pyrazol-3-yl)-3-(trifluoromethoxy)pyridin-2-amine | | 452.16 | A |
| 126 | 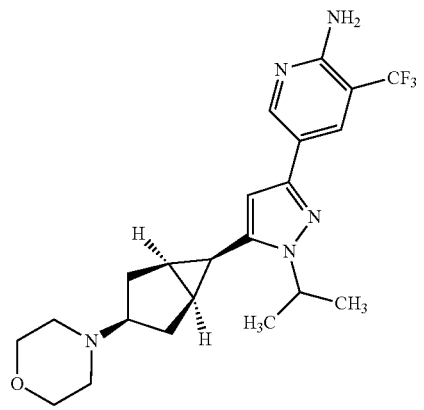 [SMILES: CC(C)n1nc(-c2cnc(N)c(C(F)(F)F)c2)cc1[C@@H]1[C@@H]2C[C@H](N3CCOCC3)C[C@@H]21]<br>5-(1-isopropyl-5-((1R,5S,6s)-3-morpholinobicyclo[3.1.0]hexan-6-yl)-1H-pyrazol-3-yl)-3-(trifluoromethyl)pyridin-2-amine | | 436.31 | A |
| 127 | 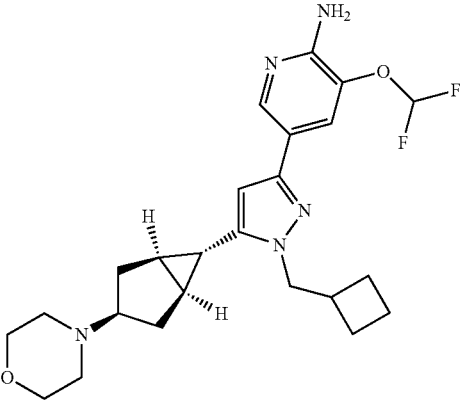 [SMILES: Nc1ncc(-c2cc([C@H]3[C@@H]4C[C@H](N5CCOCC5)C[C@@H]43)n(CC3CCC3)n2)cc1OC(F)F]<br>5-(1-(cyclobutylmethyl)-5-((1R,3r,5S,6r)-3-morpholinobicyclo[3.1.0]hexan-6-yl)-1H-pyrazol-3-yl)-3-(difluoromethoxy)pyridin-2-amine | (400 MHz, DMSO-d₆), δ: 8.14 (d, J = 1.9 Hz, 1 H), 7.56 (d, J = 1.7 Hz, 1 H), 7.15 (t, $J_{HF}$ = 73.8 Hz, 1 H), 6.14 (s, 1 H), 6.09 (br s, 2 H), 4.13 (d, J = 7.1 Hz, 2 H), 3.56 (t, J = 4.6 Hz, 4 H), 2.70-2.81 (m, 2 H), 2.35 (m, 4 H), 2.03-2.09 (m, 3 H), 1.94-2.01 (m, 2 H), 1.76-1.89 (m, 6 H), 1.58 (m, 2 H) | 460.4 | D |

TABLE A-continued

| Cmpd No. | Structure | $^1$H NMR | MS [MH]$^+$ | Method |
|---|---|---|---|---|
| 128 | 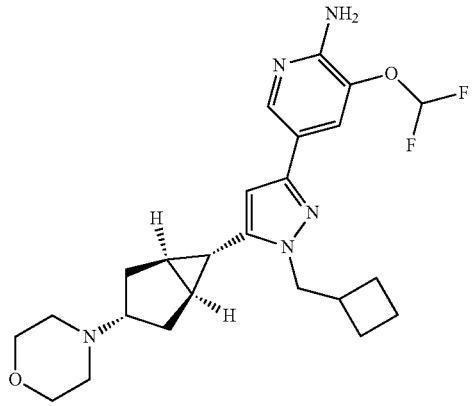 [SMILES: Nc1ncc(-c2cc([C@H]3[C@@H]4C[C@@H](N5CCOCC5)C[C@@H]43)n(CC3CCC3)n2)cc1OC(F)F]<br>5-(1-(cyclobutylmethyl)-5-((1R, 3s,5S,6r)-3-morpholinobicyclo [3.1.0]hexan-6-yl)-1H-pyrazol-3-yl)-3-(difluoromethoxy)pyridin-2-amine | (400 MHz, DMSO-d$_6$) δ: 8.14 (d, J = 1.9 Hz, 1H), 7.60-7.49 (m, 1H), 7.37-6.93 (m, 1H), 6.19 (d, J = 0.5 Hz, 1H), 6.09 (s, 2H), 4.13 (d, J = 7.1 Hz, 2H), 3.60-3.52 (m, 4H), 2.34 (m, 5H), 2.15-2.03 (m, 2H), 2.03-1.93 (m, 1H), 1.89-1.59 (m, 11H) | 460.2 | D |
| 129 | 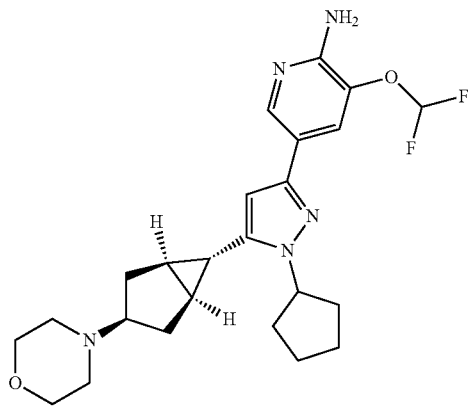 [SMILES: Nc1ncc(-c2cc([C@H]3[C@@H]4C[C@H](N5CCOCC5)C[C@@H]43)n(C3CCCC3)n2)cc1OC(F)F]<br>5-(1-cyclopentyl-5-((1R,3r,5S,6r)-3-morpholinobicyclo[3.1.0] hexan-6-yl)-1H-pyrazol-3-yl)-3-(difluoromethoxy)pyridin-2-amine | (400 MHz, DMSO-d$_6$) δ: 8.19-8.08 (m, 1H), 7.59-7.51 (m, 1H), 7.15 (t, J = 73.9 Hz, 1H), 6.21-6.14 (m, 1H), 6.08 (s, 2H), 4.86-4.77 (m, 1H), 3.55 (t, J = 4.6 Hz, 4H), 2.84-2.69 (m, 1H), 2.42-2.26 (m, 4H), 2.14-1.93 (m, 7H), 1.89-1.81 (m, 2H), 1.76-1.57 (m, 6H) | 460.2 | D |
| 130 | 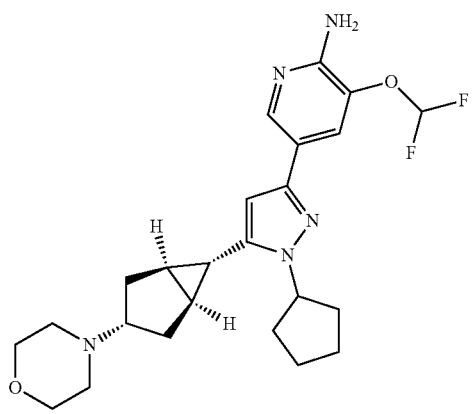 [SMILES: Nc1ncc(-c2cc([C@H]3[C@@H]4C[C@@H](N5CCOCC5)C[C@@H]43)n(C3CCCC3)n2)cc1OC(F)F]<br>5-(1-cyclopentyl-5-((1R,3s,5S,6r)-3-morpholinobicyclo[3.1.0] hexan-6-yl)-1H-pyrazol-3-yl)-3-(difluoromethoxy)pyridin-2-amine | (400 MHz, DMSO-d$_6$) δ: 8.19-8.12 (m, 1H), 7.61-7.50 (m, 1H), 7.36-6.95 (m, 1H), 6.27-6.18 (m, 1H), 6.08 (s, 2H), 4.91-4.76 (m, 1H), 3.60-3.53 (m, 4H), 2.39-2.30 (m, 5H), 2.17-1.58 (m, 15H) | 460.2 | D |

TABLE A-continued

| Cmpd No. | Structure | ¹H NMR | MS [MH]⁺ | Method |
|---|---|---|---|---|
| 131 | 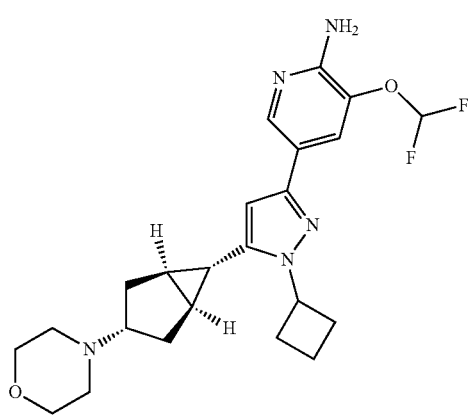 [SMILES: Nc1ncc(-c2cc([C@H]3[C@@H]4C[C@@H](N5CCOCC5)C[C@@H]43)n(C3CCC3)n2)cc1OC(F)F]<br>5-(1-cyclobutyl-5-((1R,3s,5S,6r)-3-morpholinobicyclo[3.1.0]hexan-6-yl)-1H-pyrazol-3-yl)-3-(difluoromethoxy)pyridin-2-amine | (400 MHz, CDCl₃) δ: 8.25 (d, J = 1.9 Hz, 1H), 7.75-7.59 (m, 1H), 6.55 (t, J = 73.6 Hz, 1H), 6.00 (d, J = 0.7 Hz, 1H), 4.91-4.77 (m, 1H), 4.71 (s, 2H), 3.80-3.67 (m, 4H), 2.87-2.67 (m, 2H), 2.52-2.31 (m, 8H), 2.29-2.16 (m, 2H), 2.00-1.73 (m, 4H), 1.71-1.60 (m, 2H), 1.57-1.46 (m, 1H) | 446.2 | D |
| 132 | 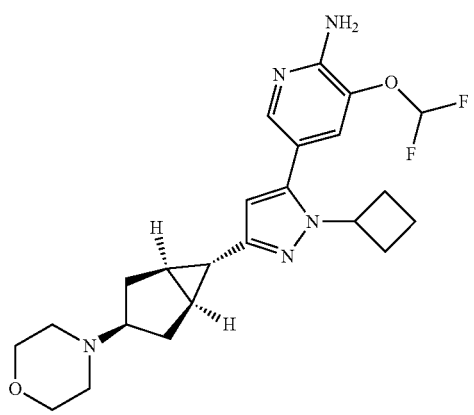 [SMILES: Nc1ncc(-c2cc([C@H]3[C@@H]4C[C@H](N5CCOCC5)C[C@@H]43)nn2C2CCC2)cc1OC(F)F]<br>5-(1-cyclobutyl-3-((1R,3r,5S,6r)-3-morpholinobicyclo[3.1.0]hexan-6-yl)-1H-pyrazol-5-yl)-3-(difluoromethoxy)pyridin-2-amine | (400 MHz, CDCl₃) δ: 7.88 (d, J = 1.9 Hz, 1H), 7.24-7.13 (m, 1H), 6.53 (t, J = 72.8 Hz, 1H), 5.77 (s, 1H), 4.86 (s, 2H), 4.67-4.44 (m, 1H), 3.75 (s, 4H), 2.86-2.66 (m, 2H), 2.60-2.34 (m, 2H), 2.33-2.14 (m, 4H), 1.93-1.81 (m, 2H), 1.76-1.58 (m, 9H) | 446.2 | D |
| 133 | 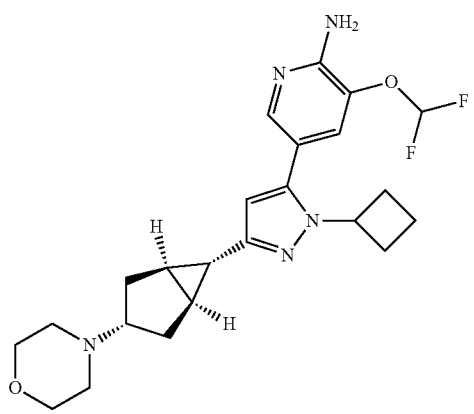 [SMILES: Nc1ncc(-c2cc([C@H]3[C@@H]4C[C@@H](N5CCOCC5)C[C@@H]43)nn2C2CCC2)cc1OC(F)F]<br>5-(1-cyclobutyl-3-((1R,3s,5S,6r)-3-morpholinobicyclo[3.1.0]hexan-6-yl)-1H-pyrazol-5-yl)-3-(difluoromethoxy)pyridin-2-amine | (400 MHz, CDCl₃) δ: 7.88 (d, J = 1.9 Hz, 1H), 7.24-7.16 (m, 1H), 6.53 (t, J = 72.8 Hz, 1H), 5.82 (s, 1H), 4.85 (s, 2H), 4.65-4.47 (m, 1H), 3.86-3.63 (m, 4H), 2.85-2.69 (m, 2H), 2.34-2.16 (m, 4H), 1.75-1.51 (m, 13H) | 446.2 | D |

TABLE A-continued

| Cmpd No. | Structure | ¹H NMR | MS [MH]⁺ | Method |
|---|---|---|---|---|
| 134 | 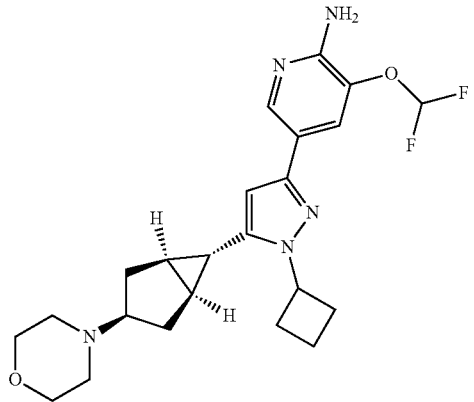 [SMILES: Nc1ncc(-c2cc([C@H]3[C@@H]4C[C@H](N5CCOCC5)C[C@@H]43)n(C3CCC3)n2)cc1OC(F)F]<br>5-(1-cyclobutyl-5-((1R,3r,5S,6r)-3-morpholinobicyclo[3.1.0]hexan-6-yl)-1H-pyrazol-3-yl)-3-(difluoromethoxy)pyridin-2-amine | (400 MHz, DMSO-$d_6$) δ: 8.17 (d, J = 1.9 Hz, 1H), 7.63-7.57 (m, 1H), 7.16 (t, J = 73.9 Hz, 1H), 6.20 (d, J = 0.6 Hz, 1H), 6.10 (s, 2H), 5.02-4.81 (m, 1H), 3.56 (t, J = 4.6 Hz, 4H), 2.84-2.71 (m, 1H), 2.63-2.53 (m, 3H), 2.41-2.30 (m, 6H), 2.14-2.05 (m, 2H), 1.97-1.86 (m, 1H), 1.86-1.76 (m, 2H), 1.75-1.65 (m, 2H), 1.61-1.52 (m, 2H) | 446.2 | D |
| 135 | 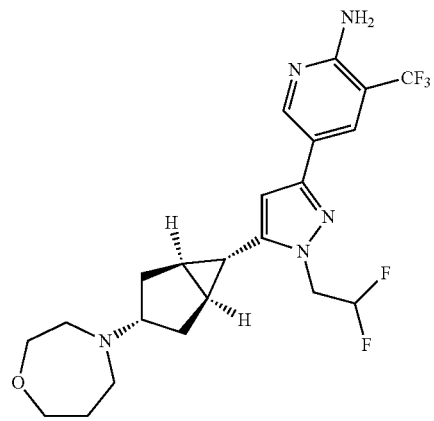 [SMILES: Nc1ncc(-c2cc([C@H]3[C@@H]4C[C@@H](N5CCCOCC5)C[C@@H]43)n(CC(F)F)n2)cc1C(F)(F)F]<br>5-(5-((1R,3s,5S,6r)-3-(1,4-oxazepan-4-yl)bicyclo[3.1.0]hexan-6-yl)-1-(2,2-difluoroethyl)-1H-pyrazol-3-yl)-3-(trifluoromethyl)pyridin-2-amine | (400 MHz, CDCl₃), δ: 8.53 (s, 1 H), 8.06 (d, J = 1.2 Hz, 1 H), 6.35-6.02 (m, 1 H), 6.06 (s, 1 H), 5.03 (br s, 2 H), 4.53-4.43 (m, 2 H), 3.79 (t, J = 6.0 Hz, 2 H), 3.74 (t, J = 4.8 Hz, 2 H), 2.82-2.74 (m, 1 H), 2.73-2.67 (m, 4 H), 2.42-2.17 (m, 2 H), 1.92-1.81 (m, 4 H), 1.72-1.66 (m, 2 H), 1.57 (t, J = 2.8 Hz, 1 H) | 472.1 | E |
| 136 | 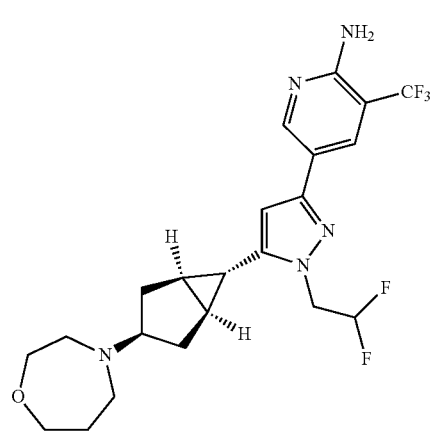 [SMILES: Nc1ncc(-c2cc([C@H]3[C@@H]4C[C@H](N5CCCOCC5)C[C@@H]43)n(CC(F)F)n2)cc1C(F)(F)F]<br>5-(5-((1R,3r,5S,6r)-3-(1,4-oxazepan-4-yl)bicyclo[3.1.0]hexan-6-yl)-1-(2,2-difluoroethyl)-1H-pyrazol-3-yl)-3-(trifluoromethyl)pyridin-2-amine | (400 MHz, CDCl₃), δ: 8.53 (d, J = 1.2 Hz, 1 H), 8.06 (d, J = 1.2 Hz, 1 H), 6.34-6.02 (m, 1 H), 6.01 (s, 1 H), 5.03 (br s, 2 H), 4.55-4.45 (m, 2 H), 3.78 (t, J = 6.0 Hz, 2 H), 3.73 (t, J = 4.8 Hz, 2 H), 3.35-3.25 (m, 1 H), 2.74-2.65 (m, 4 H), 2.33-2.23 (m, 2 H), 1.91-1.84 (m, 2 H), 1.82 (t, J = 3.0 Hz, 1 H), 1.70-1.61 (m, 4 H) | 472.1 | E |

TABLE A-continued

| Cmpd No. | Structure | ¹H NMR | MS [MH]⁺ | Method |
|---|---|---|---|---|
| 137 | 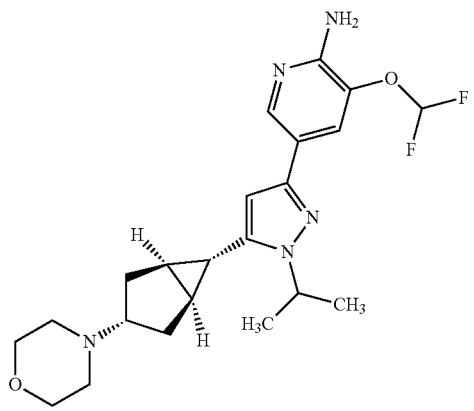 [SMILES: CC(C)n1nc(-c2cnc(N)c(OC(F)F)c2)cc1[C@H]1[C@@H]2C[C@@H](N3CCOCC3)C[C@@H]21]<br>3-(difluoromethoxy)-5-(1-isopropyl-5-((1R,3s,5S,6r)-3-morpholino-bicyclo[3.1.0]hexan-6-yl)-1H-pyrazol-3-yl)pyridin-2-amine | (400 MHz, CDCl$_3$) δ: 8.22 (s, 1 H), 7.69 (s, 1 H), 6.54 (t, J$_{HF}$ = 73.6 Hz, 1 H), 5.98 (s, 1 H), 4.69 (s, 2H), 4.61-4.58 (m, 1 H), 3.73-3.71 (m, 4 H), 2.45-2.24 (m, 5 H), 2.22-2.18 (m, 2 H), 1.85-1.82 (m, 2 H), 1.67-1.54 (m, 2 H), 1.53-1.50 (m, 7 H) | 434.2 | A |
| 138 | 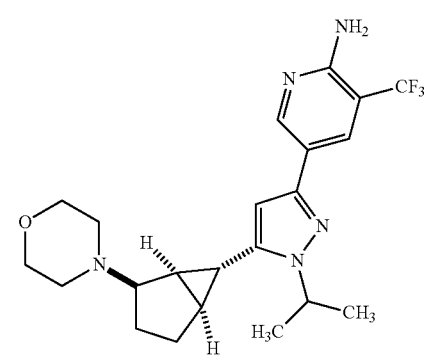 [SMILES: CC(C)n1nc(-c2cnc(N)c(C(F)(F)F)c2)cc1[C@@H]1[C@H]2CC[C@@H](N3CCOCC3)[C@H]21]<br>5-(1-isopropyl-5-(2-morpholino bicyclo[3.1.0]hexan-6-yl)-1H-pyrazol-3-yl)-3-(trifluoromethyl) pyridin-2-amine (Exo-anti enantiomer 2) | | 436.1 | F |
| 139 | 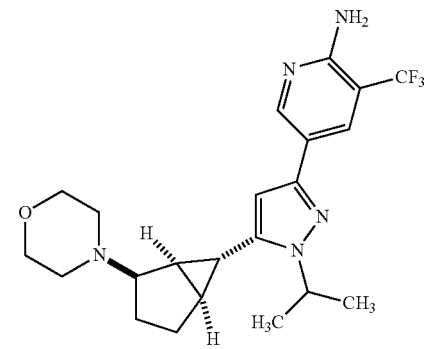 [SMILES: CC(C)n1nc(-c2cnc(N)c(C(F)(F)F)c2)cc1[C@@H]1[C@H]2CC[C@@H](N3CCOCC3)[C@H]21]<br>5-(1-isopropyl-5-(2-morpholino bicyclo[3.1.0]hexan-6-yl)-1H-pyrazol-3-yl)-3-(trifluoromethyl) pyridin-2-amine (Exo-anti enantiomer 1) | (400 MHz, CDCl$_3$) δ: 8.53 (s, 1 H), 8.10 (s, 1 H), 5.96 (s, 1 H), 4.95 (s, 2 H), 4.72 (m, 1 H), 3.74 (m, 4 H), 2.90 (s, 1 H), 2.63-2.55 (m, 4 H), 2.05-1.85 (m, 5 H), 1.70 (m, 2 H), 1.56-1.51 (m, 6 H) | 436.1 | F |

TABLE A-continued

| Cmpd No. | Structure | ¹H NMR | MS [MH]⁺ | Method |
|---|---|---|---|---|
| 140 | 5-(1-isopropyl-5-((1'R,2r,5'S,6'r)-1-(oxetan-3-yl)spiro[azetidine-2,3'-bicyclo[3.1.0]hexan]-6'-yl)-1H-pyrazol-3-yl)-3-(trifluoromethoxy)pyridin-2-amine | (400 MHz, CDCl₃), δ: 8.30 (s, 1 H), 7.81 (s, 1 H), 5.96 (s, 1 H), 4.78-4.68 (m, 2 H), 4.67-4.59 (m, 5 H), 4.05-4.00 (m, 1 H), 3.44-3.40 (m, 2 H), 2.27-2.19 (m, 4 H), 1.59 (m, 4 H), 1.54-1.52 (d, J = 8 Hz, 6 H), 1.39 (m, 1 H) | 464.2 | G |
| 141 | 5-(1-isopropyl-5-((1'R,5'S,6'r)-1-(2-methoxyethyl)spiro[azetidine-3,3'-bicyclo[3.1.0]hexan]-6'-yl)-1H-pyrazol-3-yl)-3-(trifluoromethyl)pyridin-2-amine | (400 MHz, CDCl₃), δ: 8.53 (s, 1 H), 8.11 (s, 1 H), 6.03 (s, 1 H), 5.08 (s, 2 H), 4.51-4.57 (m, 1 H), 3.82 (t, J = 4.4 Hz, 2 H), 3.37 (s, 3 H), 3.26 (t, J = 4.2 Hz, 2 H), 2.20-2.24 (m, 2 H), 1.71 (s, 2 H), 1.51 (d, J = 7.2 Hz, 6 H), 1.26-1.29 (m, 6 H), 0.98 (m, 1 H) | 450.0 | H |
| 142 | 6-(3-(6-amino-5-trifluoromethyl pyridin-3-yl)-1-isopropyl-1H-pyrazol-5-yl)bicyclo[3.1.0]hexan-2-ol (Exo-syn enantiomer 2) | (400 MHz, CDCl₃) δ: 8.55 (s, 1 H), 8.12 (s, 1 H), 6.07 (s, 1 H), 4.97 (s, 2H), 4.61-4.56 (m, 1 H), 4.47-4.46 (d, J = 4.4 Hz, 1 H), 2.20-2.11 (m, 1 H), 1.94-1.90 (m, 1 H), 1.80-1.74 (m, 4 H), 1.54-1.52 (m, 6 H), 1.43 (m, 1 H) | 367.0 | I |

TABLE A-continued

| Cmpd No. | Structure | ¹H NMR | MS [MH]⁺ | Method |
|---|---|---|---|---|
| 143 | 6-(3-(6-amino-5-trifluoromethyl pyridin-3-yl)-1-isopropyl-1H-pyrazol-5-yl)bicyclo[3.1.0]hexan-2-ol (Exo-syn enantiomer 1) | (400 MHz, CDCl$_3$) δ: 8.55 (s, 1 H), 8.12 (s, 1 H), 6.07 (s, 1 H), 4.97 (s, 2 H), 4.63-4.56 (m, 1 H), 4.47-4.46 (d, J = 4.8 Hz, 1 H), 2.20-2.11 (m, 1 H), 1.96-1.94 (m, 1 H), 1.80-1.74 (m, 4 H), 1.54-1.52 (m, 6H), 1.43 (m, 1 H) | 367.0 | I |
| 144 | 5-(1-(2,2-difluoroethyl)-5-((1R,3r,5S,6r)-3-(3-methoxyazetidin-1-yl)bicyclo[3.1.0]hexan-6-yl)-1H-pyrazol-3-yl)-3-(trifluoromethyl)pyridin-2-amine | (400 MHz, Methanol-d$_4$), δ: 8.51 (d, J = 2 Hz, 1 H), 8.11 (d, J = 2 Hz, 1 H), 6.37-6.09 (m, 2 H), 4.63-4.55 (m, 2 H), 4.00-3.90 (m, 1 H), 3.54-3.50 (m, 2 H), 3.25 (s, 3 H), 2.80-2.76 (m, 1 H), 2.76-2.70 (m, 2 H), 2.36-2.34 (m, 1 H), 2.10-1.90 (m, 2 H), 1.77-1.67 (m, 4 H) | 458.2 | E |
| 145 | 5-(1-(2,2-difluoroethyl)-5-((1R,3r,5S,6S)-3-((S)-3-methoxy pyrrolidin-1-yl)bicyclo[3.1.0]hexan-6-yl)-1H-pyrazol-3-yl)-3-(trifluoromethyl)pyridin-2-amine | (400 MHz, Methanol-d$_4$), δ: 8.51 (m, 1 H), 8.11 (s, 1 H), 6.38-6.08 (m, 2 H), 4.65-4.56 (m, 2 H), 4.00-3.80 (m, 1 H), 3.27 (s, 3 H), 3.00-2.90 (m, 1 H), 2.65-2.63 (m, 3 H), 2.50-2.00 (m, 5 H), 1.80-1.70 (m, 5 H) | 472.2 | E |

TABLE A-continued

| Cmpd No. | Structure | ¹H NMR | MS [MH]⁺ | Method |
|---|---|---|---|---|
| 146 | 5-(1-isopropyl-5-((1'R,2r,5'S,6'r)-1-(2-methoxyethyl)spiro[azetidine-2,3'-bicyclo[3.1.0]hexan]-6-yl)-1H-pyrazol-3-yl)-3-(trifluoromethoxy)pyridin-2-amine | (400 MHz, CDCl$_3$), δ: 8.31 (s, 1 H), 7.80 (s, 1 H), 5.96 (s, 1 H), 4.75 (s, 2 H), 4.61-4.68 (m, 1H), 3.40 (t, J = 5.6 Hz, 2 H), 3.34 (s, 3 H), 3.21 (t, J = 7.0 Hz, 2 H), 2.62 (t, J = 5.8 Hz, 2 H), 2.24 (m, 1 H), 2.16-2.21 (m, 3 H), 1.88 (m, 2 H), 1.57 (m, 2 H), 1.53 (d, J = 6.8 Hz, 6H), 1.40 (t, J = 3.0 Hz, 1 H) | 466.0 | X |
| 147 | 5-(5-((1'R,2r,5'S,6'r)-1-(2,2-difluoroethyl)spiro[azetidine-2,3'-bicyclo[3.1.0]hexan]-6'-yl)-1-isopropyl-1H-pyrazol-3-yl)-3-(trifluoromethoxy)pyridin-2-amine | (400 MHz, CDCl$_3$), δ: 8.31 (s, 1 H), 7.80 (s, 1 H), 5.96 (s, 1 H), 5.74 (tt, J$_{HF}$ = 56.2 Hz, J = 4.2 Hz, 1 H), 4.80 (s, 2 H), 4.61-4.62 (m, 1 H), 3.27 (t, J = 7.0 Hz, 2 H), 2.71-2.80 (m, 2 H), 2.18-2.26 (m, 4 H), 1.75 (d, J = 13.6 Hz, 2 H), 1.58 (s, 2 H), 1.53 (d, J = 6.8 Hz, 6 H), 1.38 (t, J = 3.0 Hz, 1 H) | 472.1 | X |
| 148 | 5-(5-((1'R,2r,5'S,6'r)-1-(2,2-difluoroethyl)spiro[azetidine-2,3'-bicyclo[3.1.0]hexan]-6-yl)-1-isopropyl-1H-pyrazol-3-yl)-3-(trifluoromethyl)pyridin-2-amine | (400 MHz, CDCl$_3$), δ: 8.52 (s, 1 H), 8.12 (s, 1 H), 5.98 (s, 1 H), 5.79 (tt, J$_{HF}$ = 55.8 Hz, J = 4.4 Hz, 1 H), 5.09 (s, 2 H), 4.61-4.67 (m, 1 H), 3.31 (t, J = 7.0 Hz, 2 H), 2.75-2.83 (m, 2 H), 2.21-2.29 (m, 4 H), 1.80 (d, J = 14.0 Hz, 2 H), 1.60 (m, 2 H), 1.54 (d, J = 6.8 Hz, 6 H), 1.40 (t, J = 3.2 Hz, 1H) | 456.1 | X |

TABLE A-continued

| Cmpd No. | Structure | ¹H NMR | MS [MH]⁺ | Method |
|---|---|---|---|---|
| 149 | 5-(1-(2,2-difluoroethyl)-5-((1R,3s,5S,6r)-3-(3-methoxyazetidin-1-yl)bicyclo[3.1.0]hexan-6-yl)-1H-pyrazol-3-yl)-3-(trifluoromethyl)pyridin-2-amine | (400 MHz, Methanol-$d_4$), δ: 8.15 (d, J = 2 Hz, 1 H), 8.11 (d, J = 2 Hz, 1 H), 6.37-6.08 (m, 2 H), 4.64-4.56 (m, 2 H), 4.02-3.80 (m, 1 H), 3.56-3.54(m, 2 H), 3.25 (s, 3 H), 3.03-3.01 (m, 2 H), 2.80-2.70 (m, 1 H), 2.19-2.13 (m, 2 H), 1.75-1.65 (m, 5 H) | 458.2 | E |
| 150 | 5-(1-(2,2-difluoroethyl)-5-((1R,3s,5S,6S)-3-((S)-3-methoxy-pyrrolidin-1-yl)bicyclo[3.1.0]hexan-6-yl)-1H-pyrazol-3-yl)-3-(trifluoromethyl)pyridin-2-amine | (400 MHz, Methanol-$d_4$), δ: 8.51 (s, 1 H), 8.12 (d, J = 1.6 Hz, 1 H), 6.38-6.07 (m, 2 H), 4.63-4.56 (m, 2 H), 4.00-3.80 (m, 1 H), 3.28 (s, 3 H), 2.72-2.69 (m, 3 H), 2.50-2.40 (m, 2 H), 2.26-2.22 (m, 2 H), 2.10-2.00 (m, 1 H), 1.83-1.74 (m, 6 H) | 472.2 | E |
| 151 | 5-(1-isopropyl-5-((1'R,2r,5'S,6'r)-1-(oxetan-3-yl)spiro[azetidine-2,3'-bicyclo[3.1.0]hexan]-6'-yl)-1H-pyrazol-3-yl)-3-(trifluoromethyl)pyridin-2-amine | (400 MHz, CDCl₃), δ: 8.52 (s, 1 H), 8.09 (s, 1 H), 5.97 (s, 1 H), 5.03 (s, 2 H), 4.60-4.68 (m, 5 H), 3.96-4.03 (m, 1 H), 3.39 (t, J = 7.0 Hz, 2H), 2.17-2.26 (m, 4 H), 1.57-1.58 (m, 2 H), 1.49-1.57 (m, 8 H), 1.29 (m, 1 H) | 448.1 | G |

TABLE A-continued

| Cmpd No. | Structure | ¹H NMR | MS [MH]⁺ | Method |
|---|---|---|---|---|
| 152 | 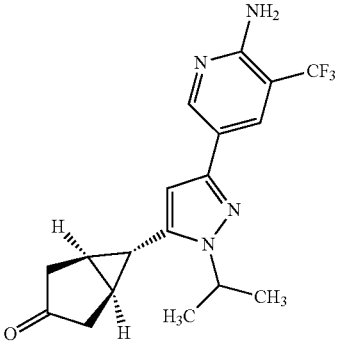 [SMILES: CC(C)n1nc(-c2cnc(N)c(C(F)(F)F)c2)cc1[C@H]1[C@@H]2CC(=O)C[C@@H]21]<br>(1R,5S,6r)-6-(3-(6-amino-5-(trifluoromethyl)pyridin-3-yl)-1-isopropyl-1H-pyrazol-5-yl)bicyclo[3.1.0]hexan-3-one | (400 MHz, CDCl₃), δ: 8.56 (d, J = 2.0 Hz, 1 H), 8.11 (d, J = 2.1 Hz, 1 H), 6.09 (s, 1 H), 5.02 (br s, 2 H), 4.58 (m, 1 H), 2.73-2.80 (m, 2 H), 2.38-2.43 (m, 2 H), 1.94 (m, 2 H), 1.81 (m, 1 H), 1.52 (d, J = 6.7 Hz, 6 H), 1.37 (t, J = 3.6 Hz, 1 H) | | A |
| 153 | 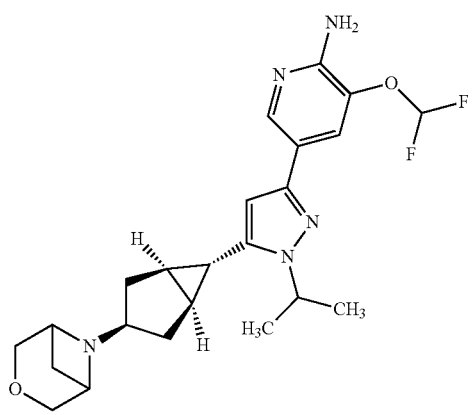 [SMILES: CC(C)n1nc(-c2cnc(N)c(OC(F)F)c2)cc1[C@H]1[C@@H]2C[C@H](N3C4COCC3C4)C[C@@H]21]<br>5-(5-((1R,3r,5S,6r)-3-(3-oxa-6-azabicyclo[3.1.1]heptan-6-yl)bicyclo[3.1.0]hexan-6-yl)-1-isopropyl-1H-pyrazol-3-yl)-3-(difluoromethoxy)pyridin-2-amine | (400 MHz, CDCl₃) δ: 8.25 (s, 1 H), 7.71 (s, 1 H), 6.55 (t, J = 73.6 Hz, 1 H), 5.96 (s, 1 H), 4.68-4.62 (m, 3 H), 4.18 (d, J = 10.4 Hz, 2 H), 3.75-3.68 (m, 3 H) 3.50-3.47 (d, J = 4.8 Hz, 2 H), 2.62-2.60 (m, 1 H), 2.50 (m, 1 H), 2.08-2.03 (m, 2 H), 1.79-1.76 (m, 3 H), 1.65 (m, 1 H), 1.54 (d, J = 6.8 Hz, 6 H) | 446.9 | A |
| 154 | 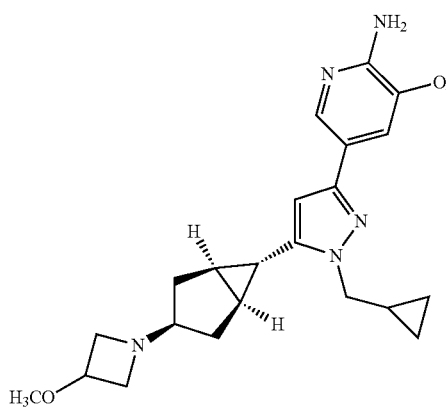<br>5-(1-(cyclopropylmethyl)-5-((1R,3r,5S,6r)-3-(3-methoxyazetidin-1-yl)bicyclo[3.1.0]hexan-6-yl)-1H-pyrazol-3-yl)-3-(difluoromethoxy)pyridin-2-amine | (400 MHz, Methanol-d₄), δ: 8.13 (d, J = 2 Hz, 1 H), 7.69 (s, 1 H), 6.86 (t, J$_{HF}$ = 73.2 Hz, 1 H), 6.06 (s, 1 H), 4.07-4.05 (m, 2 H), 3.97-3.96 (m, 1 H), 3.53-3.50 (m, 2 H), 3.25 (s, 3 H), 3.00-2.90 (m, 1 H), 2.79-2.75 (m, 2 H), 2.43-2.41 (m, 1 H), 2.10-2.00 (m, 2 H), 1.80-1.50 (m, 4 H), 1.35-1.25 (m, 1 H), 0.61-0.59 (m, 2 H), 0.50-0.46 (m, 2 H) | 446.2 | E |

TABLE A-continued

| Cmpd No. | Structure | ¹H NMR | MS [MH]⁺ | Method |
|---|---|---|---|---|
| 155 | 5-(1-(cyclopropylmethyl)-5-((1R,3s,5S,6r)-3-(3-methoxyazetidin-1-yl)bicyclo[3.1.0]hexan-6-yl)-1H-pyrazol-3-yl)-3-(difluoromethoxy)pyridin-2-amine | (400 MHz, Methanol-$d_4$), δ: 8.14 (s, 1 H), 7.69 (s, 1 H), 6.86 (t, $J_{HF}$ = 73.2 Hz, 1 H), 6.14 (s, 1 H), 4.08-4.02 (m, 3 H), 3.58-3.54 (m, 2 H), 3.25 (s, 3 H), 3.05-3.02 (m, 2 H), 2.76-2.60 (m, 1 H), 2.18-2.13 (m, 2 H), 1.73-1.64 (m, 4 H), 1.31-1.29 (m, 2 H), 0.62-0.57 (m, 2 H), 0.44-0.42 (m, 2 H) | 446.2 | E |
| 156 | (±)-5-(1-isopropyl-5-(4-methyl-octahydro-2H-cyclopropa[4,5]cyclopenta[1,2-b][1,4]oxazin-6-yl)-1H-pyrazol-3-yl)-3-(trifluoromethyl)pyridin-2-amine | (400 MHz, Methanol-$d_4$, 1.5:1 mixture of diastereomers) δ: 8.52 (d, J = 3.6 Hz, 1 H), 8.32 (s, 1 H), 8.13 (s, 1 H), 6.31 (s, 0.6 H), 6.22 (s, 0.4 H), 4.85-4.82 (m, 1 H), 4.06-4.02 (m, 1 H), 3.85-3.70 (m, 1.6 H), 3.50-3.45 (m, 0.4 H), 3.40-3.30 (m, 0.6 H), 3.20-3.17 (m, 0.4 H), 2.90-2.85 (m, 0.6 H), 2.79-2.65 (m, 3.4 H), 2.60 (s, 1 H), 2.37-2.36 (m, 1.6 H), 2.05-1.95 (m, 2H), 1.90-1.80 (m, 1 H), 1.55-1.52 (m, 6 H) | 422.0 | J |
| 157 | 5-(5-((1R,3s,5S,6r)-3-(3-oxa-6-azabicyclo[3.1.1]heptan-6-yl)bicyclo[3.1.0]hexan-6-yl)-1-isopropyl-1H-pyrazol-3-yl)-3-(difluoromethoxy)pyridin-2-amine | (400 MHz, CDCl₃) δ: 8.24 (s, 1 H), 7.71 (s, 1 H), 6.55 (t, $J_{HF}$ = 73.6 Hz, 1 H), 5.99 (s, 1 H), 4.71 (s, 2 H), 4.64-4.59 (m, 1 H), 4.24 (d, J = 10.8 Hz, 2 H), 3.74 (d, J = 10.8 Hz, 2 H) 3.50-3.48 (d, J = 6.0 Hz, 2 H), 3.29-3.24 (m, 1 H), 2.64 (m, 1 H), 2.17-2.12 (m, 2 H), 1.87-1.80 (m, 3 H), 1.72-1.60 (m, 3 H), 1.54 (d, J = 6.8 Hz, 6 H) | 446.9 | S |

TABLE A-continued

| Cmpd No. | Structure | ¹H NMR | MS [MH]⁺ | Method |
|---|---|---|---|---|
| 158 | 5-(1-(cyclopropylmethyl)-5-((1R,3r,5S,6S)-3-((S)-3-methoxy-pyrrolidin-1-yl)bicyclo[3.1.0]hexan-6-yl)-1H-pyrazol-3-yl)-3-(difluoromethoxy)pyridin-2-amine | (400 MHz, Methanol-$d_4$), δ: 8.13 (s, 1 H), 7.69 (s, 1 H), 6.86 (t, $J_{HF}$ = 73.2 Hz, 1 H), 6.07 (s, 1 H), 4.07 (d, J = 7.2 Hz, 2 H), 3.94-3.80 (m, 1 H), 3.28 (s, 3 H), 2.90-2.80 (m, 1 H), 2.71-2.62 (m, 3 H), 2.50-2.00 (m, 5 H), 1.81-1.60 (m, 5 H), 1.40-1.30 (m, 1 H), 0.60-0.56 (m, 2 H), 0.47-0.44 (m, 2 H) | 460.2 | E |
| 159 | 5-(1-(cyclopropylmethyl)-5-((1R,3s,5S,6S)-3-((S)-3-methoxy-pyrrolidin-1-yl)bicyclo[3.1.0]hexan-6-yl)-1H-pyrazol-3-yl)-3-(difluoromethoxy)pyridin-2-amine | (400 MHz, Methanol-$d_4$), δ: 8.14 (d, J = 1.6 Hz, 1 H), 7.69 (s, 1 H), 6.87 (t, $J_{HF}$ = 13.2 Hz, 1 H), 6.15 (s, 1 H), 4.06 (d, J = 6.8 Hz, 2 H), 3.94-3.93 (m, 1 H), 3.28 (s, 3 H), 2.72-2.69 (m, 3 H), 2.50-2.45 (m, 2 H), 2.24-2.20 (m, 2 H), 2.20-2.00 (m, 1 H), 1.76-1.72 (m, 6 H), 1.40-1.30 (m, 1 H), 0.60-0.57 (m, 2 H), 0.45-0.41 (m, 2 H) | 460.2 | E |
| 160 | 5-(1-(2,2-difluoroethyl)-5-((1R,3s,5S,6r)-3-morpholinobicyclo[3.1.0]hexan-6-yl)-1H-pyrazol-3-yl)-3-(difluoromethoxy)pyridin-2-amine | (400 MHz, CDCl₃,), δ: 8.22 (d, J = 1.6 Hz, 1 H), 7.66 (s, 1 H), 6.54 (t, $J_{HF}$ = 73.2 Hz, 1 H), 6.17 (m, 1 H), 5.99 (s, 1 H), 4.78 (s, 2 H), 4.51-4.45 (m, 2 H), 3.70 (t, J = 4.4 Hz, 4 H), 2.92-2.81 (m, 1 H), 2.43 (m, 4 H), 2.27-2.18 (m, 2 H), 1.92 (t, J = 3.2 Hz, 1 H), 1.76-1.71 (m, 2 H), 1.65 (s, 2 H) | 456.3 | W |

TABLE A-continued

| Cmpd No. | Structure | ¹H NMR | MS [MH]⁺ | Method |
|---|---|---|---|---|
| 161 | 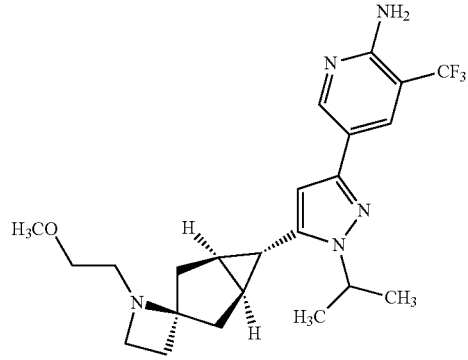 [SMILES: COCCN1CC[C@@]12C[C@@H]1[C@H](C2)[C@H]1c1cc(-c2cnc(N)c(C(F)(F)F)c2)nn1C(C)C]<br>5-(1-isopropyl-5-((1'R,2r,5'S,6'r)-1-(2-methoxyethyl)spiro[azetidine-2,3'-bicyclo[3.1.0]hexan]-6'-yl)-1H-pyrazol-3-yl)-3-(trifluoromethyl)pyridin-2-amine | (400 MHz, Methanol-$d_4$), δ: 8.49 (s, 1 H), 8.44 (s, 1 H), 8.10 (s, 1 H), 6.21 (s, 1 H), 4.75-4.80 (m, 1 H), 4.01 (t, J = 8.0 Hz, 2 H), 3.62 (t, J = 4.8 Hz, 2 H), 3.40 (s, 3 H), 3.34 (t, J = 4.8 Hz, 2 H), 2.60 (t, J = 8.0 Hz, 2 H), 2.46-2.55 (m, 4 H), 1.84 (m, 2 H), 1.66 (t, J = 3.0 Hz, 1 H), 1.52 (d, J = 6.8 Hz, 6 H) | 450.2 | X |
| 162 | 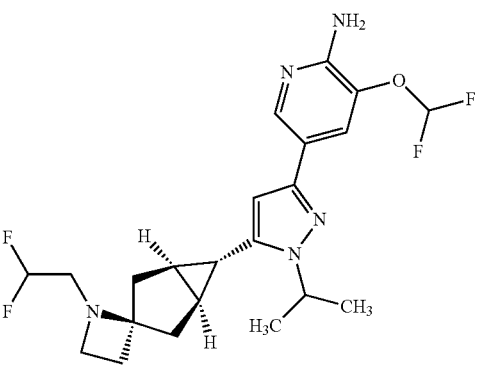 [SMILES: CC(C)n1nc(-c2cnc(N)c(OC(F)F)c2)cc1[C@H]1[C@@H]2C[C@@]3(CCN3CC(F)F)C[C@@H]21]<br>5-(5-((1'R,2r,5'S,6'r)-1-(2,2-difluoroethyl)spiro[azetidine-2,3'-bicyclo[3.1.0]hexan]-6'-yl)-1-isopropyl-1H-pyrazol-3-yl)-3-(difluoromethoxy)pyridin-2-amine | (400 MHz, CDCl₃), δ: 8.23 (d, J = 1.6 Hz, 1 H), 7.71 (s, 1 H), 6.55 (t, $J_{HF}$ = 73.6 Hz, 1 H), 5.97 (s, 1 H), 5.76 (t, J = 69.4 Hz, 1 H), 4.75 (s, 2 H), 4.65-4.61 (m, 1 H), 3.28 (t, J = 6.8 Hz, 2 H), 2.81-2.73 (m, 2 H), 2.26-2.18 (m, 4 H), 1.78-1.26 (m, 11 H) | 454.1 | X |
| 163 | 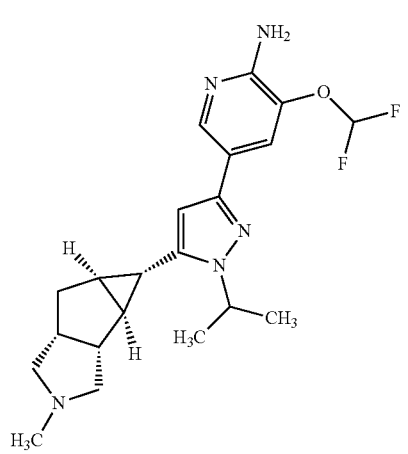 [SMILES: CC(C)n1nc(-c2cnc(N)c(OC(F)F)c2)cc1[C@H]1[C@@H]2C[C@H]3CN(C)C[C@H]3[C@@H]21]<br>(±)-3-(difluoromethoxy)-5-(1-isopropyl-5-((3aS,3bR,4S,4aR,5aR)-2-methyloctahydro-1H-cyclopropa[3,4]cyclopenta[1,2-c]pyrrol-4-yl)-1H-pyrazol-3-yl)pyridin-2-amine | (400 MHz, Methanol-$d_4$) δ: 8.39 (s, 1 H), 8.11 (s, 1 H), 7.69 (s, 1 H), 6.85 (t, J = 73.6 Hz, 1 H), 6.14 (s, 1 H), 4.75-4.70 (m, 1 H), 3.50-3.74 (m, 2 H), 3.32-3.29 (m, 2 H), 3.18-3.16 (m, 1 H), 2.92 (s, 3 H), 2.90-2.80 (m, 1 H), 2.38-2.25 (m, 1 H), 1.86-1.75 (m, 3 H), 1.63 (t, J = 6.4 Hz, 1 H), 1.53 (m, 6H) | 404.0 | K |

TABLE A-continued

| Cmpd No. | Structure | ¹H NMR | MS [MH]⁺ | Method |
|---|---|---|---|---|
| 164 | 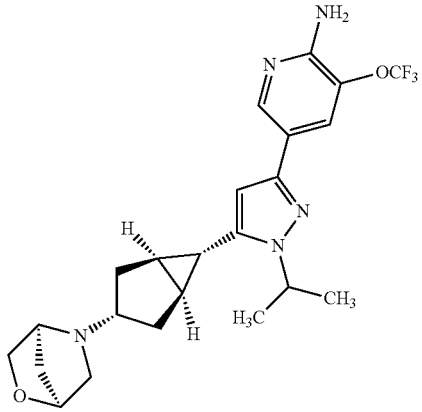 [SMILES: CC(C)n1nc(-c2cnc(N)c(OC(F)(F)F)c2)cc1[C@H]1[C@@H]2C[C@@H](N3C[C@@H]4C[C@H]3CO4)C[C@@H]21]<br>5-(5-((1R,3s,5S,6S)-3-((1S,4S)-2-oxa-5-azabicyclo[2.2.1]heptan-5-yl)bicyclo[3.1.0]hexan-6-yl)-1-isopropyl-1H-pyrazol-3-yl)-3-(trifluoromethoxy)pyridin-2-amine | (400 MHz, CDCl₃) d: 8.32 (d, J = 1.6 Hz, 1 H), 7.80 (s, 1 H), 5.98 (s, 1 H), 4.71 (s, 2H), 4.61 (m, J = 6.8 Hz, 1 H), 4.40 (s, 1 H), 4.07 (d, J = 8.0 Hz, 1 H), 3.62 (d, J = 6.8 Hz, 1 H), 3.50 (s, 1 H), 3.00 (d, J = 10.0 Hz, 1 H), 2.81 (m, J = 7.6 Hz, 1 H), 2.46 (d, J = 10.4 Hz, 1 H), 2.22 (dd, J = 12.4 Hz, 6.8 Hz, 1 H), 2.11 (dd, J = 12.4 Hz, 7.2 Hz, 1 H), 1.90-1.80 (m, 3 H), 1.75 (d, J = 10 Hz, 2 H), 1.70-1.67 (m, 1 H), 1.59 (t, J = 3.2 Hz, 1 H), 1.52 (d, J = 6.8 Hz, 6 H) | 464.0 | A |
| 165 | 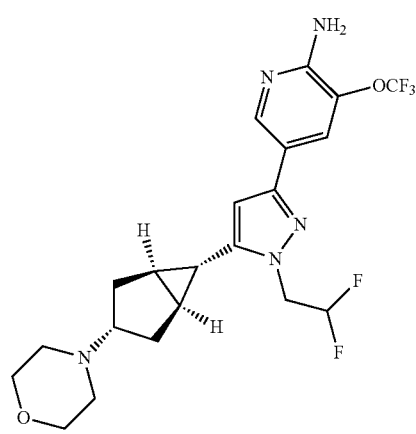 [SMILES: Nc1ncc(-c2cc([C@H]3[C@@H]4C[C@@H](N5CCOCC5)C[C@@H]43)n(CC(F)F)n2)cc1OC(F)(F)F]<br>5-(1-(2,2-difluoroethyl)-5-((1R,3s,5S,6r)-3-morpholinobicyclo[3.1.0]hexan-6-yl)-1H-pyrazol-3-yl)-3-(trifluoromethoxy)pyridin-2-amine | (400 MHz, CDCl₃) δ: 8.30 (s, 1 H), 7.77 (s, 1 H), 6.30-6.05 (m, 2 H), 4.77 (s, 2 H), 4.51-4.37 (m, 2 H), 3.74 (m, 4 H), 2.45 (m, 4 H), 2.35-2.21 (m, 3 H), 1.85-1.81 (m, 2 H), 1.71 (m, 2 H), 1.57 (d, J = 2.8 Hz, 1 H) | 474.2 | W |
| 166 | 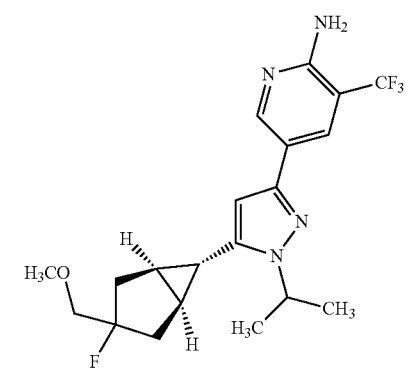<br>5-(5-((1R,5S,6r)-3-fluoro-3-(methoxymethyl)bicyclo[3.1.0]hexan-6-yl)-1-isopropyl-1H-pyrazol-3-yl)-3-(trifluoromethyl)pyridin-2-amine | (400 MHz, CDCl₃), δ: 8.56 (s, 1 H), 8.38 (s, 1 H), 7.51 (br s, 2 H), 6.07 (s, 1 H), 4.59 (t, J = 6.4 Hz, 1 H), 3.47-3.41 (m, 2 H), 3.39 (s, 3 H), 2.49-2.34 (m, 2 H), 2.08-1.94 (m, 2 H), 1.83 (m, 2 H), 1.48 (d, J = 6.8 Hz, 6 H), 1.39 (m, 1 H). | 413.1 | L |

TABLE A-continued

| Cmpd No. | Structure | ¹H NMR | MS [MH]⁺ | Method |
|---|---|---|---|---|
| 167 | 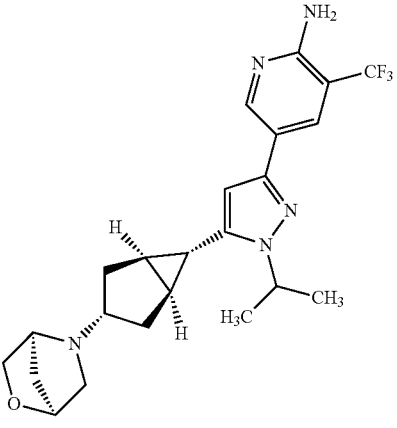 [SMILES: CC(C)n1nc(-c2cnc(N)c(C(F)(F)F)c2)cc1[C@H]1[C@@H]2C[C@@H](N3C[C@@H]4C[C@H]3CO4)C[C@@H]21]<br>5-(5-((1R,3s,5S,6S)-3-((1S,4S)-2-oxa-5-azabicyclo[2.2.1]heptan-5-yl)bicyclo[3.1.0]hexan-6-yl)-1-isopropyl-1H-pyrazol-3-yl)-3-(trifluoromethyl)pyridin-2-amine | (400 MHz, DMSO-$d_6$), δ: 8.53 (s, 1 H), 7.97 (s, 1 H), 6.48 (s, 2 H), 6.29 (s, 1 H), 4.67-4.74 (m, 1 H), 4.29 (s, 1 H), 3.91 (d, J = 1.2 Hz, 1 H), 3.46 (d, J = 6.8 Hz, 2 H), 2.79-2.84 (m, 2 H), 2.31 (d, J = 10 Hz, 1 H), 2.11-2.16 (m, 1 H), 2.01-2.06 (m, 1 H), 1.84 (m, 1 H), 1.53-1.70 (m, 6 H), 1.40 (d, J = 6.4 Hz, 6 H). | 448.2 | A |
| 168 | 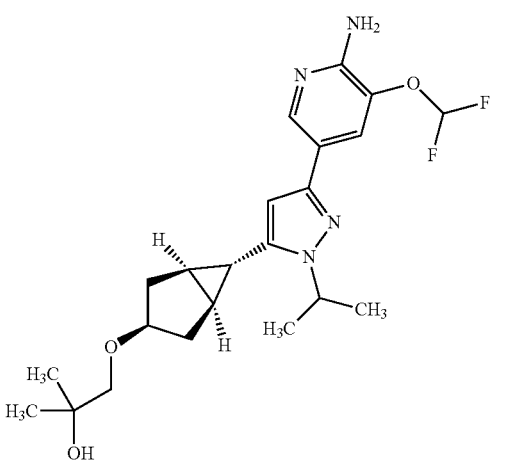 [SMILES: CC(C)n1nc(-c2cnc(N)c(OC(F)F)c2)cc1[C@H]1[C@@H]2C[C@H](OCC(C)(C)O)C[C@@H]21]<br>1-(((1R,3r,5S,6r)-6-(3-(6-amino-5-(difluoromethoxy)pyridin-3-yl)-1-isopropyl-1H-pyrazol-5-yl)bicyclo[3.1.0]hexan-3-yl)oxy)-2-methylpropan-2-ol | (400 MHz, CD$_3$OD), δ: 8.19 (s, 1 H), 8.06 (d, J = 1.2 Hz, 1 H), 7.13 (t, $J_{HF}$ = 72.0 Hz, 1 H), 6.29 (s, 1 H), 4.82-4.72 (m, 1 H), 4.02 (t, J = 5.6 Hz, 1 H), 3.21 (s, 2 H), 2.20-2.06 (m, 5 H), 1.69 (m, 2 H), 1.50 (d, J = 6.8 Hz, 6 H), 1.20 (s, 6 H). | 437.2 | M |

TABLE A-continued

| Cmpd No. | Structure | ¹H NMR | MS [MH]⁺ | Method |
|---|---|---|---|---|
| 169 | 3-(difluoromethoxy)-5-(5-((1R,5S,6r)-3-(6-fluoro-1,4-oxazepan-4-yl)bicyclo[3.1.0]hexan-6-yl)-1-isopropyl-1H-pyrazol-3-yl)pyridin-2-amine (Stereoisomer 1) | (400 MHz, CDCl₃) δ: 8.24 (s, 1 H), 7.72 (s, 1 H), 6.56 (t, $J_{HF}$ = 13.2 Hz, 1 H), 6.00 (s, 1 H), 4.81-4.69 (m, 3 H), 4.62-4.59 (m, 1 H), 4.02-3.86 (m, 3 H), 3.70-3.67 (m, 1 H), 3.00-2.96 (m, 3 H), 2.80-2.76 (m, 2 H), 2.25-2.18 (m, 2 H), 1.87 (m, 2 H), 1.73 (m, 3 H), 1.52 (d, J = 6.4 Hz, 6 H) | 466.0 | A |
| 170 | 3-(difluoromethoxy)-5-(1-isopropyl-5-((1R,5S,6r)-spiro[bicyclo[3.1.0]hexane-3,3'-oxetan]-6-yl)-1H-pyrazol-3-yl)pyridin-2-amine | (400 MHz, DMSO-d₆) δ: 8.13 (s, 1 H), 7.66 (s, 1 H), 7.38-7.01 (m, 1 H), 6.57 (br s, 1 H), 6.29 (s, 2 H), 4.62-4.56 (m, 1 H), 4.49 (s, 2 H), 4.39 (s, 2 H), 2.76 (m, 1H), 2.44-2.37 (m, 2 H), 2.05-2.02 (m, 2 H), 1.60 (m, 2 H), 1.40-1.39 (m, 6 H). | 391.0 | N |
| 171 | 3-(difluoromethoxy)-5-(5-((1R,5S,6r)-3-(3-fluoro-3-(methoxymethyl)pyrrolidin-1-yl)bicyclo[3.1.0]hexan-6-yl)-1-isopropyl-1H-pyrazol-3-yl)pyridin-2-amine (Stereoisomer 1) | (400 MHz, Methanol-d₄) δ : 8.13 (s, 1 H), 7.70 (s, 1 H), 6.87 (t, J = 73.2 Hz, 1 H), 6.13 (s, 1 H), 4.75-4.72 (m, 1 H), 3.58-3.51 (m, 2 H), 3.41 (s, 3 H), 2.92-2.76 (m, 2 H), 2.75-2.66 (m, 1 H), 2.56-2.52 (m, 2 H), 2.26-2.23 (m, 2 H), 2.16-2.08 (m, 2 H), 1.87-1.85 (m, 2 H), 1.74-1.72 (m, 3 H), 1.50 (d, J = 6.8 Hz, 6 H). | 480.2 | A |

TABLE A-continued

| Cmpd No. | Structure | ¹H NMR | MS [MH]⁺ | Method |
|---|---|---|---|---|
| 172 | 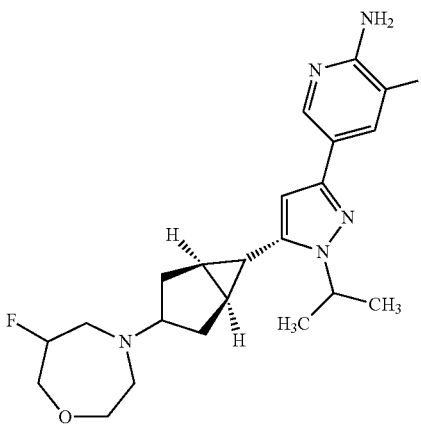<br>3-(difluoromethoxy)-5-(5-((1R,5S,6r)-3-(6-fluoro-1,4-oxazepan-4-yl)bicyclo[3.1.0]hexan-6-yl)-1-isopropyl-1H-pyrazol-3-yl)pyridin-2-amine (Stereoisomer 1) | (400 MHz, CDCl₃) δ: 8.24 (s, 1 H), 7.70 (s, 1 H), 6.55 (t, $J_{HF}$ = 74.0 Hz, 1 H), 5.96 (s, 1 H), 4.81-4.64 (m, 4 H), 3.95 (m, 2 H), 3.85-3.81 (m, 1 H), 3.67-3.63 (m, 1 H), 3.41-3.89 (m, 1 H), 2.95 (m, 2 H), 2.90-2.62 (m, 2 H), 2.30-2.28 (m, 2 H), 1.75 (d, J = 3.2 Hz, 1 H), 1.64-1.62 (m, 4 H), 1.53 (d, J = 6.8 Hz, 6 H) | 465.9 | A |
| 173 | 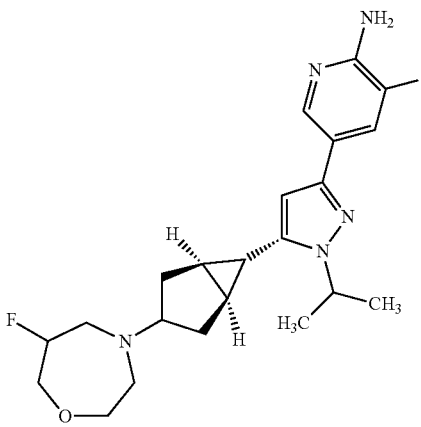<br>3-(difluoromethoxy)-5-(5-((1R,5S,6r)-3-(6-fluoro-1,4-oxazepan-4-yl)bicyclo[3.1.0]hexan-6-yl)-1-isopropyl-1H-pyrazol-3-yl)pyridin-2-amine (Stereoisomer 2) | (400 MHz, CDCl₃) δ: 8.22 (s, 1 H), 7.70 (s, 1 H), 6.54 (t, J = 73.6 Hz, 1 H), 5.94 (s, 1 H), 4.74-4.63 (m, 4 H), 3.95 (m, 2 H), 3.82-3.81 (m, 1 H), 3.70-3.65 (m, 1 H), 3.45-3.40 (m, 1 H), 2.97 (m, 2 H), 2.80-2.66 (m, 2 H), 2.32-2.27 (m, 2 H), 1.78 (m, 1 H), 1.63 (m, 4H), 1.52 (d, J = 6.8 Hz, 6 H) | 465.9 | A |

TABLE A-continued

| Cmpd No. | Structure | ¹H NMR | MS [MH]⁺ | Method |
|---|---|---|---|---|
| 174 | 3-(difluoromethoxy)-5-(5-((1R,5S,6r)-3-(3-fluoro-3-(methoxymethyl)pyrrolidin-1-yl)bicyclo[3.1.0]hexan-6-yl)-1-isopropyl-1H-pyrazol-3-yl)pyridin-2-amine (Stereoisomer 2) | (400 MHz, Methanol-$d_4$) δ: 8.13 (s, 1 H), 7.70 (s, 1 H), 6.87 (t, J = 73.2 Hz, 1 H), 6.13 (s, 1 H), 4.75-4.72 (m, 1 H), 3.58-3.51 (m, 2 H), 3.41 (s, 3 H), 2.92-2.76 (m, 2 H), 2.75-2.66 (m, 1 H), 2.56-2.52 (m, 2 H), 2.26-2.23 (m, 2 H), 2.16-2.08 (m, 2 H), 1.87-1.85 (m, 2 H), 1.74-1.72 (m, 3 H), 1.50 (d, J = 6.8 Hz, 6 H). | 480.2 | A |
| 175 | 3-(difluoromethoxy)-5-(5-((1R,5S,6r)-3-(6-fluoro-1,4-oxazepan-4-yl)bicyclo[3.1.0]hexan-6-yl)-1-isopropyl-1H-pyrazol-3-yl)pyridin-2-amine (Stereoisomer 3) | (400 MHz, CDCl$_3$) δ: 8.24 (s, 1 H), 7.70 (s, 1 H), 6.55 (t, J$_{HF}$ = 73.4 Hz, 1 H), 6.00 (s, 1 H), 4.81-4.69 (m, 3 H), 4.62-4.59 (m, 1 H), 4.02-3.86 (m, 3 H), 3.70-3.67 (m, 1 H), 3.00-2.96 (m, 3 H), 2.80-2.76 (m, 2 H), 2.25-2.18 (m, 2 H), 1.87 (m, 2 H), 1.73 (m, 3 H), 1.52 (d, J = 6.4 Hz, 6 H) | 465.9 | A |

TABLE A-continued

| Cmpd No. | Structure | ¹H NMR | MS [MH]⁺ | Method |
|---|---|---|---|---|
| 176 | 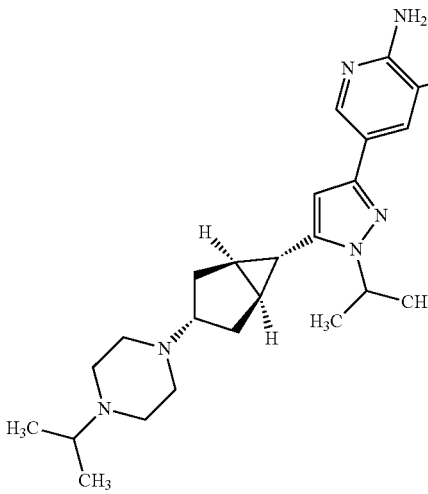<br>3-(difluoromethoxy)-5-(1-isopropyl-5-((1R,3s,5S,6r)-3-(4-isopropyl-piperazin-1-yl)bicyclo[3.1.0]hexan-6-yl)-1H-pyrazol-3-yl)pyridin-2-amine | (400 MHz, DMSO-$d_6$) δ: 8.15 (d, J = 1.9 Hz, 1H), 7.57 (d, J = 1.8 Hz, 1H), 7.15 (t, J = 73.9 Hz, 1H), 6.21 (s, 1H), 6.08 (s, 2H), 4.74-4.61 (m, 1H), 2.46-2.28 (m, 10H), 2.15-2.06 (m, 2H), 1.74-1.57 (m, 5H), 1.40 (d, J = 6.5 Hz, 6H), 0.95 (d, J = 6.5 Hz, 6H) | 475.3 | D |
| 177 | 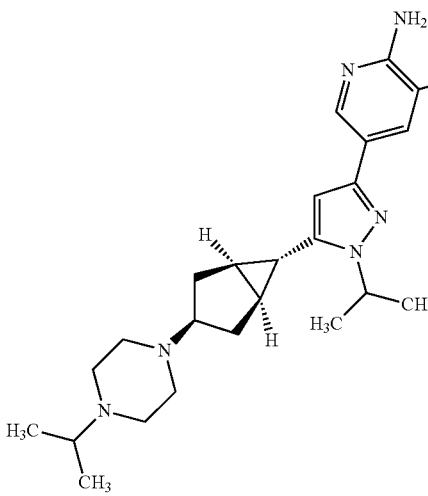<br>3-(difluoromethoxy)-5-(1-isopropyl-5-((1R,3r,5S,6r)-3-(4-isopropyl-piperazin-1-yl)bicyclo[3.1.0]hexan-6-yl)-1H-pyrazol-3-yl)pyridin-2-amine | (400 MHz, DMSO-$d_6$) δ: 8.15 (d, J = 1.9 Hz, 1H), 7.60-7.54 (m, 1H), 7.15 (t, J = 73.9 Hz, 1H), 6.17 (s, 1H), 6.08 (s, 2H), 4.72-4.60 (m, 1H), 2.81-2.69 (m, 1H), 2.60-2.51 (m, 1H), 2.42-2.37 (m, 6H), 2.36-2.31 (m, 2H), 2.15-2.03 (m, 2H), 1.99-1.92 (m, 1H), 1.74-1.64 (m, 2H), 1.62-1.55 (m, 2H), 1.43 (d, J = 6.6 Hz, 6H), 0.94 (d, J = 6.5 Hz, 6H) | 475.3 | D |

TABLE A-continued

| Cmpd No. | Structure | ¹H NMR | MS [MH]⁺ | Method |
|---|---|---|---|---|
| 178 | 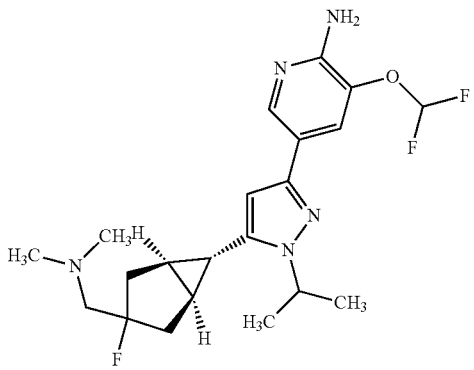<br>3-(difluoromethoxy)-5-(5-((1R,5S,6r)-3-((dimethylamino)methyl)-3-fluorobicyclo[3.1.0]hexan-6-yl)-1-isopropyl-1H-pyrazol-3-yl)pyridin-2-amine (Mixture of diastereomers) | (400 MHz, CDCl₃), δ: 8.24 (s, 1 H), 7.71 (s, 1 H), 6.56 (t, $J_{HF}$ = 13.6 Hz, 1 H), 6.00 (s, 1 H), 4.78-4.63 (m, 3 H), 2.73-2.71 (m, 2 H), 2.58-2.52 (m, 7 H), 2.10-2.02 (m, 3 H), 1.90 (s, 2 H), 1.52 (d, J = 6.8 Hz, 6 H), 1.26 (m, 1 H). | 423.9 | O |
| 179 | 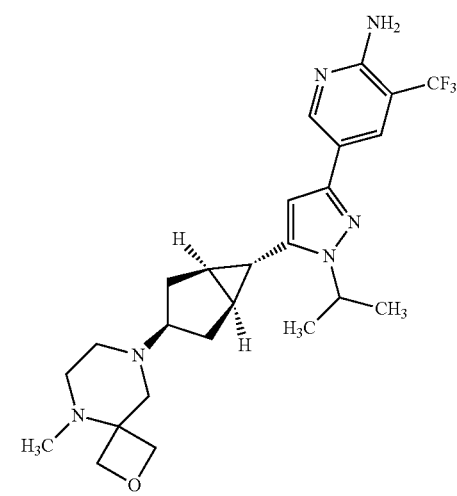 [SMILES: CC(C)n1nc(-c2cnc(N)c(C(F)(F)F)c2)cc1[C@H]1[C@@H]2C[C@H](N3CCN(C)C4(COC4)C3)C[C@@H]21]<br>5-(1-isopropyl-5-((1R,3r,5S,6r)-3-(5-methyl-2-oxa-5,8-diazaspiro[3.5]nonan-8-yl)bicyclo[3.1.0]hexan-6-yl)-1H-pyrazol-3-yl)-3-(trifluoromethyl)pyridin-2-amine | (400 MHz, DMSO-d₆) δ: 8.56-8.51 (m, 1H), 7.97 (d, J = 2.2 Hz, 1H), 6.46 (s, 2H), 6.28 (s, 1H), 4.72-4.58 (m, 3H), 4.12 (d, J = 6.6 Hz, 2H), 2.85-2.73 (m, 1H), 2.57-2.52 (m, 1H), 2.43-2.33 (m, 8H), 2.17-2.05 (m, 2H), 1.98-1.91 (m, 1H), 1.84-1.74 (m, 2H), 1.65-1.58 (m, 2H), 1.42 (d, J = 6.6 Hz, 6H) | 491.3 | D |

TABLE A-continued

| Cmpd No. | Structure | ¹H NMR | MS [MH]⁺ | Method |
|---|---|---|---|---|
| 180 | 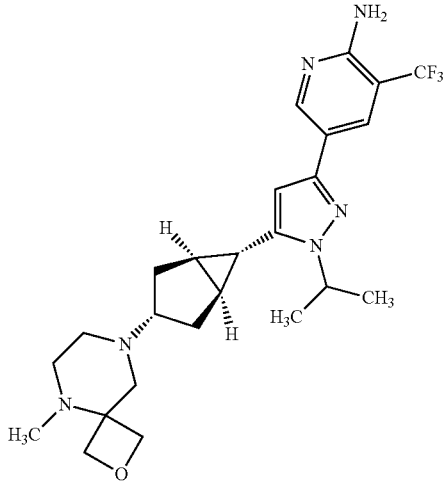 [SMILES: CC(C)n1nc(-c2cnc(N)c(C(F)(F)F)c2)cc1[C@H]1[C@@H]2C[C@@H](N3CCN(C)C4(COC4)C3)C[C@@H]21]<br>5-(1-isopropyl-5-((1R,3s,5S,6r)-3-(5-methyl-2-oxa-5,8-diazaspiro[3.5]nonan-8-yl)bicyclo[3.1.0]hexan-6-yl)-1H-pyrazol-3-yl)-3-(trifluoromethyl)pyridin-2-amine | (400 MHz, DMSO-$d_6$) δ: 8.54 (dd, J = 2.3, 0.9 Hz, 1H), 7.98 (d, J = 2.1 Hz, 1H), 6.46 (s, 2H), 6.31 (s, 1H), 4.75-4.62 (m, 3H), 4.11 (d, J = 6.7 Hz, 2H), 2.62-2.52 (m, 2H), 2.46-2.34 (m, 8H), 2.20-2.11 (m, 2H), 1.79-1.59 (m, 5H), 1.41 (d, J = 6.5 Hz, 6H) | 491.3 | D |
| 181 | 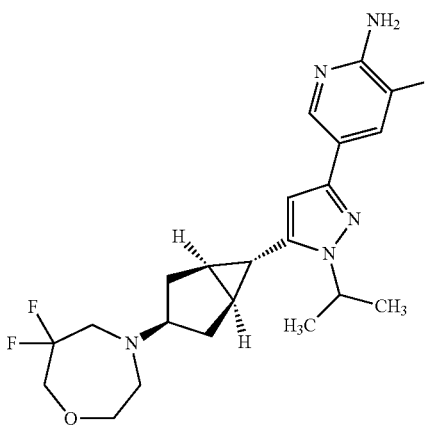<br>5-(5-((1R,3r,5S,6r)-3-(6,6-difluoro-1,4-oxazepan-4-yl)bicyclo[3.1.0]hexan-6-yl)-1-isopropyl-1H-pyrazol-3-yl)-3-(difluoromethoxy)pyridin-2-amine | (400 MHz, CDCl₃) δ: 8.24 (s, 1 H), 7.70 (s, 1 H), 6.55 (t, $J_{HF}$ = 73.6 Hz, 1 H), 5.99 (s, 1 H), 4.69-4.63 (m, 3 H), 3.93 (t, J = 13.2 Hz, 2 H), 3.81 (t, J = 4.8 Hz, 2 H), 3.45-3.42 (m, 1 H), 3.06 (t, J = 14.4 Hz, 2 H), 2.79 (t, J = 4.2 Hz, 2 H), 2.30-2.28 (m, 2 H), 1.77 (d, J = 3.2 Hz, 1 H), 1.67 (m, 2H), 1.62 (m, 2 H) 1.53 (d, J = 6.8 Hz, 6 H) | 484.2 | A |

TABLE A-continued

| Cmpd No. | Structure | ¹H NMR | MS [MH]⁺ | Method |
|---|---|---|---|---|
| 182 | 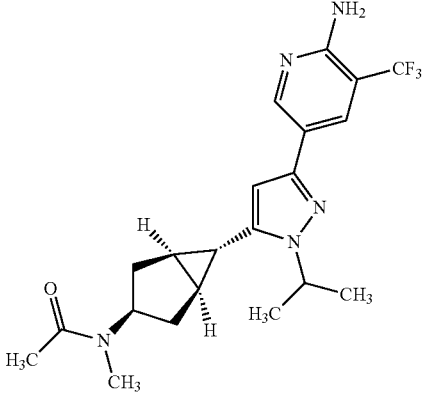 [SMILES: CC(=O)N(C)[C@H]1C[C@@H]2[C@H](C1)[C@H]2c1cc(-c2cnc(N)c(C(F)(F)F)c2)nn1C(C)C]<br>N-((1R,5S,6r)-6-(3-(6-amino-5-(trifluoromethyl)pyridin-3-yl)-1-isopropyl-1H-pyrazol-5-yl)bicyclo[3.1.0]hexan-3-yl)-N-methylacetamide | (400 MHz, Methanol-$d_4$) δ: 8.50 (s, 1 H), 8.10 (s, 1 H), 6.17 (s, 1 H), 4.84-4.81 (m, 2 H), 2.92-2.78 (m, 3 H), 2.38-2.31 (m, 2 H), 2.18-2.08 (m, 3 H), 1.81-1.68 (m, 5 H), 1.54 (d, J = 6.4 Hz, 6 H). | 422.2 | P |
| 183 | 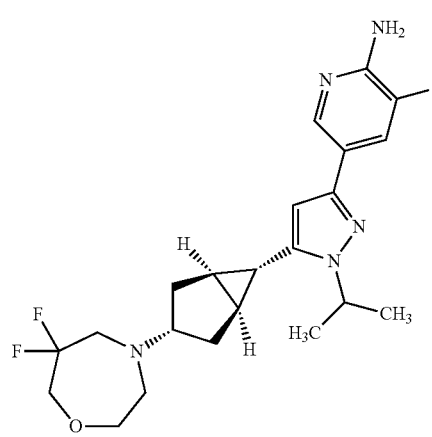<br>5-(5-((1R,3s,5S,6r)-3-(6,6-difluoro-1,4-oxazepan-4-yl)bicyclo[3.1.0]hexan-6-yl)-1-isopropyl-1H-pyrazol-3-yl)-3-(difluoromethoxy)pyridin-2-amine | (400 MHz, CDCl₃) δ: 8.24 (s, 1 H), 7.70 (s, 1 H), 6.55 (t, $J_{HF}$ = 73.6 Hz, 1 H), 5.99 (s, 1 H), 4.69 (s, 2H), 4.60-4.51 (m, 1 H), 3.94 (t, J = 10.6 Hz, 2 H), 3.81 (t, J = 4.8 Hz, 2 H), 3.08-2.97 (m, 3 H), 2.80 (t, J = 4.2 Hz, 2 H), 2.19 (m, 2 H), 1.83-1.75 (m, 2 H), 1.67 (m, 2 H), 1.57-1.51 (m, 7 H) | 484.2 | A |

TABLE A-continued

| Cmpd No. | Structure | $^1$H NMR | MS [MH]$^+$ | Method |
|---|---|---|---|---|
| 184 | 5-(5-((1R,5S,6r)-3-(hexahydropyrazino[2,1-c][1,4]oxazin-8(1H)-yl)bicyclo[3.1.0]hexan-6-yl)-1-isopropyl-1H-pyrazol-3-yl)-3-(trifluoromethyl)pyridin-2-amine (Stereoisomers 1 and 2) | (400 MHz, CDCl$_3$), δ: 8.53 (s, 1 H), 8.10 (s, 1 H), 5.95 (s, 1 H), 4.93 (br s, 2 H), 4.67-4.59 (m, 1 H), 3.85 (d, J = 11.2 Hz, 1 H), 3.73-3.65 (m, 2 H), 3.24 (t, J = 10.4 Hz, 1 H), 2.96-2.86 (m, 2 H), 2.75 (d, J = 11.2 Hz, 1 H), 2.67 (t, J = 11.2 Hz, 2 H), 2.41-2.24 (m, 5 H), 2.21-2.12 (m, 1 H), 1.77-1.73 (m, 1 H), 1.68 (t, J = 10.8 Hz, 2 H), 1.64-1.62 (m, 3H), 1.53 (d, J = 6.8 Hz, 6H). | 491.3 | A |
| 185 | 5-(1-isopropyl-5-((1R,3r,5S,6R)-3-((R)-3-methoxypyrrolidin-1-yl)bicyclo[3.1.0]hexan-6-yl)-1H-pyrazol-3-yl)-3-(trifluoromethyl)pyridin-2-amine | (400 MHz, CDCl$_3$), δ: 8.53 (s, 1 H), 8.10 (s, 1 H), 5.95 (s, 1 H), 4.95 (br s, 2 H), 4.68-4.58 (m, 1 H), 3.88 (t, J = 6.6 Hz, 1 H), 3.28 (s, 3 H), 2.90-2.80 (m, 1 H), 2.70-2.61 (m, 2 H), 2.55 (dd, J = 10.3, 2.9 Hz, 1 H), 2.46-2.38 (m, 1 H), 2.24-2.15 (m, 2 H), 2.06-1.97 (m, 2 H), 1.83-1.76 (m, 3 H), 1.61 (d, J = 2.0 Hz, 2 H), 1.52 (d, J = 6.6 Hz, 6 H). | 450.2 | A |

TABLE A-continued

| Cmpd No. | Structure | ¹H NMR | MS [MH]⁺ | Method |
|---|---|---|---|---|
| 186 | 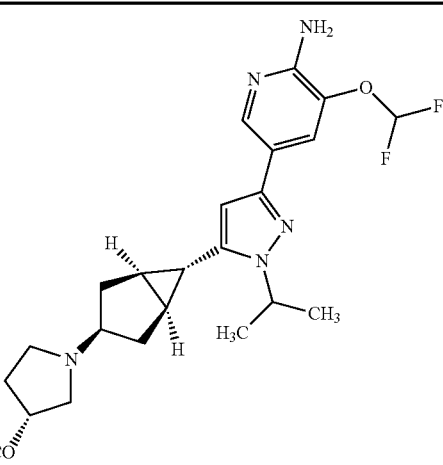<br>3-(difluoromethoxy)-5-(1-isopropyl-5-((1R,3r,5S,6R)-3-((R)-3-methoxypyrrolidin-1-yl)bicyclo[3.1.0]hexan-6-yl)-1H-pyrazol-3-yl)pyridin-2-amine | (400 MHz, CDCl$_3$), δ: 8.24 (d, J = 2 Hz, 1 H), 7.69 (s, 1 H), 6.54 (t, J$_{HF}$ = 13.6 Hz, 1 H), 5.93 (s, 1 H), 4.70 (s, 2 H), 4.67-4.59 (m, 1 H), 3.92-3.86 (m, 1 H), 3.28 (s, 3 H), 2.91-2.82 (m, 1 H) 2.71-2.62 (m, 2 H), 2.56 (dd, J = 10.4, 2.8 Hz, 1 H), 2.49-2.38 (m, 1 H), 2.25-2.15 (m, 2 H), 2.09-1.97 (m, 2 H), 1.85-1.76 (m, 3 H), 1.63-1.59 (m, 2 H), 1.51 (d, J = 6.8 Hz, 6 H). | 448.2 | A |
| 187 | 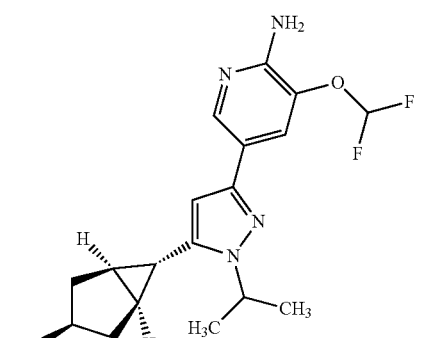<br>3-(difluoromethoxy)-5-(1-isopropyl-5-((1R,3r,5S,6r)-3-methoxy-bicyclo[3.1.0]hexan-6-yl)-1H-pyrazol-3-yl)pyridin-2-amine | (400 MHz, Methanol-d$_4$) δ: 8.13 (s, 1H), 7.71 (s, 1H), 6.87 (t, J = 73.6 Hz, 1H), 6.10 (s, 1 H), 4.74-4.67 (m, 1 H), 3.91 (m, 1 H), 3.25 (s, 3 H), 2.10- 2.03 (m, 4 H), 2.00-1.93 (m, 1 H), 1.66 (m, 2 H), 1.50 (d, J = 6.8 Hz, 6 H) | 379.2 | Q |
| 188 | 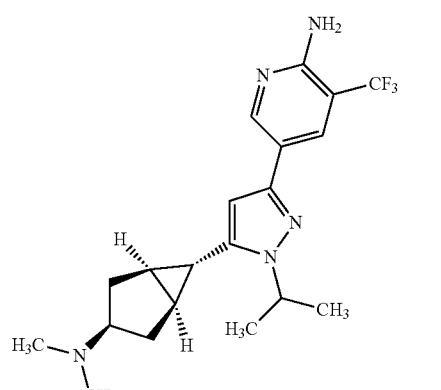<br>5-(5-((1R,3r,5S,6r)-3-(dimethylamino)bicyclo[3.1.0]hexan-6-yl)-1-isopropyl-1H-pyrazol-3-yl)-3-(trifluoromethyl)pyridin-2-amine | (400 MHz, CDCl$_3$), δ: 8.54 (s, 1 H), 8.10 (s, 1 H), 5.96 (s, 1 H), 4.97 (s, 2 H), 4.62-4.69 (m, 1 H), 2.78-2.86 (m, 1 H), 2.28-2.37 (m, 2 H), 2.18-2.23 (m, 6 H), 2.01-2.04 (m, 1 H), 1.60-1.68 (m, 4 H), 1.53 (d, J = 6.8 Hz, 6 H). | 394.2 | A |

TABLE A-continued

| Cmpd No. | Structure | ¹H NMR | MS [MH]⁺ | Method |
|---|---|---|---|---|
| 189 | 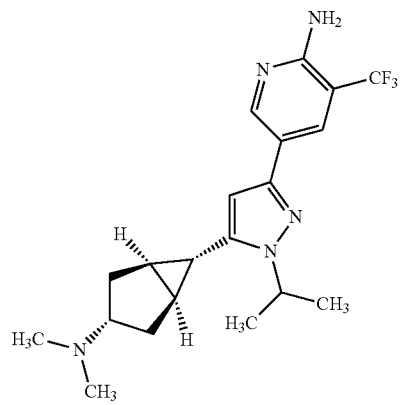 [SMILES: CC(C)n1nc(-c2cnc(N)c(C(F)(F)F)c2)cc1[C@H]1[C@@H]2C[C@@H](N(C)C)C[C@@H]21]<br>5-(5-((1R,3s,5S,6r)-3-(dimethyl amino)bicyclo[3.1.0]hexan-6-yl)-1-isopropyl-1H-pyrazol-3-yl)-3-(trifluoromethyl)pyridin-2-amine | (400 MHz, CDCl₃), δ: 8.55 (s, 1 H), 8.11 (s, 1 H), 6.01 (s, 1 H), 4.96 (s, 2 H), 4.59-4.66 (m, 1 H), 2.18-2.26 (m, 9 H), 1.84-1.86 (m, 4 H), 1.67 (m, 1 H), 1.53 (d, J = 6.4 Hz, 6 H). | 394.2 | A |
| 190 | 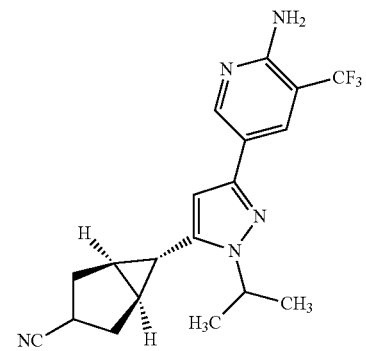<br>(1R,5S,6r)-6-(3-(6-amino-5-(trifluoromethyl)pyridin-3-yl)-1-isopropyl-1H-pyrazol-5-yl)bicyclo[3.1.0]hexane-3-carbonitrile<br>(Diastereomer 2) | (400 MHz, CDCl₃), δ: 8.56 (m, 1 H), 8.12 (m, 1 H), 6.03 (s, 1 H), 4.95 (s, 2 H), 4.67-4.63 (m, 1 H), 3.13-3.10 (m, 1 H), 2.38-2.37 (m, 4 H), 2.12-2.10 (m, 1 H), 1.83 (m, 2 H), 1.58-1.55 (m, 6 H). | 376.2 | R |
| 191 | 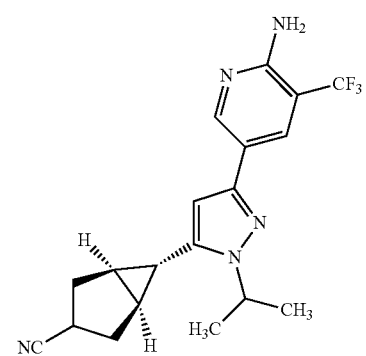<br>(1R,5S,6r)-6-(3-(6-amino-5-(trifluoromethyl)pyridin-3-yl)-1-isopropyl-1H-pyrazol-5-yl)bicyclo[3.1.0]hexane-3-carbonitrile<br>(Diastereomer 1) | (400 MHz, CDCl₃), δ: 8.54 (s, 1 H), 8.11-8.10 (m, 1 H), 6.05 (s, 1 H), 4.96 (s, 2 H), 4.57-4.54 (m, 1 H), 2.57-2.46 (m, 3H), 2.31-2.28 (m, 2 H), 1.81-1.80 (m, 2 H), 1.59-1.51 (m, 7 H). | 376.2 | R |

| Cmpd No. | Structure | ¹H NMR | MS [MH]⁺ | Method |
|---|---|---|---|---|
| 192 | 5-(1-isopropyl-5-((1R,3s,5S,6R)-3-((R)-3-methoxypyrrolidin-1-yl)bicyclo[3.1.0]hexan-6-yl)-1H-pyrazol-3-yl)-3-(trifluoromethyl)pyridin-2-amine | (400 MHz, CDCl$_3$), δ: 8.53 (s, 1 H), 8.10 (d, J = 1.5 Hz, 1 H), 6.00 (s, 1 H), 4.94 (s, 2 H), 4.66-4.56 (m, 1 H), 3.95-3.95 (m, 1 H), 3.29 (s, 3 H), 2.72-2.62 (m, 2 H), 2.61-2.55 (m, 1 H), 2.45-2.37 (m, 1 H), 2.36-2.27 (m, 1 H), 2.22-2.14 (m, 2 H), 2.12-2.01 (m, 1 H), 1.96-1.87 (m, 2 H), 1.86-1.79 (m, 1 H), 1.66 (m, 2 H), 1.56 (t, J = 3.2 Hz, 1 H), 1.52 (d, J = 6.6 Hz, 6 H). | 450.2 | A |
| 193 | 5-(1-isopropyl-5-((1R,3s,5S,6R)-3-((R)-3-methoxypyrrolidin-1-yl)bicyclo[3.1.0]hexan-6-yl)-1H-pyrazol-3-yl)-3-(trifluoromethoxy)pyridin-2-amine | (400 MHz, CDCl$_3$), δ: 8.32 (d, J = 1.6 Hz, 1 H), 7.80 (s, 1 H), 5.98 (s, 1 H), 4.70 (br s, 2 H), 4.66-4.56 (m, 1 H), 3.95-3.88 (m, 1 H), 3.29 (s, 3 H), 2.74-2.63 (m, 2 H), 2.62-2.55 (m, 1 H), 2.42 (d, J = 6.8 Hz, 1 H), 2.33 (t, J = 7.6 Hz, 1 H), 2.12-2.01 (m, 1 H), 1.97-1.86 (m, 2 H), 1.66 (m, 2 H), 1.56 (t, J = 3.2 Hz, 1 H), 1.85-1.78 (m, 1 H), 1.66 (m, 2 H), 1.52 (d, J = 6.4 Hz, 6H). | 466.2 | A |

TABLE A-continued

| Cmpd No. | Structure | ¹H NMR | MS [MH]⁺ | Method |
|---|---|---|---|---|
| 194 | 3-(difluoromethoxy)-5-(1-isopropyl-5-((1R,3s,5S,6R)-3-((R)-3-methoxypyrrolidin-1-yl)bicyclo[3.1.0]hexan-6-yl)-1H-pyrazol-3-yl)pyridin-2-amine | (400 MHz, CDCl₃) δ: 8.24 (d, J = 1.6 Hz, 1 H), 7.70 (s, 1 H), 6.54 (t, $J_{HF}$ = 73.8 Hz, 1 H), 5.98 (s, 1 H), 4.70 (br s, 2 H), 4.66-4.55 (m, 1 H), 3.95-3.87 (m, 1 H), 3.29 (s, 3 H), 2.73-2.62 (m, 2 H), 2.62-2.55 (m, 1 H), 2.46-2.37 (m, 1 H), 2.36-2.27 (m, 1 H), 2.22-2.14 (m, 2 H), 2.12-2.01 (m, 1 H), 1.97-1.85 (m, 2 H), 1.85-1.77 (m, 1 H), 1.66 (m, 2 H), 1.58-1.55 (m, 1 H), 1.52 (d, J = 6.5 Hz, 6 H). | 448.2 | A |
| 195 | 3-(difluoromethoxy)-5-(1-isopropyl-5-((1R,3s,5S,6r)-3-methoxy-bicyclo[3.1.0]hexan-6-yl)-1H-pyrazol-3-yl)pyridin-2-amine | (400 MHz, Methanol-d₄) δ: 8.14 (s, 1 H), 7.71 (s, 1 H), 6.87 (t, J = 13.2 Hz, 1 H), 6.12 (s, 1 H), 4.76-4.70 (m, 1 H), 3.81-3.74 (m, 1 H), 3.31 (s, 3 H), 2.42-2.37 (m, 2 H), 1.84-1.79 (m, 2 H), 1.69 (m, 2 H), 1.57 (m, 1 H), 1.50 (d, J = 6.8 Hz, 6 H). | 379.2 | Q |
| 196 | 5-(5-((1R,5S,6r)-3-(hexahydro-pyrazino[2,1-c][1,4]oxazin-8(1H)-yl)bicyclo[3.1.0]hexan-6-yl)-1-isopropyl-1H-pyrazol-3-yl)-3-(trifluoromethyl)pyridin-2-amine (Stereoisomers 3 and 4) | (400 MHz, CDCl₃) δ: 8.53 (s, 1 H), 8.09 (s, 1 H), 6.00 (s, 1 H), 4.94 (br s, 2 H), 4.62-4.55 (m, 1 H), 3.86 (d, J = 9.2 Hz, 1 H), 3.71-3.65 (m, 2 H), 3.25 (t, J = 10.4 Hz, 1 H), 2.89-2.79 (m, 1 H), 2.77 (d, J = 11.2 Hz, 1 H), 2.73-2.61 (m, 2 H), 2.40 (t, J = 10.8 Hz, 4 H), 2.31-2.23 (m, 4 H), 2.17 (m, 2 H), 1.88 (m, 1 H), 1.76 (m, 2 H), 1.68 (m, 2 H), 1.52 (d, J = 6.8 Hz, 6 H). | 491.3 | A |

TABLE A-continued

| Cmpd No. | Structure | ¹H NMR | MS [MH]⁺ | Method |
|---|---|---|---|---|
| 197 | 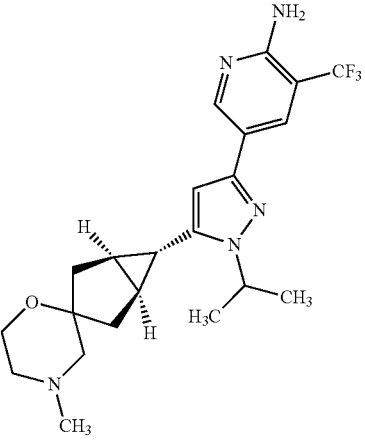<br>5-(1-isopropyl-5-((1R,5S,6r)-4'-methylspiro[bicyclo[3.1.0]hexane-3,2'-morpholin]-6-yl)-1H-pyrazol-3-yl)-3-(trifluoromethyl)pyridin-2-amine (Single diastereomer) | (400 MHz, CDCl₃), δ: 8.45 (s, 1 H), 8.30 (s, 2 H), 8.14 (s, 1 H), 5.97 (s, 1 H), 5.64 (m, 2 H), 4.63-4.60 (m, 1 H), 3.90 (m, 2 H), 2.81-2.75 (m, 4 H), 2.53 (s, 3 H), 2.33-2.29 (m, 2 H), 2.06 (s, 3 H), 1.67 (m, 2 H), 1.51 (d, J = 6.0 Hz, 6 H). | 436.2 | S |
| 198 | 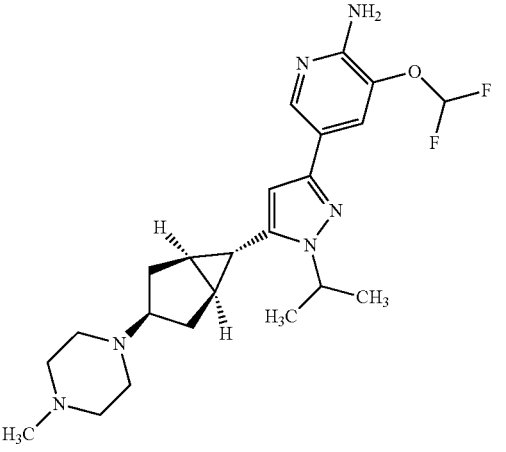 [SMILES: CC(C)n1nc(-c2cnc(N)c(OC(F)F)c2)cc1[C@H]1[C@@H]2C[C@H](N3CCN(C)CC3)C[C@@H]21]<br>3-(difluoromethoxy)-5-(1-isopropyl-5-((1R,3r,5S,6r)-3-(4-methylpiperazin-1-yl)bicyclo[3.1.0]hexan-6-yl)-1H-pyrazol-3-yl)pyridin-2-amine | (400 MHz, DMSO-d₆) δ: 8.15 (d, J = 1.9 Hz, 1H), 7.57 (m, 1H), 7.15 (t, J = 73.9 Hz, 1H), 6.17 (s, 1H), 6.08 (s, 2H), 4.72-4.60 (m, 1H), 2.30 (m, 8H), 2.16-2.04 (m, 5H), 1.96-1.90 (m, 1H), 1.73-1.63 (m, 2H), 1.62-1.55 (m, 2H), 1.43 (d, J = 6.6 Hz, 6H) | 447.4 | D |

TABLE A-continued

| Cmpd No. | Structure | ¹H NMR | MS [MH]⁺ | Method |
|---|---|---|---|---|
| 199 | 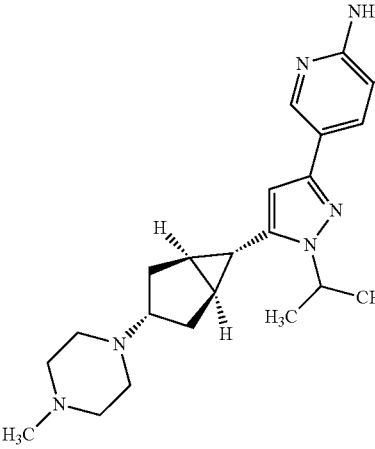<br>3-(difluoromethoxy)-5-(1-isopropyl-5-((1R,3s,5S,6r)-3-(4-methyl-piperazin-1-yl)bicyclo[3.1.0]hexan-6-yl)-1H-pyrazol-3-yl)pyridin-2-amine | (400 MHz, DMSO-d₆) δ: 8.15 (d, J = 1.9 Hz, 1H), 7.57 (m, 1H), 7.15 (t, J = 73.9 Hz, 1H), 6.17 (s, 1H), 6.08 (s, 2H), 4.72-4.60 (m, 1H), 2.30 (m, 8H), 2.16-2.04 (m, 5H), 1.96-1.90 (m, 1H), 1.73-1.63 (m, 2H), 1.62-1.55 (m, 2H), 1.43 (d, J = 6.6 Hz, 6H) | 447.4 | D |
| 200 | 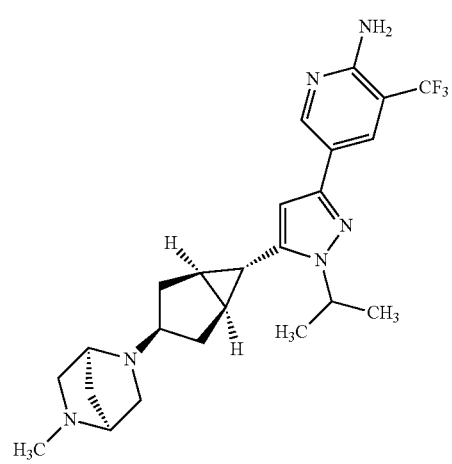 [SMILES: CC(C)n1nc(-c2cnc(N)c(C(F)(F)F)c2)cc1[C@H]1[C@@H]2C[C@H](N3C[C@@H]4C[C@H]3CN4C)C[C@@H]21]<br>5-(1-isopropyl-5-((1R,3r,5S,6S)-3-((1S,4S)-5-methyl-2,5-diazabicyclo[2.2.1]heptan-2-yl)bicyclo[3.1.0]hexan-6-yl)-1H-pyrazol-3-yl)-3-(trifluoromethyl)pyridin-2-amine | (400 MHz, DMSO-d₆) δ: 8.53 (d, 1H), 7.97 (d, J = 2.2 Hz, 1H), 6.46 (s, 2H), 6.26 (s, 1H), 4.68-4.54 (m, 1H), 3.43-3.33 (m, 1H), 3.16-3.05 (m, 2H), 2.69- 2.51 (m, 5H), 2.49-2.45 (m, 1H), 2.23 (s, 3H), 2.07-1.79 (m, 4H), 1.63-1.51 (m, 3H), 1.44 (d, J = 6.6 Hz, 6H) | 461.4 | D |

TABLE A-continued

| Cmpd No. | Structure | ¹H NMR | MS [MH]⁺ | Method |
|---|---|---|---|---|
| 201 | 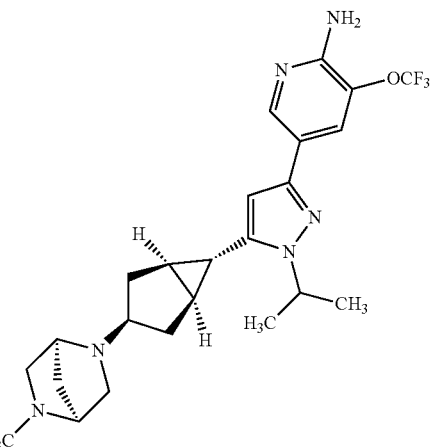 5-(1-isopropyl-5-((1R,3r,5S,6S)-3-((1S,4S)-5-methyl-2,5-diazabicyclo[2.2.1]heptan-2-yl)bicyclo[3.1.0]hexan-6-yl)-1H-pyrazol-3-yl)-3-(trifluoromethoxy)pyridin-2-amine | (400 MHz, DMSO-d₆) δ: 8.28 (d, J = 1.9 Hz, 1H), 7.70 (d, J = 1.6 Hz, 1H), 6.41 (s, 2H), 6.21 (s, 1H), 4.67-4.55 (m, 1H), 3.41-3.36 (m, 1H), 3.16-3.04 (m, 2H), 2.64-2.51 (m, 4H), 3.31-3.29 (m, 1H), 2.49-2.43 (m, 2H), 2.23 (s, 3H), 2.05-1.93 (m, 1H), 1.97-1.79 (m, 3H), 1.62-1.50 (m, 3H), 1.43 (d, J = 6.7 Hz, 6H) | 477.4 | D |
| 202 | 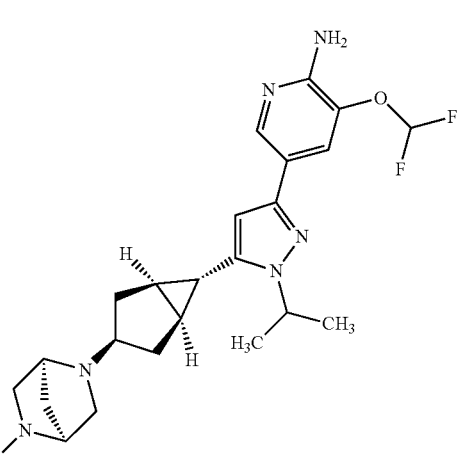 3-(difluoromethoxy)-5-(1-isopropyl-5-((1R,3r,5S,6S)-3-((1S,4S)-5-methyl-2,5-diazabicyclo[2.2.1]heptan-2-yl)bicyclo[3.1.0]hexan-6-yl)-1H-pyrazol-3-yl)pyridin-2-amine | (400 MHz, DMSO-d₆) δ: 8.15 (d, J = 1.9 Hz, 1H), 7.57 (m, 1H), 7.15 (t, J = 73.9 Hz, 1H), 6.16 (s, 1H), 6.07 (s, 2H), 4.67-4.54 (m, 1H), 3.46-3.32 (m, 1H), 3.16-3.04 (m, 2H), 2.64-2.51 (m, 4H), 2.49-2.44 (m, 2H), 2.23 (s, 3H), 2.07-1.79 (m, 4H), 1.64-1.50 (m, 3H), 1.44 (d, J = 6.7 Hz, 6H) | 459.4 | D |

TABLE A-continued

| Cmpd No. | Structure | ¹H NMR | MS [MH]⁺ | Method |
|---|---|---|---|---|
| 203 | 5-(1-isopropyl-5-((1R,3s,5S,6r)-3-(4-methyl-1,4-diazepan-1-yl)bicyclo[3.1.0]hexan-6-yl)-1H-pyrazol-3-yl)-3-(trifluoromethoxy)pyridin-2-amine | (400 MHz, DMSO-$d_6$) δ: 8.28 (d, J = 1.9 Hz, 1H), 7.70 (d, J = 1.7 Hz, 1H), 6.41 (s, 2H), 6.24 (s, 1H), 4.75-4.60 (m, 1H), 2.93-2.80 (m, 1H), 2.68-2.52 (m, 5H), 2.49-2.40 (m, 3H), 2.22 (s, 3H), 2.12-2.01 (m, 2H), 1.76-1.53 (m, 7H), 1.40 (d, J = 6.6 Hz, 6H) | 479.4 | D |
| 204 | 5-(1-isopropyl-5-((1R,3r,5S,6r)-3-(4-methyl-1,4-diazepan-1-yl)bicyclo[3.1.0]hexan-6-yl)-1H-pyrazol-3-yl)-3-(trifluoromethoxy)pyridin-2-amine | (400 MHz, DMSO-$d_6$) δ: 8.28 (d, J = 1.9 Hz, 1H), 7.70 (d, J = 1.6 Hz, 1H), 6.42 (s, 2H), 6.21 (s, 1H), 4.77-4.63 (m, 1H), 3.25-3.11 (m, 1H), 2.66-2.56 (m, 4H), 2.49-2.45 (m, 4H), 2.22 (s, 3H), 2.15-2.03 (m, 2H), 2.00-1.94 (m, 1H), 1.75-1.51 (m, 6H), 1.43 (d, J = 6.5 Hz, 6H) | 479.4 | D |

| Cmpd No. | Structure | ¹H NMR | MS [MH]⁺ | Method |
|---|---|---|---|---|
| 205 | 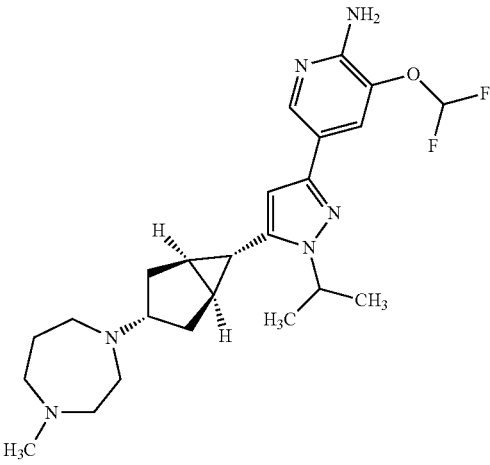 [SMILES: CC(C)n1nc(-c2cnc(N)c(OC(F)F)c2)cc1[C@H]1[C@@H]2C[C@@H](N3CCCN(C)CC3)C[C@@H]21]<br>3-(difluoromethoxy)-5-(1-isopropyl-5-((1R,3s,5S,6r)-3-(4-methyl-1,4-diazepan-1-yl)bicyclo[3.1.0]hexan-6-yl)-1H-pyrazol-3-yl)pyridin-2-amine | (400 MHz, DMSO-$d_6$) δ: 8.15 (d, J = 1.9 Hz, 1H), 7.57 (m, 1H), 7.15 (t, J = 73.9 Hz, 1H), 6.17 (s, 1H), 6.08 (s, 2H), 4.77-4.62 (m, 1H), 3.25-3.13 (m, 1H), 2.67-2.50 (m, 5H), 2.51-2.43 (m, 3H), 2.22 (s, 3H), 2.15-2.03 (m, 2H), 2.00-1.93 (m, 1H), 1.75-1.60 (m, 4H), 1.61-1.52 (m, 2H), 1.43 (d, J = 6.5 Hz, 6H) | 461.4 | D |
| 206 | 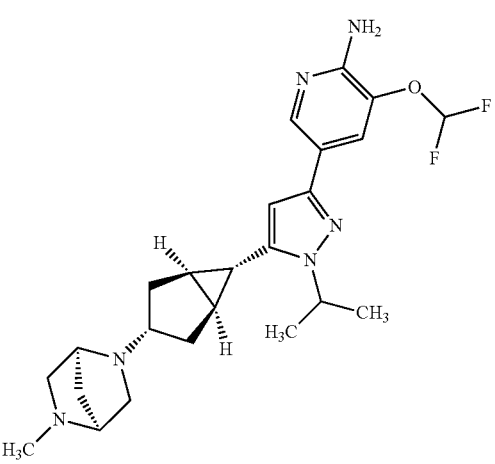 [SMILES: CC(C)n1nc(-c2cnc(N)c(OC(F)F)c2)cc1[C@H]1[C@@H]2C[C@@H](N3C[C@@H]4C[C@H]3CN4C)C[C@@H]21]<br>3-(difluoromethoxy)-5-(1-isopropyl-5-((1R,3s,5S,6S)-3-((1S,4S)-5-methyl-2,5-diazabicyclo[2.2.1]heptan-2-yl)bicyclo[3.1.0]hexan-6-yl)-1H-pyrazol-3-yl)pyridin-2-amine | (400 MHz, DMSO-$d_6$) δ: 8.16 (d, J = 1.9 Hz, 1H), 7.57 (d, J = 1.8 Hz, 1H), 7.15 (t, J = 73.9 Hz, 1H), 6.20 (s, 1H), 6.07 (s, 2H), 4.77-4.64 (m, 1H), 3.22-3.17 (m, 1H), 3.07-3.02 (m, 1H), 2.84-2.71 (m, 1H), 2.73-2.58 (m, 2H), 2.50-2.35 (m, 2H), 2.23 (s, 3H), 2.19-2.08 (m, 1H), 2.04-1.95 (m, 1H), 1.83-1.77 (m, 1H), 1.69-1.47 (m, 6H), 1.40 (d, J = 6.5 Hz, 6H) | 459.4 | D |

TABLE A-continued

| Cmpd No. | Structure | ¹H NMR | MS [MH]⁺ | Method |
|---|---|---|---|---|
| 207 | 5-(1-isopropyl-5-((1R,3s,5S,6S)-3-((1S,4S)-5-methyl-2,5-diazabicyclo[2.2.1]heptan-2-yl)bicyclo[3.1.0]hexan-6-yl)-1H-pyrazol-3-yl)-3-(trifluoromethyl)pyridin-2-amine | (400 MHz, DMSO-$d_6$) δ: 8.56-8.51 (m, 1H), 7.97 (d, J = 2.2 Hz, 1H), 6.46 (s, 2H), 6.29 (s, 1H), 4.78-4.63 (m, 1H), 3.24-3.17 (m, 1H), 3.07-3.02 (m, 1H), 2.84-2.58 (m, 3H), 2.50-2.35 (m, 2H), 2.23 (s, 3H), 2.17-2.08 (m, 1H), 2.05-1.95 (m, 1H), 1.84-1.78 (m, 1H), 1.67-1.45 (m, 6H), 1.41 (dd, J = 6.5, 1.1 Hz, 6H) | 461.4 | D |
| 208 | 3-(difluoromethoxy)-5-(1-isopropyl-5-((1R,3r,5S,6r)-3-(4-methyl-1,4-diazepan-1-yl)bicyclo[3.1.0]hexan-6-yl)-1H-pyrazol-3-yl)pyridin-2-amine | (400 MHz, DMSO-$d_6$) δ: 8.16 (d, J = 1.9 Hz, 1H), 7.57 (m, 1H), 7.15 (t, J = 73.9 Hz, 1H), 6.20 (s, 1H), 6.07 (s, 2H), 4.73-4.61 (m, 1H), 2.93-2.80 (m, 1H), 2.66-2.55 (m, 4H), 2.50-2.45 (m, 4H), 2.22 (s, 3H), 2.10-2.01 (m, 2H), 1.76-1.52 (m, 7H), 1.40 (d, J = 6.5 Hz, 6H) | 461.4 | D |

TABLE A-continued

| Cmpd No. | Structure | ¹H NMR | MS [MH]⁺ | Method |
|---|---|---|---|---|
| 209 | 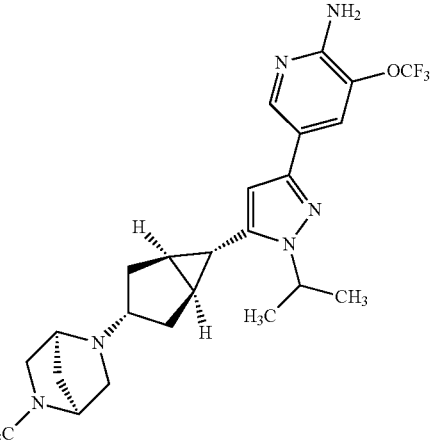<br>5-(1-isopropyl-5-((1R,3s,5S,6S)-3-((1S,4S)-5-methyl-2,5-diazabicyclo[2.2.1]heptan-2-yl)bicyclo[3.1.0]hexan-6-yl)-1H-pyrazol-3-yl)-3-(trifluoromethoxy)pyridin-2-amine | (400 MHz, DMSO-$d_6$) δ: 8.28 (d, J = 1.9 Hz, 1H), 7.70 (d, J = 1.6 Hz, 1H), 6.41 (s, 2H), 6.24 (s, 1H), 4.77-4.64 (m, 1H), 3.22-3.17 (m, 1H), 3.07-3.02 (m, 1H), 2.84-2.58 (m, 3H), 2.49-2.35 (m, 2H), 2.23 (s, 3H), 2.17-2.08 (m, 1H), 2.04-1.95 (m, 1H), 1.83-1.77 (m, 1H), 1.67-1.45 (m, 6H), 1.40 (d, J = 6.4 Hz, 6H) | 477.3 | D |
| 210 | 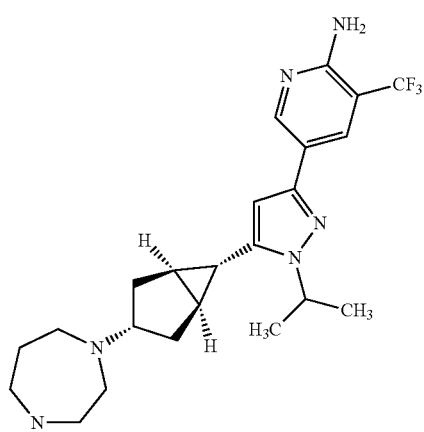<br>5-(1-isopropyl-5-((1R,3s,5S,6r)-3-(4-methyl-1,4-diazepan-1-yl)bicyclo[3.1.0]hexan-6-yl)-1H-pyrazol-3-yl)-3-(trifluoromethyl)pyridin-2-amine | (400 MHz, DMSO-$d_6$) δ: 8.54 (d, J = 2.2 Hz, 1H), 7.97 (d, J = 2.2 Hz, 1H), 6.46 (s, 2H), 6.29 (s, 1H), 4.76-4.61 (m, 1H), 2.93-2.80 (m, 1H), 2.66-2.53 (m, 5H), 2.51-2.43 (m, 3H), 2.22 (s, 3H), 2.11-2.01 (m, 2H), 1.77-1.55 (m, 7H), 1.40 (d, J = 6.5 Hz, 6H) | 463.4 | D |

TABLE A-continued

| Cmpd No. | Structure | ¹H NMR | MS [MH]⁺ | Method |
|---|---|---|---|---|
| 211 | 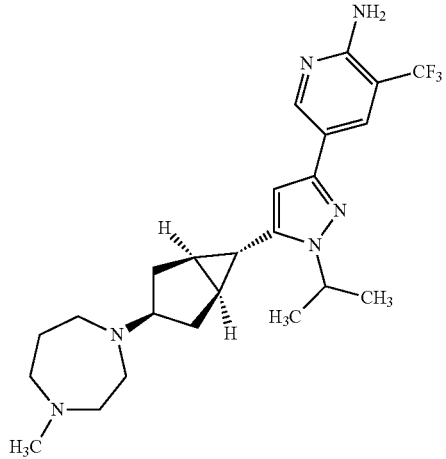 [SMILES: CC(C)n1nc(-c2cnc(N)c(C(F)(F)F)c2)cc1[C@H]1[C@@H]2C[C@H](N3CCCN(C)CC3)C[C@@H]21]<br>5-(1-isopropyl-5-((1R,3r,5S,6r)-3-(4-methyl-1,4-diazepan-1-yl)bicyclo[3.1.0]hexan-6-yl)-1H-pyrazol-3-yl)-3-(trifluoromethyl)pyridin-2-amine | (400 MHz, DMSO-$d_6$) δ: 8.54 (d, J = 2.2 Hz, 1H), 7.97 (d, J = 2.2 Hz, 1H), 6.46 (s, 2H), 6.26 (s, 1H), 4.78-4.63 (m, 1H), 3.27-3.13 (m, 1H), 2.67-2.52 (m, 5H), 2.51-2.44 (m, 3H), 2.22 (s, 3H), 2.15-2.04 (m, 2H), 2.01-1.95 (m, 1H), 1.75-1.53 (m, 6H), 1.43 (d, J = 6.5 Hz, 6H) | 463.4 | D |
| 212 | 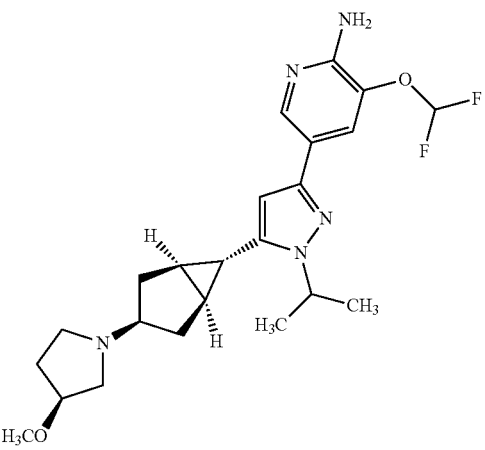 [SMILES: CO[C@H]1CCN([C@H]2C[C@@H]3[C@H](C2)[C@H]3c2cc(-c3cnc(N)c(OC(F)F)c3)nn2C(C)C)C1]<br>3-(difluoromethoxy)-5-(1-isopropyl-5-((1R,3r,5S,6S)-3-((S)-3-methoxypyrrolidin-1-yl)bicyclo[3.1.0]hexan-6-yl)-1H-pyrazol-3-yl)pyridin-2-amine | (400 MHz, CDCl₃), δ: 8.16 (s, 1 H), 7.71 (s, 1 H), 6.55 (t, $J_{HF}$ = 73.6 Hz, 1 H), 5.90 (s, 1 H), 5.16 (m, 2 H), 4.68-4.65 (m, 1 H), 4.01 (m, 1 H), 3.61-3.56 (m, 2 H), 3.30 (m, 4 H), 2.91-2.81 (m, 2 H), 2.48-2.45 (m, 2 H), 2.05-1.97 (m, 5 H), 1.66 (m, 2 H), 1.50 (d, J = 6.4 Hz, 6 H). | 448.1 | A |

TABLE A-continued

| Cmpd No. | Structure | ¹H NMR | MS [MH]⁺ | Method |
|---|---|---|---|---|
| 213 | 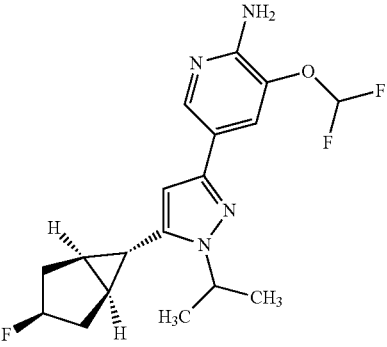 [SMILES: CC(C)n1nc(-c2cnc(N)c(OC(F)F)c2)cc1[C@H]1[C@@H]2C[C@H](F)C[C@@H]21]<br>3-(difluoromethoxy)-5-(5-((1R,3r,5S,6r)-3-fluorobicyclo[3.1.0]hexan-6-yl)-1-isopropyl-1H-pyrazol-3-yl)pyridin-2-amine | (400 MHz, Methanol-d₄), δ: 8.14 (m, 1 H), 7.71 (m, 1 H), 6.87 (t, $J_{HF}$ = 73.2 Hz, 1 H), 6.15 (s, 1 H), 5.26-5.11 (m, 1 H), 4.73-4.68 (m, 1 H), 2.29-2.20 (m, 4 H), 1.81-1.76 (m, 3 H), 1.52-1.48 (m, 6 H) | 367.2 | T |
| 214 | 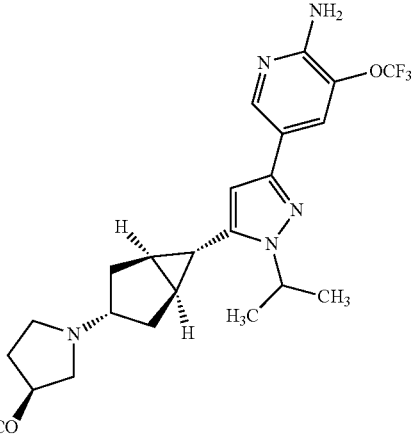<br>5-(1-isopropyl-5-((1R,3s,5S,6S)-3-((S)-3-methoxypyrrolidin-1-yl)bicyclo[3.1.0]hexan-6-yl)-1H-pyrazol-3-yl)-3-(trifluoromethoxy)pyridin-2-amine | (400 MHz, CDCl₃), δ: 8.30 (s, 1 H), 7.81 (s, 1 H), 6.00 (s, 1 H), 4.87 (s, 2 H), 4.61-4.54 (m, 1 H), 4.03 (m, 1 H), 3.45 (m, 1 H), 3.32 (s, 3 H), 3.21 (m, 1 H), 2.90-2.77 (m, 3 H), 2.31-2.05 (m, 6 H), 1.74 (m, 2 H), 1.51 (d, J = 6.4 Hz, 6 H). | 466.0 | A |
| 215 | 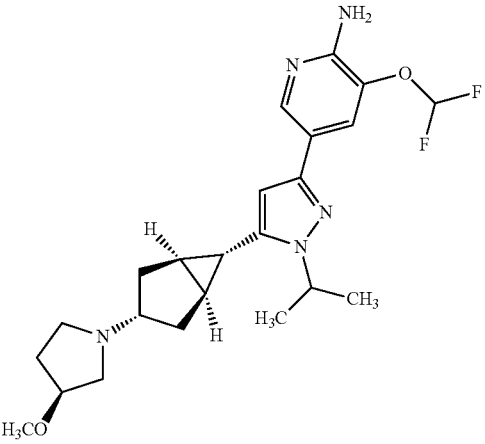 [SMILES: CO[C@H]1CCN([C@@H]2C[C@@H]3[C@H](C2)[C@H]3c2cc(-c3cnc(N)c(OC(F)F)c3)nn2C(C)C)C1]<br>3-(difluoromethoxy)-5-(1-isopropyl-5-((1R,3s,5S,6S)-3-((S)-3-methoxypyrrolidin-1-yl)bicyclo[3.1.0]hexan-6-yl)-1H-pyrazol-3-yl)pyridin-2-amine | (400 MHz, CDCl₃), δ: 8.15 (s, 1 H), 7.71 (s, 1 H), 6.56 (t, $J_{HF}$ = 73.2 Hz, 1 H), 5.98 (s, 1 H), 5.35 (m, 2 H), 4.56-4.53 (m, 1 H), 4.05 (m, 1 H), 3.76-3.74 (m, 1 H), 3.51 (m, 1 H), 3.31 (s, 3 H), 3.13-2.87 (m, 3 H), 2.32 (m, 4 H), 2.10 (m, 2 H), 1.75 (m, 2 H), 1.49 (d, J = 6 Hz, 6 H). | 448.1 | A |

| Cmpd No. | Structure | ¹H NMR | MS [MH]⁺ | Method |
|---|---|---|---|---|
| 216 | 5-(5-((1R,5S,6r)-3,3-difluorobicyclo[3.1.0]hexan-6-yl)-1-isopropyl-1H-pyrazol-3-yl)-3-(difluoromethoxy)pyridin-2-amine | (400 MHz, Methanol-d$_4$), δ: 8.14 (d, J = 2 Hz, 1 H), 7.71 (m, 1 H), 6.87 (t, J$_{HF}$ = 73.6 Hz, 1 H), 6.19 (s, 1 H), 4.72-4.66 (m, 1 H), 2.57-2.31 (m, 4 H), 1.83-1.77 (m, 3 H), 1.51 (d, J = 6.8 Hz, 6 H) | 385.4 | U |
| 217 | 3-(difluoromethoxy)-5-(5-((1R,3s,5S,6r)-3-fluorobicyclo[3.1.0]hexan-6-yl)-1-isopropyl-1H-pyrazol-3-yl)pyridin-2-amine | (400 MHz, Methanol-d$_4$), δ: 8.13 (d, J = 1.6 Hz, 1 H), 7.70 (m, 1 H), 6.87 (t, J$_{HF}$ = 13.6 Hz, 1 H), 6.13 (s, 1 H), 5.13-5.09 (m, 1 H), 4.74-4.68 (m, 1 H), 2.37-2.13 (m, 4 H), 1.78 (m, 2 H), 1.52-1.48 (m, 7 H) | 367.0 | T |
| 218 | 5-(1-isopropyl-5-((1R,3s,5S,6r)-3-(8-methyl-5-oxa-2,8-diazaspiro[3.5]nonan-2-yl)bicyclo[3.1.0]hexan-6-yl)-1H-pyrazol-3-yl)-3-(trifluoromethyl)pyridin-2-amine | (400 MHz, DMSO-d$_6$) δ: 8.50 (d, J = 2.1 Hz, 1H), 8.18 (m, 1H), 6.03 (s, 1H), 5.40 (s, 2H), 4.61-4.48 (m, 1H), 3.72-3.67 (m, 2H), 3.44-3.39 (m, 1H), 2.78-2.52 (m, 5H), 2.52-2.30 (m, 5H), 2.13-2.01 (m, 1H), 1.88-1.81 (m, 2H), 1.55-1.47 (m, 11H), | 491.4 | D |

| Cmpd No. | Structure | ¹H NMR | MS [MH]⁺ | Method |
|---|---|---|---|---|
| 219 | 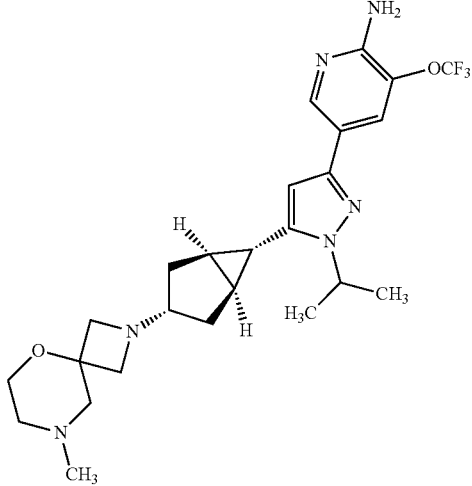 [SMILES: CC(C)n1nc(-c2cnc(N)c(OC(F)(F)F)c2)cc1[C@H]1[C@@H]2C[C@@H](N3CC4(CN(C)CCO4)C3)C[C@@H]21]<br>5-(1-isopropyl-5-((1R,3s,5S,6r)-3-(8-methyl-5-oxa-2,8-diazaspiro[3.5]nonan-2-yl)bicyclo[3.1.0]hexan-6-yl)-1H-pyrazol-3-yl)-3-(trifluoromethoxy)pyridin-2-amine | (400 MHz, DMSO-d₆) δ: 8.28 (d, J = 1.9 Hz, 1H), 7.70 (d, J = 1.6 Hz, 1H), 6.39 (s, 2H), 6.24 (s, 1H), 4.73-4.61 (m, 1H), 3.53-3.45 (m, 2H), 3.22-3.15 (m, 2H), 2.83-2.76 (m, 2H), 2.78-2.67 (m, 1H), 2.41-2.36 (m, 2H), 2.25-2.13 (m, 5H), 2.05-1.95 (m, 2H), 1.75-1.69 (m, 1H), 1.62-1.48 (m, 4H), 1.40 (d, J = 6.5 Hz, 6H) | 507.4 | D |
| 220 | 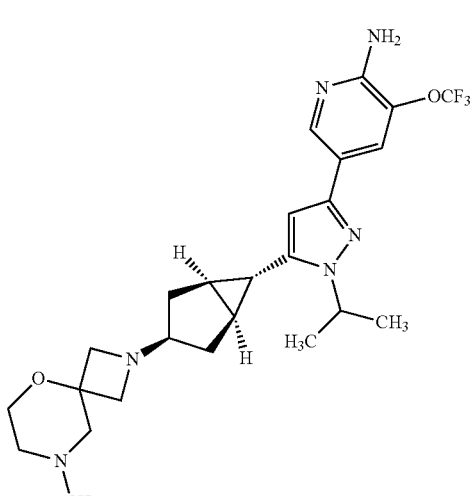<br>5-(1-isopropyl-5-((1R,3r,5S,6r)-3-(8-methyl-5-oxa-2,8-diazaspiro[3.5]nonan-2-yl)bicyclo[3.1.0]hexan-6-yl)-1H-pyrazol-3-yl)-3-(trifluoromethoxy)pyridin-2-amine | (400 MHz, DMSO-d₆) δ: 8.28 (m, 1H), 7.70 (d, J = 2.5 Hz, 1H), 6.39 (s, 2H), 6.21 (s, 1H), 4.64-4.52 (m, 1H), 3.49 (t, J = 4.4 Hz, 2H), 3.29-3.22 (m, 2H), 2.90-2.81 (m, 1H), 2.62-2.50 (m, 3H), 2.40-2.35 (m, 2H), 2.27-2.21 (m, 2H), 2.17 (s, 3H), 1.92-1.82 (m, 2H), 1.77-1.69 (m, 2H), 1.63-1.57 (m, 2H), 1.44 (d, J = 6.6 Hz, 6H) | 507.4 | D |

TABLE A-continued

| Cmpd No. | Structure | ¹H NMR | MS [MH]⁺ | Method |
|---|---|---|---|---|
| 221 | 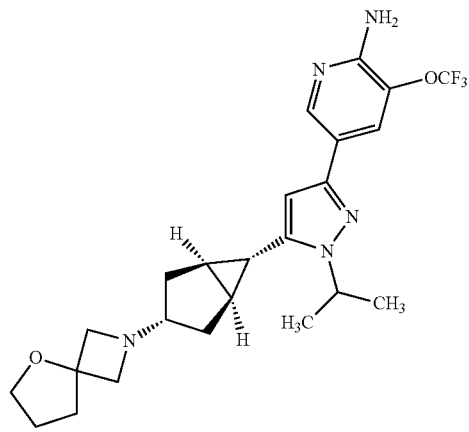 [SMILES: CC(C)n1nc(-c2cnc(N)c(OC(F)(F)F)c2)cc1[C@H]1[C@@H]2C[C@@H](N3CC4(CCCO4)C3)C[C@@H]21]<br>5-(5-((1R,3s,5S,6r)-3-(5-oxa-2-azaspiro[3.4]octan-2-yl)bicyclo[3.1.0]hexan-6-yl)-1-isopropyl-1H-pyrazol-3-yl)-3-(trifluoromethoxy)pyridin-2-amine | (400 MHz, DMSO-$d_6$) δ: 8.28 (d, J = 1.9 Hz, 1H), 7.72-7.67 (m, 1H), 6.39 (s, 2H), 6.23 (s, 1H), 4.73-4.61 (m, 1H), 3.69-3.59 (m, 2H), 3.22-3.13 (m, 2H), 2.97-2.89 (m, 2H), 2.68-2.59 (m, 1H), 2.04-1.90 (m, 4H), 1.85-1.69 (m, 3H), 1.61-1.48 (m, 4H), 1.37 (d, J = 6.5 Hz, 6H) | 478.4 | D |
| 222 | 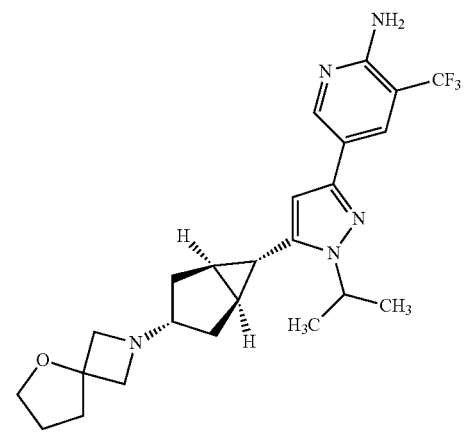 [SMILES: CC(C)n1nc(-c2cnc(N)c(C(F)(F)F)c2)cc1[C@H]1[C@@H]2C[C@@H](N3CC4(CCCO4)C3)C[C@@H]21]<br>5-(5-((1R,3s,5S,6r)-3-(5-oxa-2-azaspiro[3.4]octan-2-yl)bicyclo[3.1.0]hexan-6-yl)-1-isopropyl-1H-pyrazol-3-yl)-3-(trifluoromethyl)pyridin-2-amine | (400 MHz, DMSO-$d_6$) δ: 8.53 (s, 1H), 7.97 (s, 1H), 6.43 (s, 2H), 6.28 (s, 1H), 4.77-4.56 (m, 1H), 3.65 (t, J = 6.7 Hz, 2H), 3.18 (d, J = 6.8 Hz, 2H), 2.94 (d, J = 7.0 Hz, 2H), 2.68-2.59 (m, 1H), 2.04-1.93 (m, 4H), 1.85-1.70 (m, 3H), 1.61-1.48 (m, 4H), 1.40 (d, J = 6.5 Hz, 6H) | 462.3 | D |

TABLE A-continued

| Cmpd No. | Structure | ¹H NMR | MS [MH]⁺ | Method |
|---|---|---|---|---|
| 223 | 5-(5-((1R,3s,5S,6r)-3-(5-oxa-2-azaspiro[3.4]octan-2-yl)bicyclo[3.1.0]hexan-6-yl)-1-isopropyl-1H-pyrazol-3-yl)-3-(difluoromethoxy)pyridin-2-amine | (400 MHz, DMSO-$d_6$) δ: 8.15 (d, J = 1.9 Hz, 1H), 7.60-7.54 (m, 1H), 7.14 (t, J = 73.9 Hz, 1H), 6.19 (s, 1H), 6.05 (s, 2H), 4.72-4.61 (m, 1H), 3.64 (t, J = 6.7 Hz, 2H), 3.23-3.15 (m, 2H), 2.97-2.90 (m, 2H), 2.68-2.57 (m, 1H), 2.04-1.93 (m, 4H), 1.85-1.68 (m, 3H), 1.61-1.48 (m, 4H), 1.40 (d, J = 6.5 Hz, 6H) | 460.4 | D |
| 224 | 3-(difluoromethoxy)-5-(1-isopropyl-5-((1R,3s,5S,6r)-3-(8-methyl-5-oxa-2,8-diazaspiro[3.5]nonan-2-yl)bicyclo[3.1.0]hexan-6-yl)-1H-pyrazol-3-yl)pyridin-2-amine | (400 MHz, DMSO-$d_6$) δ: 8.15 (d, J = 1.9 Hz, 1H), 7.57 (m, 1H), 7.15 (t, J = 73.9 Hz, 1H), 6.17 (s, 1H), 6.05 (s, 2H), 4.64-4.53 (m, 1H), 3.53-3.46 (m, 2H), 3.29-3.22 (m, 3H), 2.90-2.82 (m, 1H), 2.63-2.51 (m, 2H), 2.40-2.35 (m, 2H), 2.27-2.20 (m, 2H), 2.17 (s, 3H), 1.93-1.82 (m, 2H), 1.77-1.69 (m, 2H), 1.63-1.56 (m, 2H), 1.44 (d, J = 6.6 Hz, 6H) | 489.4 | D |

TABLE A-continued

| Cmpd No. | Structure | ¹H NMR | MS [MH]⁺ | Method |
|---|---|---|---|---|
| 225 | 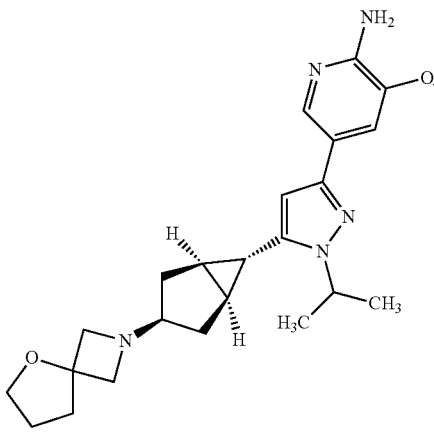 5-(5-((1R,3r,5S,6r)-3-(5-oxa-2-azaspiro[3.4]octan-2-yl)bicyclo[3.1.0]hexan-6-yl)-1-isopropyl-1H-pyrazol-3-yl)-3-(difluoromethoxy)pyridin-2-amine | (400 MHz, DMSO-$d_6$) δ: 8.15 (d, J = 1.9 Hz, 1H), 7.57 (m, 1H), 7.15 (t, J = 73.9 Hz, 1H), 6.17 (s, 1H), 6.05 (s, 2H), 4.64-4.52 (m, 1H), 3.70-3.61 (m, 2H), 3.28-3.19 (m, 2H), 2.83-2.71 (m, 3H), 2.59-2.52 (m, 1H), 2.01-1.92 (m, 2H), 1.92-1.75 (m, 4H), 1.74-1.66 (m, 2H), 1.59-1.56 (m, 2H), 1.48-1.41 (m, 6H) | 460.1 | D |
| 226 | 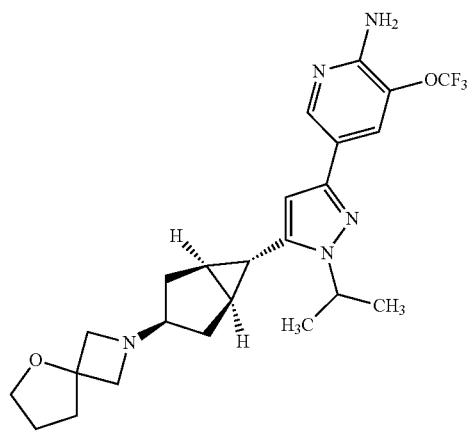 [SMILES: CC(C)n1nc(-c2cnc(N)c(OC(F)(F)F)c2)cc1[C@H]1[C@@H]2C[C@H](N3CC4(CCCO4)C3)C[C@@H]21] 5-(5-((1R,3r,5S,6r)-3-(5-oxa-2-azaspiro[3.4]octan-2-yl)bicyclo[3.1.0]hexan-6-yl)-1-isopropyl-1H-pyrazol-3-yl)-3-(trifluoromethoxy)pyridin-2-amine | (400 MHz, DMSO-$d_6$) δ: 8.28 (d, J = 1.9 Hz, 1H), 7.73-7.67 (m, 1H), 6.39 (s, 2H), 6.21 (s, 1H), 4.64-4.53 (m, 1H), 3.70-3.61 (m, 2H), 3.26-3.19 (m, 2H), 2.83-2.71 (m, 3H), 2.59-2.53 (m, 1H), 2.01-1.92 (m, 2H), 1.92-1.75 (m, 4H), 1.75-1.66 (m, 2H), 1.64-1.55 (m, 2H), 1.45 (d, J = 6.7 Hz, 6H) | 478.4 | D |

| Cmpd No. | Structure | ¹H NMR | MS [MH]⁺ | Method |
|---|---|---|---|---|
| 227 | 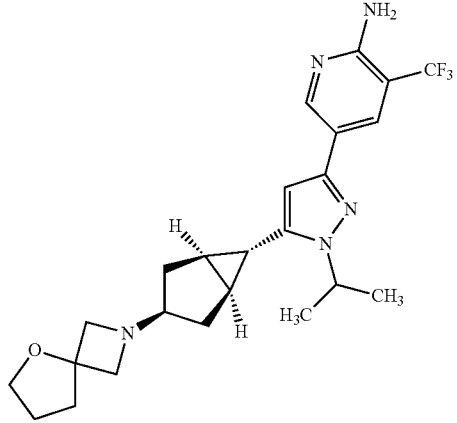 [SMILES: CC(C)n1nc(-c2cnc(N)c(C(F)(F)F)c2)cc1[C@H]1[C@@H]2C[C@H](N3CC4(CCCO4)C3)C[C@@H]21]<br>5-(5-((1R,3r,5S,6r)-3-(5-oxa-2-azaspiro[3.4]octan-2-yl)bicyclo[3.1.0]hexan-6-yl)-1-isopropyl-1H-pyrazol-3-yl)-3-(trifluoromethyl)pyridin-2-amine | (400 MHz, DMSO-d₆) δ: 8.56-8.50 (m, 1H), 7.97 (d, J = 2.3 Hz, 1H), 6.43 (s, 2H), 6.26 (s, 1H), 4.65-4.53 (m, 1H), 3.70-3.61 (m, 2H), 3.26-3.19 (m, 2H), 2.83-2.71 (m, 3H), 2.60-2.53 (m, 1H), 2.01-1.93 (m, 2H), 1.87-1.75 (m, 4H), 1.75-1.66 (m, 2H), 1.63-1.56 (m, 2H), 1.45 (d, J = 6.6, 6H) | 462.4 | D |
| 228 | 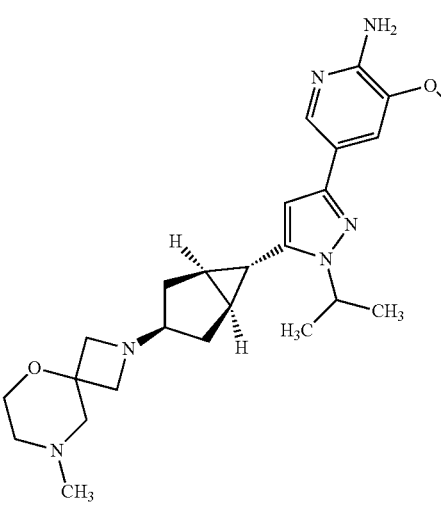<br>3-(difluoromethoxy)-5-(1-isopropyl-5-((1R,3r,5S,6r)-3-(8-methyl-5-oxa-2,8-diazaspiro[3.5]nonan-2-yl)bicyclo[3.1.0]hexan-6-yl)-1H-pyrazol-3-yl)pyridin-2-amine | (400 MHz, DMSO-d₆) δ: 8.15 (d, J = 1.9 Hz, 1H), 7.57 (d, J = 1.9 Hz, 1H), 7.14 (t, J = 73.9 Hz, 1H), 6.19 (s, 1H), 6.05 (s, 2H), 4.73-4.61 (m, 1H), 3.53-3.45 (m, 2H), 3.22-3.15 (m, 2H), 2.83-2.67 (m, 3H), 2.41-2.36 (m, 2H), 2.25-2.14 (m, 5H), 2.05-1.95 (m, 2H), 1.75-1.68 (m, 1H), 1.61-1.48 (m, 4H), 1.40 (d, J = 6.5 Hz, 6H) | 489.4 | D |

TABLE A-continued
| Cmpd No. | Structure | ¹H NMR | MS [MH]⁺ | Method |
|---|---|---|---|---|
| 229 | 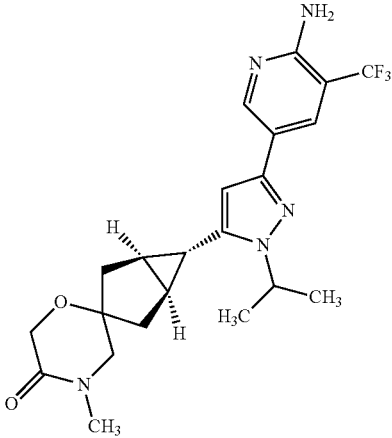<br>(1R,5S,6r)-6-(3-(6-amino-5-(tri-fluoromethyl)pyridin-3-yl)-1-iso propyl-1H-pyrazol-5-yl)-4'-methylspiro[bicyclo[3.1.0]hexane-3,2'-morpholin]-5'-one | (400 MHz, Methanol-d₄), δ: 8.49 (s, 1 H), 8.10 (s, 1 H), 6.18 (s, 1 H), 4.87-4.70 (m, 1 H), 4.19 (s, 2 H), 3.39 (s, 2 H), 2.98 (s, 3 H), 2.34-2.30 (m, 2 H), 2.10-2.05 (m, 3 H), 1.79-1.78 (m, 2 H), 1.51 (d, J = 6.8 Hz, 6 H). | 449.9 | S |
| 230 | 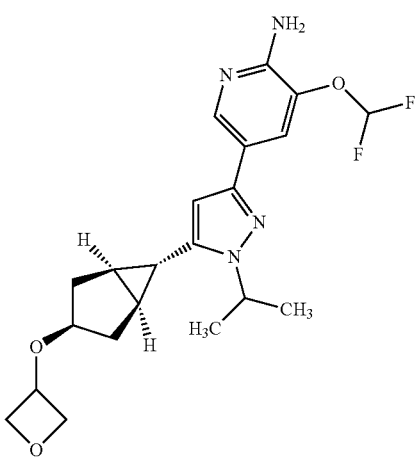 [SMILES: CC(C)n1nc(-c2cnc(N)c(OC(F)F)c2)cc1[C@H]1[C@@H]2C[C@H](OC3COC3)C[C@@H]21]<br>3-(difluoromethoxy)-5-(1-iso-oprpyl-5-((1R,3r,5S,6r)-3-(oxetan-3-yloxy)bicyclo[3.1.0]hexan-6-yl)-1H-pyrazol-3-yl)pyridin-2-amine | (400 MHz, CDCl₃), δ: 8.24 (s, 1 H), 7.78 (s, 1 H), 6.50 (t, J = 73.4 Hz, 1 H), 5.97 (s, 1 H), 4.92-4.78 (m, 1 H), 4.76 (m, 2 H), 4.64-4.55 (m, 4 H), 3.99-3.96 (m, 1 H), 2.12-2.06 (m, 3 H), 2.00-1.97 (m, 2 H), 1.54-1.53 (m, 7 H). | 421.2 | Q |

TABLE A-continued

| Cmpd No. | Structure | ¹H NMR | MS [MH]⁺ | Method |
|---|---|---|---|---|
| 231 | 3-(difluoromethoxy)-5-(1-isopropyl-5-((1R,3s,5S,6r)-3-(oxetan-3-yloxy)bicyclo[3.1.0]hexan-6-yl)-1H-pyrazol-3-yl)pyridin-2-amine | (400 MHz, CDCl₃), δ: 8.20 (s, 1 H), 7.69 (s, 1 H), 6.72-6.35 (t, $J_{HF}$ = 73.4 Hz, 1 H), 5.97 (s, 1 H), 4.75-4.72 (m, 2 H), 4.62-4.59 (m, 2 H), 4.55-4.52 (m, 2 H), 3.70-3.66 (m, 1 H), 2.30-2.25 (m, 2 H), 1.91-1.87 (m, 2 H), 1.65 (m, 2 H), 1.50-1.48 (d, J = 6.4 Hz, 6 H), 1.36-1.35 (m, 1 H). | 421.2 | Q |
| 232 | 5-(5-((1R,3s,5S,6r)-3-(1,4-oxazepan-4-yl)bicyclo[3.1.0]hexan-6-yl)-1-(2,2-difluoroethyl)-1H-pyrazol-3-yl)-3-(difluoromethoxy)pyridin-2-amine | (400 MHz, Methanl-d₄), δ: 8.40 (s, 1 H), 8.16-8.15 (m, 1 H), 7.72 (s, 1 H), 6.87 (t, $J_{HF}$ = 73.2 Hz, 1H), 6.38-6.10 (m, 2 H), 4.90-4.60 (m, 2 H), 3.92-3.81 (m, 4 H), 3.42-3.38 (m, 1 H), 3.32-3.30 (m, 4 H), 2.55-2.50 (m, 2 H), 2.16-2.14 (m, 4 H), 1.89-1.83 (m, 3 H). | 470.0 | E |

TABLE A-continued

| Cmpd No. | Structure | ¹H NMR | MS [MH]⁺ | Method |
|---|---|---|---|---|
| 233 | 5-(5-((1R,3r,5S,6r)-3-(1,4-oxazepan-4-yl)bicyclo[3.1.0]hexan-6-yl)-1-(2,2-difluoroethyl)-1H-pyrazol-3-yl)-3-(difluoromethoxy)pyridin-2-amine | (400 MHz, Methanol-$d_4$), δ: 8.41 (s, 1 H), 8.15 (s, 1 H), 7.72 (s, 1 H), 6.86 (t, $J_{HF}$ = 73.6 Hz, 1 H), 6.40-6.11 (m, 2 H), 4.89-4.59 (m, 2 H), 3.88-3.81 (m, 5 H), 3.32-3.25 (m, 4 H), 2.10-2.07 (m, 2 H), 1.84-1.83 (m, 2 H), 1.79-1.73 (m, 5 H). | 470.0 | E |
| 234 | 5-(1-isopropyl-5-((1R,3r,5S,6S)-3-((S)-3-methylpiperazin-1-yl)bicyclo[3.1.0]hexan-6-yl)-1H-pyrazol-3-yl)-3-(trifluoromethyl)pyridin-2-amine | (400 MHz, DMSO-$d_6$) δ: 8.53 (d, J = 2.1 Hz, 1H), 7.97 (d, J = 2.2 Hz, 1H), 6.44 (s, 2H), 6.30 (s, 1H), 4.74-4.62 (m, 1H), 2.80-2.72 (m, 1H), 2.71-2.58 (m, 4H), 2.43-2.34 (m, 1H), 2.15-2.05 (m, 2H), 1.87-1.77 (m, 1H), 1.76-1.57 (m, 5H), 1.54-1.36 (m, 7H), 0.90 (d, J = 6.2 Hz, 3H) | 449.4 | D |
| 235 | 5-(1-isopropyl-5-((1R,3s,5S,6S)-3-((S)-3-methylpiperazin-1-yl)bicyclo[3.1.0]hexan-6-yl)-1H-pyrazol-3-yl)-3-(trifluoromethyl)pyridin-2-amine | (400 MHz, DMSO-$d_6$) δ: 8.53 (s, 1H), 7.97 (d, J = 2.2 Hz, 1H), 6.44 (s, 2H), 6.26 (s, 1H), 4.71-4.63 (m, 1H), 2.82-2.72 (m, 4H), 2.63-2.56 (m, 2H), 2.12-2.07 (m, 3H), 1.96-1.90 (m, 1H), 1.79-1.52 (m, 5H), 1.43 (d, J = 6.6 Hz, 6H), 0.91 (d, J = 6.3 Hz, 3H) | 449.4 | D |

TABLE A-continued

| Cmpd No. | Structure | ¹H NMR | MS [MH]⁺ | Method |
|---|---|---|---|---|
| 236 | 5-(5-((1R,3s,5S,6r)-3-chlorobicyclo[3.1.0]hexan-6-yl)-1-isopropyl-1H-pyrazol-3-yl)-3-(difluoromethoxy)pyridin-2-amine | (400 MHz, DMSO- $d_6$) δ: 8.16 (d, J = 1.9 Hz, 1H), 7.57 (d, J = 1.8 Hz, 1H), 7.14 (t, J = 73.9 Hz, 1H), 6.23 (s, 1H), 6.07 (s, 2H), 4.73-4.62 (m, 1H), 4.35-4.22 (m, 1H), 2.55-2.50 (m, 1H), 2.50-2.45 (m, 1H), 2.10-1.99 (m, 2H), 1.93-1.86 (m, 1H), 1.74-1.67 (m, 2H), 1.40 (d, J = 6.5 Hz, 6H) | 282.2 | D |
| 237 | 5-(5-((1R,3s,5S,6S)-3-((S)-2,4-dimethylpiperazin-1-yl)bicyclo[3.1.0]hexan-6-yl)-1-isopropyl-1H-pyrazol-3-yl)-3-(trifluoromethoxy)pyridin-2-amine | (400 MHz, CDCl₃) δ: 8.32 (d, J = 1.9 Hz, 1H), 7.80 (d, J = 1.7 Hz, 1H), 5.99 (s, 1H), 4.70-4.53 (m, 3H), 3.03-2.80 (m, 2H), 2.77-2.64 (m, 1H), 2.57-2.29 (m, 6H), 2.28-2.23 (m, 3H), 2.18-2.08 (m, 1H), 2.07-1.97 (m, 1H), 1.96-1.84 (m, 2H), 1.72-1.59 (m, 2H), 1.57-1.47 (m, 6H), 1.11 (d, J = 6.5 Hz, 3H) | 479.4 | D |
| 238 | 3-(difluoromethoxy)-5-(5-((1R,3r,5S,6S)-3-((S)-2,4-dimethyl-piperazin-1-yl)bicyclo[3.1.0]hexan-6-yl)-1-isopropyl-1H-pyrazol-3-yl)pyridin-2-amine | (400 MHz, DMSO- $d_6$) δ: 8.15 (d, J = 1.9 Hz, 1H), 7.57 (d, J = 1.7 Hz, 1H), 7.15 (t, J = 73.9 Hz, 1H), 6.16 (s, 1H), 6.06 (s, 2H), 4.73-4.61 (m, 1H), 3.27-3.22 (m, 1H), 2.86-2.81 (m, 1H), 2.49-2.38 (m, 3H), 2.29-2.24 (m, 1H), 2.20-2.03 (m, 6H), 2.04-1.99 (m, 1H), 1.93-1.86 (m, 1H), 1.75-1.54 (m, 4H), 1.43 (d, J = 6.6 Hz, 6H), 0.98 (d, J = 6.4 Hz, 3H) | 461.4 | D |

| Cmpd No. | Structure | ¹H NMR | MS [MH]⁺ | Method |
|---|---|---|---|---|
| 239 | 5-(5-((1R,3s,5S,6S)-3-((S)-2,4-dimethylpiperazin-1-yl)bicyclo[3.1.0]hexan-6-yl)-1-isopropyl-1H-pyrazol-3-yl)-3-(trifluoromethyl)pyridin-2-amine | (400 MHz, DMSO-$d_6$) δ: 8.56-8.51 (m, 1H), 7.97 (d, J = 2.2 Hz, 1H), 6.44 (s, 2H), 6.29 (s, 1H), 4.76-4.64 (m, 1H), 2.97-2.92 (m, 1H), 2.76-2.71 (m, 1H), 2.40-2.32 (m, 2H), 2.28-2.20 (m, 1H), 2.20-2.15 (m, 3H), 2.12-1.87 (m, 5H), 1.82-1.53 (m, 5H), 1.41 (d, J = 6.6, 2.0 Hz, 6H), 1.00 (d, J = 6.4 Hz, 3H) | 463.4 | D |
| 240 | 5-(5-((1R,3r,5S,6S)-3-((S)-2,4-dimethylpiperazin-1-yl)bicyclo[3.1.0]hexan-6-yl)-1-isopropyl-1H-pyrazol-3-yl)-3-(trifluoromethoxy)pyridin-2-amine | (400 MHz, DMSO-$d_6$) δ: 8.28 (d, J = 1.9 Hz, 1H), 7.70 (d, J = 1.6 Hz, 1H), 6.39 (s, 2H), 6.21 (s, 1H), 4.73-4.61 (m, 1H), 2.86-2.81 (m, 1H), 2.46-2.39 (m, 3H), 2.29-2.24 (m, 2H), 2.20-2.04 (m, 7H), 1.93-1.86 (m, 1H), 1.75-1.54 (m, 4H), 1.42 (d, J = 6.6 Hz, 6H), 0.98 (d, J = 6.4 Hz, 3H) | 479.4 | D |

TABLE A-continued

| Cmpd No. | Structure | ¹H NMR | MS [MH]⁺ | Method |
|---|---|---|---|---|
| 241 | 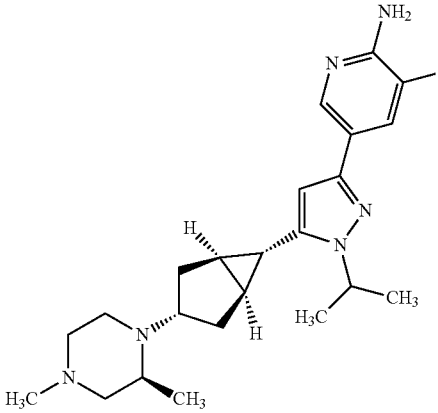<br>3-(difluoromethoxy)-5-(5-((1R,3s,5S,6S)-3-((S)-2,4-dimethyl-piperazin-1-yl)bicyclo[3.1.0]hexan-6-yl)-1-isopropyl-1H-pyrazol-3-yl)pyridin-2-amine | (400 MHz, DMSO-$d_6$) δ: 8.16 (d, J = 1.9 Hz, 1H), 7.60-7.55 (m, 1H), 7.15 (t, J = 73.9 Hz, 1H), 6.20 (s, 1H), 6.05 (s, 2H), 4.75-4.63 (m, 1H), 2.96-2.91 (m, 1H), 2.76-2.71 (m, 1H), 2.40-2.32 (m, 2H), 2.28-2.15 (m, 4H), 2.12-1.89 (m, 5H), 1.81-1.52 (m, 5H), 1.40 (d, J = 6.6, 6H), 1.00 (d, J = 6.4 Hz, 3H) | 461.4 | D |
| 242 | 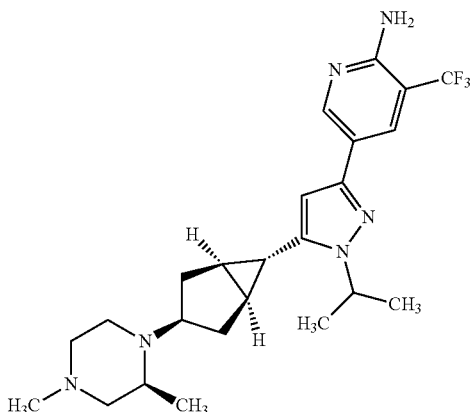<br>5-(5-((1R,3r,5S,6S)-3-((S)-2,4-dimethylpiperazin-1-yl)bicyclo[3.1.0]hexan-6-yl)-1-isopropyl-1H-pyrazol-3-yl)-3-(trifluoromethyl)pyridin-2-amine | (400 MHz, DMSO-$d_6$) δ: 8.56-8.50 (m, 1H), 7.97 (d, J = 2.1 Hz, 1H), 6.44 (s, 2H), 6.26 (s, 1H), 4.74-4.62 (m, 1H), 3.27-3.22 (m, 2H), 2.86-2.81 (m, 1H), 2.49-2.38 (m, 3H), 2.35-2.20 (m, 1H), 2.20-1.96 (m, 6H), 1.94-1.87 (m, 1H), 1.75-1.54 (m, 4H), 1.43 (d, J = 6.5 Hz, 6H), 0.98 (d, J = 6.4 Hz, 3H | 463.4 | D |

TABLE A-continued

| Cmpd No. | Structure | ¹H NMR | MS [MH]⁺ | Method |
|---|---|---|---|---|
| 243 | 5-(5-((1R,3s,5S,6r)-3-(1,4-oxazepan-4-yl)bicyclo[3.1.0]hexan-6-yl)-1-(2,2-difluoroethyl)-1H-pyrazol-3-yl)-3-(trifluoromethoxy)pyridin-2-amine | (400 MHz, CDCl$_3$) δ: 8.31 (s, 1 H), 8.29 (s, 1 H), 7.79 (s, 1 H), 6.35-6.05 (m, 2 H), 5.01 (s, 2 H), 4.52-4.46 (m, 2 H), 3.90 (t, J = 4.0 Hz, 2 H), 3.83 (t, J = 6.0 Hz, 2 H), 3.12-3.07 (m, 5 H), 2.36-2.27 (m, 4 H), 2.18-2.15 (m, 2 H), 1.79 (m, 2 H), 1.56 (m, 1 H) | 488.1 | W |
| 244 | 5-(1-isopropyl-5-((1R,3r,5S,6r)-3-(piperazin-1-yl)bicyclo[3.1.0]hexan-6-yl)-1H-pyrazol-3-yl)-3-(trifluoromethoxy)pyridin-2-amine | (400 MHz, CDCl$_3$), δ: 8.32 (s, 1 H), 7.80 (s, 1 H), 5.98 (s, 1 H), 4.70 (br s, 2 H), 4.65-4.55 (m, 1 H), 2.91 (t, J = 4.6 Hz, 4 H), 2.51-2.29 (m, 5 H), 2.22 (dd, J = 12.4, 7.2 Hz, 2 H), 1.83 (t, J = 9.4 Hz, 2 H), 1.67 (m, 3 H), 1.55-1.49 (m, 7 H). | 451.2 | A |

TABLE A-continued
| Cmpd No. | Structure | ¹H NMR | MS [MH]⁺ | Method |
|---|---|---|---|---|
| 245 | 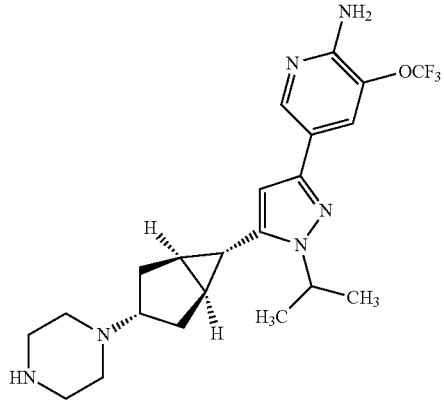 [SMILES: CC(C)n1nc(-c2cnc(N)c(OC(F)(F)F)c2)cc1[C@H]1[C@@H]2C[C@@H](N3CCNCC3)C[C@@H]21]<br>5-(1-isopropyl-5-((1R,3s,5S,6r)-3-(piperazin-1-yl)bicyclo[3.1.0]hexan-6-yl)-1H-pyrazol-3-yl)-3-(trifluoromethoxy)pyridin-2-amine | (400 MHz, CDCl₃), δ: 8.32 (s, 1 H), 7.80 (s, 1 H), 5.98 (s, 1 H), 4.70 (br s, 2 H), 4.65-4.56 (m, 1 H), 2.91 (t, J = 4.6 Hz, 4 H), 2.29-2.49 (m, 5 H), 2.22 (dd, J = 12.4, 7.0 Hz, 2 H), 1.83 (t, J = 9.4 Hz, 2 H), 1.67 (m, 3 H), 1.55-1.50 (m, 7 H). | 451.2 | A |
| 246 | 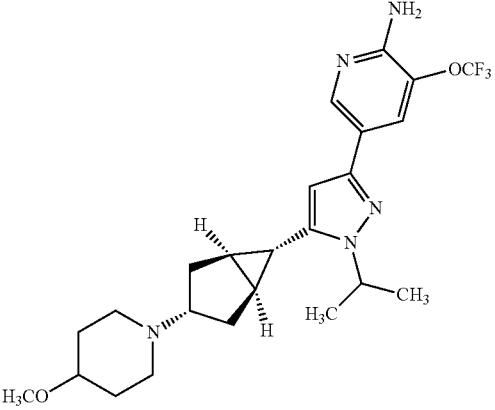 [SMILES: COC1CCN([C@@H]2C[C@@H]3[C@H](C2)[C@H]3c2cc(-c3cnc(N)c(OC(F)(F)F)c3)nn2C(C)C)CC1]<br>5-(1-isopropyl-5-((1R,3s,5S,6r)-3-(4-methoxypiperidin-1-yl)bicyclo[3.1.0]hexan-6-yl)-1H-pyrazol-3-yl)-3-(trifluoromethoxy)pyridin-2-amine | (400 MHz, DMSO-d₆) δ: 8.28 (d, J = 1.9 Hz, 1H), 7.73-7.67 (m, 1H), 6.39 (s, 2H), 6.25 (s, 1H), 4.72-4.61 (m, 1H), 3.21 (s, 3H), 3.18-3.07 (m, 1H), 2.71-2.63 (m, 2H), 2.48-2.39 (m, 1H), 2.15-1.96 (m, 4H), 1.85-1.76 (m, 2H), 1.76-1.56 (m, 5H), 1.40 (m, 8H) | 480.2 | D |

TABLE A-continued

| Cmpd No. | Structure | ¹H NMR | MS [MH]⁺ | Method |
|---|---|---|---|---|
| 247 | 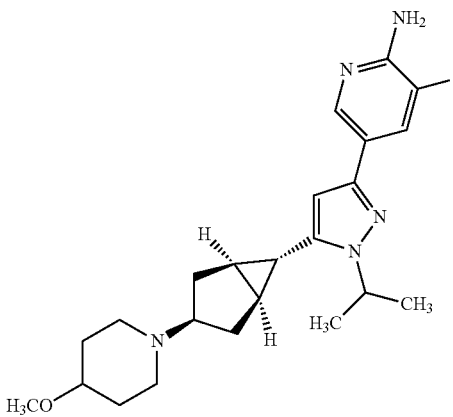<br>3-(difluoromethoxy)-5-(1-isopropyl-5-((1R,3r,5S,6r)-3-(4-methoxypiperidin-1-yl)bicyclo[3.1.0]hexan-6-yl)-1H-pyrazol-3-yl)pyridin-2-amine | (400 MHz, DMSO-$d_6$) δ: 8.15 (d, J = 1.9 Hz, 1H), 7.60-7.57 (m, 1H), 7.57 (d, J = 1.9 Hz, 1H), 7.15 (t, J = 73.9 Hz, 1H), 6.16 (s, 1H), 6.05 (s, 2H), 4.73-4.61 (m, 1H), 3.21 (s, 3H), 3.18-3.07 (m, 1H), 2.88-2.75 (m, 1H), 2.72-2.65 (m, 2H), 2.20-2.08 (m, 2H), 2.03-1.93 (m, 2H), 1.88-1.76 (m, 3H), 1.66-1.54 (m, 4H), 1.46-1.28 (m, 8H) | 462.2 | D |
| 248 | 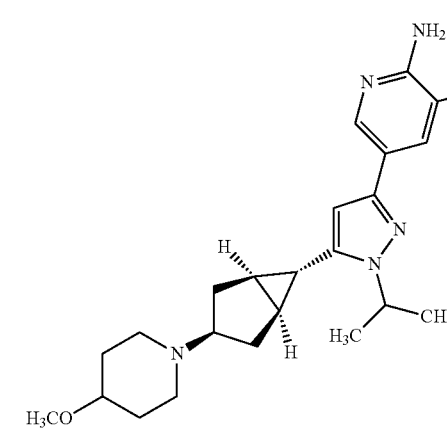<br>5-(1-isopropyl-5-((1R,3r,5S,6r)-3-(4-methoxypiperidin-1-yl)bicyclo[3.1.0]hexan-6-yl)-1H-pyrazol-3-yl)-3-(trifluoromethoxy)pyridin-2-amine | (400 MHz, DMSO-$d_6$) δ: 8.28 (d, J = 1.9 Hz, 1H), 7.73-7.66 (m, 1H), 6.39 (s, 2H), 6.21 (s, 1H), 4.75-4.60 (m, 1H), 3.21 (s, 3H), 3.18-3.07 (m, 1H), 2.87-2.78 (m, 1H), 2.73-2.65 (m, 2H), 2.20-2.09 (m, 2H), 2.04-1.93 (m, 2H), 1.88-1.77 (m, 3H), 1.67-1.55 (m, 4H), 1.47-1.29 (m, 8H) | 480.2 | D |

TABLE A-continued

| Cmpd No. | Structure | $^1$H NMR | MS [MH]$^+$ | Method |
|---|---|---|---|---|
| 249 | 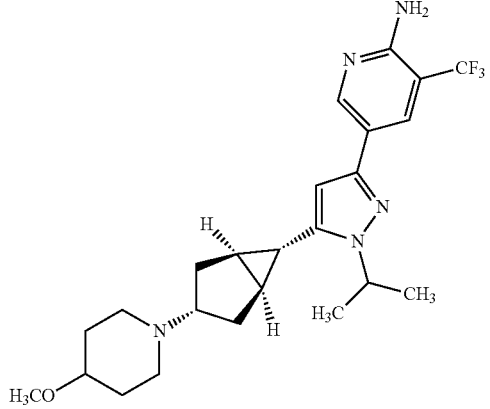 [SMILES: COC1CCN([C@@H]2C[C@@H]3[C@H](C2)[C@H]3c2cc(-c3cnc(N)c(C(F)(F)F)c3)nn2C(C)C)CC1]<br>5-(1-isopropyl-5-((1R,3s,5S,6r)-3-(4-methoxypiperidin-1-yl)bicyclo[3.1.0]hexan-6-yl)-1H-pyrazol-3-yl)-3-(trifluoromethyl)pyridin-2-amine | (400 MHz, DMSO-$d_6$) δ: 8.53 (d, 1H), 7.97 (d, J = 2.2 Hz, 1H), 6.43 (s, 2H), 6.29 (s, 1H), 4.73-4.62 (m, 1H), 3.21 (s, 3H), 3.18-3.07 (m, 1H), 2.72-2.62 (m, 2H), 2.49-2.36 (m, 1H), 2.15-1.96 (m, 4H), 1.85-1.54 (m, 7H), 1.40 (m, 8H) | 464.2 | D |
| 250 | 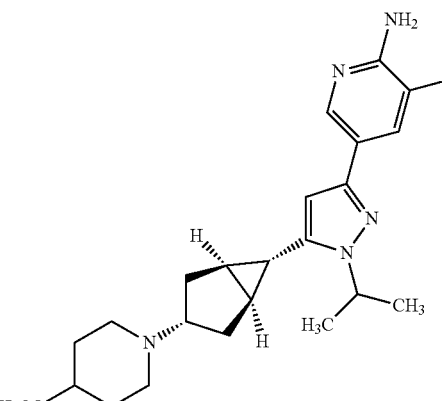<br>3-(difluoromethoxy)-5-(1-isopropyl-5-((1R,3s,5S,6r)-3-(4-methoxypiperidin-1-yl)bicyclo[3.1.0]hexan-6-yl)-1H-pyrazol-3-yl)pyridin-2-amine | (400 MHz, DMSO-$d_6$) δ: 8.15 (d, J = 1.9 Hz, 1H), 7.56 (d, J = 2.0 Hz, 1H), 7.37-6.89 (m, 1H), 6.20 (s, 1H), 6.08 (s, 2H), 4.72-4.61 (m, 1H), 3.21 (s, 3H), 3.18-3.04 (m, 1H), 2.72-2.64 (m, 2H), 2.46-2.41 (m, 1H), 2.18-2.05 (m, 2H), 2.02-1.97 (m, 2H), 1.85-1.77 (m, 3H), 1.74-1.62 (m, 4H), 1.62-1.55 (m, 2H), 1.43-1.37 (m, 6H) | 462.2 | D |

TABLE A-continued

| Cmpd No. | Structure | ¹H NMR | MS [MH]⁺ | Method |
|---|---|---|---|---|
| 251 | 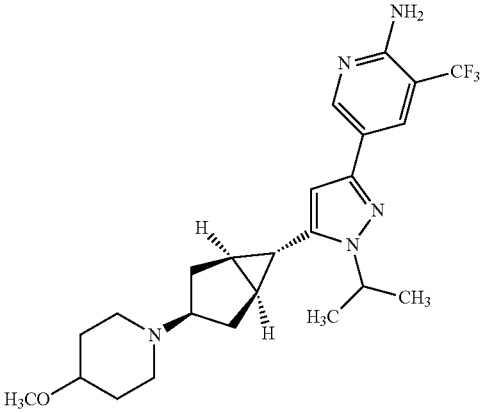 [SMILES: COC1CCN([C@H]2C[C@@H]3[C@H](C2)[C@H]3c2cc(-c3cnc(N)c(C(F)(F)F)c3)nn2C(C)C)CC1]<br>5-(1-isopropyl-5-((1R,3r,5S,6r)-3-(4-methoxypiperidin-1-yl)bicyclo[3.1.0]hexan-6-yl)-1H-pyrazol-3-yl)-3-(trifluoromethyl)pyridin-2-amine | (400 MHz, DMSO-d₆) δ: 8.53 (d, 1H), 7.97 (d, J = 2.3 Hz, 1H), 6.44 (s, 2H), 6.26 (s, 1H), 4.74-4.62 (m, 1H), 3.21 (s, 3H), 3.18-3.07(m, 1H), 2.88-2.75 (m, 1H), 2.74-2.65 (m, 1H), 2.20-2.08 (m, 2H), 2.03-1.93 (m, 2H), 1.89-1.77 (m, 3H), 1.67-1.55 (m, 4H), 1.47-1.29 (m, 8H) | 464.3 | D |
| 252 | 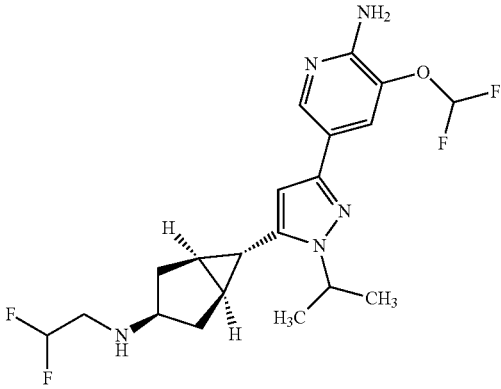 [SMILES: CC(C)n1nc(-c2cnc(N)c(OC(F)F)c2)cc1[C@H]1[C@@H]2C[C@H](NCC(F)F)C[C@@H]21]<br>5-(5-((1R,3r,5S,6r)-3-((2,2-difluoroethyl)amino)bicyclo[3.1.0]hexan-6-yl)-1-isopropyl-1H-pyrazol-3-yl)-3-(difluoromethoxy)pyridin-2-amine | (400 MHz, Methanol-d₄), δ: 8.12 (s, 1 H), 7.70 (s, 1 H), 6.86 (t, J = 73.6 Hz, 1 H), 6.07 (s, 1 H), 6.00-5.70 (m, 1 H), 4.78-4.72 (m, 1 H), 3.45-3.42 (m, 1 H), 2.93-2.85 (m, 2 H), 2.33-2.24 (m, 3 H), 1.78-1.66 (m, 4 H), 1.51 (d, J = 6.8 Hz, 6 H) | 428.2 | V |
| 253 | 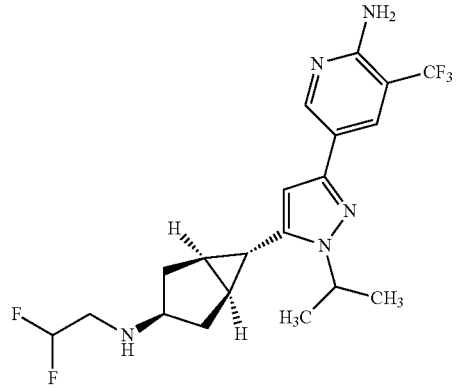 [SMILES: CC(C)n1nc(-c2cnc(N)c(C(F)(F)F)c2)cc1[C@H]1[C@@H]2C[C@H](NCC(F)F)C[C@@H]21]<br>5-(5-((1R,3r,5S,6r)-3-((2,2-difluoroethyl)amino)bicyclo[3.1.0]hexan-6-yl)-1-isopropyl-1H-pyrazol-3-yl)-3-(trifluoromethyl)pyridin-2-amine | (400 MHz, Methanol-d₄), δ: 8.48 (s, 1 H), 8.10 (s, 1 H), 6.12 (s, 1 H), 6.01-5.72 (m, 1 H), 4.78-4.73 (m, 1 H), 3.43-3.40 (m, 1 H), 2.94-2.86 (m, 2 H), 2.34-2.25 (m, 3 H), 1.78-1.67 (m, 4 H), 1.51 (d, J = 6.8 Hz, 6 H) | 430.2 | V |

TABLE A-continued

| Cmpd No. | Structure | $^1$H NMR | MS [MH]$^+$ | Method |
|---|---|---|---|---|
| 254 | 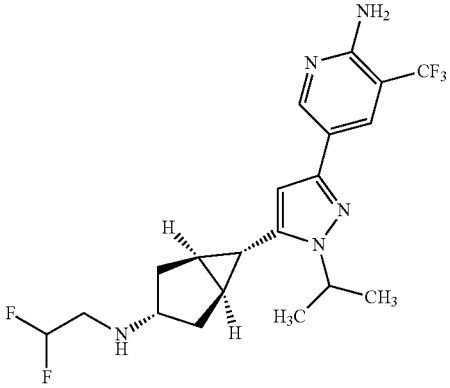 [SMILES: CC(C)n1nc(-c2cnc(N)c(C(F)(F)F)c2)cc1[C@H]1[C@@H]2C[C@@H](NCC(F)F)C[C@@H]21]<br>5-(5-((1R,3s,5S,6r)-3-((2,2-difluoroethyl)amino)bicyclo[3.1.0]hexan-6-yl)-1-isopropyl-1H-pyrazol-3-yl)-3-(trifluoromethyl)pyridin-2-amine | (400 MHz, Methanol-d$_4$), δ: 8.49 (m, 1 H), 8.10 (d, J = 2 Hz, 1 H), 6.17 (s, 1 H), 6.05-5.74 (m, 1 H), 4.78-4.72 (m, 1 H), 3.06-2.88 (m, 3 H), 2.37-2.32 (m, 2 H), 1.72-1.66 (m, 5 H), 1.50 (d, J = 7.2 Hz, 6 H) | 430.2 | V |
| 255 | 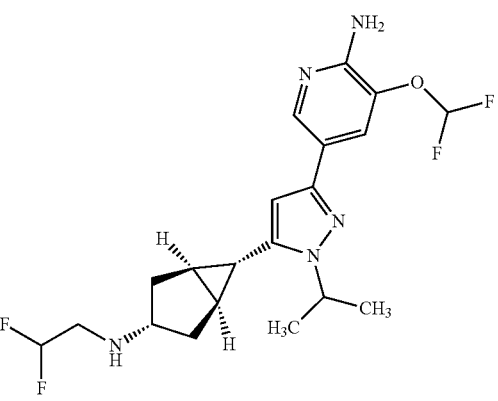 [SMILES: CC(C)n1nc(-c2cnc(N)c(OC(F)F)c2)cc1[C@H]1[C@@H]2C[C@@H](NCC(F)F)C[C@@H]21]<br>5-(5-((1R,3s,5S,6r)-3-((2,2-difluoroethyl)amino)bicyclo[3.1.0]hexan-6-yl)-1-isopropyl-1H-pyrazol-3-yl)-3-(difluoromethoxy)pyridin-2-amine | (400 MHz, Methanol-d$_4$), δ: 8.13 (s, 1 H), 7.70 (s, 1 H), 6.86 (t, J$_{HF}$ = 73.6 Hz, 1 H), 6.12 (s, 1 H), 6.04-5.74 (m, 1 H), 4.83-4.69 (m, 1 H), 3.04-2.88 (m, 3 H), 2.37-2.31 (m, 2 H), 1.71-1.66 (m, 5 H), 1.50 (d, J = 6.8 Hz, 6 H) | 428.2 | V |
| 256 | 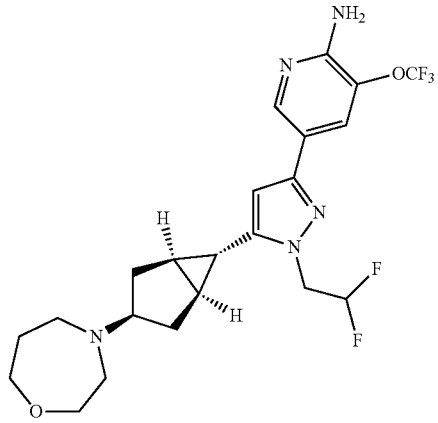 [SMILES: Nc1ncc(-c2cc([C@H]3[C@@H]4C[C@H](N5CCCOCC5)C[C@@H]43)n(CC(F)F)n2)cc1OC(F)(F)F]<br>5-(5-((1R,3r,5S,6r)-3-(1,4-oxazepan-4-yl)bicyclo[3.1.0]hexan-6-yl)-1-(2,2-difluoroethyl)-1H-pyrazol-3-yl)-3-(trifluoromethoxy)pyridin-2-amine | (400 MHz, CDCl$_3$) δ: 8.30 (s, 1 H), 7.76 (s, 1 H), 6.30-6.04 (m, 1 H), 5.99 (s, 1 H), 4.75 (s, 2 H), 4.53-4.46 (m, 2 H), 3.79-3.72 (m, 4 H), 3.33-3.29 (m, 1 H), 2.71 (m, 4 H), 2.30-2.27 (m, 2 H), 1.88-1.82 (m, 3 H), 1.68-1.64 (m, 4 H) | 488.1 | W |

TABLE A-continued

| Cmpd No. | Structure | ¹H NMR | MS [MH]⁺ | Method |
|---|---|---|---|---|
| 257 | 5-(5-((1R,3s,5S,6r)-3-(4-(2,2-difluoro-ethyl)piperazin-1-yl)bicyclo[3.1.0]hexan-6-yl)-1-isopropyl-1H-pyrazol-3-yl)-3-(difluoromethoxy)pyridin-2-amine | (400 MHz, DMSO-d₆) δ: 8.16 (d, J = 1.9 Hz, 1H), 7.60-7.54 (m, 1H), 7.15 (t, J = 73.9 Hz, 1H), 6.20 (s, 1H), 6.11 (m, 1H), 6.06 (s, 2H), 4.73-4.61 (m, 1H), 2.75-2.61 (m, 2H), 2.55-2.50 (m, 3H), 2.51-2.34 (m, 6H), 2.16-2.06 (m, 2H), 1.76-1.57 (m, 5H), 1.40 (d, J = 6.5 Hz, 6H) | 497.3 | D |
| 258 | 3-(difluoromethoxy)-5-(5-((1R,3s,5S,6r)-3-(hexahydropyrrolo[1,2-a]pyrazin-2(1H)-yl)bicyclo[3.1.0]hexan-6-yl)-1-isopropyl-1H-pyrazol-3-yl)pyridin-2-amine (Stereoisomer 1) | (400 MHz, DMSO-d₆) δ: 8.16 (d, J = 1.9 Hz, 1H), 7.60-7.54 (m, 1H), 7.15 (t, J = 73.9 Hz, 1H), 6.21 (s, 1H), 6.06 (s, 2H), 4.73-4.61 (m, 1H), 2.95-2.83 (m, 3H), 2.78-2.71 (m, 1H), 2.49-2.42 (m, 2H), 2.20-1.80 (m, 5H), 1.78-1.52 (m, 9H), 1.40 (d, J = 6.5 Hz, 6H), 1.29-1.19 (m, 1H) | 473.3 | D |

TABLE A-continued

| Cmpd No. | Structure | ¹H NMR | MS [MH]⁺ | Method |
|---|---|---|---|---|
| 259 | 3-(difluoromethoxy)-5-(5-((1R,3s,5S,6r)-3-(hexahydropyrrolo[1,2-a]pyrazin-2(1H)-yl)bicyclo[3.1.0]hexan-6-yl)-1-isopropyl-1H-pyrazol-3-yl)pyridin-2-amine (Stereoisomer 2) | (400 MHz, DMSO-$d_6$) δ: 8.15 (d, J = 1.9 Hz, 1H), 7.60-7.54 (m, 1H), 7.15 (t, J = 73.9 Hz, 1H), 6.17 (s, 1H), 6.06 (s, 2H), 4.72-4.61 (m, 1H), 3.36-3.24 (m, 1H), 3.01-2.77 (m, 5H), 2.17-1.86 (m, 7H), 1.77-1.55 (m, 8H), 1.42 (d, J = 6.5 Hz, 6H), 1.32-1.19 (m, 1H) | 473.3 | D |
| 260 | 3-(difluoromethoxy)-5-(5-((1R,3r,5S,6r)-3-(hexahydropyrrolo[1,2-a]pyrazin-2(1H)-yl)bicyclo[3.1.0]hexan-6-yl)-1-isopropyl-1H-pyrazol-3-yl)pyridin-2-amine (Mixture of diastereomers) | (400 MHz, DMSO-$d_6$) δ: 8.15 (d, J = 1.9 Hz, 1H), 7.60-7.54 (m, 1H), 7.15 (t, J = 73.9 Hz, 1H), 6.17 (s, 1H), 6.06 (s, 2H), 4.72-4.61 (m, 1H), 3.36-3.24 (m, 1H), 3.01-2.77 (m, 5H), 2.17-1.86 (m, 7H), 1.77-1.55 (m, 8H), 1.42 (d, J = 6.5 Hz, 6H), 1.32-1.19 (m, 1H) | 473.3 | D |

TABLE A-continued

| Cmpd No. | Structure | ¹H NMR | MS [MH]⁺ | Method |
|---|---|---|---|---|
| 261 | 5-(5-((1R,3s,5S,6r)-3-(hexahydropyrrolo[1,2-a]pyrazin-2(1H)-yl)bicyclo[3.1.0]hexan-6-yl)-1-isopropyl-1H-pyrazol-3-yl)-3-(trifluoromethyl)pyridin-2-amine (Stereoisomer 1) | (400 MHz, CDCl$_3$) δ: 8.59-8.49 (m, 1H), 8.15-8.00 (m, 1H), 6.00 (d, J = 0.6 Hz, 1H), 4.92 (s, 2H), 4.67-4.51 (m, 1H), 3.14-2.98 (m, 3H), 2.94-2.82 (m, 1H), 2.51-2.37 (m, 1H), 2.26-2.20 (m, 5H), 1.95-1.76 (m, 7H), 1.71-1.63 (m, 2H), 1.58-1.54 (m, 1H), 1.52 (d, J = 6.6 Hz, 6H), 1.42 (m, 1H) | 475.3 | D |
| 262 | 5-(5-((1R,3r,5S,6r)-3-(hexahydropyrrolo[1,2-a]pyrazin-2(1H)-yl)bicyclo[3.1.0]hexan-6-yl)-1-isopropyl-1H-pyrazol-3-yl)-3-(trifluoromethyl)pyridin-2-amine (Mixture of diastereomers) | (400 MHz, DMSO-d$_6$) δ: 8.56-8.50 (m, 1H), 7.97 (d, J = 2.2 Hz, 1H), 6.44 (s, 2H), 6.26 (s, 1H), 4.73-4.62 (m, 1H), 3.01-2.77(m, 5H), 2.20-1.81 (m, 7H), 1.77-1.56 (m, 8H), 1.43 (d, J = 6.5 Hz, 6H), 1.32-1.19 (m, 1H) | 475.3 | D |

TABLE A-continued

| Cmpd No. | Structure | ¹H NMR | MS [MH]⁺ | Method |
|---|---|---|---|---|
| 263 | 5-(5-((1R,3s,5S,6r)-3-(hexahydro-pyrrolo[1,2-a]pyrazin-2(1H)-yl)bicyclo[3.1.0]hexan-6-yl)-1-isopropyl-1H-pyrazol-3-yl)-3-(trifluoromethyl)pyridin-2-amine (Stereoisomer 2) | (400 MHz, CDCl₃) δ: 8.57-8.51 (m, 1H), 8.10 (d, J = 2.2 Hz, 1H), 6.00 (s, 1H), 4.91 (s, 2H), 4.69-4.54 (m, 1H), 3.16-2.97 (m, 3H), 2.93-2.85 (m, 1H), 2.54-2.37 (m, 1H), 2.37-1.95 (m, 4H), 1.93-1.69 (m, 7H), 1.69-1.64 (m, 3H), 1.59-1.55 (m, 1H), 1.52 (d, J = 6.6 Hz, 6H), 1.47-1.32 (m, 1H) | 475.3 | D |
| 264 | 5-(5-((1R,3r,5S,6r)-3-(4-(2,2-difluoroethyl)piperazin-1-yl)bicyclo[3.1.0]hexan-6-yl)-1-isopropyl-1H-pyrazol-3-yl)-3-(difluoromethoxy)pyridin-2-amine | (400 MHz, DMSO-d₆) δ: 8.15 (d, J = 1.9 Hz, 1H), 7.60-7.54 (m, 1H), 7.15 (t, J = 73.9 Hz, 1H), 6.17 (s, 1H), 6.11 (m, 1H), 6.06 (s, 2H), 4.72-4.60 (m, 1H), 2.84-2.61 (m, 3H), 2.55-2.46 (m, 4H), 2.39-2.34 (m, 4H), 2.16-2.05 (m, 2H), 1.95-1.88 (m, 1H), 1.73-1.63 (m, 2H), 1.64-1.55 (m, 2H), 1.43 (d, J = 6.6 Hz, 6H) | 497.3 | D |

TABLE A-continued
| Cmpd No. | Structure | ¹H NMR | MS [MH]⁺ | Method |
|---|---|---|---|---|
| 265 | 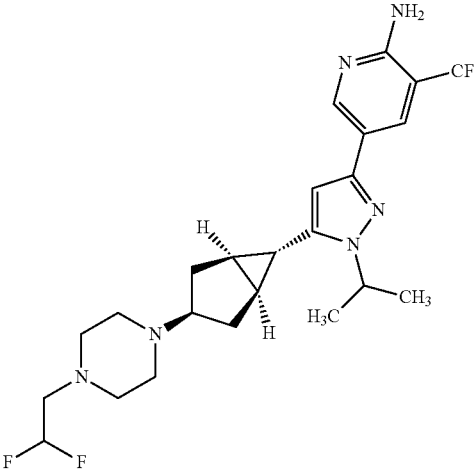<br>5-(5-((1R,3r,5S,6r)-3-(4-(2,2-difluoroethyl)piperazin-1-yl)bicyclo[3.1.0]hexan-6-yl)-1-isopropyl-1H-pyrazol-3-yl)-3-(trifluoromethyl)pyridin-2-amine | (400 MHz, DMSO-$d_6$) δ: 8.56-8.51 (m, 1H), 7.97 (d, J = 2.2 Hz, 1H), 6.45 (s, 2H), 6.35-5.84 (m, 2H), 4.73-4.61 (m, 1H), 2.81-2.76 (m, 1H), 2.75-2.62 (m, 2H), 2.55-2.45 (m, 4H), 2.39-2.34 (m, 4H), 2.13-2.08 (m, 2H), 1.95-1.88 (m, 1H), 1.74-1.64 (m, 2H), 1.62-1.57 (m, 2H), 1.43 (d, J = 6.6 Hz, 6H) | 499.3 | D |
| 266 | 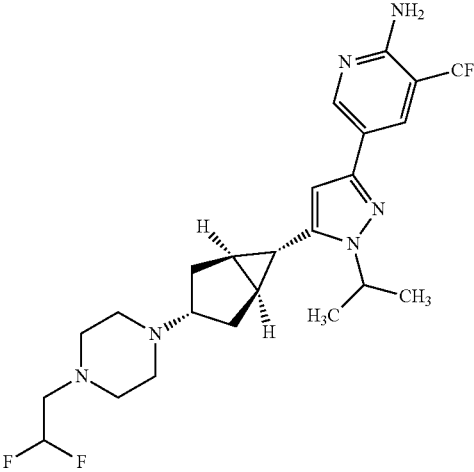 | (400 MHz DMSO-$d_6$) δ: 8.56-8.51 (m, 1H), 7.97 (d, J = 2.2 Hz, 1H), 6.44 (s, 2H), 6.30 (s, 1H), 6.28-5.90 (m, 1H), 4.74-4.62 (m, 1H), 2.75-2.62 (m, 2H), 2.55-2.50 (m, 4H), 2.39-2.34 (m, 5H), 2.16-2.06 (m, 2H), 1.77-1.58 (m, 5H), 1.40 (d, J = 6.6 Hz, 6H) | 499.3 | D |

TABLE A-continued

| Cmpd No. | Structure | ¹H NMR | MS [MH]⁺ | Method |
|---|---|---|---|---|
| 267 | 5-(1-(cyclopropylmethyl)-3-((1R,3r,5S,6r)-3-morpholinobicyclo[3.1.0]hexan-6-yl)-1H-pyrazol-5-yl)-3-(difluoromethoxy)pyridin-2-amine | (400 MHz, CDCl₃), δ: 8.28 (s, 1 H), 8.19 (s, 1 H), 6.55 (t, $J_{HF}$ = 73.6 Hz, 1 H), 5.91 (s, 1 H), 5.10 (s, 2 H), 3.88-3.82 (m, 6 H), 3.26 (m, 1 H), 2.75 (m, 1 H), 2.39-2.37 (d, J = 6.0 Hz, 2 H), 1.87-1.71 (m, 5 H), 1.14 (m, 1 H), 0.51-0.18 (m, 4 H) | 446.0 | W |
| 268 | 5-(1-(cyclopropylmethyl)-3-((1R,3s,5S,6r)-3-morpholinobicyclo[3.1.0]hexan-6-yl)-1H-pyrazol-5-yl)-3-(difluoromethoxy)pyridin-2-amine | (400 MHz, CDCl₃), δ: 7.95 (s, 1 H), 7.29 (s, 1 H), 6.54 (t, $J_{HF}$ = 73.6 Hz, 1 H), 6.00 (s, 1 H), 4.87 (s, 2 H), 3.87 (d, J = 6.8 Hz, 2 H), 3.75 (m, 4 H), 2.48-1.69 (m, 13 H), 0.52-0.20 (m, 4 H) | 446.1 | W |
| 269 | 5-(5-((1R,3r,5S,6r)-3-aminobicyclo[3.1.0]hexan-6-yl)-1-isopropyl-1H-pyrazol-3-yl)-3-(trifluoromethyl)pyridin-2-amine | (400 MHz, Methanol-d₄), δ: 8.70 (s, 1 H), 8.46 (s, 1 H), 6.39 (s, 1 H), 4.86-4.83 (m, 1 H), 4.03-3.98 (m, 1 H), 2.72-2.66 (m, 2 H), 1.90-1.81 (m, 5 H), 1.53 (d, J = 6.8 Hz, 6 H) | 365.8 | A |

TABLE A-continued

| Cmpd No. | Structure | ¹H NMR | MS [MH]⁺ | Method |
|---|---|---|---|---|
| 270 | 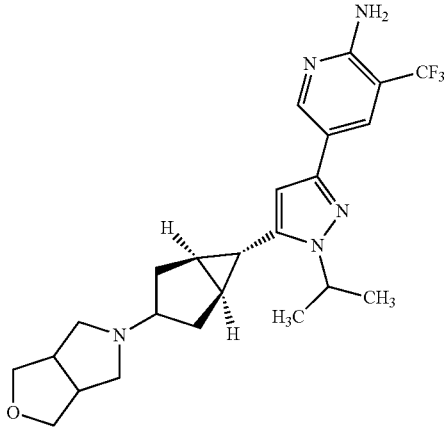<br>5-(1-isopropyl-5-((1R,5S,6r)-3-(tetrahydro-1H-furo[3,4-c]pyrrol-5(3H)-yl)bicyclo[3.1.0]hexan-6-yl)-1H-pyrazol-3-yl)-3-(trifluoromethyl)pyridin-2-amine (Stereoisomer 1) | (400 MHz, CDCl$_3$), δ: 8.54 (s, 1 H), 8.10 (s, 1 H), 5.94 (s, 1 H), 4.93 (br s, 2 H), 4.68-4.59 (m, 1H), 3.87 (t, J = 6.8 Hz, 2 H), 3.49 (d, J = 6.1 Hz, 2 H), 2.75 (m, 3 H), 2.46 (m, 4 H), 2.18 (m, 1 H), 2.12 (m, 2 H), 1.85-1.94 (m, 2 H), 1.61 (m, 2 H), 1.53 (d, J = 6.4 Hz, 6 H) | 462.2 | A |
| 271 | 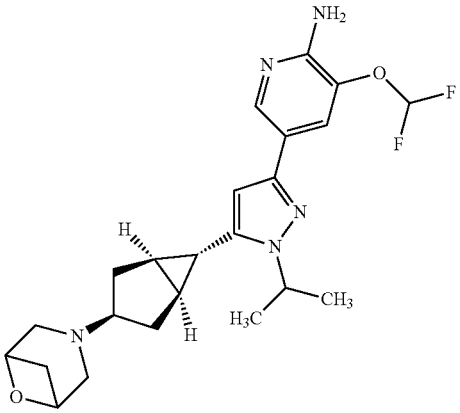 [SMILES: CC(C)n1nc(-c2cnc(N)c(OC(F)F)c2)cc1[C@H]1[C@@H]2C[C@H](N3CC4CC(C3)O4)C[C@@H]21]<br>5-(5-((1R,3r,5S,6r)-3-(6-oxa-3-azabicyclo[3.1.1]heptan-3-yl)bicyclo[3.1.0]hexan-6-yl)-1-isopropyl-1H-pyrazol-3-yl)-3-(difluoromethoxy)pyridin-2-amine | (400 MHz, CDCl$_3$), δ: 8.25 (s, 1H), 7.71 (s, 1H), 6.55 (t, J$_{HF}$ = 74 Hz, 1 H), 5.97 (s, 1 H), 4.70-4.53 (m, 3 H), 4.51-4.45 (m, 2 H), 3.19-3.16 (m, 2 H), 3.02-3.00 (m, 1 H), 2.70-2.67 (m, 2 H), 2.23-1.98 (m, 7 H), 1.65-1.24 (m, 8 H) | 446.2 | A |
| 272 | 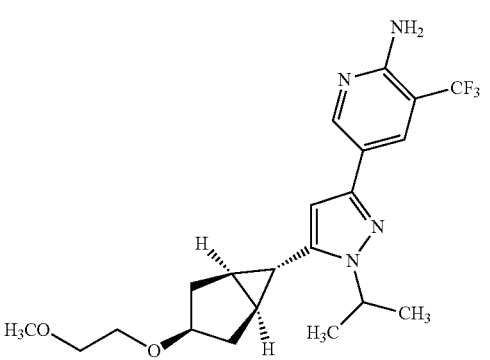 [SMILES: COCCO[C@H]1C[C@@H]2[C@H](C1)[C@H]2c1cc(-c2cnc(N)c(C(F)(F)F)c2)nn1C(C)C]<br>5-(1-isopropyl-5-((1R,3r,5S,6r)-3-(2-methoxyethoxy)bicyclo[3.1.0]hexan-6-yl)-1H-pyrazol-3-yl)-3-(trifluoromethyl)pyridin-2-amine | (400 MHz, CDCl$_3$) δ: 8.54 (s, 1 H), 8.10 (s, 1 H), 5.97 (s, 1 H), 4.91 (s, 2 H), 4.70-4.63 (m, 1 H), 4.03 (t, J = 5.6 Hz, 1 H), 3.51 (m, 4 H), 3.38 (m, 1 H), 2.11-2.04 (m, 5 H), 1.61-1.57 (m, 2 H), 1.52 (d, J = 6.4 Hz, 6 H) | 425.2 | Q |

| Cmpd No. | Structure | ¹H NMR | MS [MH]⁺ | Method |
|---|---|---|---|---|
| 273 | 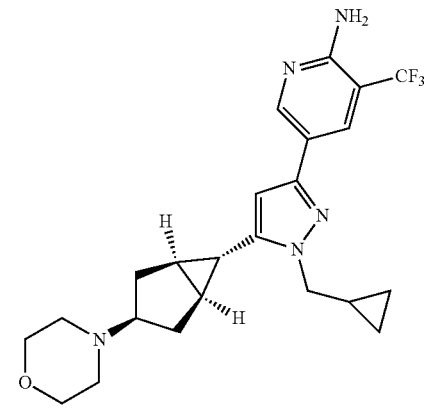 [SMILES: Nc1ncc(-c2cc([C@H]3[C@@H]4C[C@H](N5CCOCC5)C[C@@H]43)n(CC3CC3)n2)cc1C(F)(F)F]<br>5-(1-(cyclopropylmethyl)-5-((1R,3r,5S,6r)-3-morpholinobicyclo[3.1.0]hexan-6-yl)-1H-pyrazol-3-yl)-3-(trifluoromethyl)pyridin-2-amine | (400 MHz, CDCl$_3$) δ: 8.55 (s, 1 H), 8.09 (s, 1 H), 5.95 (s, 1 H), 4.95 (s, 2 H), 4.05 (d, J = 7.2 Hz, 2 H), 3.72 (m, 4 H), 2.87 (m, 1 H), 2.45 (m, 4 H), 2.25-2.17 (m, 2 H) 1.89 (m, 1 H) 1.72-1.61 (m, 4 H) 1.34-1.26 (m, 1 H) 0.62-0.42 (m, 4 H) | 448.0 | W |
| 274 | 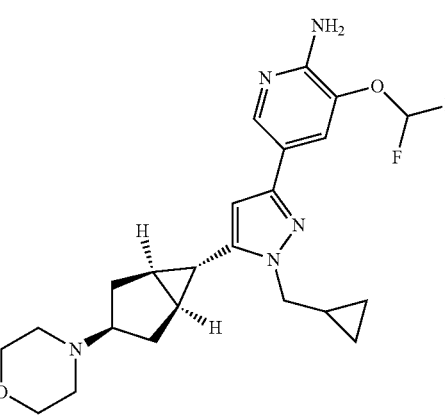<br>5-(1-(cyclopropylmethyl)-5-((1R,3r,5S,6r)-3-morpholinobicyclo[3.1.0]hexan-6-yl)-1H-pyrazol-3-yl)-3-(difluoromethoxy)pyridin-2-amine | (400 MHz, CDCl$_3$), δ: 8.24 (s, 1 H), 7.69 (s, 1 H), 6.55 (t, J$_{HF}$ = 73.6 Hz, 1 H), 5.94 (s, 1 H), 4.73 (s, 2 H), 4.05 (d, J = 6.8 Hz, 2 H), 3.73 (m, 4 H), 2.90-1.33 (m, 13 H), 0.62-0.42 (m, 4 H) | 446.2 | W |
| 275 | 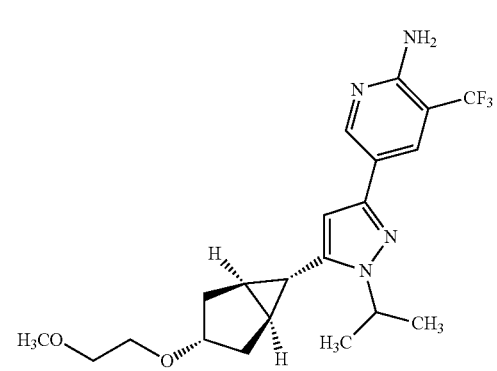 [SMILES: COCCO[C@@H]1C[C@@H]2[C@H](C1)[C@H]2c1cc(-c2cnc(N)c(C(F)(F)F)c2)nn1C(C)C]<br>5-(1-isopropyl-5-((1R,3s,5S,6r)-3-(2-methoxyethoxy)bicyclo[3.1.0]hexan-6-yl)-1H-pyrazol-3-yl)-3-(trifluoromethyl)pyridin-2-amine | (400 MHz, CDCl$_3$) δ: 8.53 (s, 1 H), 8.09 (s, 1 H), 6.00 (s, 1 H), 4.92 (s, 2 H), 4.62-4.57 (m, 1 H), 3.85-3.3.79 (m, 1 H), 3.56-3.52 (m, 4 H), 3.39 (s, 3 H), 2.37 (dd, J = 7.6 Hz, 13.2 Hz, 2 H), 1.95-1.92 (m, 2 H), 1.65 (m, 2 H), 1.51 (d, J = 6.8 Hz, 6 H), 1.38 (m, 1 H) | 425.2 | Q |

TABLE A-continued

| Cmpd No. | Structure | ¹H NMR | MS [MH]⁺ | Method |
|---|---|---|---|---|
| 276 | 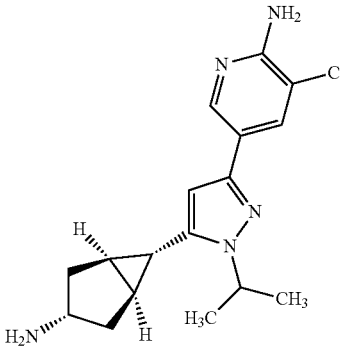 5-(5-((1R,3s,5S,6r)-3-aminobicyclo[3.1.0]hexan-6-yl)-1-isopropyl-1H-pyrazol-3-yl)-3-(trifluoromethyl)pyridin-2-amine | (400 MHz, Methanol-$d_4$), δ: 8.61 (s, 1 H), 8.45 (s, 1 H), 6.37 (s, 1 H), 4.78-4.75 (m, 1 H), 3.50-3.45 (m, 1 H), 2.51-2.45 (m, 2 H), 2.01-1.96 (m, 2 H), 1.85 (m, 3 H), 1.51 (d, J = 6.8 Hz, 6 H) | 365.9 | A |
| 277 | 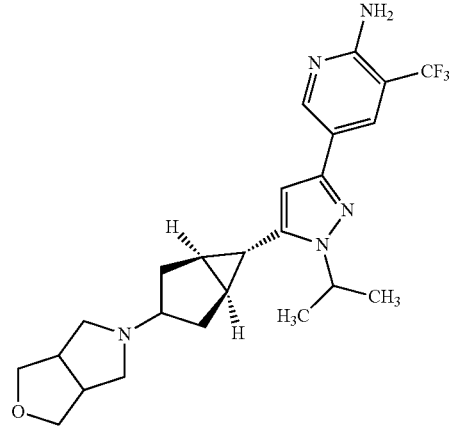 5-(1-isopropyl-5-((1R,5S,6r)-3-(tetrahydro-1H-furo[3,4-c]pyrrol-5(3H)-yl)bicyclo[3.1.0]hexan-6-yl)-1H-pyrazol-3-yl)-3-(trifluoromethyl)pyridin-2-amine (Stereoisomer 2) | (400 MHz, CDCl$_3$), δ: 8.54 (s, 1 H) 8.10 (s, 1 H), 6.00 (s, 1 H), 4.95 (br s, 2 H), 4.65-4.56 (m, 1 H), 3.69-3.78 (m, 2 H), 3.61 (d, J = 8.3 Hz, 2 H), 2.71-2.85 (m, 4H), 2.14-2.28 (m, 5 H), 1.86 (t, J = 9.7 Hz, 2H), 1.65 (m, 2H), 1.56 (m, 1 H), 1.52 (d, J = 6.6 Hz, 6 H) | 462.2 | A |
| 278 | 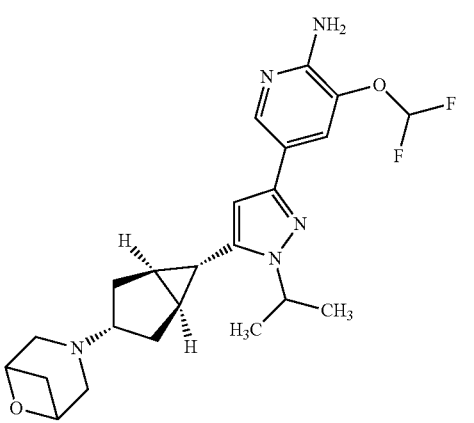 [SMILES: CC(C)n1nc(-c2cnc(N)c(OC(F)F)c2)cc1[C@H]1[C@@H]2C[C@@H](N3CC4CC(C3)O4)C[C@@H]21] 5-(5-((1R,3s,5S,6r)-3-(6-oxa-3-azabicyclo[3.1.1]heptan-3-yl)bicyclo[3.1.0]hexan-6-yl)-1-isopropyl-1H-pyrazol-3-yl)-3-(difluoromethoxy)pyridin-2-amine | (400 MHz, Methanol-$d_4$), δ: 8.13 (s, 1 H), 7.71 (s, 1 H), 6.87 (t, $J_{HF}$ = 73.6 Hz, 1 H), 6.14 (s, 1 H), 4.90-4.74 (m, 1 H), 4.60-4.51 (m, 2 H), 3.26-3.14 (m, 2 H), 3.02-3.00 (m, 1 H), 2.79-2.75 (m, 3 H), 2.33-2.28 (m, 3 H), 1.94-1.91 (m, 2 H), 1.89-1.74 (m, 3 H), 1.51 (d, J = 6.8 Hz, 6 H) | 446.2 | A |

| Cmpd No. | Structure | ¹H NMR | MS [MH]⁺ | Method |
|---|---|---|---|---|
| 279 | 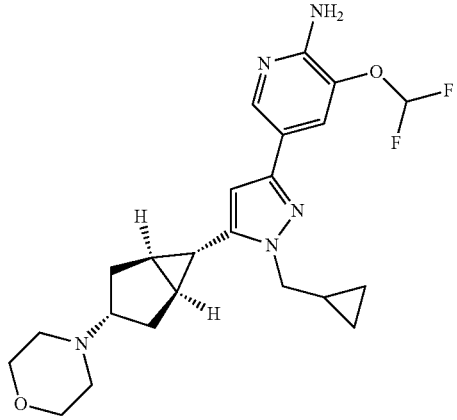 [SMILES: Nc1ncc(-c2cc([C@H]3[C@@H]4C[C@@H](N5CCOCC5)C[C@@H]43)n(CC3CC3)n2)cc1OC(F)F]<br>5-(1-(cyclopropylmethyl)-5-((1R,3s,5S,6r)-3-morpholinobicyclo[3.1.0]hexan-6-yl)-1H-pyrazol-3-yl)-3-(difluoromethoxy)pyridin-2-amine | (400 MHz, CDCl$_3$), δ: 8.27 (s, 1 H), 8.18 (s, 1 H), 7.12 (s, 1 H), 6.56 (t, J$_{HF}$ = 73.6 Hz, 1 H), 6.00 (s, 1 H), 5.24 (s, 2 H), 4.04 (d, J = 6.8 Hz, 2 H), 3.78 (d, J = 4.4 Hz, 4 H), 2.63-1.31 (m, 13 H), 0.64-0.41 (m, 4 H) | 446.0 | W |
| 280 | 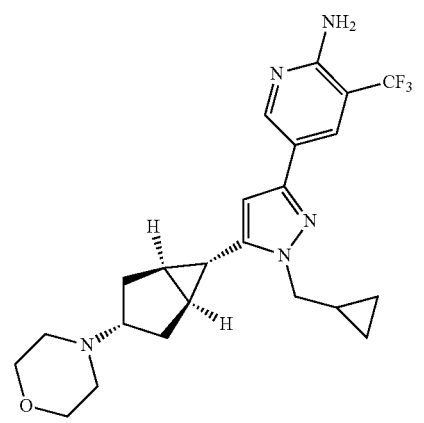 [SMILES: Nc1ncc(-c2cc([C@H]3[C@@H]4C[C@@H](N5CCOCC5)C[C@@H]43)n(CC3CC3)n2)cc1C(F)(F)F]<br>5-(1-(cyclopropylmethyl)-5-((1R,3s,5S,6r)-3-morpholinobicyclo[3.1.0]hexan-6-yl)-1H-pyrazol-3-yl)-3-(trifluoromethyl)pyridin-2-amine | (400 MHz, CDCl$_3$), δ: 8.23 (s, 1 H), 8.25 (s, 1 H), 8.10 (s, 1 H), 6.02 (s, 1 H), 5.18 (s, 2 H), 4.05 (d, J = 6.8 Hz, 2 H), 3.79-3.77 (m, 4 H), 2.58-2.47 (m, 4 H), 2.46 (m, 1 H), 2.27-2.22 (m, 2 H), 2.0-1.98 (m, 2 H), 1.95-1.73 (m, 2 H), 1.57 (m, 1 H), 1.32 (m, 1 H), 0.63-0.60 (m, 2 H), 0.43-0.40 (m, 2 H) | 448.2 | W |
| 281 | 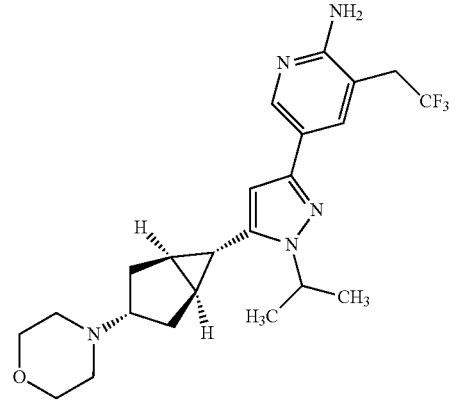 [SMILES: CC(C)n1nc(-c2cnc(N)c(CC(F)(F)F)c2)cc1[C@H]1[C@@H]2C[C@@H](N3CCOCC3)C[C@@H]21]<br>5-(1-isopropyl-5-((1R,3s,5S,6r)-3-morpholinobicyclo[3.1.0]hexan-6-yl)-1H-pyrazol-3-yl)-3-(2,2,2-trifluoroethyl)pyridin-2-amine | (400 MHz, CDCl$_3$), δ: 8.40 (s, 1 H), 7.82 (s, 1 H), 6.01 (s, 1 H), 4.65-4.57 (m, 1 H), 4.53 (br s, 2 H), 3.77 (m, 4H), 3.33 (q, J = 10.8 Hz, 2 H), 2.51 (m, 4 H), 2.41 (m, 1H), 2.24 (dd, J = 12.3, 7.0 Hz, 2 H), 1.89 (m, 2 H), 1.70 (m, 3 H), 1.53 (d, J = 6.5 Hz, 6 H) | 450.2 | A |

TABLE A-continued

| Cmpd No. | Structure | $^1$H NMR | MS [MH]$^+$ | Method |
|---|---|---|---|---|
| 282 | 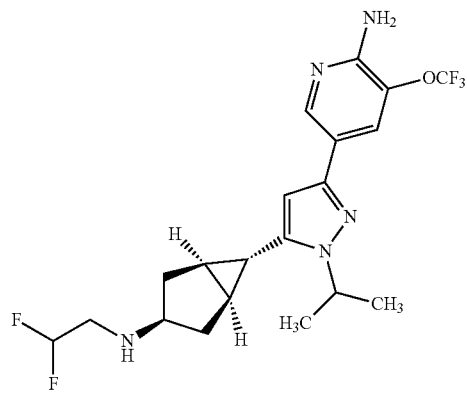 [SMILES: CC(C)n1nc(-c2cnc(N)c(OC(F)(F)F)c2)cc1[C@H]1[C@@H]2C[C@H](NCC(F)F)C[C@@H]21]<br>5-(5-((1R,3r,5S,6r)-3-((2,2-difluoroethyl)amino)bicyclo[3.1.0]hexan-6-yl)-1-isopropyl-1H-pyrazol-3-yl)-3-(trifluoromethoxy)pyridin-2-amine | (400 MHz, Methanol-d$_4$), δ: 8.24 (d, J = 2 Hz, 1 H), 7.82 (s, 1 H), 6.09 (s, 1 H), 6.01-5.71 (m, 1 H), 4.83-4.74 (m, 1 H), 3.43-3.40 (m, 1 H), 2.93-2.85 (m, 2 H), 2.34-2.21 (m, 3 H), 1.78-1.77 (m, 2 H), 1.75-1.67 (m, 2 H), 1.51 (d, J = 6.8 Hz, 6 H) | 446.2 | V |
| 283 | 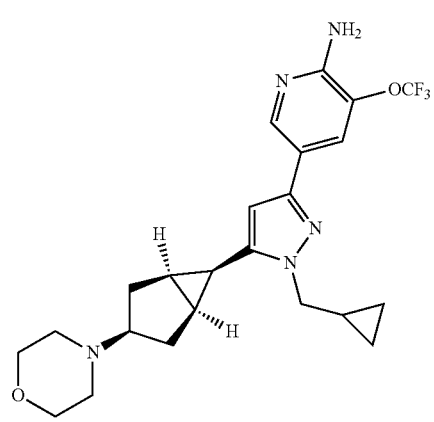 [SMILES: Nc1ncc(-c2cc([C@@H]3[C@@H]4C[C@H](N5CCOCC5)C[C@@H]43)n(CC3CC3)n2)cc1OC(F)(F)F]<br>5-(1-(cyclopropylmethyl)-5-((1R,3r,5S,6s)-3-morpholinobicyclo[3.1.0]hexan-6-yl)-1H-pyrazol-3-yl)-3-(trifluoromethoxy)pyridin-2-amine | (400 MHz, CDCl$_3$), δ: 8.00 (s, 1 H), 7.39 (s, 1 H), 5.90 (s, 1 H), 4.92 (s, 2 H), 3.88-3.77 (m, 6H), 3.04 (m, 1H), 2.56 (m, 4 H), 2.31 (m, 2H), 1.90 (s, 1 H), 1.67 (m, 4 H), 1.14 (m, 1 H), 0.48 (m, 2 H), 0.16 (m, 2 H) | 463.9 | W |
| 284 | 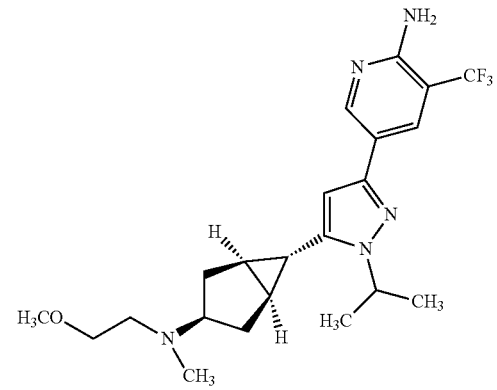 [SMILES: COCCN(C)[C@H]1C[C@@H]2[C@H](C1)[C@H]2c1cc(-c2cnc(N)c(C(F)(F)F)c2)nn1C(C)C]<br>5-(1-isopropyl-5-((1R,3r,5S,6r)-3-((2-methoxyethyl)(methyl)amino)bicyclo[3.1.0]hexan-6-yl)-1H-pyrazol-3-yl)-3-(trifluoromethyl)pyridin-2-amine | (400 MHz, CDCl$_3$), δ: 8.53 (s, 1 H), 8.09 (s, 1 H), 5.94 (s, 1 H), 4.97 (br s, 2 H), 4.72-4.58 (m, 1 H), 3.47 (t, J = 5.6 Hz, 2 H), 3.35 (s, 3 H), 3.19-3.06 (m, 1 H), 2.56 (t, J = 5.6 Hz, 2 H), 2.35-2.26 (m, 2 H), 2.24 (s, 3 H), 1.70-1.56 (m, 5 H), 1.52 (d, J = 6.6 Hz, 6 H) | 438.2 | A |

TABLE A-continued

| Cmpd No. | Structure | ¹H NMR | MS [MH]⁺ | Method |
|---|---|---|---|---|
| 285 | 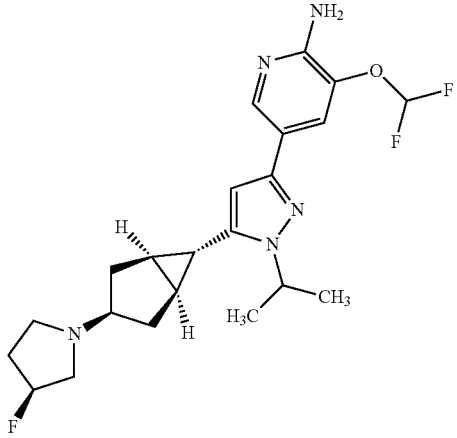 [SMILES: CC(C)n1nc(-c2cnc(N)c(OC(F)F)c2)cc1[C@H]1[C@@H]2C[C@H](N3CC[C@H](F)C3)C[C@@H]21]<br>3-(difluoromethoxy)-5-(5-((1R,3r,5S,6S)-3-((S)-3-fluoropyrrolidin-1-yl)bicyclo[3.1.0]hexan-6-yl)-1-isopropyl-1H-pyrazol-3-yl)pyridin-2-amine | (400 MHz, CD₃OD), δ: 8.12 (s, 1 H), 7.70 (s, 1 H), 6.86 (t, $J_{HF}$ = 73.2 Hz, 1 H), 6.07 (s, 1 H), 5.26-5.06 (m. 1 H), 4.80-4.72 (m, 1 H), 3.11-2.90 (m, 4 H), 2.72-2.54 (m, 1 H), 2.46-2.36 (m, 1 H), 2.35-2.24 (m, 3 H), 2.06 (m, 1 H), 1.85-1.75 (m, 3 H), 1.69 (m, 2 H), 1.51 (d, J = 6.60 Hz, 6 H) | 436.2 | A |
| 286 | 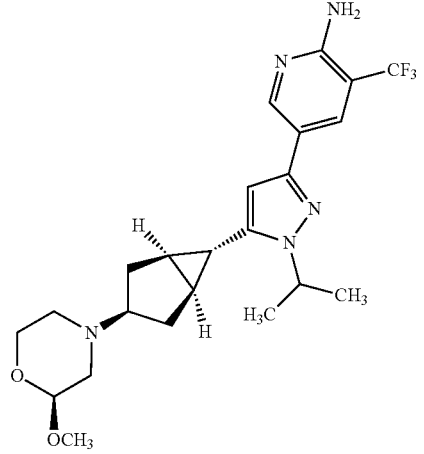 [SMILES: CO[C@@H]1CN([C@H]2C[C@@H]3[C@H](C2)[C@H]3c2cc(-c3cnc(N)c(C(F)(F)F)c3)nn2C(C)C)CCO1]<br>5-(1-isopropyl-5-((1R,3r,5S,6S)-3-((S)-3-methoxypiperidin-1-yl)bicyclo[3.1.0]hexan-6-yl)-1H-pyrazol-3-yl)-3-(trifluoromethyl)pyridin-2-amine | (400 MHz, CDCl₃), δ: 8.53 (s, 1 H), 8.09 (s, 1 H), 5.94 (s, 1 H), 4.95 (br s, 2 H), 4.68-4.59 (m, 1 H), 3.37 (s, 3 H), 3.32-3.23 (m, 1 H), 2.96 (t, J = 8.0 Hz, 1 H), 2.87 (d, J = 8.0 Hz, 1 H), 2.67-2.57 (m, 1 H), 2.38-2.27 (m, 2 H), 2.08-1.97 (m, 2 H), 1.94-1.87 (m, 1 H), 1.79-1.71 (m, 2 H), 1.71-1.67 (m, 1 H), 1.65-1.58 (m, 4 H), 1.52 (d, J = 6.8 Hz, 6 H), 1.33-1.23 (m, 1 H) | 464.2 | A |
| 287 | 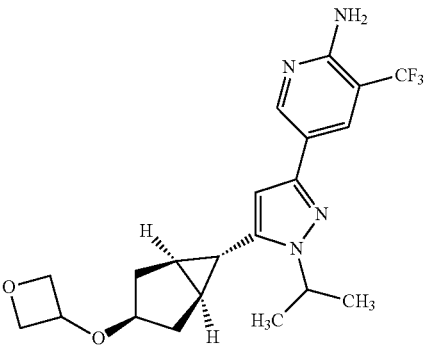 [SMILES: CC(C)n1nc(-c2cnc(N)c(C(F)(F)F)c2)cc1[C@H]1[C@@H]2C[C@H](OC3COC3)C[C@@H]21]<br>5-(1-isopropyl-5-((1R,3r,5S,6r)-3-(oxetan-3-yloxy)bicyclo[3.1.0]hexan-6-yl)-1H-pyrazol-3-yl)-3-(trifluoromethyl)pyridin-2-amine | (400 MHz, CDCl₃) δ: 8.56 (s, 1 H), 8.12 (s, 1 H), 6.00 (s, 1 H), 4.96 (s, 2 H), 4.80-4.77 (m, 2 H), 4.66-4.56 (m, 4 H), 3.98 (t, J = 6.0 Hz, 1 H), 2.12-2.07 (m, 3 H), 2.02 (m, 1 H), 1.98 (m, 1 H), 1.65 (m, 2 H), 1.55 (d, J = 6.8 Hz, 6 H) | 423.2 | Q |

| Cmpd No. | Structure | ¹H NMR | MS [MH]⁺ | Method |
|---|---|---|---|---|
| 288 | 5-(5-((1R,3s,5S,6r)-3-((2,2-udifloroethyl)amino)bicyclo[3.1.0]hexan-6-yl)-1-isopropyl-1H-pyrazol-3-yl)-3-(tritluoromethoxy)pyridin-2-amine | (400 MHz, Methanol-d₄), δ: 8.24 (d, J = 2 Hz, 1 H), 7.82 (m, 1 H), 6.14 (s, 1 H), 6.10-5.70 (m, 1 H), 4.74-4.70 (m, 1 H), 3.04-2.88 (m, 3 H), 2.37-2.32 (m, 2 H), 2.01 (m, 1 H), 1.72-1.68 (m, 4 H), 1.49 (d, J = 6.4 Hz, 6 H) | 446.2 | V |
| 289 | 3-(difluoromethoxy)-5-(5-((1R,3s,5S,6S)-3-((S)-3-fluoropyrrolidin-1-yl)bicyclo[3.1.0]hexan-6-yl)-1-isopropyl-1H-pyrazol-3-yl)pyridin-2-amine | (400 MHz, CDCl₃) δ: 8.24 (d, J = 1.5 Hz, 1 H), 7.69 (m, 1 H), 6.54 (t, J$_{HF}$ = 73.2 Hz, 1 H), 5.99 (s, 1 H), 5.28-5.07 (m, 1 H), 4.71 (br s, 2 H), 4.65-4.55 (m, 1 H), 2.95-2.82 (m, 2 H), 2.78-2.62 (m, 1 H), 2.47-2.35 (m, 2 H), 2.16-2.24 (m, 3H), 2.07-2.14 (m, 1 H), 2.06-1.98 (m, 1 H), 1.86-1.97 (m, 2 H), 1.75-1.69 (m, 1 H), 1.58-1.55 (m, 1 H), 1.52 (d, J = 6.6 Hz, 6 H) | 436.2 | A |

TABLE A-continued

| Cmpd No. | Structure | ¹H NMR | MS [MH]⁺ | Method |
|---|---|---|---|---|
| 290 | 5-(1-isopropyl-5-((1R,3s,5S,6S)-3-((S)-3-methoxypiperidin-1-yl)bicyclo[3.1.0]hexan-6-yl)-1H-pyrazol-3-yl)-3-(trifluoromethyl)pyridin-2-amine | (400 MHz, CDCl₃), δ: 8.53 (s, 1 H), 8.09 (s, 1 H), 5.99 (s, 1 H), 4.96 (br s, 2 H), 4.65-4.56 (m, 1 H), 3.37 (s, 3 H), 3.31 (m, 1 H), 2.92-2.84 (m, 1 H), 2.70-2.57 (m, 1 H), 2.45-2.33 (m, 1 H), 2.55-2.17 (m, 2 H), 2.10-1.73 (m, 8 H), 1.66 (m, 2 H), 1.52 (d, J = 6.4 Hz, 6 H), 1.35-1.22 (m, 1 H) | 464.2 | A |
| 291 | 5-(1-isopropyl-5-((1R,3s,5S,6r)-3-((2-methoxyethyl)(methyl)amino)bicyclo[3.1.0]hexan-6-yl)-1H-pyrazol-3-yl)-3-(trifluoromethyl)pyridin-2-amine | (400 MHz, CDCl₃), δ: 8.54 (s, 1 H), 8.10 (s, 1 H), 6.00 (s, 1 H), 4.95 (br s, 2 H), 4.65-4.57 (m, 1 H), 3.50 (t, J = 5.6 Hz, 2 H), 3.36 (s, 3 H), 2.65-2.57 (m, 3 H), 2.28 (s, 3 H), 2.20 (dd, J = 12.4 Hz, 7.2 Hz, 2 H), 1.90 (t, J = 10.4 Hz, 2 H), 1.66 (m, 2 H), 1.52 (m, 7 H) | 438.2 | A |
| 292 | 5-(1-(cyclopropylmethyl)-5-((1R,3s,5S,6r)-3-morpholinobicyclo[3.1.0]hexan-6-yl)-1H-pyrazol-3-yl)-3-(trifluoromethoxy)pyridin-2-amine | (400 MHz, CDCl₃) δ: 8.32 (s, 1 H), 7.80 (s, 1 H), 6.00 (s, 1 H), 4.81 (br s, 2 H), 4.03 (d, J = 6.8 Hz, 2 H), 3.76 (m, 4 H), 2.51 (m, 4 H), 2.41-2.39 (m, 1 H), 2.25-2.20 (m, 2 H), 1.92-1.90 (m, 2 H), 1.72-1.68 (m, 2 H), 1.57 (m, 1 H), 1.32 (m, 1 H), 0.61 (m, 2 H), 0.43 (m, 2 H) | 464.0 | W |

| Cmpd No. | Structure | ¹H NMR | MS [MH]⁺ | Method |
|---|---|---|---|---|
| 293 | 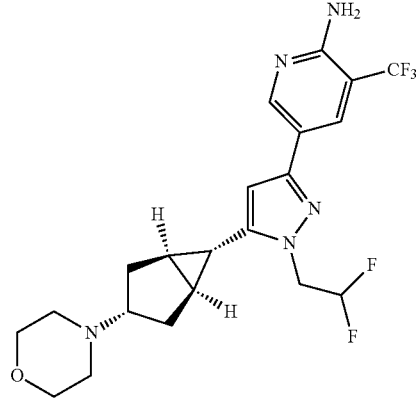 [SMILES: Nc1ncc(-c2cc([C@H]3[C@@H]4C[C@@H](N5CCOCC5)C[C@@H]43)n(CC(F)F)n2)cc1C(F)(F)F]<br>5-(1-(2,2-difluoroethyl)-5-((1R,3s,5S,6r)-3-morpholinobicyclo[3.1.0]hexan-6-yl)-1H-pyrazol-3-yl)-3-(trifluoromethyl)pyridin-2-amine | (400 MHz, CDCl₃) δ: 8.54 (s, 1 H), 8.08 (s, 1 H), 6.34-6.08 (m, 2 H), 5.02 (s, 2 H), 4.53-4.46 (m, 2 H), 3.74 (m, 4 H), 2.47 (m, 4 H), 2.39-2.35 (m, 1 H), 2.27-2.22 (m, 2 H), 1.87-1.84 (m, 2 H), 1.73 (m, 2 H), 1.63 (m, 1 H) | 458.0 | W |
| 294 | 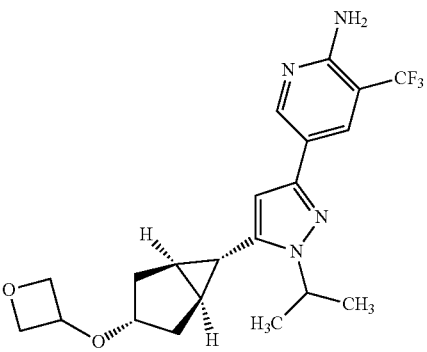 [SMILES: CC(C)n1nc(-c2cnc(N)c(C(F)(F)F)c2)cc1[C@H]1[C@@H]2C[C@@H](OC3COC3)C[C@@H]21]<br>5-(1-isopropyl-5-((1R,3s,5S,6r)-3-(oxetan-3-yloxy)bicyclo[3.1.0]hexan-6-yl)-1H-pyrazol-3-yl)-3-(trifluoromethyl)pyridin-2-amine | (400 MHz, CDCl₃) δ: 8.54 (s, 1 H), 8.10 (s, 1 H), 6.01 (s, 1 H), 4.97 (s, 2 H), 4.76 (t, J = 6.4 Hz, 2 H), 4.63-4.57 (m, 3 H), 4.16-4.10 (m, 1 H), 3.73-3.69 (m, 1 H), 2.32-2.28 (m, 2 H), 1.91 (m, 2 H), 1.52 (d, J = 6.8 Hz, 6 H), 1.38 (m, 1H), 1.27 (t, J = 6.8 Hz, 2 H) | 423.2 | Q |
| 295 | 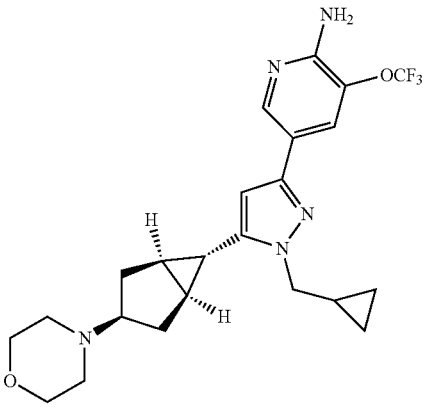 [SMILES: Nc1ncc(-c2cc([C@H]3[C@@H]4C[C@H](N5CCOCC5)C[C@@H]43)n(CC3CC3)n2)cc1OC(F)(F)F]<br>5-(1-(cyclopropylmethyl)-5-((1R,3r,5S,6r)-3-morpholinobicyclo[3.1.0]hexan-6-yl)-1H-pyrazol-3-yl)-3-(trifluoromethoxy)pyridin-2-amine | (400 MHz, CDCl₃) δ: 8.33 (s, 1 H), 7.80 (s, 1 H), 5.96 (s, 1 H), 4.71 (s, 2 H), 4.04 (d, J = 6.8 Hz, 2 H), 3.72 (m, 4 H), 2.89-2.87 (m, 1 H), 2.46 (m, 4 H), 2.25-2.20 (m, 2 H), 1.89 (m, 1 H), 1.73-1.66 (m, 4 H), 1.32 (m, 1 H), 0.61 (m, 2 H), 0.43 (m, 2 H) | 463.9 | W |

Example 4

DLK TR-FRET inhibition assay: DLK kinase reactions (20 µL) containing 5 nM N-terminally GST-tagged DLK (catalytic domain amino acid 1-520) (Carna Bioscience), 40 nM N-terminally HIS-tagged MKK4 K131M substrate, and 30 µM ATP in kinase reaction buffer (50 mM HEPES, pH 7.5, 0.01% Triton X-100, 0.01% Bovine γ-Globulins, 2 mM DTT, 10 mM $MgCl_2$ and 1 mM EGTA), and testing compound 1:3 serial diluted starting at 20 uM were incubated at ambient temperature for 60 minutes in 384 well OptiPlate (Perkin Elmer). To quench kinase reactions and detect phosphorylated MKK4, 15 µL of TR-FRET antibody mixture containing 2 nM anti-phosphorylated MKK4 labeled with Europium cryptate (Cisbio) and 23 nM anti-HIS labeled with D2 (Cisbio) in detection buffer (25 mM Tris pH 7.5, 100 mM NaCl, 100 mM EDTA, 0.01% Tween-20, and 200 mM KF) was added to the reaction mixture. The detection mixture was incubated for 3 hours at ambient temperature and the TR-FRET was detected with an EnVision multilabel plate reader (Perkin-Elmer) using the LANCE/DELFIA Dual Enh label from Perkin-Elmer (excitation filter: UV2 (TRF) 320 and emission filters: APC 665 and Europium 615). Compounds of formula 0 as set forth in Table A inhibited the DLK kinase with the $K_i$s in micromolar (µM) as provided in Table B below.

TABLE B

| Cmpd No. | DLK ($K_i$) µM |
|---|---|
| 1 | 0.00228 |
| 2 | 0.00206 |
| 3 | |
| 4 | 0.00451 |
| 5 | 0.0188 |
| 6 | 0.0144 |
| 7 | 0.00463 |
| 8 | 0.00336 |
| 9 | 0.004 |
| 10 | 0.00328 |
| 11 | 0.00187 |
| 12 | 0.00177 |
| 13 | 0.00189 |
| 14 | 0.00172 |
| 15 | 0.00358 |
| 16 | 0.0091 |
| 17 | 0.00292 |
| 18 | 0.00381 |
| 19 | 0.00297 |
| 20 | 0.00439 |
| 21 | 0.0042 |
| 22 | 0.00157 |
| 23 | 0.00098 |
| 24 | 0.00034 |
| 25 | 0.0706 |
| 26 | 0.0756 |
| 27 | 0.00014 |
| 28 | 0.00254 |
| 29 | 0.00283 |
| 30 | 0.00359 |
| 31 | 0.0794 |
| 32 | 0.00408 |
| 33 | 0.123 |
| 34 | 0.00419 |
| 35 | 0.003 |
| 36 | 0.00153 |
| 37 | 0.00237 |
| 38 | 0.00145 |
| 39 | 0.00206 |
| 40 | 0.00182 |
| 41 | 0.0069 |
| 42 | 0.00453 |
| 43 | 0.00305 |
| 44 | 0.0082 |
| 45 | 0.0033 |
| 46 | 0.00185 |
| 47 | 0.00411 |
| 48 | 0.0031 |
| 49 | 0.0042 |
| 50 | 0.00283 |
| 51 | 0.00355 |
| 52 | 0.00397 |
| 53 | 0.00472 |
| 54 | 0.00768 |
| 55 | 0.0054 |
| 56 | 0.00481 |
| 57 | 0.00188 |
| 58 | 0.00186 |
| 59 | 0.00306 |
| 60 | 0.00226 |
| 61 | 0.00305 |
| 62 | 0.00273 |
| 63 | 0.00221 |
| 64 | 0.000763 |
| 65 | 0.00113 |
| 66 | 0.00226 |
| 67 | 0.00393 |
| 68 | 0.0012 |
| 69 | 0.00297 |
| 70 | 0.0029 |
| 71 | 0.00362 |
| 72 | 0.00348 |
| 73 | 0.00181 |
| 74 | 0.00375 |
| 75 | 0.00074 |
| 76 | 0.00217 |
| 77 | 0.0013 |
| 78 | 0.00052 |
| 79 | 0.0011 |
| 80 | 0.0006 |
| 81 | 0.00143 |
| 82 | 0.00143 |
| 83 | 0.00012 |
| 84 | 0.00168 |
| 85 | 0.0478 |
| 86 | 0.0016 |
| 87 | 0.00064 |
| 88 | 0.0014 |
| 89 | 0.00642 |
| 90 | 0.00595 |
| 91 | 0.00379 |
| 92 | 0.0094 |
| 93 | 0.00122 |
| 94 | 0.00145 |
| 95 | 0.00213 |
| 96 | 0.019 |
| 97 | 0.00412 |
| 98 | 0.00489 |
| 99 | 0.00116 |
| 100 | 0.00103 |
| 101 | 0.00044 |
| 102 | 0.00079 |
| 103 | 0.00128 |
| 104 | 0.00243 |
| 105 | 0.0183 |
| 106 | >0.321 |
| 107 | >0.321 |
| 108 | 0.0016 |
| 109 | 0.00159 |
| 110 | 0.00389 |
| 111 | 0.00861 |
| 112 | 0.00587 |
| 113 | 0.00423 |
| 114 | 0.0151 |
| 115 | 0.00919 |
| 116 | 0.00779 |
| 117 | 0.00526 |
| 118 | 0.00375 |
| 119 | 0.00664 |
| 120 | 0.00691 |
| 121 | 0.00668 |
| 122 | >0.321 |

TABLE B-continued

| Cmpd No. | DLK ($K_i$) μM |
|---|---|
| 123 | >0.321 |
| 124 | >1.6 |
| 125 | >1.6 |
| 126 | >1.6 |
| 127 | 0.00355 |
| 128 | 0.00506 |
| 129 | 0.00452 |
| 130 | 0.00482 |
| 131 | 0.0035 |
| 132 | 0.258 |
| 133 | 0.321 |
| 134 | 0.00158 |
| 135 | 0.00557 |
| 136 | 0.0071 |
| 137 | 0.00334 |
| 138 | 0.0129 |
| 139 | 0.0657 |
| 140 | 0.00659 |
| 141 | 0.00852 |
| 142 | 0.0622 |
| 143 | 0.0319 |
| 144 | 0.0028 |
| 145 | 0.0033 |
| 146 | 0.0043 |
| 147 | 0.0057 |
| 148 | 0.0089 |
| 149 | 0.0041 |
| 150 | 0.0036 |
| 151 | 0.009 |
| 152 | |
| 153 | 0.0009 |
| 154 | 0.0007 |
| 155 | 0.0033 |
| 156 | 0.0135 |
| 157 | 0.0031 |
| 158 | 0.0012 |
| 159 | 0.0019 |
| 160 | 0.0024 |
| 161 | 0.0025 |
| 162 | 0.0026 |
| 163 | 0.0028 |
| 164 | 0.0033 |
| 165 | 0.0016 |
| 166 | 0.0067 |
| 167 | 0.0014 |
| 168 | 0.0027 |
| 169 | 0.0041 |
| 170 | 0.0045 |
| 171 | 0.0054 |
| 172 | 0.0042 |
| 173 | 0.0045 |
| 174 | 0.0052 |
| 175 | 0.0055 |
| 176 | 0.0018 |
| 177 | 0.0011 |
| 178 | 0.0021 |
| 179 | 0.0043 |
| 180 | 0.0058 |
| 181 | 0.0024 |
| 182 | 0.003 |
| 183 | 0.0045 |
| 184 | 0.0021 |
| 185 | 0.0016 |
| 186 | 0.0016 |
| 187 | 0.0022 |
| 188 | 0.0028 |
| 189 | 0.0029 |
| 190 | 0.0048 |
| 191 | 0.0078 |
| 192 | 0.0026 |
| 193 | 0.0014 |
| 194 | 0.002 |
| 195 | 0.0064 |
| 196 | 0.0034 |
| 197 | 0.0013 |
| 198 | 0.0021 |
| 199 | 0.0018 |
| 200 | 0.002 |
| 201 | 0.0013 |
| 202 | 0.0012 |
| 203 | 0.0009 |
| 204 | 0.0012 |
| 205 | 0.0029 |
| 206 | 0.0021 |
| 207 | 0.0036 |
| 208 | 0.0015 |
| 209 | 0.0026 |
| 210 | 0.0020 |
| 211 | 0.0032 |
| 212 | 0.0044 |
| 213 | 0.0051 |
| 214 | 0.0015 |
| 215 | 0.0014 |
| 216 | 0.0066 |
| 217 | 0.0042 |
| 218 | |
| 219 | 0.0022 |
| 220 | 0.0021 |
| 221 | 0.002 |
| 222 | 0.0027 |
| 223 | 0.0026 |
| 224 | 0.0038 |
| 225 | 0.0042 |
| 226 | 0.0032 |
| 227 | 0.0045 |
| 228 | 0.0028 |
| 229 | 0.0039 |
| 230 | 0.0034 |
| 231 | 0.0055 |
| 232 | 0.0011 |
| 233 | 0.0018 |
| 234 | 0.0049 |
| 235 | 0.0038 |
| 236 | 0.0158 |
| 237 | 0.0011 |
| 238 | 0.0016 |
| 239 | 0.0017 |
| 240 | 0.0021 |
| 241 | 0.002 |
| 242 | 0.0021 |
| 243 | 0.0011 |
| 244 | 0.0011 |
| 245 | 0.0026 |
| 246 | 0.0018 |
| 247 | 0.0029 |
| 248 | 0.0028 |
| 249 | 0.0026 |
| 250 | 0.0020 |
| 251 | 0.0027 |
| 252 | 0.0030 |
| 253 | 0.0034 |
| 254 | 0.0024 |
| 255 | 0.0015 |
| 256 | 0.0011 |
| 257 | 0.0007 |
| 258 | 0.0009 |
| 259 | 0.0007 |
| 260 | 0.0004 |
| 261 | 0.0012 |
| 262 | <0.0001 |
| 263 | 0.0010 |
| 264 | 0.0018 |
| 265 | 0.0025 |
| 266 | 0.0011 |
| 267 | 0.220 |
| 268 | 0.221 |
| 269 | 0.0041 |
| 270 | 0.0028 |
| 271 | 0.0026 |
| 272 | 0.0056 |
| 273 | 0.0013 |
| 274 | 0.0013 |
| 275 | 0.0047 |
| 276 | 0.0018 |
| 277 | 0.0023 |
| 278 | 0.0014 |

TABLE B-continued

| Cmpd No. | DLK ($K_i$) μM |
|---|---|
| 279 | 0.0016 |
| 280 | 0.0011 |
| 281 | 0.0184 |
| 282 | 0.0077 |
| 283 | 0.209 |
| 284 | 0.0057 |
| 285 | 0.0043 |
| 286 | 0.0034 |
| 287 | 0.0063 |
| 288 | 0.0063 |
| 289 | 0.0044 |
| 290 | 0.0077 |
| 291 | 0.0047 |
| 292 | 0.0046 |
| 293 | 0.0030 |
| 294 | 0.0089 |
| 295 | 0.0024 |

It is to be understood that the invention is not limited to the particular embodiments of the invention described above, as variations of the particular embodiments may be made and still fall within the scope of the appended claims. All documents cited to or relied upon herein are expressly incorporated by reference.

We claim:
1. A compound of formula 0:

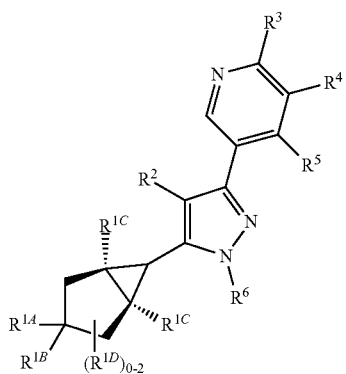

and salts thereof; wherein in formula 0
$R^{1A}$ is selected from the group consisting of H, —F, —Cl, a 3 to 12 membered heterocycloalkyl, 5 or 6 membered heteroaryl, —$(X^{1A})_{0-1}$—$OR^{1A-1}$, —$(X^{1A})_{0-1}$—$SR^{1A-1}$, —$(X^{1A})_{0-1}$—$S(O)R^{1A-1}$, —$(X^{1A})_{0-1}$—$S(O)_2R^{1A-1}$ and —$(X^{1A})_{0-1}$—$N(R^{1A-1})_2$, each $X^{1A}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{1A-1}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl-, 3-7 membered heterocycloalkyl, 3-7 membered heterocycloalkyl-$C_{1-4}$ alkyl-, 5-6 membered heteroaryl, 5-6 membered heteroaryl-$C_{1-4}$ alkyl-, phenyl and phenyl-$C_{1-4}$ alkyl-, or any two $R^{1A-1}$ groups attached to the same nitrogen atom are optionally combined to form a 3 to 6 membered heterocyclic ring optionally comprising 1 to 2 additional heteroatom selected from N, O and S, and wherein a $R^{1A}$ group at each occurrence is independently optionally further substituted with 1 to 5 $R^{1A-2}$ substituents independently selected from the group consisting of —F, —Cl, —Br, —I, —OH, —CN, —$NO_2$, —$SF_5$, —$NH_2$, $C_{1-6}$ alkoxy, $C_{1-6}$ alkylamino, $C_{1-6}$ dialkylamino, $C_{1-6}$ alkyl, $C_{1-6}$ heteroalkyl, $C_{1-6}$ haloalkyl, oxo, —$S(=O)_{1-2}$—$C_{1-6}$ alkyl and 3 to 7 membered heterocycloalkyl;

$R^{1B}$ is selected from the group consisting of H, —OH, —F, —Cl, —Br, —I, —CN, —$NH_2$, —$N(CH_3)C(O)CH_3$, $C_{1-6}$ alkylamino, $C_{1-6}$ dialkylamino, $C_{1-6}$ alkoxy, $C_{1-6}$ alkyl, $C_{1-6}$ haloalkyl and $C_{1-6}$ heteroalkyl;

or $R^{1A}$ and $R^{1B}$ together form an oxo group or a 3 to 7 membered heterocycloalkyl comprising 1 to 2 heteroatoms selected from N, O and S and wherein said 3 to 7 membered heterocycloalkyl is optionally further substituted with 1 to 5 $R^{1A-2}$ substituents independently selected from the group consisting of —F, —Cl, —Br, —I, —OH, —CN, —$NO_2$, —$SF_5$, —$NH_2$, $C_{1-6}$ alkoxy, $C_{1-6}$ alkylamino, $C_{1-6}$ dialkylamino, $C_{1-6}$ alkyl, $C_{1-6}$ heteroalkyl, $C_{1-6}$ haloalkyl, oxo, —$S(=O)_{1-2}$—$C_{1-6}$ alkyl and 3 to 7 membered heterocycloalkyl;

$R^{1C}$ at each occurrence is independently selected from the group consisting of hydrogen, —F, —Cl, —Br, —I, $C_{1-4}$ alkyl and $C_{1-4}$ haloalkyl;

$R^{1D}$ at each occurrence is independently selected from the group consisting of hydrogen, —F, —Cl, —Br, —I, —OH, $C_{1-4}$ alkyl, $C_{1-4}$ haloalkyl, 3 to 7 membered heterocycloalkyl;

or $R^{1A}$ and $R^{1D}$ together form a 3-7 membered cycloalkyl or 3-7 membered heterocycloalkyl, each optionally substituted by $C_{1-4}$ alkyl;

$R^2$ is selected from the group consisting of hydrogen, —F, —Cl, —Br, —I, —$NO_2$, —CN, $C_{1-6}$ alkyl and $C_{1-6}$ haloalkyl;

$R^3$ is $N(R^{3A})_2$, wherein each $R^{3A}$ is independently selected from the group consisting of hydrogen, $C_{1-6}$ alkyl, and $C_{1-6}$ haloalkyl;

$R^4$ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^4)_{0-1}$—CN, —$(X^4)_{0-1}$—$NO_2$, —$(X^4)_{0-1}$—$SF_5$, —$(X^4)_{0-1}$—$OSF_5$, —$(X^4)_{0-1}$—$OR^{4A}$, —$(X^4)_{0-1}$—$N(R^{4A})_2$, —$(X^4)_{0-1}$—$SR^{4A}$, —$(X^4)_{0-1}$—$CF_3$, 3 to 7 membered cycloalkyl-$(X^4)_{0-1}$—, 3 to 7 membered heterocycloalkyl-$(X^4)_{0-1}$—, 5 to 6 membered heteroaryl-$(X^4)_{0-1}$—, phenyl-$(X^4)_{0-1}$—, —$(X^4)_{0-1}$—C(=O)N($R^{4A}$)($R^{4A}$), —$(X^4)_{0-1}$—C(=O)$OR^{4A}$, —$(X^4)_{0-1}$—N($R^{4A}$)C(=O)($R^{4A}$), —$(X^4)_{0-1}$—N($R^{4A}$)C(=O)$OR^{4A}$, —$(X^4)_{0-1}$—S(=O)$_{1-2}$—$R^{4A}$, —$(X^4)_{0-1}$—N($R^{4A}$)S(=O)$_{1-2}$—$R^{4A}$, —$(X^4)_{0-1}$—S(=O)$_{1-2}$N($R^{4A}$)$_2$, —$(X^4)_{0-1}$—C(=O)$R^{4A}$, —$(X^4)_{0-1}$—C(=NOR$^{4A}$)$R^{4A}$, —$(X^4)_{0-1}$—N($R^{4A}$)C(=O)N($R^{4A}$)$_2$, —$(X^4)_{0-1}$—OC(=O)$R^{4A}$, —$(X^4)_{0-1}$—OP(=O)(OR$^{4A}$)$_2$, —$(X^4)$—SC(=O)$OR^{4A}$ and —$(X^4)$—SC(=O)N($R^{4A}$)$_2$, each $X^4$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring optionally comprising 1 to 2 additional heteroatoms selected from N, O and S, and wherein a $R^4$ group is independently optionally further substituted with 1 to 5 $R^{4A-1}$ substituents independently selected from the group consisting of —F, —Cl, —Br, —I, —OH, —CN, —$NO_2$, —$SF_5$, —$NH_2$, $C_{1-6}$ alkoxy, $C_{1-6}$ alkylamino, $C_{1-6}$ alkyl and $C_{1-6}$ dialkylamino;

or $R^3$ and $R^4$ together with the atoms to which they are attached form a 5 or 6 membered heteroaryl wherein the 5 or 6 membered heteroaryl is optionally substituted with 1 to 3 $R^{3/4cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^{3/4})_{0-1}$—CN, —$(X^{3/4})_{0-1}$—$NO_2$, —$(X^{3/4})_{0-1}$—$SF_5$, —$(X^{3/4})_{0-1}$—$OSF_5$, —$(X^{3/4})_{0-1}$—$OR^{3/4.4}$, —$(X^{3/4})_{0-1}$—$N(R^{3/4.4})_2$, —$(X^{3/4})_{0-1}$—$SR^{3/4.4}$, —$(X^{3/4})_{0-1}$—$CF_3$, 3 to 12 membered cycloalkyl-$(X^{3/4})_{0-1}$—, 3 to 12 membered heterocycloalkyl-$(X^{3/4})_{0-1}$—, 5 to 6 membered heteroaryl-$(X^{3/4})_{0-1}$—, phenyl-$(X^{3/4})_{0-1}$—, —$(X^{3/4})_{0-1}$—C(=O)N$(R^{3/4.4})(R^{3/4.4})$, —$(X^{3/4})_{0-1}$—C(=O)$OR^{3/4.4}$, —$(X^{3/4})_{0-1}$—$N(R^{3/4.4})C(=O)(R^{3/4.4})$, —$(X^{3/4})_{0-1}$—$N(R^{3/4.4})C(=O)OR^{3/4.4}$, —$(X^{3/4})_{0-1}$—$S(=O)_{1-2}$—$R^{3/4.4}$, —$(X^{3/4})_{0-1}$—$N(R^{3/4.4})S(=O)_{1-2}$—$R^{3/4.4}$, —$(X^{3/4})_{0-1}$—$S(=O)_{1-2}N(R^{3/4.4})_2$, —$(X^{3/4})_{0-1}$—$C(=O)R^{3/4.4}$, —$(X^{3/4})_{0-1}$—$C(=NOR^{3/4.4})R^{3/4.4}$, —$(X^{3/4})_{0-1}$—$N(R^{3/4.4})C(=O)N(R^{3/4.4})_2$ and —$(X^{3/4})_{0-1}$—OC(=O)$R^{3/4.4}$, —$(X^{3/4})_{0-1}$—OP(=O)$(OR^{3/4.4})_2$, —$(X^{3/4})$—SC(=O)$OR^{3/4.4}$ and $(X^{3/4})$—SC(=O)$N(R^{3/4.4})_2$, each $X^{3/4}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{3/4.4}$ at each occurrence is each independently selected from the group consisting of hydrogen, $C_{1-6}$ alkyl, $C_{1-6}$ haloalkyl and $C_{1-6}$ heteroalkyl, or any two $R^{3/4.4}$ groups attached to the same nitrogen atom are optionally combined to form a 3 to 6 membered heterocyclic ring optionally comprising 1 to 2 additional heteroatom selected from N, O and S, and wherein a $R^{3/4cy}$ substituent at each occurrence is independently optionally further substituted with 1 to 5 $R^{3/4cy-1}$ substituents independently selected from the group consisting of —F, —Cl, —Br, —I, —OH, —CN, —$NO_2$, —$SF_5$, —$NH_2$, $C_{1-6}$ alkoxy, $C_{1-6}$ alkylamino, $C_{1-6}$ alkyl and $C_{1-6}$ dialkylamino;

$R^5$ is hydrogen, —F, —Cl, —Br or —I; and $R^6$ is selected from the group consisting of $C_{1-12}$ alkyl, $C_{1-12}$ haloalkyl, $C_{1-12}$ heteroalkyl-$(L)_{0-1}$-, $C_{2-12}$ alkenyl-$(L)_{0-1}$-, $C_{2-12}$ alkynyl-$(L)_{0-1}$-, 3 to 12 membered cycloalkyl-$(L)_{0-1}$- and 3 to 12 membered heterocycloalkyl-$(L)_{0-1}$-, wherein L is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, wherein a $R^6$ group is optionally further substituted with 1 to 5 $R^{6A}$ substituents independently selected from the group consisting of —F, —Cl, —Br, —I, —OH, —CN, —$NO_2$, —$SF_5$, —$OSF_5$, —$NH_2$, $C_{1-6}$ alkyl, $C_{1-6}$ haloalkyl, 3 to 5 membered cycloalkyl, 3 to 5 membered heterocycloalkyl, $C_{1-6}$ alkoxy, $C_{1-6}$ alkylthio, $C_{1-6}$ alkylamino and $C_{1-6}$ dialkylamino.

2. A compound of claim 1, which is a compound of formula I:

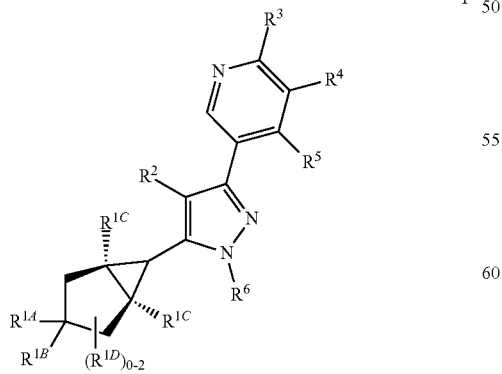

and salts thereof; wherein in formula I $R^{1A}$ is selected from the group consisting of a 3 to 12 membered heterocycloalkyl, 5 or 6 membered heteroaryl, —$(X^{1A})_{0-1}$—$OR^{1A-1}$, —$(X^{1A})_{0-1}$—$SR^{1A-1}$, —$(X^{1A})_{0-1}$—$S(O)R^{1A-1}$—$(X^{1A})_{0-1}$—$S(O)_2R^{1A-1}$ and —$(X^{1A})_{0-1}$—$N(R^{1A-1})_2$, each $X^{1A}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{1A-1}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl-, 3-7 membered heterocycloalkyl, 3-7 membered heterocycloalkyl-$C_{1-4}$ alkyl-, 5-6 membered heteroaryl, 5-6 membered heteroaryl-$C_{1-4}$ alkyl-, phenyl and phenyl-$C_{1-4}$ alkyl-, or any two $R^{1A-1}$ groups attached to the same nitrogen atom are optionally combined to form a 3 to 6 membered heterocyclic ring optionally comprising 1 to 2 additional heteroatom selected from N, O and S, and wherein a $R^{1A}$ group at each occurrence is independently optionally further substituted with 1 to 5 $R^{1A-2}$ substituents independently selected from the group consisting of —F, —Cl, —Br, —I, —OH, —CN, —$NO_2$, —$SF_5$, —$NH_2$, $C_{1-6}$ alkoxy, $C_{1-6}$ alkylamino, $C_{1-6}$ dialkylamino, $C_{1-6}$ alkyl, oxo, —$S(=O)_{1-2}$—$C_{1-6}$ alkyl and 3 to 7 membered heterocycloalkyl;

$R^{1B}$ is selected from the group consisting of H, —OH, —F, —Cl, —Br, —I, —CN, $NH_2$, $C_{1-6}$ alkylamino, $C_{1-6}$ dialkylamino, $C_{1-6}$ alkoxy, $C_{1-6}$ alkyl, $C_{1-6}$ haloalkyl and $C_{1-6}$ heteroalkyl;

or $R^{1A}$ and $R^{1B}$ together form an oxo group or a 3 to 7 membered heterocycloalkyl comprising 1 to 2 heteroatoms selected from N, O and S and wherein said 3 to 7 membered heterocycloalkyl is optionally further substituted with 1 to 5 $R^{1A-2}$ substituents independently selected from the group consisting of —F, —Cl, —Br, —I, —OH, —CN, —$NO_2$, —$SF_5$, —$NH_2$, $C_{1-6}$ alkoxy, $C_{1-6}$ alkylamino, $C_{1-6}$ dialkylamino, $C_{1-6}$ alkyl, oxo, —$S(=O)_{1-2}$—$C_{1-6}$ alkyl and 3 to 7 membered heterocycloalkyl;

$R^{1C}$ at each occurrence is independently selected from the group consisting of hydrogen, —F, —Cl, —Br, —I, $C_{1-4}$ alkyl and $C_{1-4}$ haloalkyl;

$R^{1D}$ at each occurrence is independently selected from the group consisting of hydrogen, —F, —Cl, —Br, —I, $C_{1-4}$ alkyl and $C_{1-4}$ haloalkyl;

$R^2$ is selected from the group consisting of hydrogen, —F, —Cl, —Br, —I, —$NO_2$, —CN, $C_{1-6}$ alkyl and $C_{1-6}$ haloalkyl;

$R^3$ is $N(R^{3A})_2$, wherein each $R^{3A}$ is independently selected from the group consisting of hydrogen, $C_{1-6}$ alkyl, and $C_{1-6}$ haloalkyl;

$R^4$ is selected from the group consisting of $C_{1-2}$ alkyl, $C_{1-2}$ haloalkyl, $C_{2-12}$ alkenyl, $C_{2-12}$ alkynyl, —F, —Cl, —Br, —I, —$(X^4)_{0-1}$—CN, —$(X^4)_{0-1}$—$NO_2$, —$(X^4)_{0-1}$—$SF_5$, —$(X^4)_{0-1}$—$OSF_5$, —$(X^4)_{0-1}$—$OR^{4.4}$, —$(X^4)_{0-1}$—$N(R^{4.4})_2$, —$(X^4)_{0-1}$—$SR^{4.4}$, —$(X^4)_{0-1}$—$CF_3$, 3 to 7 membered cycloalkyl-$(X^4)_{0-1}$—, 3 to 7 membered heterocycloalkyl-$(X^4)_{0-1}$—, 5 to 6 membered heteroaryl-$(X^4)_{0-1}$—, phenyl-$(X^4)_{0-1}$—, —$(X^4)_{0-1}$—C(=O)N$(R^{4.4})(R^{4.4})$, —$(X^4)_{0-1}$—C(=O)$OR^{4.4}$, —$(X^4)_{0-1}$—$N(R^{4.4})C(=O)(R^{4.4})$, —$(X^4)_{0-1}$—$N(R^{4.4})C(=O)OR^{4.4}$, —$(X^4)_{0-1}$—$S(=O)_{1-2}$—$R^{4.4}$, —$(X^4)_{0-1}$—$N(R^{4.4})S(=O)_{1-2}$—$R^{4.4}$, —$(X^4)_{0-1}$—$S(=O)_{1-2}N(R^{4.4})_2$, —$(X^4)_{0-1}$—$C(=O)R^{4.4}$, —$(X^4)_{0-1}$—$C(=NOR^{4.4})R^{4.4}$, —$(X^4)_{0-1}$—$N(R^{4.4})C(=O)N(R^{4.4})_2$, —$(X^4)_{0-1}$—OC(=O)$R^{4.4}$, —$(X^4)_{0-1}$—OP(=O)$(OR^{4.4})_2$, —$(X^4)$—SC(=O)$OR^{4.4}$ and —$(X^4)$—SC(=O)$N(R^{4.4})_2$, each $X^4$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{4.4}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring optionally comprising 1 to 2 additional heteroatoms selected from N, O and S, and wherein a $R^4$ group is independently optionally further substituted with 1 to 5 $R^{4A-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ alkyl and $C_{1-6}$ dialkylamino;

or $R^3$ and $R^4$ together with the atoms to which they are attached form a 5 or 6 membered heteroaryl wherein the 5 or 6 membered heteroaryl is optionally substituted with 1 to 3 $R^{3/4cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^{3/4})_{0-1}$—CN, —$(X^{3/4})_{0-1}$—NO$_2$, —$(X^{3/4})_{0-1}$—SF$_5$, —$(X^{3/4})_{0-1}$—OSF$_5$, —$(X^{3/4})_{0-1}$—OR$^{3/4A}$, —$(X^{3/4})_{0-1}$—N(R$^{3/4A}$)$_2$, —$(X^{3/4})_{0-1}$—SR$^{3/4A}$, —$(X^{3/4})_{0-1}$—CF$_3$, 3 to 12 membered cycloalkyl-$(X^{3/4})_{0-1}$—, 3 to 12 membered heterocycloalkyl-$(X^{3/4})_{0-1}$—, 5 to 6 membered heteroaryl-$(X^{3/4})_{0-1}$—, phenyl-$(X^{3/4})_{0-1}$—, —$(X^{3/4})_{0-1}$—C(=O)N(R$^{3/4A}$)(R$^{3/4A}$), —$(X^{3/4})_{0-1}$—C(=O)OR$^{3/4A}$, —$(X^{3/4})_{0-1}$—N(R$^{3/4A}$)C(=O)(R$^{3/4A}$), —$(X^{3/4})_{0-1}$—N(R$^{3/4A}$)C(=O)OR$^{3/4A}$, —$(X^{3/4})_{0-1}$—S(=O)$_{1-2}$—R$^{3/4A}$, —$(X^{3/4})_{0-1}$—N(R$^{3/4A}$) S(=O)$_{1-2}$—R$^{3/4A}$, —$(X^{3/4})_{0-1}$—S(=O)$_{1-2}$N(R$^{3/4A}$)$_2$, —$(X^{3/4})_{0-1}$—C(=O)R$^{3/4A}$, —$(X^{3/4})_{0-1}$—C(=NOR$^{3/4A}$)R$^{3/4A}$, —$(X^{3/4})_{0-1}$—N(R$^{3/4A}$)C(=O)N(R$^{3/4A}$)$_2$ and —$(X^{3/4})_{0-1}$—OC(=O)R$^{3/4A}$, —$(X^{3/4})_{0-1}$—OP(=O)(OR$^{3/4A}$)$_2$, —$(X^{3/4})$—SC(=O)OR$^{3/4A}$ and —$(X^{3/4})$—SC(=O)N(R$^{3/4A}$)$_2$, each $X^{3/4}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{3/4A}$ at each occurrence is each independently selected from the group consisting of hydrogen, $C_{1-6}$ alkyl, $C_{1-6}$ haloalkyl and $C_{1-6}$ heteroalkyl, or any two $R^{3/4A}$ groups attached to the same nitrogen atom are optionally combined to form a 3 to 6 membered heterocyclic ring optionally comprising 1 to 2 additional heteroatom selected from N, O and S, and wherein a $R^{3/4cy}$ substituent at each occurrence is independently optionally further substituted with 1 to 5 $R^{3/4cy-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ alkyl and $C_{1-6}$ dialkylamino;

$R^5$ is hydrogen, —F, —Cl, —Br or —I; and $R^6$ is selected from the group consisting of $C_{1-12}$ alkyl, $C_{1-12}$ haloalkyl, $C_{1-12}$ heteroalkyl-(L)$_{0-1}$-, $C_{2-12}$ alkenyl-(L)$_{0-1}$-, $C_{2-12}$ alkynyl-(L)$_{0-1}$-, 3 to 12 membered cycloalkyl-(L)$_{0-1}$- and 3 to 12 membered heterocycloalkyl-(L)$_{0-1}$-, wherein L is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, wherein a $R^6$ group is optionally further substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ alkyl, $C_{1-6}$ haloalkyl, 3 to 5 membered cycloalkyl, 3 to 5 membered heterocycloalkyl, $C_{1-6}$ alkoxy, $C_{1-6}$ alkylthio, $C_{1-6}$ alkylamino and $C_{1-6}$ dialkylamino.

3. The compound of claim 1, wherein $R^2$ is hydrogen.

4. The compound of claim 1, wherein $R^5$ is hydrogen or —F.

5. The compound of claim 1, wherein $R^{1C}$ and $R^{1D}$ at each occurrence are each hydrogen.

6. The compound of claim 1, which is a compound of formula Id:

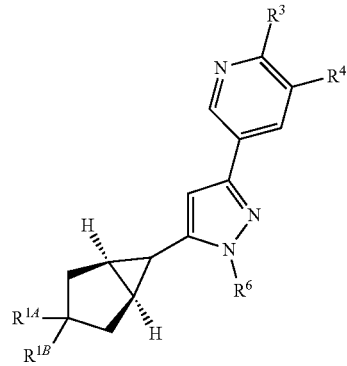

or a salt thereof.

7. The compound of claim 1, which is a compound of formula Ie:

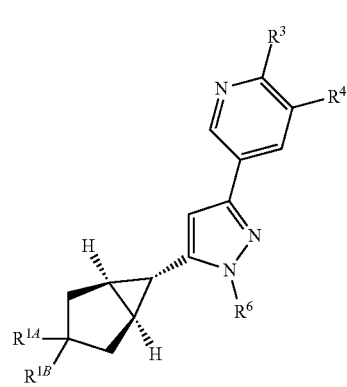

or a salt thereof.

8. The compound of claim 1, wherein $R^6$ is $C_{1-12}$ alkyl or a 3 to 7 membered cycloalkyl-(L)$_{0-1}$, wherein L is a $C_{1-4}$ alkylene, and wherein said $C_{1-12}$ alkyl group and 3 to 7 membered cycloalkyl-(L)$_{0-1}$ are each independently optionally substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ haloalkyl, $C_{1-6}$ alkoxy, $C_{1-6}$ alkylthio, $C_{1-6}$ alkylamino and $C_{1-6}$ dialkylamino.

9. The compound of claim 1, wherein $R^6$ is $C_{1-6}$ alkyl, wherein the $C_{1-6}$ alkyl is optionally substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ haloalkyl, $C_{1-6}$ alkoxy, $C_{1-6}$ alkylthio, $C_{1-6}$ alkylamino and $C_{1-6}$ dialkylamino.

10. The compound of claim 1, wherein $R^6$ is —CH(CH$_3$)$_2$ or —CH$_2$CHF$_2$.

11. The compound of claim 1, wherein $R^6$ is 3 to 7 membered cycloalkyl-(L)$_{0-1}$, wherein L is $C_{1-4}$ alkylene; and wherein $R^6$ is optionally substituted with 1 to 5 $R^{6A}$ substituents independently selected from the group consisting of —F, —Cl, —Br, —I, —OH, —CN, —NO$_2$, —SF$_5$, —OSF$_5$, —NH$_2$, $C_{1-6}$ haloalkyl, $C_{1-6}$ alkoxy, $C_{1-6}$ alkylthio, $C_{1-6}$ alkylamino and $C_{1-6}$ dialkylamino.

12. The compound of claim 1, wherein $R^6$ is selected from the group consisting of:

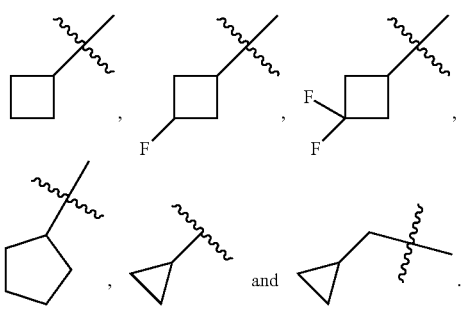

13. The compound of claim 1, wherein $R^3$ is $N(R^{3A})_2$, and $R^4$ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^4)_{0-1}$—CN, —$(X^4)_{0-1}$—NO$_2$, —$(X^4)_{0-1}$—SF$_5$, —$(X^4)_{0-1}$—OSF$_5$, —$(X^4)_{0-1}$—OR$^{4A}$, —$(X^4)_{0-1}$—N(R$^{4A}$)$_2$, —$(X^4)_{0-1}$—SR$^{4A}$, —$(X^4)_{0-1}$—CF$_3$, 3 to 7 membered cycloalkyl-$(X^4)_{0-1}$—, 3 to 7 membered heterocycloalkyl-$(X^4)_{0-1}$—, 5 to 6 membered heteroaryl-$(X^4)_{0-1}$—, phenyl-$(X^4)_{0-1}$, —$(X^4)_{0-1}$—C(=O)N(R$^{4A}$)(R$^{4A}$), —$(X^4)_{0-1}$—C(=O)OR$^{4A}$, —$(X^4)_{0-1}$—N(R$^{4A}$)C(=O)(R$^{4A}$), —$(X^4)_{0-1}$—N(R$^{4A}$)C(=O)OR$^{4A}$, —$(X^4)_{0-1}$—S(=O)$_{1-2}$—R$^{4A}$, —$(X^4)_{0-1}$—N(R$^{4A}$)S(=O)$_{1-2}$—R$^{4A}$, —$(X^4)_{0-1}$—S(=O)$_{1-2}$N(R$^{4A}$)$_2$, —$(X^4)_{0-1}$—C(=O)R$^{4A}$, —$(X^4)_{0-1}$—C(=NOR$^{4A}$)R$^{4A}$, —$(X^4)_{0-1}$—N(R$^{4A}$)C(=O)N(R$^{4A}$)$_2$, —$(X^4)_{0-1}$—OC(=O)R$^{4A}$, —$(X^4)_{0-1}$—OP(=O)(OR$^{4A}$)$_2$, —$(X^4)$—SC(=O)OR$^{4A}$ and —$(X^4)$—SC(=O)N(R$^{4A}$)$_2$, each $X^4$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatoms selected from N, O and S; and wherein a $R^4$ group is independently optionally further substituted with 1 to 5 $R^{4A-1}$ substituents independently selected from the group consisting of —F, —Cl, —Br, —I, —OH, —CN, —NO$_2$, —SF$_5$, —NH$_2$, $C_{1-6}$ alkoxy and $C_{1-6}$ alkylamino.

14. The compound of claim 1, wherein each $R^{3A}$ is independently selected from the group consisting of hydrogen and methyl.

15. The compound of claim 1, wherein $R^3$ is —NH$_2$.

16. The compound of claim 1, which is a compound of formula Ii:

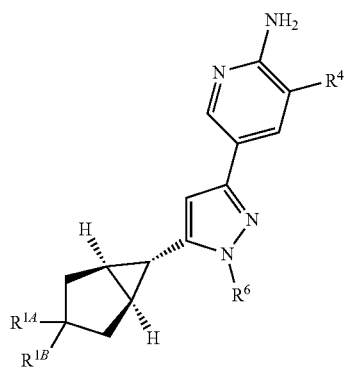

Ii or a salt thereof.

17. The compound of claim 1, wherein $R^4$ is selected from the group consisting of $C_{1-12}$ alkyl, $C_{1-12}$ haloalkyl, $C_{2-12}$ alkenyl, $C_{2-12}$ alkenyl, —$(X^4)_{0-1}$—OR$^{4A}$, —$(X^4)_{0-1}$—SR$^{4A}$ and —$(X^4)_{0-1}$—C(=O)N(R$^{4A}$)(R$^{4A}$); each $X^4$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatoms selected from N, O and S, and wherein a $R^4$ group is independently optionally further substituted with 1 to 5 $R^{4A-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ alkyl and $C_{1-6}$ dialkylamino.

18. The compound of claim 1, wherein $R^4$ is selected from the group consisting of $C_{1-6}$ alkyl, $C_{1-6}$ haloalkyl, $C_{2-6}$ alkenyl, $C_{2-6}$ alkynyl, —OR$^{4A}$, —SR$^{4A}$ and —C(=O)N(R$^{4A}$)(R$^{4A}$), $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatoms selected from N, O and S, and wherein a $R^4$ group is independently optionally further substituted with 1 to 5 $R^{4A-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ alkyl and $C_{1-6}$ dialkylamino.

19. The compound of claim 1, wherein $R^4$ is selected from the group consisting of $C_{1-6}$ haloalkyl, —OC$_{1-6}$ haloalkyl, —SC$_{1-6}$ haloalkyl and —C(=O)N(R$^{4A}$)(R$^{4A}$) and the two $R^{4A}$ groups attached to the same nitrogen atom are combined to form a 3 to 6 membered heterocyclic ring comprising 1 to 2 additional heteroatoms selected from N, O and S.

20. The compound of claim 1, wherein $R^4$ is selected from the group consisting of $C_{1-3}$ haloalkyl, —O(C$_{1-3}$ haloalkyl) and —S(C$_{1-3}$ haloalkyl).

21. The compound of claim 1, wherein $R^4$ is selected from the group consisting of CF$_3$, —OCF$_3$, —OCHF$_2$, —OCH$_2$CF$_3$, —SCF$_3$ and —C(=O)-(pyrrolidin-1-yl).

22. The compound of claim 1, wherein $R^3$ and $R^4$ together with the atoms to which they are attached form a 5 membered heteroaryl, wherein the 5 membered heteroaryl is optionally substituted with 1 to 3 $R^{3/4cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^{3/4})_{0-1}$—CN, —$(X^{3/4})_{0-1}$—NO$_2$, —$(X^{3/4})_{0-1}$—SF$_5$, —$(X^{3/4})_{0-1}$—OSF$_5$, —$(X^{3/4})_{0-1}$—OR$^{3/4A}$, —$(X^{3/4})_{0-1}$—N(R$^{3/4A}$)$_2$, —$(X^{3/4})_{0-1}$—SR$^{3/4A}$, —$(X^{3/4})_{0-1}$—CF$_3$, 3 to 12 membered cycloalkyl-$(X^{3/4})_{0-1}$—, 3 to 12 membered heterocycloalkyl-$(X^{3/4})_{0-1}$—, 5 to 6 membered heteroaryl-$(X^{3/4})_{0-1}$—, phenyl-$(X^{3/4})_{0-1}$—, —$(X^{3/4})_{0-1}$—C(=O)N(R$^{3/4A}$)(R$^{3/4A}$), —$(X^{3/4})_{0-1}$—C(=O)OR$^{3/4A}$, —$(X^{3/4})_{0-1}$—N(R$^{3/4A}$)C(=O)(R$^{3/4A}$), —$(X^{3/4})_{0-1}$—N(R$^{3/4A}$)C(=O)OR$^{3/4A}$, —$(X^{3/4})_{0-1}$—S(=O)$_{1-2}$—R$^{3/4A}$, —$(X^{3/4})_{0-1}$—N(R$^{3/4A}$)S(=O)$_{1-2}$—R$^{3/4A}$, —$(X^{3/4})_{0-1}$—S(=O)$_{1-2}$N(R$^{3/4A}$)$_2$, —$(X^{3/4})_{0-1}$—C(=O)R$^{3/4A}$, —$(X^{3/4})_{0-1}$—C(=NOR$^{3/4A}$)R$^{3/4A}$, —$(X^{3/4})_{0-1}$—N(R$^{3/4A}$)C(=O)N(R$^{3/4A}$)$_2$ and —$(X^{3/4})_{0-1}$—C(=O)R$^{3/4A}$, —$(X^{3/4})_{0-1}$—OP(=O)(OR$^{3/4A}$)$_2$, —$(X^{3/4})$—SC(=O)OR$^{3/4A}$ and —$(X^{3/4})$—SC(=O)N(R$^{3/4A}$)$_2$, each $X^{3/4}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{3/4A}$ at each occurrence is each independently selected from the group consisting of hydrogen, $C_{1-6}$ alkyl, $C_{1-6}$ haloalkyl and $C_{1-6}$ heteroalkyl, or any two $R^{3/4A}$ groups attached to the same nitrogen atom are optionally combined to form a 3 to 6 membered heterocyclic ring comprising 1 to 2 additional heteroatom selected from N, O and S, and wherein a $R^{3/4cy}$ substituent at each occurrence is independently optionally further substituted with 1 to 5 $R^{3/4cy-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino.

23. The compound of claim 1, wherein $R^3$ and $R^4$ together with the atoms to which are attached and the remainder of the compound of formula 0 form a compound of formula II:

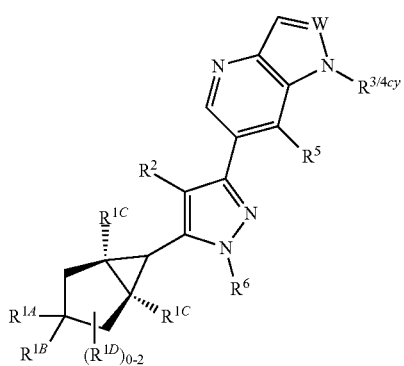

II wherein W is CH or N, or a salt thereof.

24. The compound of claim 1, wherein $R^3$ and $R^4$ together with the atoms to which are attached and the remainder of the compound of formula 0 form a compound of formula IIe:

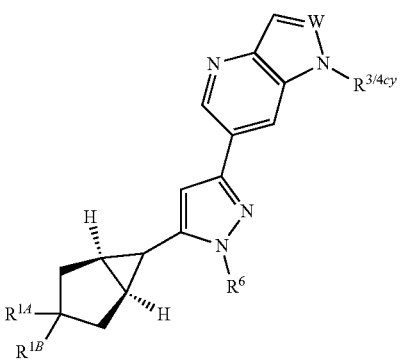

IIe wherein W is CH or N, or a salt thereof.

25. The compound of claim 1, wherein each $R^{3/4cy}$ substituent is selected from the group consisting of 3 to 12 membered cycloalkyl-$(X^{3/4})_{0-1}$—, 3 to 12 membered heterocycloalkyl-$(X^{3/4})_{0-1}$, 5 to 6 membered heteroaryl-$(X^{3/4})_{0-1}$— and phenyl-$(X^{3/4})_{0-1}$—, each $X^{3/4}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, and wherein a $R^{3/4cy}$ substituent at each occurrence is independently optionally further substituted with 1 to 5 $R^{3/4cy-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino.

26. The compound of claim 1, wherein each $R^{3/4cy}$ substituent is selected from the group consisting of 5 to 6 membered heteroaryl-$(X^{3/4})_{0-1}$— and phenyl-$(X^{3/4})_{0-1}$—, each $X^{3/4}$ is $C_{1-4}$ alkylene, and wherein a $R^{3/4cy}$ substituent at each occurrence is independently optionally further substituted with 1 to 5 $R^{3/4cy-1}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino.

27. The compound of claim 1, wherein each $R^{3/4cy}$ is pyridinyl-$(X^{3/4})_1$—, wherein $X^{3/4}$ is $C_{1-4}$ alkylene.

28. The compound of claim 1, wherein $R^{3/4cy}$ is:

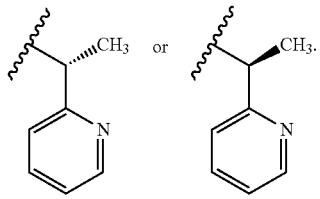

29. The compound of claim 1, wherein $R^{1A}$ is selected from the group consisting of 3 to 12 membered heterocycloalkyl, 5 or 6 membered heteroaryl, —$(X^{1A})_{0-1}$—$OR^{1A-1}$ and —$(X^{1A})_{0-1}$—$N(R^{1A-1})_2$, wherein each $X^{1A}$ is independently selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{1A-1}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, phenyl and phenyl-$C_{1-4}$ alkyl, or any two $R^{1A-1}$ groups attached to the same nitrogen atom are optionally combined to form a 3 to 6 membered heterocyclic ring comprising 1 to 2 additional heteroatom selected from N, O and S, and wherein a $R^{1A}$ group at each occurrence is independently optionally further substituted with 1 to 5 $R^{1A-2}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ dialkylamino, $C_{1-6}$ alkyl, oxo, —S(═O)$_{1-2}$—$C_{1-6}$ alkyl, and $R^{1b}$ is H.

30. The compound of claim 1, wherein $R^{1A}$ is selected from the group consisting of 3 to 12 membered heterocycloalkyl and 5 or 6 membered heteroaryl, wherein the 3 to 12 membered heterocycloalkyl and 5 or 6 membered heteroaryl at each occurrence is independently optionally further substituted with 1 to 5 $R^{1A-2}$ substituents independently selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ dialkylamino, $C_{1-6}$ alkyl, oxo, —S(═O)$_{1-2}$—$C_{1-6}$ alkyl, and $R^{1b}$ is H.

31. The compound of claim 1, wherein $R^{1A}$ is selected from the group consisting of 3 to 12 membered heterocycloalkyl, 5 or 6 membered heteroaryl, —$(X^{1A})_{0-1}$—$OR^{1A-1}$ and —$(X^{1A})_{0-1}$—$N(R^{1A-1})_2$, wherein each $X^{1A}$ is independently selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene, $R^{1A-1}$ at each occurrence is each independently selected from the group consisting of hydrogen, $C_{1-6}$ alkyl, 3-7 membered heterocycloalkyl and 3-7 membered heterocycloalkyl-$C_{1-4}$ alkyl-, and wherein a $R^{1A}$ group at each occurrence is independently optionally further substituted with 1 to 5 $R^{1A-2}$ substituents independently selected from the group consisting of —F, —Cl, —Br, —I, —OH, —CN, —NO$_2$, —SF₅, —NH₂, C₁₋₆ alkoxy, C₁₋₆ alkylamino, C₁₋₆ dialkylamino, C₁₋₆ alkyl, oxo and —S(=O)₁₋₂—C₁₋₆ alkyl, and R$^{1b}$ is H.

32. The compound of claim 1, wherein R$^{1A}$ is selected from the group consisting of 3 to 12 membered heterocycloalkyl, 5 or 6 membered heteroaryl, —OR$^{1A-1}$ and —N(R$^{1A-1}$)₂, wherein R$^{1A-1}$ at each occurrence is each independently selected from the group consisting of hydrogen, C₁₋₆ alkyl, 3-7 membered heterocycloalkyl and 3-7 membered heterocycloalkyl-C₁₋₄ alkyl-, and wherein a R$^{1A}$ group at each occurrence is independently optionally further substituted with 1 to 5 R$^{1A-2}$ substituents independently selected from the group consisting of —F, —Cl, —Br, —I, —OH, —CN, —NO₂, —SF₅, —NH₂, C₁₋₆ alkoxy, C₁₋₆ alkylamino, C₁₋₆ dialkylamino, C₁₋₆ alkyl, oxo and —S(=O)₁₋₂—C₁₋₆ alkyl, and R$^{1b}$ is H.

33. The compound of claim 1, wherein R$^{1A}$ is selected from the group consisting of morpholinyl, thiomorpholinyl, thiomorpholinyl-1,1-dioxide, piperazinyl, azetidinyl, pyrrolidin-2-onyl, 2-oxa-6-azaspiro[3.3]heptanyl, (1R,4R)-2-oxa-5-azabicyclo[2.2.1]heptanyl, oxazolidin-2-only, piperazinyl, (1S,4S)-2-oxa-5-azabicyclo[2.2.1]heptanyl, pyrrolidinyl, 1,4-oxazepanyl, octahydropyrrolo[1,2-a]pyrazinyl, pyrazolyl, —OH and —N(R$^{1A-1}$)₂, wherein R$^{1A-1}$ at each occurrence is each independently selected from the group consisting of hydrogen, C₁₋₆ alkyl, 3-7 membered heterocycloalkyl and 3-7 membered heterocycloalkyl-C₁₋₄ alkyl-, and wherein a R$^{1A}$ group at each occurrence is independently optionally further substituted with 1 to 5 R$^{1A-2}$ substituents selected from the group consisting of —F, —Cl, —Br, —I, —OH, —CN, —NO₂, —SF₅, —NH₂, C₁₋₆ alkoxy, C₁₋₆ alkylamino, C₁₋₆ dialkylamino, C₁₋₆ alkyl, oxo and —S(=O)₁₋₂—C₁₋₆ alkyl, and R$^{1b}$ is H.

34. The compound of claim 1, wherein R$^{1B}$ is H, and R$^{1A}$ is:

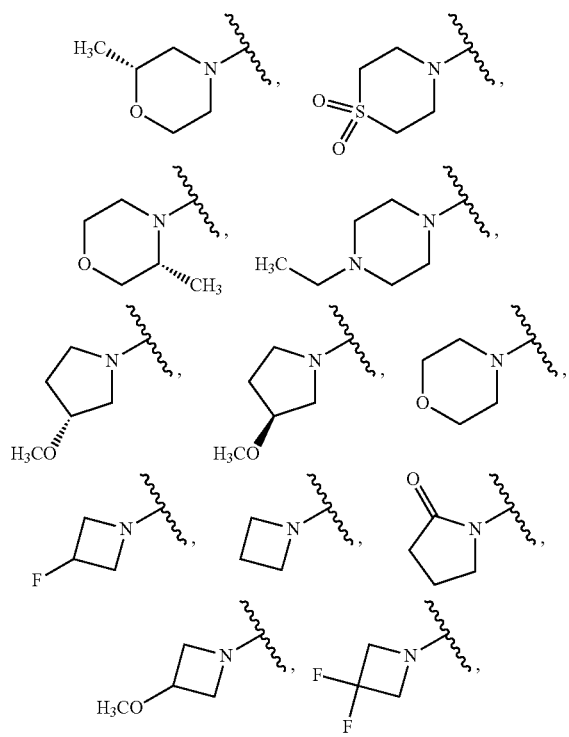
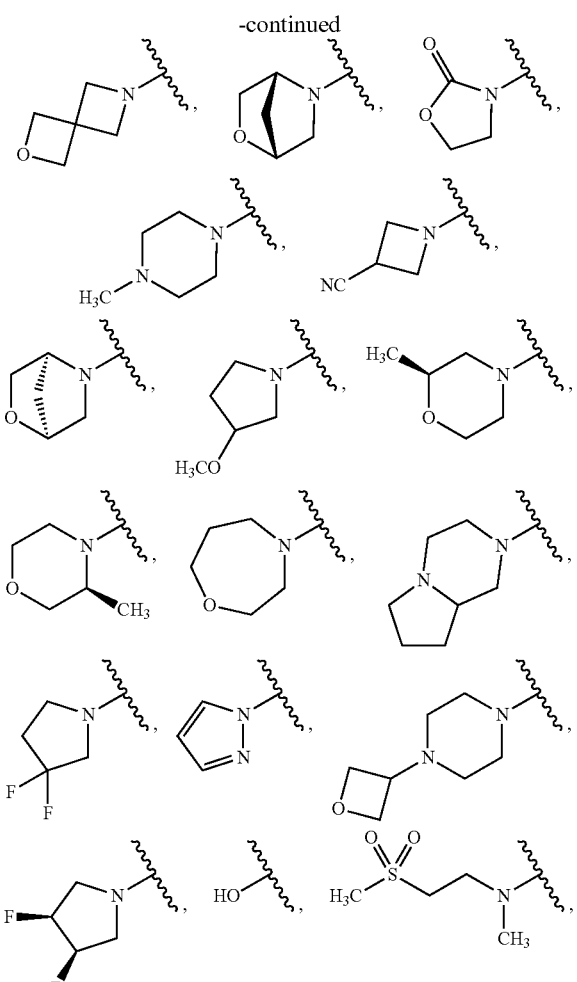

35. The compound of claim 1, wherein R$^{1B}$ is H, and R$^{1A}$ is:

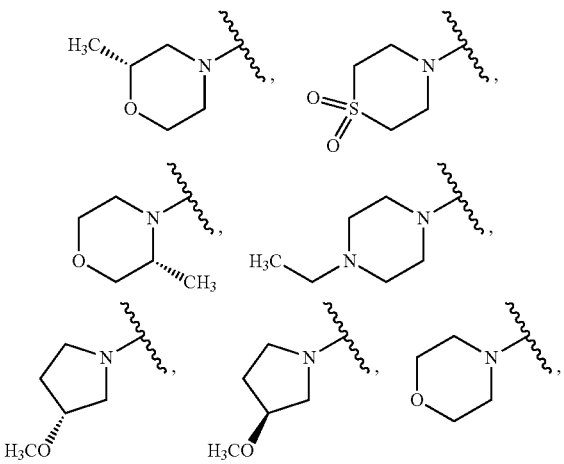

-continued

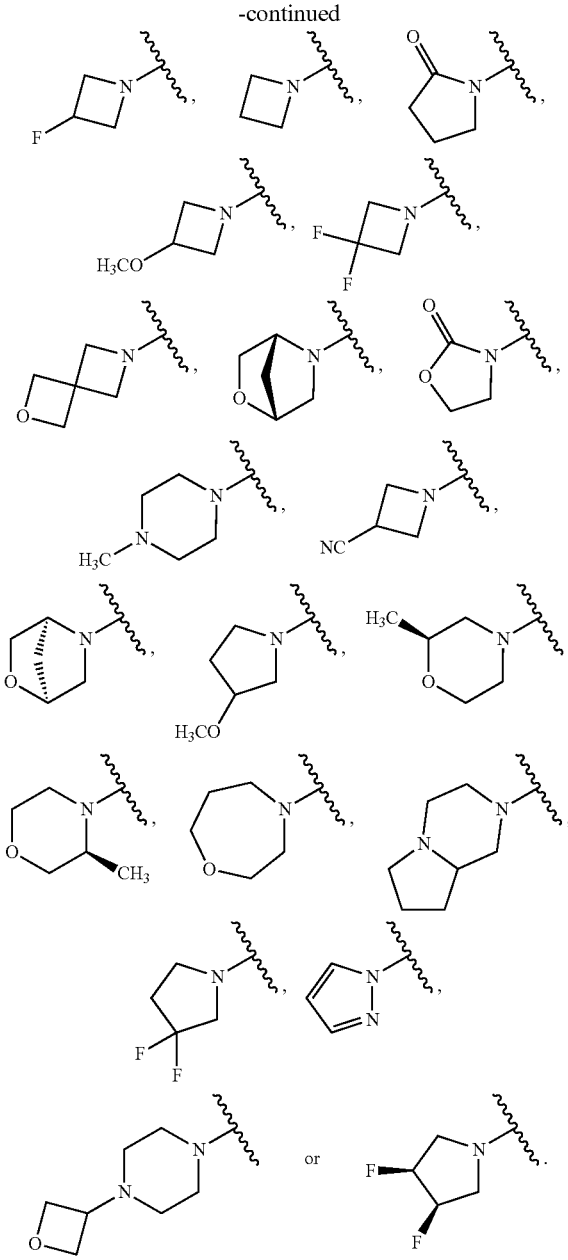

36. The compound of claim 1, wherein $R^{1B}$ is H, and $R^{1A}$ is:

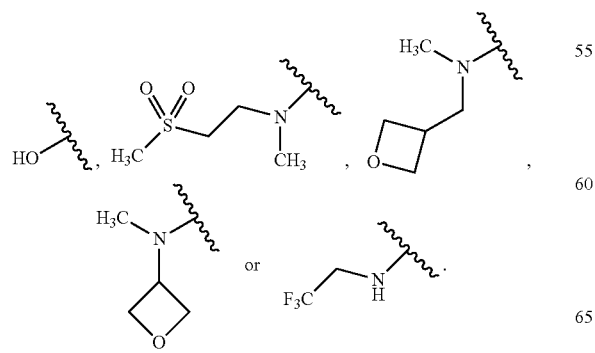

37. The compound of claim 1, wherein or $R^{1A}$ and $R^{1B}$ together form an oxo group.

38. The compound of claim 1, wherein or $R^{1A}$ and $R^{1B}$ together form a 3 to 7 membered heterocycloalkyl comprising 1 to 2 heteroatoms selected from N, O and S and wherein said 3 to 7 membered heterocycloalkyl is optionally further substituted with 1 to 5 $R^{1A-2}$ substituents independently selected from the group consisting of —F, —Cl, —Br, —I, —OH, —CN, —NO$_2$, —SF$_5$, —NH$_2$, C$_{1-6}$ alkoxy, C$_{1-6}$ alkylamino, C$_{1-6}$ dialkylamino, C$_{1-6}$ alkyl, oxo, —S(=O)$_{1-2}$—C$_{1-6}$ alkyl and $R^{1b}$ is H.

39. The compound of claim 1 selected from:

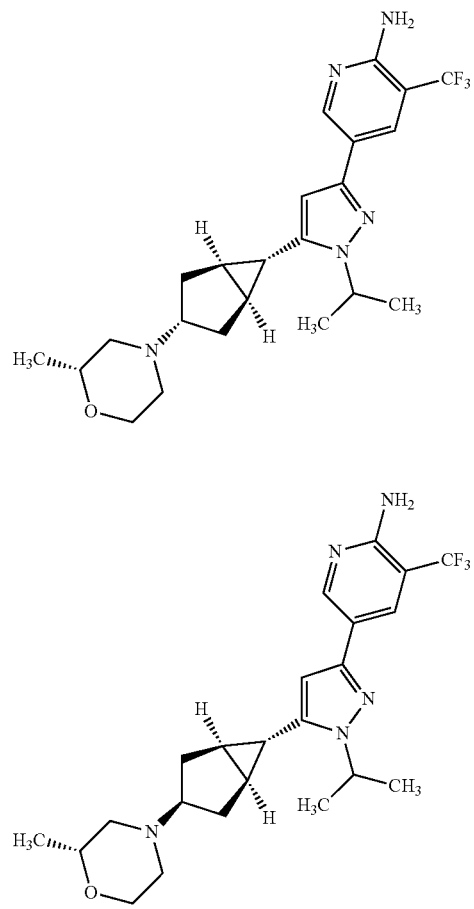

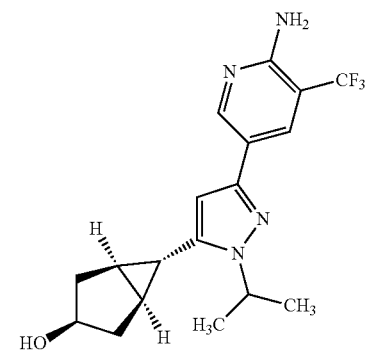

443
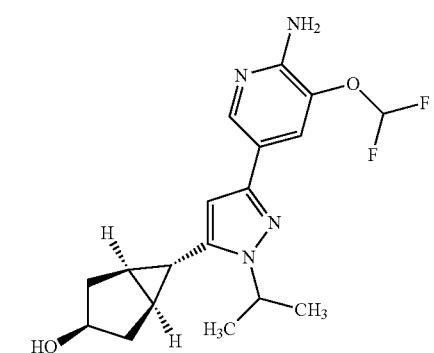
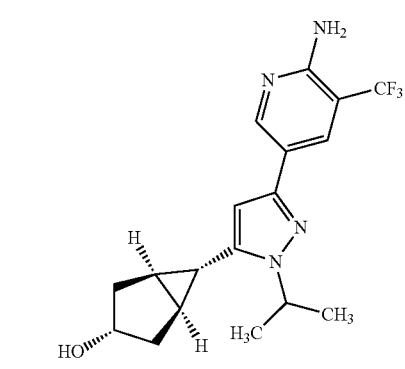
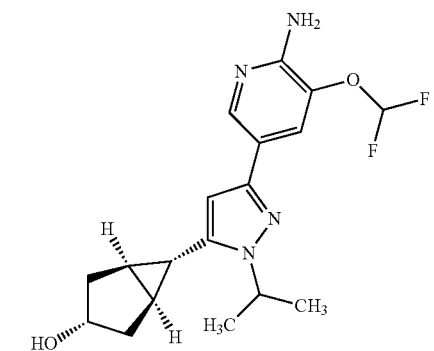
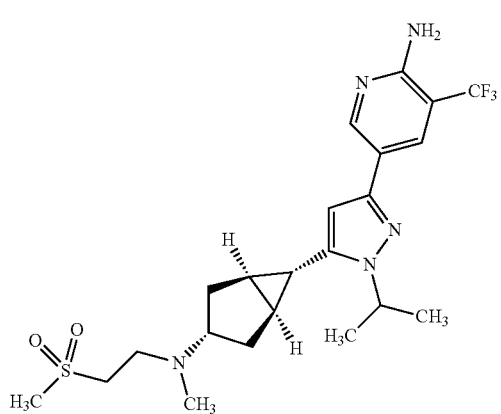
444
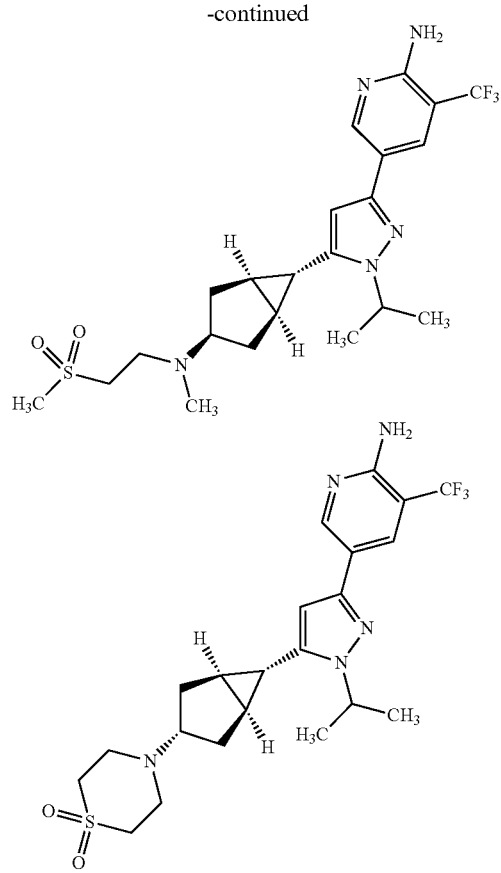
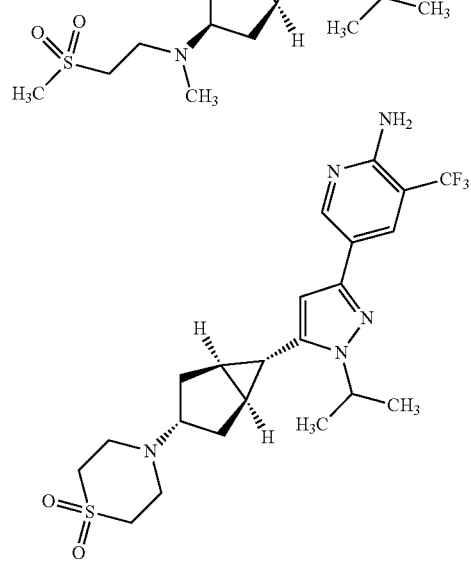
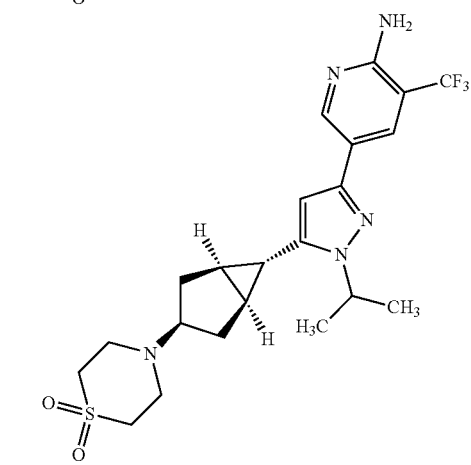
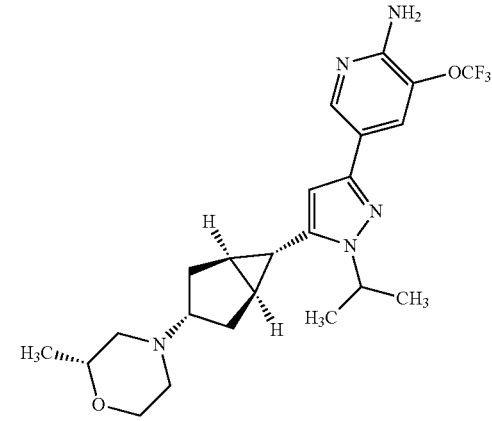

-continued
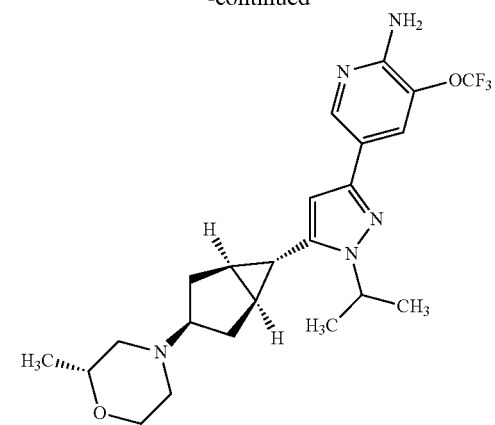
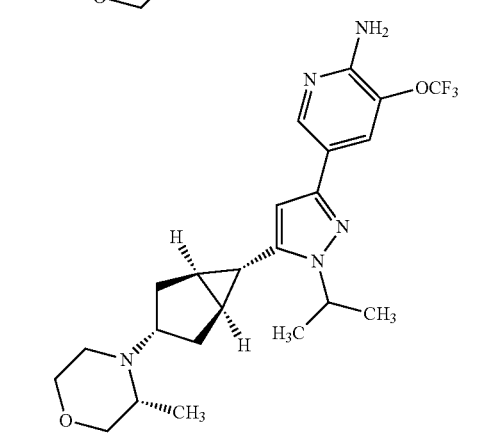
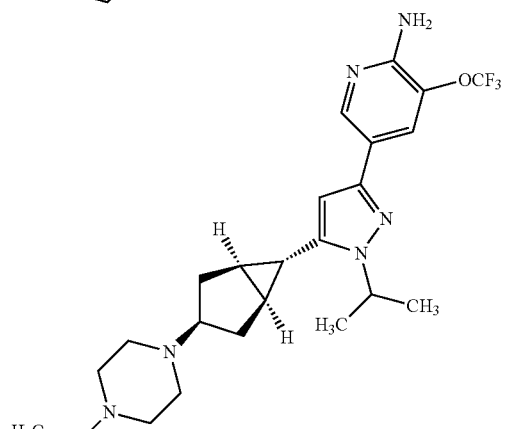
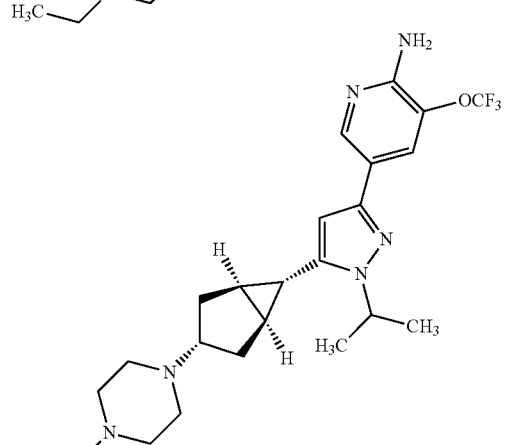
-continued
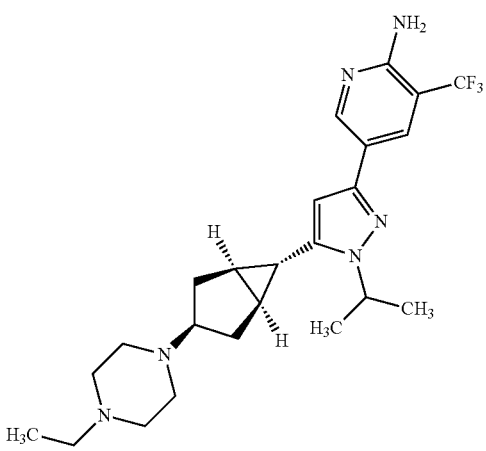
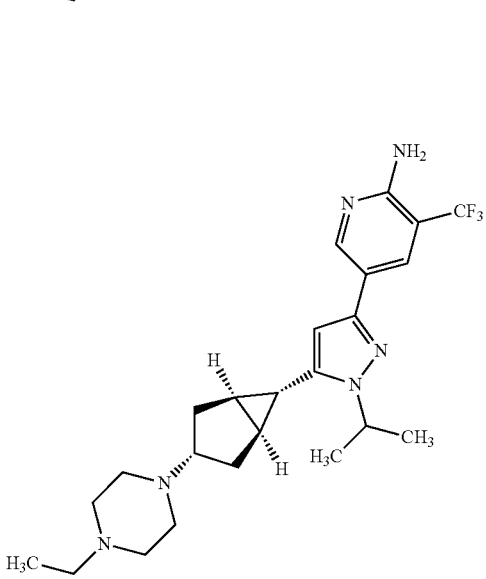
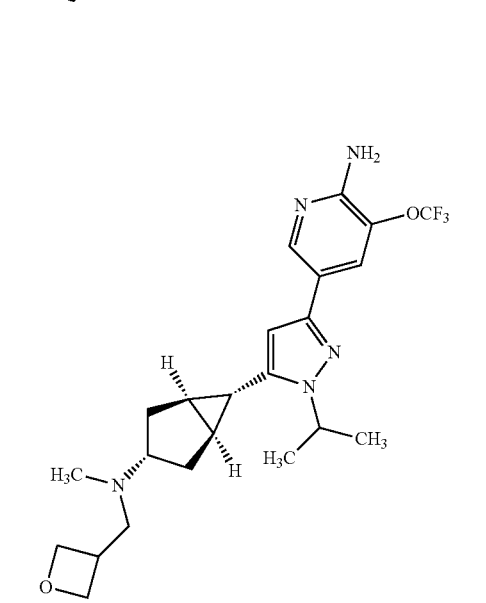

447
-continued
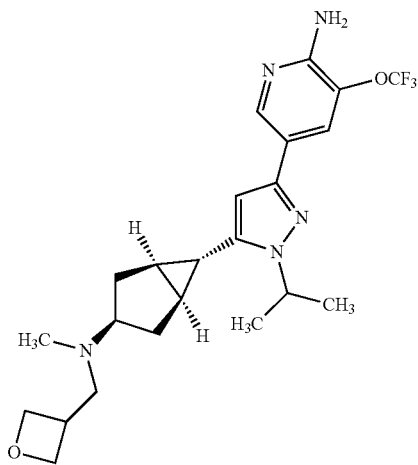
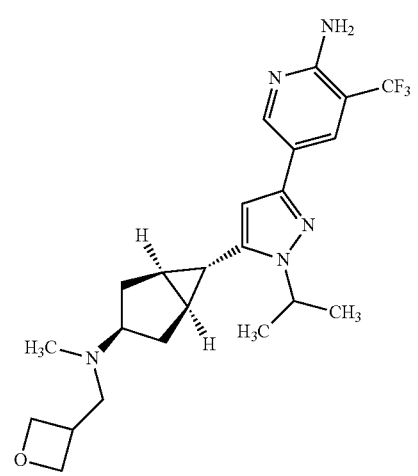
448
-continued
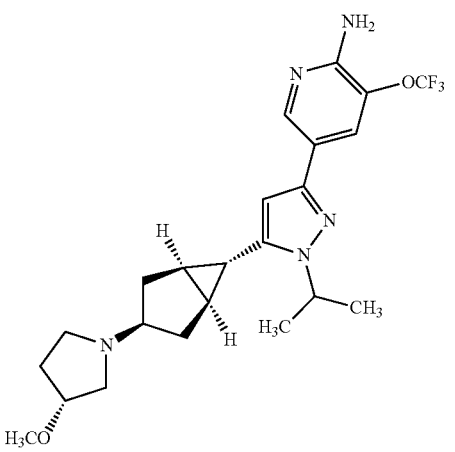
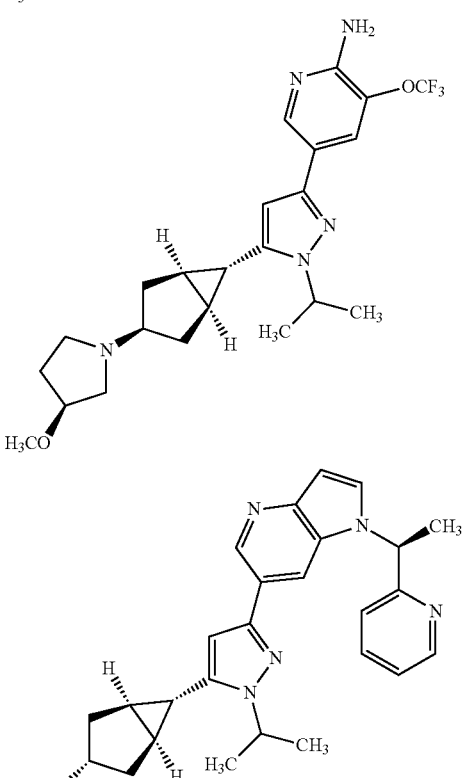
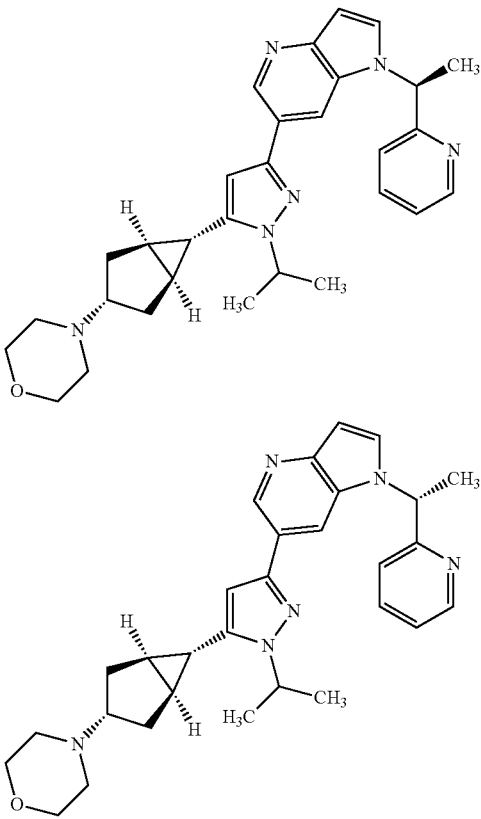

449
-continued
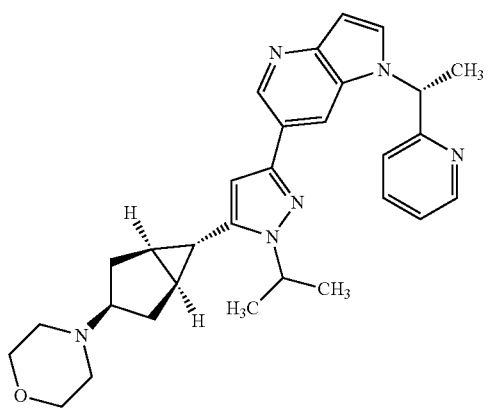
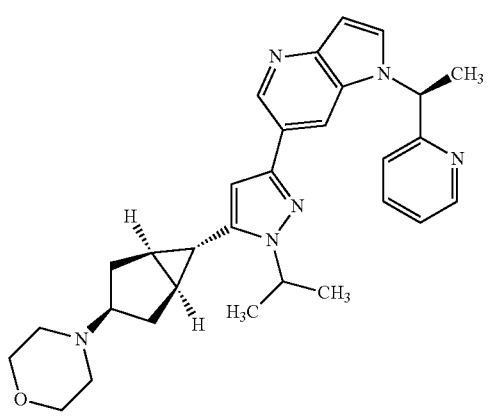
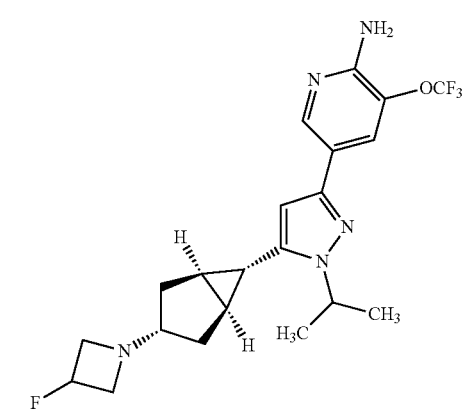
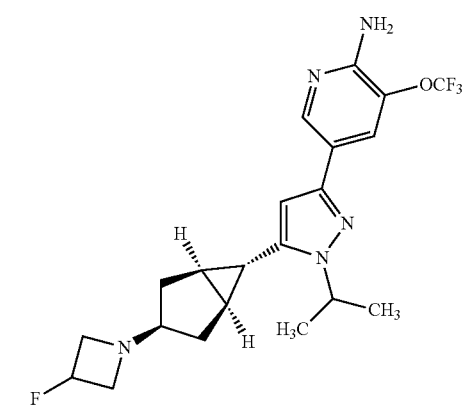
450
-continued
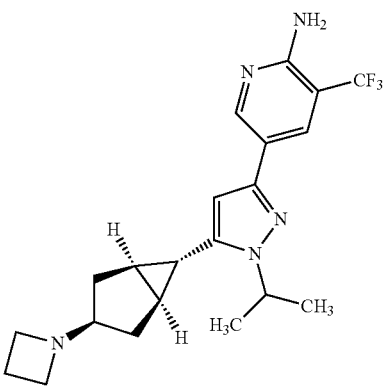
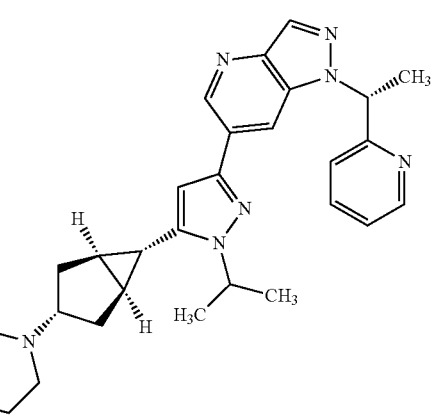
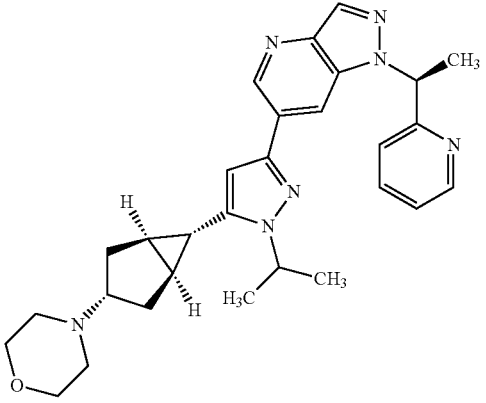
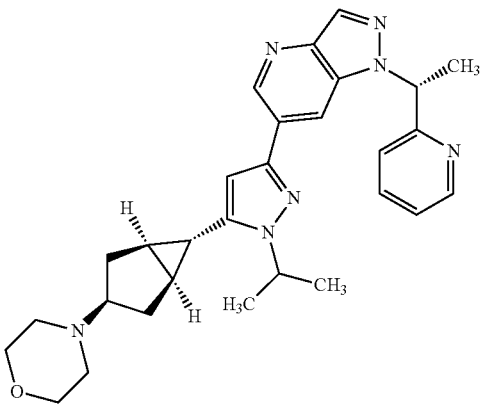

451
-continued
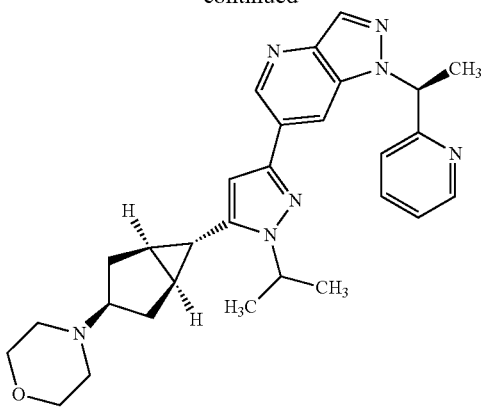
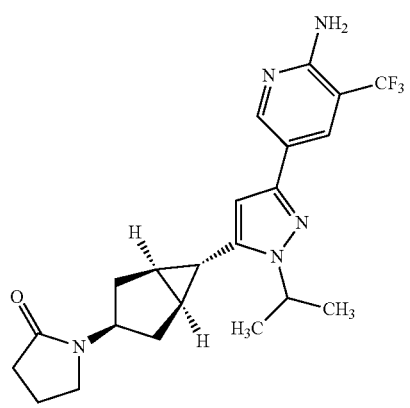
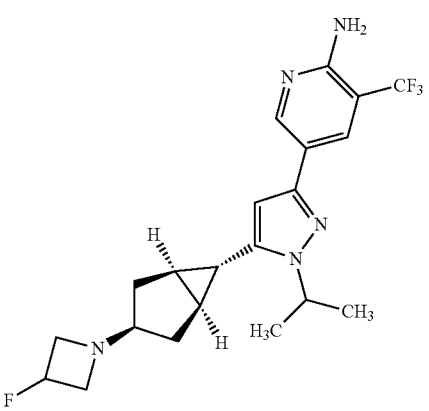
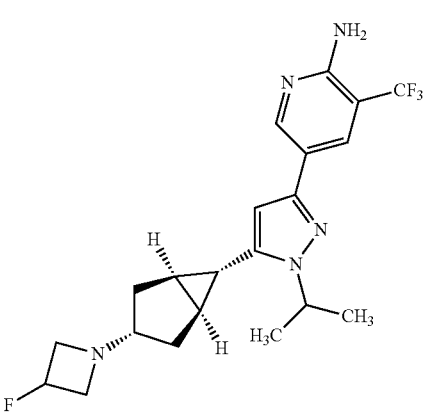
452
-continued
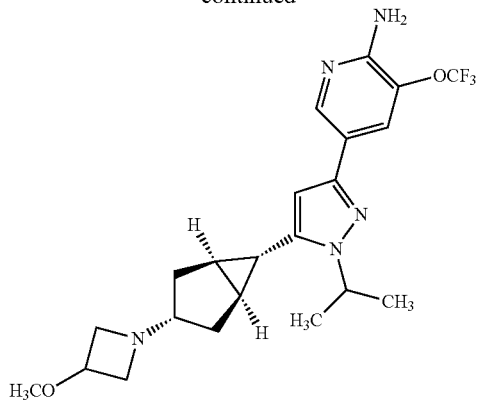
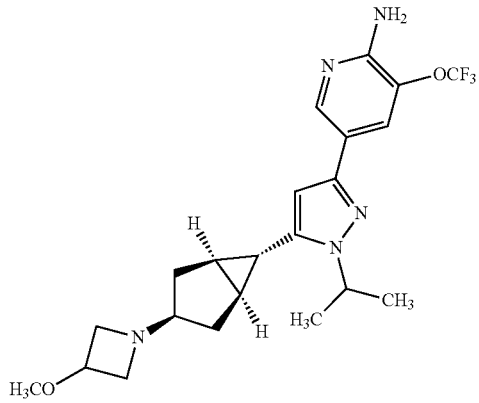
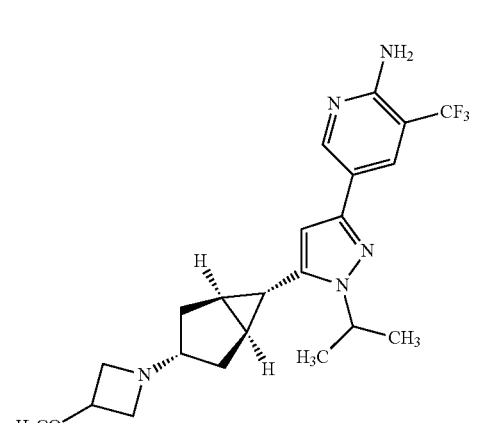
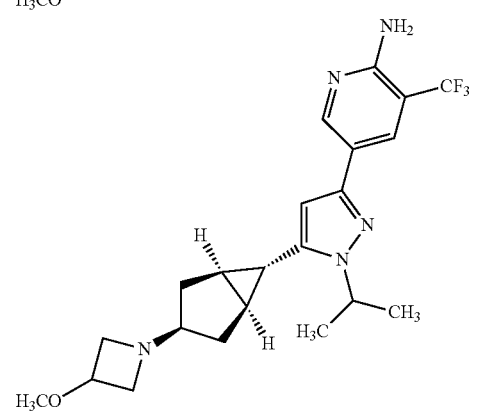

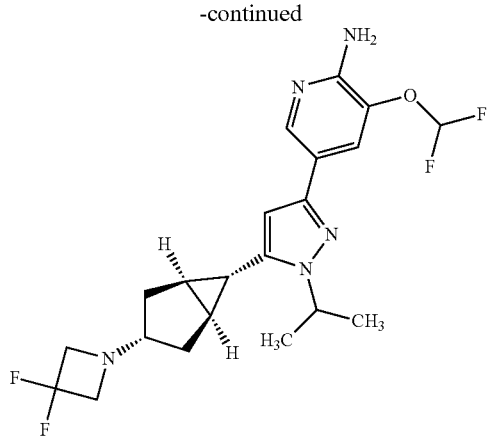
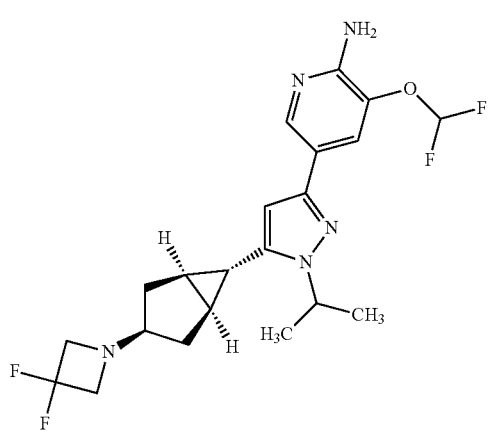
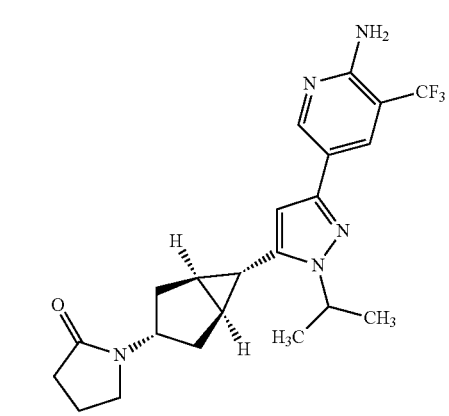
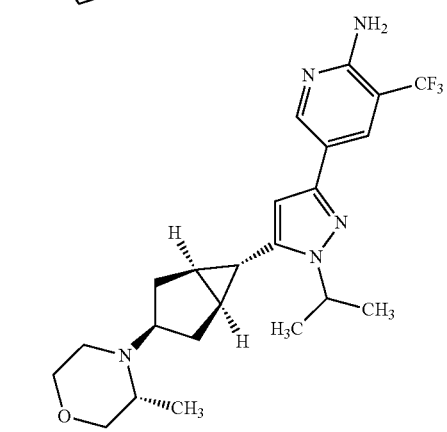
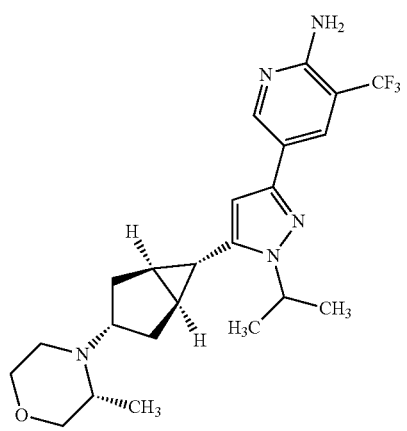
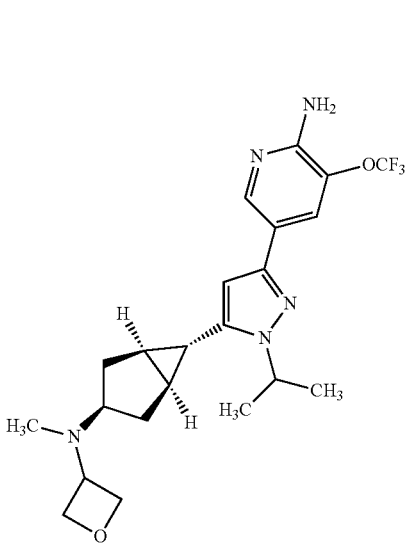
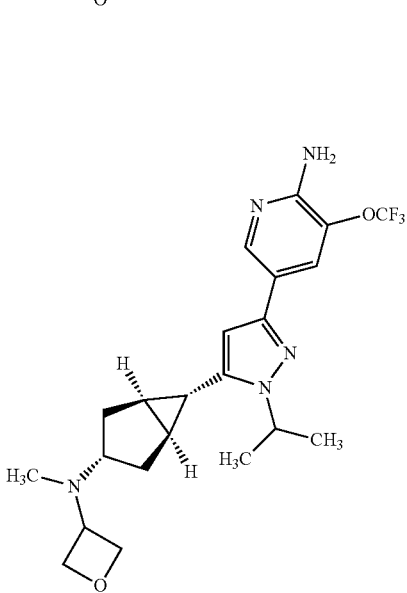

455
-continued
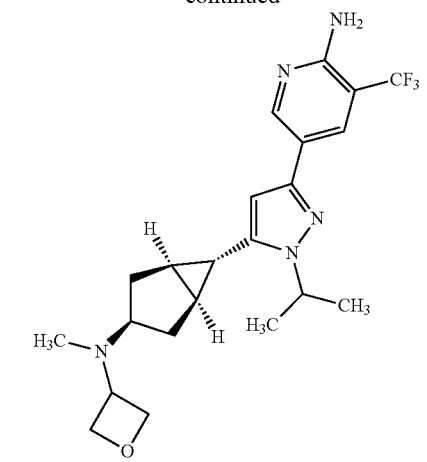
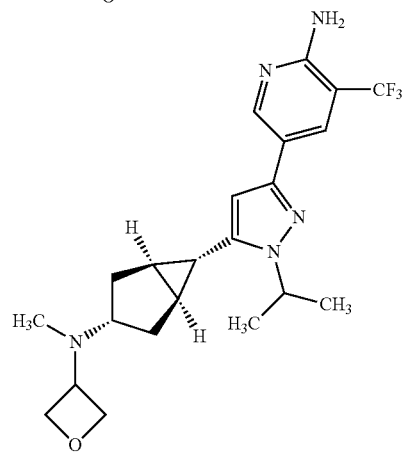
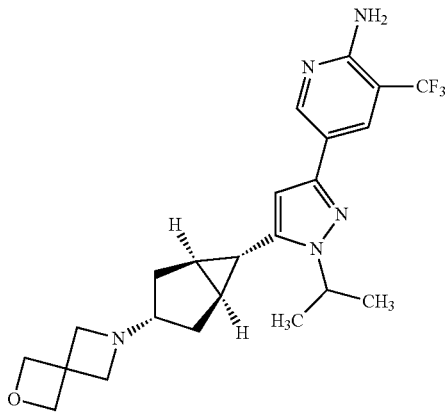
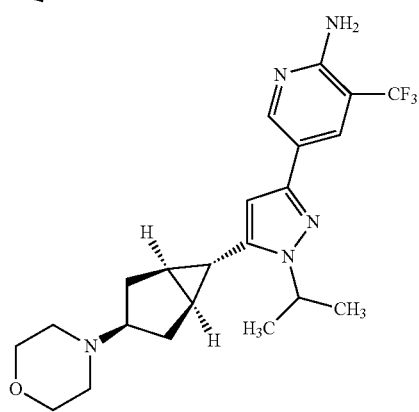
456
-continued
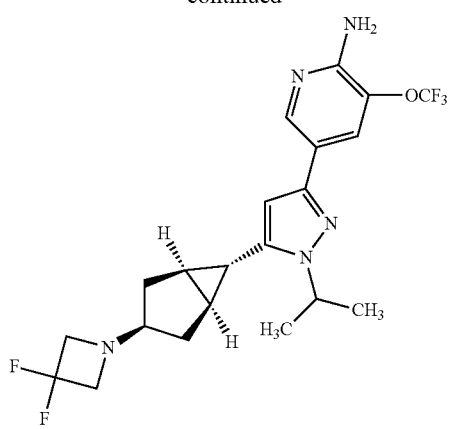
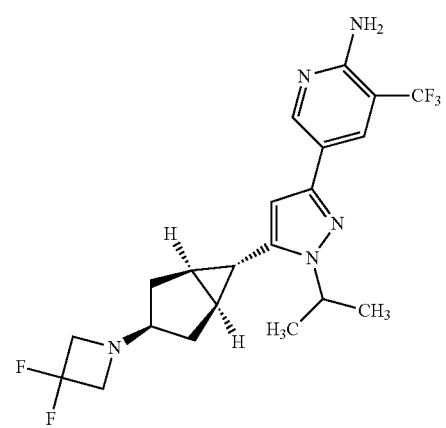
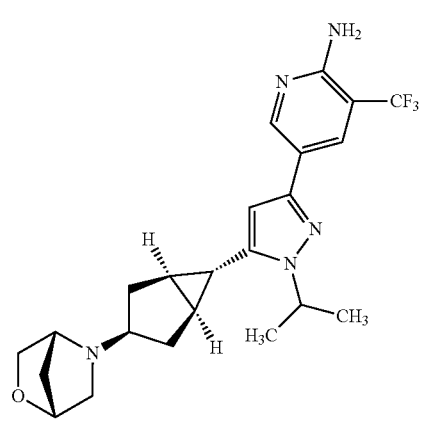
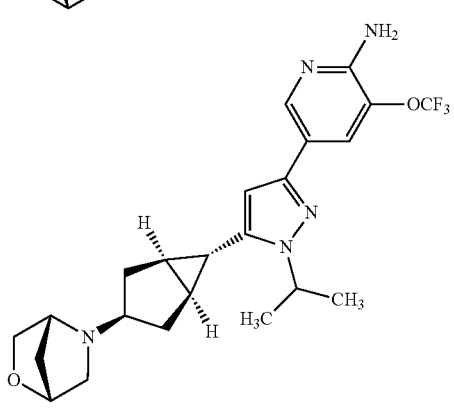

457
-continued
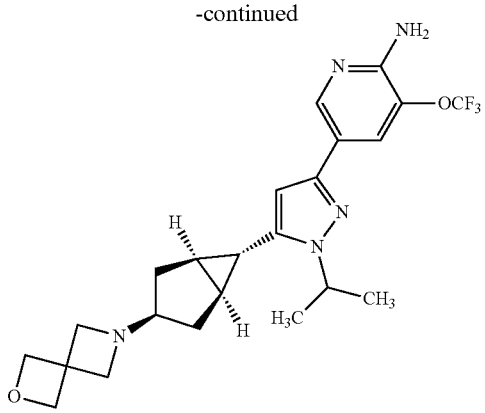
458
-continued
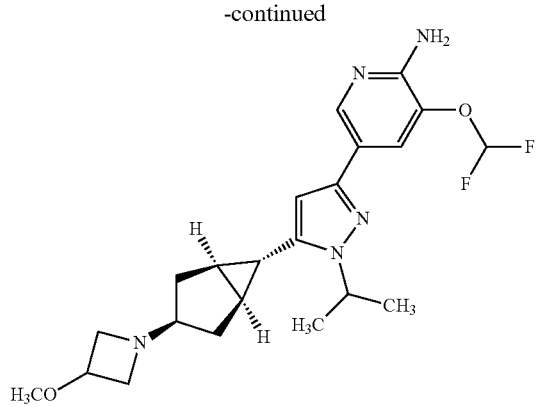
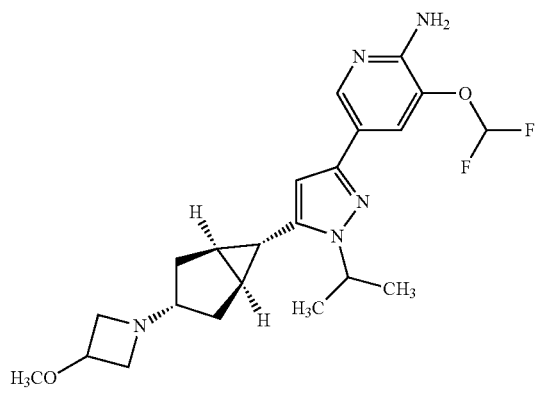
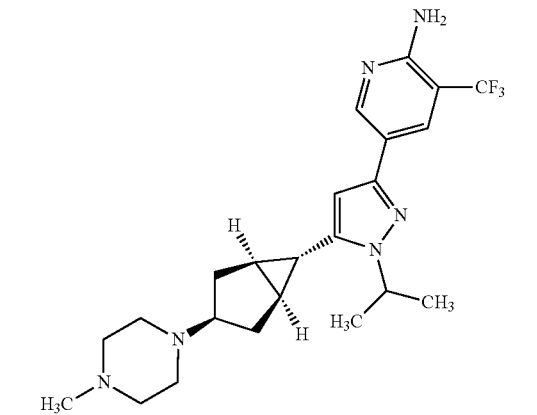

459
-continued
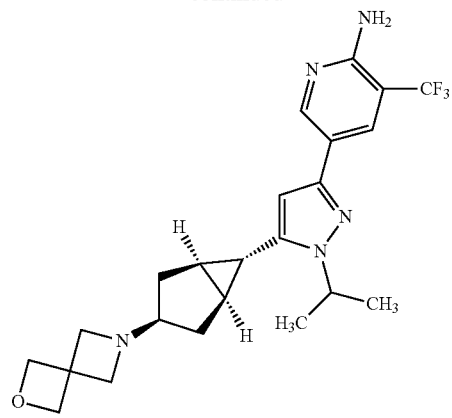
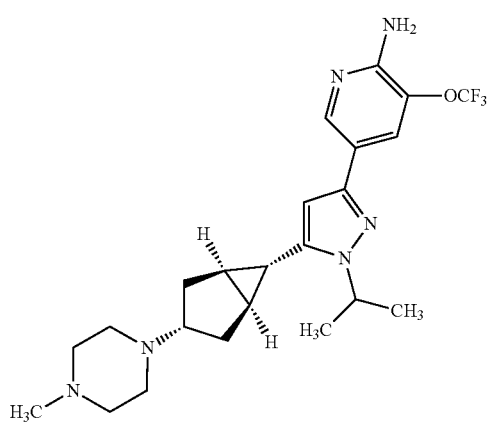
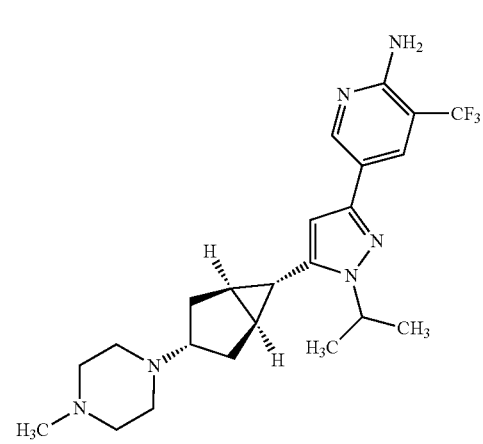
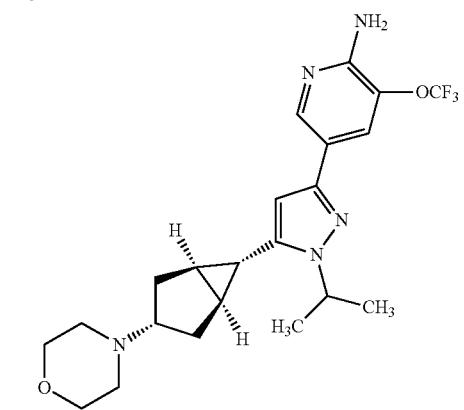
460
-continued
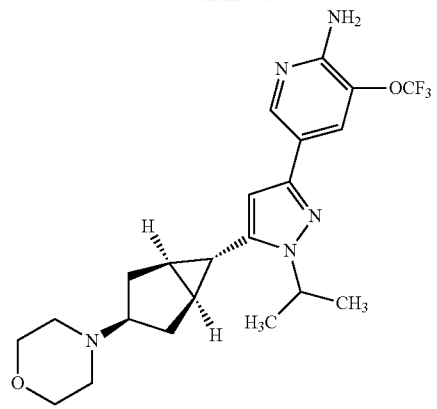
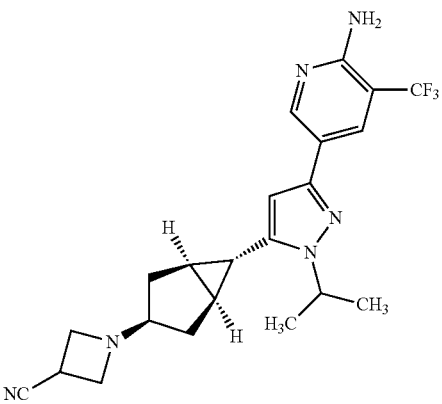
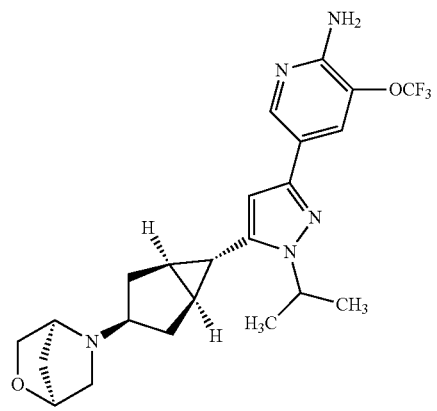
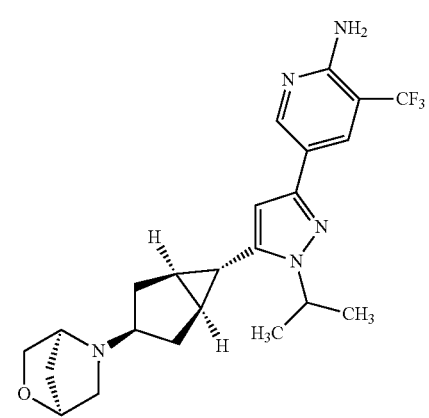

461
-continued
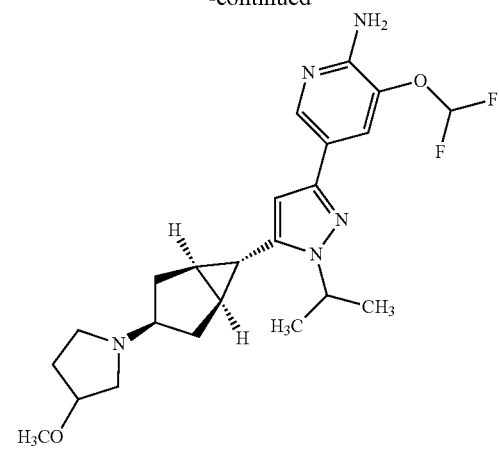
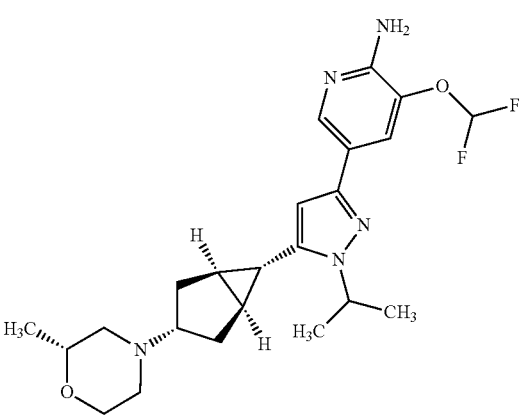
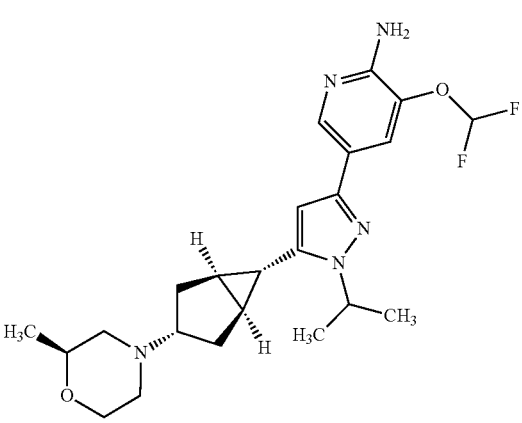
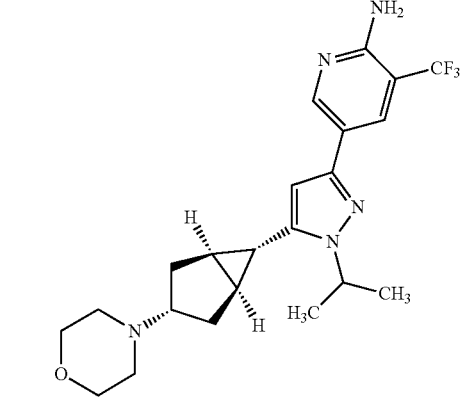
462
-continued
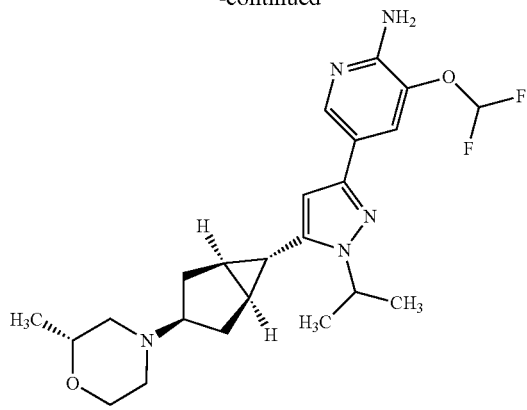
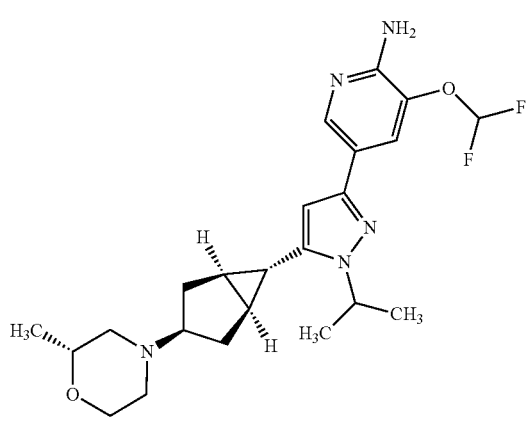
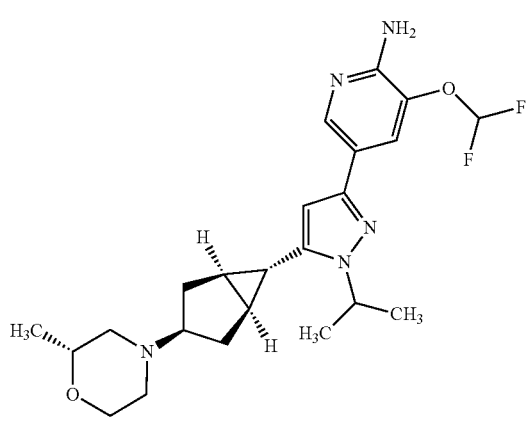
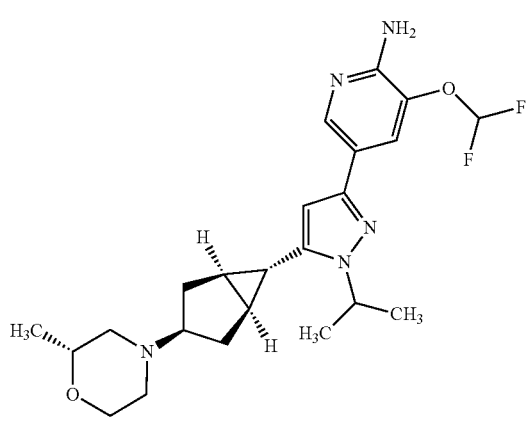

463
-continued
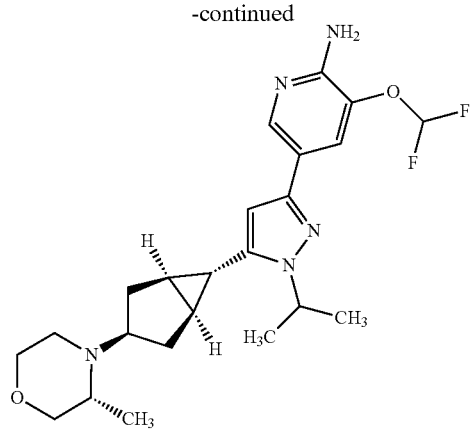
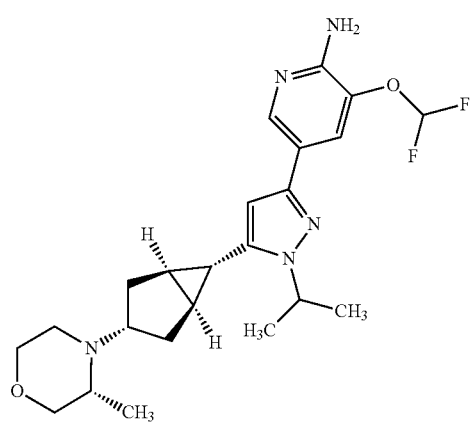
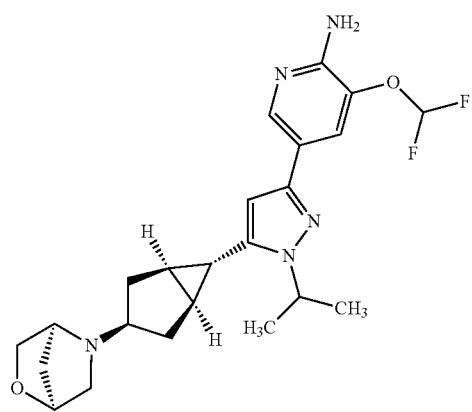
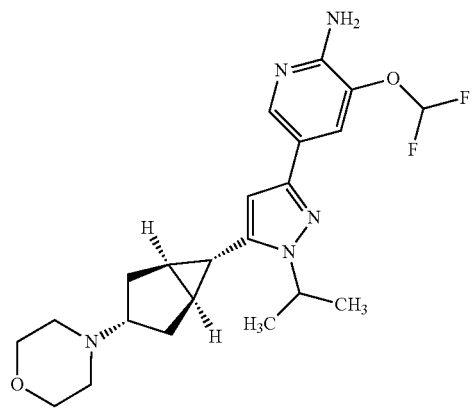
464
-continued
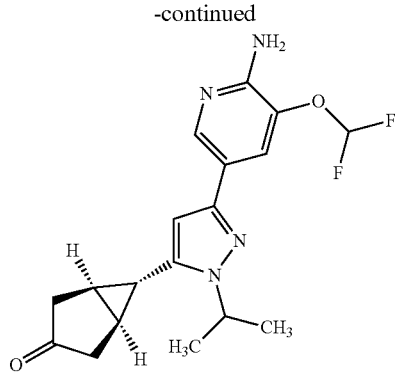
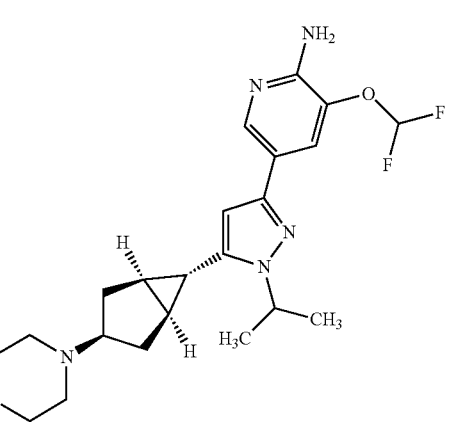
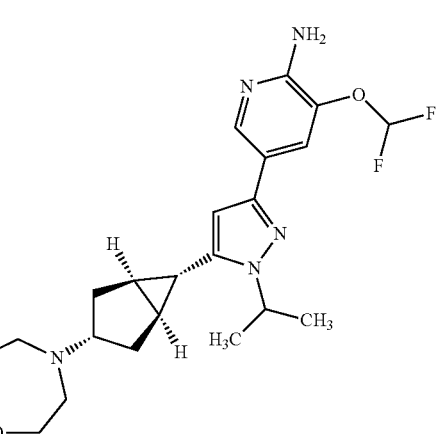
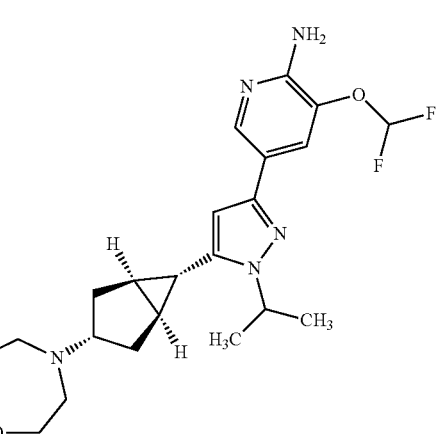

465
-continued
466
-continued
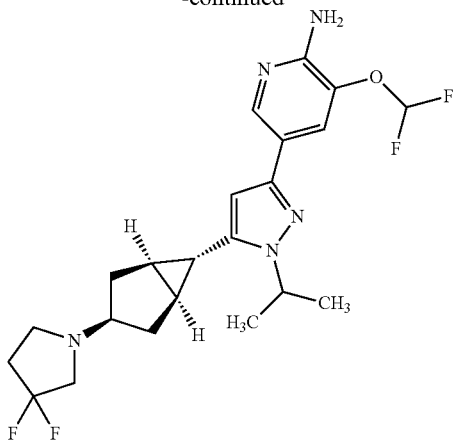
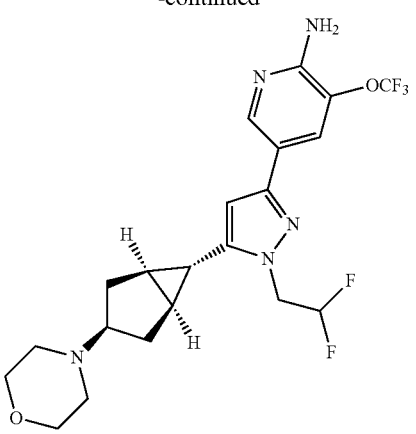

467
-continued
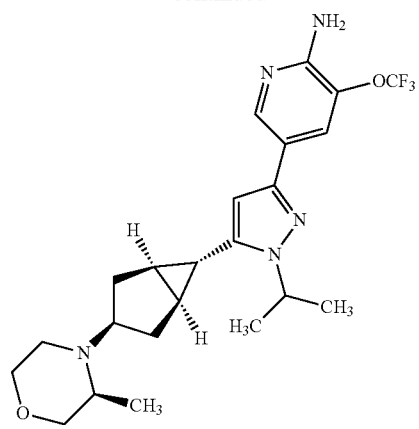
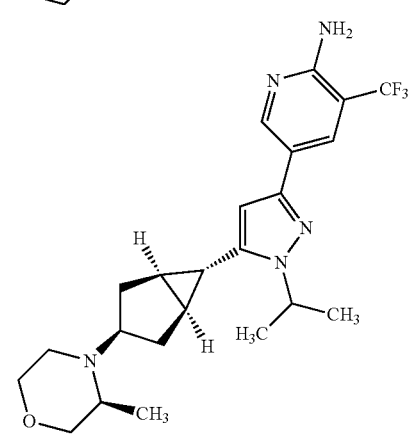
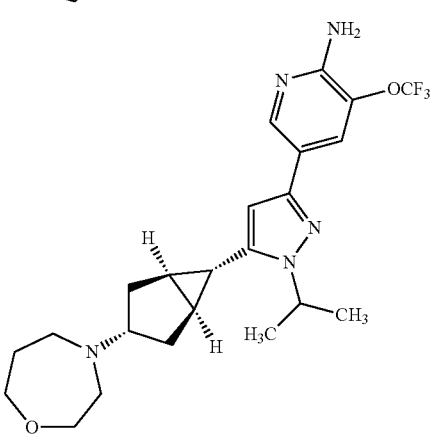
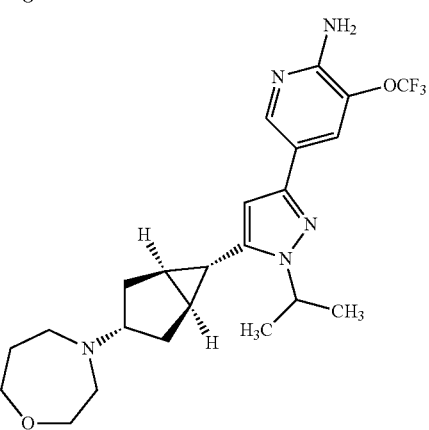
468
-continued
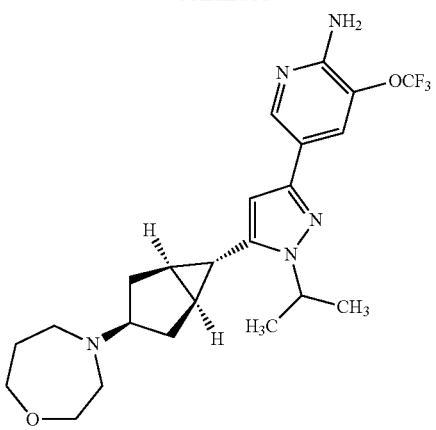
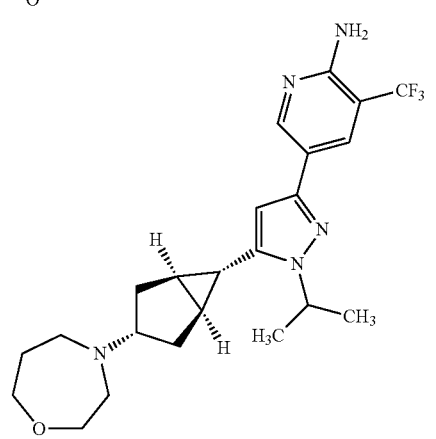
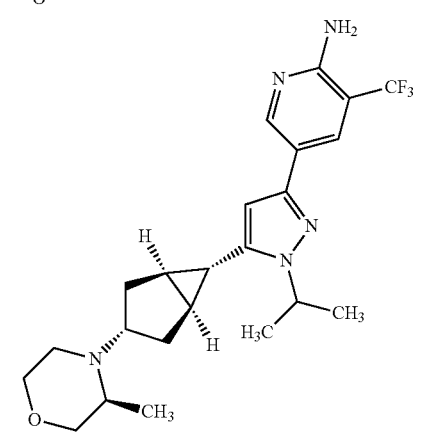
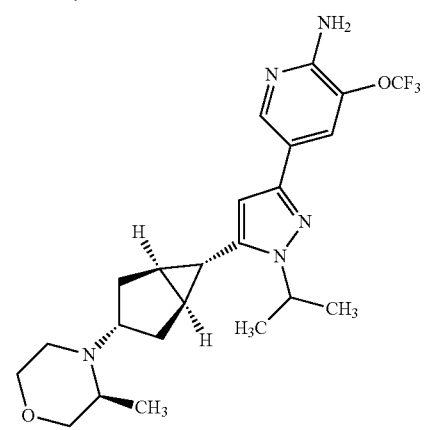

469
-continued
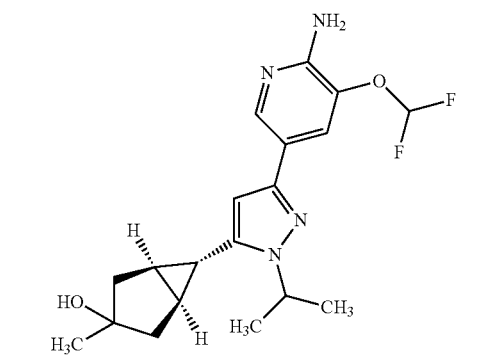
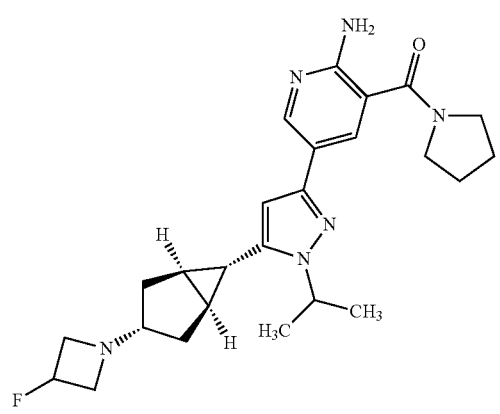
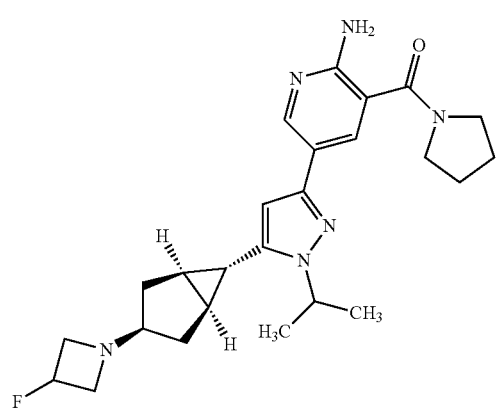
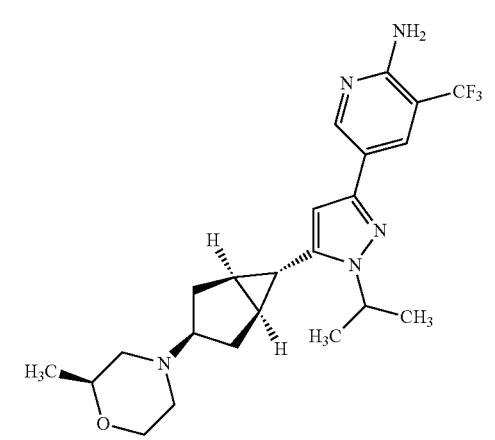
470
-continued
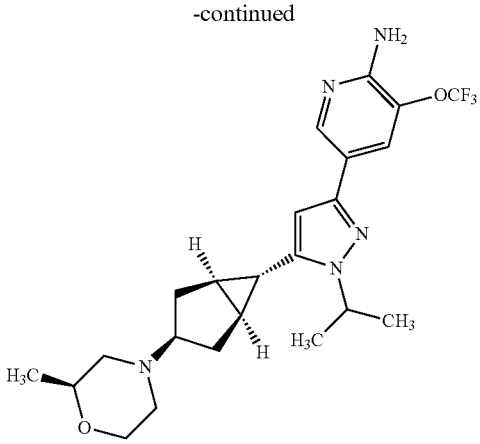
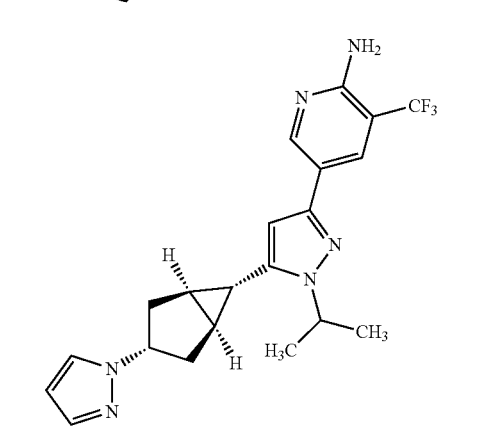
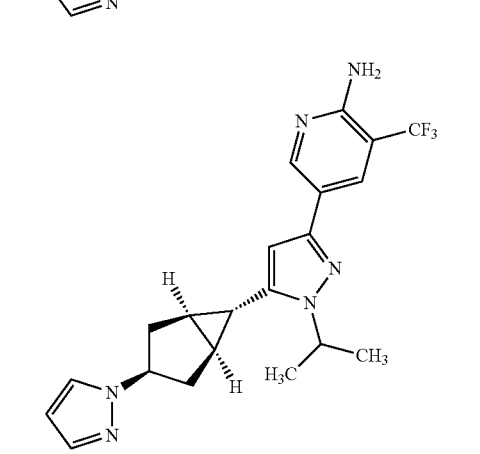
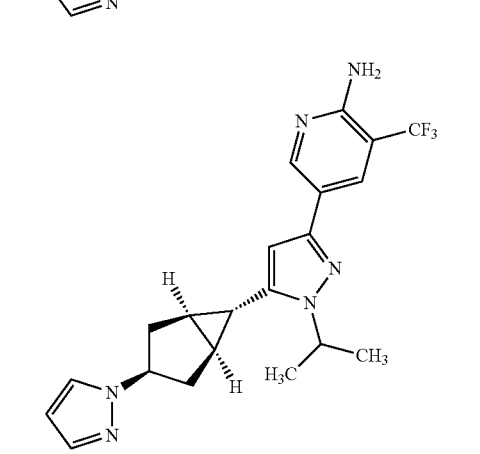

471
-continued
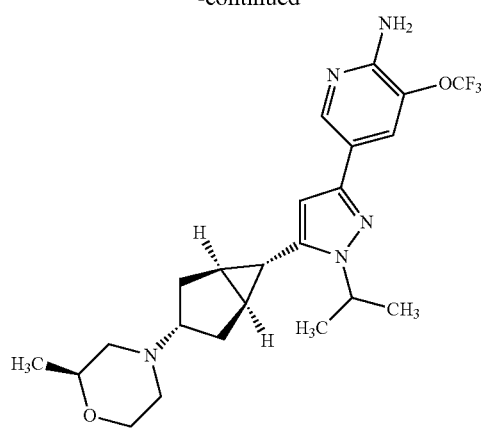
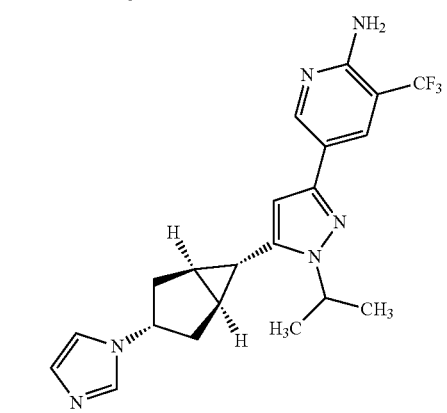
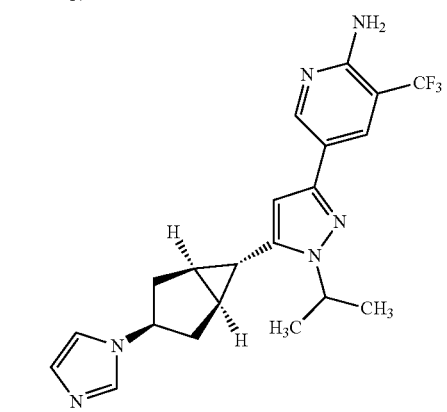
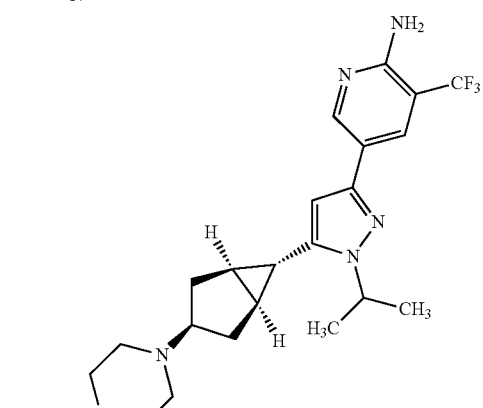
472
-continued
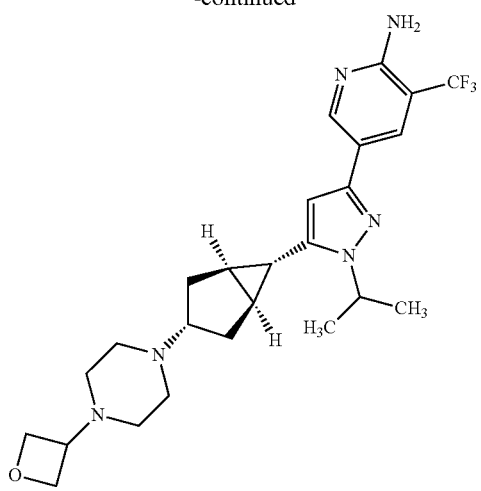
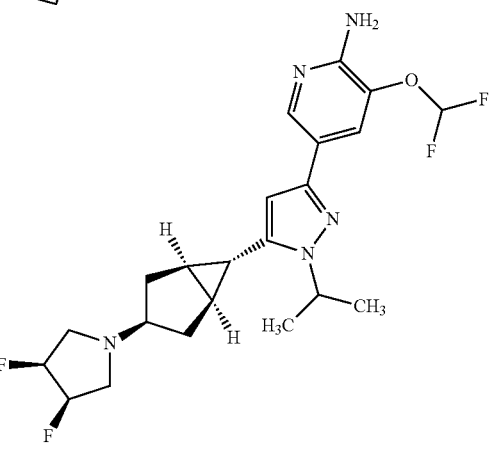
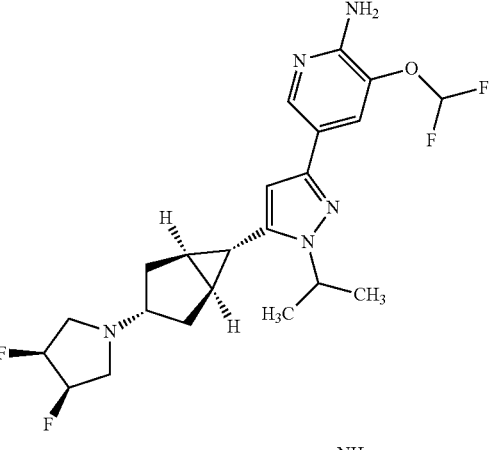
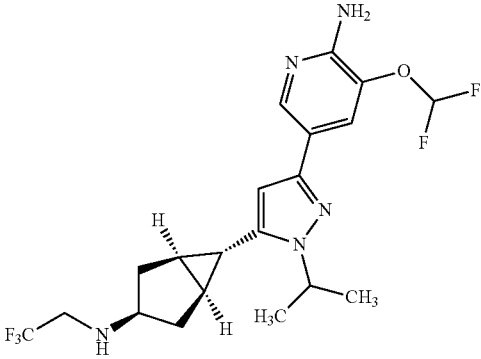

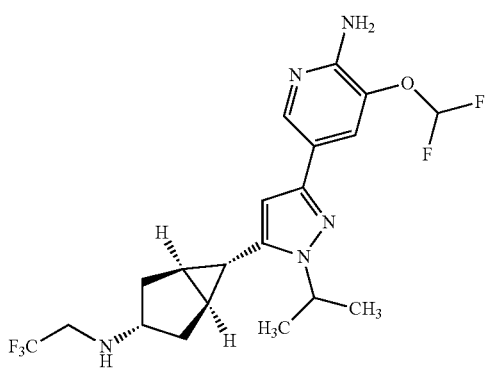
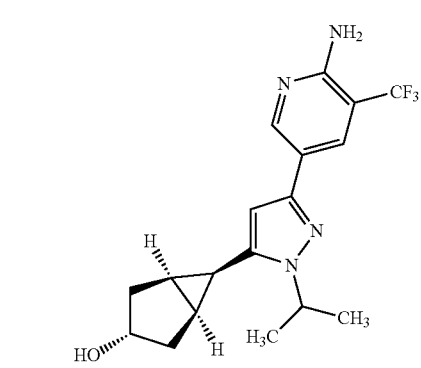
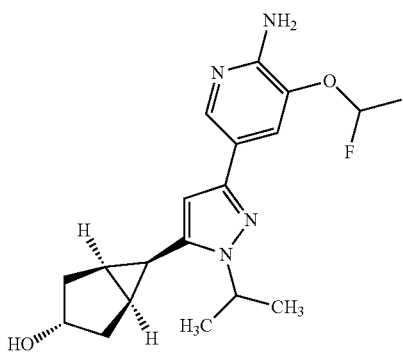
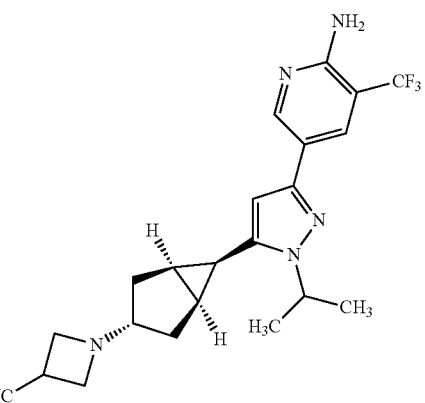
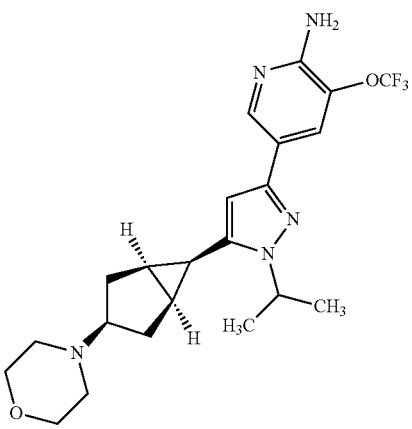
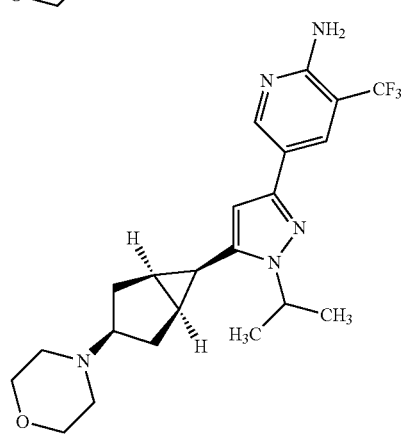
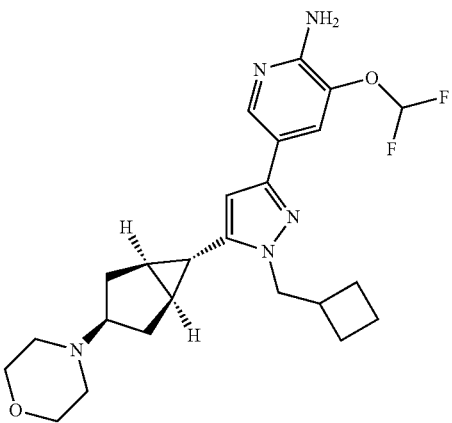
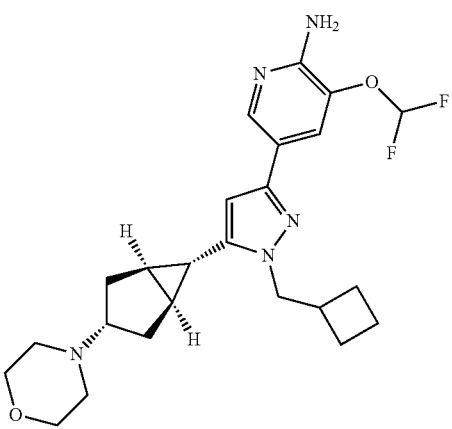

475
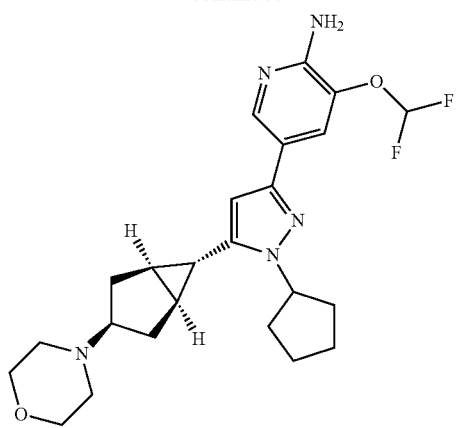
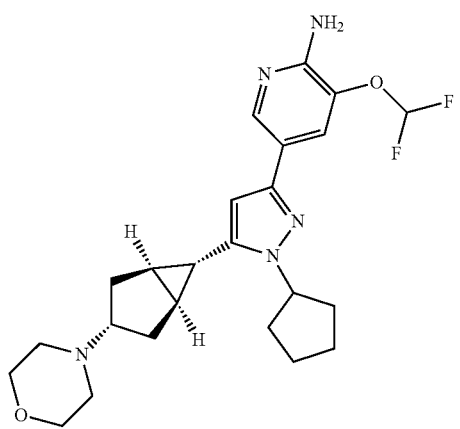
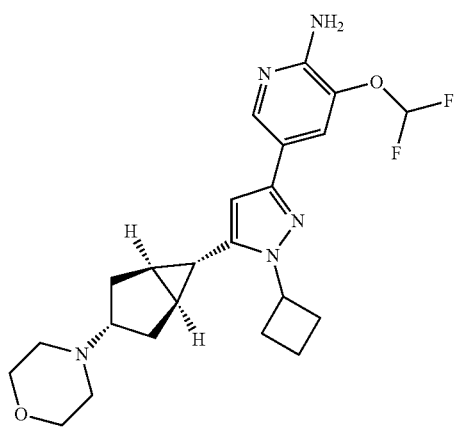
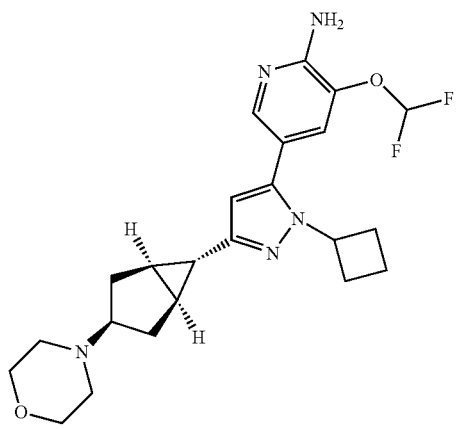
476
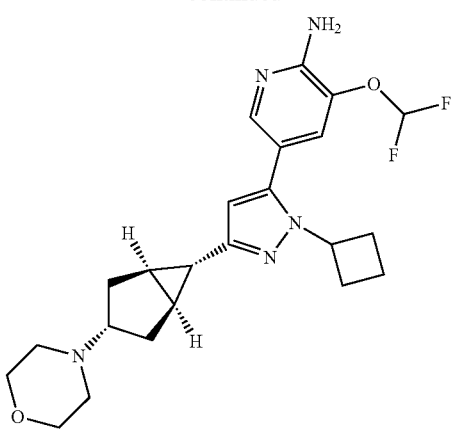
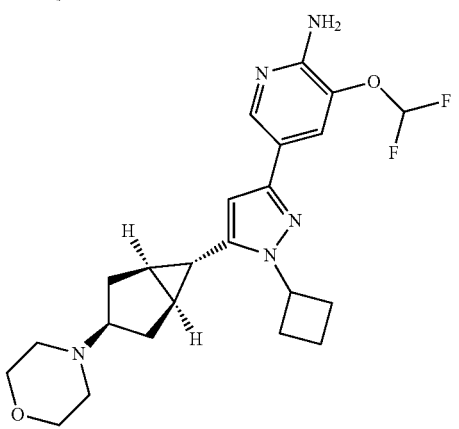
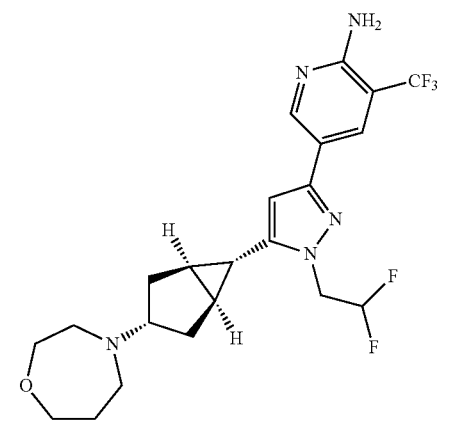
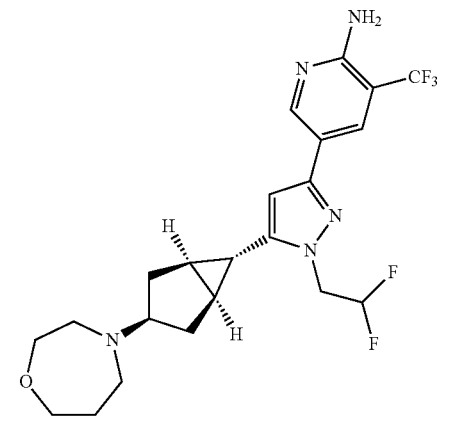

477
-continued
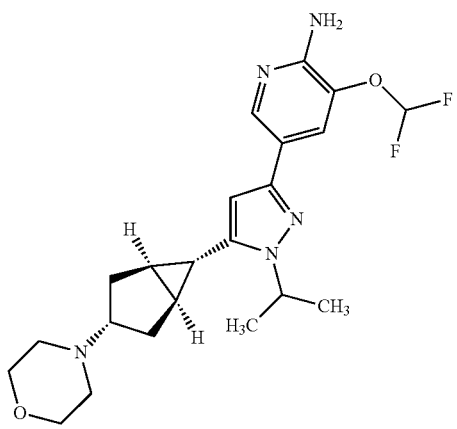
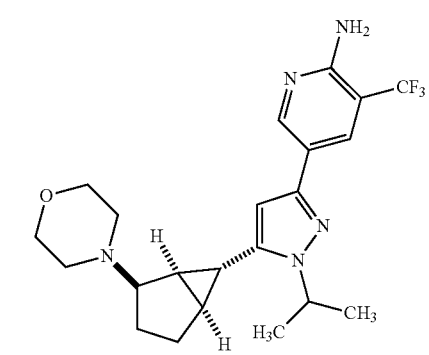
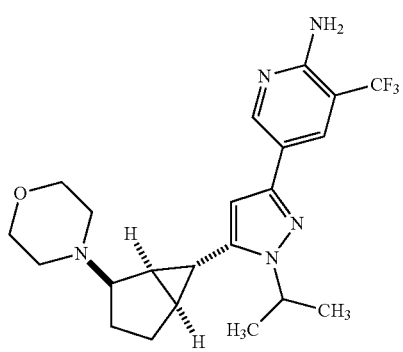
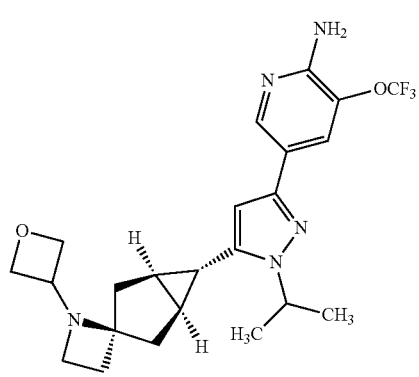
478
-continued
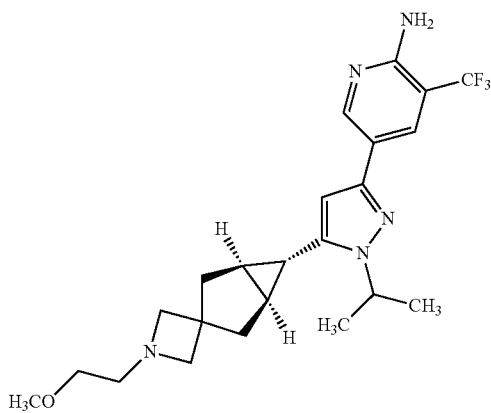
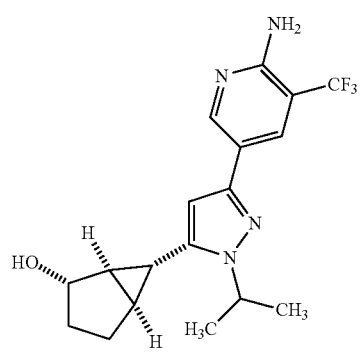
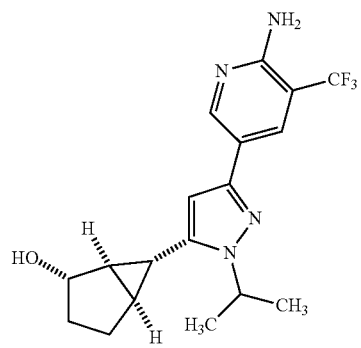
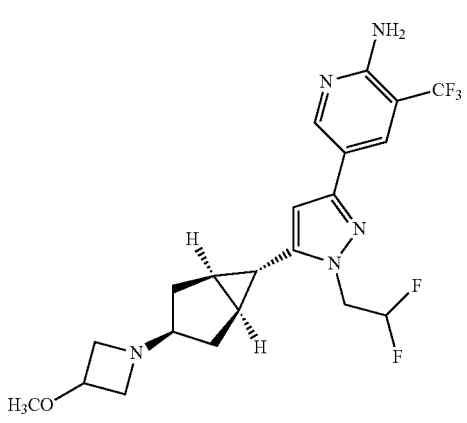

479
-continued
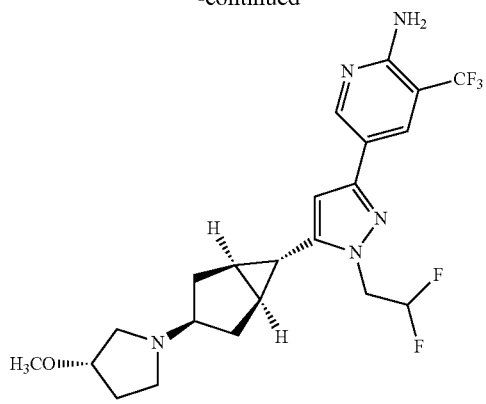
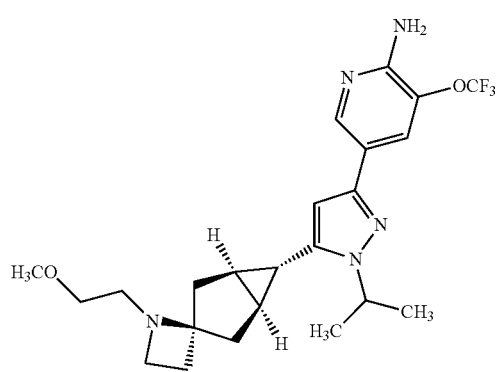
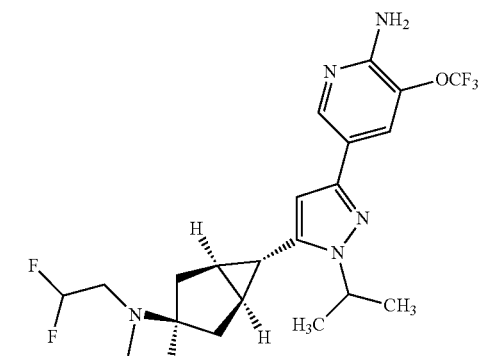
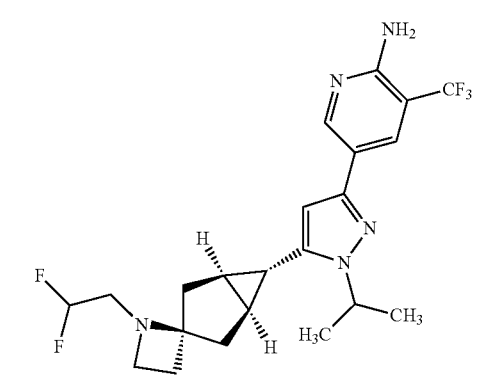
480
-continued
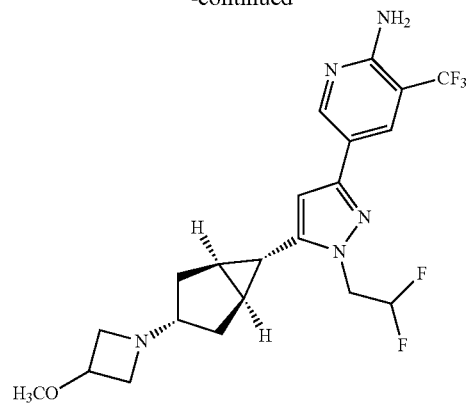
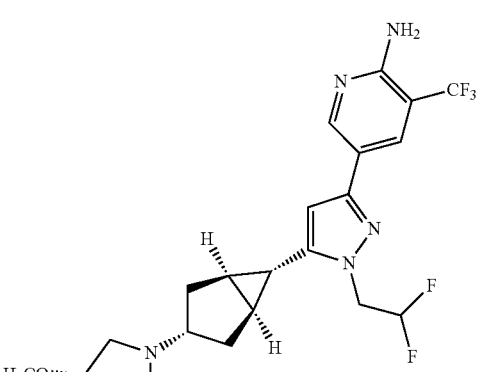
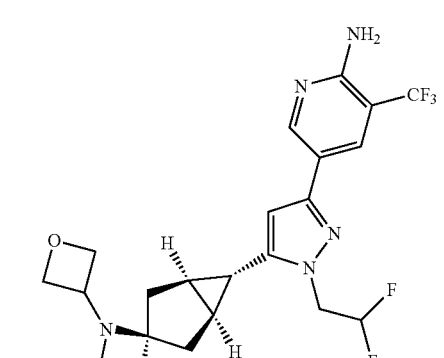
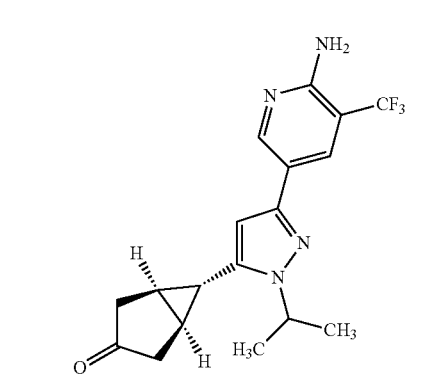

481
-continued
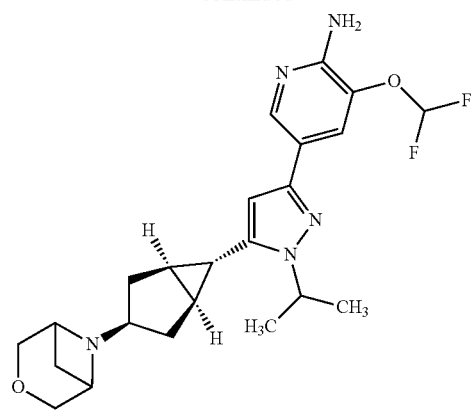
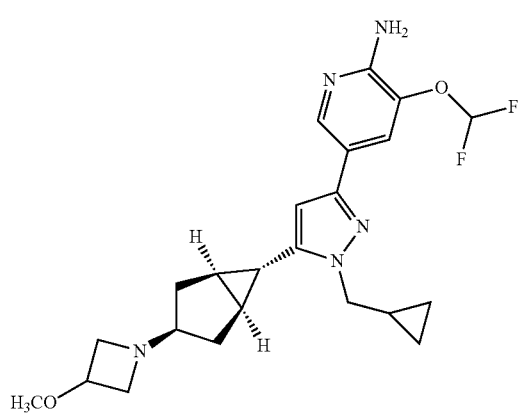
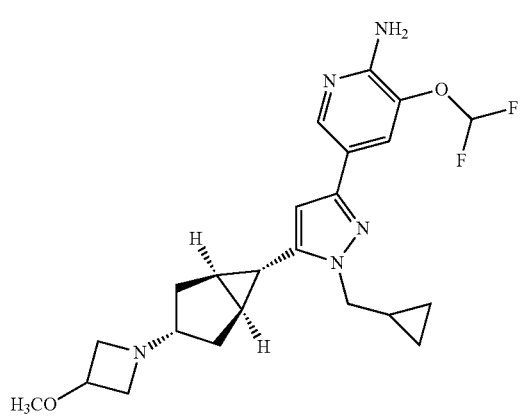
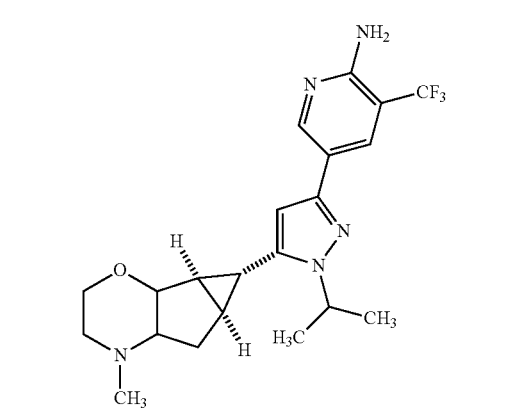
482
-continued
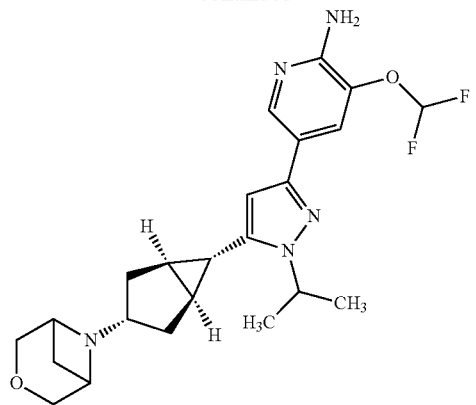
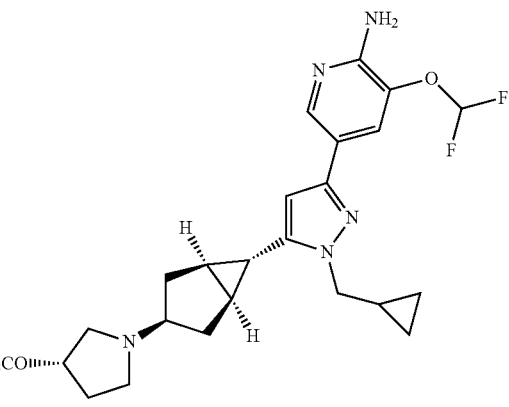
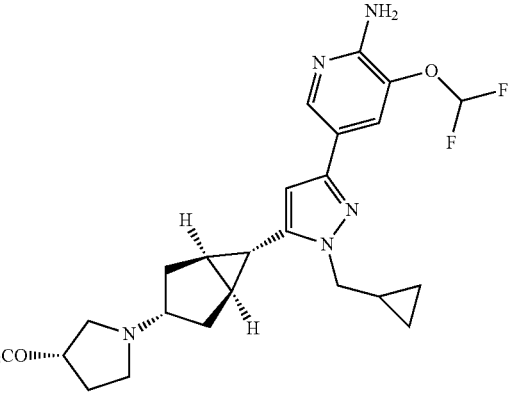
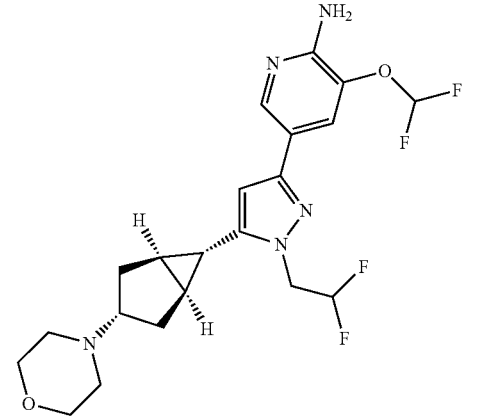

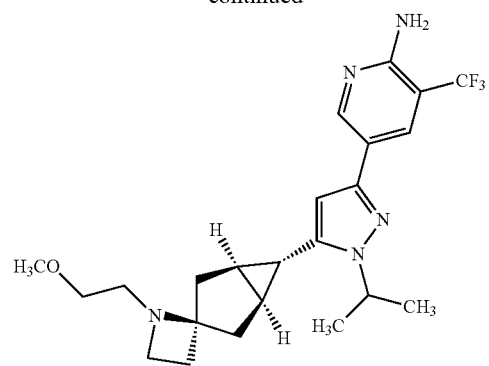
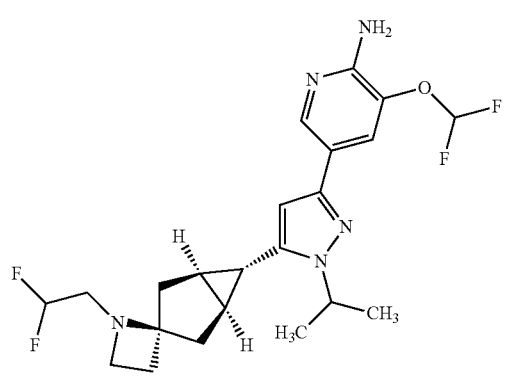
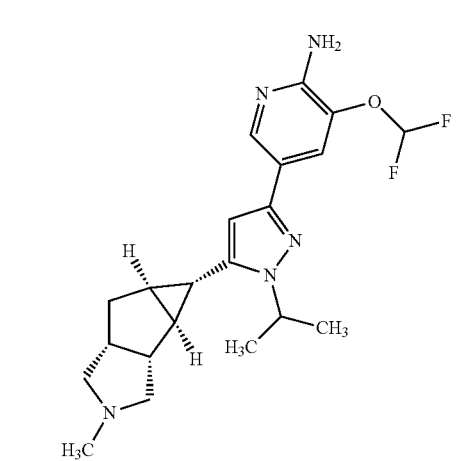
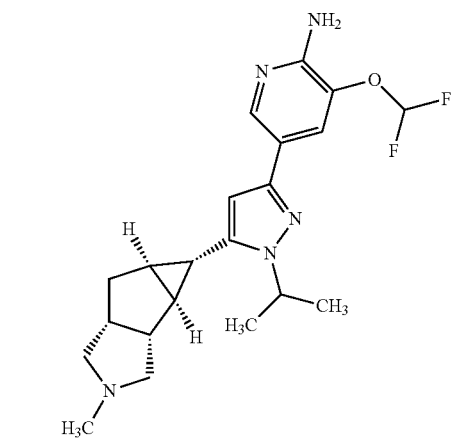
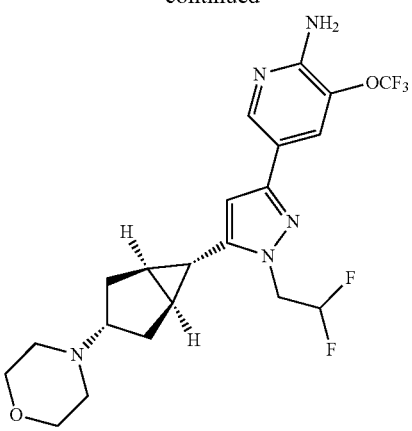
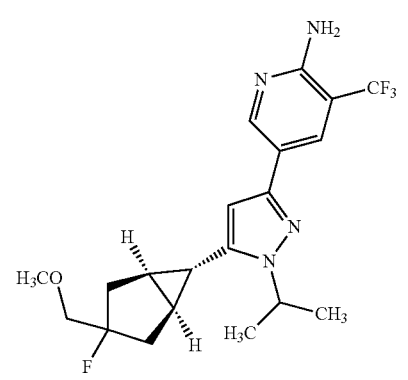
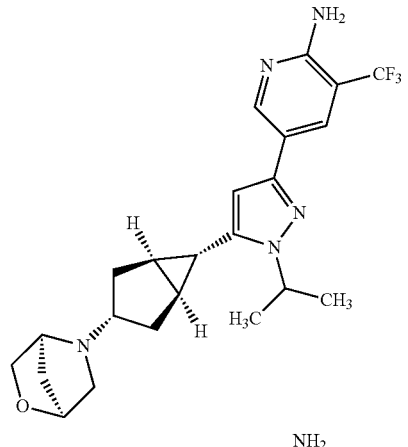
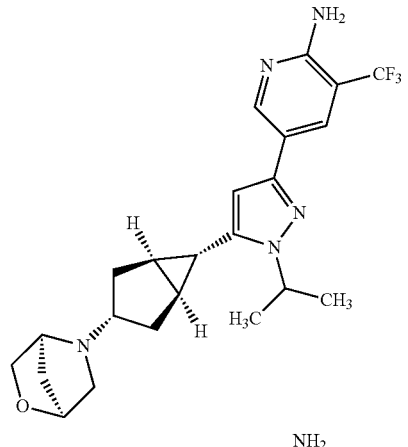

485
-continued
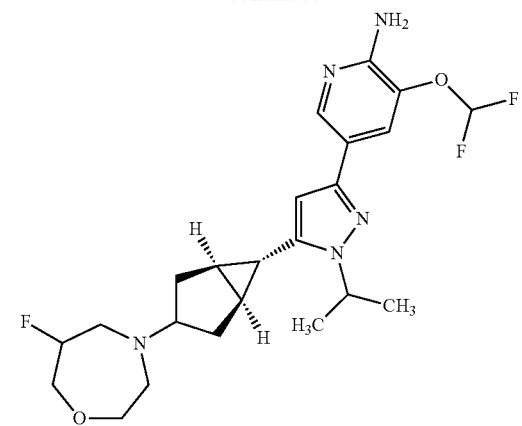
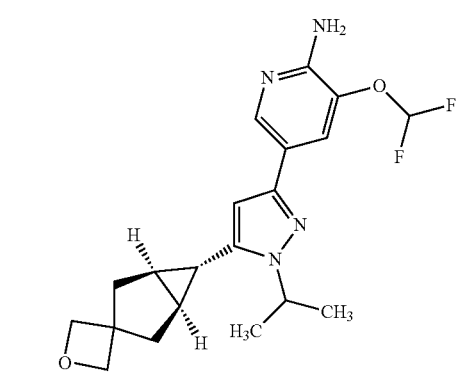
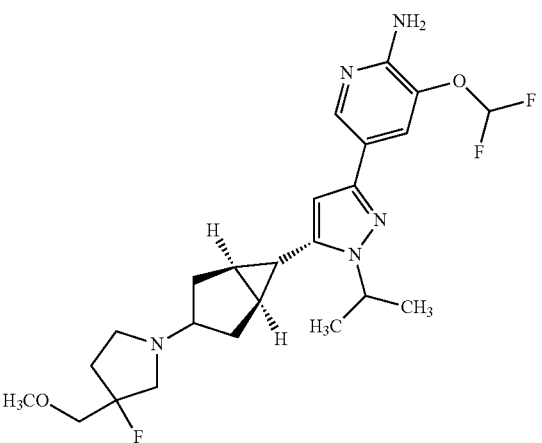
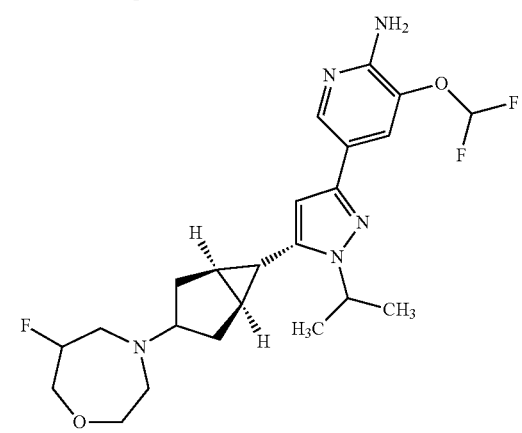
486
-continued
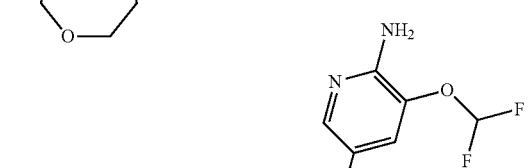
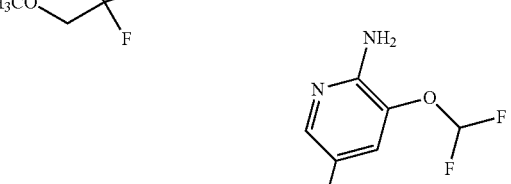

487
-continued
488
-continued
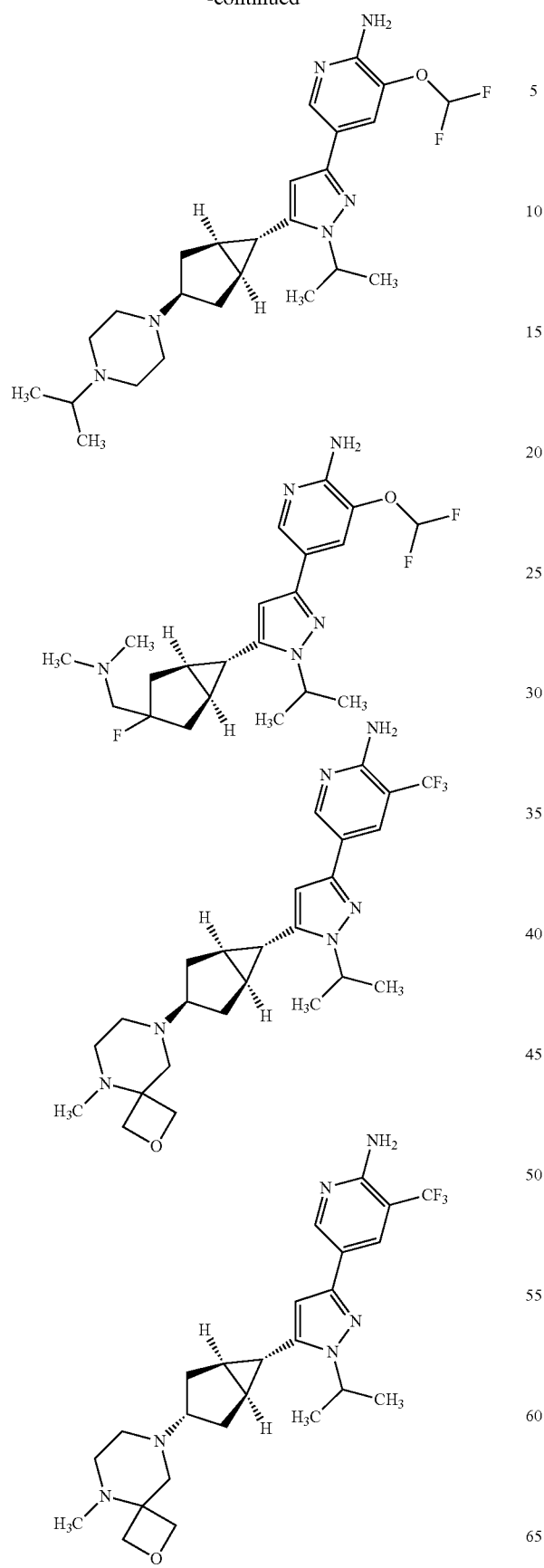
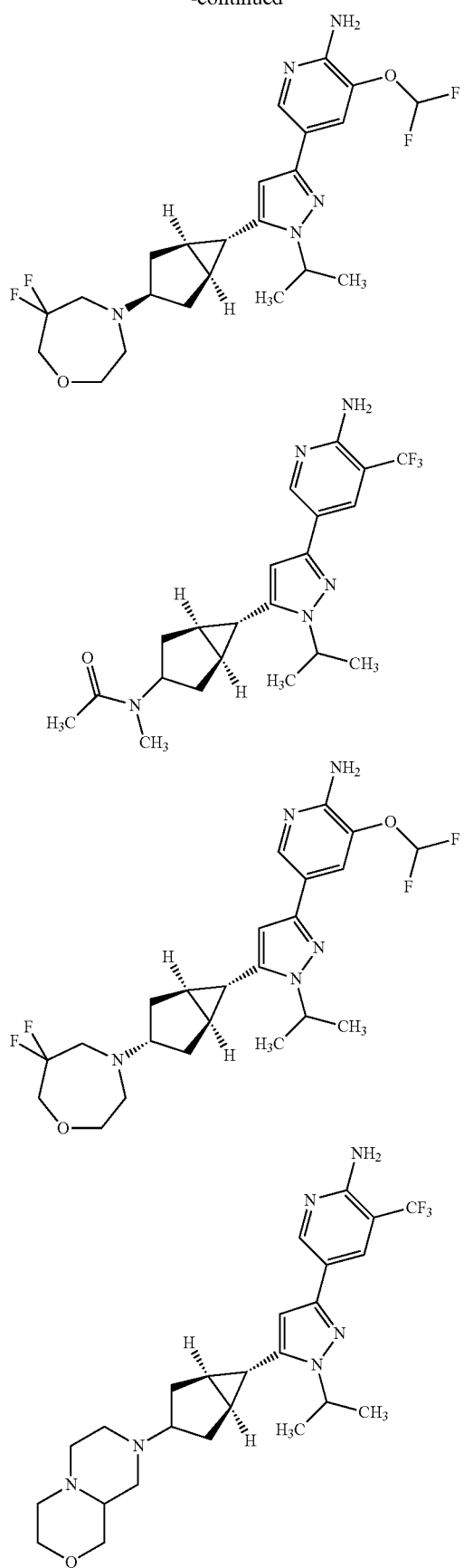

489
-continued
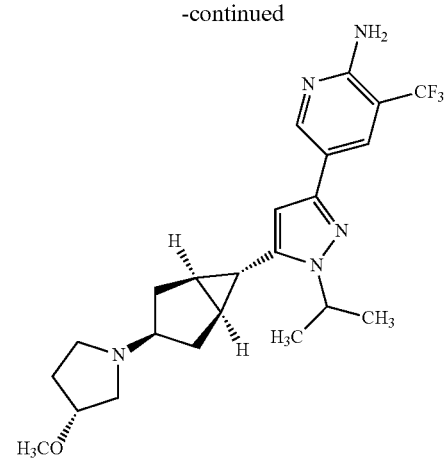
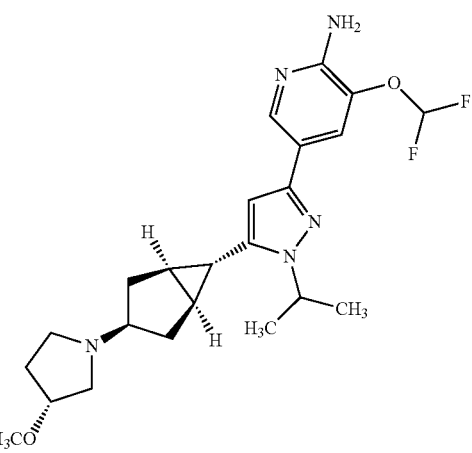
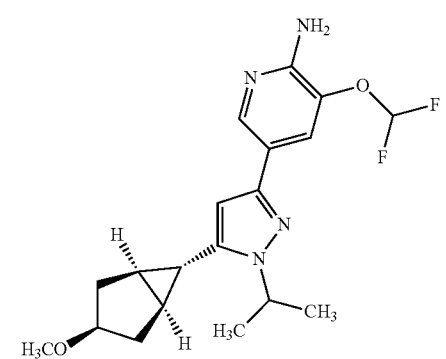
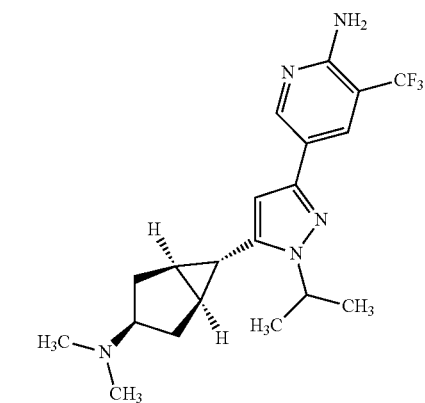
490
-continued
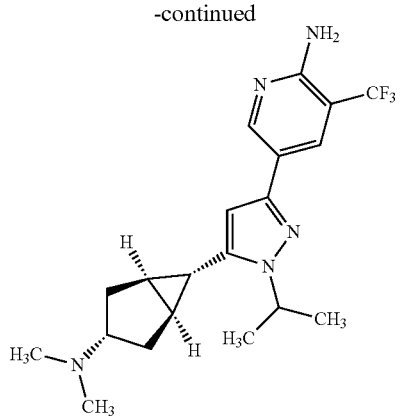
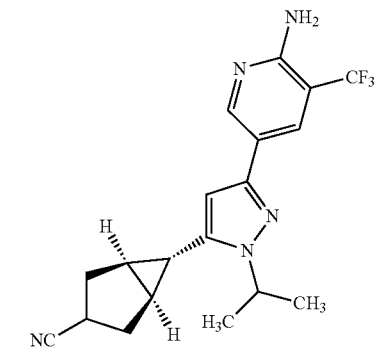
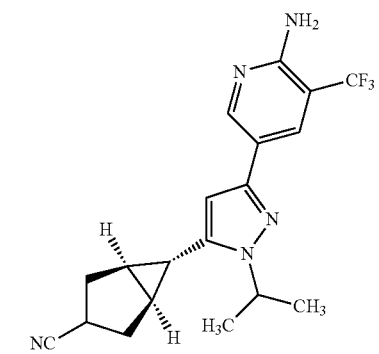
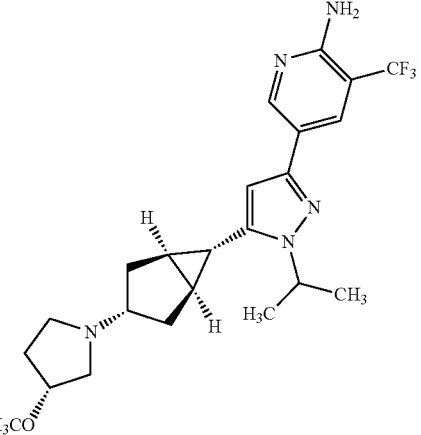

| 491 | 492 |
|---|---|
| -continued | -continued |
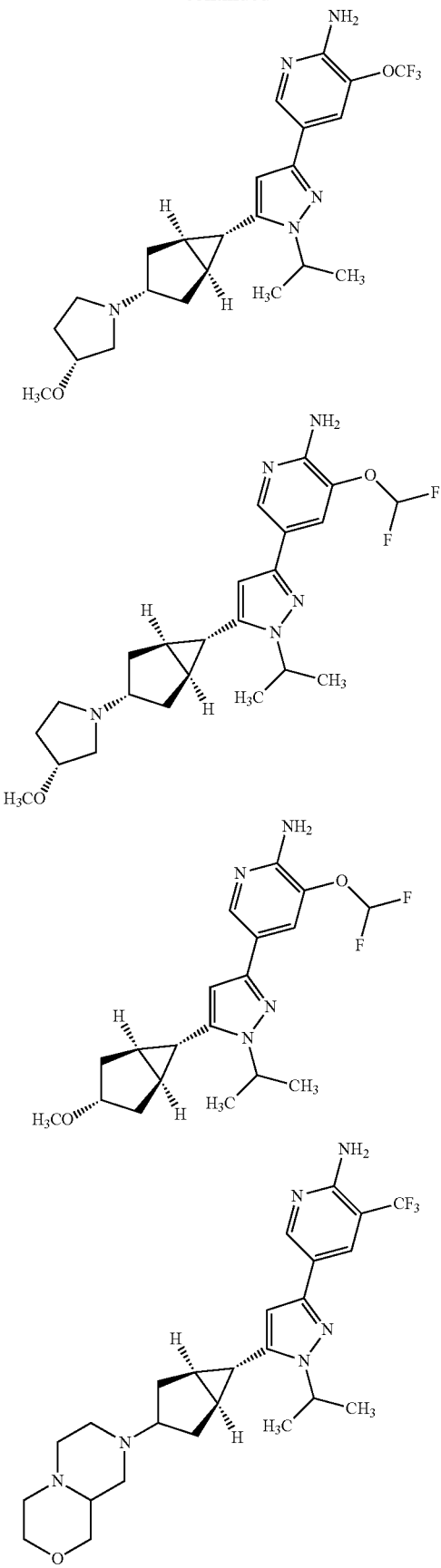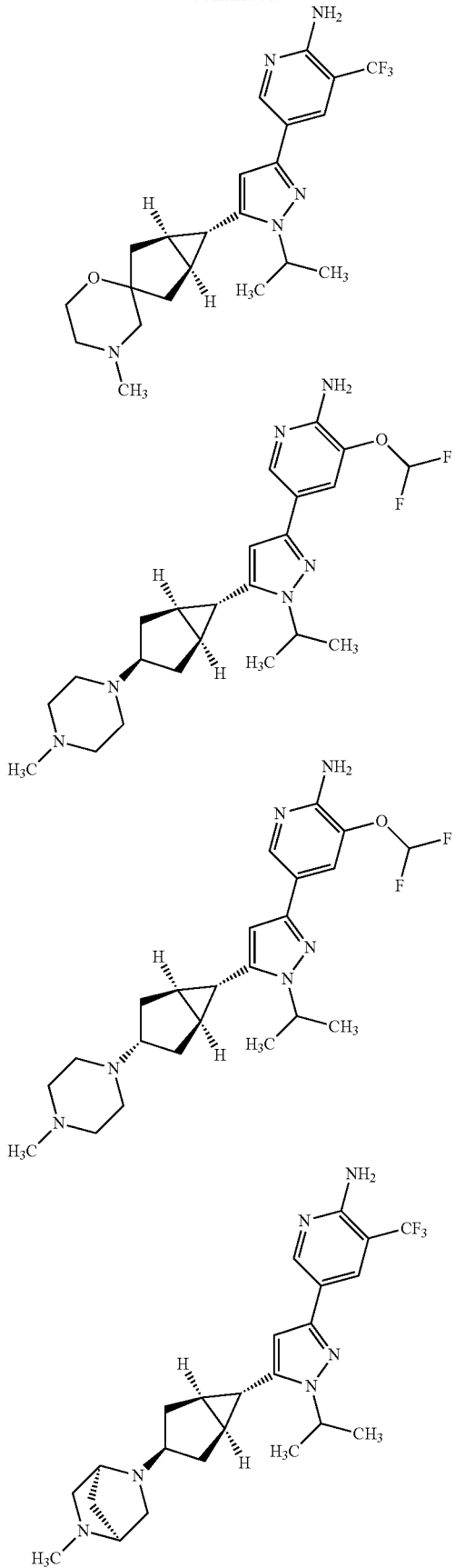

493
-continued
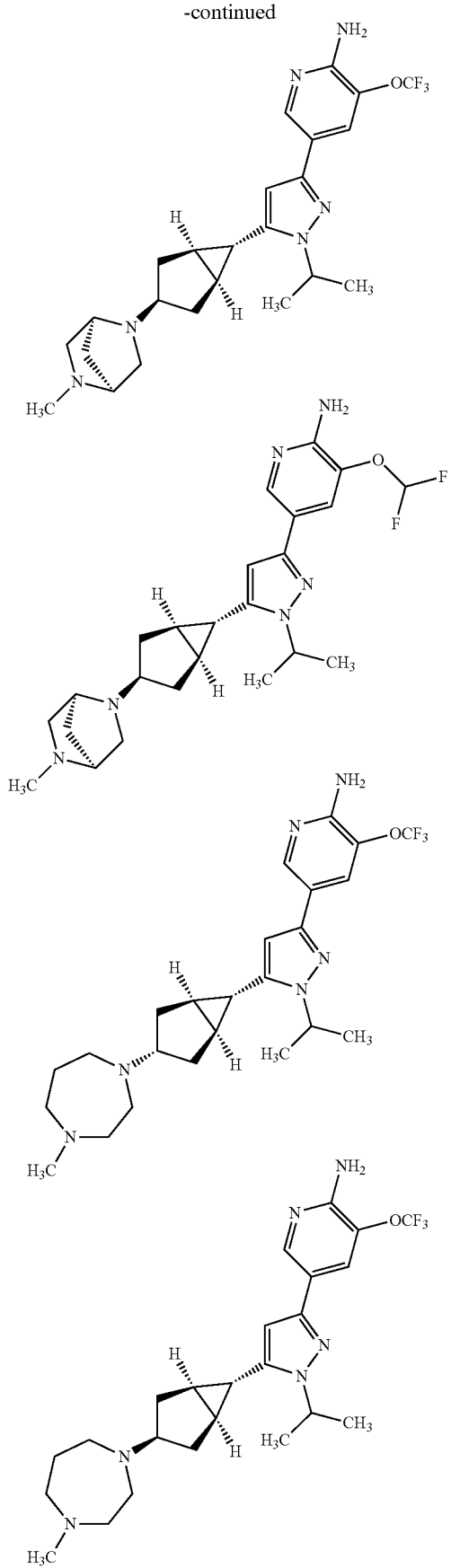
494
-continued
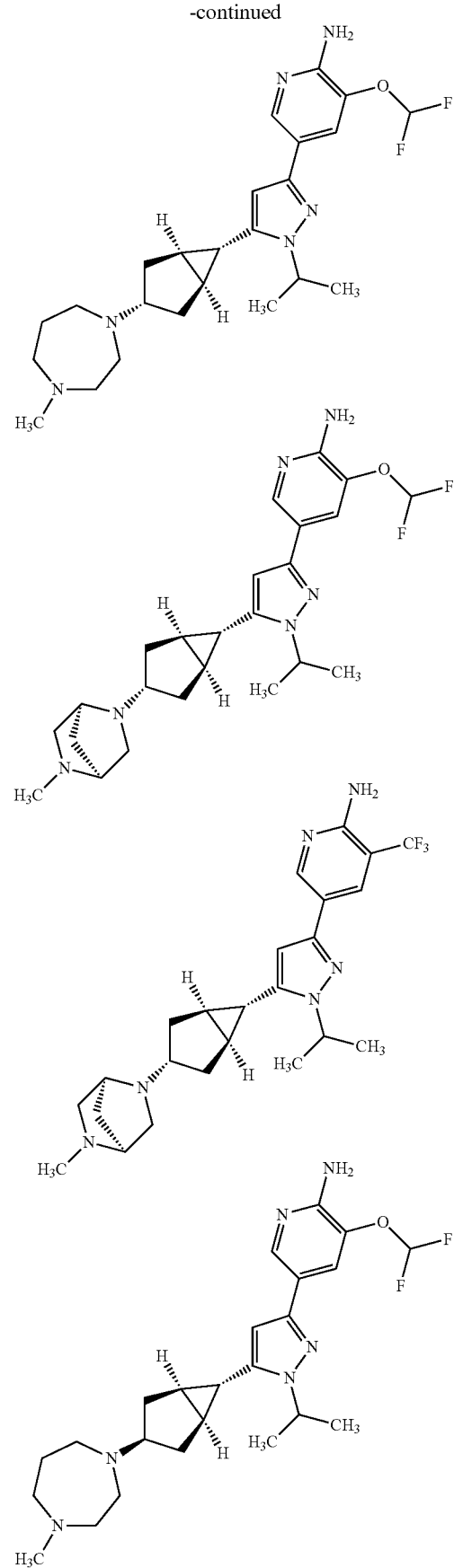

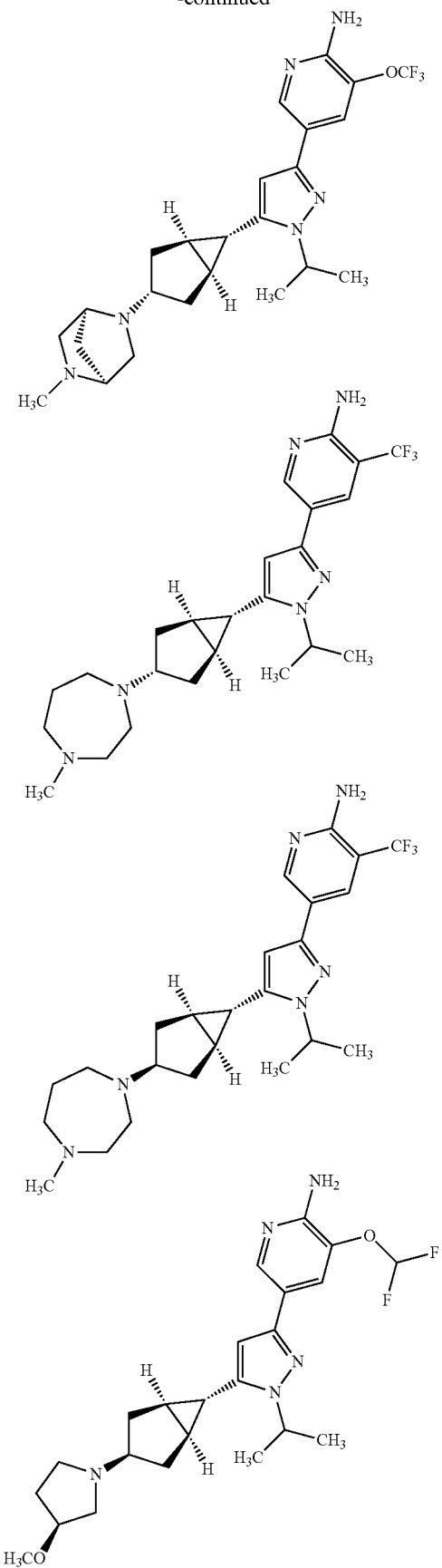
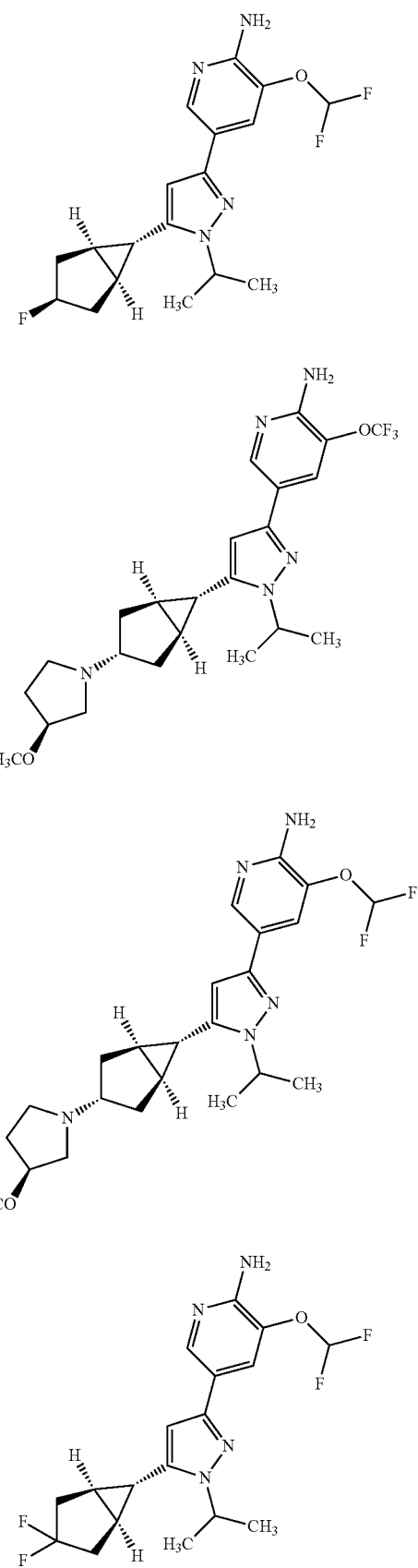

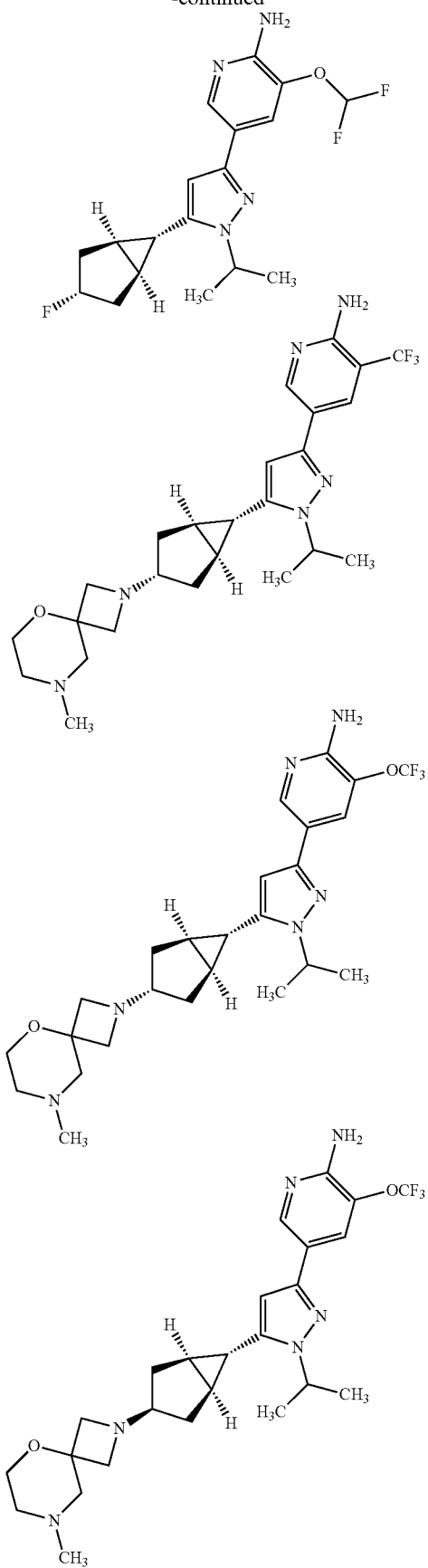
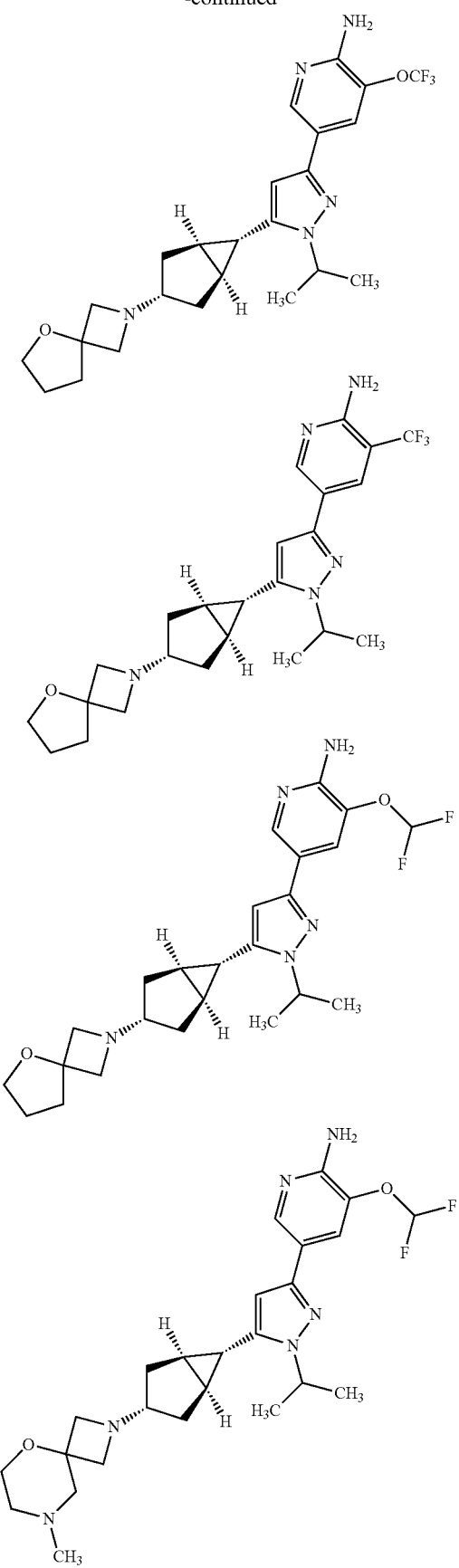

499
-continued
500
-continued
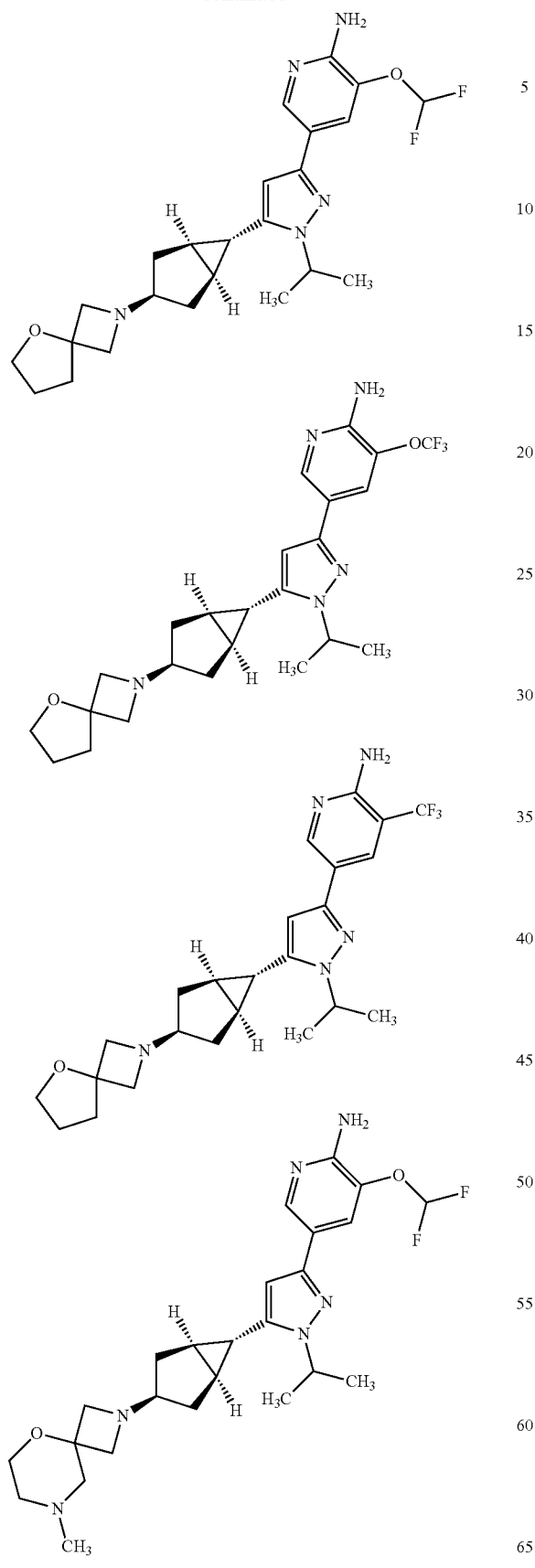
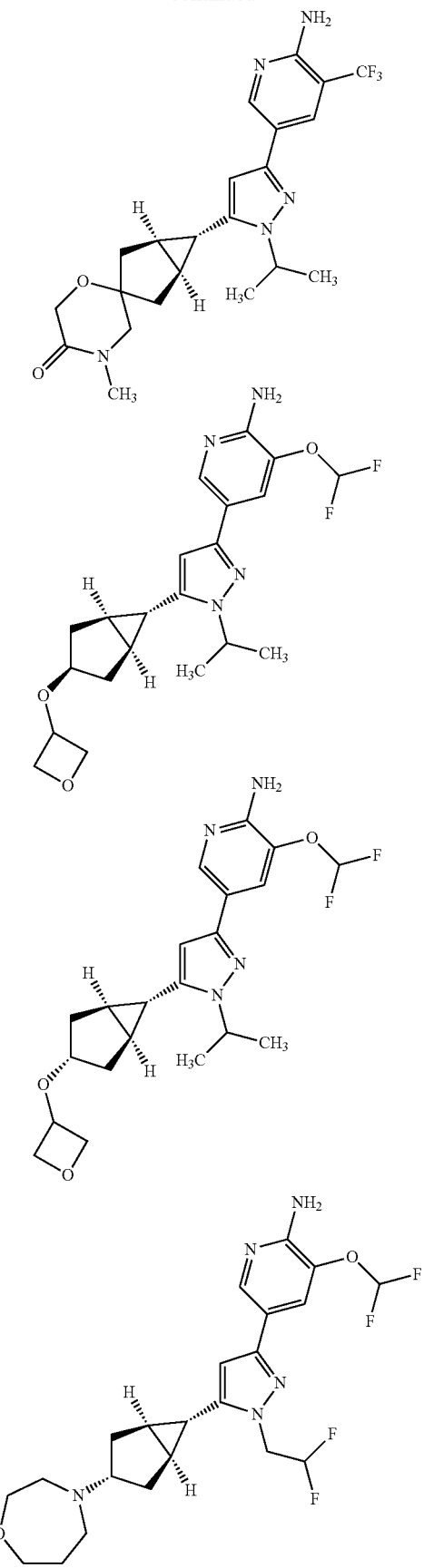

501
-continued
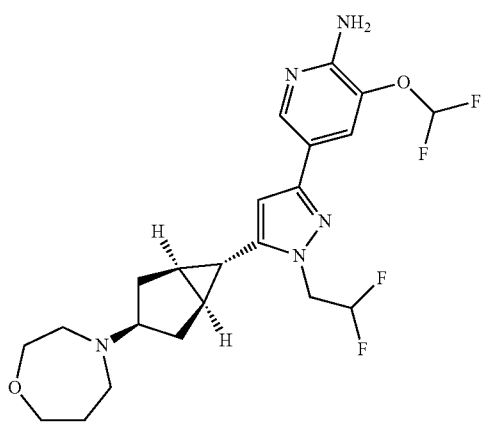
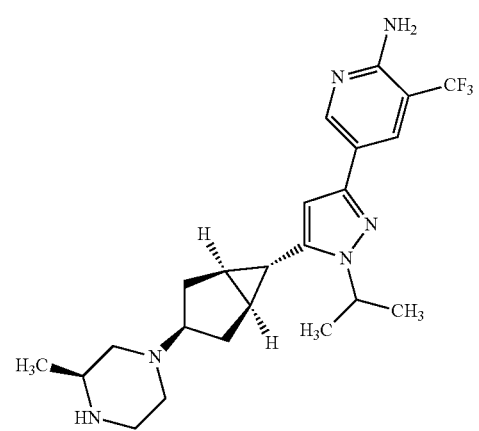
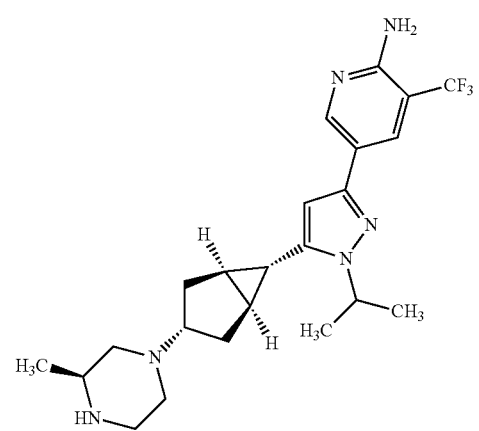
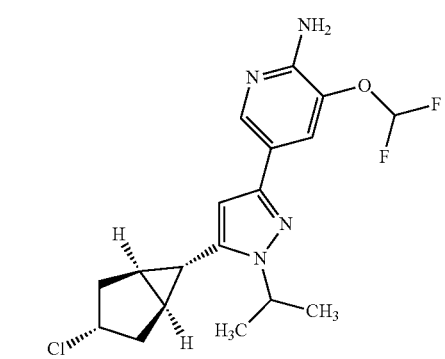
502
-continued
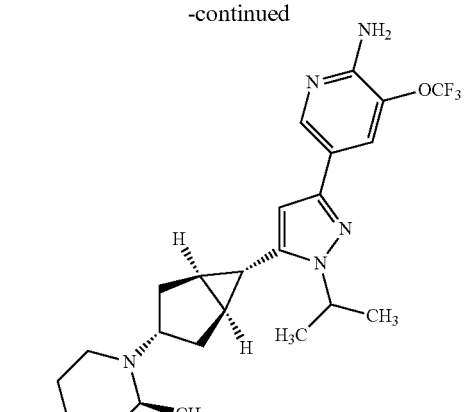
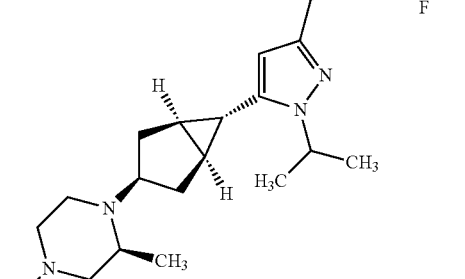
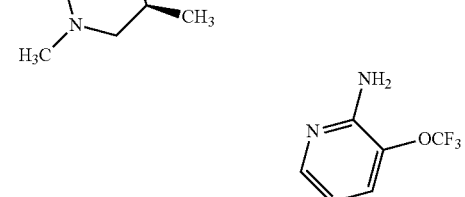
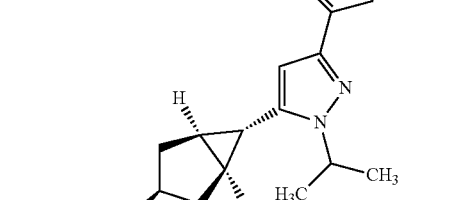

503
-continued
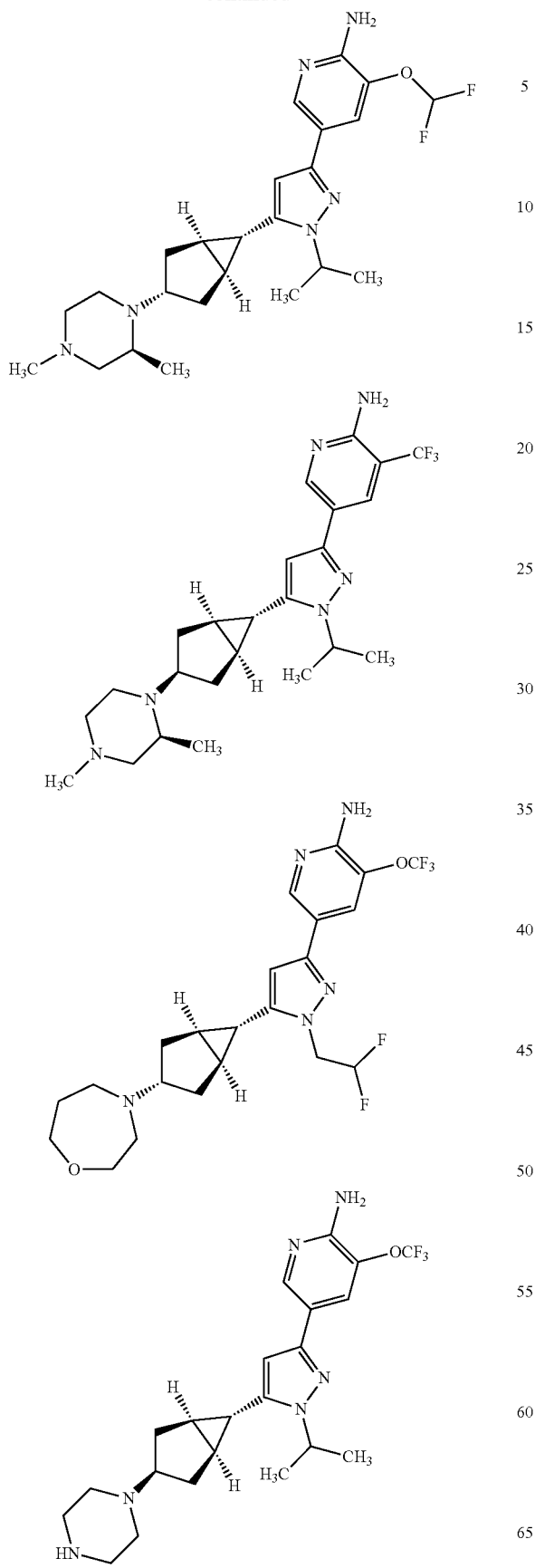
504
-continued
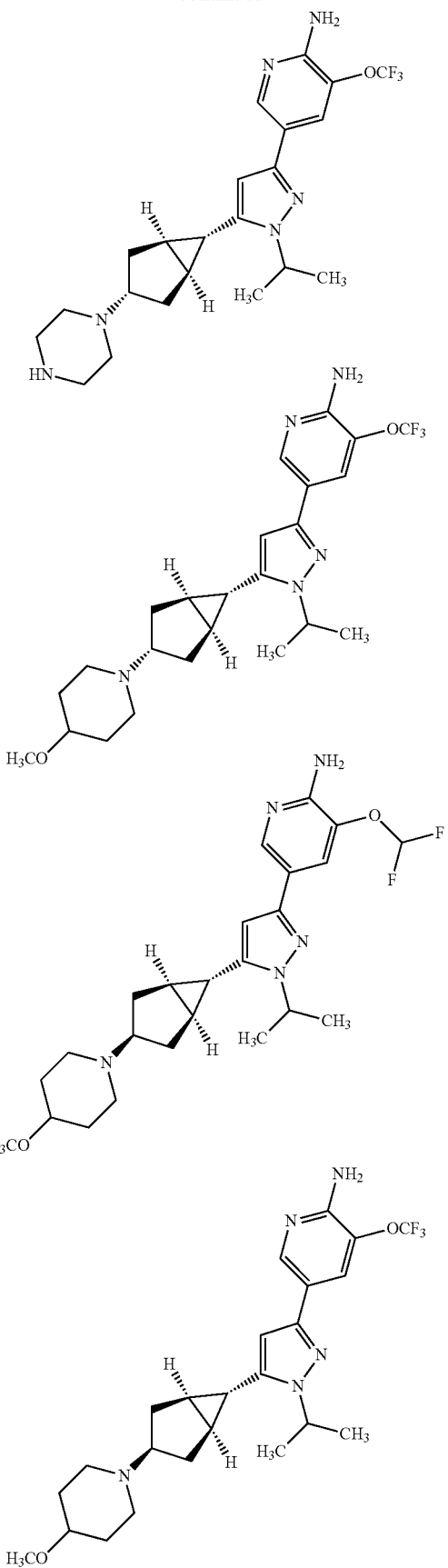

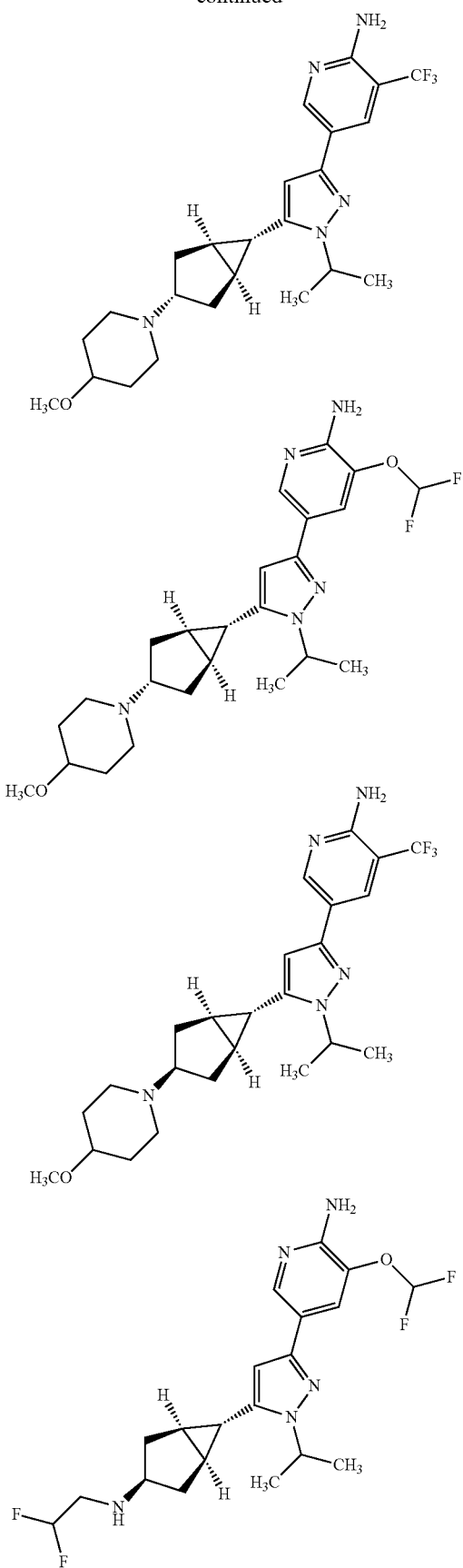

507
-continued
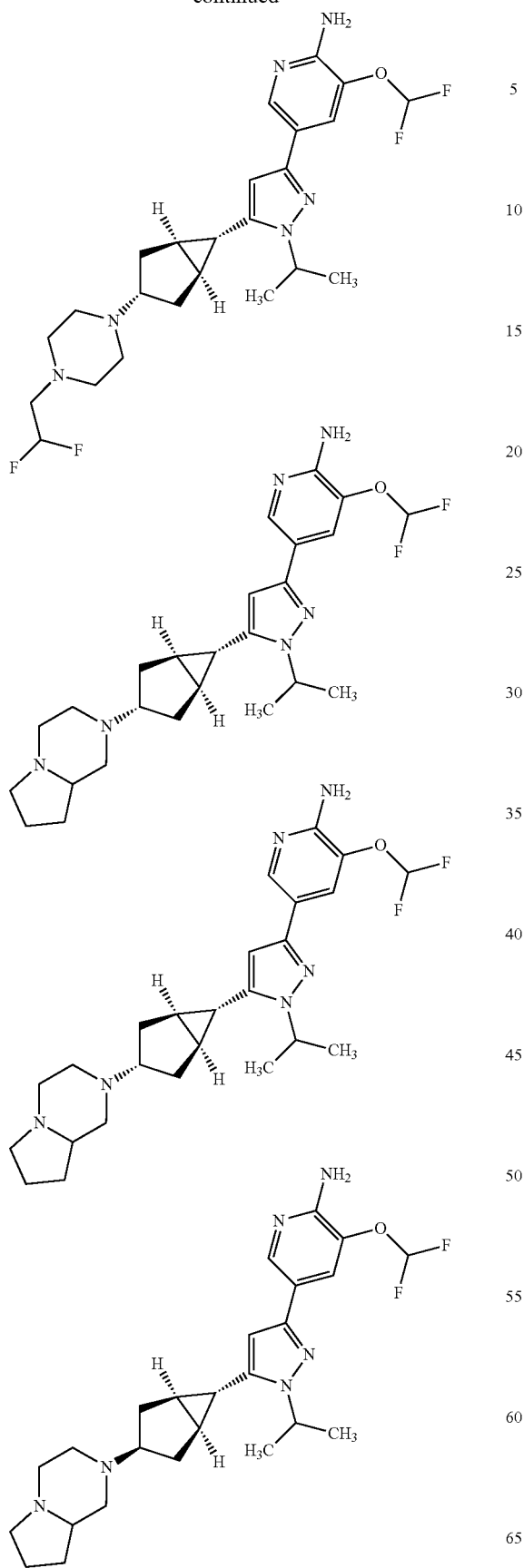
508
-continued
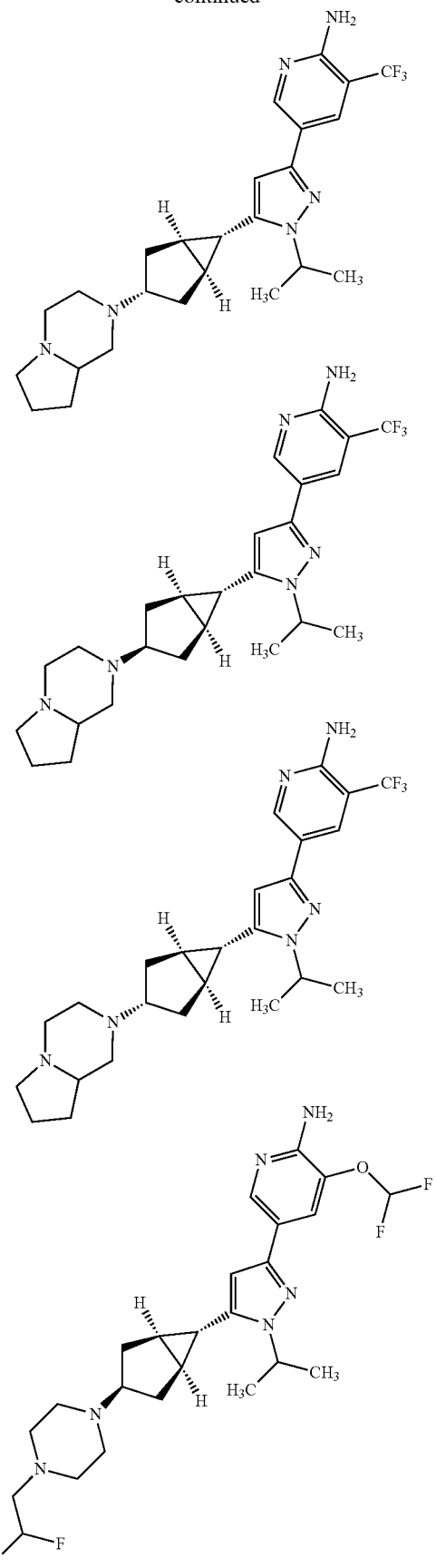

509
-continued
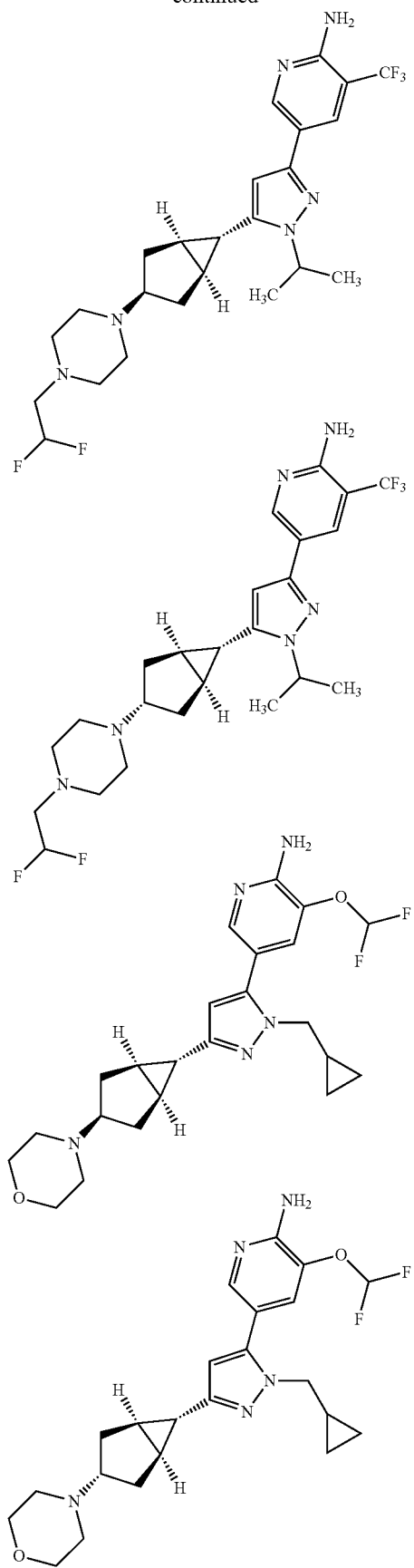
510
-continued
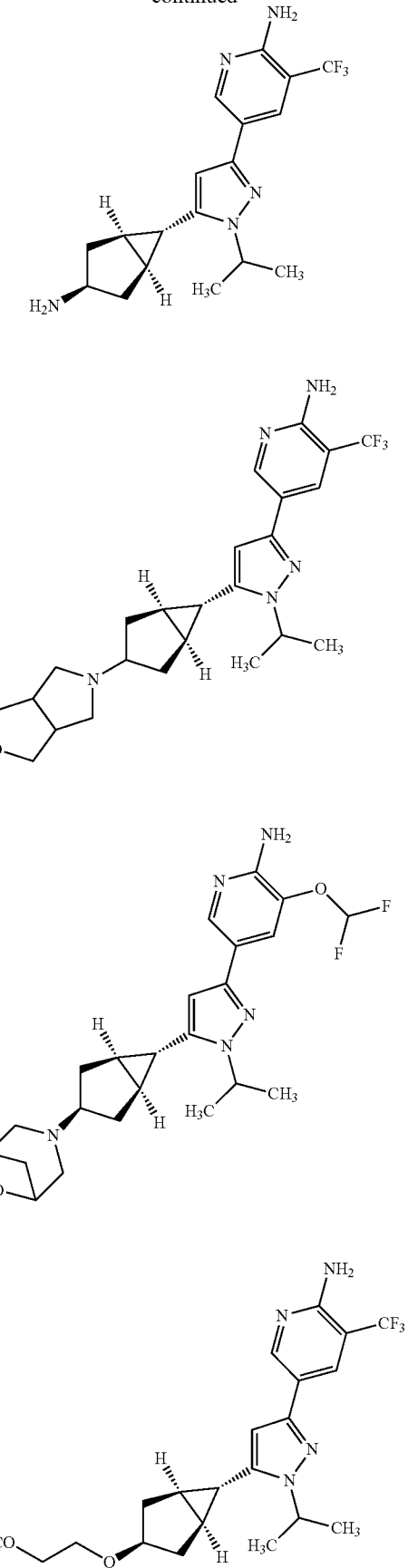

| 511 | 512 |
|---|---|
| -continued | -continued |
| 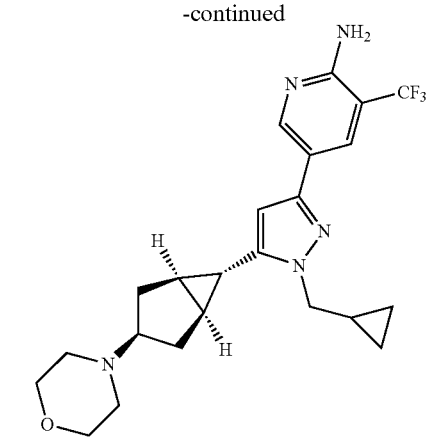 | 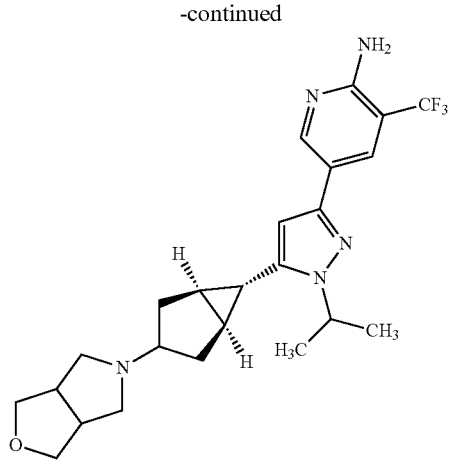 |
| 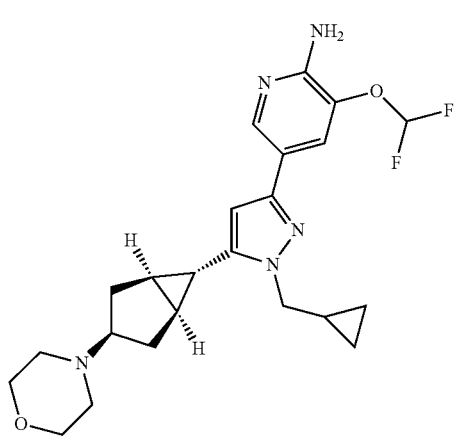 | 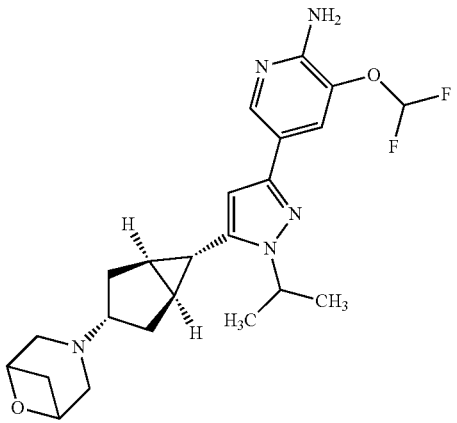 |
| 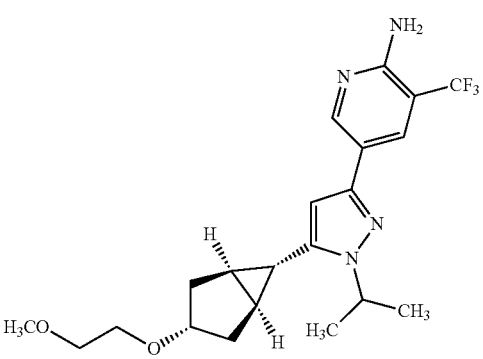 | 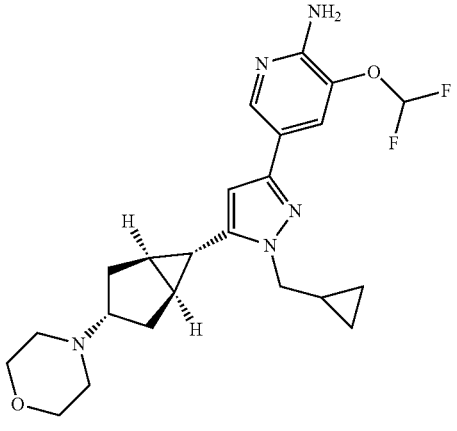 |
| 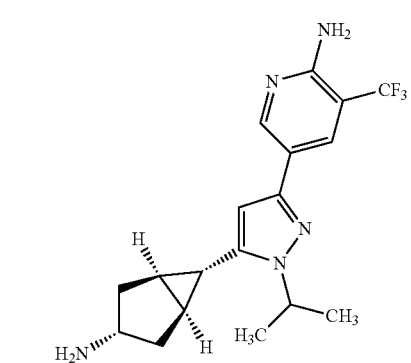 | 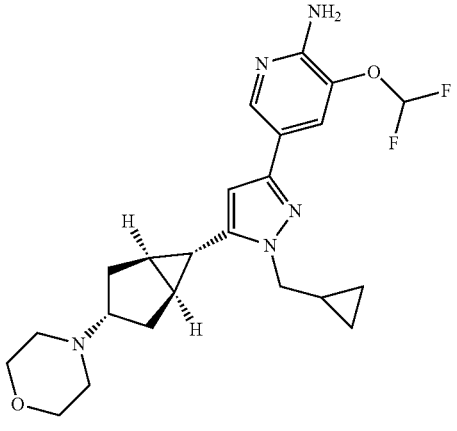 |

513 -continued
514 -continued
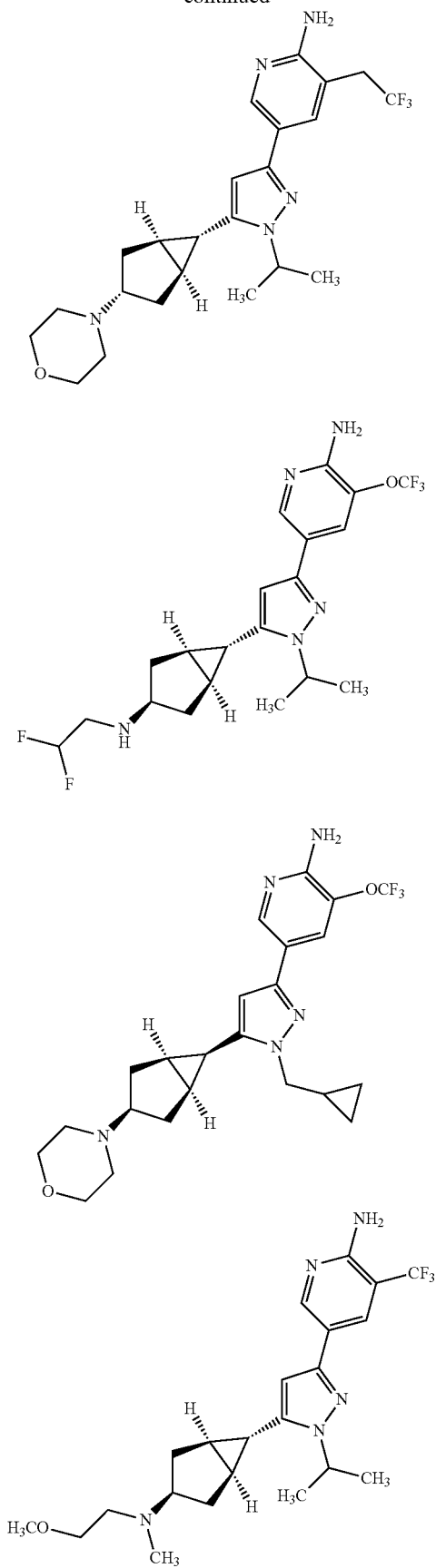
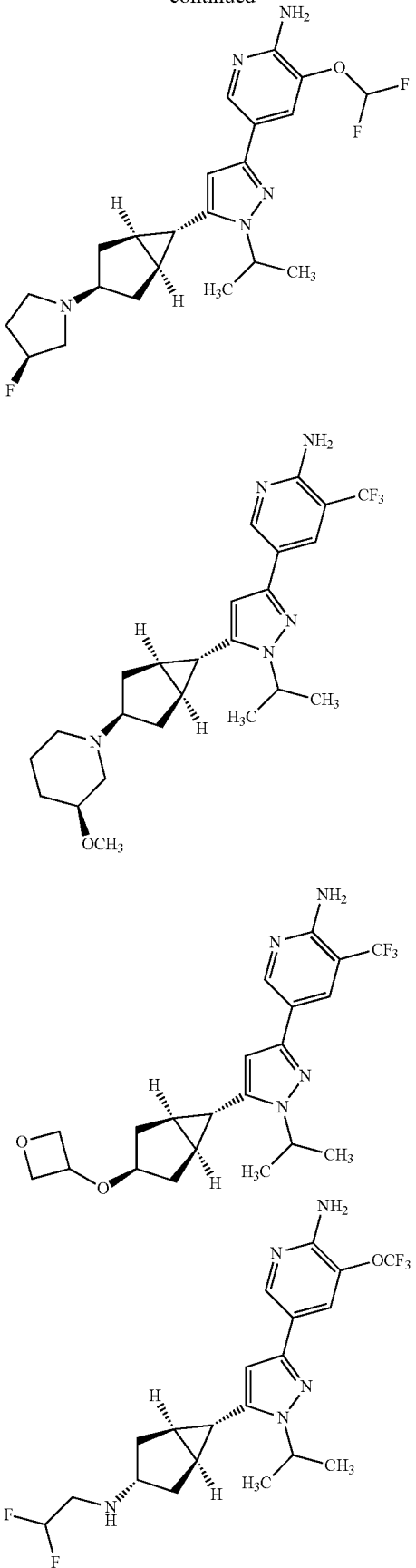

515
-continued
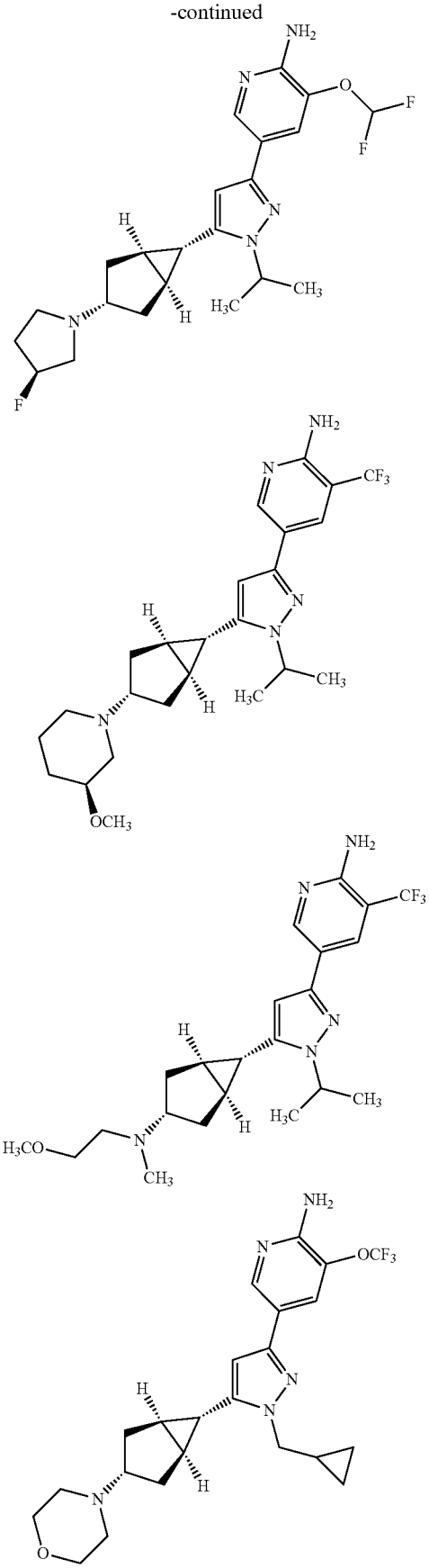
516
-continued
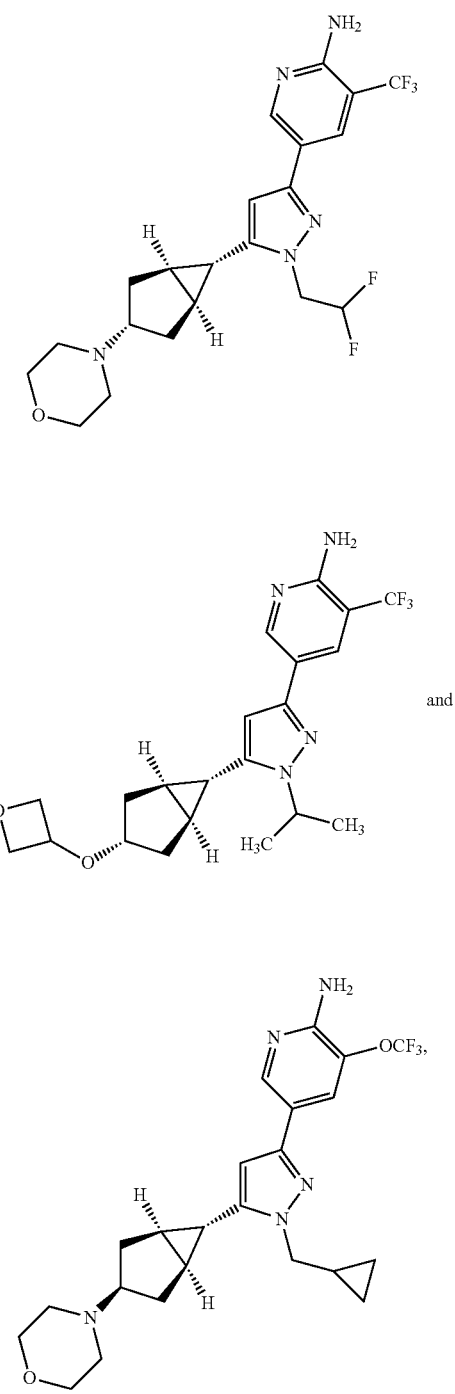
and salts thereof.
40. A pharmaceutical composition comprising a compound of formula 0 as described in claim 1, or a pharmaceutically acceptable salt thereof and a pharmaceutically acceptable carrier, diluent or excipient.
\* \* \* \* \*